US012522565B2

(12) United States Patent
Fleetham et al.

(10) Patent No.: US 12,522,565 B2
(45) Date of Patent: Jan. 13, 2026

(54) ORGANIC ELECTROLUMINESCENT MATERIALS AND DEVICES

(71) Applicant: Universal Display Corporation, Ewing, NJ (US)

(72) Inventors: Tyler Fleetham, Yardley, PA (US); Nicholas J. Thompson, New Hope, PA (US); Jason Brooks, Philadelphia, PA (US); Ivan Milas, Summit, NJ (US); Jerald Feldman, Cherry Hill, NJ (US); Siva Kumar Talluri, Wilmington, DE (US); Mahesh Paudyal, Middletown, DE (US); Douglas Williams, Mullica Hill, NJ (US); Eric A. Margulies, Philadelphia, PA (US); Chun Lin, Yardley, PA (US); Bin Ma, Plainsboro, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 860 days.

(21) Appl. No.: 17/672,934

(22) Filed: Feb. 16, 2022

(65) Prior Publication Data

US 2022/0181561 A1 Jun. 9, 2022

Related U.S. Application Data

(63) Continuation-in-part of application No. 17/063,884, filed on Oct. 6, 2020, now Pat. No. 11,919,914.

(Continued)

(51) Int. Cl.

| | |
|---|---|
| ***H01L 51/50*** | (2006.01) |
| ***C07D 209/86*** | (2006.01) |

(Continued)

(52) U.S. Cl.

CPC ........... *C07D 209/86* (2013.01); *C07F 5/027* (2013.01); *C07F 7/0812* (2013.01);

(Continued)

(58) Field of Classification Search

None

See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |

(Continued)

FOREIGN PATENT DOCUMENTS

| | | |
|---|---|---|
| CN | 109378392 | 2/2019 |
| CN | 112909197 | 6/2021 |

(Continued)

OTHER PUBLICATIONS

Partial European Search Report Issued May 10, 2024 In Corresponding European Application No. 23205921.2.

(Continued)

*Primary Examiner* — Gregory D Clark

(74) *Attorney, Agent, or Firm* — DUANE MORRIS LLP

(57) ABSTRACT

High performance OLED that includes deuterated compounds in the emissive layer are disclosed. The OLED includes an anode; a cathode; and an emissive layer, disposed between the anode and the cathode. In the OLED, the emissive layer includes a first phosphorescent emitter and a first host; the first phosphorescent emitter is a metal complex; the first host is partially or fully deuterated; and at least one additional condition is true.

19 Claims, 2 Drawing Sheets

Related U.S. Application Data

(60) Provisional application No. 63/229,748, filed on Aug. 5, 2021, provisional application No. 63/220,429, filed on Jul. 9, 2021, provisional application No. 63/154,320, filed on Feb. 26, 2021, provisional application No. 62/982,883, filed on Feb. 28, 2020, provisional application No. 62/971,295, filed on Feb. 7, 2020, provisional application No. 62/926,035, filed on Oct. 25, 2019.

(51) Int. Cl.

| | |
|---|---|
| ***C07F 5/02*** | (2006.01) |
| ***C07F 7/08*** | (2006.01) |
| ***C07F 15/00*** | (2006.01) |
| ***C09K 11/02*** | (2006.01) |
| ***C09K 11/06*** | (2006.01) |
| ***H10K 85/30*** | (2023.01) |
| ***H10K 85/40*** | (2023.01) |
| ***H10K 85/60*** | (2023.01) |
| *H10K 50/11* | (2023.01) |
| *H10K 101/00* | (2023.01) |
| *H10K 101/10* | (2023.01) |

(52) U.S. Cl.

CPC ...... *C07F 15/0033* (2013.01); *C07F 15/0086* (2013.01); *C09K 11/02* (2013.01); *C09K 11/06* (2013.01); *H10K 85/342* (2023.02); *H10K 85/346* (2023.02); *H10K 85/40* (2023.02); *H10K 85/654* (2023.02); *H10K 85/6572* (2023.02); *C07B 2200/05* (2013.01); *C09K 2211/1007* (2013.01); *C09K 2211/1011* (2013.01); *C09K 2211/1014* (2013.01); *C09K 2211/1022* (2013.01); *C09K 2211/1029* (2013.01); *C09K 2211/1033* (2013.01); *C09K 2211/1044* (2013.01); *C09K 2211/1055* (2013.01); *C09K 2211/185* (2013.01); *H10K 50/11* (2023.02); *H10K 85/658* (2023.02); *H10K 2101/10* (2023.02); *H10K 2101/90* (2023.02)

(56) References Cited

U.S. PATENT DOCUMENTS

| | | | |
|---|---|---|---|
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,528,187 | B1 | 3/2003 | Okada |
| 6,687,266 | B1 | 2/2004 | Ma et al. |
| 6,835,469 | B2 | 12/2004 | Kwong et al. |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |
| 7,250,226 | B2 | 7/2007 | Tokito et al. |
| 7,279,704 | B2 | 10/2007 | Walters et al. |
| 7,332,232 | B2 | 2/2008 | Ma et al. |
| 7,338,722 | B2 | 3/2008 | Thompson et al. |
| 7,393,599 | B2 | 7/2008 | Thompson et al. |
| 7,396,598 | B2 | 7/2008 | Takeuchi et al. |
| 7,431,968 | B1 | 10/2008 | Shtein et al. |
| 7,445,855 | B2 | 11/2008 | Mackenzie et al. |
| 7,534,505 | B2 | 5/2009 | Lin et al. |
| 8,012,609 | B2 | 9/2011 | Takeda |
| 9,391,288 | B2 | 7/2016 | Nagao et al. |
| 9,496,506 | B2 | 11/2016 | Lecloux et al. |
| 2002/0034656 | A1 | 3/2002 | Thompson et al. |
| 2002/0134984 | A1 | 9/2002 | Igarashi |
| 2002/0158242 | A1 | 10/2002 | Son et al. |
| 2003/0138657 | A1 | 7/2003 | Li et al. |
| 2003/0152802 | A1 | 8/2003 | Tsuboyama et al. |
| 2003/0162053 | A1 | 8/2003 | Marks et al. |
| 2003/0175553 | A1 | 9/2003 | Thompson et al. |
| 2003/0230980 | A1 | 12/2003 | Forrest et al. |
| 2004/0036077 | A1 | 2/2004 | Ise |
| 2004/0137267 | A1 | 7/2004 | Igarashi et al. |
| 2004/0137268 | A1 | 7/2004 | Igarashi et al. |
| 2004/0174116 | A1 | 9/2004 | Lu et al. |
| 2005/0025993 | A1 | 2/2005 | Thompson et al. |
| 2005/0112407 | A1 | 5/2005 | Ogasawara et al. |
| 2005/0238919 | A1 | 10/2005 | Ogasawara |
| 2005/0244673 | A1 | 11/2005 | Satoh et al. |
| 2005/0260441 | A1 | 11/2005 | Thompson et al. |
| 2005/0260449 | A1 | 11/2005 | Walters et al. |
| 2006/0008670 | A1 | 1/2006 | Lin et al. |
| 2006/0202194 | A1 | 9/2006 | Jeong et al. |
| 2006/0240279 | A1 | 10/2006 | Adamovich et al. |
| 2006/0251923 | A1 | 11/2006 | Lin et al. |
| 2006/0263635 | A1 | 11/2006 | Ise |
| 2006/0280965 | A1 | 12/2006 | Kwong et al. |
| 2007/0190359 | A1 | 8/2007 | Knowles et al. |
| 2007/0278938 | A1 | 12/2007 | Yabunouchi et al. |
| 2008/0015355 | A1 | 1/2008 | Schafer et al. |
| 2008/0018221 | A1 | 1/2008 | Egen et al. |
| 2008/0106190 | A1 | 5/2008 | Yabunouchi et al. |
| 2008/0124572 | A1 | 5/2008 | Mizuki et al. |
| 2008/0220265 | A1 | 9/2008 | Xia et al. |
| 2008/0297033 | A1 | 12/2008 | Knowles et al. |
| 2009/0008605 | A1 | 1/2009 | Kawamura et al. |
| 2009/0009065 | A1 | 1/2009 | Nishimura et al. |
| 2009/0017330 | A1 | 1/2009 | Iwakuma et al. |
| 2009/0030202 | A1 | 1/2009 | Iwakuma et al. |
| 2009/0039776 | A1 | 2/2009 | Yamada et al. |
| 2009/0045730 | A1 | 2/2009 | Nishimura et al. |
| 2009/0045731 | A1 | 2/2009 | Nishimura et al. |
| 2009/0058279 | A1 | 3/2009 | Takeda |
| 2009/0101870 | A1 | 4/2009 | Prakash et al. |
| 2009/0108737 | A1 | 4/2009 | Kwong et al. |
| 2009/0115316 | A1 | 5/2009 | Zheng et al. |
| 2009/0165846 | A1 | 7/2009 | Johannes et al. |
| 2009/0167162 | A1 | 7/2009 | Lin et al. |
| 2009/0179554 | A1 | 7/2009 | Kuma et al. |
| 2010/0084967 | A1 * | 4/2010 | Takeda .................. C09K 11/06 313/504 |
| 2011/0037381 | A1 | 2/2011 | Rostovtsev |
| 2011/0101312 | A1 † | 5/2011 | LeCloux et al. |
| 2014/0070204 | A1 | 3/2014 | Nagao |
| 2014/0374728 | A1 | 12/2014 | Adamovich |
| 2016/0099422 | A1 | 4/2016 | Zeng et al. |
| 2017/0338432 | A1 | 11/2017 | Adamovich |
| 2018/0094000 | A1 | 4/2018 | Hatakeyama |
| 2018/0134954 | A1 | 5/2018 | Tsai |
| 2018/0138425 | A1 | 5/2018 | Ma |
| 2018/0301639 | A1 | 10/2018 | Zeng et al. |
| 2019/0115538 | A1 | 4/2019 | Lim |
| 2019/0211042 | A1 | 7/2019 | Lee |
| 2019/0214577 | A1 | 7/2019 | Pan |
| 2020/0091431 | A1 | 3/2020 | Hatakeyama |
| 2020/0136059 | A1 | 4/2020 | Hong |
| 2020/0185633 | A1 | 6/2020 | Hong |
| 2020/0199164 | A1 | 6/2020 | Kim |
| 2021/0032278 | A1 | 2/2021 | Tsai |
| 2021/0066613 | A1 | 3/2021 | Cheng |
| 2021/0098721 | A1 | 4/2021 | Jung |
| 2021/0104682 | A1 | 4/2021 | Shin |
| 2021/0104698 | A1 | 4/2021 | Kim et al. |
| 2021/0122765 | A1 † | 4/2021 | Wolohan et al. |
| 2021/0193936 | A1 | 6/2021 | Li |
| 2021/0202876 | A1 | 7/2021 | Kim |
| 2021/0284906 | A1 | 9/2021 | Nam |

(56) References Cited

U.S. PATENT DOCUMENTS

| | | | |
|---|---|---|---|
| 2021/0367168 | A1 | 11/2021 | Heechoon |
| 2022/0006022 | A1 | 1/2022 | Suh |
| 2022/0029108 | A1 | 1/2022 | Kim |
| 2022/0037591 | A1 | 2/2022 | Hatakeyama |
| 2022/0056062 | A1 | 2/2022 | Chen |
| 2022/0158096 | A1 | 5/2022 | Fleetham |
| 2022/0177492 | A1 | 6/2022 | Fleetham |
| 2022/0285625 | A1 | 9/2022 | Tasaki |
| 2022/0298193 | A1 | 9/2022 | Thompson |
| 2023/0189635 | A1 | 6/2023 | Heechoon |
| 2023/0247902 | A1 | 8/2023 | No |
| 2023/0329021 | A1 | 10/2023 | Sharifidehsari |
| 2023/0337533 | A1 | 10/2023 | Choi et al. |

FOREIGN PATENT DOCUMENTS

| | | | | |
|---|---|---|---|---|
| CN | 115064647 | | | 9/2022 |
| EP | 0650955 | | | 5/1995 |
| EP | 1725079 | | | 11/2006 |
| EP | 2034538 | | | 3/2009 |
| EP | 2129739 | | | 6/2011 |
| EP | 2709181 | | † | 3/2014 |
| EP | 3862355 | | † | 8/2021 |
| EP | 4059941 | | | 9/2022 |
| EP | 4190778 | | † | 6/2023 |
| JP | 200511610 | | | 1/2005 |
| JP | 2007123392 | | | 5/2007 |
| JP | 2007254297 | | | 10/2007 |
| JP | 2008074939 | | | 4/2008 |
| JP | 2009231516 | | † | 10/2009 |
| JP | 2013145811 | | | 7/2013 |
| KR | 10-2010-0014603 | | | 2/2010 |
| KR | 2012-0101032 | | | 9/2012 |
| KR | 10-2014-0040133 | | | 4/2014 |
| KR | 20190038303 | A | † | 4/2019 |
| KR | 10-2054806 | | | 12/2019 |
| KR | 10-2021-0048977 | | | 5/2021 |
| KR | 20210092513 | | | 7/2021 |
| KR | 102349311 | | | 1/2022 |
| KR | 10-2022-0013910 | | | 2/2022 |
| KR | 1020220023700 | | | 3/2022 |
| KR | 10-2022-0122512 | | | 9/2022 |
| WO | 01/39234 | | | 5/2001 |
| WO | 02/02714 | | | 1/2002 |
| WO | 02015654 | | | 2/2002 |
| WO | 03040257 | | | 5/2003 |
| WO | 03060956 | | | 7/2003 |
| WO | 2004093207 | | | 10/2004 |
| WO | 2004107822 | | | 12/2004 |
| WO | 2005014551 | | | 2/2005 |
| WO | 2005019373 | | | 3/2005 |
| WO | 2005030900 | | | 4/2005 |
| WO | 2005089025 | | | 9/2005 |
| WO | 2005123873 | | | 12/2005 |
| WO | 2006009024 | | | 1/2006 |
| WO | 2006056418 | | | 6/2006 |
| WO | 2006072002 | | | 7/2006 |
| WO | 2006082742 | | | 8/2006 |
| WO | 2006098120 | | | 9/2006 |
| WO | 2006100298 | | | 9/2006 |
| WO | 2006103874 | | | 10/2006 |
| WO | 2006114966 | | | 11/2006 |
| WO | 2006132173 | | | 12/2006 |
| WO | 2007002683 | | | 1/2007 |
| WO | 2007004380 | | | 1/2007 |
| WO | 2007063754 | | | 6/2007 |
| WO | 2007063796 | | | 6/2007 |
| WO | 2008056746 | | | 5/2008 |
| WO | 2008101842 | | | 8/2008 |
| WO | 2008117889 | | | 10/2008 |
| WO | 2008132085 | | | 11/2008 |
| WO | 2009000673 | | | 12/2008 |
| WO | 2009003898 | | | 1/2009 |
| WO | 2009008311 | | | 1/2009 |
| WO | 2009018009 | | | 2/2009 |
| WO | 2009021126 | | | 2/2009 |
| WO | 2009050290 | | | 4/2009 |
| WO | 2009062578 | | | 5/2009 |
| WO | 2009063833 | | | 5/2009 |
| WO | 2009066778 | | | 5/2009 |
| WO | 2009066779 | | | 5/2009 |
| WO | 2009086028 | | | 7/2009 |
| WO | 2009100991 | | | 8/2009 |
| WO | 2015102118 | | | 7/2015 |
| WO | 2018103744 | A1 | † | 6/2018 |
| WO | 2021025328 | | | 2/2021 |
| WO | 2021029616 | | | 2/2021 |
| WO | 2022/255241 | | | 12/2022 |

OTHER PUBLICATIONS

Third Party Observation for European Application No. EP20220158225, Submitted On Aug. 29, 2023.

Liu, Xiaojie et al., "Isotope Effect in the Magneto-Optoelectronic Response of Organic Light-Emitting Diodes Based on Donor-Acceptor Exciplexes", Adv. Mater. 2020, 32, 2004421, 8 pages.

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1: 15-20 (2000).

Hamada, Yuji et al., "High Luminance in Organic Electroluminescent Devices with Bis(10-hydroxybenzo[h]quinolinato) beryllium as an Emitter, " Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi et al., "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

(56) References Cited

OTHER PUBLICATIONS

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18 (21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota, Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based On Silole Derivatives And Their Exciplexes," Organic Electronics, 4:113-121 (2003).
Paulose, Betty Marie Jennifer S. et al., "First Examples of Alkenyl Pyridines as Organic Ligands for Phosphorescent ridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing N∧C∧N-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes Of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2- α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Yumaio, S., et al., "The Applications of Carbazole and Carbazole-Related Compounds in Blue Emitting Organic Light-Emitting Diodes," Chemistry progress, Issue 10, pp. 1384-1399.
Aubouy, L., et al., "Molecular engineering to improve the charge carrier balance in single-layer silole-based OLEDs", New Journal of Chemistry, Royal Society of Chemistry, GB, vol. 33, Apr. 27, 2009.
Pourtaghi-Zahed, H. et al., "Synthesis and characterization of ethylene-propylene copolymer and polyethylene using [alpha]-diimine nickel catal", Journal of Polymer Research, Kluwer Academic Publishers—Consultants Bureau, NL, vol. 19, No. 11, Oct. 31, 2012.
Liu et al., Advanced Materials (2020), vol. 32, 2004421, pp. 1-8 are enclosed.†

* cited by examiner
† cited by third party

ORGANIC ELECTROLUMINESCENT MATERIALS AND DEVICES

CROSS-REFERENCE TO RELATED APPLICATIONS

This application is a continuation-in-part of U.S. patent application Ser. No. 17/063,884, filed Oct. 6, 2020, which claims priority under 35 U.S.C. § 119(e) to U.S. Provisional Applications No. 62/926,035, filed on Oct. 25, 2019, U.S. Provisional Application No. 62/971,295, filed on Feb. 7, 2020, U.S. Provisional Application No. 62/982,883, filed on Feb. 28, 2020, the entire contents of which are incorporated herein by reference. This application also claims priority under 35 U.S.C. § 119(e) to U.S. Provisional Applications No. 63/154,320, filed on Feb. 26, 2021, No. 63/220,429, filed on Jul. 9, 2021, and No. 63/229,748, filed on Aug. 5, 2021, the entire contents of which are incorporated herein by reference.

FIELD

The present disclosure generally relates to organometallic compounds and formulations and their various uses including as emitters in devices such as organic light emitting diodes and related electronic devices.

BACKGROUND

Opto-electronic devices that make use of organic materials are becoming increasingly desirable for various reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials.

OLEDs make use of thin organic films that emit light when voltage is applied across the device. OLEDs are becoming an increasingly interesting technology for use in applications such as flat panel displays, illumination, and backlighting.

One application for phosphorescent emissive molecules is a full color display. Industry standards for such a display call for pixels adapted to emit particular colors, referred to as "saturated" colors. In particular, these standards call for saturated red, green, and blue pixels. Alternatively, the OLED can be designed to emit white light. In conventional liquid crystal displays emission from a white backlight is filtered using absorption filters to produce red, green and blue emission. The same technique can also be used with OLEDs. The white OLED can be either a single emissive layer (EML) device or a stack structure. Color may be measured using CIE coordinates, which are well known to the art.

SUMMARY

In one aspect, the present disclosure provides an organic electroluminescent device (OLED) comprising: an anode; a cathode; and an emissive layer, disposed between the anode and the cathode; wherein the emissive layer comprises a first phosphorescent emitter and a first host; wherein the first phosphorescent emitter is a metal complex; and wherein the first host is partially or fully deuterated. In some embodiments, the first phosphorescent emitter is partially or fully deuterated and the first host is independently partially or fully deuterated. In some embodiments the metal complex is a metal carbene complex.

In some embodiments, an OLED is disclosed that comprises, an anode; a cathode; and an emissive layer, disposed between the anode and the cathode; wherein the emissive layer comprises a first compound and a second compound; wherein the first compound and the second compound form an exciplex; wherein the first compound is not an organometallic compound; and wherein the first compound is fully or partially deuterated, with the proviso that neither the first nor the second compound is the following compound:

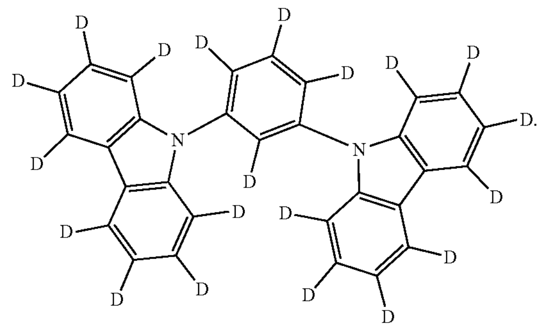

In yet another aspect, the present disclosure provides a consumer product comprising an OLED as described herein.

DETAILED DESCRIPTION

A. Terminology

Figure 1:
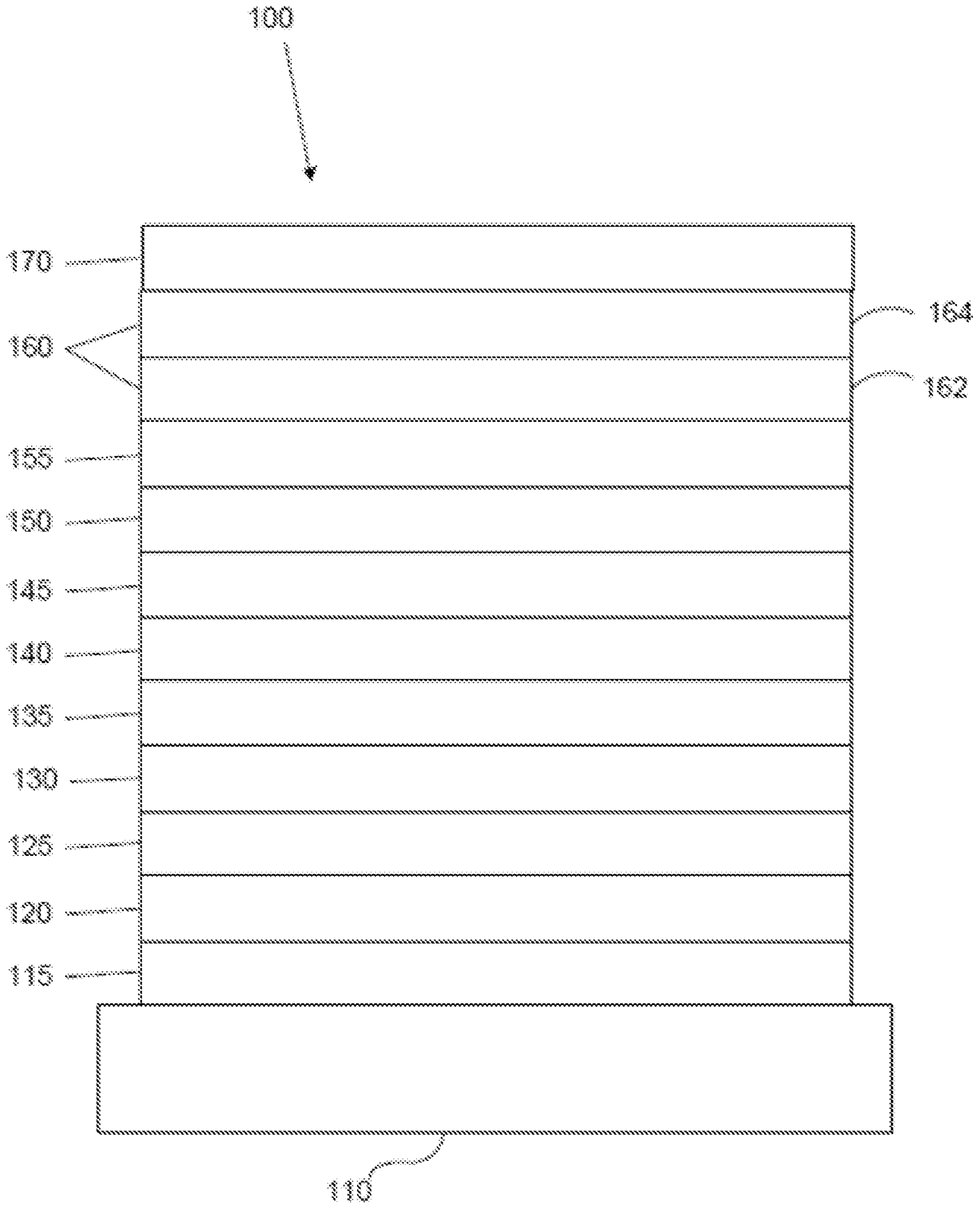
FIG. 1 shows an organic light emitting device.

Unless otherwise specified, the below terms used herein are defined as follows:

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate.

Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

The terms "halo," "halogen," and "halide" are used interchangeably and refer to fluorine, chlorine, bromine, and iodine.

The term "acyl" refers to a substituted carbonyl radical (C(O)—$R_s$).

The term "ester" refers to a substituted oxycarbonyl (—O—C(O)—$R_s$ or —C(O)—O—$R_s$) radical.

The term "ether" refers to an —$OR_s$ radical.

The terms "sulfanyl" or "thio-ether" are used interchangeably and refer to a —$SR_s$ radical.

The term "selenyl" refers to a —$SeR_s$ radical.

The term "sulfinyl" refers to a —S(O)—$R_s$ radical.

The term "sulfonyl" refers to a —$SO_2$—$R_s$ radical.

The term "phosphino" refers to a —$P(R_s)_3$ radical, wherein each $R_s$ can be same or different.

The term "silyl" refers to a —$Si(R_s)_3$ radical, wherein each $R_s$ can be same or different.

The term "germyl" refers to a —$Ge(R_s)_3$ radical, wherein each $R_s$ can be same or different.

The term "boryl" refers to a —$B(R_s)_2$ radical or its Lewis adduct —$B(R_s)_3$ radical, wherein $R_s$ can be same or different.

In each of the above, $R_s$ can be hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, and combination thereof. Preferred $R_s$ is selected from the group consisting of alkyl, cycloalkyl, aryl, heteroaryl, and combination thereof.

The term "alkyl" refers to and includes both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group may be optionally substituted.

The term "cycloalkyl" refers to and includes monocyclic, polycyclic, and spiro alkyl radicals. Preferred cycloalkyl groups are those containing 3 to 12 ring carbon atoms and includes cyclopropyl, cyclopentyl, cyclohexyl, bicyclo[3.1.1]heptyl, spiro[4.5]decyl, spiro[5.5]undecyl, adamantyl, and the like. Additionally, the cycloalkyl group may be optionally substituted.

The terms "heteroalkyl" or "heterocycloalkyl" refer to an alkyl or a cycloalkyl radical, respectively, having at least one carbon atom replaced by a heteroatom. Optionally the at least one heteroatom is selected from O, S, N, P, B, Si and Se, preferably, O, S or N. Additionally, the heteroalkyl or heterocycloalkyl group may be optionally substituted.

The term "alkenyl" refers to and includes both straight and branched chain alkene radicals. Alkenyl groups are essentially alkyl groups that include at least one carbon-carbon double bond in the alkyl chain. Cycloalkenyl groups are essentially cycloalkyl groups that include at least one carbon-carbon double bond in the cycloalkyl ring. The term "heteroalkenyl" as used herein refers to an alkenyl radical having at least one carbon atom replaced by a heteroatom. Optionally the at least one heteroatom is selected from O, S, N, P, B, Si, and Se, preferably, O, S, or N. Preferred alkenyl, cycloalkenyl, or heteroalkenyl groups are those containing two to fifteen carbon atoms. Additionally, the alkenyl, cycloalkenyl, or heteroalkenyl group may be optionally substituted.

The term "alkynyl" refers to and includes both straight and branched chain alkyne radicals. Alkynyl groups are essentially alkyl groups that include at least one carbon-carbon triple bond in the alkyl chain. Preferred alkynyl groups are those containing two to fifteen carbon atoms. Additionally, the alkynyl group may be optionally substituted.

The terms "aralkyl" or "arylalkyl" are used interchangeably and refer to an alkyl group that is substituted with an aryl group. Additionally, the aralkyl group may be optionally substituted.

The term "heterocyclic group" refers to and includes aromatic and non-aromatic cyclic radicals containing at least one heteroatom. Optionally the at least one heteroatom is selected from O, S, N, P, B, Si, and Se, preferably, O, S, or N. Hetero-aromatic cyclic radicals may be used interchangeably with heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers/thio-ethers, such as tetrahydrofuran, tetrahydropyran, tetrahydrothiophene, and the like. Additionally, the heterocyclic group may be optionally substituted.

The term "aryl" refers to and includes both single-ring aromatic hydrocarbyl groups and polycyclic aromatic ring systems. The polycyclic rings may have two or more rings in which two carbons are common to two adjoining rings (the rings are "fused") wherein at least one of the rings is an aromatic hydrocarbyl group, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group may be optionally substituted.

The term "heteroaryl" refers to and includes both single-ring aromatic groups and polycyclic aromatic ring systems that include at least one heteroatom. The heteroatoms include, but are not limited to O, S, N, P, B, Si, and Se. In many instances, O, S, or N are the preferred heteroatoms. Hetero-single ring aromatic systems are preferably single rings with 5 or 6 ring atoms, and the ring can have from one to six heteroatoms. The hetero-polycyclic ring systems can have two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. The hetero-polycyclic aromatic ring systems can have from one to six heteroatoms per ring of the polycyclic aromatic ring system. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Of the aryl and heteroaryl groups listed above, the groups of triphenylene, naphthalene, anthracene, dibenzothiophene, dibenzofuran, dibenzoselenophene, carbazole, indolocarbazole, imidazole, pyridine, pyrazine, pyrimidine, triazine, and benzimidazole, and the respective aza-analogs of each thereof are of particular interest.

The terms alkyl, cycloalkyl, heteroalkyl, heterocycloalkyl, alkenyl, cycloalkenyl, heteroalkenyl, alkynyl, aralkyl, heterocyclic group, aryl, and heteroaryl, as used herein, are independently unsubstituted, or independently substituted, with one or more general substituents.

In many instances, the general substituents are selected from the group consisting of deuterium, halogen, alkyl, cycloalkyl, heteroalkyl, heterocycloalkyl, arylalkyl, alkoxy, aryloxy, amino, silyl, germyl, boryl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, selenyl, and combinations thereof.

In some instances, the preferred general substituents are selected from the group consisting of deuterium, fluorine, alkyl, cycloalkyl, heteroalkyl, alkoxy, aryloxy, amino, silyl, boryl, alkenyl, cycloalkenyl, heteroalkenyl, aryl, heteroaryl, nitrile, isonitrile, sulfanyl, and combinations thereof.

In some instances, the more preferred general substituents are selected from the group consisting of deuterium, fluorine, alkyl, cycloalkyl, alkoxy, aryloxy, amino, silyl, aryl, heteroaryl, sulfanyl, and combinations thereof.

In yet other instances, the most preferred general substituents are selected from the group consisting of deuterium, fluorine, alkyl, cycloalkyl, aryl, heteroaryl, and combinations thereof.

The terms "substituted" and "substitution" refer to a substituent other than H that is bonded to the relevant position, e.g., a carbon or nitrogen. For example, when $R^1$ represents mono-substitution, then one $R^1$ must be other than H (i.e., a substitution). Similarly, when $R^1$ represents di-substitution, then two of $R^1$ must be other than H. Similarly, when $R^1$ represents zero or no substitution, $R^1$, for example, can be a hydrogen for available valencies of ring atoms, as in carbon atoms for benzene and the nitrogen atom in pyrrole, or simply represents nothing for ring atoms with fully filled valencies, e.g., the nitrogen atom in pyridine. The maximum number of substitutions possible in a ring structure will depend on the total number of available valencies in the ring atoms.

As used herein, "combinations thereof" indicates that one or more members of the applicable list are combined to form a known or chemically stable arrangement that one of ordinary skill in the art can envision from the applicable list. For example, an alkyl and deuterium can be combined to form a partial or fully deuterated alkyl group; a halogen and alkyl can be combined to form a halogenated alkyl substituent; and a halogen, alkyl, and aryl can be combined to form a halogenated arylalkyl. In one instance, the term substitution includes a combination of two to four of the listed groups. In another instance, the term substitution includes a combination of two to three groups. In yet another instance, the term substitution includes a combination of two groups. Preferred combinations of substituent groups are those that contain up to fifty atoms that are not hydrogen or deuterium, or those which include up to forty atoms that are not hydrogen or deuterium, or those that include up to thirty atoms that are not hydrogen or deuterium. In many instances, a preferred combination of substituent groups will include up to twenty atoms that are not hydrogen or deuterium.

The "aza" designation in the fragments described herein, i.e. aza-dibenzofuran, aza-dibenzothiophene, etc. means that one or more of the C—H groups in the respective aromatic ring can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

As used herein, "deuterium" refers to an isotope of hydrogen. Deuterated compounds can be readily prepared using methods known in the art. For example, U.S. Pat. No. 8,557,400, Patent Pub. No. WO 2006/095951, and U.S. Pat. Application Pub. No. US 2011/0037057, which are hereby incorporated by reference in their entireties, describe the making of deuterium-substituted organometallic complexes. Further reference is made to Ming Yan, et al., *Tetrahedron* 2015, 71, 1425-30 and Atzrodt et al., *Angew. Chem. Int. Ed.* (*Reviews*) 2007, 46, 7744-65, which are incorporated by reference in their entireties, describe the deuteration of the methylene hydrogens in benzyl amines and efficient pathways to replace aromatic ring hydrogens with deuterium, respectively.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In some instance, a pair of adjacent substituents can be optionally joined or fused into a ring. The preferred ring is a five, six, or seven-membered carbocyclic or heterocyclic ring, includes both instances where the portion of the ring formed by the pair of substituents is saturated and where the portion of the ring formed by the pair of substituents is unsaturated. As used herein, "adjacent" means that the two substituents involved can be on the same ring next to each other, or on two neighboring rings having the two closest available substitutable positions, such as 2, 2' positions in a biphenyl, or 1, 8 position in a naphthalene, as long as they can form a stable fused ring system.

B. The OLEDs and the Devices of the Present Disclosure

Blue OLEDs exhibit low device operational lifetimes due in part to intramolecular or intermolecular chemical reactions that occur amongst excited species in the device. This process is particularly pronounced in reactions between metal carbene complexes and other ligands.

The devices disclosed herein are designed to specifically address the possibility to greatly enhance device lifetimes by pairing metal complexes with deuterated hosts to slow the decomposition mechanism that plague carbene complexes. Additionally, in some embodiments the OLEDs are designed to form an exciplex with one of the components being deuterated to slow down the decomposition process that occurs over this bimolecular species. Additionally, Pt complexes with deuterated host components, such as those disclosed, may be important as the three-dimensional structure of Pt complexes may make them more susceptible to reactions with hosts. Similarly, Ir complexes which have pendant groups that protrude further out from the molecule maybe be reactive sites and may achieve enhancements in stability from using one or more hosts that are partially or fully deuterated.

In some embodiments the metal complexes can be metal carbene complexes.

In one aspect, the present disclosure provides an OLED that includes an anode, a cathode, and an emissive layer, disposed between the anode and the cathode. In such embodiments, the emissive layer comprises a metal carbene complex and a first host, where the first host is partially or fully deuterated. As used herein, "partially deuterated" has its ordinary meaning and for a given compound includes at least one hydrogen being replaced by deuterium, or at least two hydrogens being replaced by deuterium, or at least three hydrogens being replaced by deuterium, as well as, at least 5% of the hydrogens of the compound being replaced by deuterium, or at least 10%, or at least 15%, or at least 25%, or at least 35%, or at least 50%, or at least 60%, or at least 70%, or at least 75%, or at least 80%, or at least 90% of the hydrogens in the compound being replaced by deuterium. However, partially deuterated does not include fully deuterated.

In some embodiments, the metal carbene complex is a platinum complex.

In some embodiments, the first host comprises a moiety selected from the group consisting of triazine, pyridine, pyrimidine, pyrazine, pyridazine, dibenzofuran, dibenzothiophene, aza-dibenzofuran, aza-dibenzothiophene, triphenylene, aza-triphenylene, carbazole, indolocarbazole, aza-carbazole, aza-indolocarbazole, silyl, boryl, 5λ2-benzo[d]benzo[4,5]imidazo[3,2-a]imidazole, 5,9-dioxa-13b-boranaphtho[3,2,1-de]anthracene, and aza-(5,9-dioxa-13b-boranaphtho[3,2,1-de]anthracene).

In some embodiments, the metal carbene complex comprises a carbazole moiety.

In some embodiments, the metal carbene complex is a platinum complex comprising a tetradentate ligand, and the tetradentate ligand and the platinum atom form at least one 5-membered chelating rings. In some embodiments, the metal carbene complex is a platinum complex comprising a tetradentate ligand, and the tetradentate ligand and the platinum atom form 5-6-6 chelating rings. As an example, the following structure forms 5-6-6 chelating rings, with the numbers inside the rings

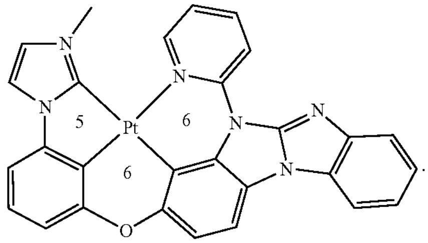

In some embodiments, the 5-6-6 chelating rings can be part of a macrocyclic ring, where a fourth chelating ring is present. The fourth chelating ring can be a 5-membered ring or a 6-membered ring. In some embodiments, the 5-6-6 chelating ring is part of a tetradentate ligand that only forms 3 chelating rings.

In some embodiments, the emissive layer has a peak emission equal to or less than 500 nm. In some embodiments, the emissive layer has a peak emission equal to or less than 490 nm. In some embodiments, the emissive layer has a peak emission equal to or less than 480 nm. In some embodiments, the emissive layer has a peak emission equal to or less than 470 nm. In some embodiments, the emissive layer has a peak emission equal to or less than 460 nm. In some embodiments, the emissive layer has a peak emission equal to or less than 450 nm.

In some embodiments, the emissive layer comprises an emitter with a peak emission equal to or less than 500 nm. In some embodiments, the emissive layer comprises an emitter with a peak emission equal to or less than 490 nm. In some embodiments, the emissive layer comprises an emitter with a peak emission equal to or less than 480 nm. In some embodiments, the emissive layer comprises an emitter with a peak emission equal to or less than 470 nm. In some embodiments, the emissive layer comprises an emitter with a peak emission equal to or less than 460 nm. In some embodiments, the emissive layer comprises an emitter with a peak emission equal to or less than 450 nm.

The emission spectrum of an emitter can be measured by photoluminescence to determine the peak wavelength of the emitter contained within the emissive layer. In this case, the photoluminescence of the emitter is measured at room temperature (~22° C.) in a solution of 2-methyl tetrahydrofuran at a concentration of less than 0.005 moles per liter. The emission peak is the wavelength of the highest energy (lowest wavelength) peak in the photoluminescence spectrum that has an intensity above 0.1 when the global maximum of the PL intensity is normalized to a value of 1. In some emission spectrums there are multiple peaks of emission and in some cases the $2^{nd}$ highest energy peak in the spectrum has the overall highest intensity, however, for the definition here, we define the peak emission as the wavelength of the higher energy peak if the intensity is above 0.1 when the spectrum is normalized to a maximum value of 1.0.

The highest occupied molecular orbital (HOMO) and lowest unoccupied molecular orbital (LUMO) are important material energy levels. Correct choice of HOMO and LUMO energy of emissive layer components are required for designing high efficiency and stability OLED devices. Here we estimated the HOMO energy from the first oxidation potential derived from cyclic voltammetry. The LUMO energy is estimated from the first reduction potential derived from cyclic voltammetry. Solution cyclic voltammetry and differential pulsed voltammetry were performed using a CH Instruments model 6201B potentiostat using anhydrous dimethylformamide solvent and tetrabutylammonium hexafluorophosphate as the supporting electrolyte. Glassy carbon, and platinum and silver wires were used as the working, counter and reference electrodes, respectively. Electrochemical potentials were referenced to an internal ferrocene-ferroconium redox couple ($Fc^+/Fc$) by measuring the peak potential differences from differential pulsed voltammetry. The $E_{HOMO}=-[(E_{ox1}$ vs $Fc^+/Fc)+4.8]$, and the $E_{LUMO}=-[(E_{red1}$ vs $Fc^+/Fc)+4.8]$, wherein $E_{ox1}$ is the first oxidation potential, and the $E_{red1}$ is the first reduction potential.

In some embodiments, a LUMO of the first host is less than −2.3 eV. In some embodiments, a LUMO of the first host is less than −2.4 eV.

In some embodiments, the HOMO of the first host is greater than −5.8 eV. In some embodiments, the HOMO of the first host is greater than −5.7 eV.

In some embodiments, the emissive layer further comprises a second host, wherein the first host has a HOMO level greater than −5.8 eV and the second host has a LUMO level less than −2.3 eV. In some embodiments, the emissive layer further comprises a second host, wherein the first host has a HOMO level greater than −5.7 eV and the second host has a LUMO level less than −2.4 eV.

In some embodiments, the metal carbene complex comprises at least one tri-aryl amine.

In some embodiments, the metal carbene complex comprises an O-linker (i.e., —O—) that is part of a ring that includes the metal. In some embodiments, the O-linker is directly bonded to the metal. In some embodiments, the O-linker is not directly bonded to the metal.

In some embodiments, the metal carbene complex comprises at least one moiety selected from the group consisting of a partially deuterated alkyl group, partially deuterated cycloalkyl group, a partially deuterated aryl or heteroaryl group, a fully deuterated alkyl group, and fully deuterated aryl or heteroaryl group.

In some embodiments, the metal carbene complex comprises at least one 5-membered chelating ring between a ligand and the metal.

In some embodiments, the metal carbene complex has a HOMO level less than −5.2 eV. In some embodiments, the metal carbene complex has a HOMO level less than −5.3 eV.

In another aspect, the present disclosure provides an OLED comprising: an anode; a cathode; and an emissive layer, disposed between the anode and the cathode; wherein the emissive layer comprises a first phosphorescent emitter and a first host; wherein the first phosphorescent emitter is a metal complex; wherein the first host is partially or fully deuterated. In some embodiments of the OLED, at least one of the following conditions is true:

(1) the metal complex is a Pt complex comprising a metal-carbene bond;

(2) the metal complex comprises at least one feature selected from the group consisting of: an imidazole moiety; a fused or unfused heteroaryl moiety comprising at least two heteroatoms; a fused-ring structure comprising at least three rings, including at least one 6-membered heteroaryl ring; a fused-ring structure having at least four rings; a pendant group comprising at least three 6-membered aromatic rings, each of which is not directly fused to another of the at least three 6-membered aromatic rings; a partially or fully deuterated 5- or 6-member carbocyclic or heterocyclic ring directly bonded to the metal; a carbazole moiety which is directly bonded to the metal; a total of at least six 6-membered aromatic rings; at least one boron atom; at least one fluorine atom; a fused ring structure comprising a benzene ring directly bonded to the metal; or a substituted or unsubstituted acetylacetonate ligand; a silicon atom; a ring structure comprising 7 or more atoms;

(3) the metal complex is a tetradentate Pt complex, wherein the tetradentate ligand forms at least three adjacent 5-membered or 6-membered chelate rings with at least two neighboring chelate rings being the same size;

(4) the metal complex is a tetradentate Pt complex, wherein the tetradentate ligand comprises at least one coordinating oxygen atom or sulfur atom trans to a coordinating carbon atom;

(5) the metal complex is partially or fully deuterated;

(6) the metal complex comprises a metal selected from the group consisting of Os, Ag, Au, Cu, and Pd;

(7) the metal complex is an Ir(III) complex comprising three different bidentate ligands;

(8) the metal complex emits light upon photoexcitation at room temperature; wherein the emitted light has an emission spectrum characterized by a peak emission wavelength $\lambda_{max}$ when measured at a mass concentration of 1% in a PMMA film; wherein the metal complex has a $\lambda_{max}$ in the range of 400-500 nm and a vertical dipole ratio (VDR) value of equal or less than 0.15, or the metal complex has a $\lambda_{max}$ in the range of 500-590 nm and a VDR value of equal or less than 0.15, or the metal complex has a $\lambda_{max}$ in the range of 590-700 nm and a VDR value of equal or less than 0.10;

(9) the metal complex has a lowest triplet energy $T1_{em}$ and a lowest singlet energy $S1_{em}$, wherein the difference between $S1_{em}-T1_{em}$ is equal or less than 0.3 eV;

(10) the first host comprises a partially or fully deuterated moiety selected from the group consisting of triphenylene, carbazole, indolocarbazole, dibenzothiophene, dibenzofuran, dibenzoselenophene, 5λ2-benzo[d]benzo[4,5]imidazo[3,2-a]imidazole, 5,9-dioxa-13b-boranaphtho[3,2,1-de]anthracene, aza-triphenylene, aza-carbazole, aza-indolocarbazole, aza-dibenzothiophene, aza-dibenzofuran, aza-dibenzoselenophene, aza-5λ2-benzo[d]benzo[4,5]imidazo[3,2-a]imidazole, and aza-(5,9-dioxa-13b-boranaphtho[3,2,1-de]anthracene);

(11) the first host comprises a boryl moiety;

(12) the first host has a lowest triplet energy $T1_{host}$ and a lowest singlet energy $S1_{host}$, wherein the difference between $S1_{host}-T1_{host}$ is equal or greater than 0.25 eV, and equal or less than 1.50 eV;

(13) the metal complex is a Pt complex and the first host has a lowest triplet energy $T1_{host}$ and a lowest singlet energy $S1_{host}$, wherein the difference between $S1_{host}-T1_{host}$ is equal or less than 0.30 eV;

(14) the first host is the only host material in the emissive layer, and the first host comprises a heteroaryl group comprising at least two nitrogen atoms;

(15) the metal complex emits light upon photoexcitation at room temperature; wherein the emitted light has an emission spectrum characterized by a peak emission wavelength $\lambda_{max}$ when measured at a mass concentration of 1% in a PMMA film; and wherein the full width at half maximum of the emission at $\lambda_{max}$ is equal to or less than 40 nm;

(16) the metal complex emits light upon photoexcitation at room temperature; wherein the emitted light has an emission spectrum characterized by a peak emission wavelength $\lambda_{max}$ when measured at a mass concentration of 1% in a PMMA film; wherein the $\lambda_{max}$ is in the range of 700-1000 nm with a PLQY value of at least 30%;

(17) the emissive layer contains two or more materials, which form an exciplex;

(18) the OLED further comprises at least one additional layer comprising at least one partially or fully deuterated material;

(19) the OLED has a first device lifetime LT95 which is measured at 10 mA/cm$^2$, wherein the first device lifetime is at least 1.5 times greater than a second device lifetime which was obtained under the exact condition as the first device lifetime except the first host is non-deuterated;

(20) at least one of the anode, the cathode, or an additional layer disposed over the emissive layer functions as an enhancement layer; wherein the enhancement layer comprises a plasmonic material exhibiting surface plasmon resonance that non-radiatively couples to the first phosphorescent emitter and transfers excited state energy from the emitter material to non-radiative mode of surface plasmon polariton; wherein the enhancement layer is provided no more than a threshold distance away from the emissive layer; and wherein the first phosphorescent emitter has a total non-radiative decay rate constant and a total radiative decay rate constant due to the presence of the enhancement layer and the threshold distance is a distance where the total non-radiative decay rate constant is equal to the total radiative decay rate constant;

(21) the concentration level of the metal complex in the emissive layer along a direction extending perpendicular to the anode toward the cathode, follows a predefined non-constant gradient profile; and

(22) any combination of two or more conditions listed above.

As used herein, "pendant group" refers to a moiety or substituent directly bonded to a moiety that is bonded to a metal, where the pendant group itself is not bonded to the metal. For instance, a methyl group bonded to the phenyl group of a phenylpyridine ligand is a pendant group.

As used herein, examples of "a pendant group comprising at least three 6-membered aromatic rings, each of which is not directly fused to another of the at least three 6-membered aromatic rings" include the following:

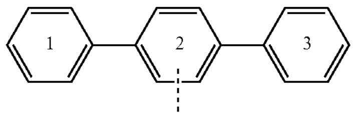

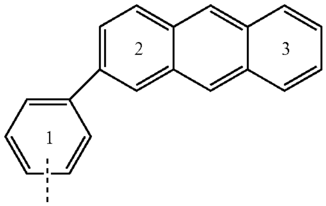

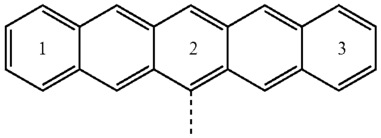

In an individual emitter compound, light emission occurs perpendicular to the triplet to ground state transition dipole moment (TDM). As such, increasing the number of emitter compound molecules whose TDM vector is horizontally aligned with respect to the OLED's substrate results in a higher light extraction efficiency, and thus higher device efficiency (external quantum efficiency—EQE). This orientation factor can be described statistically in an ensemble of emitter molecules by the ratio θ of the vertical component of the TDM vector to the sum of the vertical and horizontal components: $\theta = TDM^{\perp}/(TDM^{\perp}+TDM^{\parallel})$, hereinafter the vertical dipole ratio ("VDR").

The vertical dipole ratio (θ) may be measured by angle dependent photoluminescence measurements. By comparing the measured emission pattern of a photoexcited thin film sample, as a function of polarization, to the computationally modeled pattern, one can determine the TDM vector's orientation for a given sample.

In some embodiments, the metal complex comprises at least one polydentate ligand that forms a 5-membered chelate ring with the Pt.

In some embodiments, the at least one polydentate ligand is a tetradentate ligand.

In some embodiments, the 5-membered chelate ring includes carbene bond. In some such embodiments, the carbene is derived from imidazole or benzimidazole. In some such embodiments, the carbene is substituted by a substituent R, which can be selected from the group consisting of the General Substituents defined herein. In some such embodiments, the substituent R is partially or fully deuterated.

In some embodiments, the 5-membered chelate ring does not include a carbene bond.

In some embodiments, the metal complex is a Pt complex.

In some embodiments, the metal complex is an Ir complex.

In some embodiments, the metal complex comprises an imidazole, which can be further substituted and fused. In some embodiments, the imidazole is a benzimidazole, which can be further substituted and fused.

In some embodiments, the metal complex comprises a fused or unfused heteroaryl moiety comprising at least two N atoms.

In some embodiments, the metal complex comprises a fused or unfused heteroaryl moiety comprising at least one N and at least one O or S.

In some embodiments, the metal complex comprises a fused or unfused heteroaryl moiety comprising at least two heteroatoms on one ring.

In some embodiments, the metal complex comprises a fused or unfused heteroaryl moiety comprising at least one heteroatom on two different rings.

In some embodiments, the metal complex comprises a fused or unfused heteroaryl moiety comprising at least three heteroatoms.

In some embodiments, the fused or unfused heteroaryl moiety comprises one or more 5- or 6-membered rings.

In some embodiments, the metal complex comprises a fused-ring structure comprising at least three rings, including at least one 6-membered heteroaryl ring. In some embodiments the fused-ring structure is selected from the group consisting of aza-dibenzofuran, aza-dibenzothiophene, aza-dibenzoselephene, aza-dibenzofluorene, and aza-carbazole.

In some embodiments, the metal complex comprises a fused-ring structure comprising at least four rings. In some embodiments, such four rings are fused together in a linear fashion. In some embodiments, such four rings are fused together in a nonlinear fashion.

In some embodiments, the metal complex comprises a fused-ring structure comprising at least five rings.

In some embodiments, the metal complex comprises a fused-ring structure comprising at least six rings.

In some embodiments that include a fused-ring structure, the fused-ring structure comprises a moiety selected from the group consisting of dibenzofuran, dibenzothiophene, dibenzoselenophene, carbazole, and aza-variants thereof.

In some embodiments that include a fused-ring structure, the fused-ring structure comprises a carbene moiety.

In some embodiments that include a fused-ring structure, each of the rings in the fused ring structure is independently a 5-membered heteroaryl ring or a 6-membered aryl or heteroaryl ring.

In some such embodiments, the metal complex includes a pendant group comprising at least three 6-membered aromatic rings, each of which is not directly fused to another of the at least three 6-membered aromatic rings. In some such embodiments, the metal complex includes a pendant group comprising at least four 6-membered aromatic rings, each of which is not directly fused to another of the at least four 6-membered aromatic rings. In some such embodiments, the metal complex includes a pendant group comprising at least five 6-membered aromatic rings, each of which is not directly fused to another of the at least five 6-membered aromatic rings. In some such embodiments, the metal complex includes a pendant group comprising at least six 6-membered aromatic rings, each of which is not directly fused to another of the at least six 6-membered aromatic rings.

In some embodiments, the metal complex comprises a partially or fully deuterated 5- or 6-member carbocyclic or heterocyclic ring directly bonded to the metal. In some embodiments, the metal complex comprises a partially deuterated 5- or 6-member carbocyclic or heterocyclic ring directly bonded to the metal. In some embodiments, the metal complex comprises a fully deuterated 5- or 6-member carbocyclic or heterocyclic ring directly bonded to the metal. In some embodiments, the metal complex comprises a partially or fully deuterated 5-member heteroaryl ring directly bonded to the metal. In some embodiments, the metal complex comprises a partially or fully deuterated 6-member aryl or heteroaryl ring directly bonded to the metal.

In some embodiments, the metal complex comprises a total of at least seven 6-membered aromatic rings. In some embodiments, the metal complex comprises a total of at least eight 6-membered aromatic rings. In some embodiments, the metal complex comprises a total of at least nine 6-membered aromatic rings. In some embodiments, the metal complex comprises a total of at least ten 6-membered aromatic rings. In some embodiments, the metal complex comprises a total of at least eleven 6-membered aromatic rings. In some embodiments, the metal complex comprises a total of at least twelve 6-membered aromatic rings.

In some embodiments, the metal of the metal complex is bonded to a carbazole at the 1-position.

In some embodiments, the metal complex comprises at least one boron atom. In some embodiments, the boron atom is a three-valence boron atom. In some embodiments, the boron atom is a four-valence boron atom. In some embodiments, the boron atom is in the backbone of one ring. In some embodiments, the boron atom is in the backbone of two rings. In some embodiments, the boron atom is in the backbone of three rings.

In some embodiments, the metal complex comprises at least one fluorine atom directly bonded to a ring carbon of an aromatic or non-aromatic ring.

In some embodiments, the metal complex comprises at least one fluorine atom directly bonded to a carbon that is not part of a ring.

In some embodiments, the metal complex comprises a moiety comprising at least two benzene rings fused together that is directly bonded to the metal. In some embodiments, the metal complex comprises a moiety comprising at least three benzene rings fused together that is directly bonded to the metal. In some embodiments, the metal complex comprises a moiety comprising at least four benzene rings fused together that is directly bonded to the metal.

In some embodiments, the metal complex comprises a naphthalene moiety, that is substituted at the 4-position and coordinated to the metal at the 1-position.

In some embodiments, the metal complex comprises an acetylacetonate ligand where at least one methyl of the acetylacetonate ligand is substituted by one substituent R selected from the group consisting of the General Substituents defined herein.

In some embodiments, the metal complex comprises an acetylacetonate ligand where at least one methyl of the acetylacetonate ligand is substituted by two substituents R, wherein each R is independently selected from the group consisting of the General Substituents defined herein.

In some embodiments, the metal complex comprises an acetylacetonate ligand where each of the methyl moieties of the acetylacetonate ligand is substituted by one substituent R, wherein each R is independently selected from the group consisting of the General Substituents defined herein.

In some embodiments, the metal complex comprises an acetylacetonate ligand where each of the methyl moieties of the acetylacetonate ligand is substituted by two substituents R, wherein each R is independently selected from the group consisting of the General Substituents defined herein.

In some embodiments, the metal complex comprises a silicon atom, in some embodiments of option (2), the metal complex comprises a tetra aryl silane.

In some embodiments, the metal complex comprises a ring structure comprising 7 or more atoms, in some embodiments, the metal complex comprises s ring structure comprising 8 or more atoms, in some embodiments, the metal complex comprises s ring structure comprising 9 or more atoms.

In some embodiments, the Pt and the tetradentate ligand form at least one 5-membered chelate ring and at least one 6-membered chelate ring.

In some embodiments, the Pt and the tetradentate ligand form a 5-membered chelate ring and two 6-membered chelate rings.

In some embodiments, the Pt and the tetradentate ligand form two 5-membered chelate rings and one 6-membered chelate ring.

In some embodiments, the tetradentate ligand is a macrocyclic ligand and forms two adjacent 5-membered chelate rings and two adjacent 6-membered chelate rings.

In some embodiments, the tetradentate ligand is a macrocyclic ligand and forms three adjacent 5-membered chelate rings and one 6-membered chelate ring.

In some embodiments, the tetradentate ligand is a macrocyclic ligand and forms one 5-membered chelate rings and three adjacent 6-membered chelate rings.

In some embodiments, the tetradentate ligand comprises at least one coordinating oxygen atom trans to a coordinating carbon atom.

In some embodiments, the other two coordinating atoms are N.

In some embodiments, the coordinating carbon atom trans to the oxygen or sulfur atom is part of a phenyl ring.

In some embodiments, the metal complex is at least 10% deuterated.

In some embodiments, the metal complex is at least 30% deuterated, or at least 50% deuterated, or at least 70% deuterated, or at least 85% deuterated, or at least 90% deuterated, or at least 95% deuterated, or at least 99% deuterated, or at least 100% deuterated.

In some embodiments, the metal complex is an Os complex. In some embodiments of option (6), the metal complex is an Ag complex. In some embodiments, the metal complex is an Au complex. In some embodiments, the metal complex is an Cu complex. In some embodiments, the metal complex is an Pd complex.

In some embodiments, the Ir(III) complex has a VDR value of equal to or less than 0.15. In some embodiments, all three bidentate ligands are C^N ligands. As used herein, the X^Y nomenclature represents a ligand where an X atom and a Y atom are coordinated to the metal, Ir in this case. For example, a phenylpryidine ligand would be represented C^N, while an acetylacetonate ligand would be represented O^O.

In some embodiments, two of the bidentate ligands are C^N ligands and the remaining one is a O^O ligand.

In some embodiments, the bidentate ligands includes one C^N, one C^C, and one O^O.

In some embodiments, all three of the bidentate ligands are C^C ligands.

In some embodiments, two of the bidentate ligands are C^C ligands and the remaining one is a C^N ligand.

In some embodiments, two of the bidentate ligands are C^N ligands and the remaining one is a C^C ligand.

In some embodiments, the metal complex has a $\lambda_{max}$ in the range of 400-500 nm and a VDR value of equal or less than 0.12. In some embodiments, the metal complex has a $\lambda_{max}$ in the range of 400-500 nm and a VDR value of equal or less than 0.10. In some embodiments, the metal complex has a $\lambda_{max}$ in the range of 400-500 nm and a VDR value of equal or less than 0.08. In some embodiments, the metal complex has a $\lambda_{max}$ in the range of 400-500 nm and a VDR value of equal or less than 0.05.

In some embodiments, the metal complex has a $\lambda_{max}$ in the range of 500-590 nm and a VDR value of equal or less than 0.12. In some embodiments, the metal complex has a $\lambda_{max}$ in the range of 500-590 nm and a VDR value of equal or less than 0.10. In some embodiments, the metal complex has a $\lambda_{max}$ in the range of 500-590 nm and a VDR value of equal or less than 0.08. In some embodiments, the metal complex has a $\lambda_{max}$ in the range of 500-590 nm and a VDR value of equal or less than 0.05.

In some embodiments, the metal complex has a $\lambda_{max}$ in the range of 590-700 nm and a VDR value of equal or less than 0.08. In some embodiments, the metal complex has a $\lambda_{max}$ in the range of 590-700 nm and a VDR value of equal or less than 0.05.

In some embodiments, the difference between $S1_{em}-T1_{em}$ is equal or less than 0.25 eV. In some embodiments, the difference between $S1_{em}-T1_{em}$ is equal or less than 0.20 eV, or equal or less than 0.18 eV, or equal or less than 0.16 eV, or equal or less than 0.14 eV, or equal or less than 0.12 eV, or equal or less than 0.10 eV, or equal or less than 0.08 eV, or equal or less than 0.06 eV, or equal or less than 0.05 eV.

In some embodiments, the first host comprises two partially or fully deuterated moieties selected from the group consisting of triphenylene, carbazole, indolocarbazole, dibenzothiophene, dibenzofuran, dibenzoselenophene, 5□2-benzo[d]benzo[4,5]imidazo[3,2-a]imidazole, and 5,9-dioxa-13b-boranaphtho[3,2,1-de]anthracene.

In some embodiments, the first host comprises two partially or fully deuterated moieties selected from the group consisting of aza-triphenylene, aza-carbazole, aza-indolocarbazole, aza-dibenzothiophene, aza-dibenzofuran, aza-dibenzoselenophene, aza-5□2-benzo[d]benzo[4,5]imidazo[3,2-a]imidazole, and aza-(5,9-dioxa-13b-boranaphtho[3,2,1-de]anthracene).

In some embodiments, the first host comprises at least one partially or fully deuterated moiety selected from the group consisting of triphenylene, carbazole, indolocarbazole, dibenzothiophene, dibenzofuran, dibenzoselenophene, 5□2-benzo[d]benzo[4,5]imidazo[3,2-a]imidazole, and 5,9-dioxa-13b-boranaphtho[3,2,1-de]anthracene; and at least one partially or fully deuterated moiety selected from the group consisting of aza-triphenylene, aza-carbazole, aza-indolocarbazole, aza-dibenzothiophene, aza-dibenzofuran, aza-dibenzoselenophene, aza-5□2-benzo[d]benzo[4,5]imidazo[3,2-a]imidazole, and aza-(5,9-dioxa-13b-boranaphtho[3,2,1-de]anthracene).

In some embodiments, the first host does not comprise an indole or carbazole moiety.

In some embodiments, the boryl moiety is a three-valence boron atom.

In some embodiments, the boryl moiety is a four-valence boron atom.

In some embodiments, the boron atom is in the backbone of one ring.

In some embodiments, the boron atom is in the backbone of two rings.

In some embodiments, the boron atom is in the backbone of three rings.

In some embodiments, the difference between $S1_{host}-T1_{host}$ is equal or greater than 0.30 eV, and equal or less than 1.25 eV.

In some embodiments, the difference between $S1_{host}-T1_{host}$ is equal or greater than 0.35 eV, or equal or greater than 0.40 eV, or equal or greater than 0.45 eV, or equal or greater than 0.50 eV.

In some embodiments, the difference between $S1_{host}-T1_{host}$ is equal or less than 1.15 eV, or equal or less than 1.10 eV, or equal or less than 1.00 eV, or equal or less than 0.90 eV, or equal or less than 0.80 eV, or equal or less than 0.70 eV.

In some embodiments, the difference between $S1_{host}-T1_{host}$ is equal or less than 0.25 eV, or equal or less than 0.20 eV, or equal or less than 0.15 eV, or equal or less than 0.10 eV.

In some embodiments, the metal complex is a Pt complex.

In some embodiments, the first host comprises a heteroaryl group comprising at least two nitrogen atoms selected from the group consisting of pyrimidine, pyrazine, pyridazine, triazine, cinnoline, quinazoline, quinoxaline, phthalazine, pyridopyrazine, pyridopyridazine, and naphthyridine.

In some embodiments, the metal complex emits light upon photoexcitation at room temperature; wherein the emitted light has an emission spectrum characterized by a peak emission wavelength ax when measured at a mass concentration of 1% in a PMMA film; and wherein the full width at half maximum of the emission at $\lambda_{max}$ is equal to or less than 35 nm, or equal to or less than 30 nm, or equal to or less than 25 nm, or equal to or less than 20 nm, or equal to or less than 15 nm, or equal to or less than 10 nm.

In some embodiments, the metal complex emits light upon photoexcitation at room temperature; wherein the emitted light has an emission spectrum characterized by a peak emission wavelength ax when measured at a mass concentration of 1% in a PMMA film; wherein the $\lambda_{max}$ is in the range of 700-1000 nm with a PLQY value of at least 30%. In some such embodiments, the $\lambda_{max}$ is in the range of 700-900 nm, or 700-800 nm. In some such embodiments, the PLQY value is at least 40%, or the PLQY value is at least 50%, or the PLQY value is at least 60%, or the PLQY value is at least 70%, or the PLQY value is at least 80%, or the PLQY value is at least 90%, or the PLQY value is at least 99.9%.

In some embodiments, the emissive layer contains two or more materials, which form an exciplex.

In some embodiments, the emissive layer contains two or more host materials, which form an exciplex.

In some embodiments, the emissive layer contains at least one host material and at least one phosphorescent emitter, which form an exciplex.

In some embodiments, two or more materials form an exciplex with the same additional material. For example, the first host and second host form an exciplex and the first metal complex and second host form an exciplex.

In some embodiments, two or more materials form an exciplex and an additional material is added to the emissive layer which reduces the extent of formation of the exciplex. For example, films of the first host and second host form an exciplex as seen by a red-shift photoluminescence spectrum or a photoluminescence spectrum containing a new peak at longer wavelengths or lower energy compared to the emission of thin films of each of the components individually. However, after adding a third host, the amount of emission from the exciplex is greatly reduced, indicating a reduction of the exciplex formation rate.

In some embodiments, the blue edge of the exciplex is higher in energy than the peak wavelength of the first metal complex where the blue edge of the exciplex is the highest energy wavelength at which the PL spectrum has a value of 0.1 when the maximum of the PL spectrum is normalized to a value of one.

In some embodiments, the blue edge of the exciplex is lower in energy than the peak wavelength of the first metal complex where the blue edge of the exciplex is the highest energy wavelength at which the PL spectrum has a value of 0.1 when the maximum of the PL spectrum is normalized to a value of one.

In some embodiments, the exciplex formed by two or more materials is weakly emissive with a photoluminescence quantum yield (PLQY) less than 30%. Where the PLQY are measured on a calibrated Hamamatsu Quantaurus-QY Plus UV-NIR absolute PL quantum yield spectrometer with an excitation wavelength of 340 nm. PLQY values are taken from thin films prepared from solutions of 1% dopant by weight with PMMA in toluene which are filtered and dropcast onto Quartz substrates.

In some embodiments, the exciplex formed by two or more materials is strongly emissive with a PLQY over 50%, more preferably with a PLQY over 75%.

In some embodiments, none of the materials form an exciplex.

In some embodiments, the at least one additional layer is selected from the group consisting of a hole injection layer, a hole transport layer, an electron blocking layer, a hole blocking layer, an electron transport layer, and an electron injection layer.

In some embodiments, the at least one additional layer is adjacent the emissive layer.

In some embodiments, all materials in the at least one additional layer are partially or fully deuterated.

In some embodiments, the OLED has a first device lifetime LT95 which is measured at 10 $mA/cm^2$, wherein the first device lifetime is at least 1.5 times greater than a second device lifetime obtained under the exact condition as the first device lifetime except the first host is non-deuterated. In some embodiments, the first device lifetime is at least 2.0 times greater than a second device lifetime obtained under the exact condition as the first device lifetime except the first host is non-deuterated. In some embodiments, the first device lifetime is at least 2.5 times greater than a second device lifetime obtained under the exact condition as the first device lifetime except the first host is non-deuterated. In some embodiments, the first device lifetime is at least 3.0 times greater than a second device lifetime obtained under the exact condition as the first device lifetime except the first host is non-deuterated. In some embodiments, the first device lifetime is at least 4.5 times greater than a second device lifetime obtained under the exact condition as the first device lifetime except the first host is non-deuterated.

As used herein "LT95" is defined as the time to reach 95% of the initial device luminance when driven at a constant current density of 10 $mA/cm^2$. It should be understood that the device lifetime comparison made above could be applied to emissive layers with more than one host. In such materials, the 1.5 times, or 2.0 times, or 2.5 times, or 3.0 times, or 4.0 times, or 5.0 times greater improvement could be the result of deuteration of one of the host compounds or more than one of the host compounds. It should be understood that the device lifetime comparisons made above could be applied to emissive layers with more than one host. In such materials, the 1.5 times greater improvement could be the result of deuteration of one of the host compounds or more than one of the host compounds.

In some embodiments, at least one of the anode, the cathode, or an additional layer disposed over the emissive layer functions as an enhancement layer; wherein the enhancement layer comprises a plasmonic material exhibiting surface plasmon resonance that non-radiatively couples to the first phosphorescent emitter and transfers excited state energy from the emitter material to non-radiative mode of surface plasmon polariton; wherein the enhancement layer is provided no more than a threshold distance away from the emissive layer; and wherein the first phosphorescent emitter has a total non-radiative decay rate constant and a total radiative decay rate constant due to the presence of the enhancement layer and the threshold distance is a distance where the total non-radiative decay rate constant is equal to the total radiative decay rate constant.

In some embodiments, the concentration level of the metal complex in the emissive layer along a direction extending perpendicular to the anode toward the cathode, follows a predefined non-constant gradient profile.

In some embodiments, at least two of conditions (1) to (21) are true, or at least three of conditions (1) to (21) are true, or at least four of conditions (1) to (21) are true, or five to twenty-one of conditions (1) to (21) are true (so long as they are internally consistent).

The following embodiments apply to any of the foregoing embodiments that they are otherwise consistent with.

In some embodiments, the metal complex comprises a metal selected from the group consisting of Os, Ir, Pd, Pt, Cu, Ag, and Au. In some embodiments, the metal complex comprises a metal selected from the group consisting of Ir, Pt, and Au. In some embodiments, the metal complex is an Ir or Pt complex. In some embodiments, the metal complex is a Pt complex. In some embodiments, the Pt complex comprises a tetradentate ligand. In some embodiments, the metal complex is a Pt(II) tetradentate complex.

In some embodiments, the metal complex and the host form an exciplex.

In some embodiments, the first host is at least 10% deuterated. In some embodiments, the first host is at least 30% deuterated, or at least 50% deuterated, or at least 70% deuterated, or at least 85% deuterated, or at least 90% deuterated, or at least 95% deuterated, or at least 99% deuterated, or 100% deuterated.

In some embodiments, the OLED comprises a second host. In some embodiments, the second host is not deuterated. In some embodiments, the second host is partially or fully deuterated. In some embodiments, the second host is at least 50% deuterated, or at least 75% deuterated, or at least 90% deuterated.

In some embodiments, the metal complex is a platinum complex and the first host comprises a moiety selected from the group consisting of triazine, pyridine, pyrimidine, pyrazine, pyridazine, dibenzofuran, dibenzothiophene, aza-dibenzofuran, aza-dibenzothiophene, triphenylene, aza-triphenylene, carbazole, indolocarbazole, aza-carbazole, aza-indolocarbazole, silyl, and boryl.

In some embodiments, the metal complex is a platinum complex and the first host comprises a triazine moiety.

In some embodiments, the metal complex comprises at least one cyano substituent.

In some embodiments, the metal complex is partially fluorinated.

In some embodiments, the metal complex comprises at least one partially deuterated alkyl groups.

In some embodiments, the metal complex comprises a carbazole moiety.

In some embodiments, the metal complex is a platinum complex comprising a tetradentate ligand, and the tetradentate ligand and the platinum atom form 5-6-6 chelating rings.

In some embodiments, the emissive layer has a peak emission equal to or less than 500 nm. In some embodiments, the emissive layer comprises an emitter with a peak emission equal to or less than 500 nm.

In some embodiments, a LUMO of the first host is less than −2.3 eV. In some embodiments, the HOMO of the first host is greater than −5.8 eV.

In some embodiments, the emissive layer further comprises a second host, wherein the first host has a HOMO level greater than −5.8 eV and the second host has a LUMO level less than −2.3 eV.

In some embodiments, the metal complex comprises at least one tri-aryl amine.

In some embodiments, the metal complex comprises an O-linker (i.e., an ether) that is part of a chelating ring that includes the metal. In some embodiments, the O-linker is directly bonded to the metal. In some embodiments, the O-linker is not directly bonded to the metal.

In some embodiments, the metal complex comprises at least one moiety selected from the group consisting of a partially deuterated alkyl group, partially deuterated cycloalkyl group, a partially deuterated aryl or heteroaryl group, a fully deuterated alkyl group, and fully deuterated aryl or heteroaryl group.

In some embodiments, the metal complex comprises at least one 5-membered chelating ring between a ligand and the metal.

In some embodiments, the metal complex has a HOMO level less than −5.2 eV.

In some embodiments, the first host is selected from the group consisting of the structures in the following LIST 1:

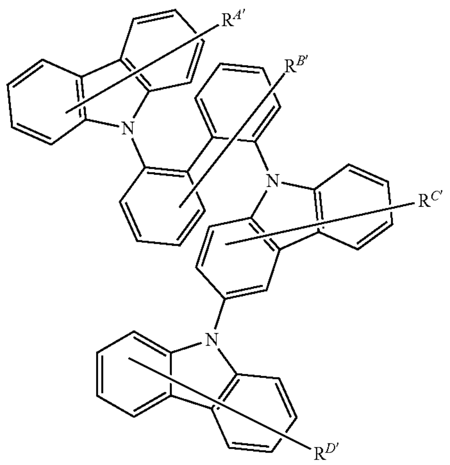

,

-continued
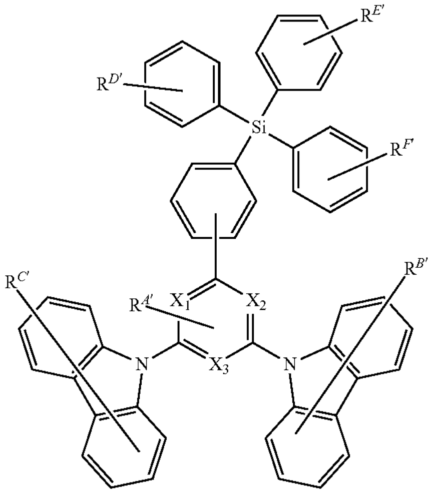
,
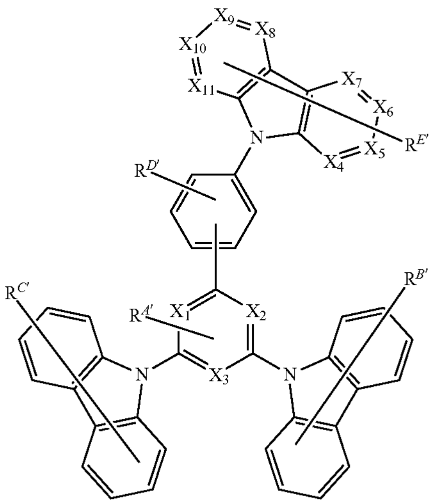
,
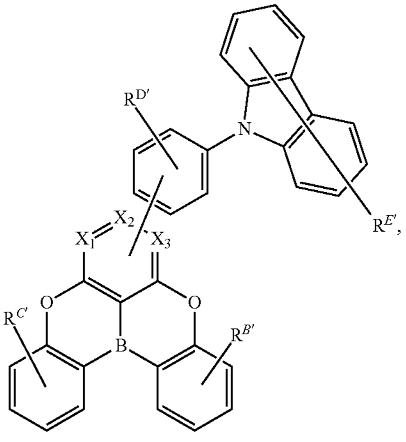
-continued
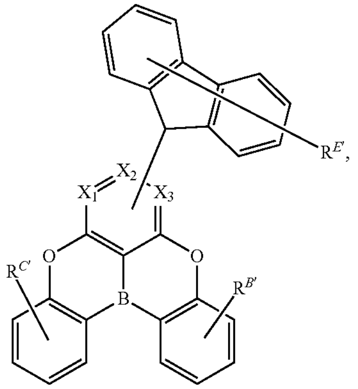
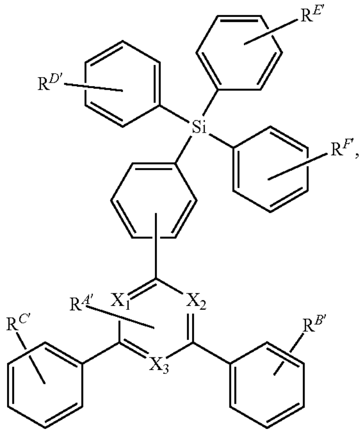
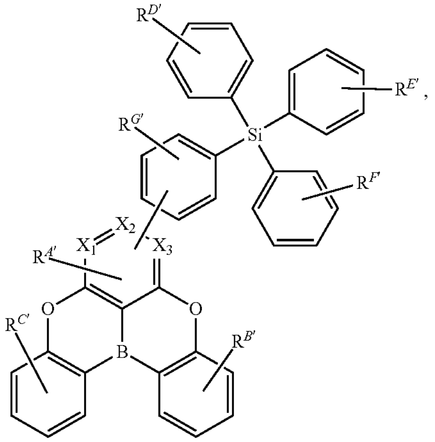
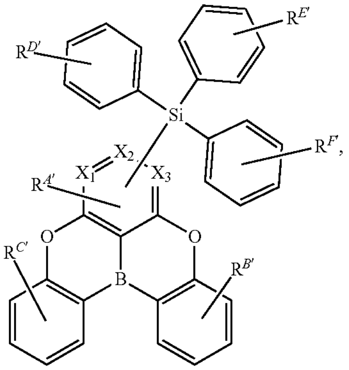

-continued
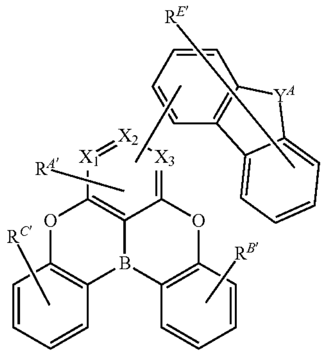
,
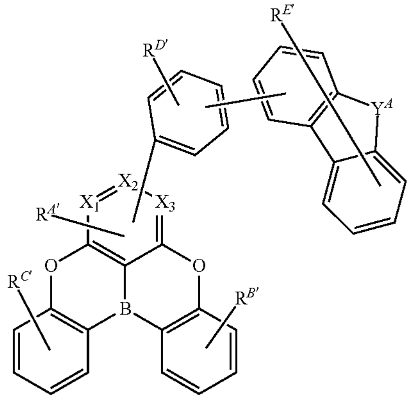
,
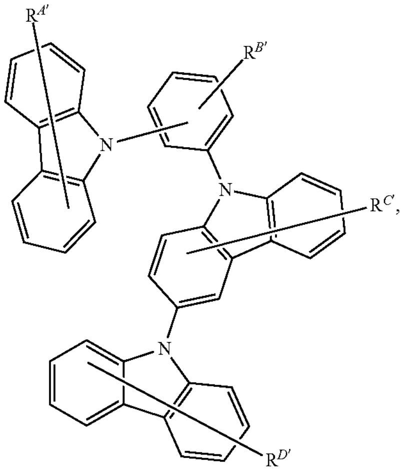
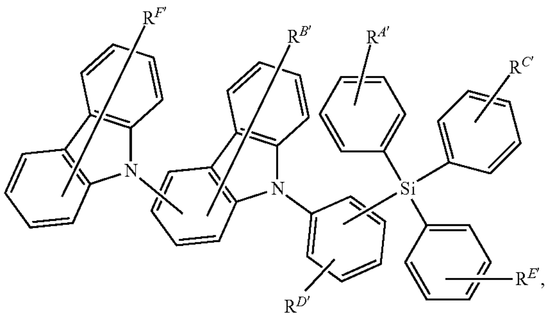
-continued
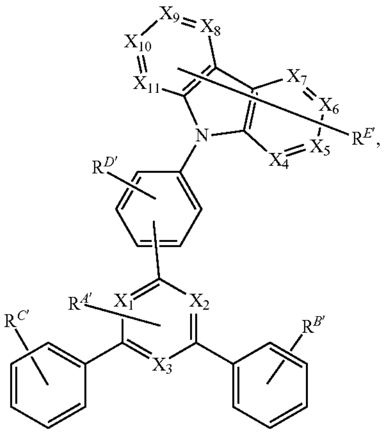
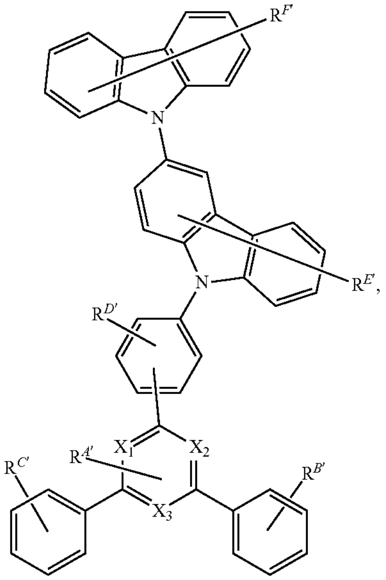
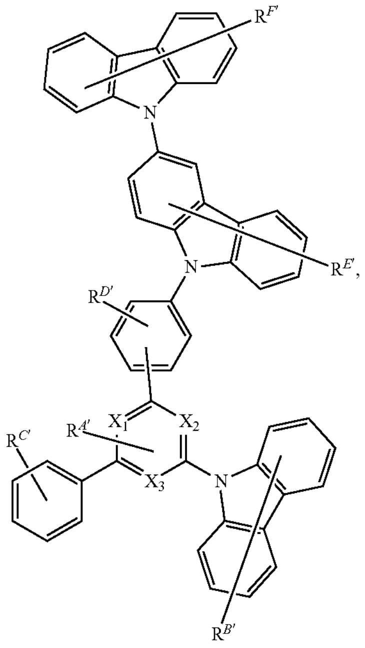

-continued
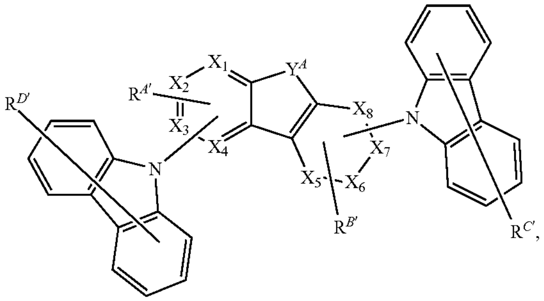
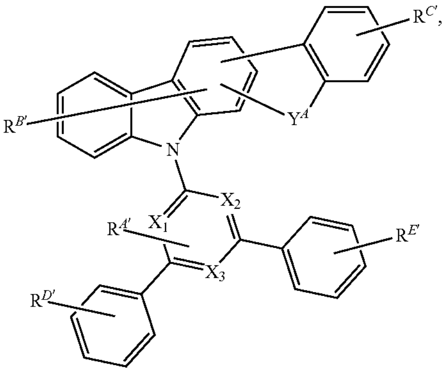
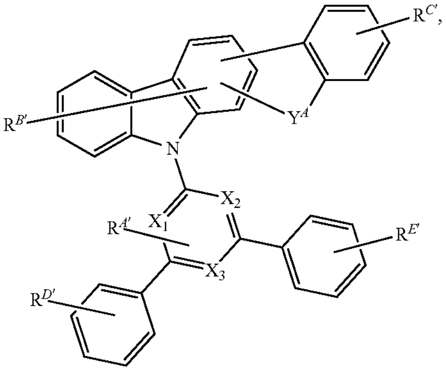
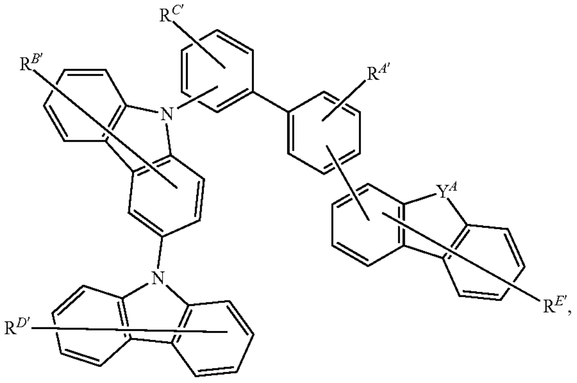
-continued
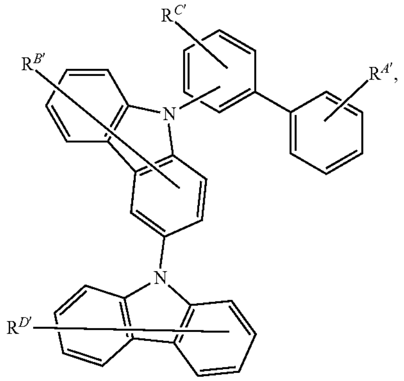
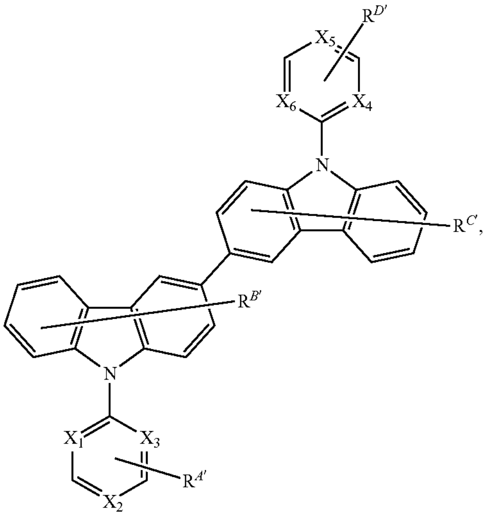
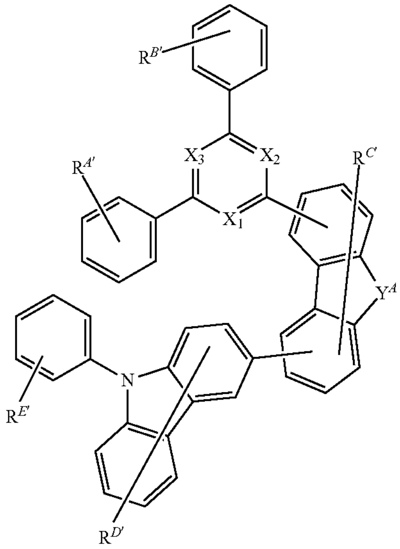
, -continued
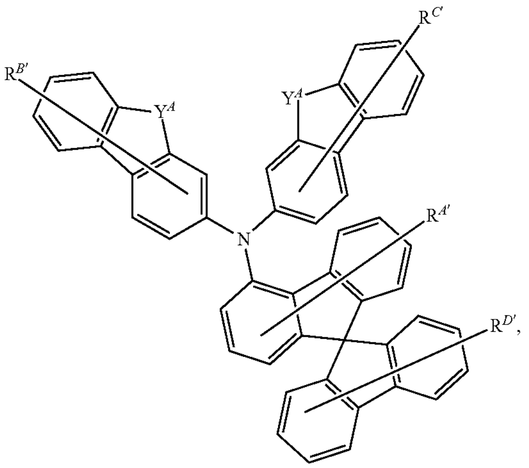
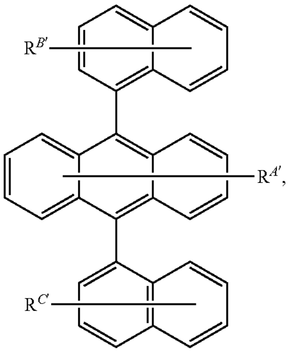
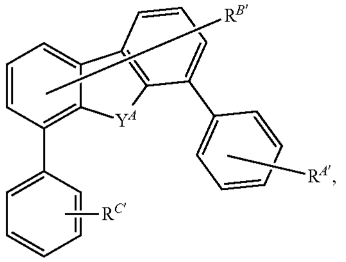
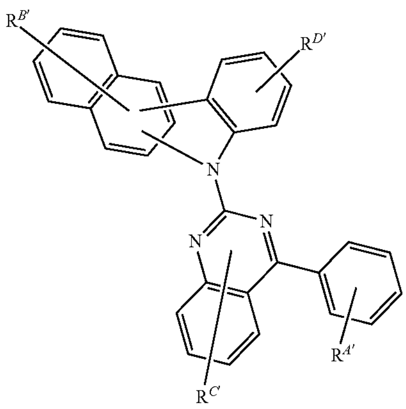
,
-continued
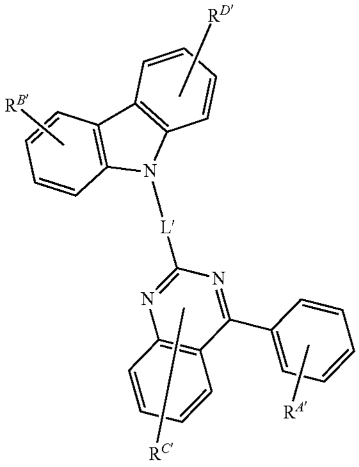
,
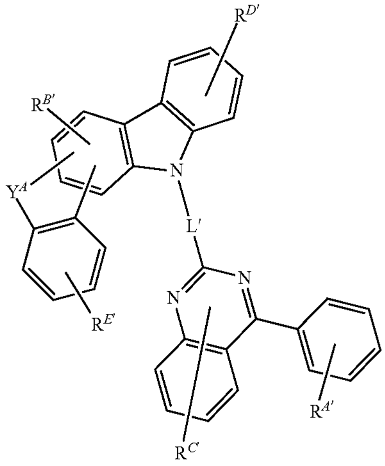
,
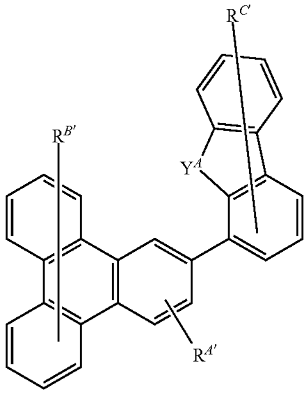
,
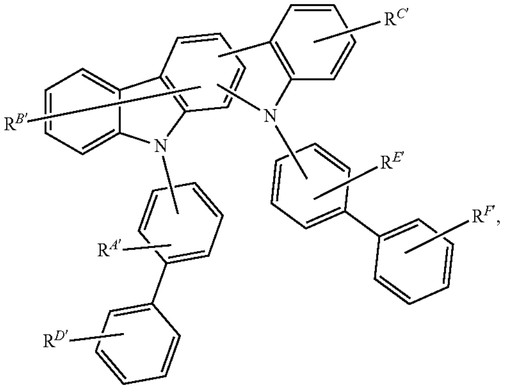

-continued
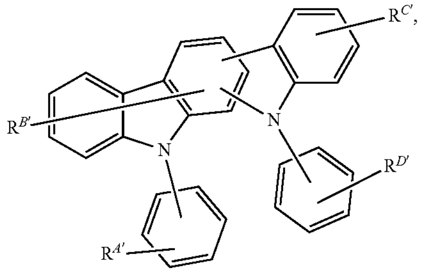
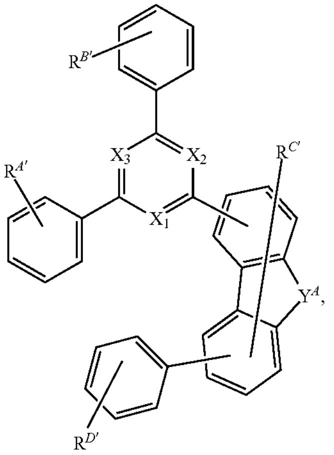
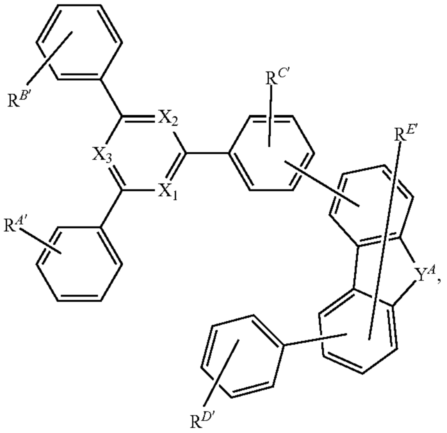
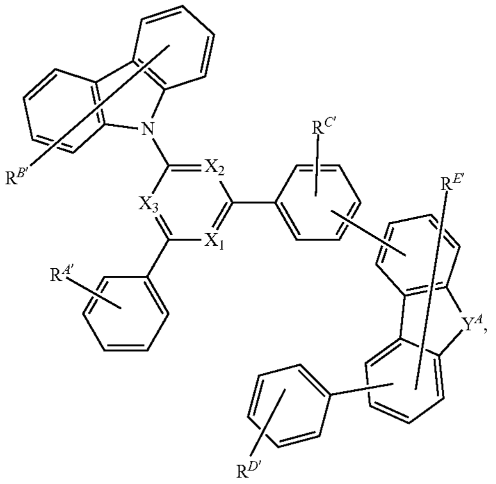
-continued
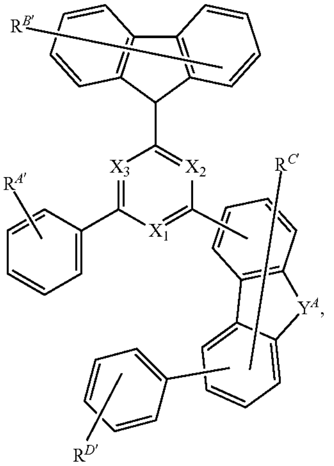
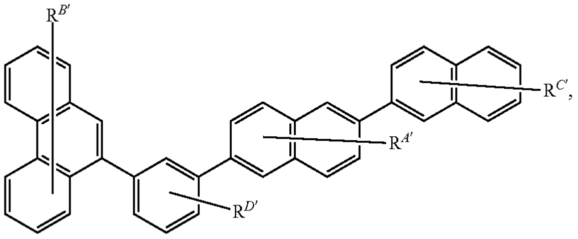
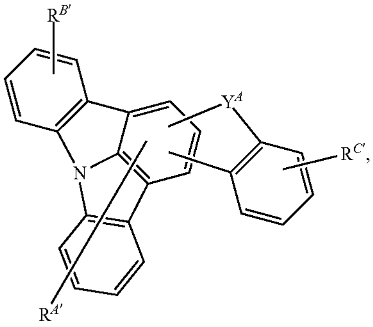
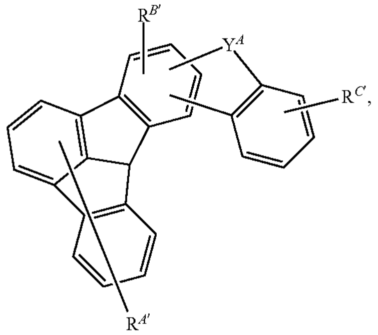
and
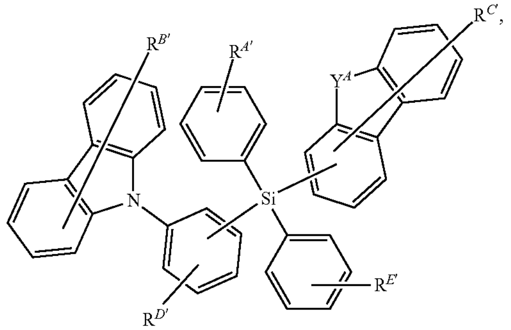

wherein:

each of $X_1$ to $X_{11}$ is independently C or N;

L' is a direct bond or is an organic linker;

each $Y^A$ is independently absent or, when present, is selected from the group consisting of O, S, Se, CRR', SiRR', NR, BR, BRR';

each of $R^{A'}$, $R^{B'}$, $R^{C'}$, $R^{D'}$, $R^{E'}$, $R^{F'}$, and $R^{G'}$ independently represents mono-, up to the maximum substitutions, or no substitutions;

each of R, R', $R^{A'}$, $R^{B'}$, $R^{C'}$, $R^{D'}$, $R^{E'}$, $R^{F'}$, and $R^{G'}$ is independently a hydrogen or a substituent selected from the group consisting of the General Substituents defined herein; and at least one R, R', $R^{A'}$, $R^{B'}$, $R^{C'}$, $R^{D'}$, $R^{E'}$, $R^{F'}$, or $R^{G'}$ comprises deuterium.

As shown in the structures of LIST 1, when present, $Y^A$ is part of a five-membered ring between two phenyl rings. Thus, in instances where $Y^A$ is absent, the two six-membered rings are bonded together by the existing single bond. In some embodiments, the first host is selected from the group consisting of the structures in the following LIST 2:

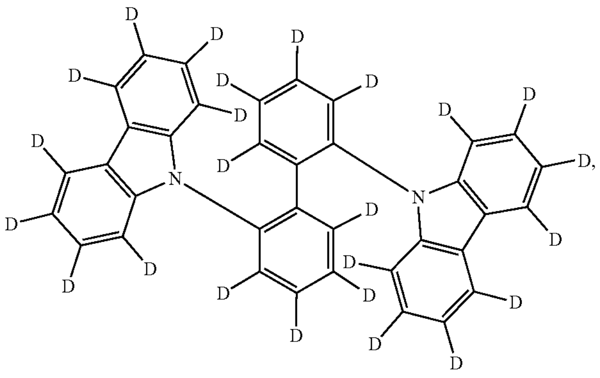

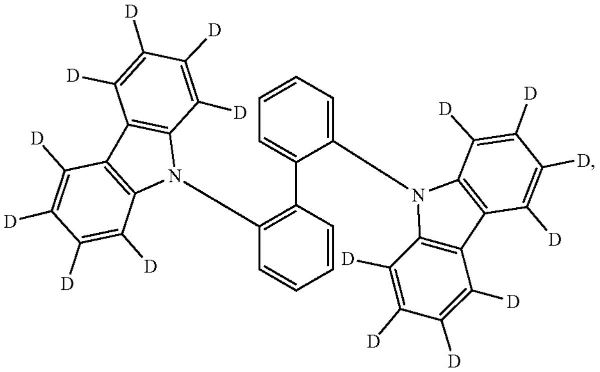

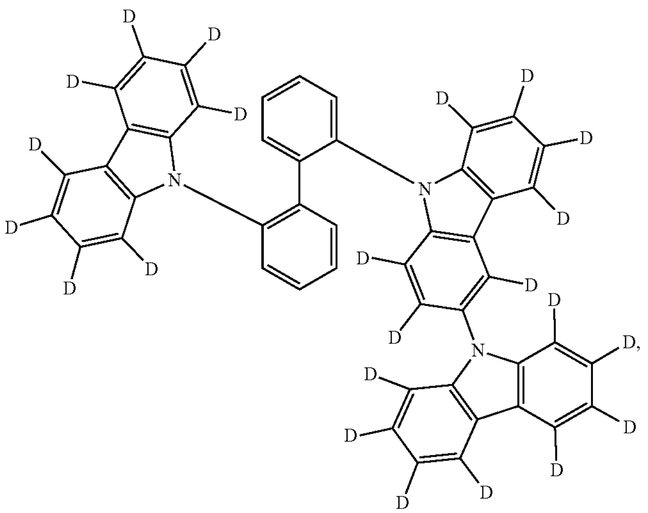

-continued
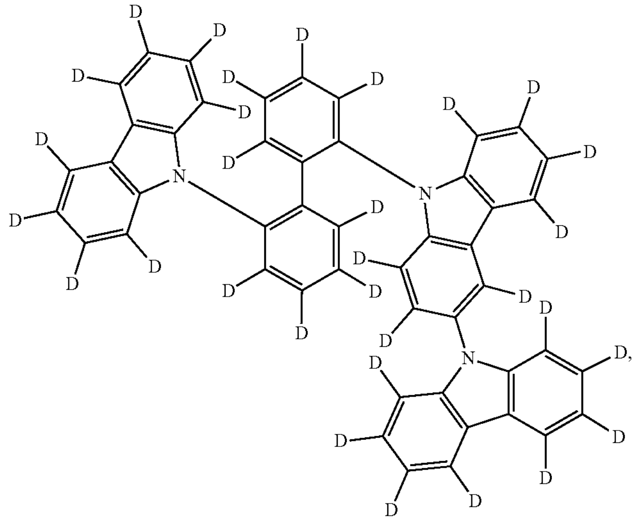
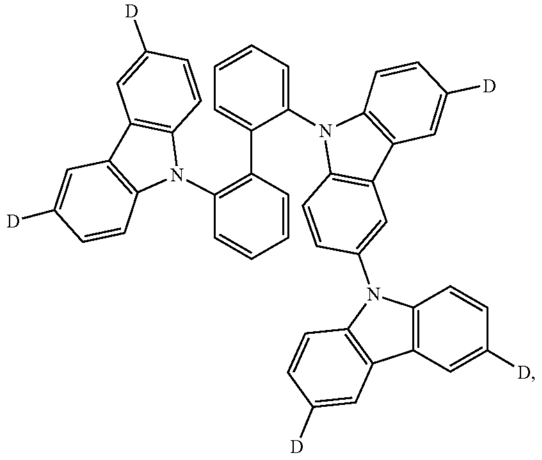
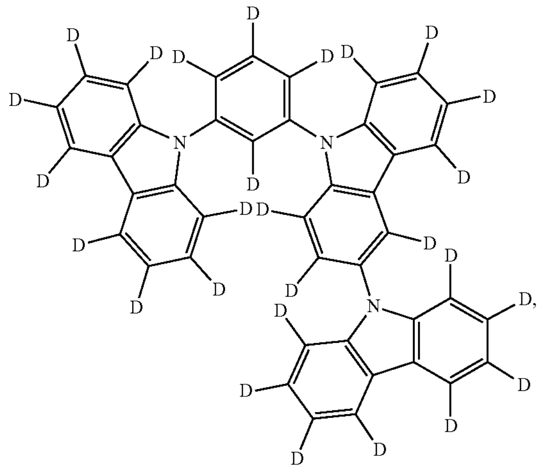
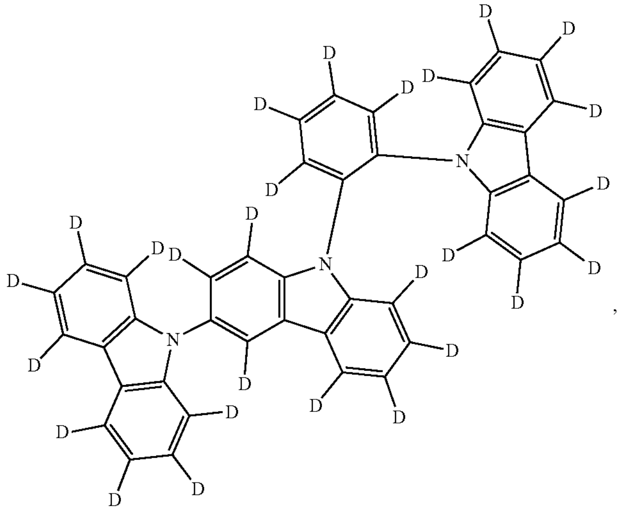
,
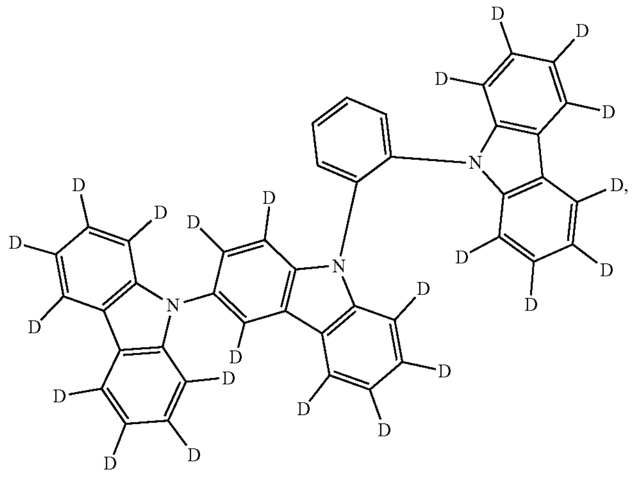

-continued
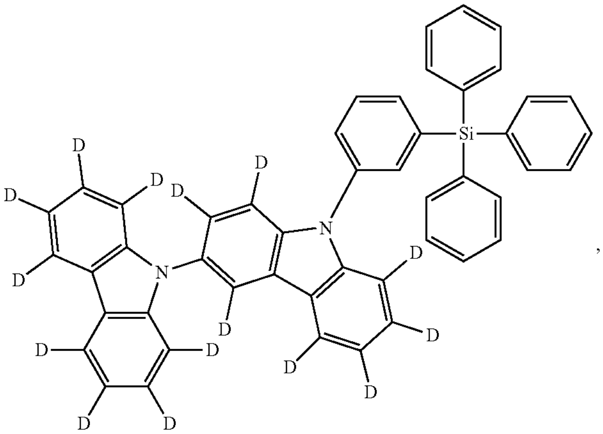
,
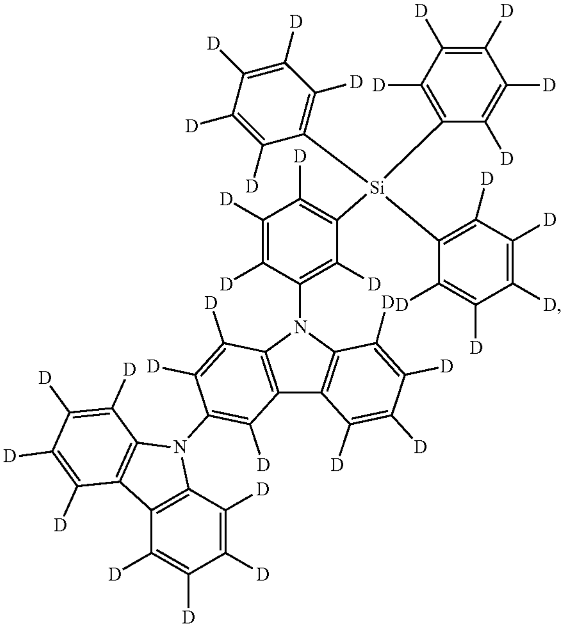
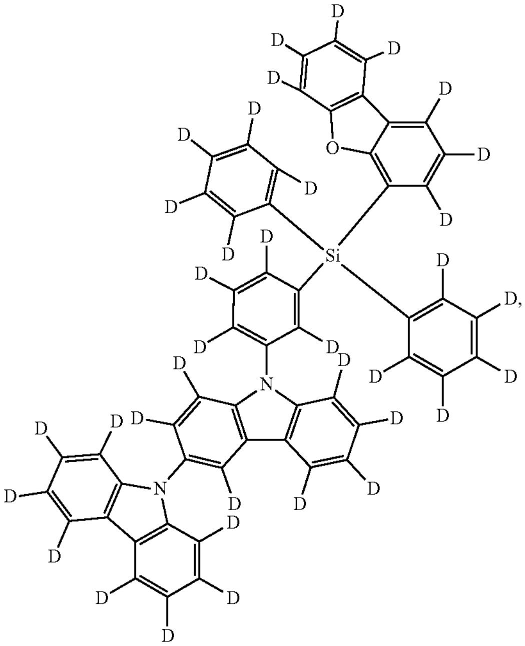

-continued
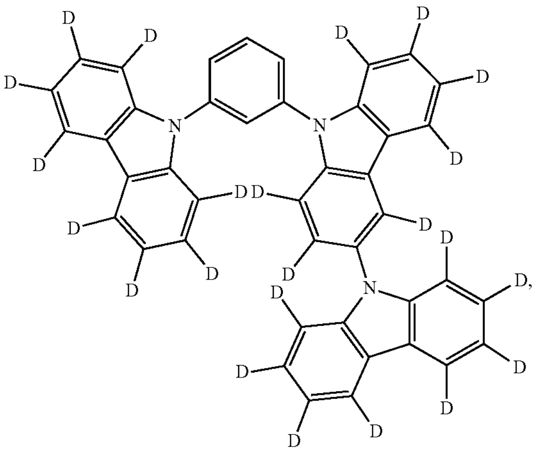
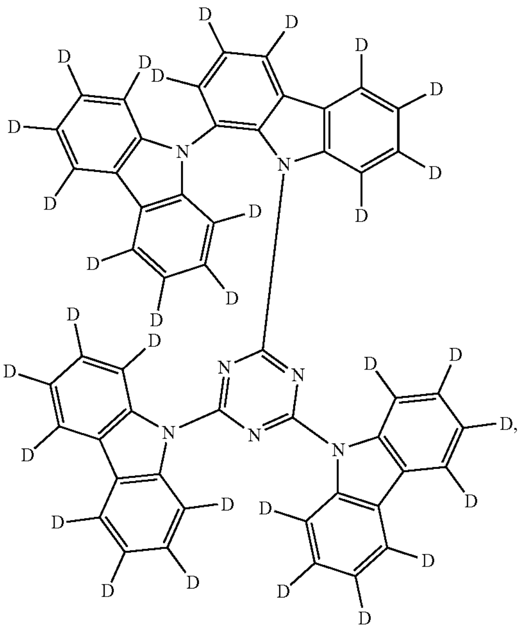
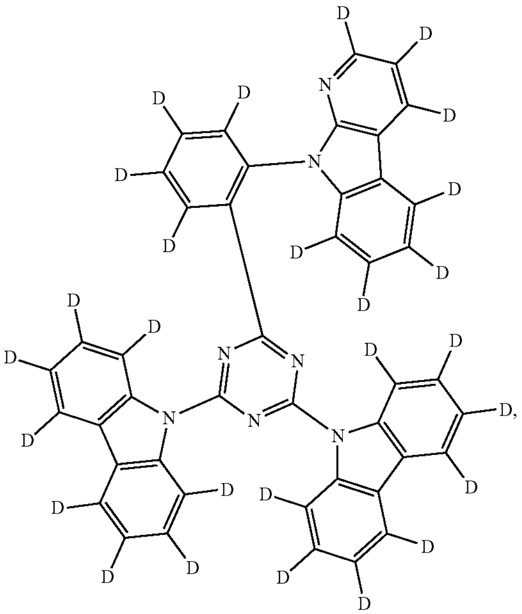
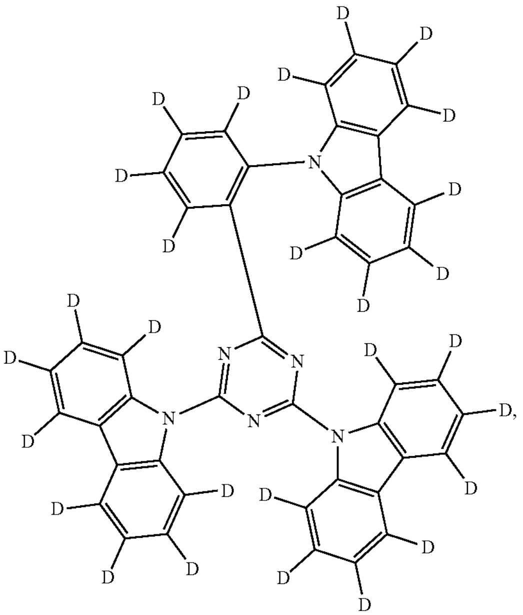

-continued
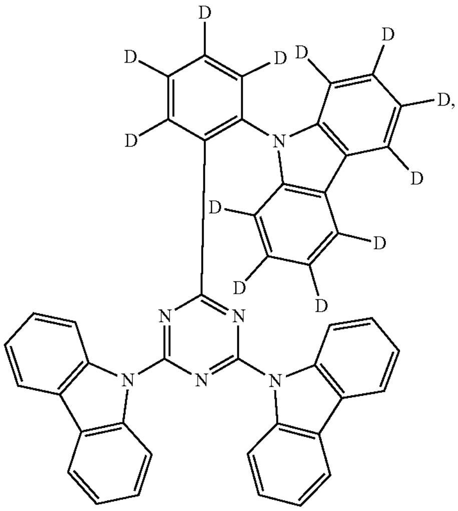
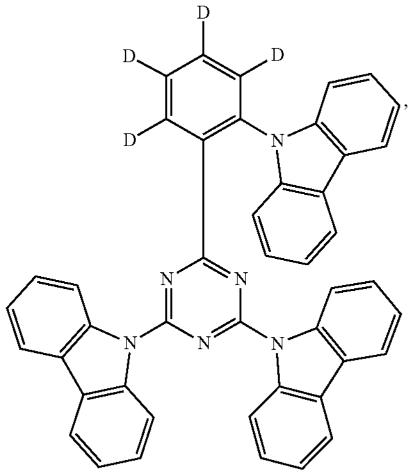
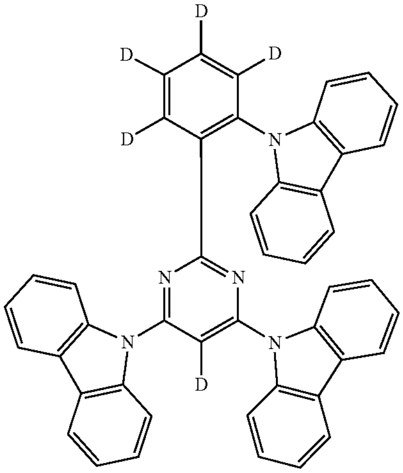
,
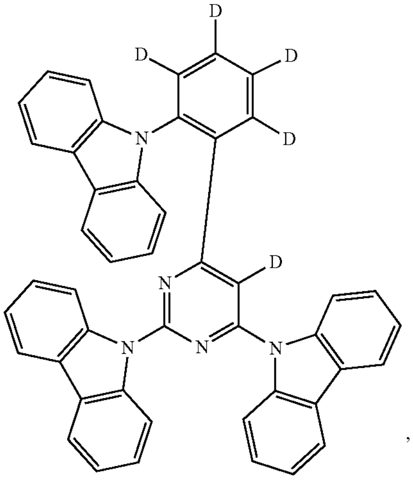
,
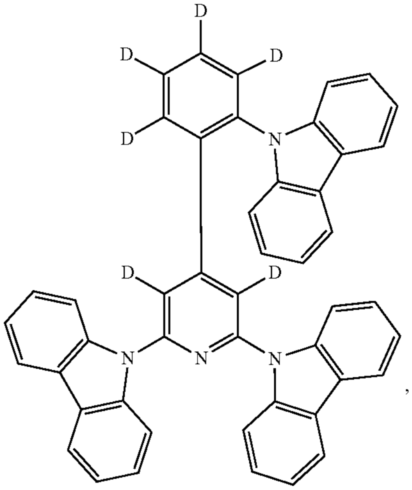
,
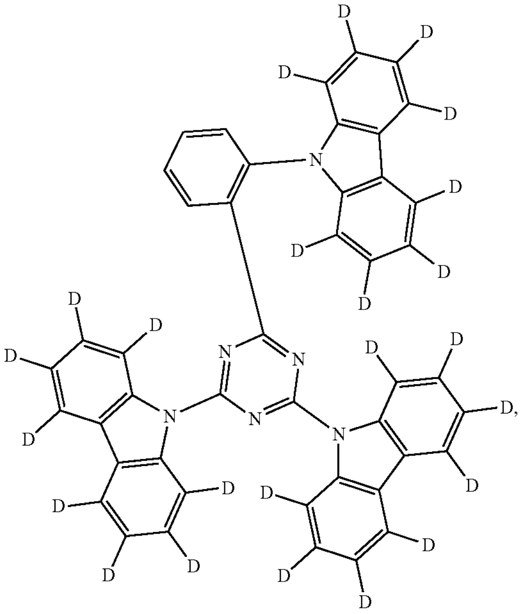

-continued
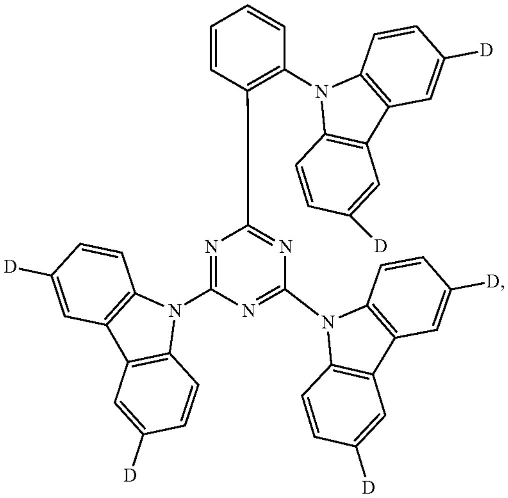
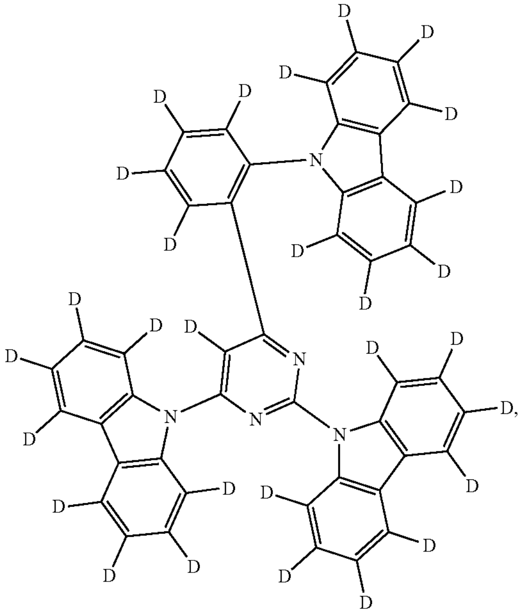
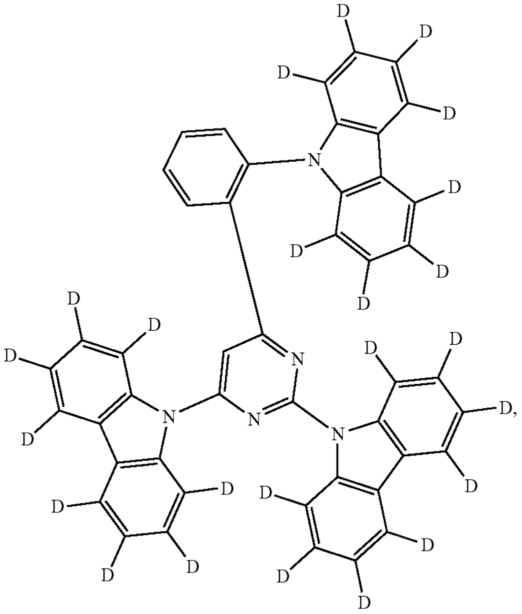
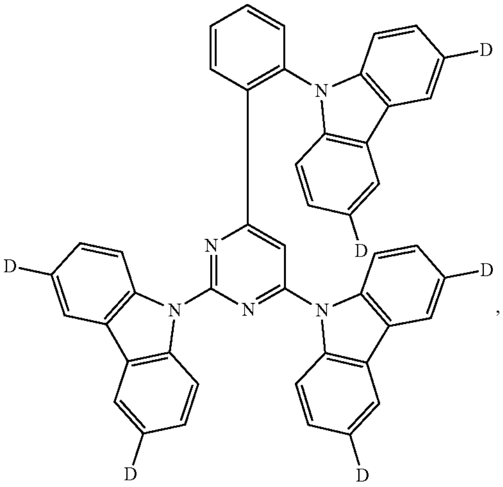
,

-continued
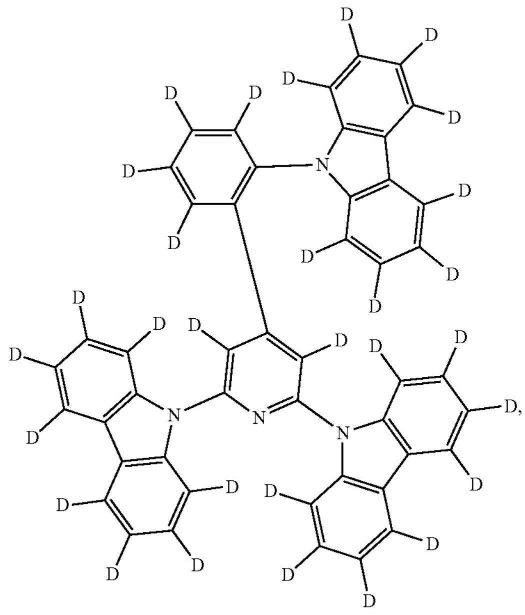,
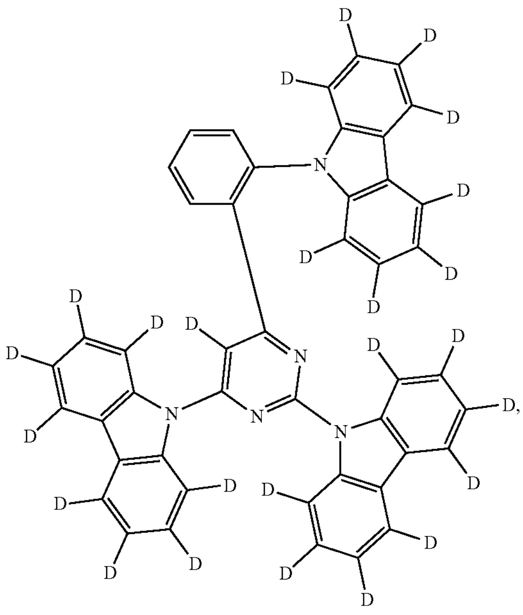,
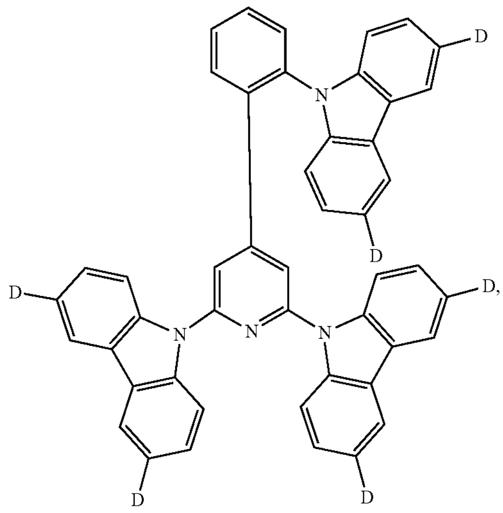,
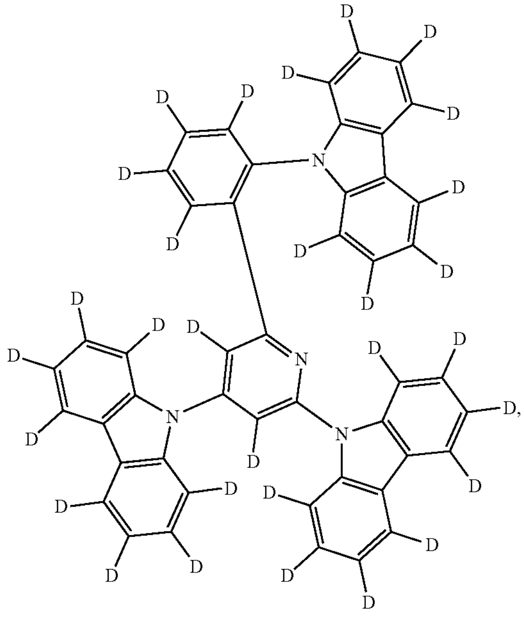,

-continued
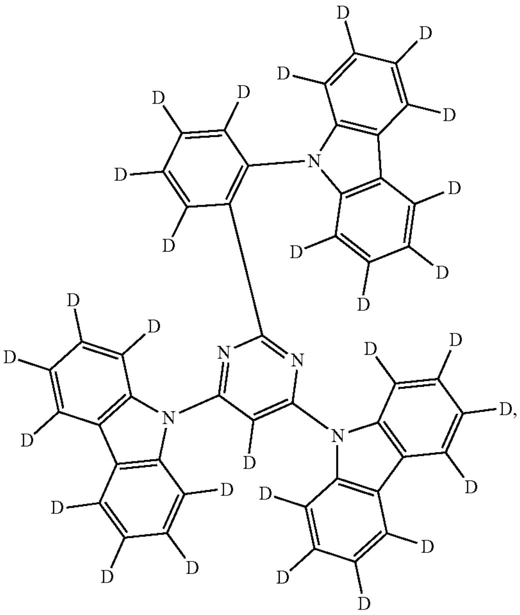,
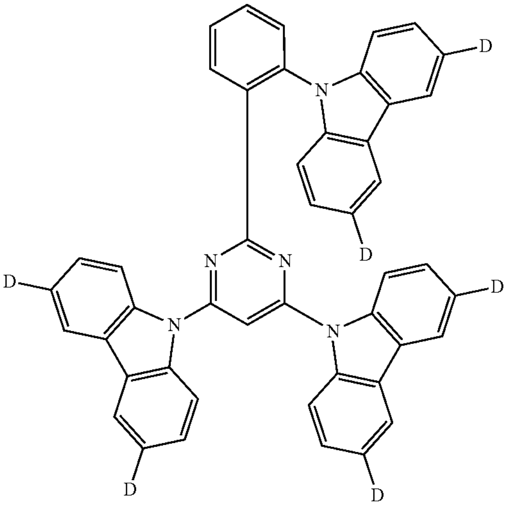,
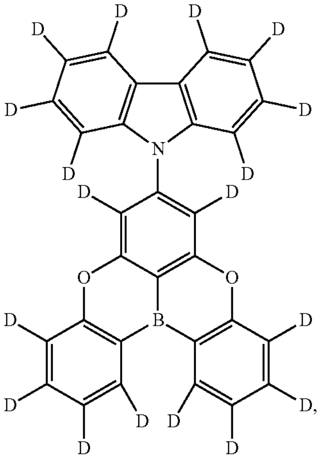,
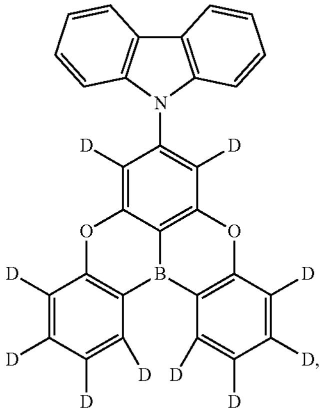,
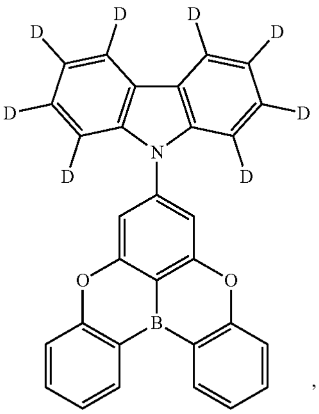,
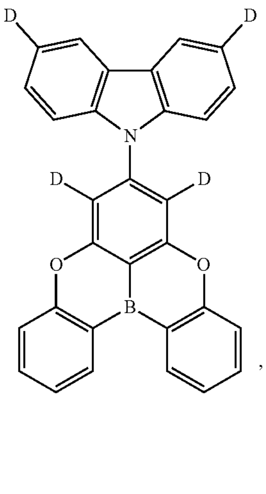,
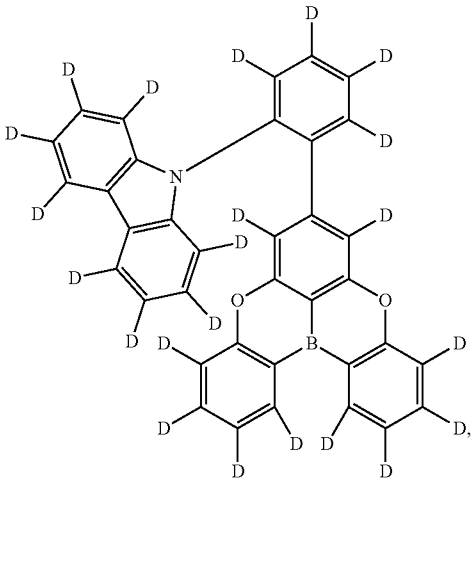, -continued
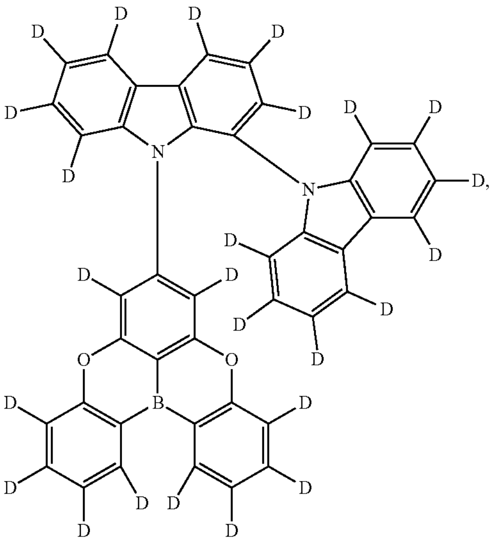
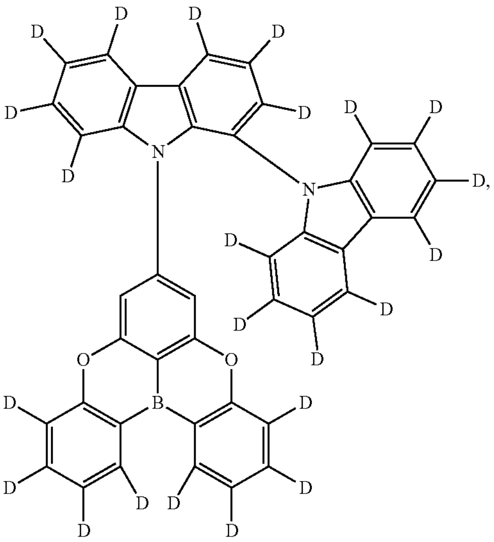
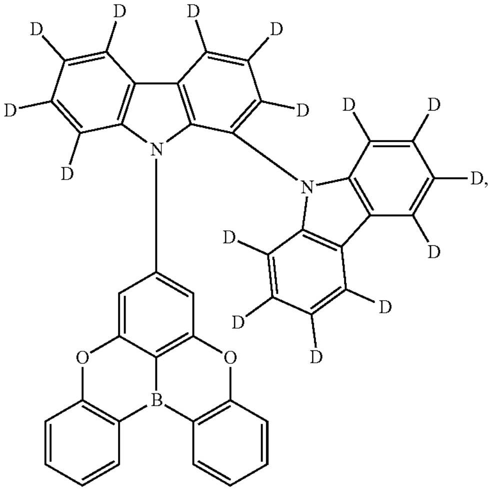
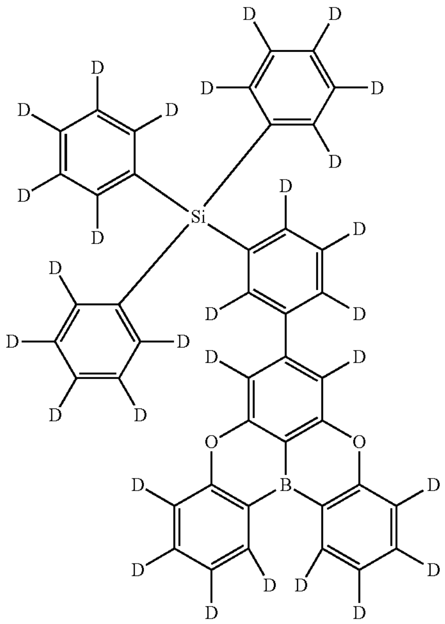
, -continued
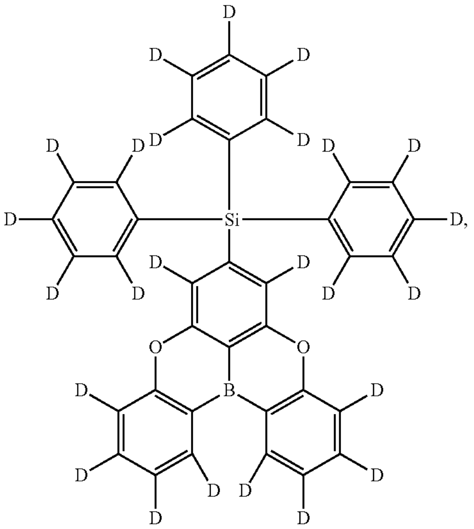
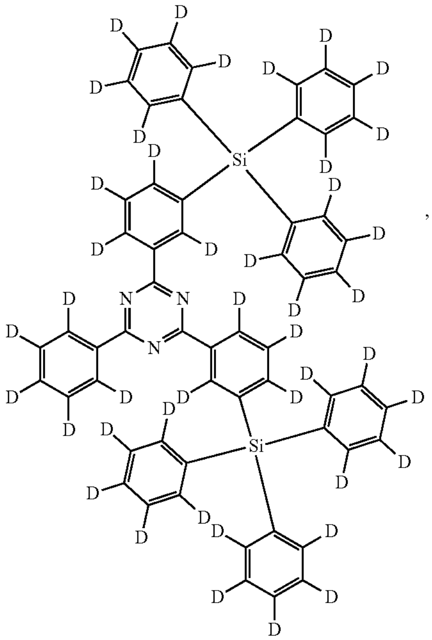
,
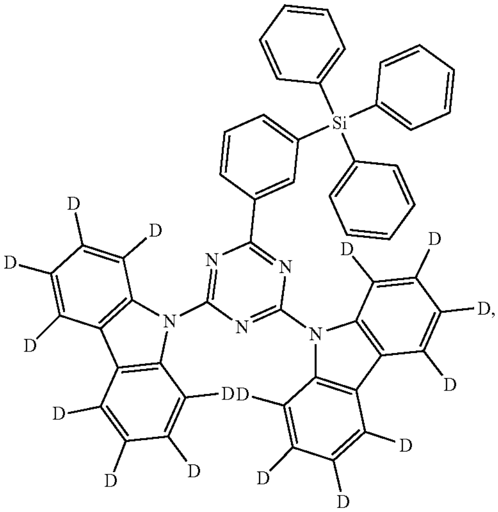
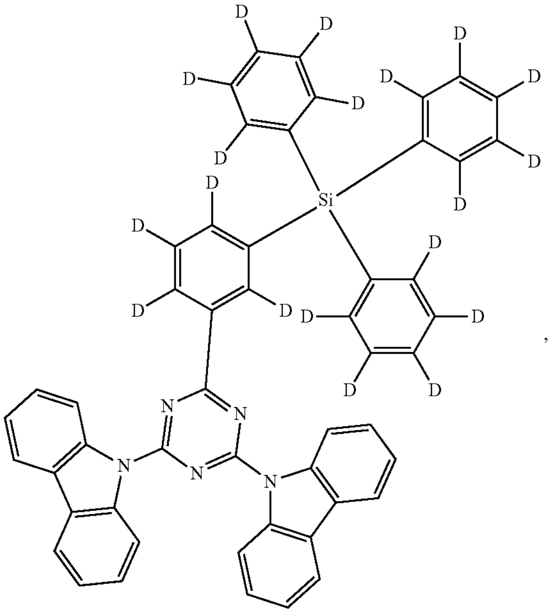
, -continued
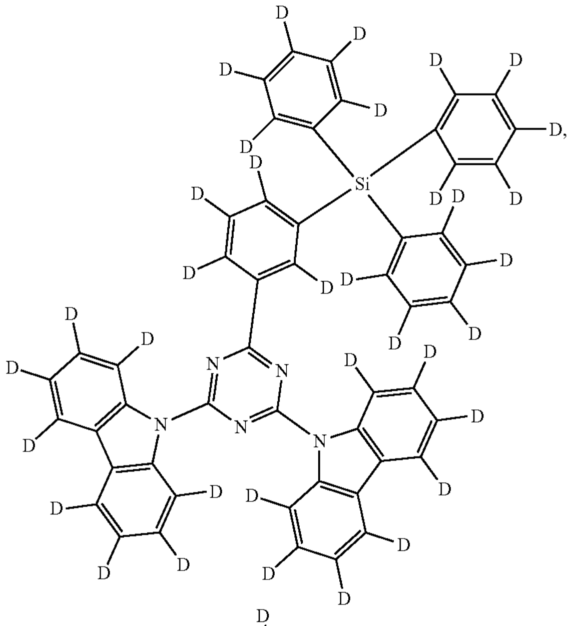
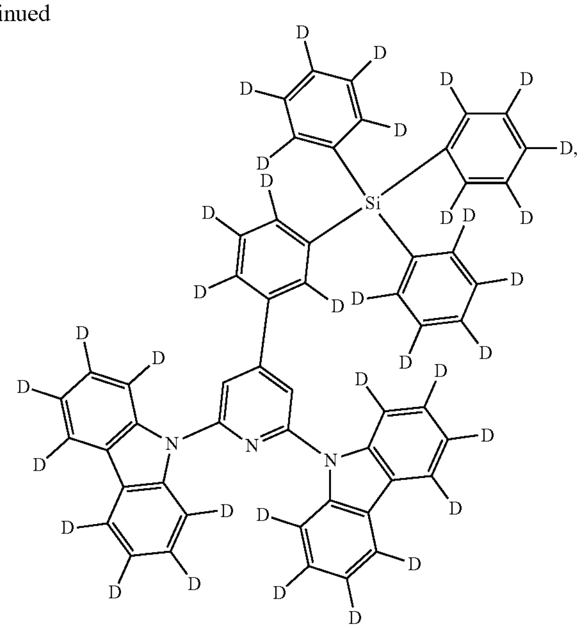
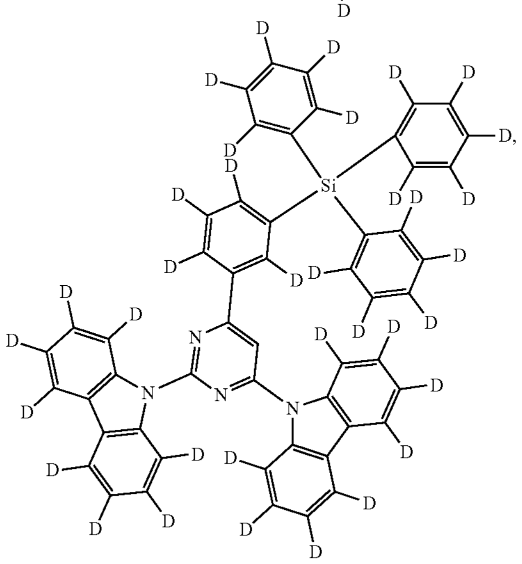
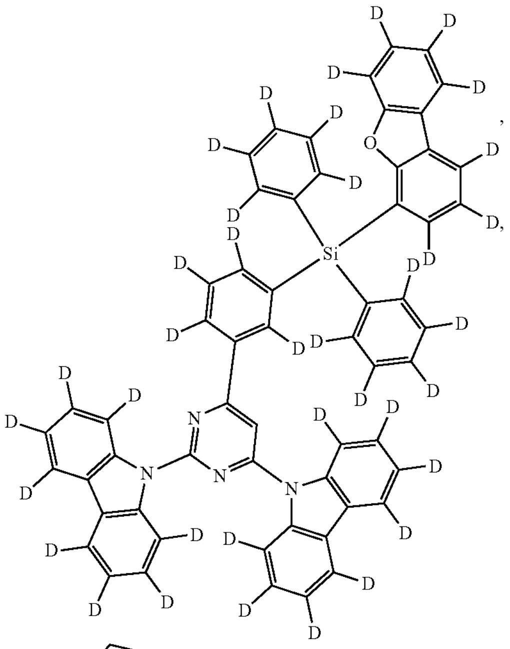
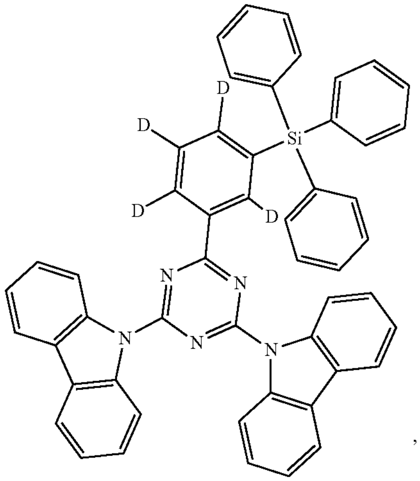
,
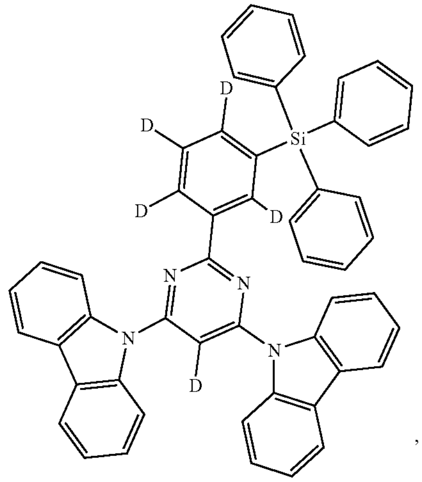
, -continued
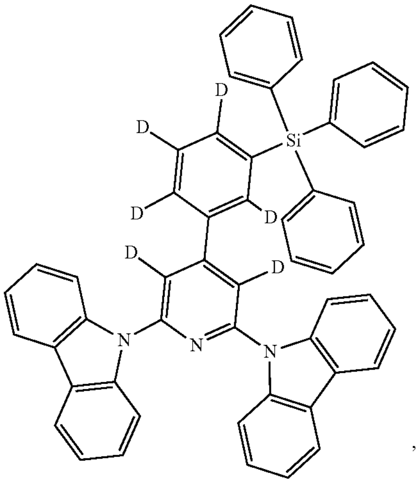
,
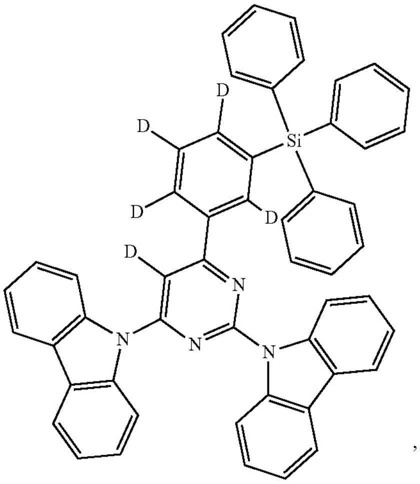
,
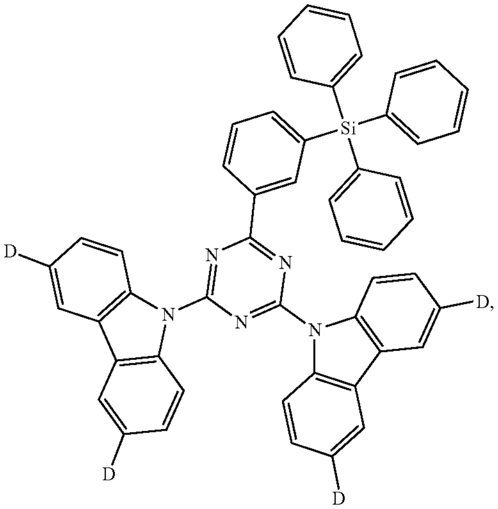
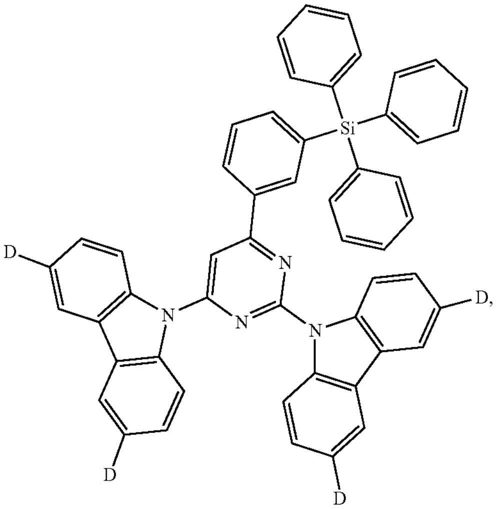
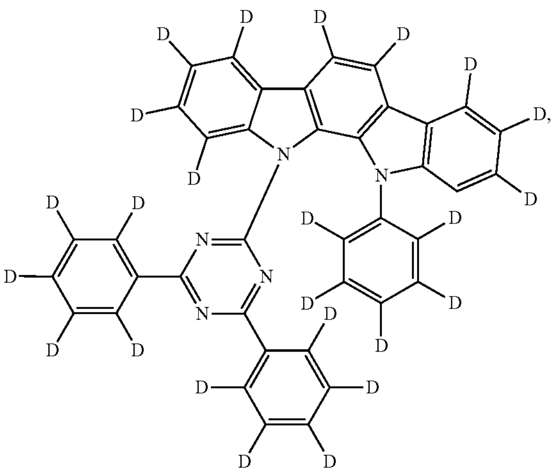
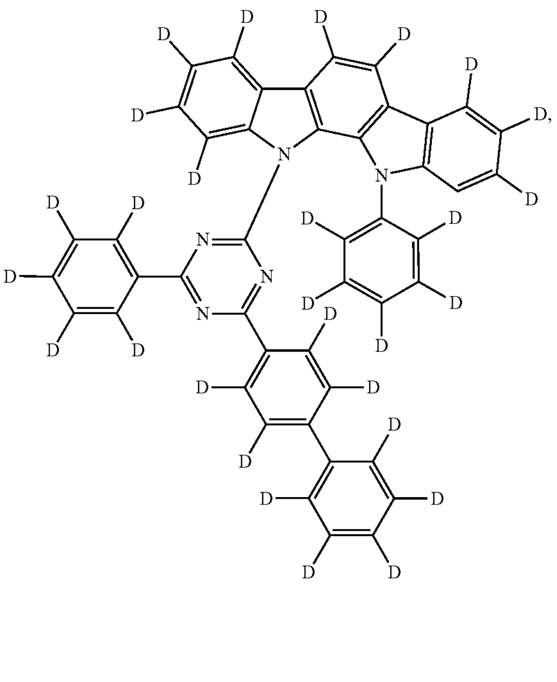

-continued
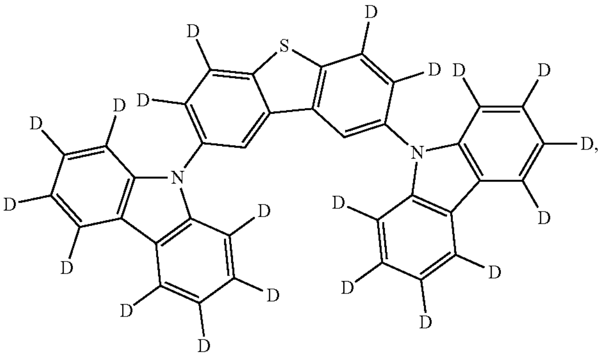
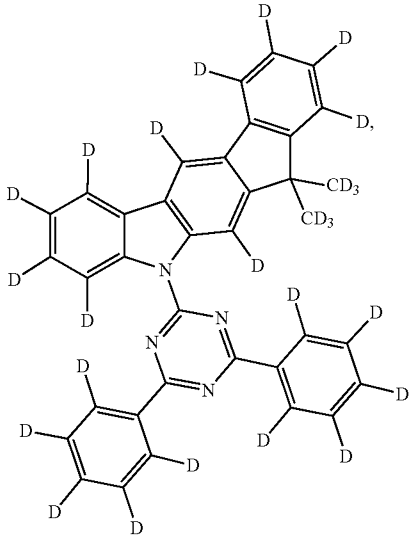
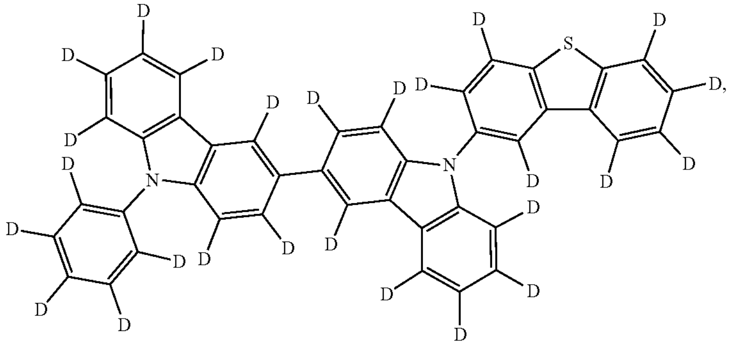
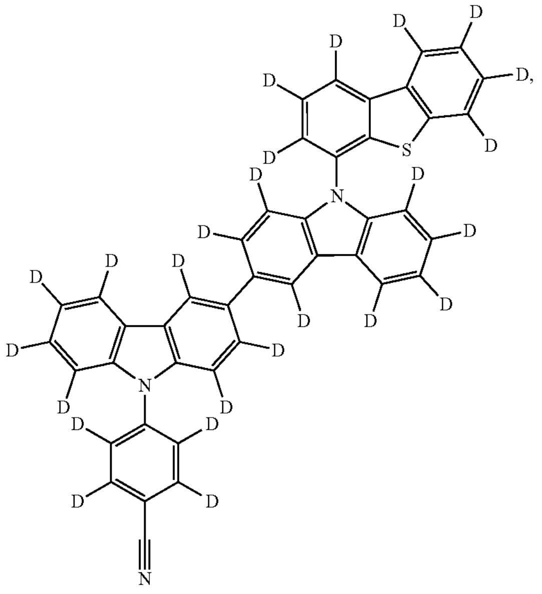
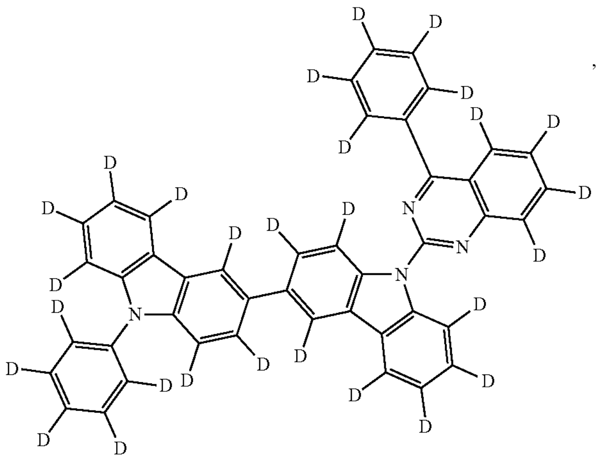
,

-continued
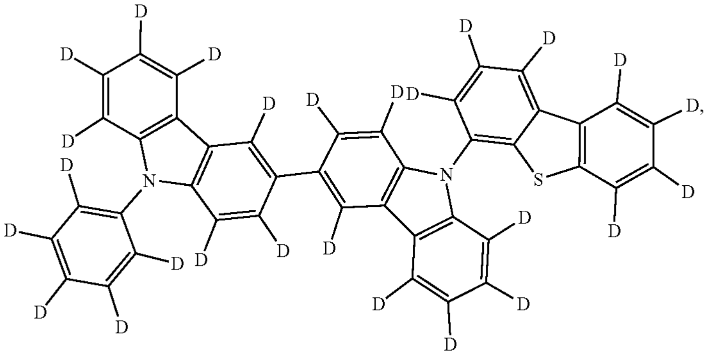
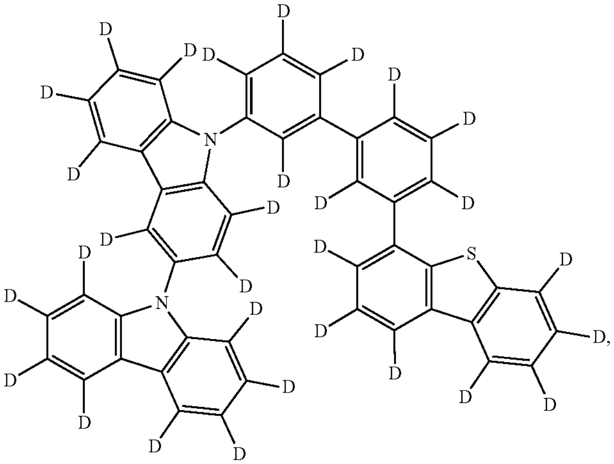
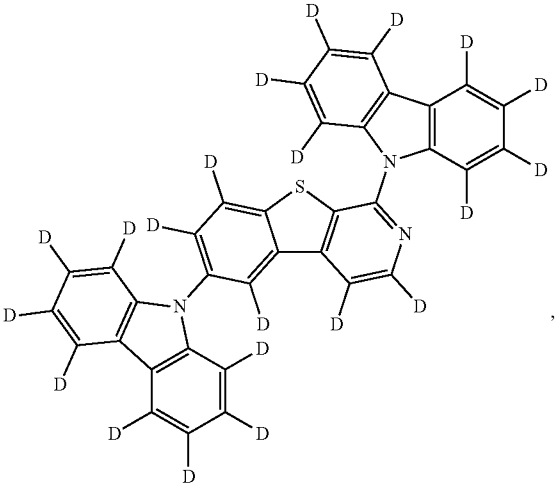
,
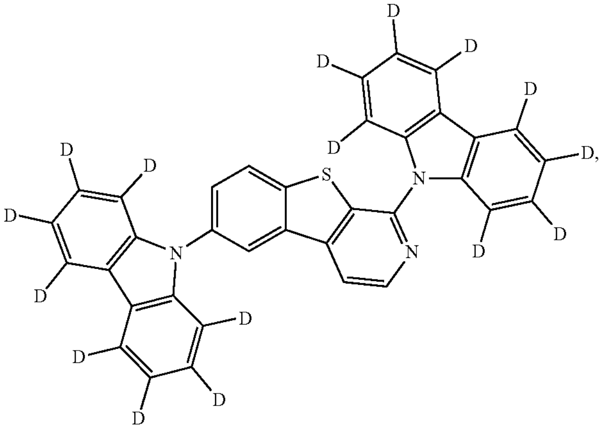
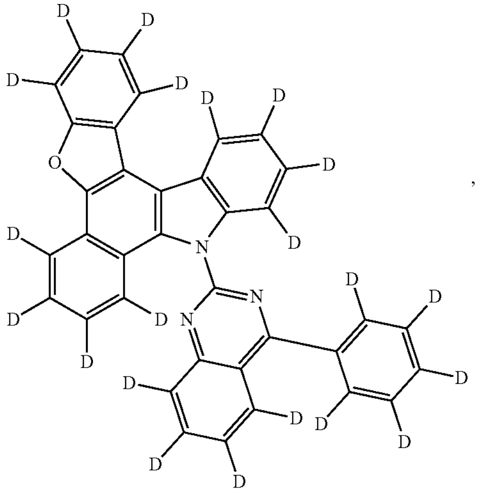
,

-continued
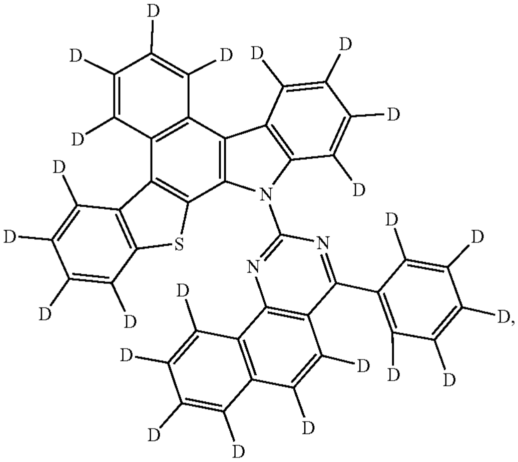
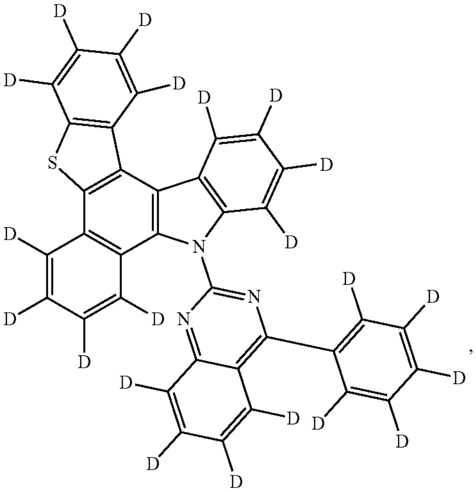
,
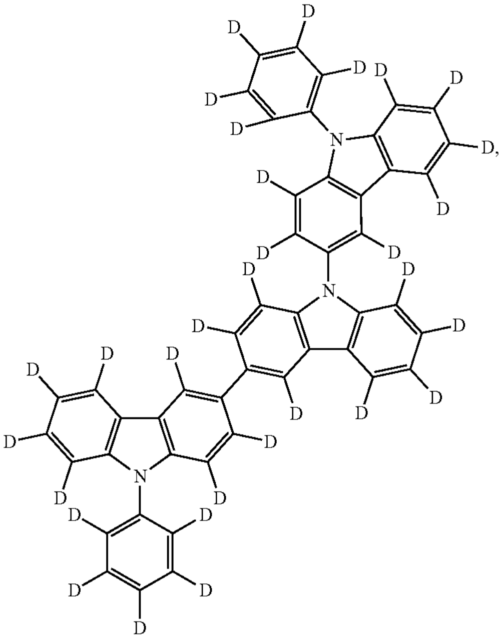
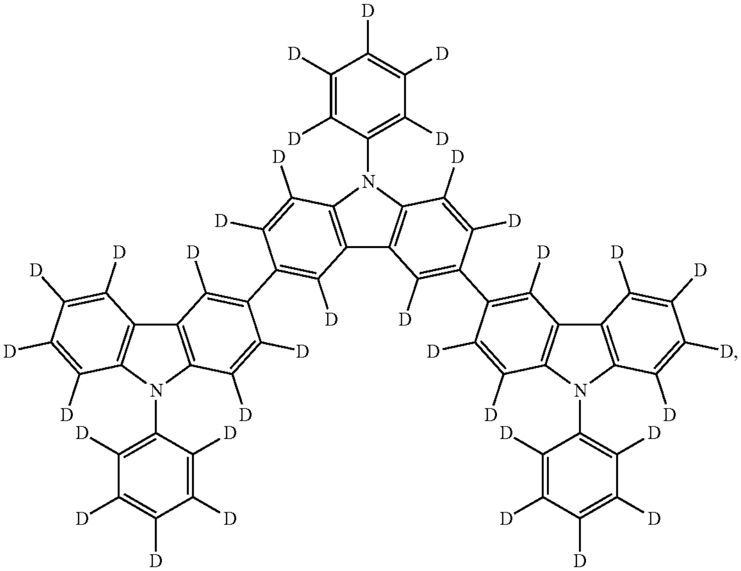

-continued
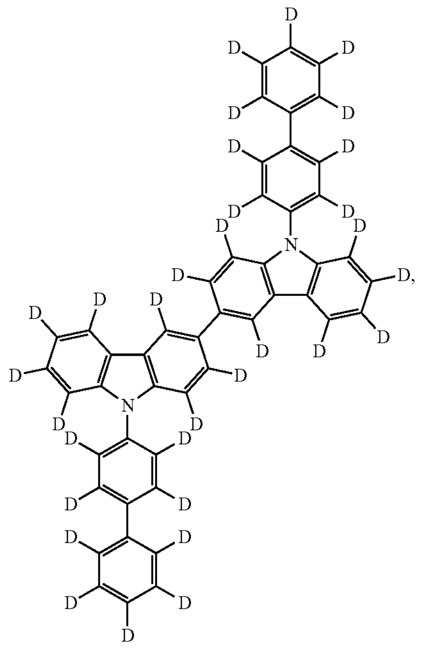
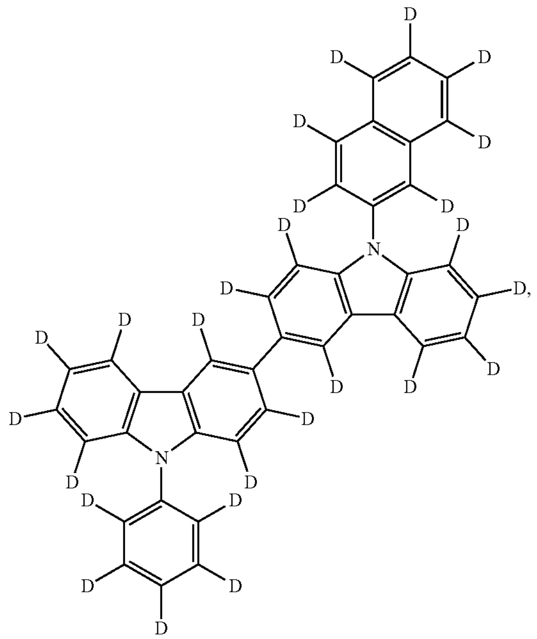
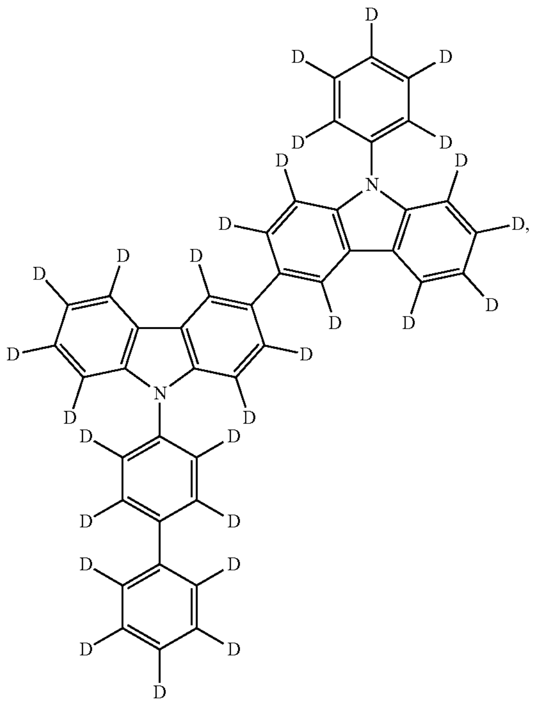

-continued
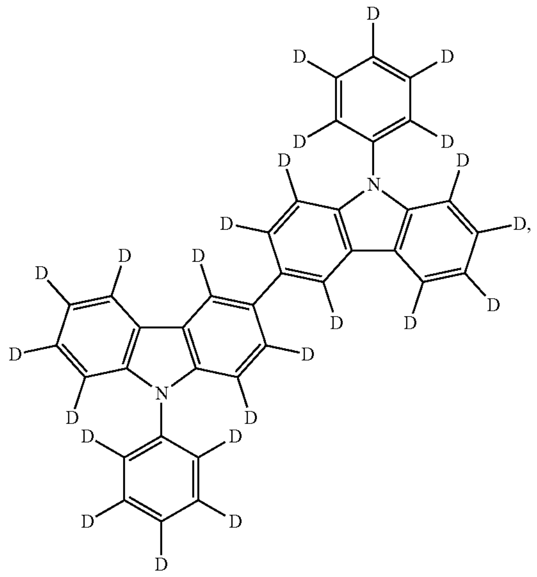
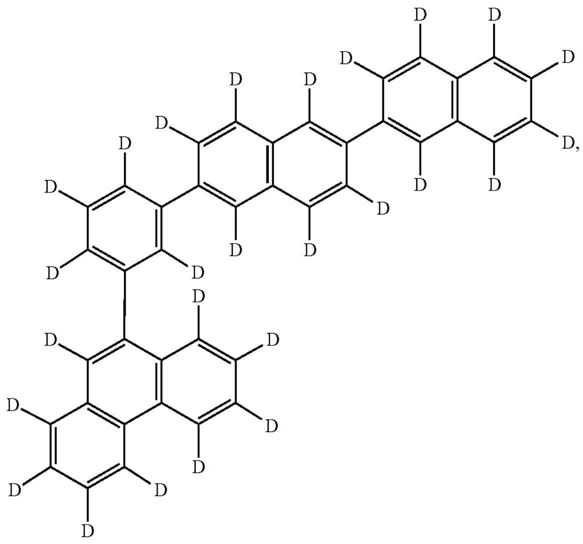
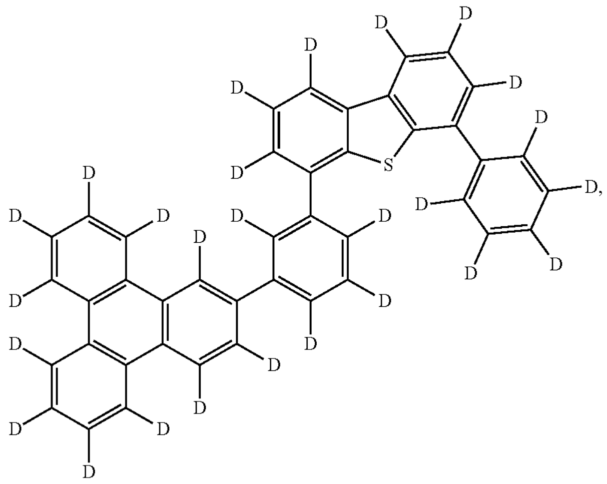
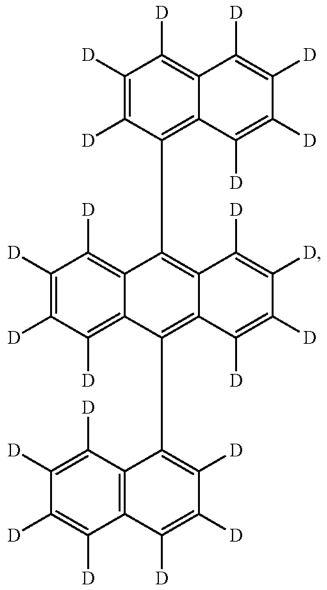

-continued
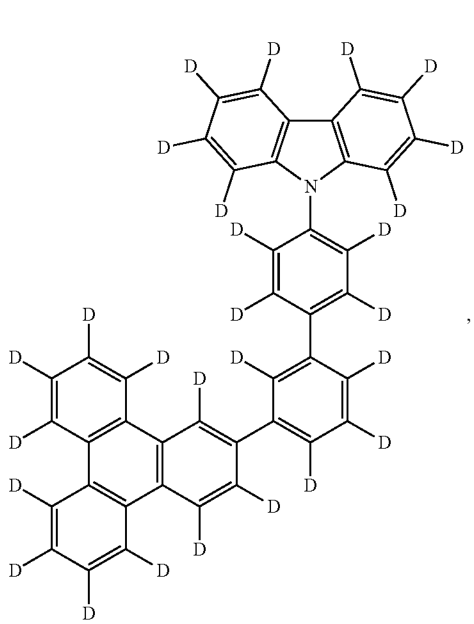
,
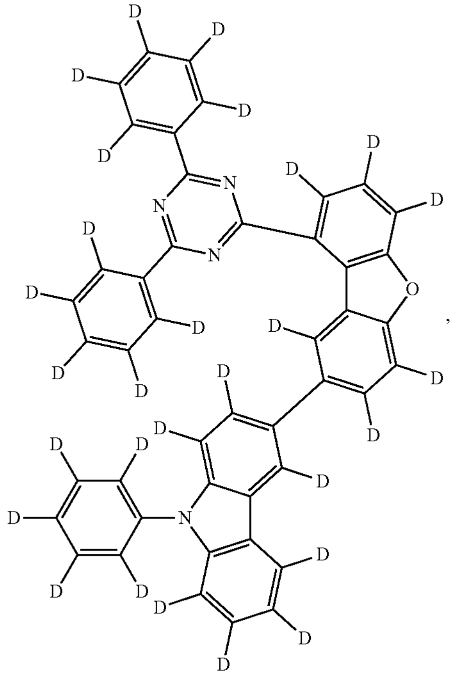
,
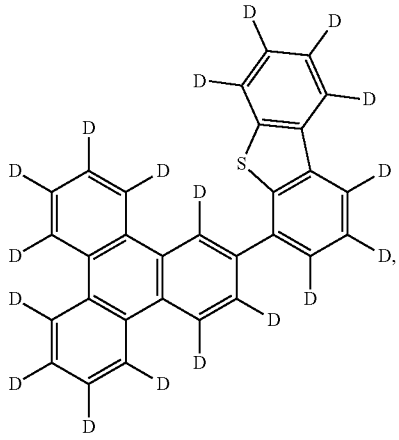
,
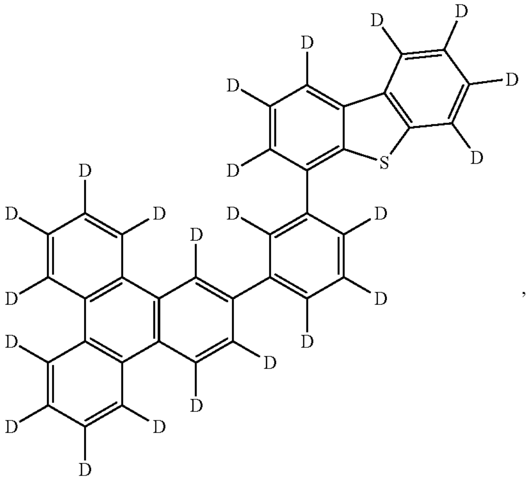
,

-continued
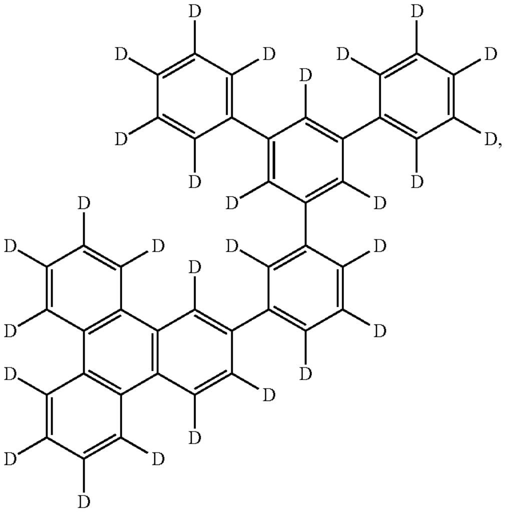
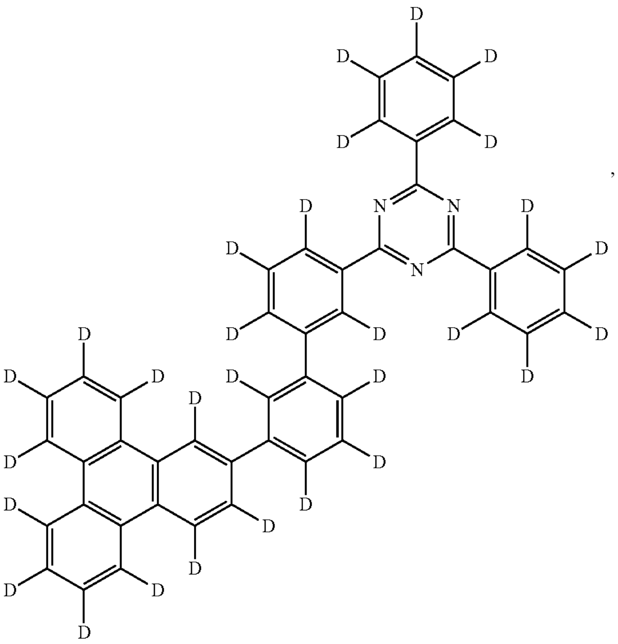
,
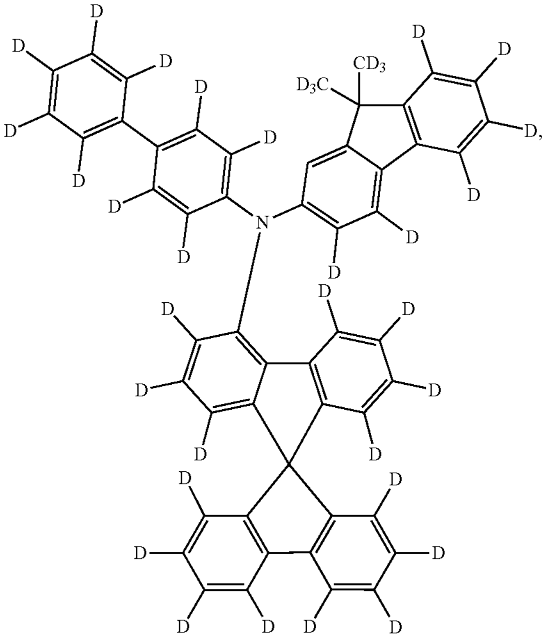
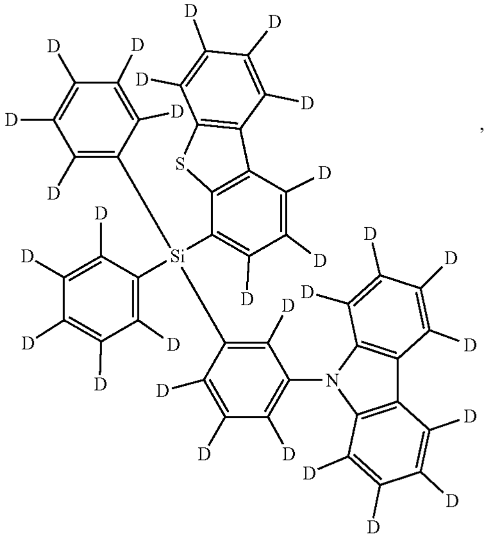
,
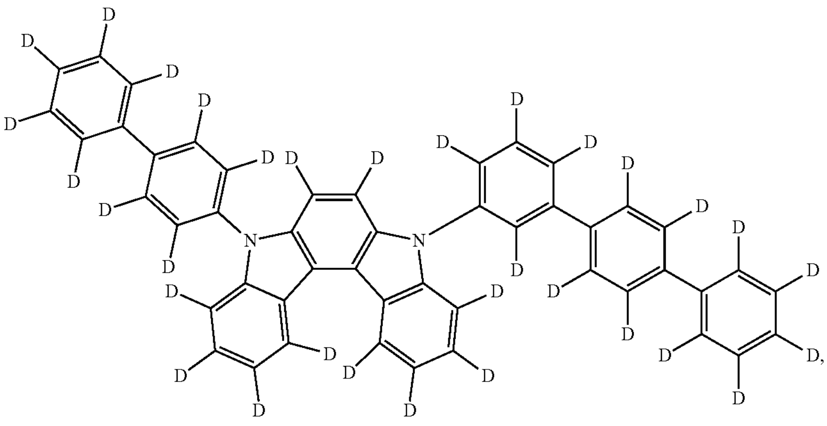

-continued
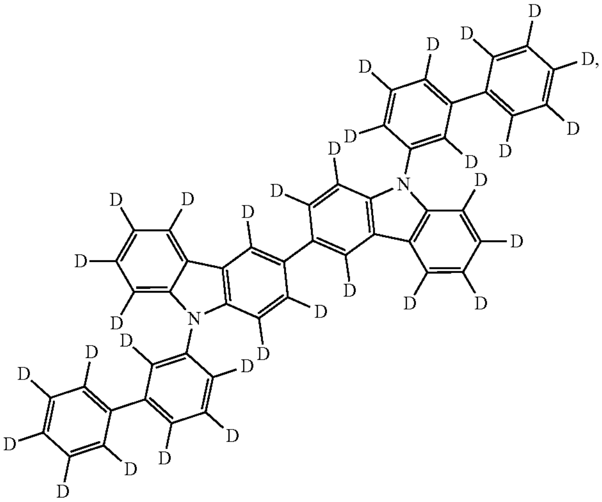
,
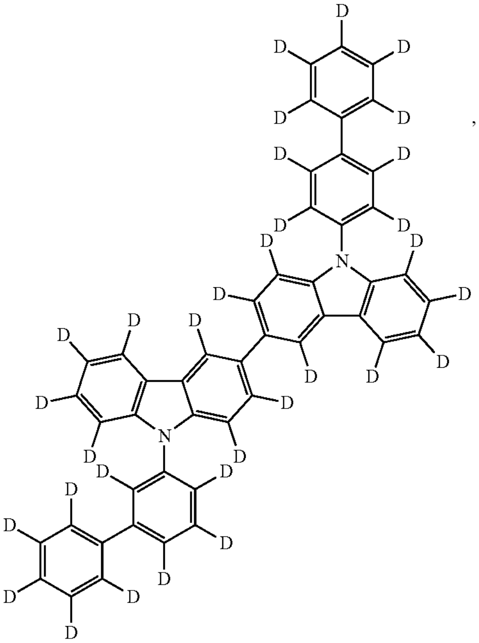
,
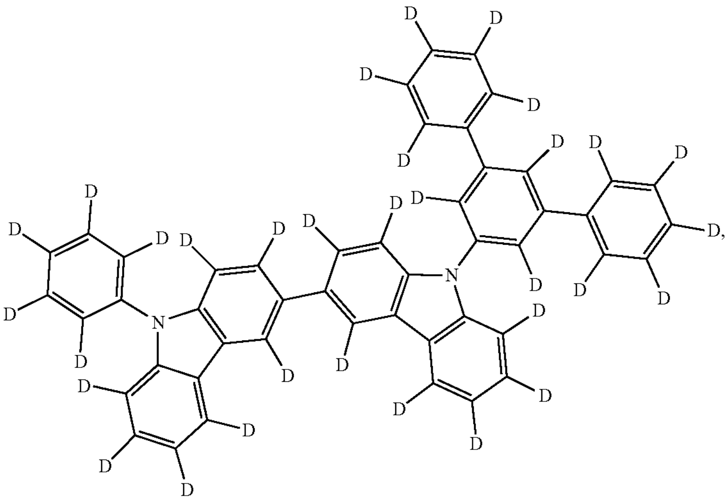
,

-continued
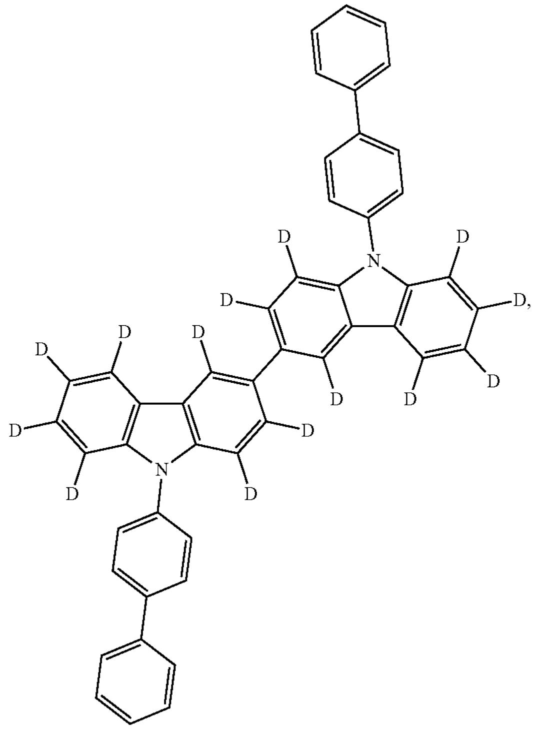
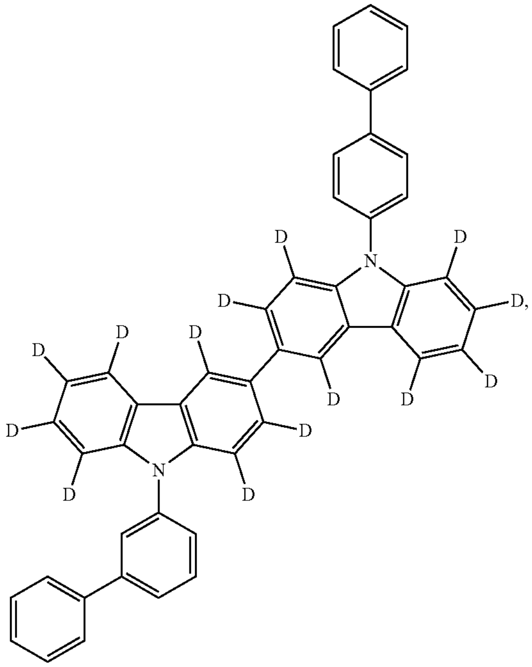
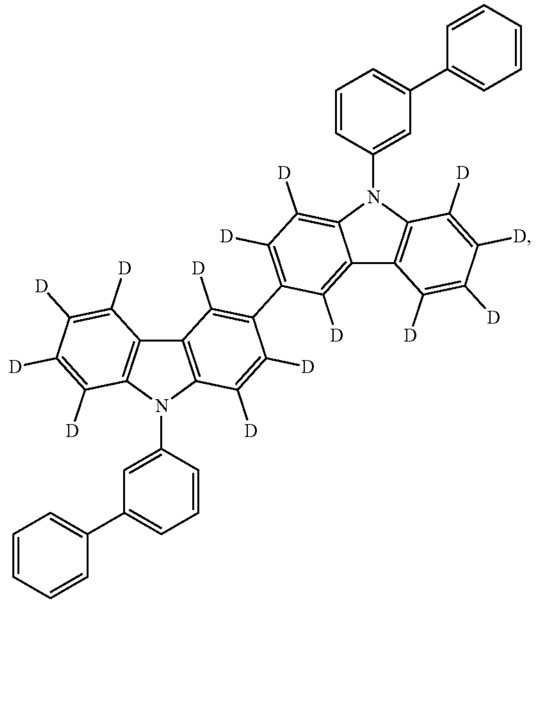
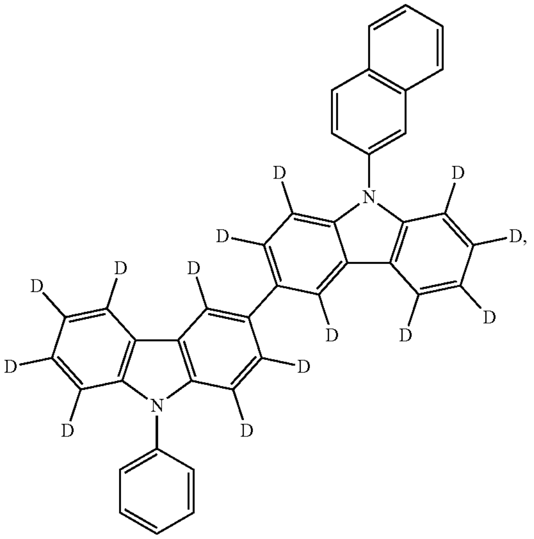

-continued
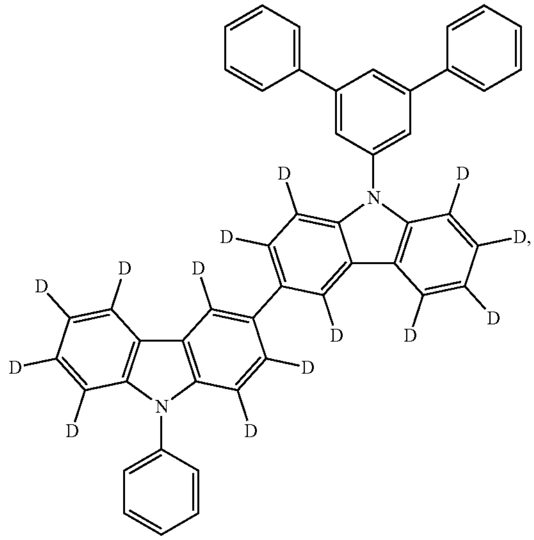
,
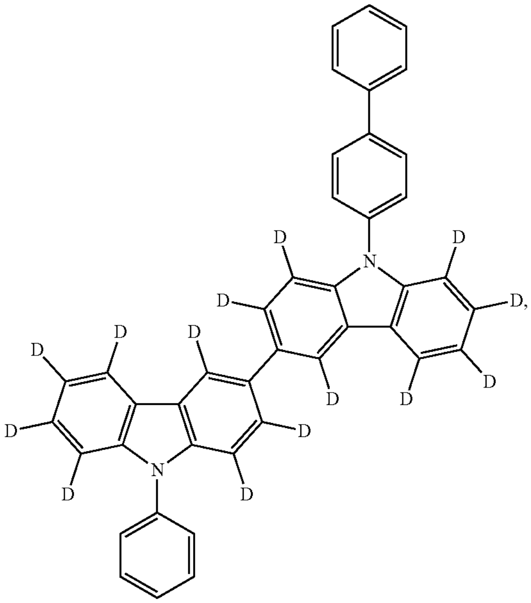
,
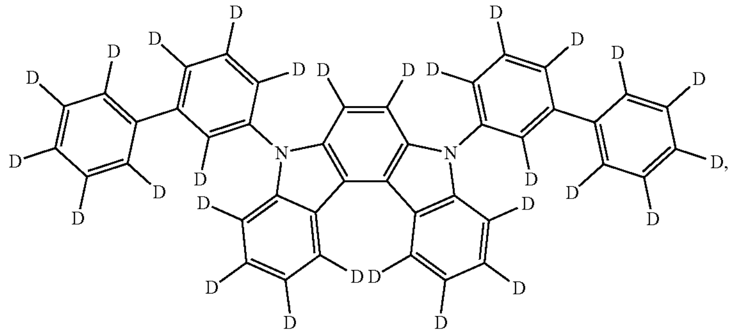
,
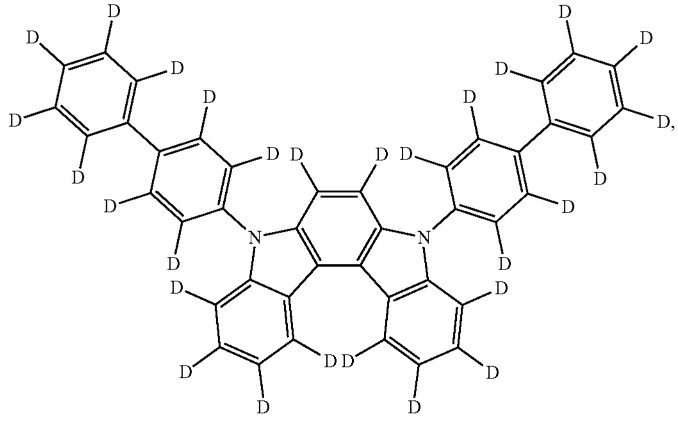
,
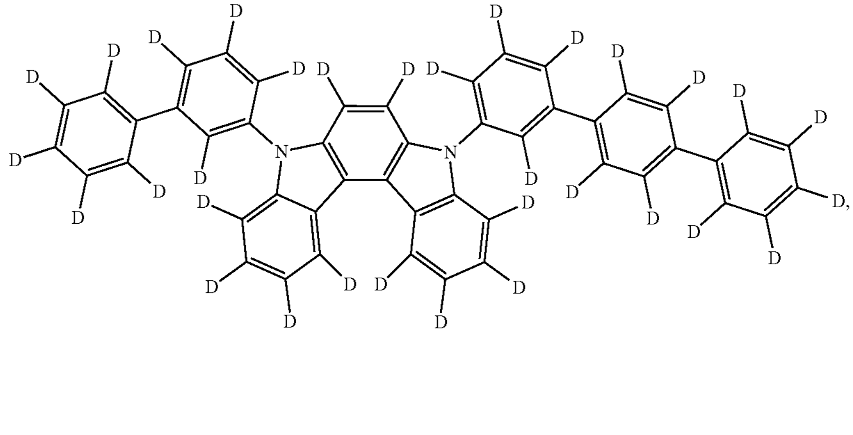
, -continued
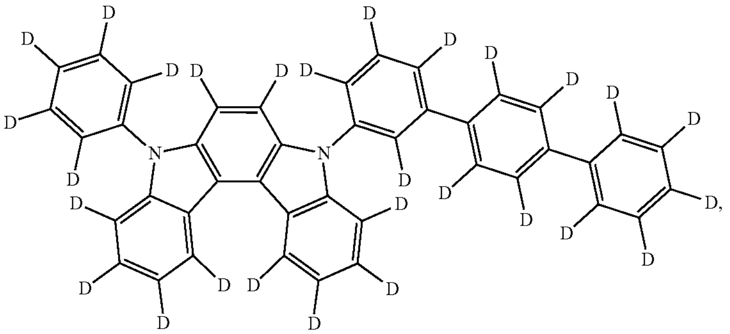
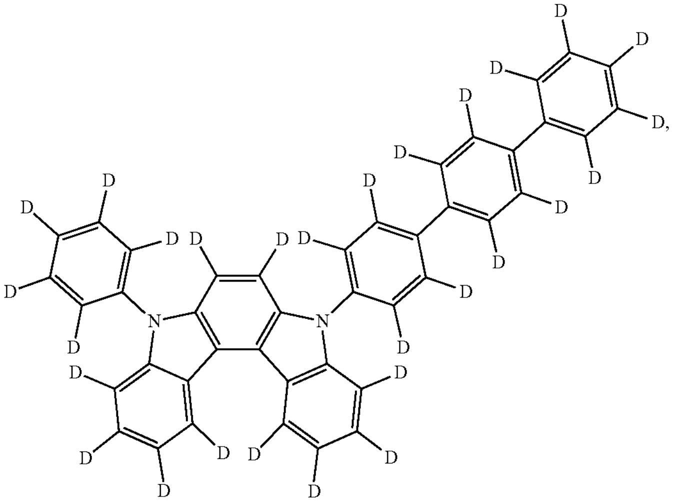
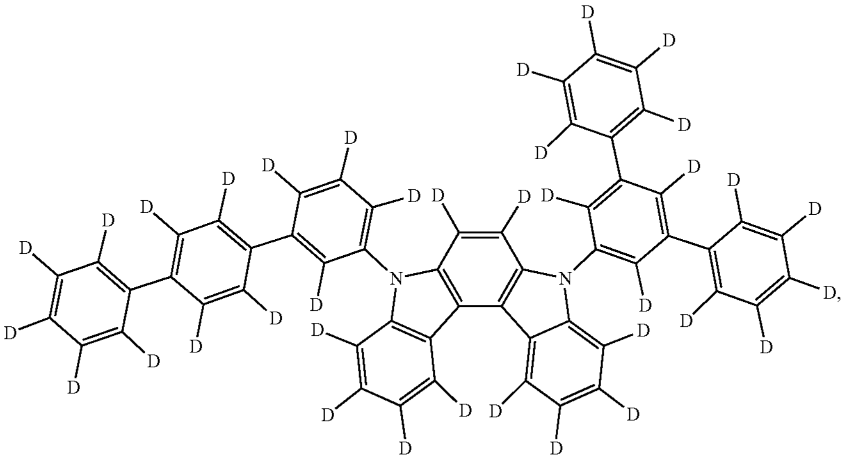
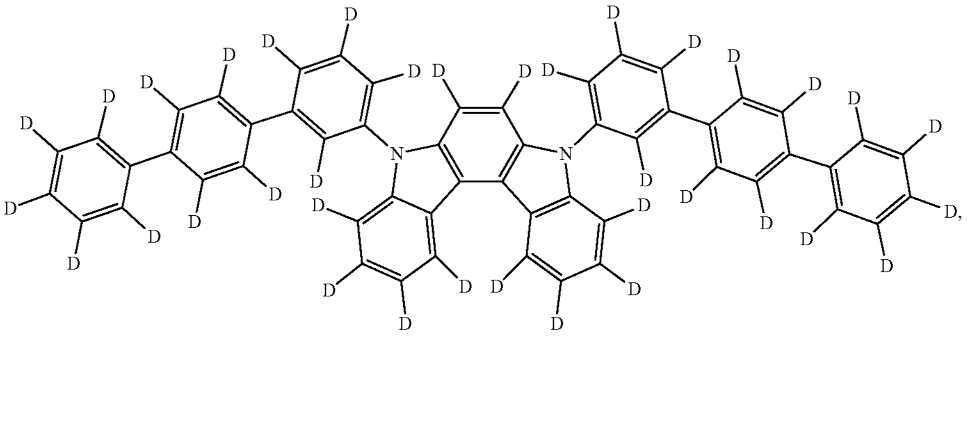

-continued
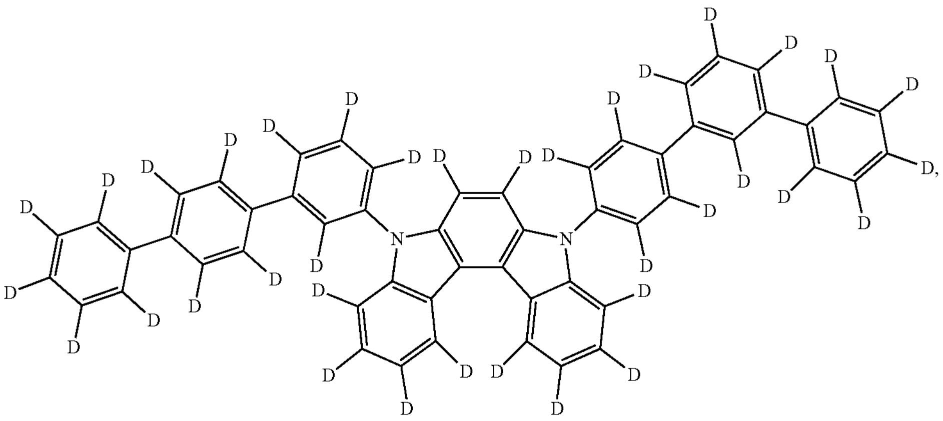
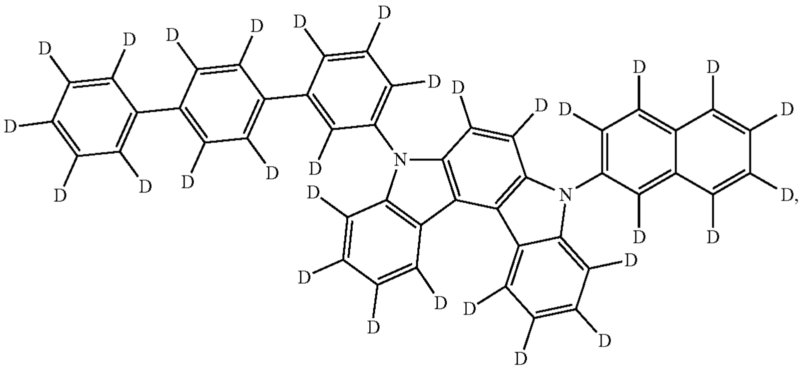
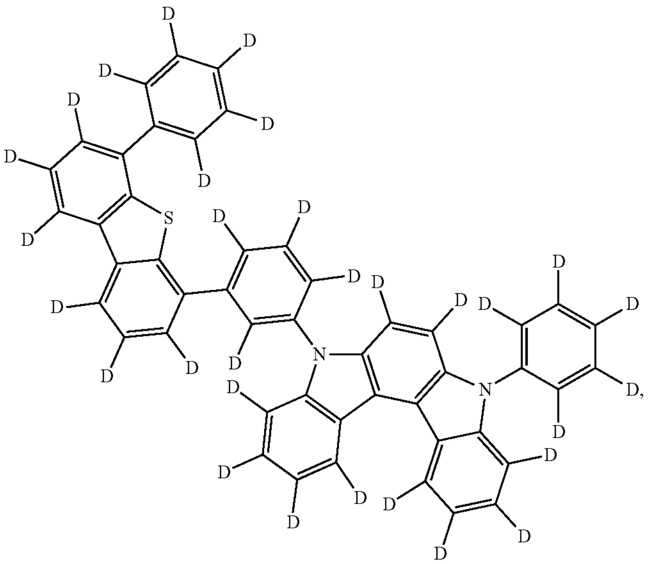

-continued
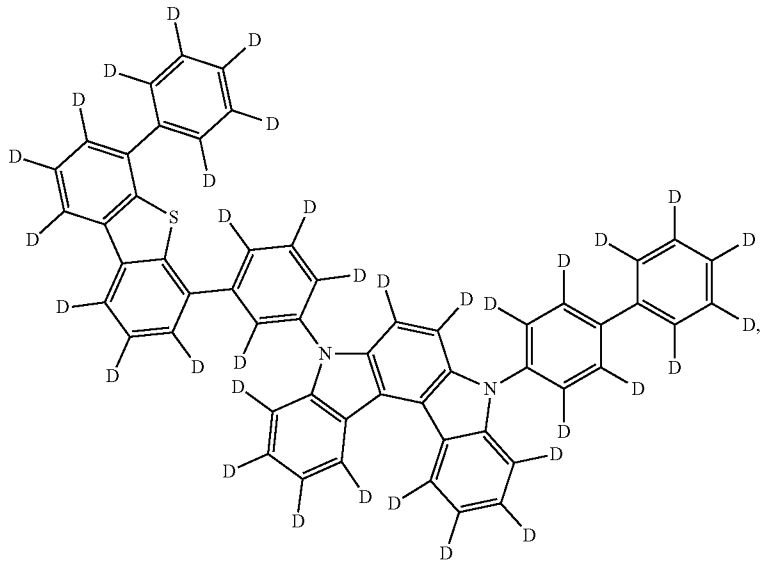
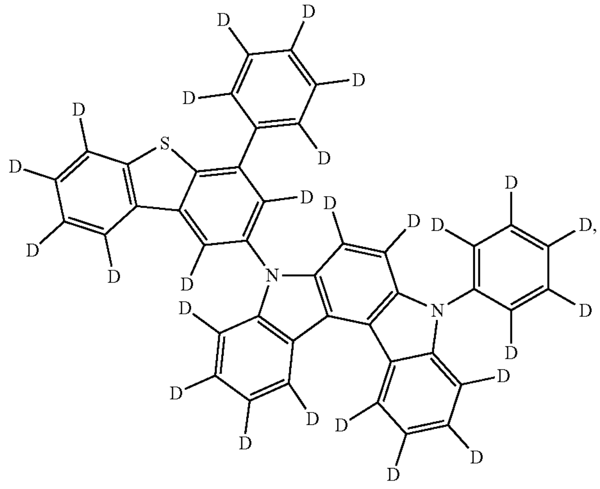
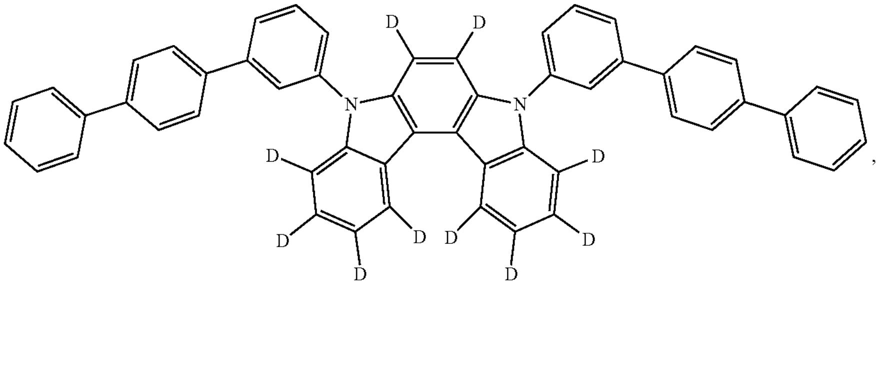
,

-continued
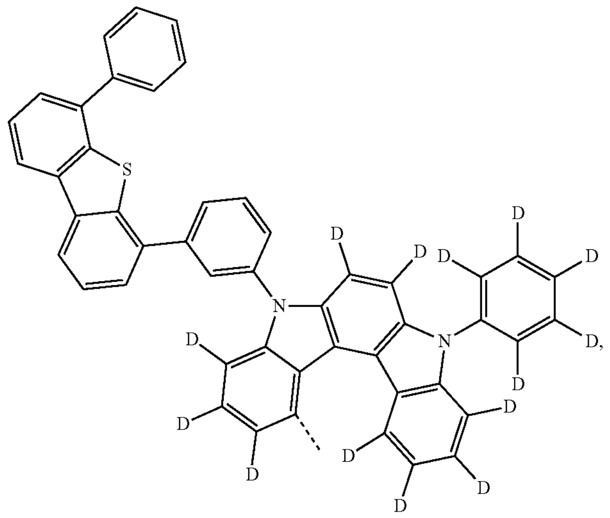
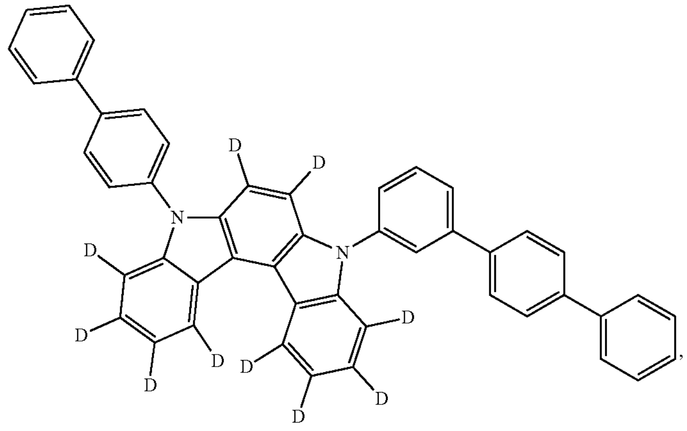
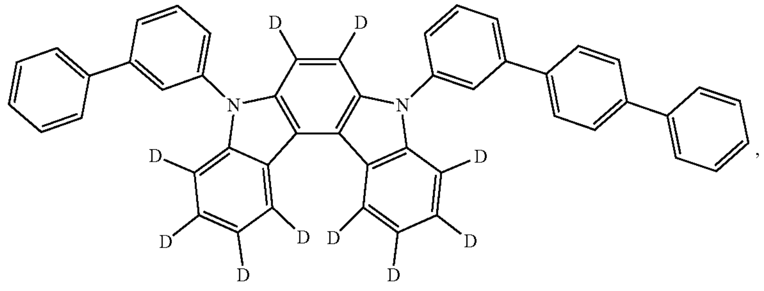
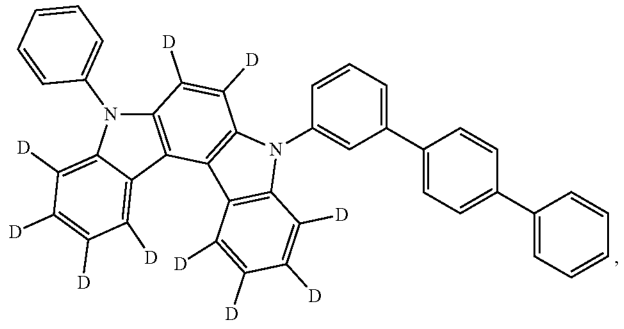

-continued
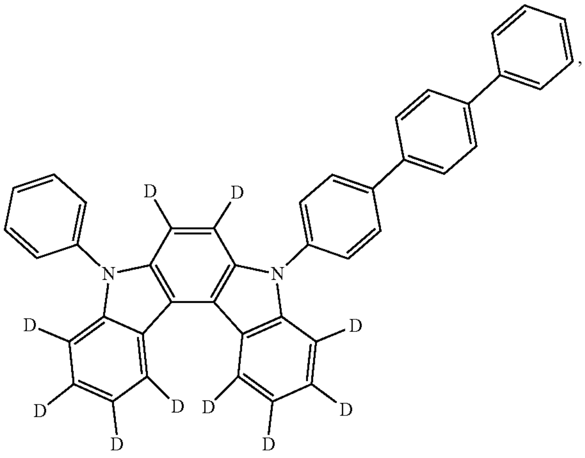
,
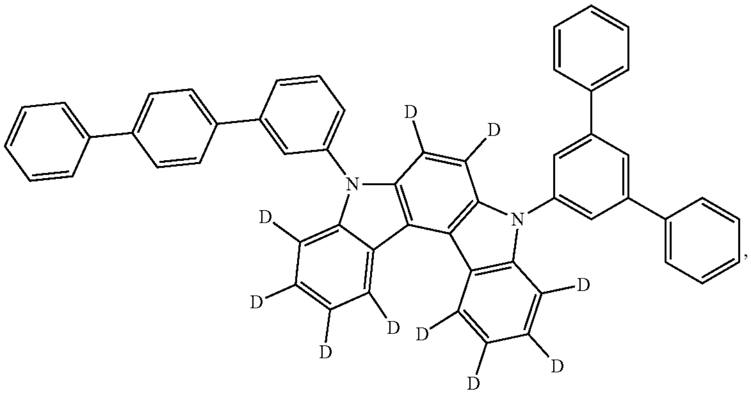
,
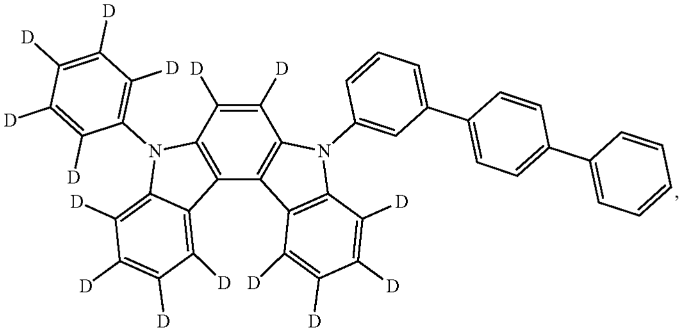
,
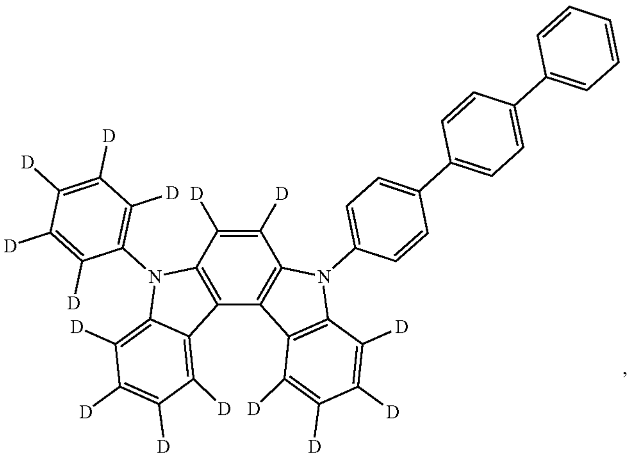
,

-continued
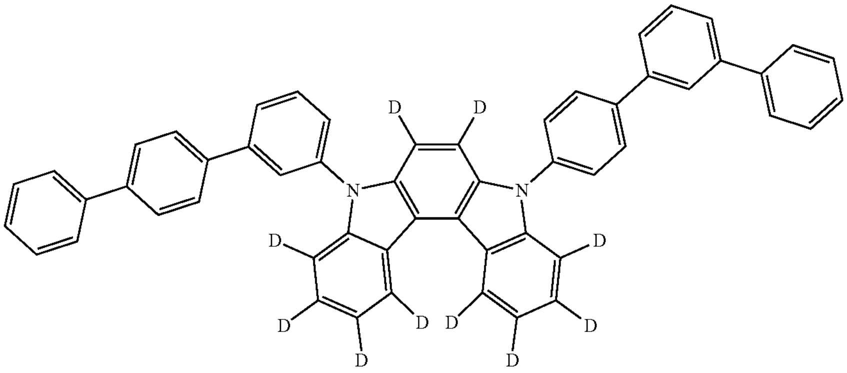
,
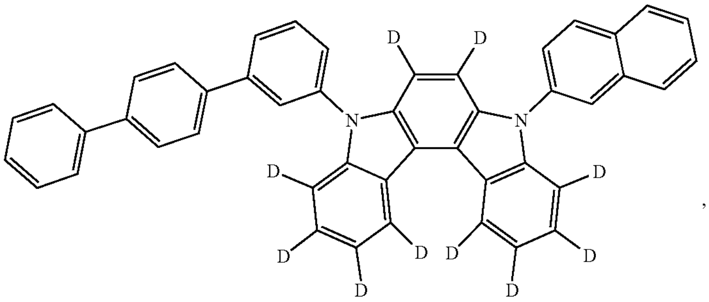
,
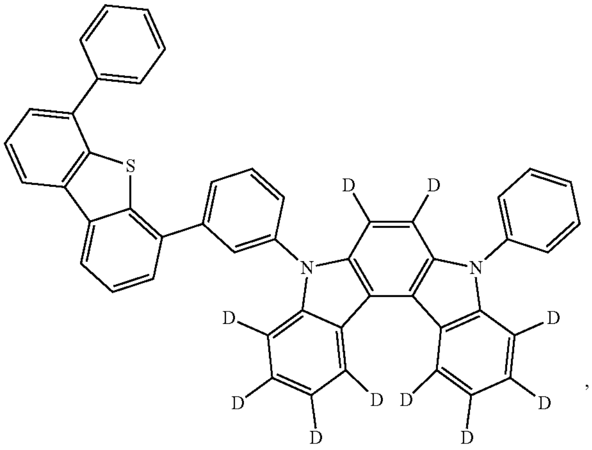
,
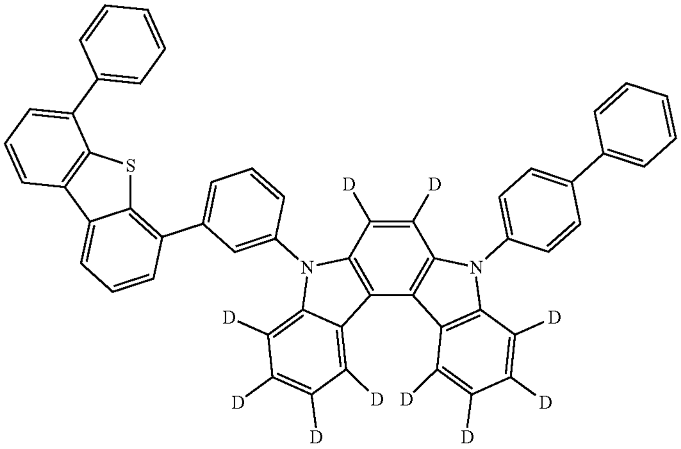
,

-continued
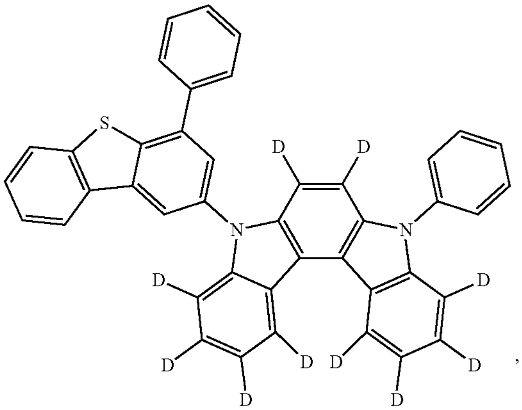
,
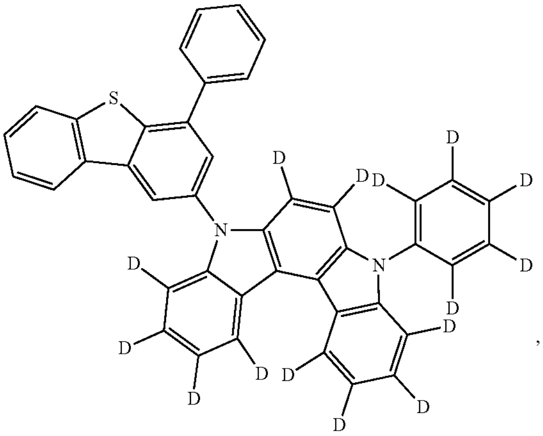
,
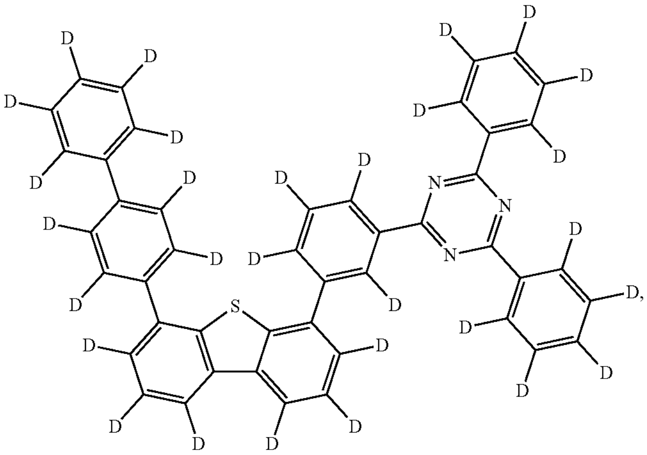
,
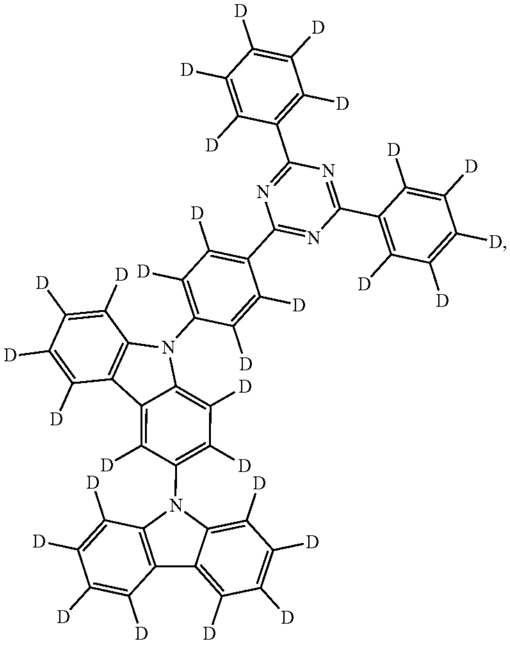
,
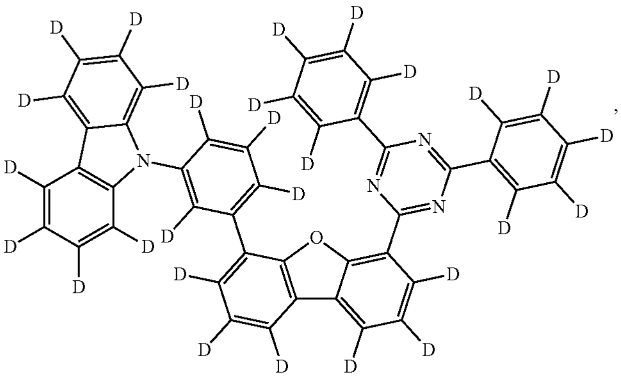
, -continued
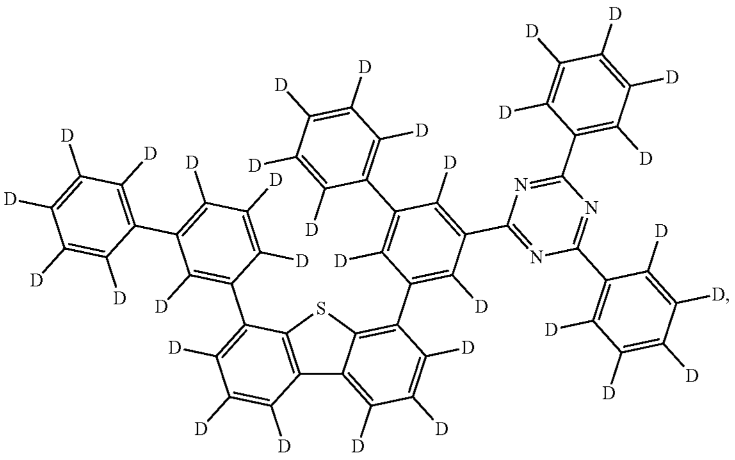
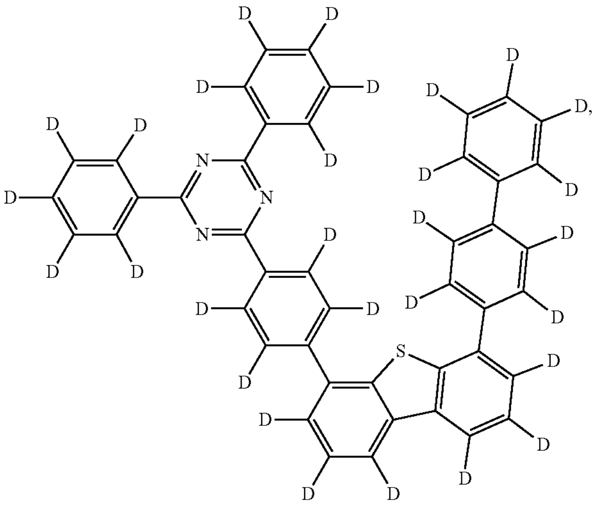
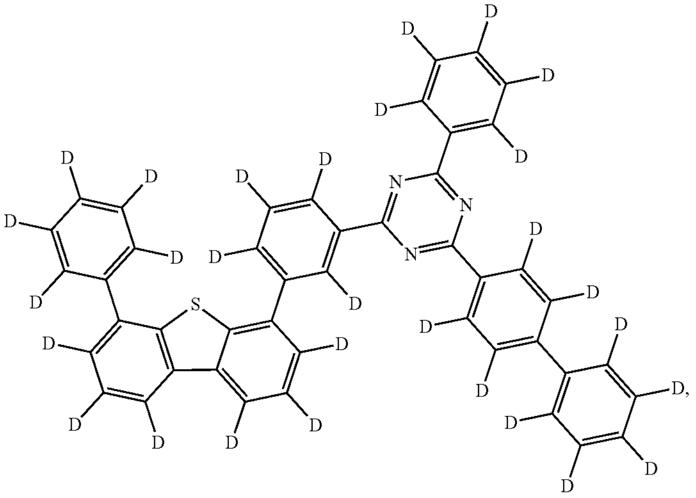

-continued
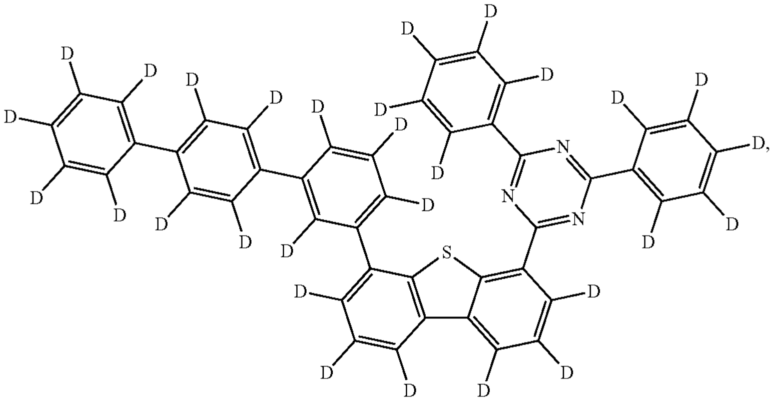
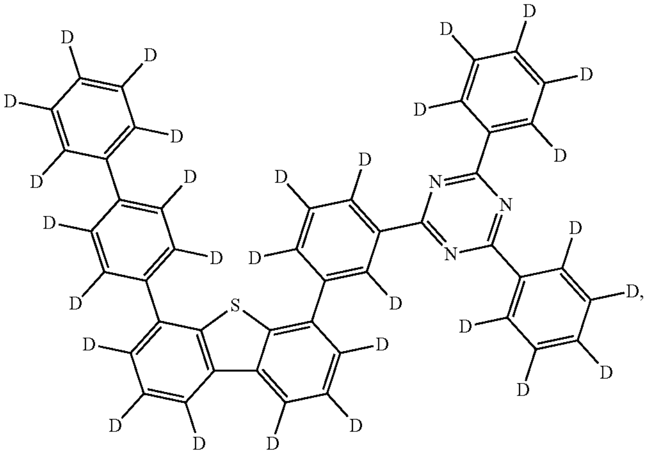
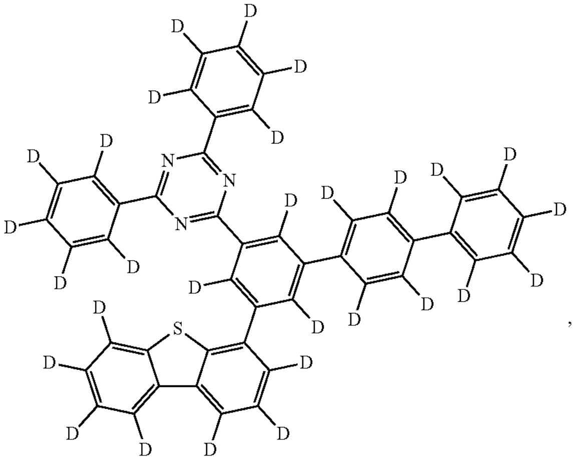
,
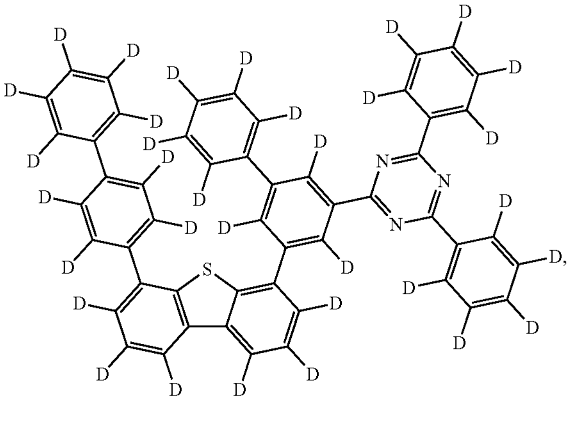

-continued
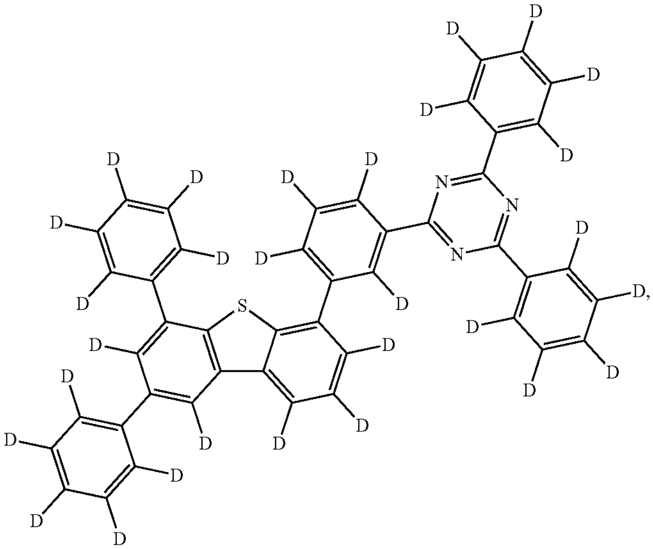
,
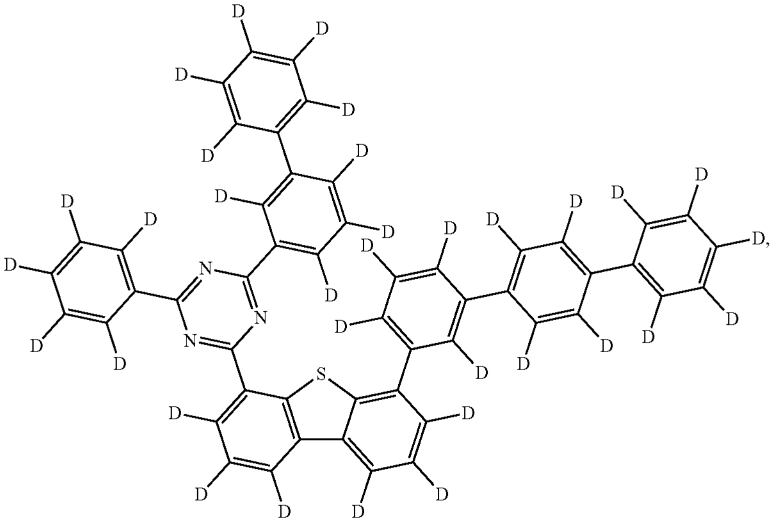
,
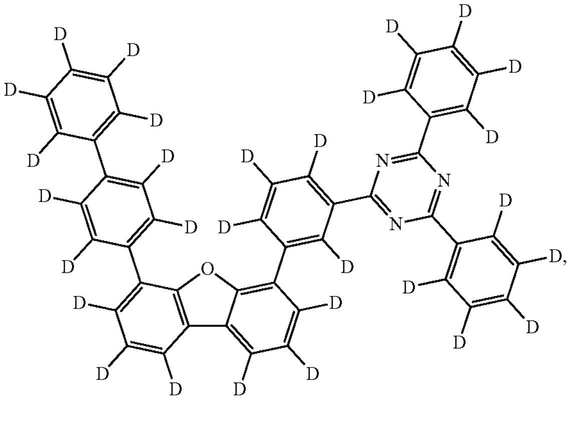
,
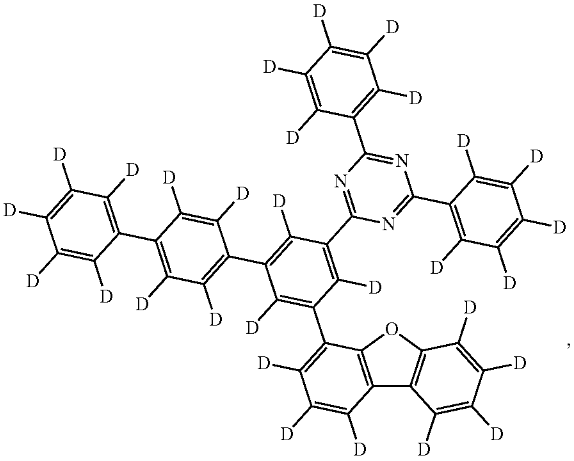
,

-continued
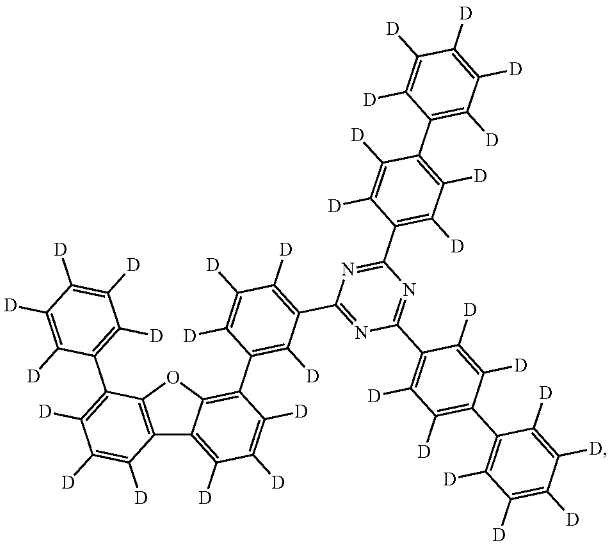
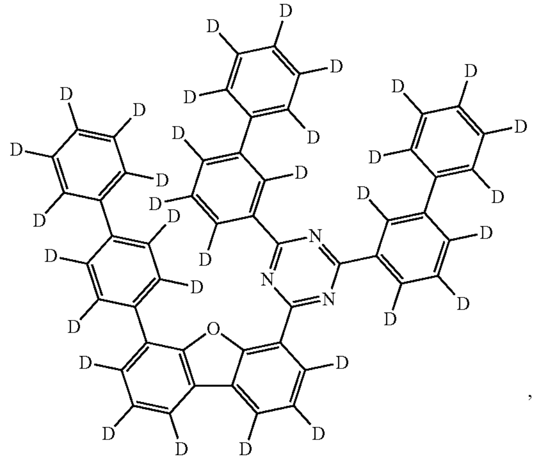
,
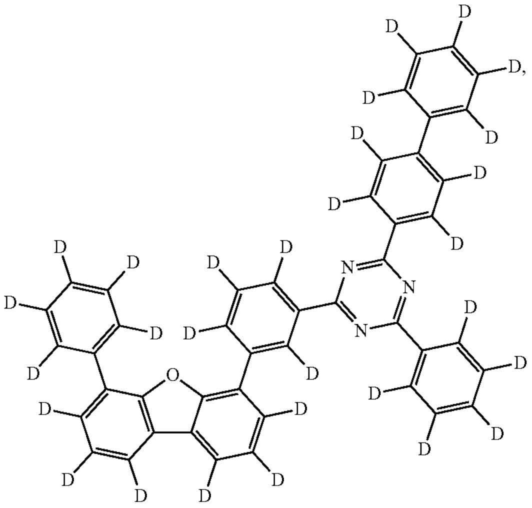
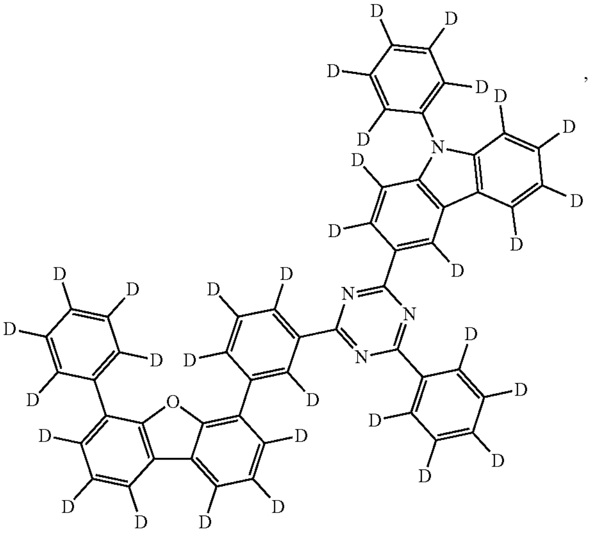
,
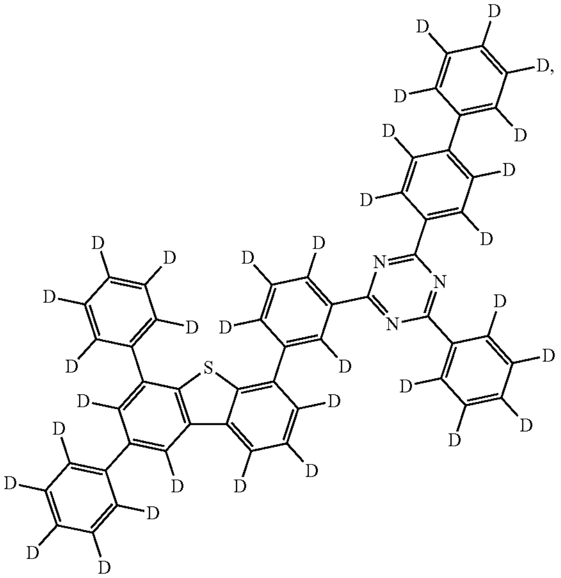
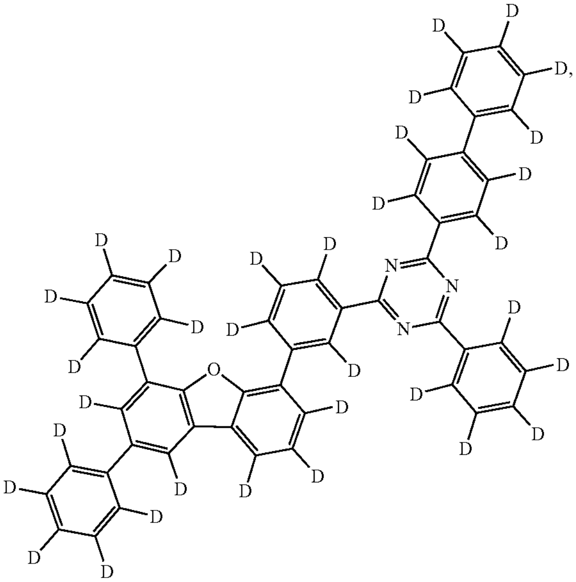

-continued
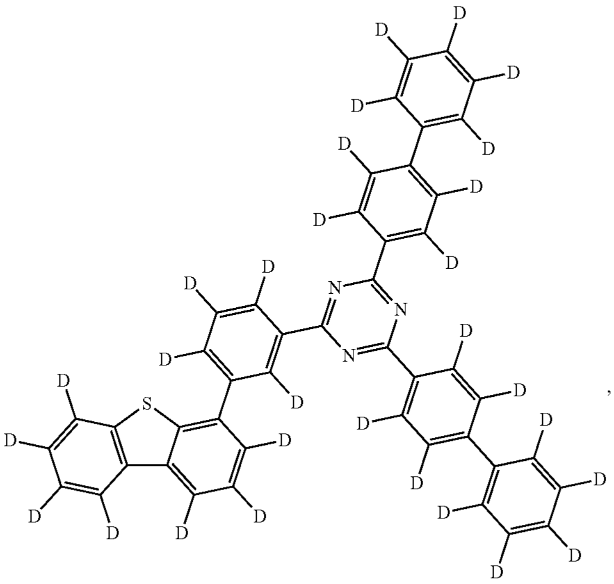
,
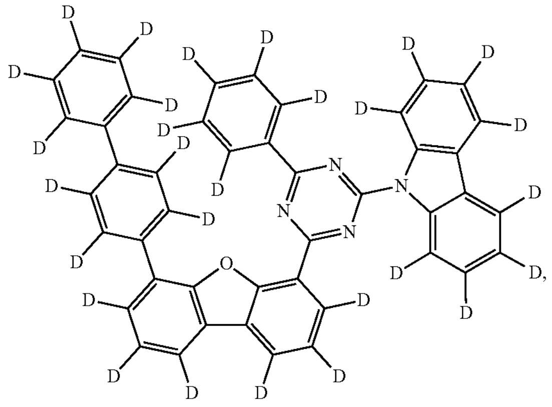
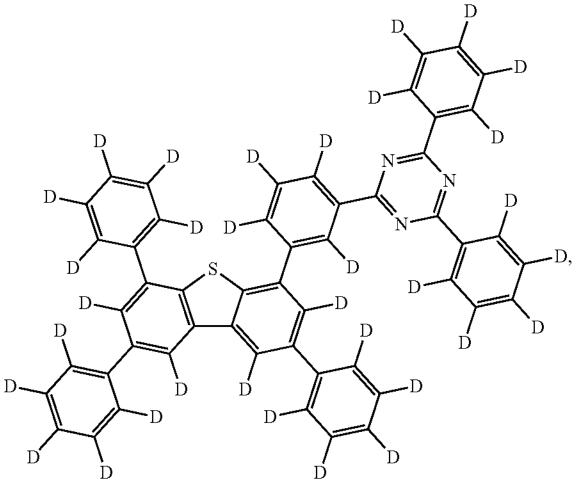
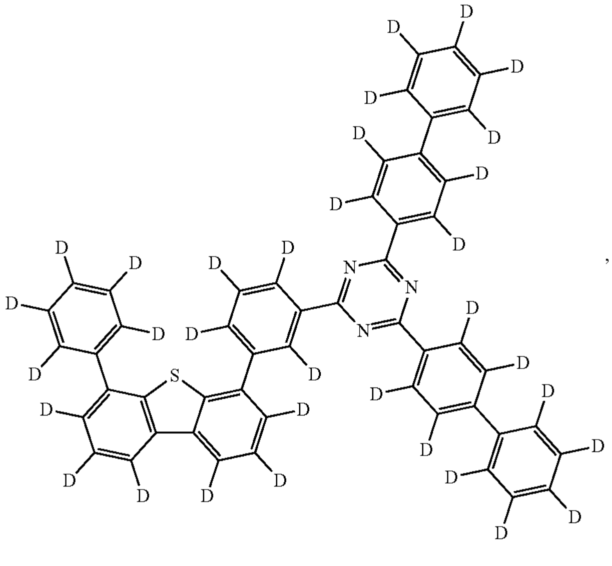
,
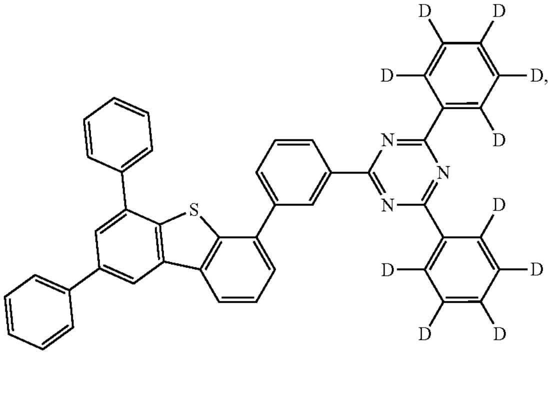
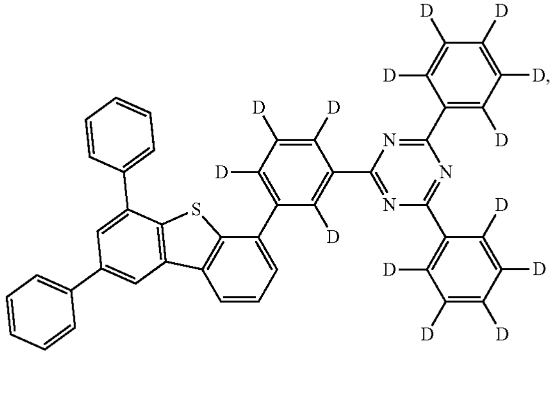

-continued
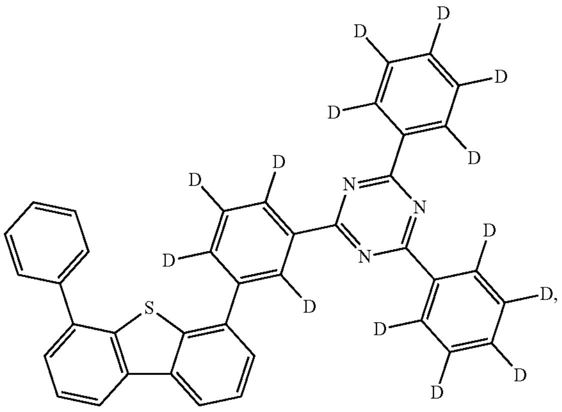
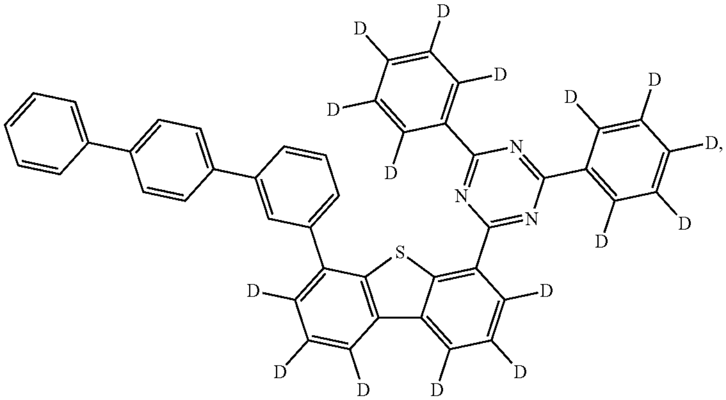
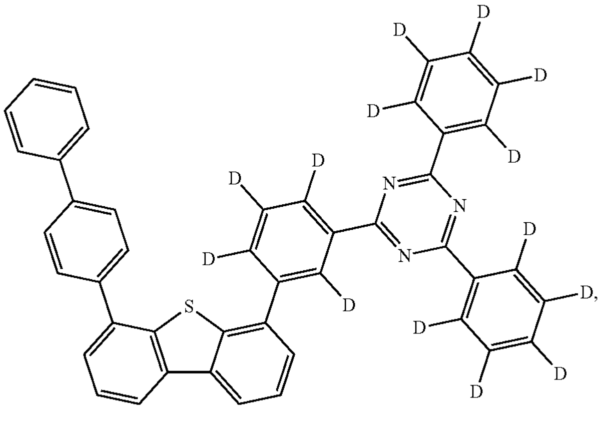
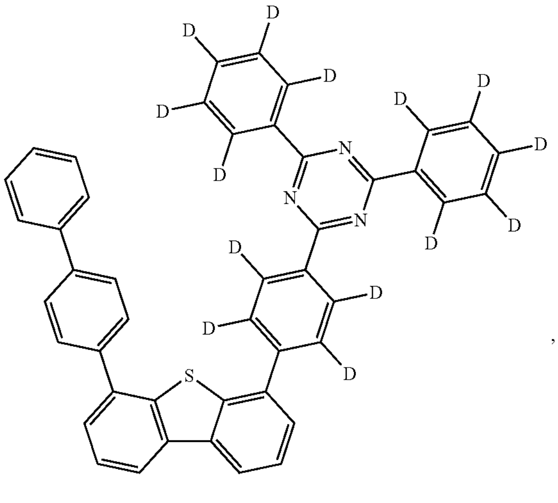
,

-continued
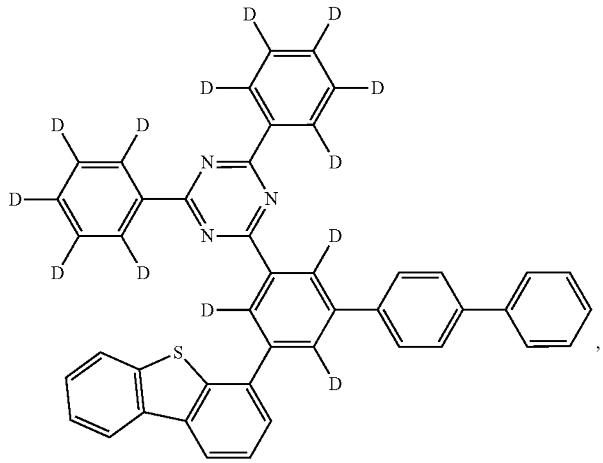
,
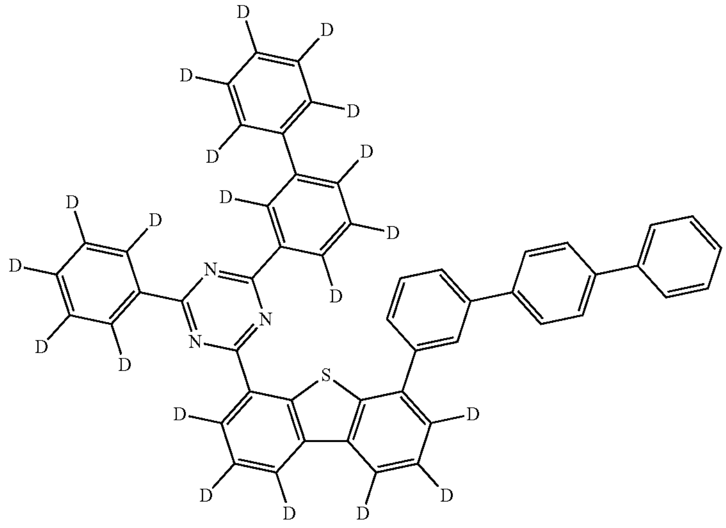
,
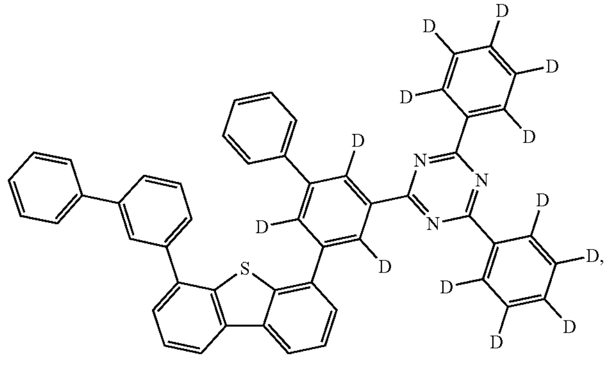
,
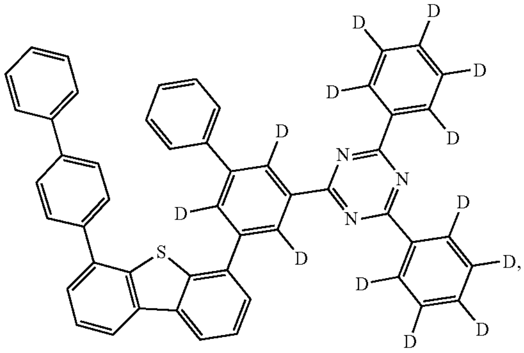
,

-continued
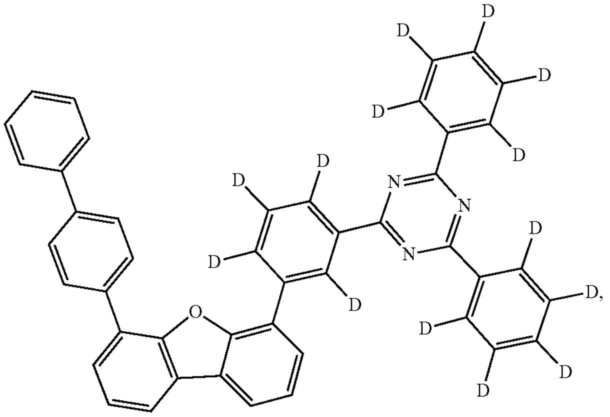
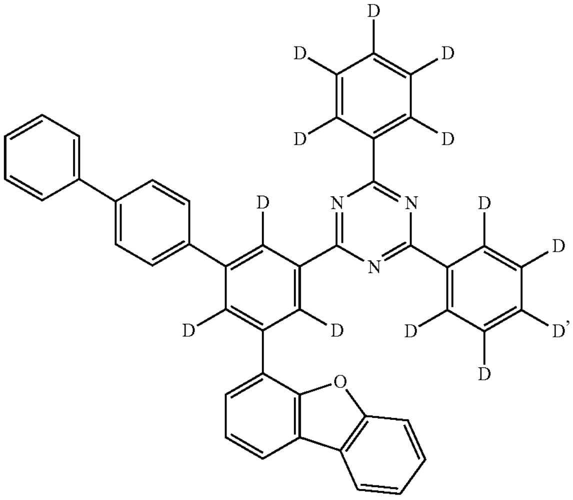
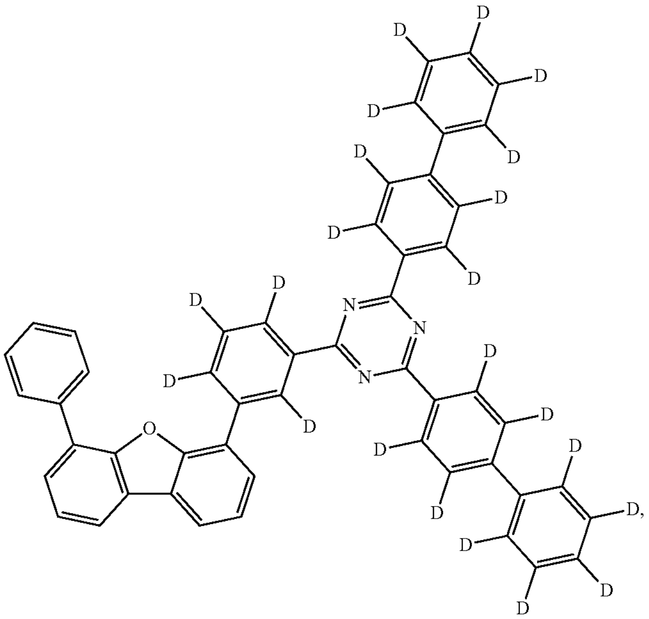
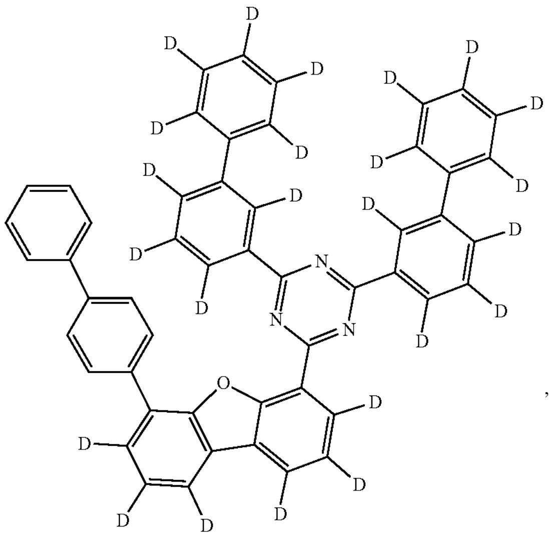
,
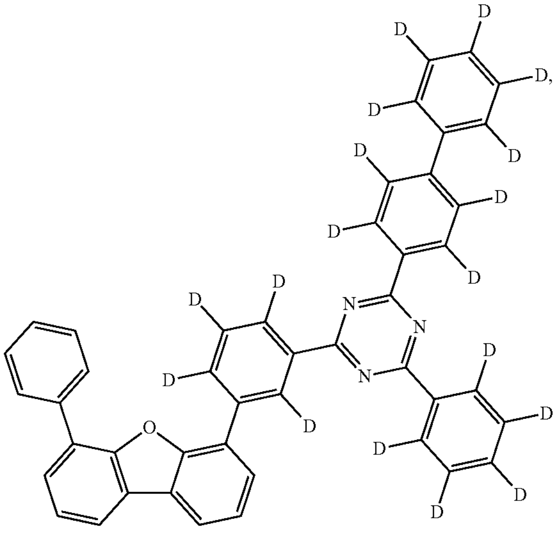
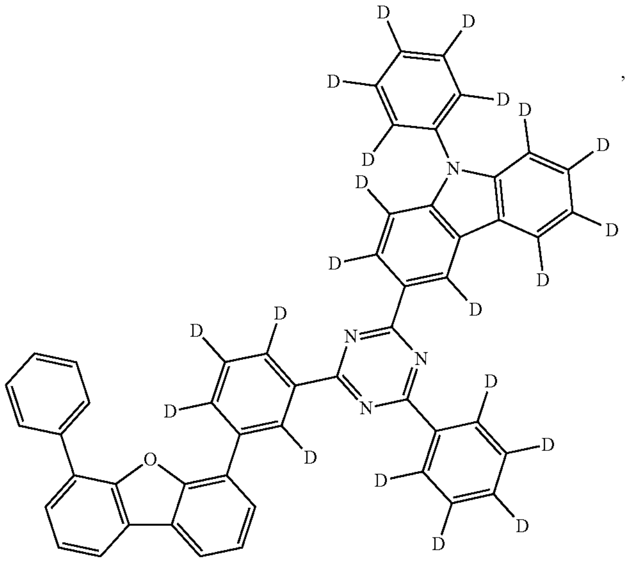
, -continued
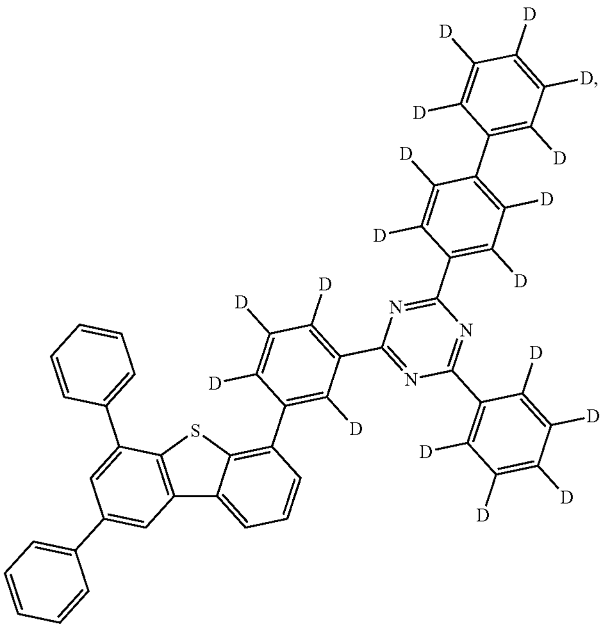
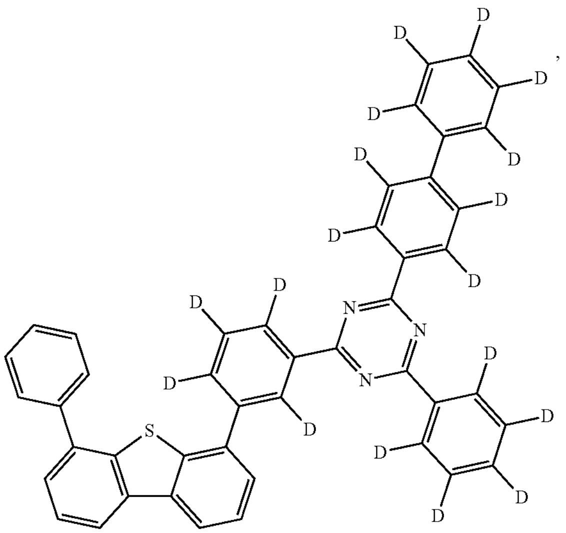
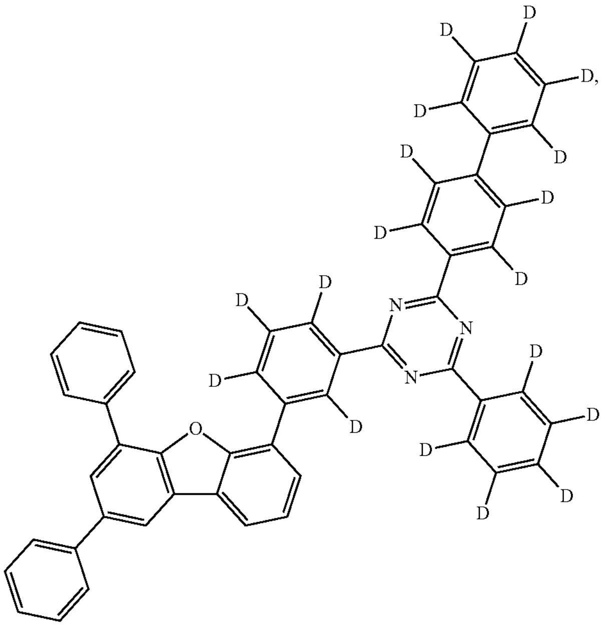

-continued
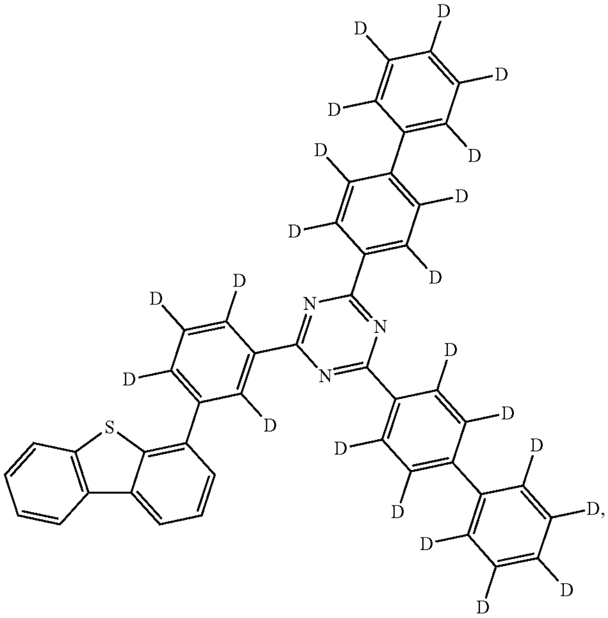
,
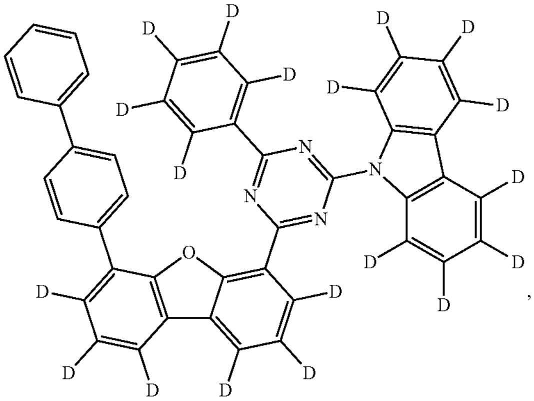
,
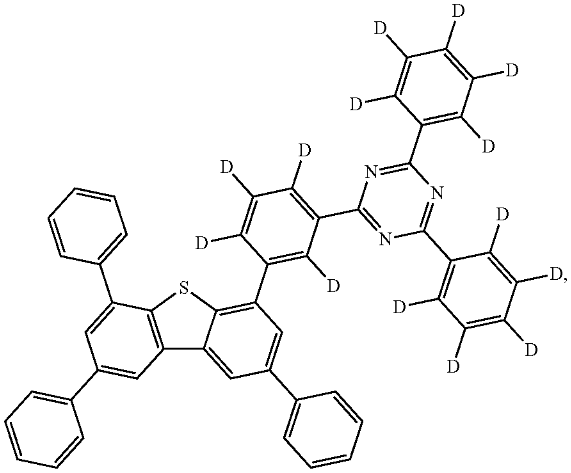
,
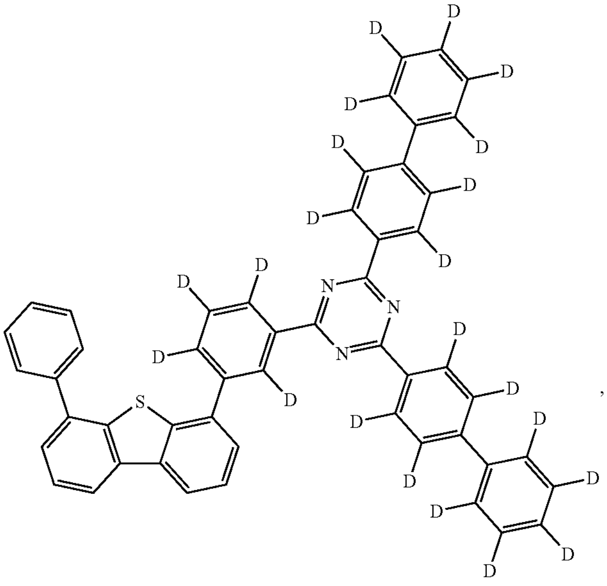
,
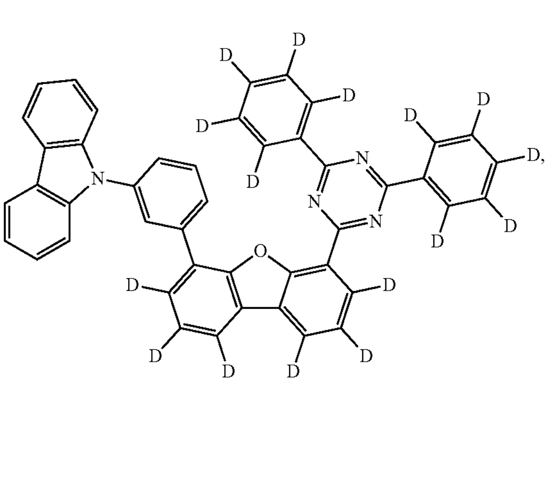
,
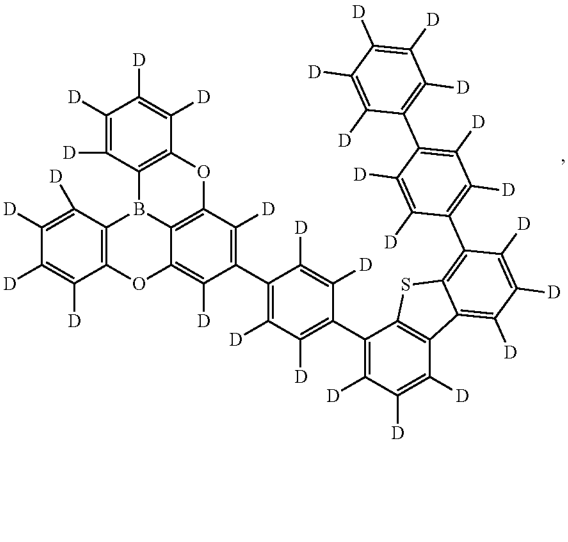
, -continued
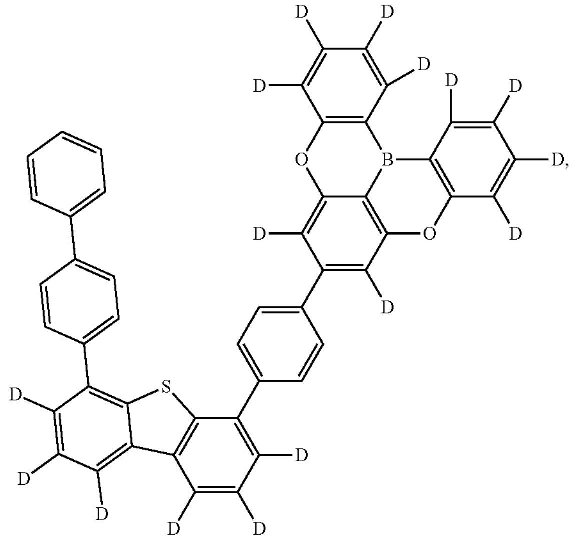
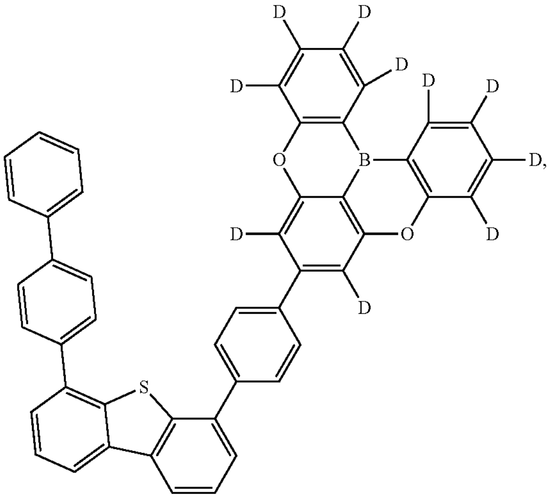
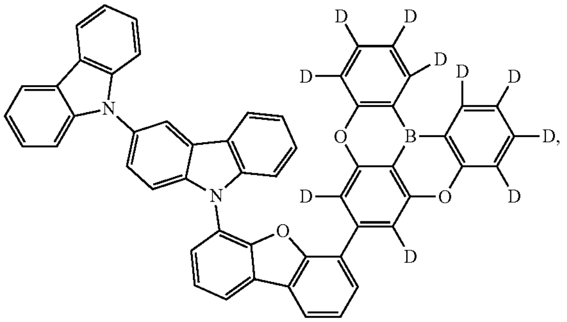
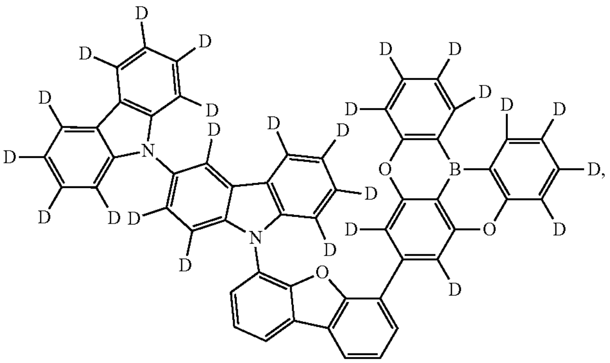
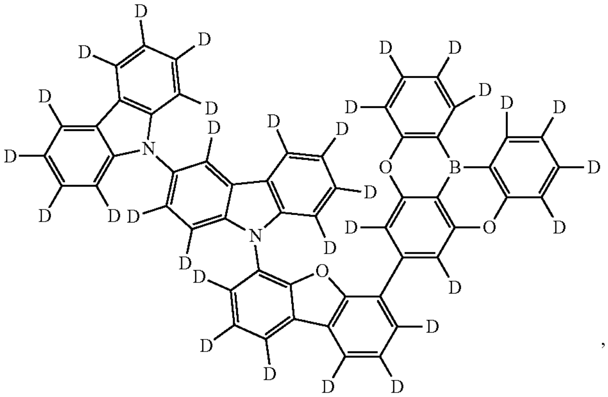
,
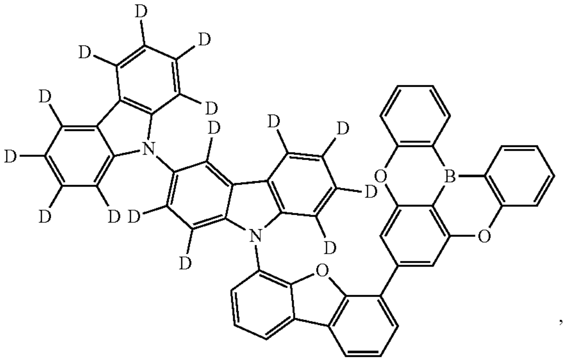
,
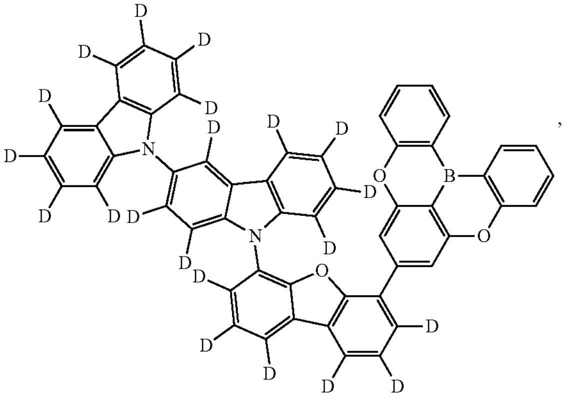
,
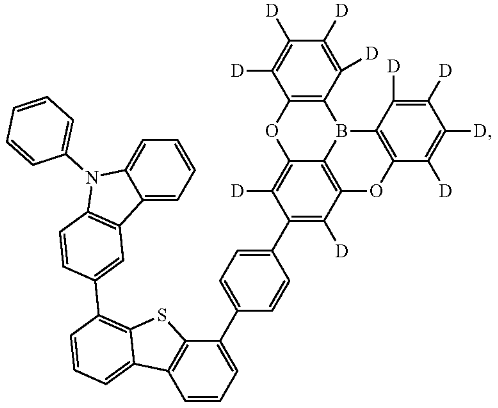

-continued
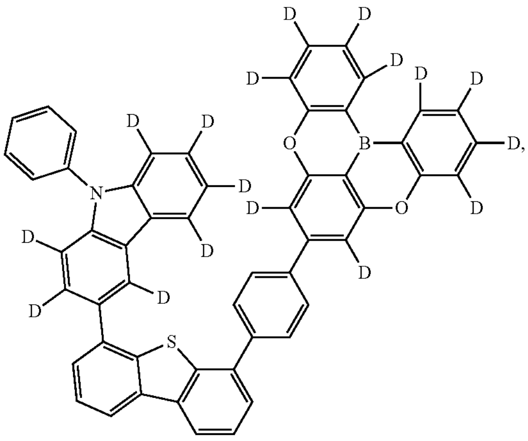
D,
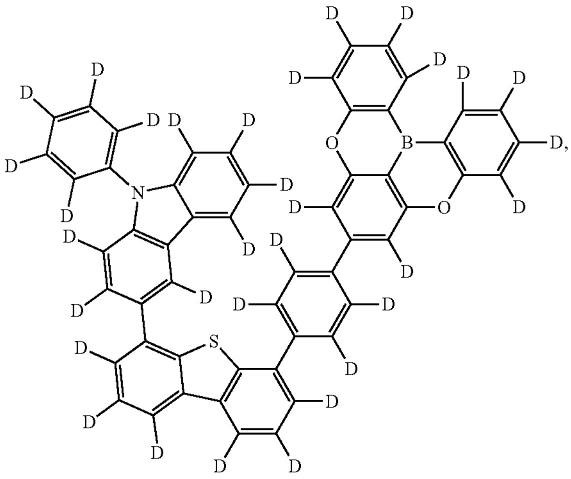
D,
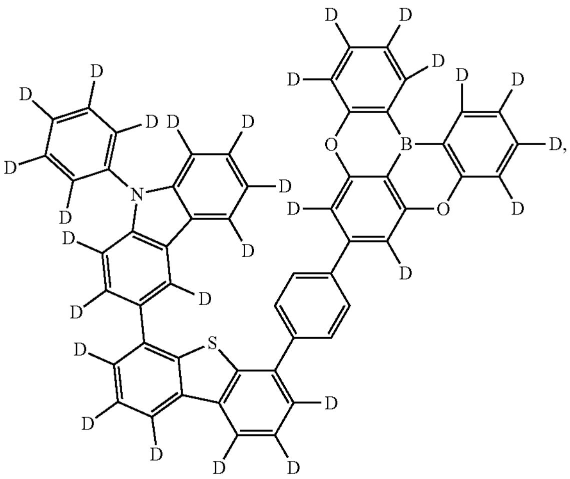
D,
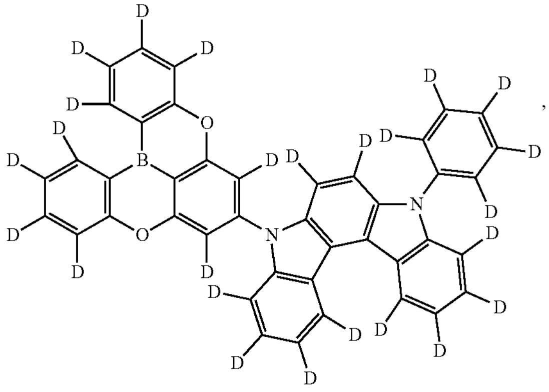
,
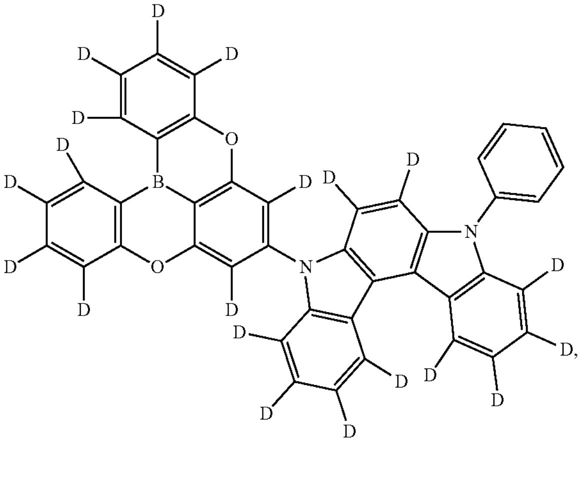
D, -continued
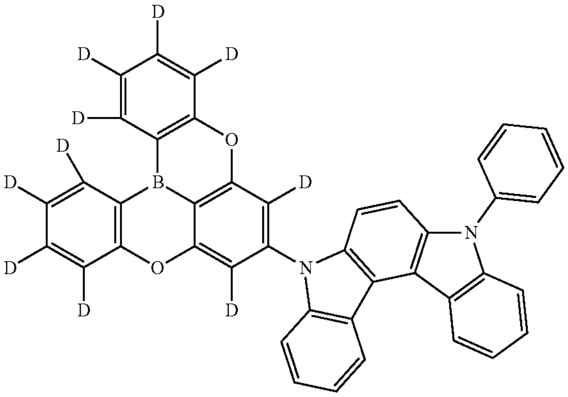
,
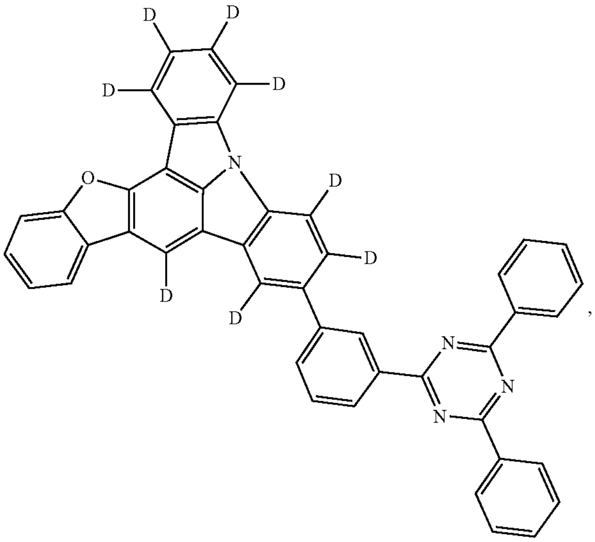
,
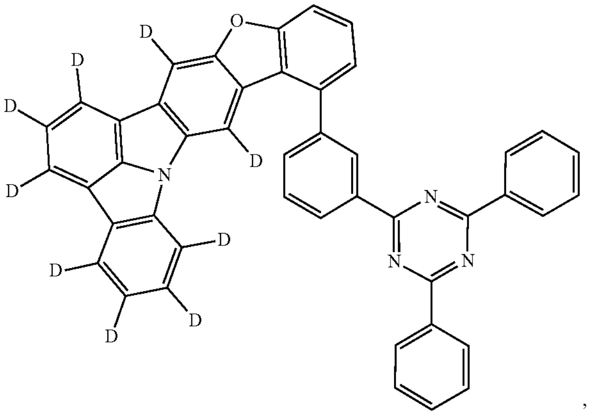
,
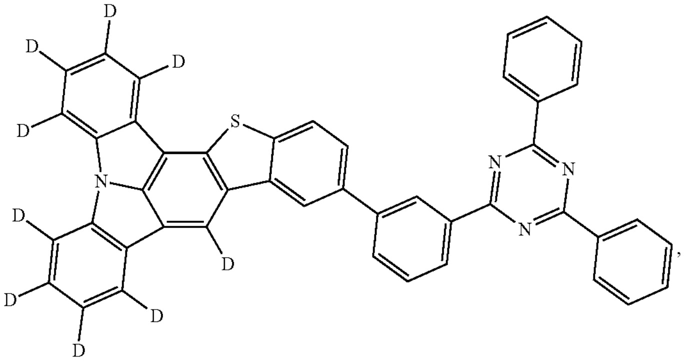
, -continued
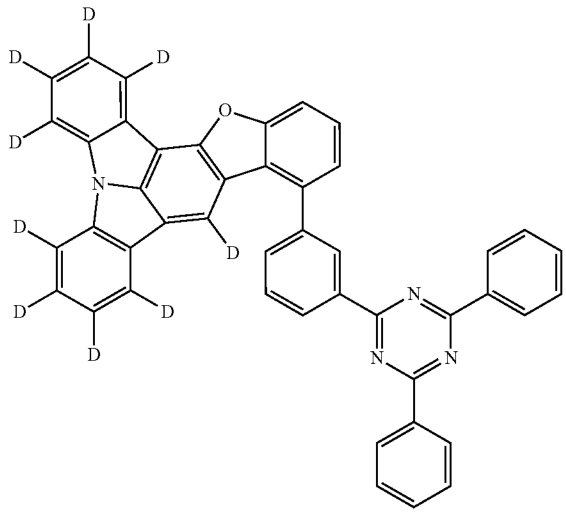
,
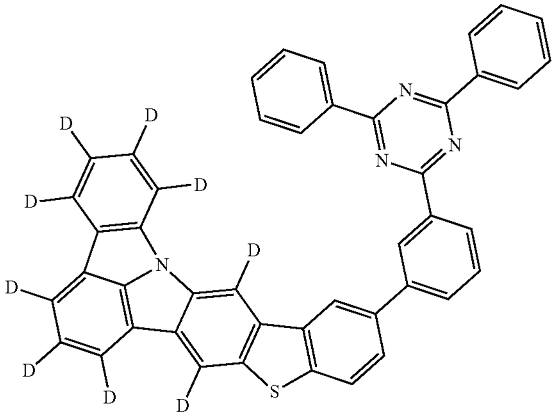
,
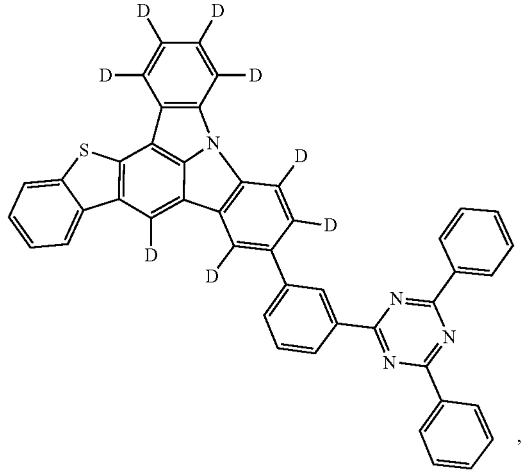
,
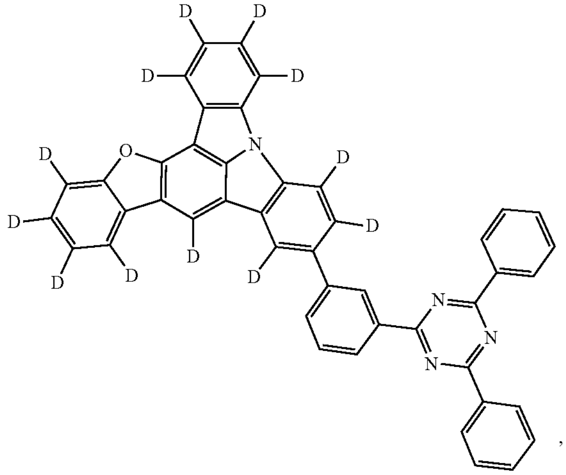
,
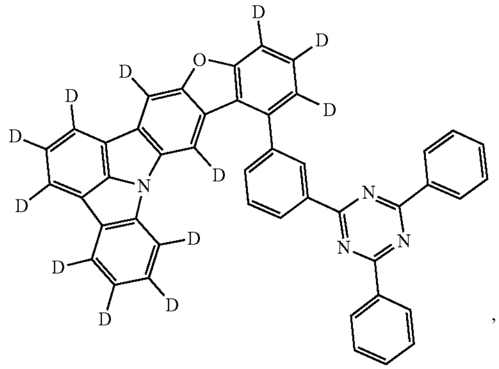
,
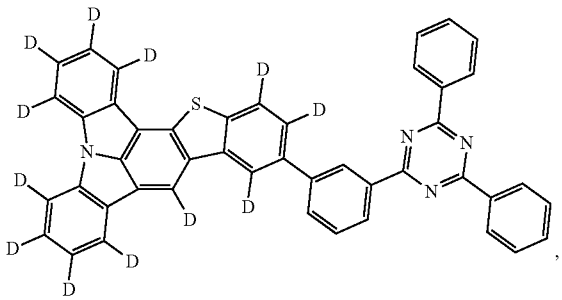
, -continued
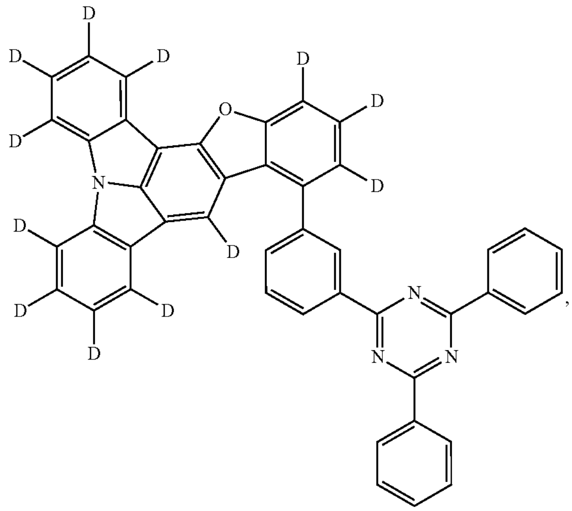
,
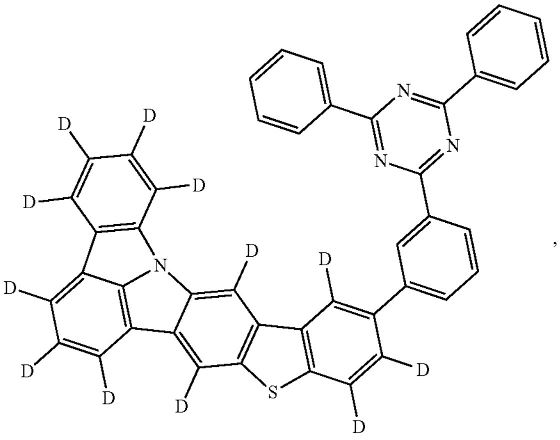
,
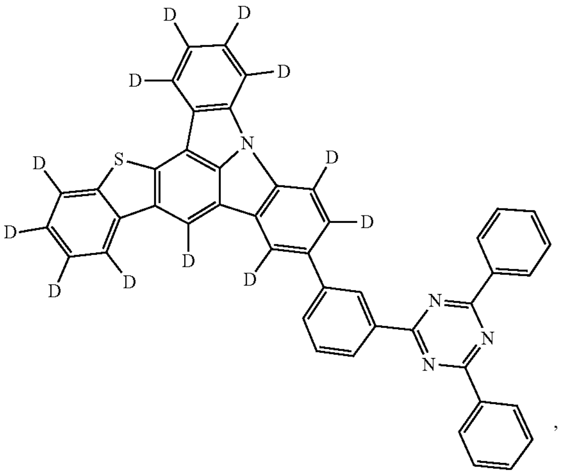
,
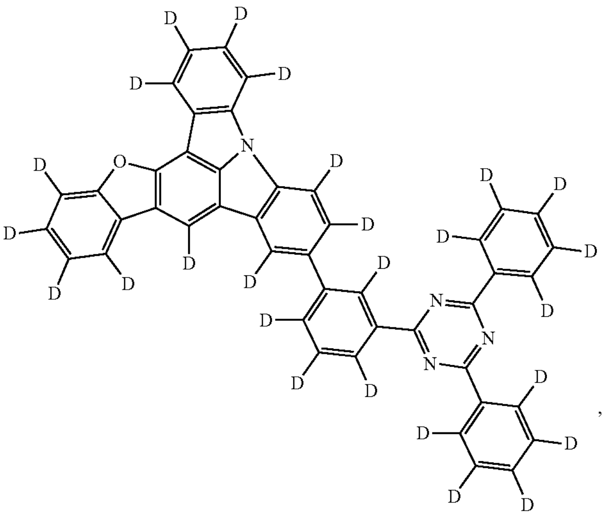
,
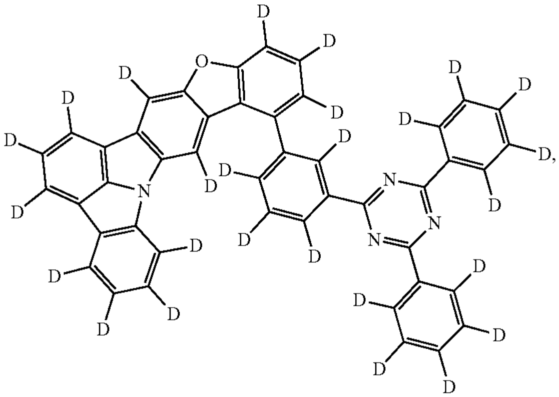
,
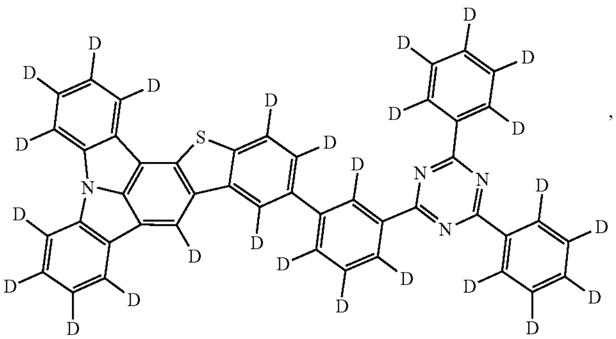
, -continued
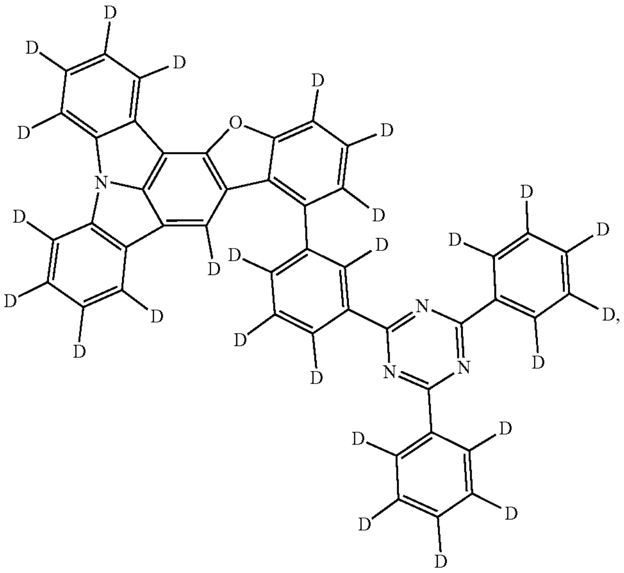
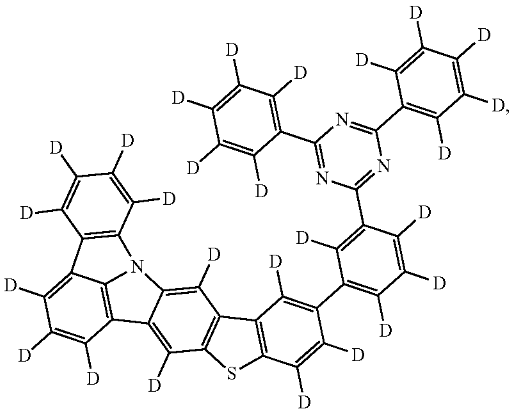
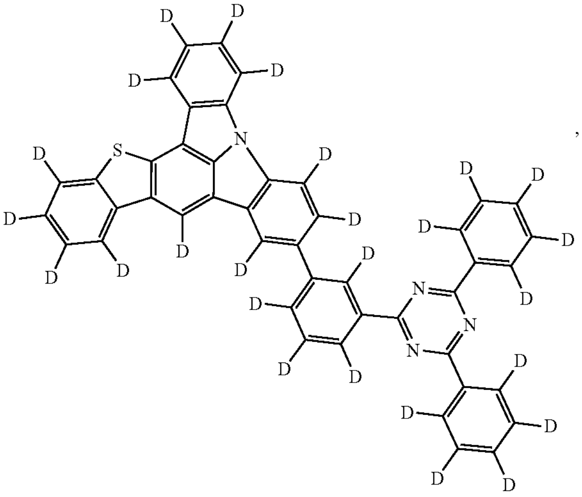
,
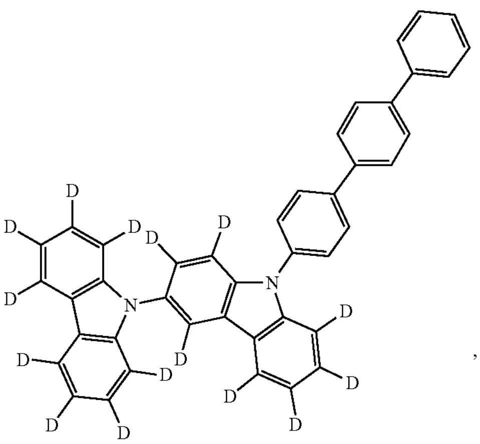
,
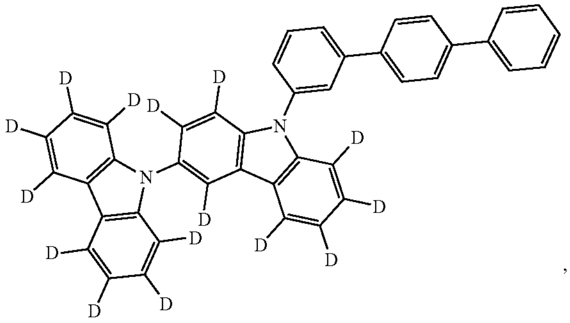
, -continued
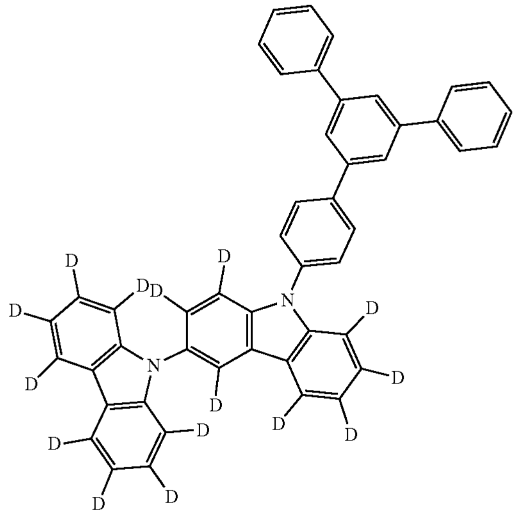
,
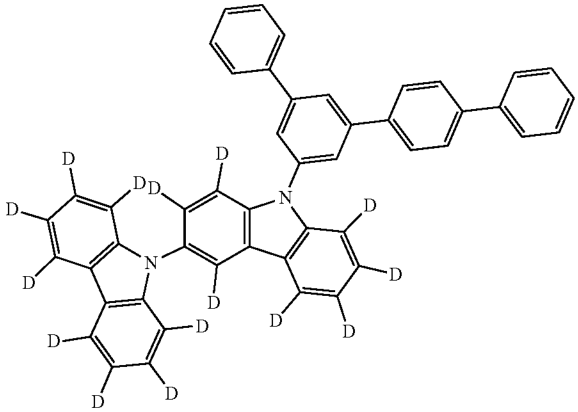
,
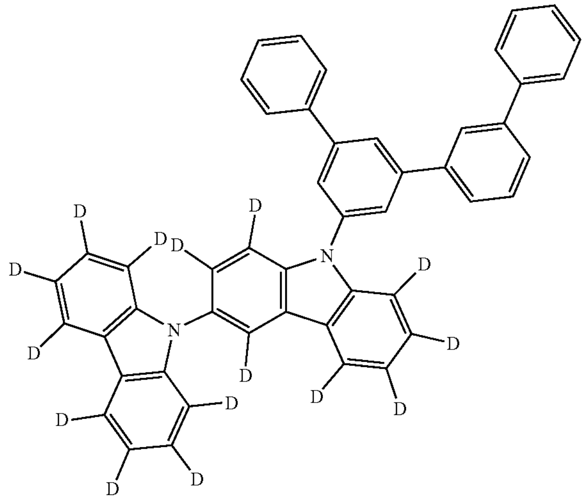
,
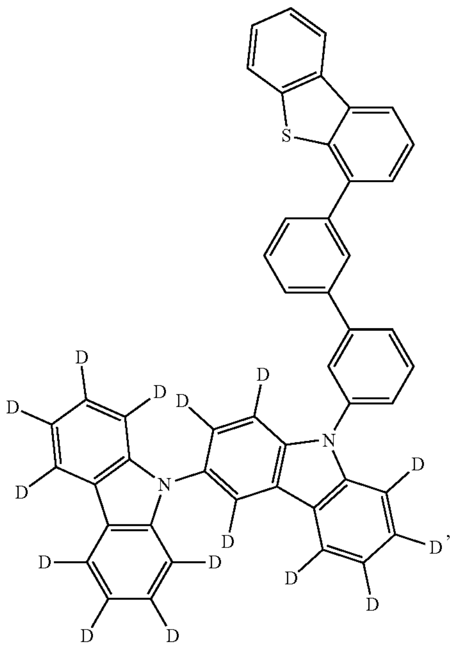
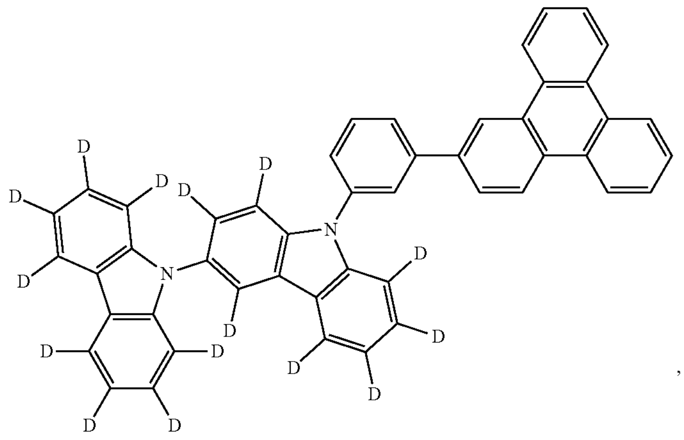
, -continued
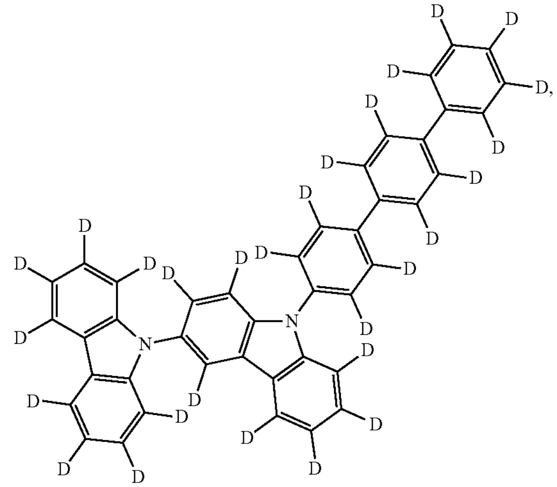
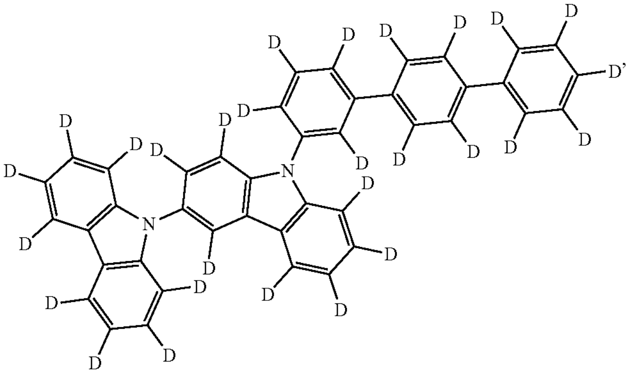
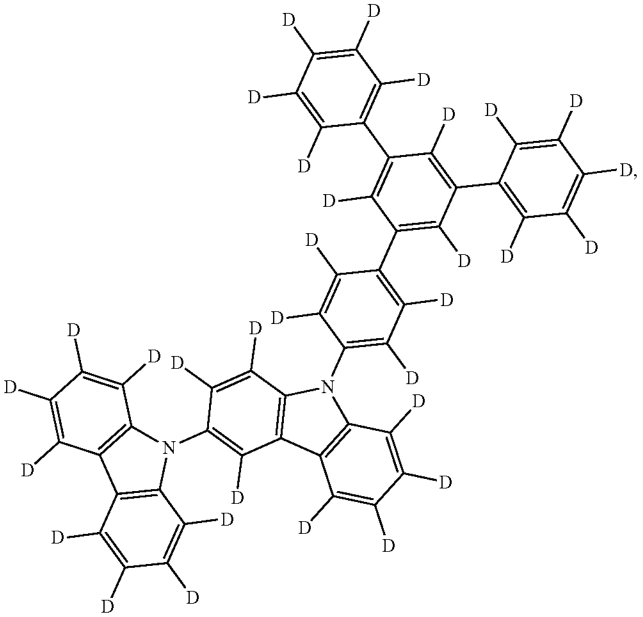
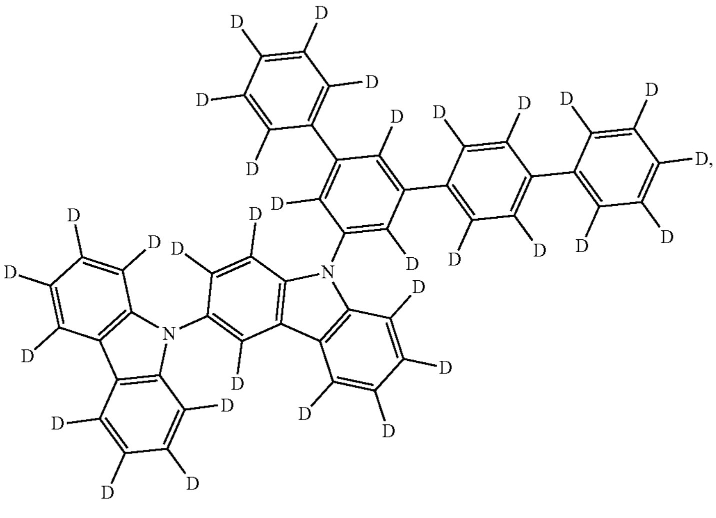

-continued
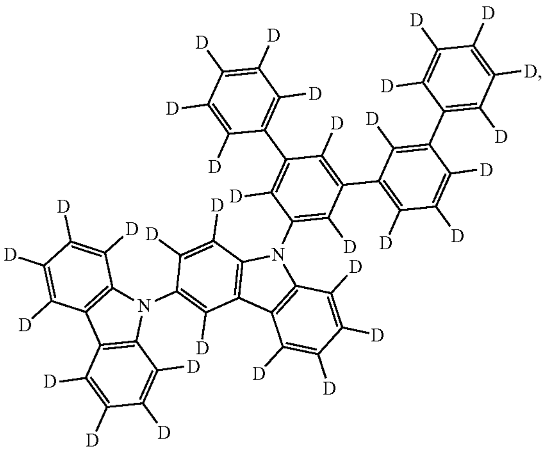
,
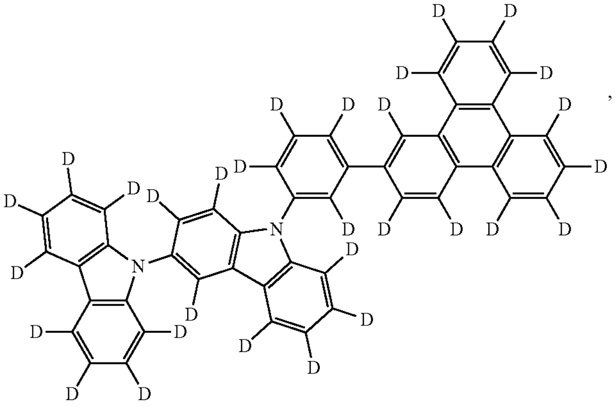
,
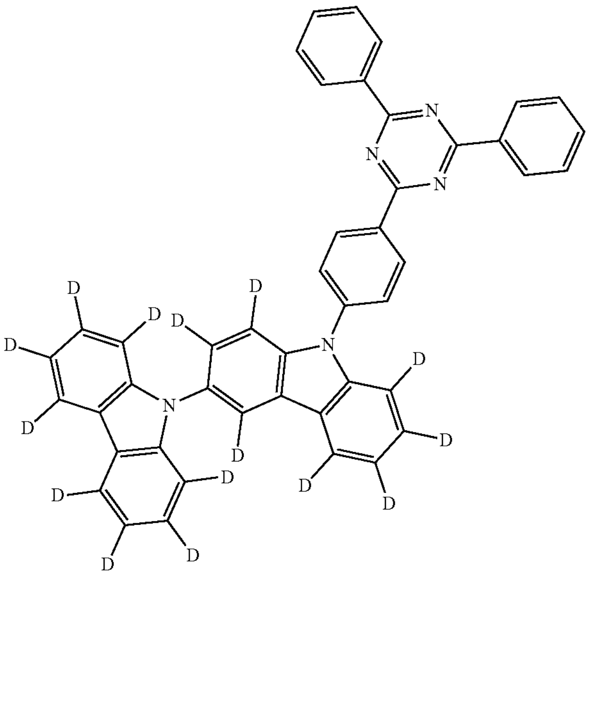
,

-continued
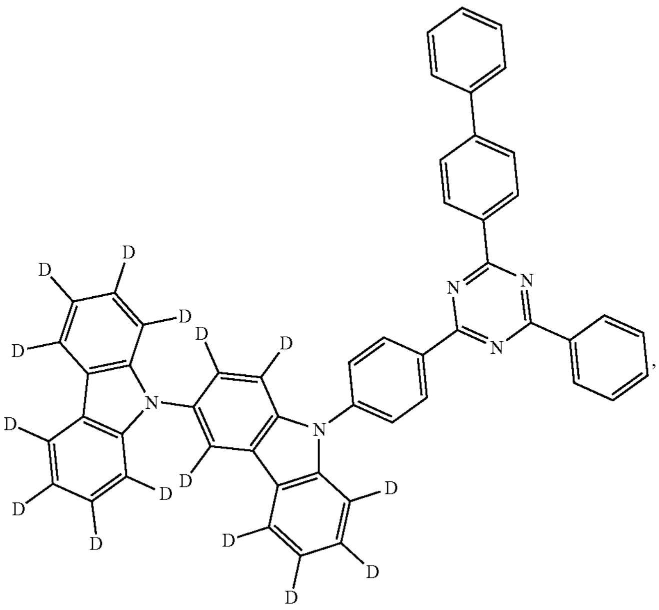,
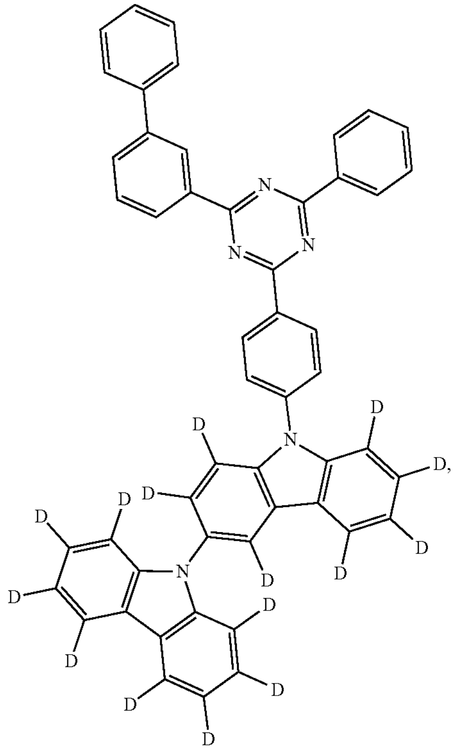,
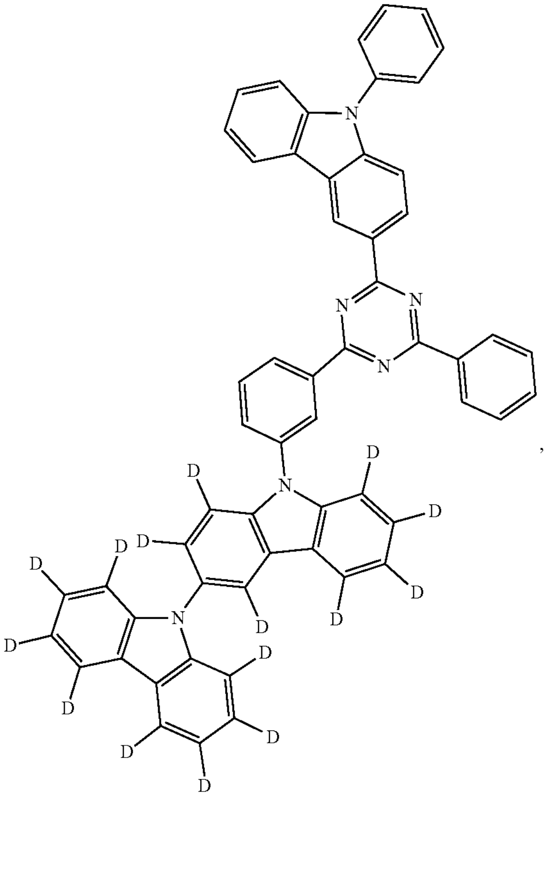,
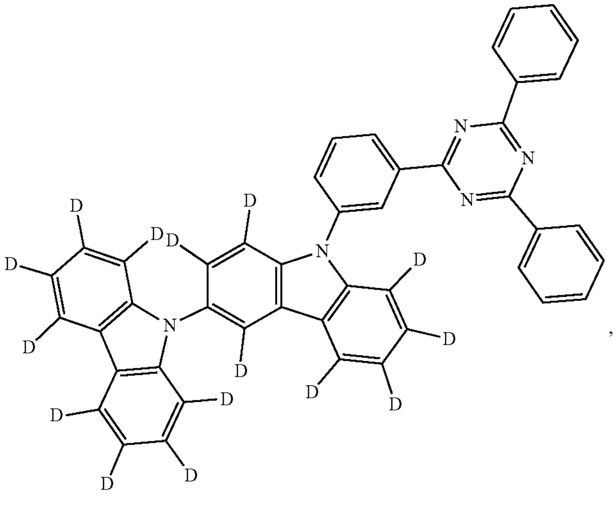,

-continued
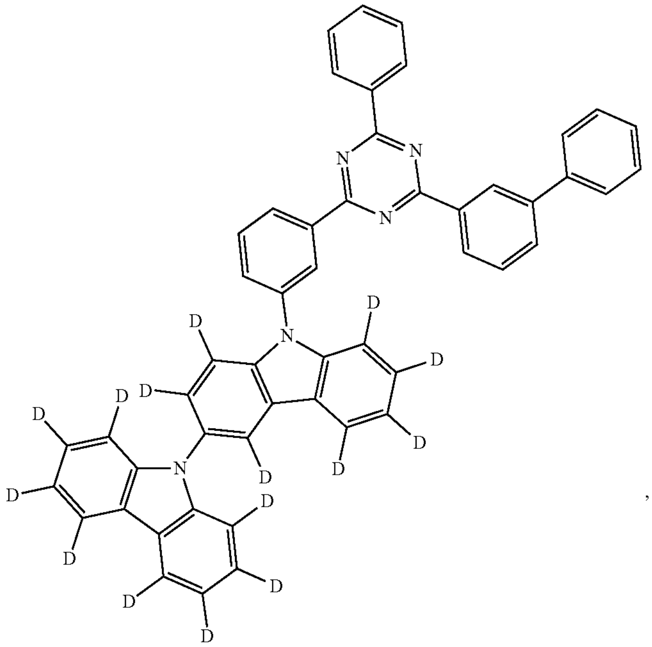
,
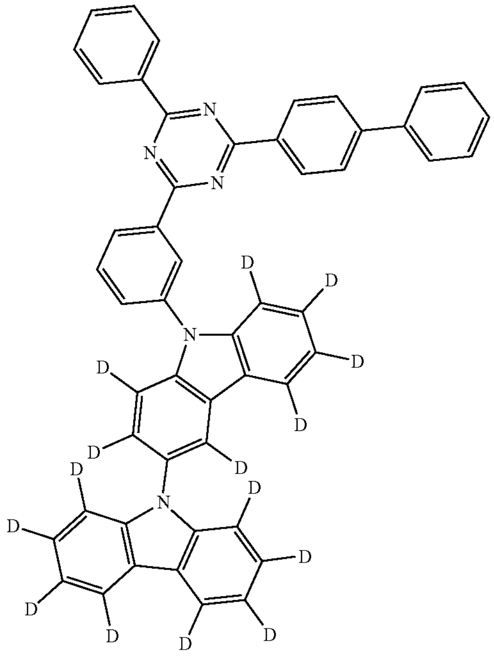
,
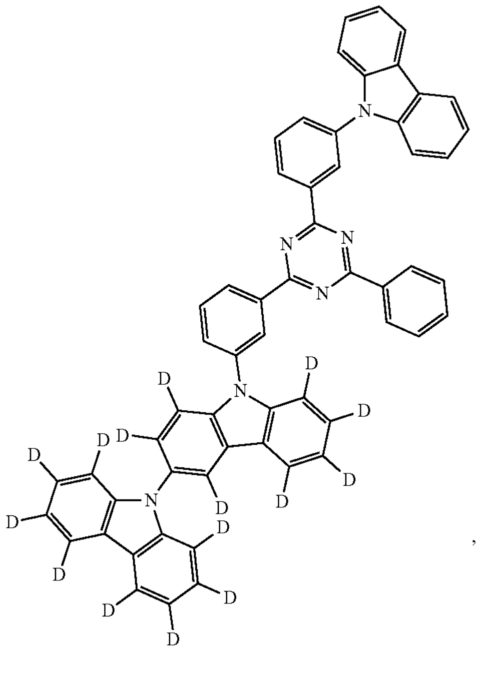
,

-continued
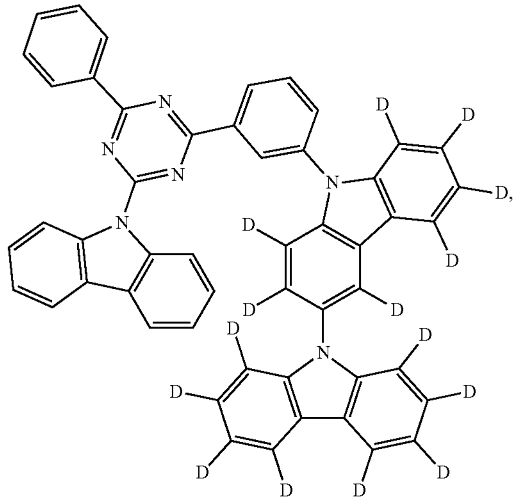
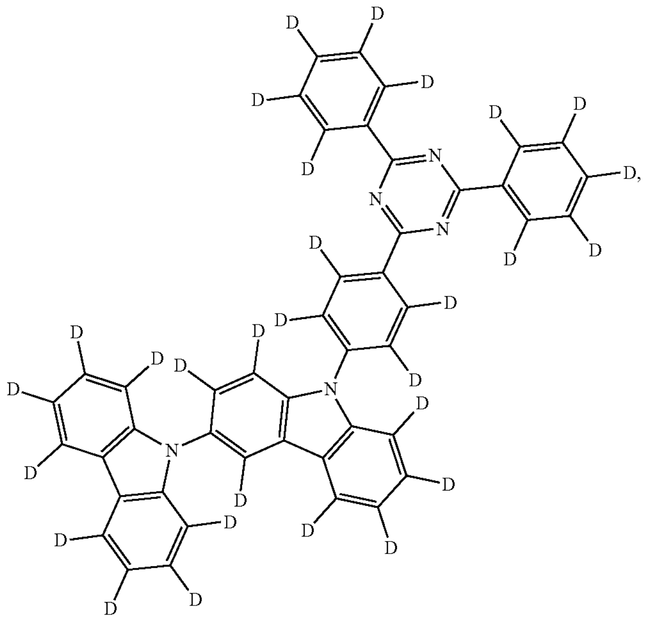
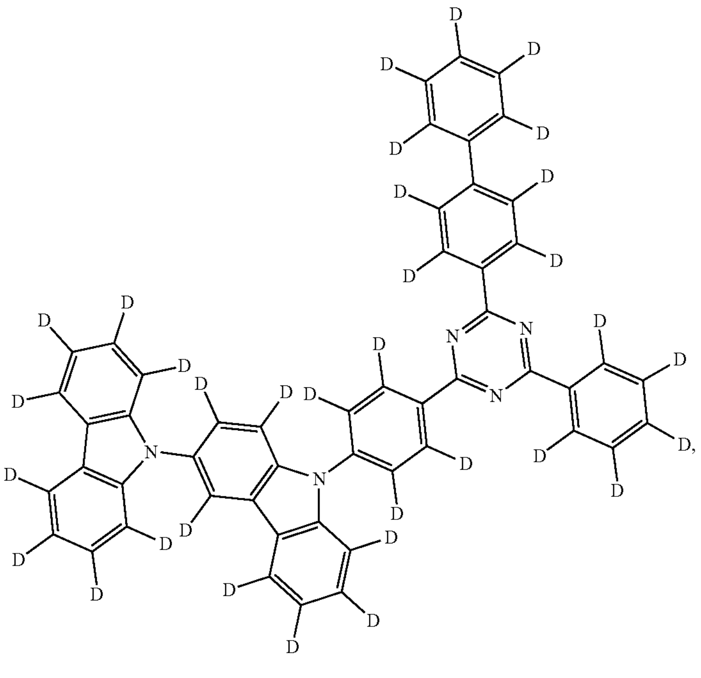

-continued
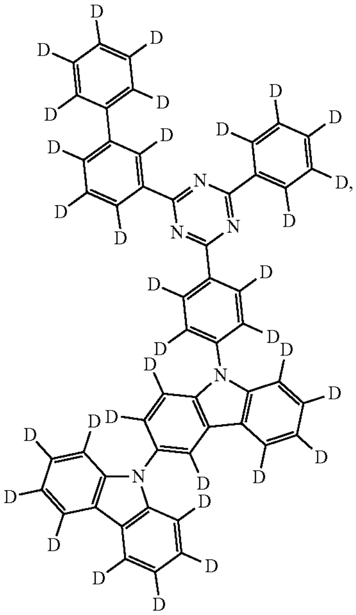
,
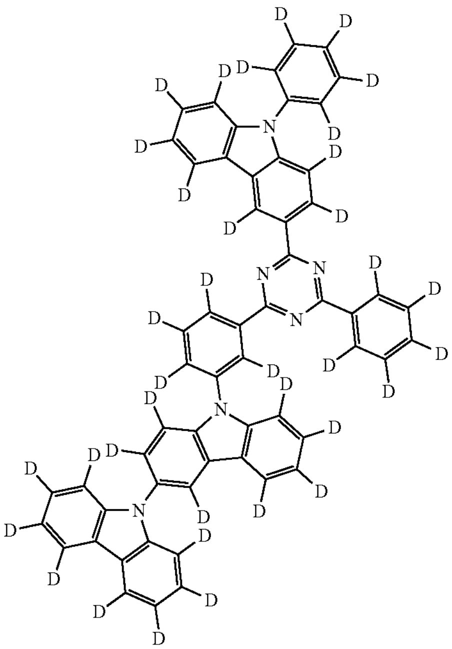
,
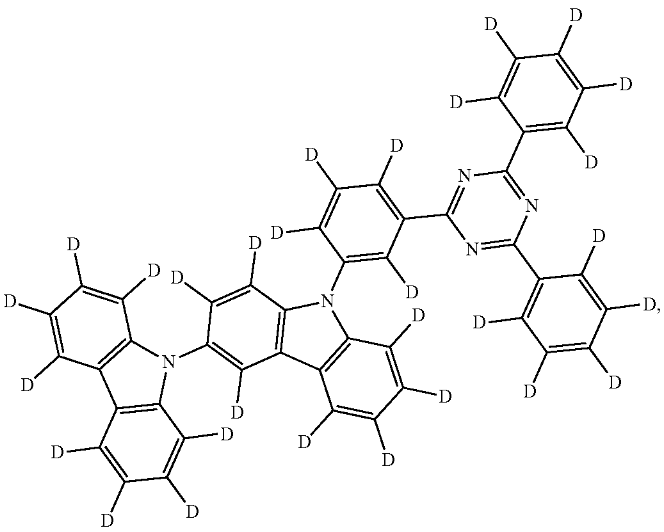
,

-continued
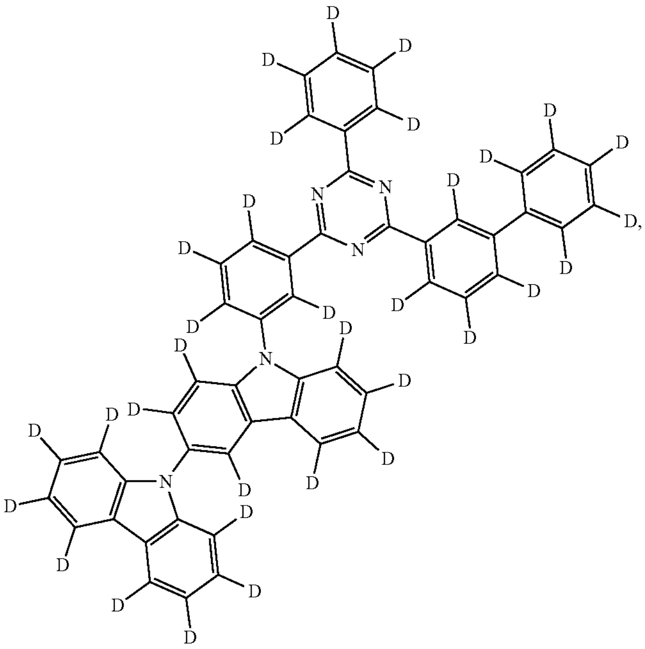,
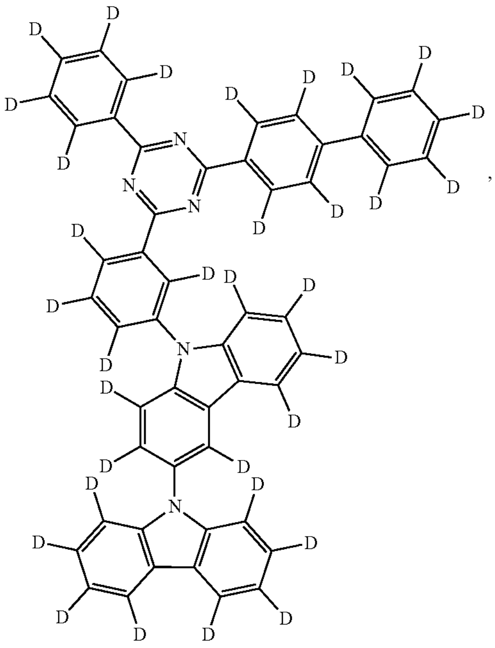,
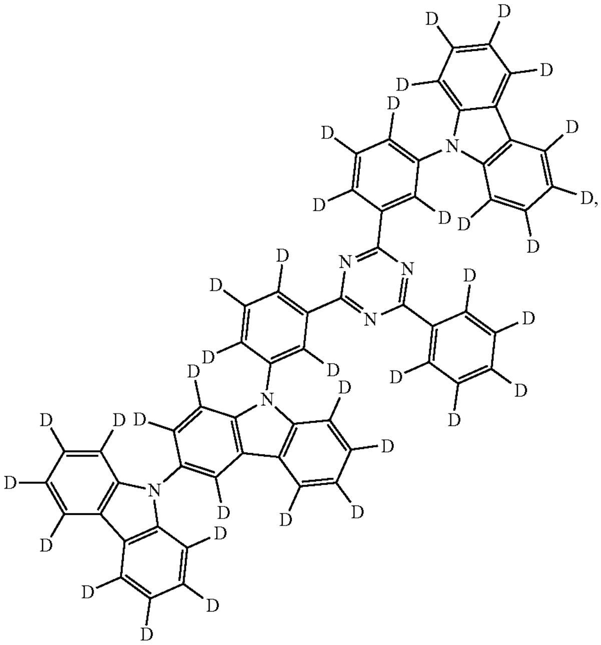,
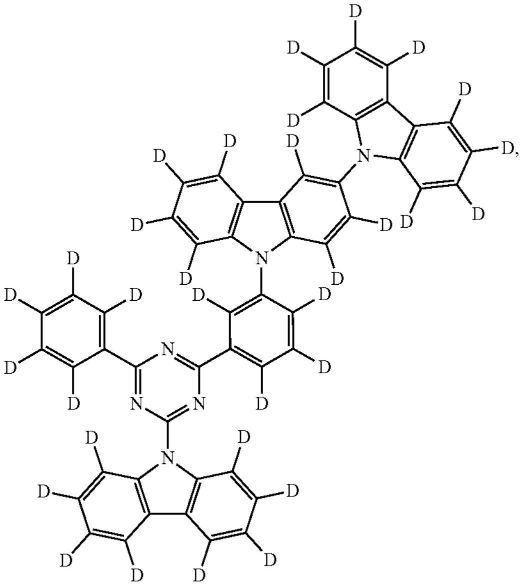,
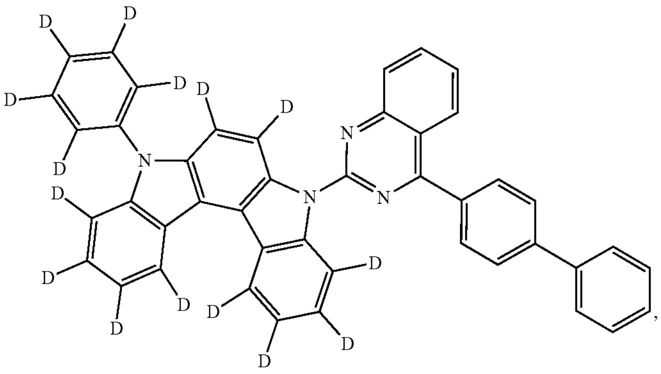,

-continued
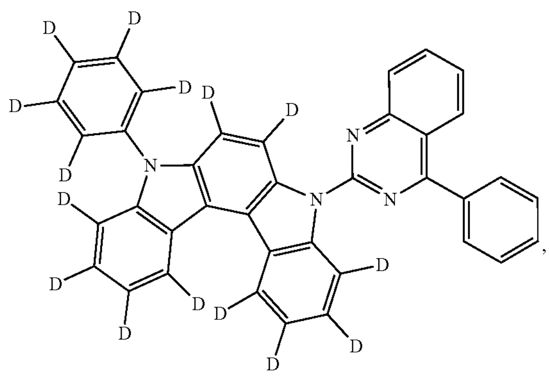,
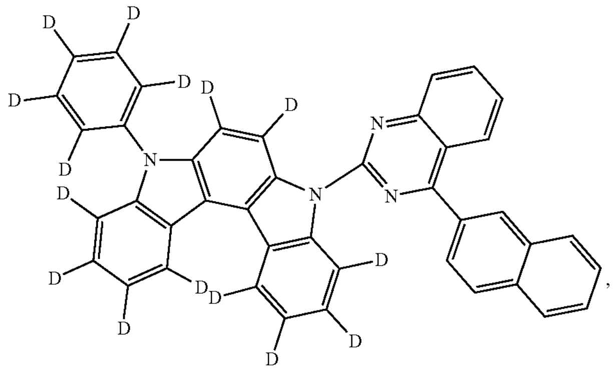,
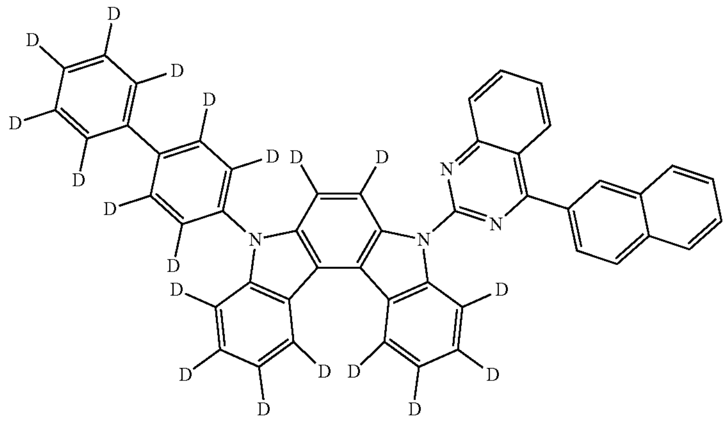,
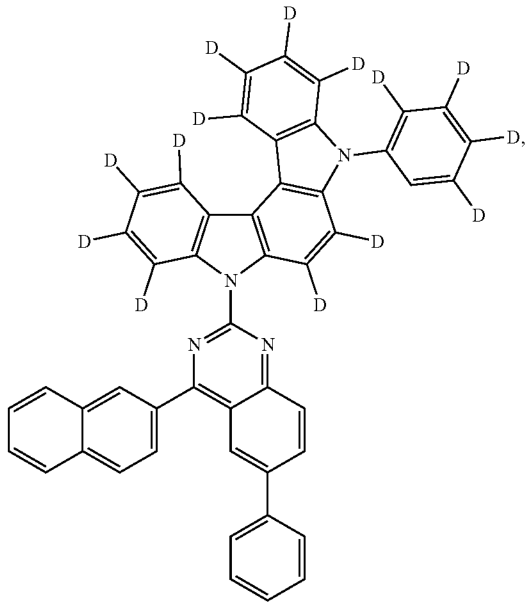,
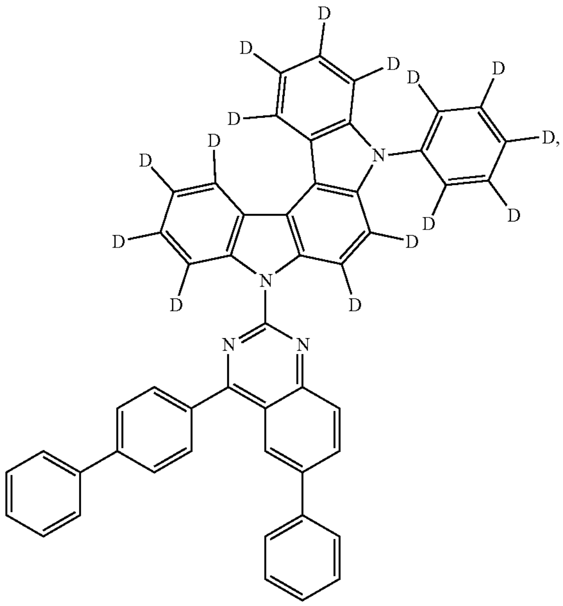,

-continued
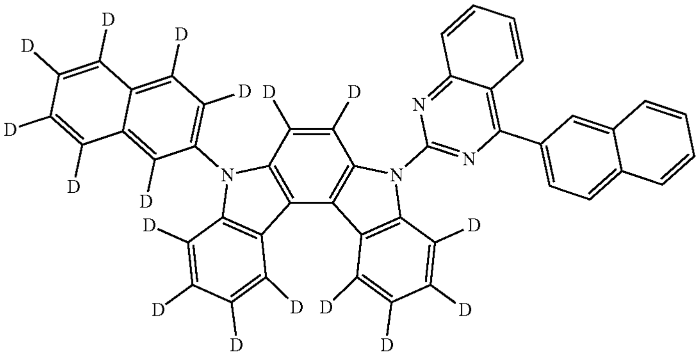
,
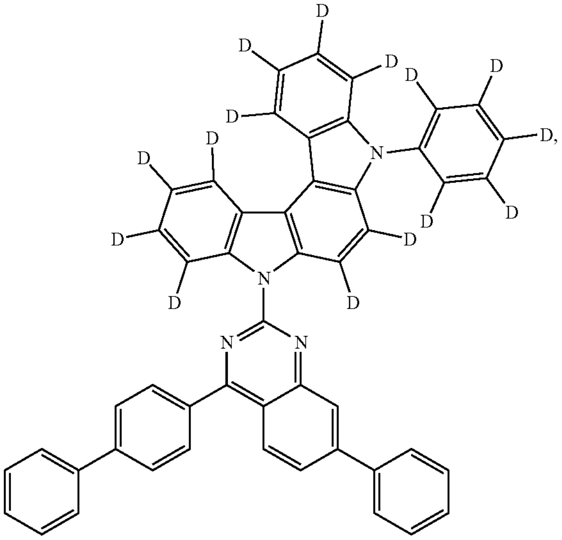
,
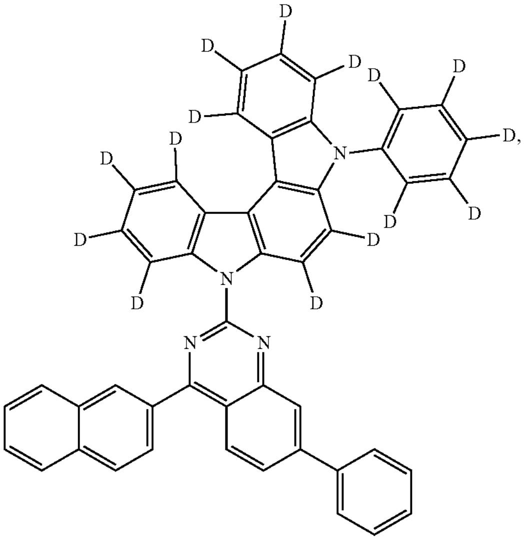
,
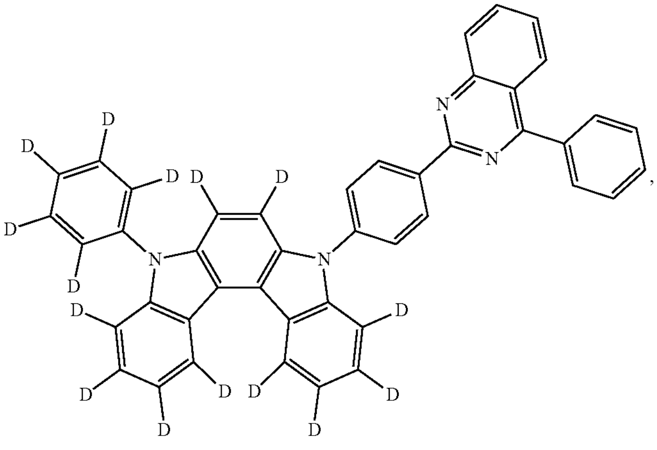
,

-continued
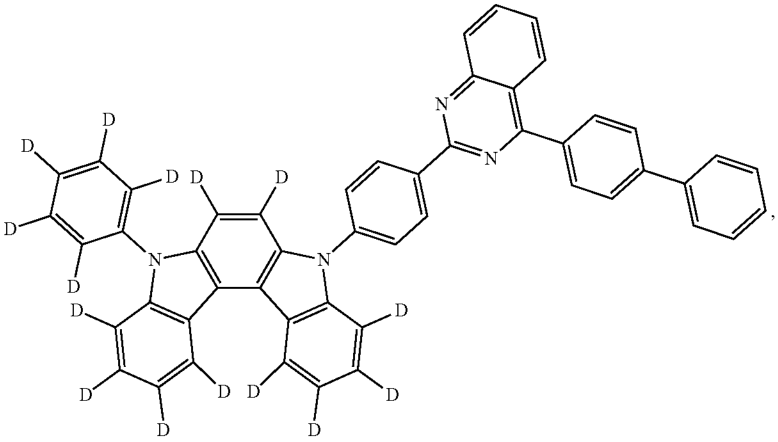
,
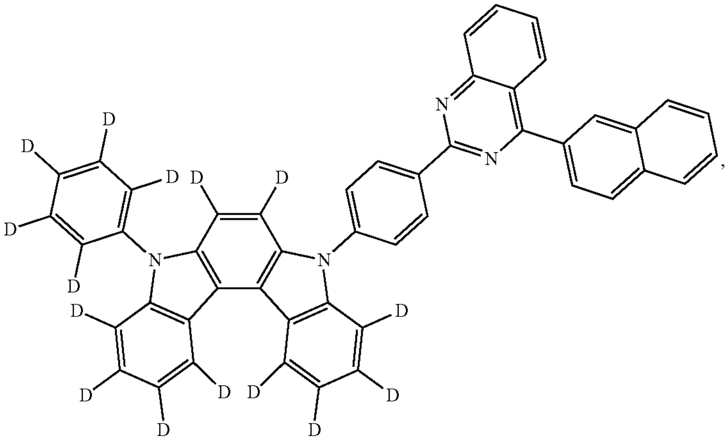
,
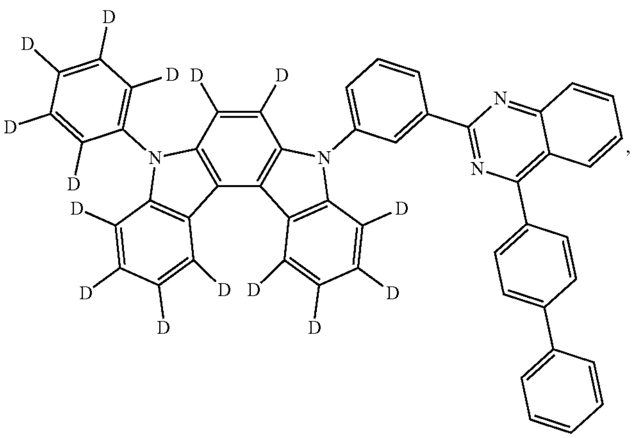
,

-continued
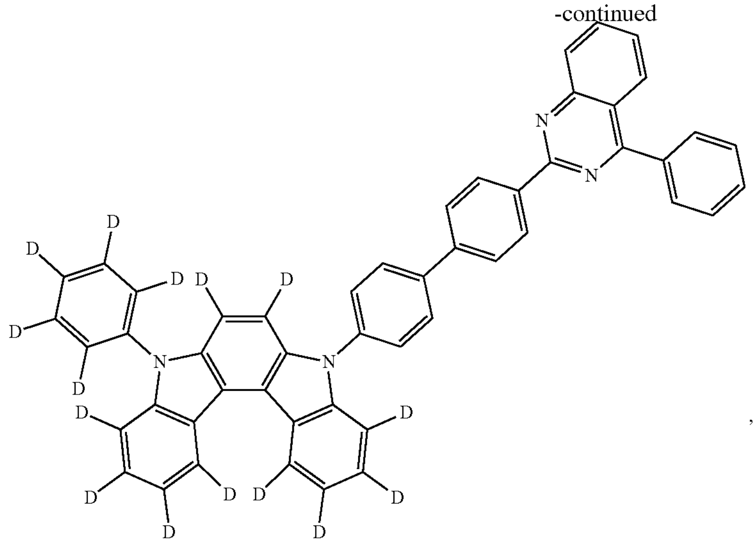
,
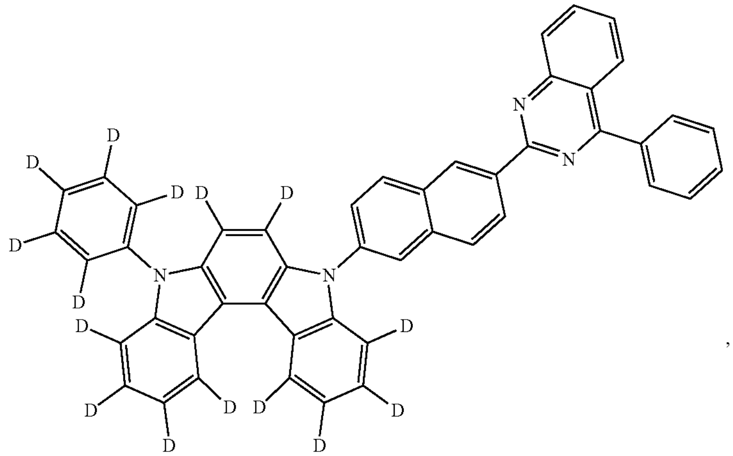
,
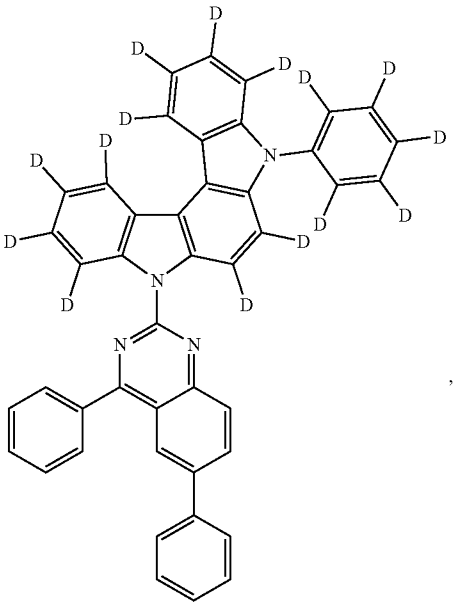
,
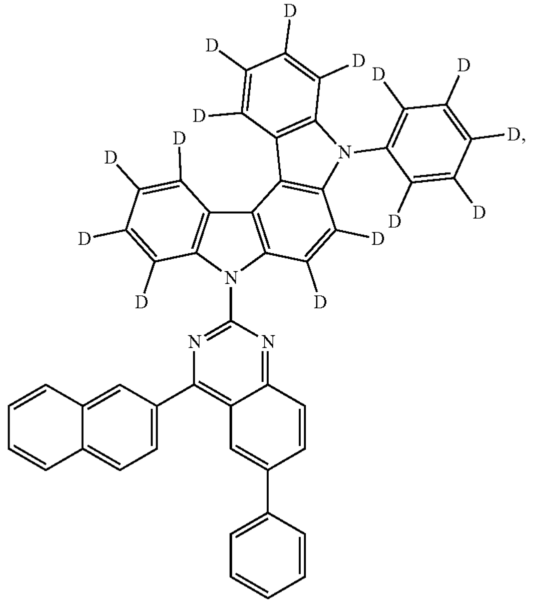
,

-continued
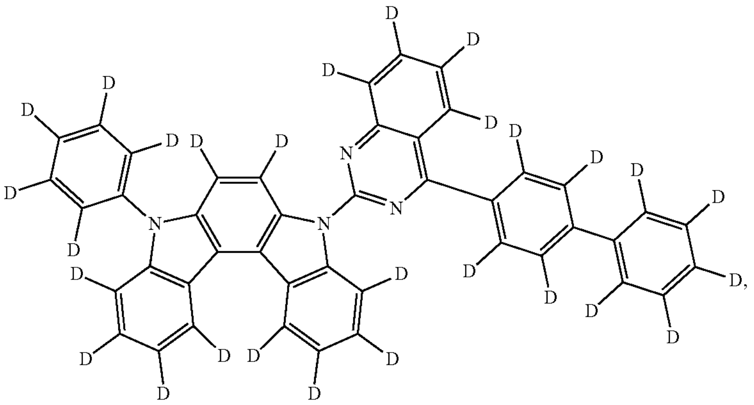
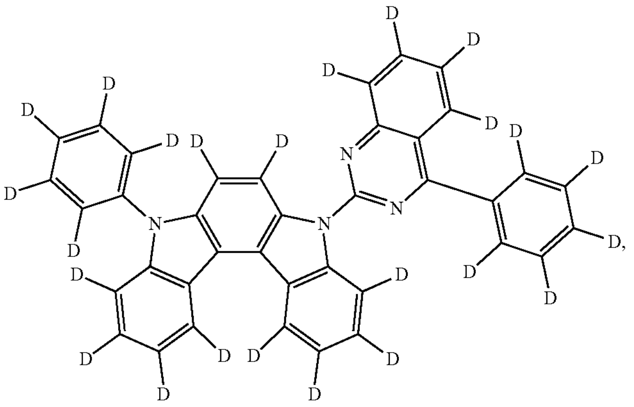
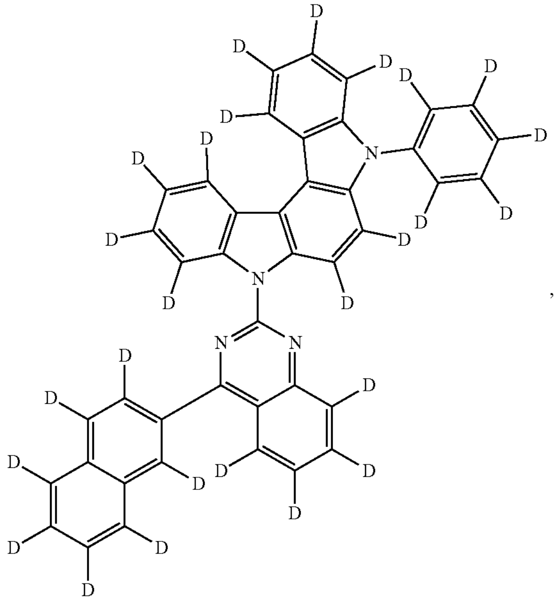
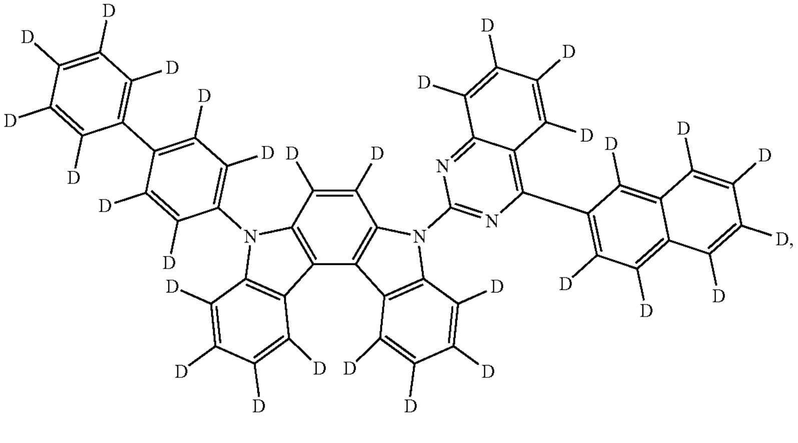

-continued
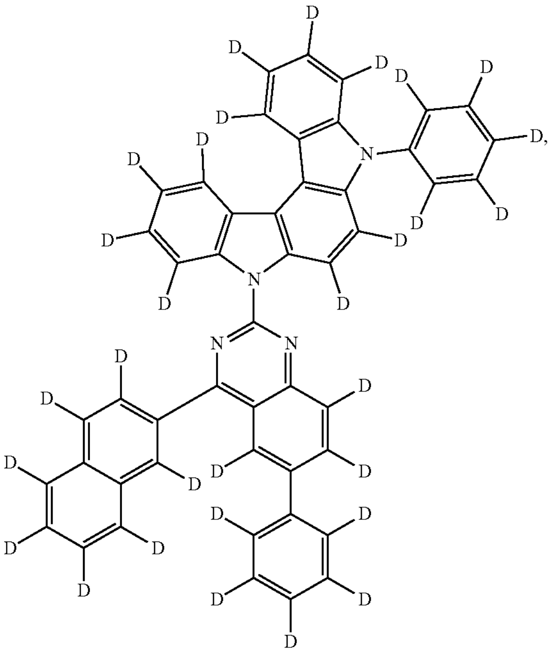
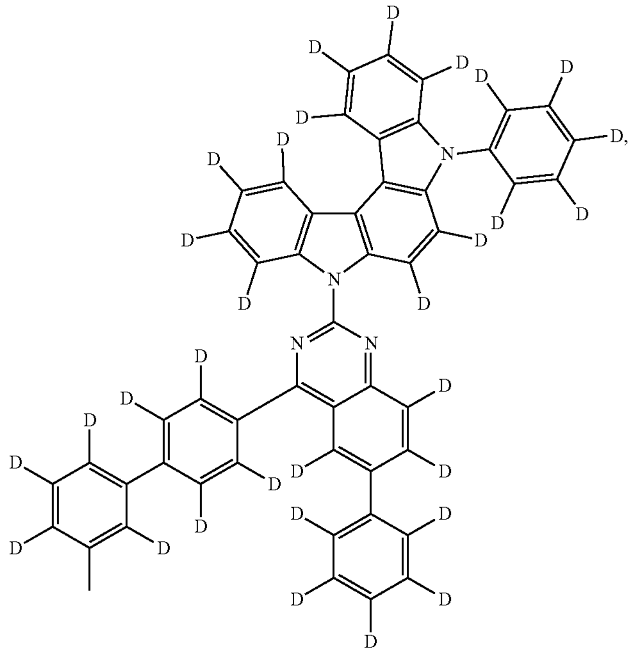
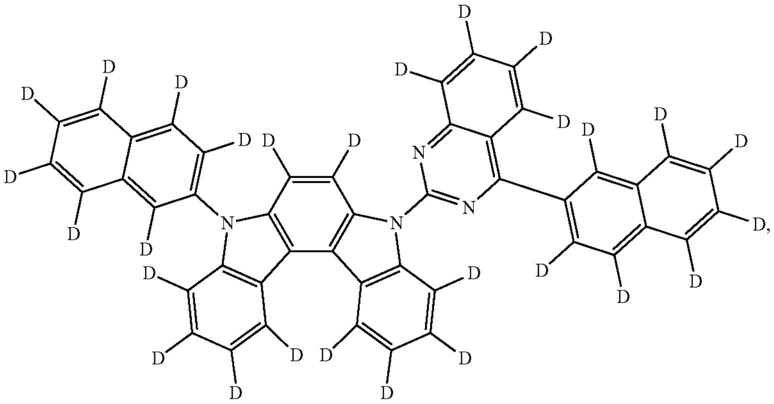
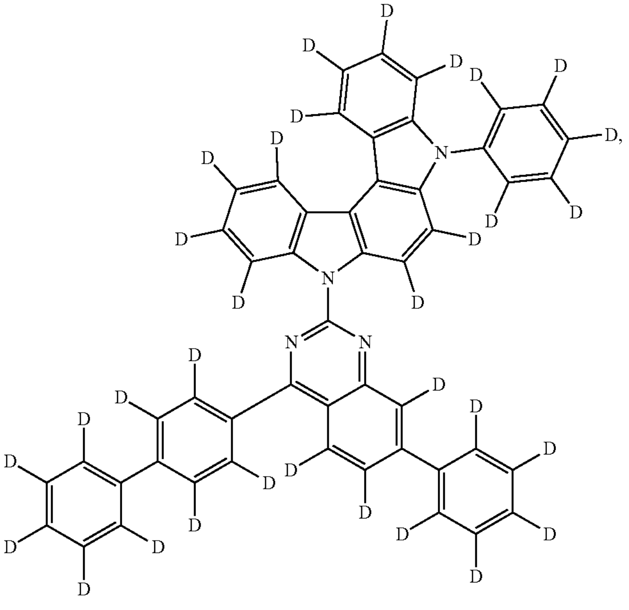
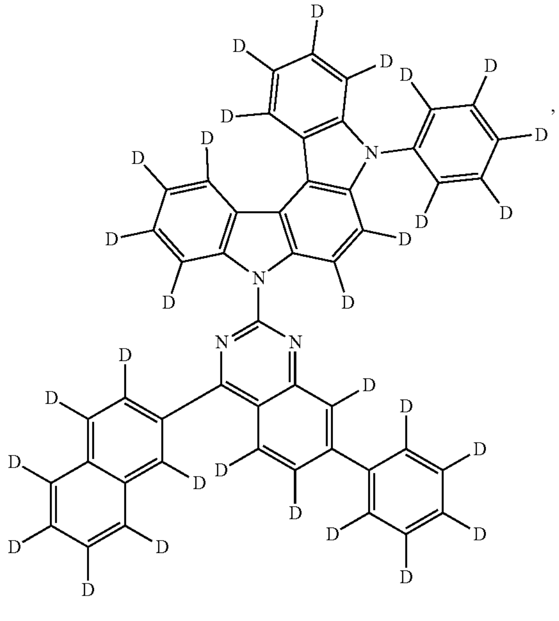

-continued
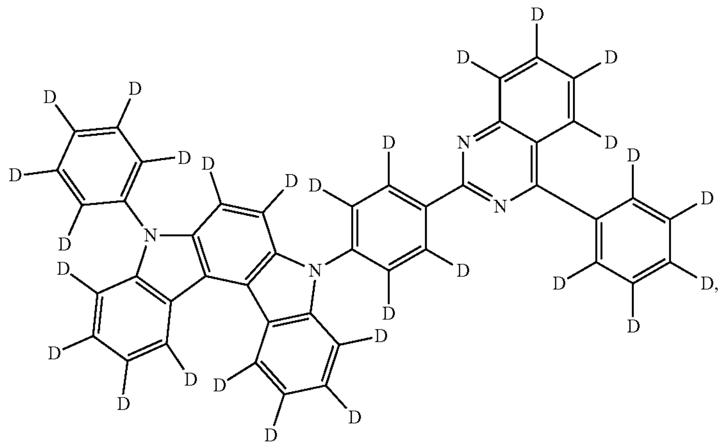
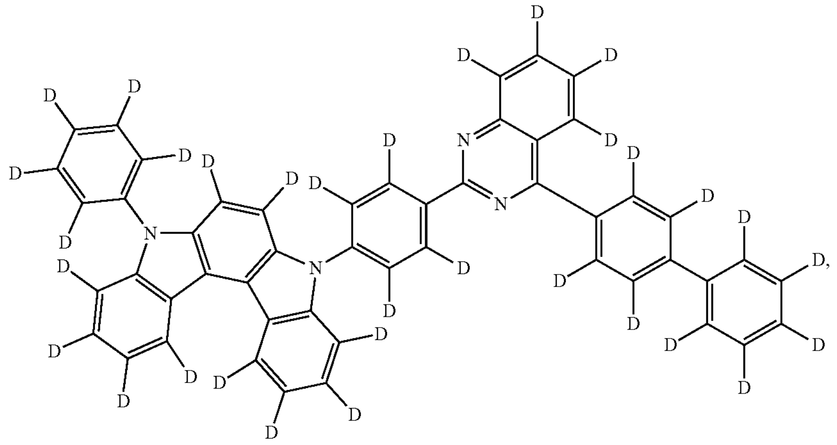
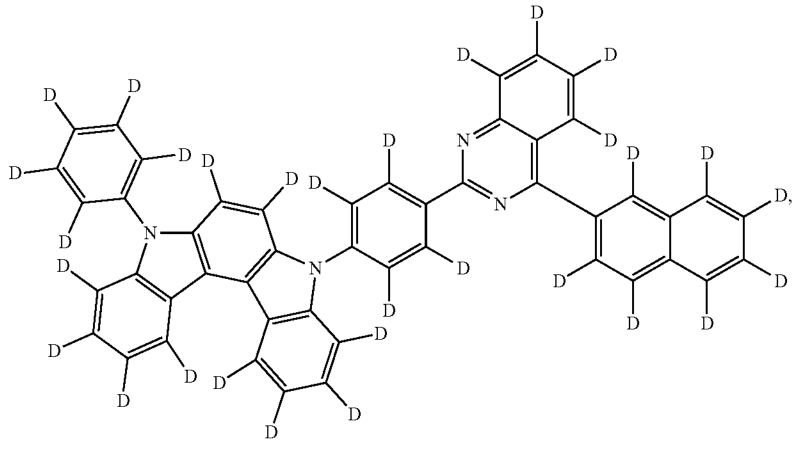

-continued
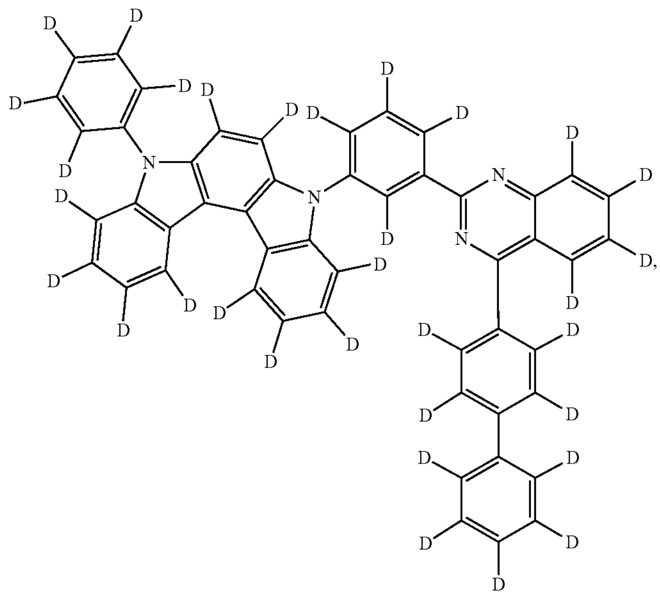
,
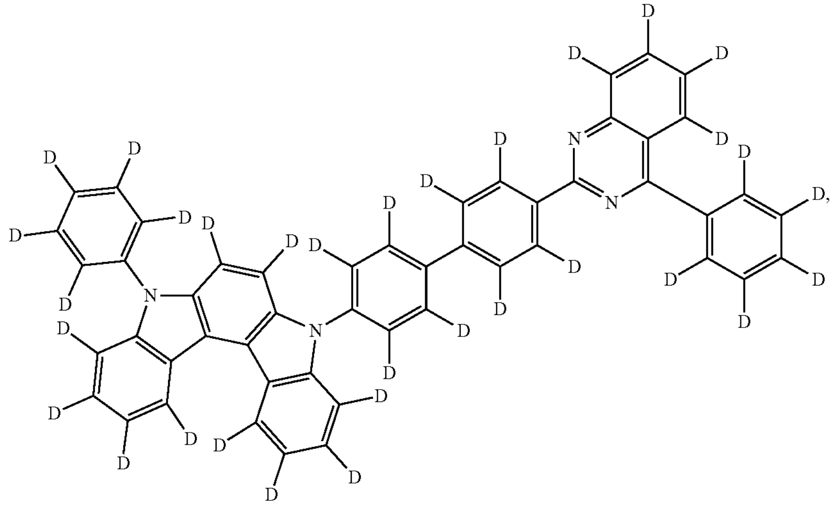
,
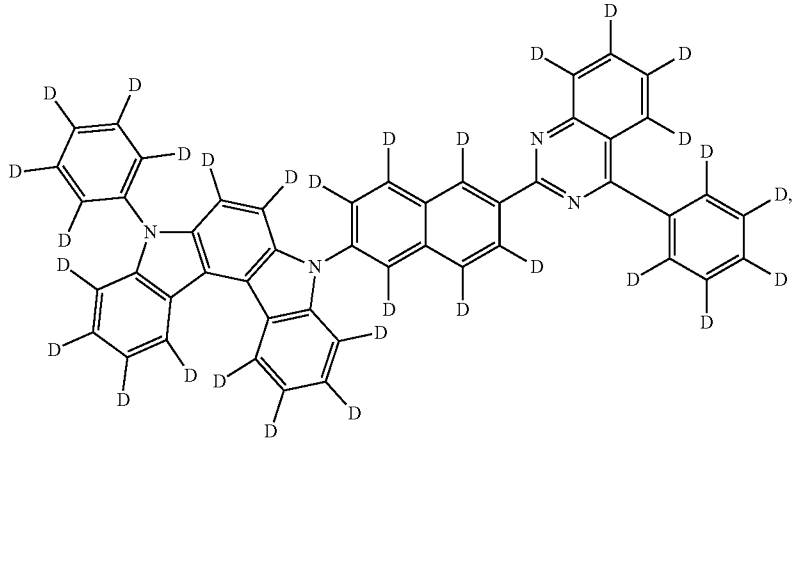
,

-continued
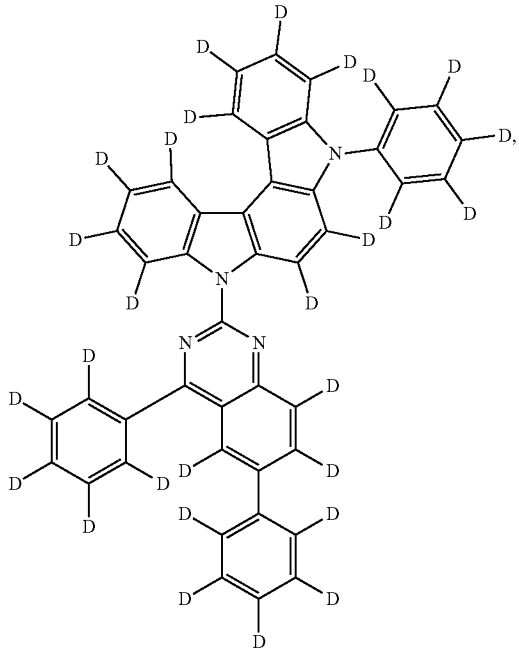
,
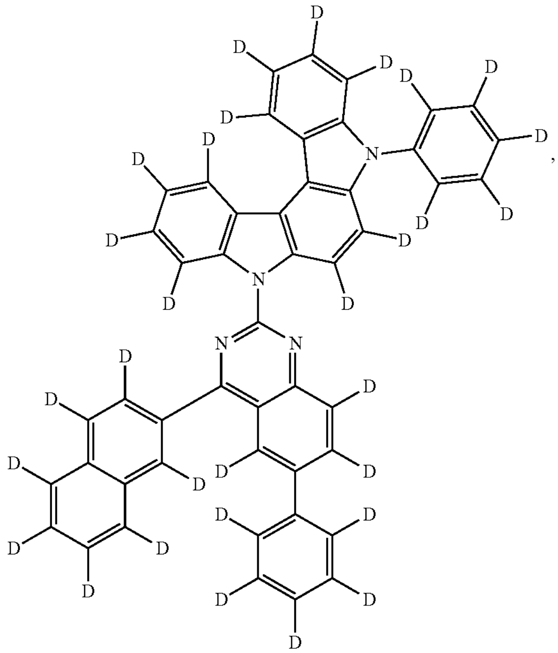
,
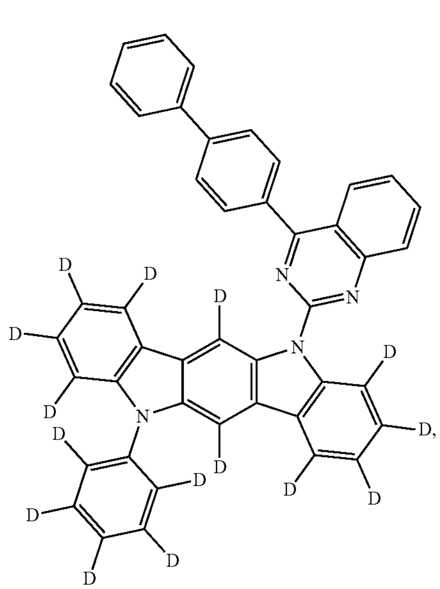
,
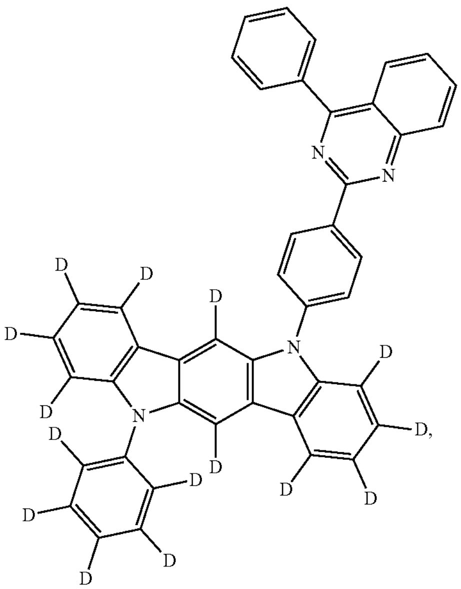
,

-continued
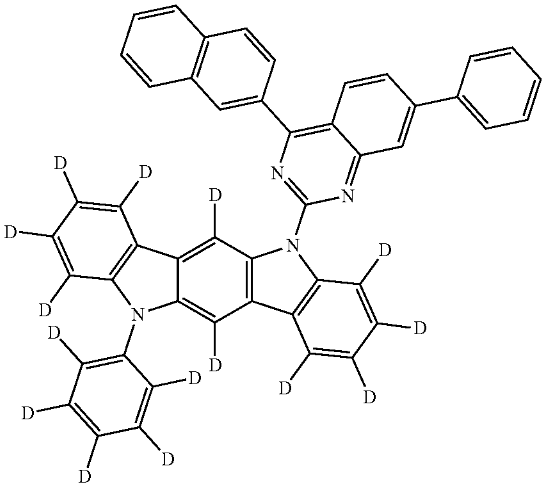
,
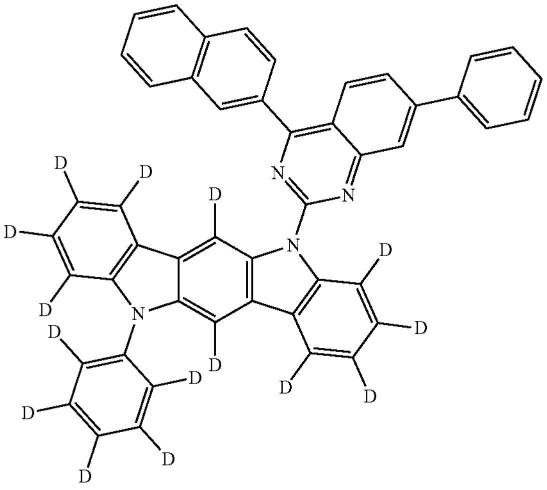
,
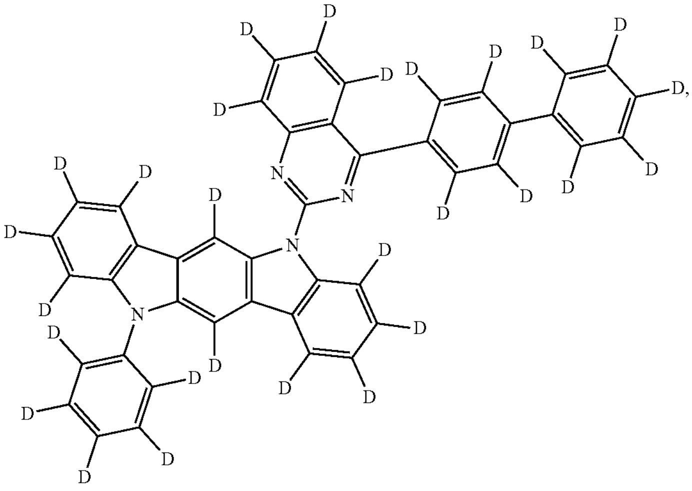
-continued
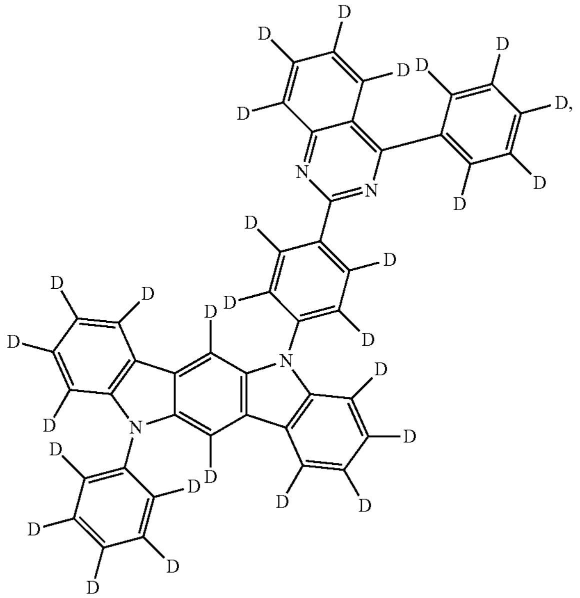
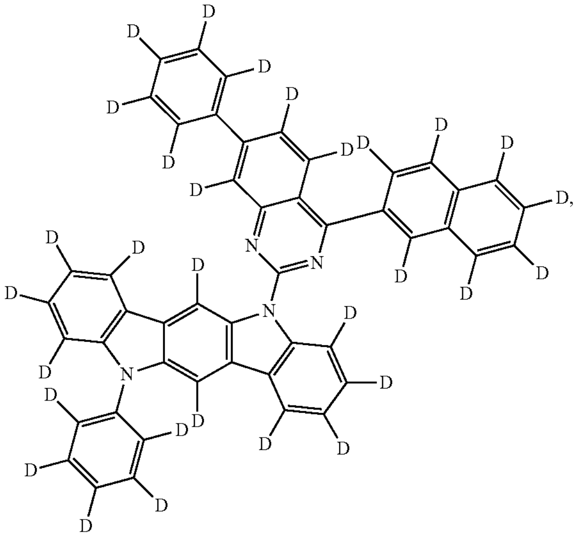

-continued
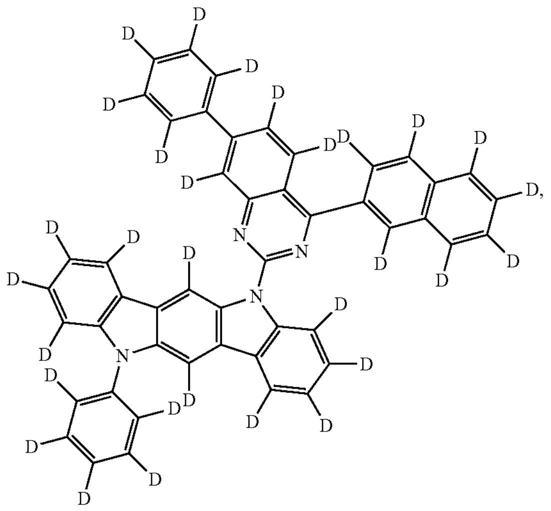
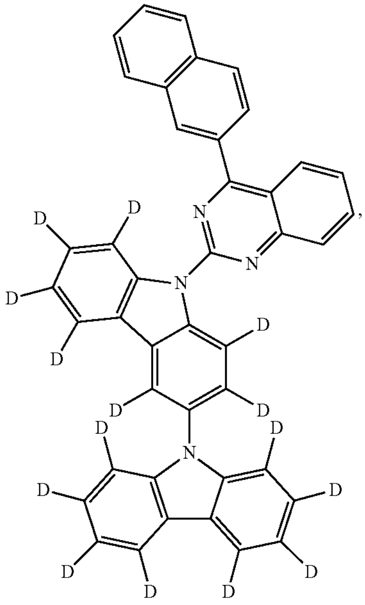
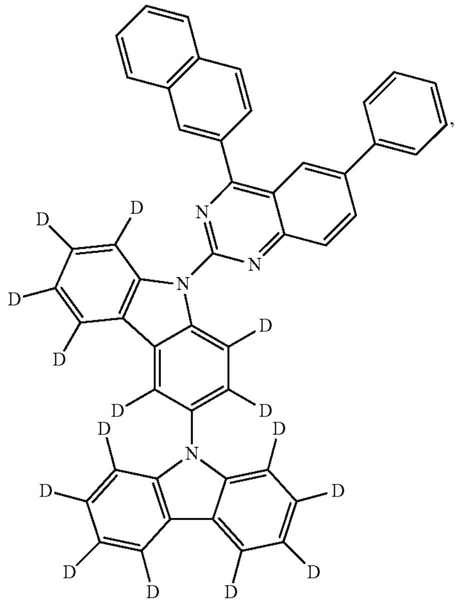
-continued
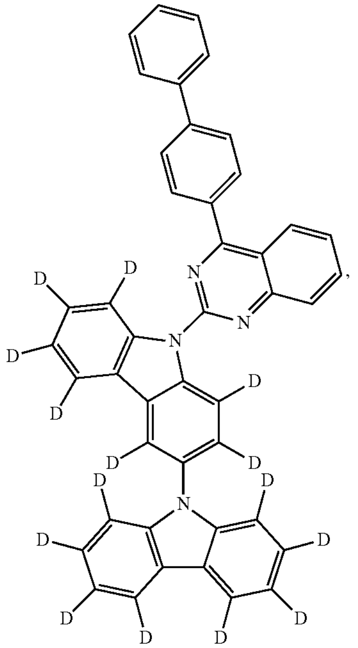
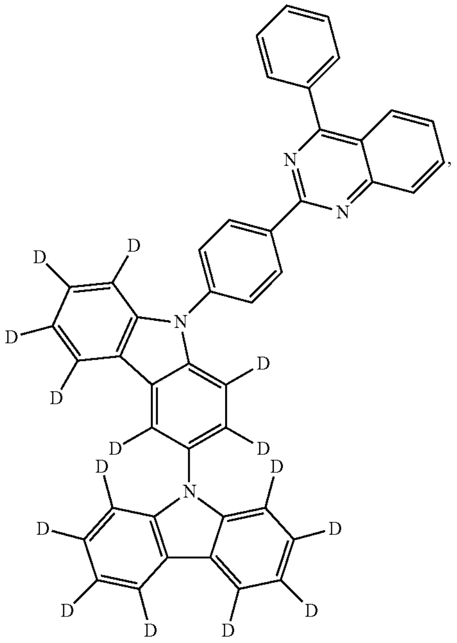

-continued
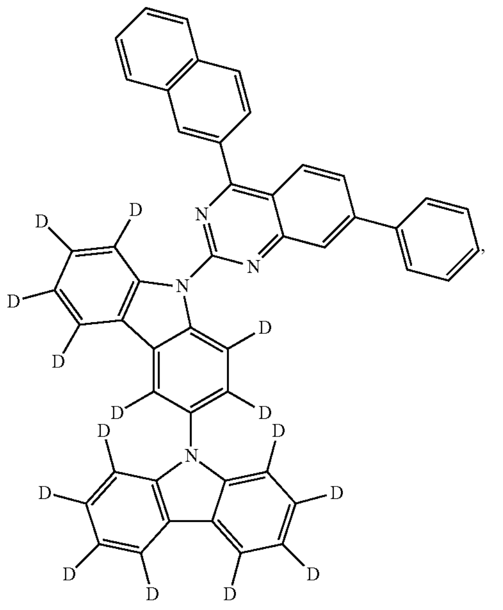
-continued
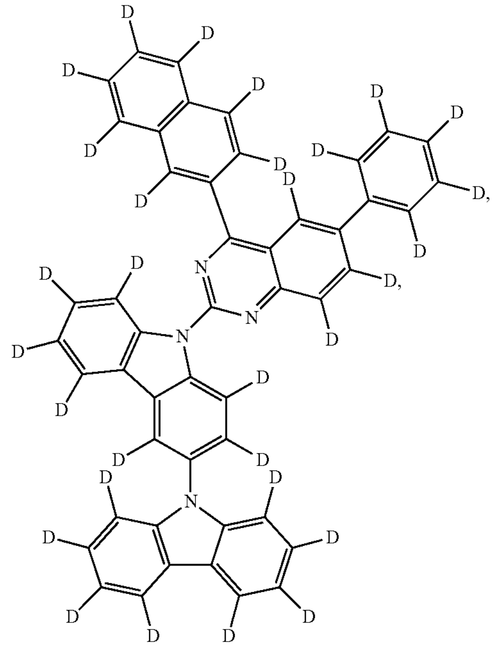
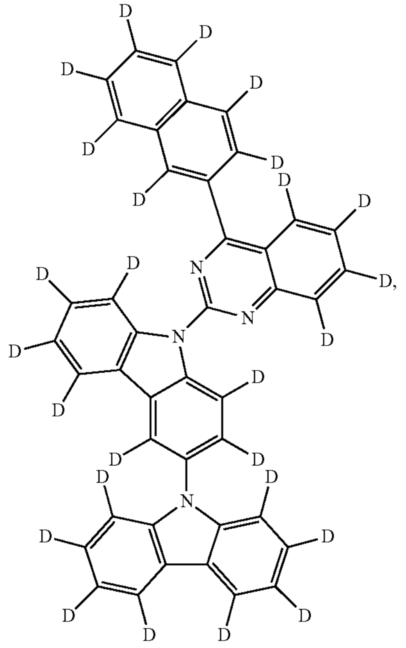
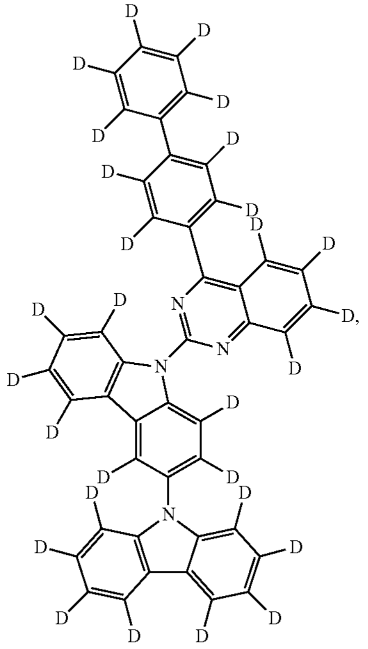

-continued

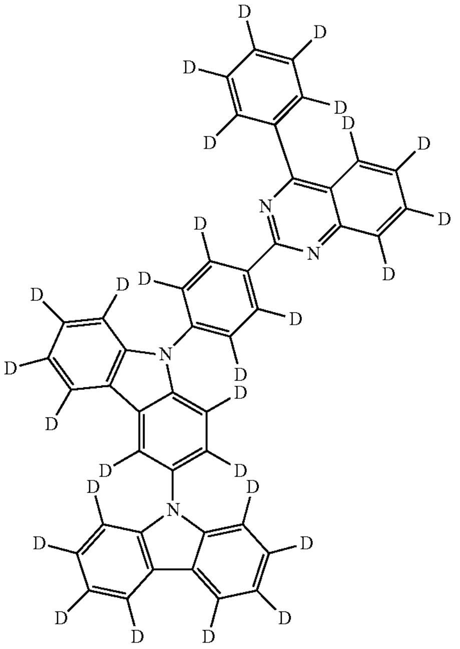

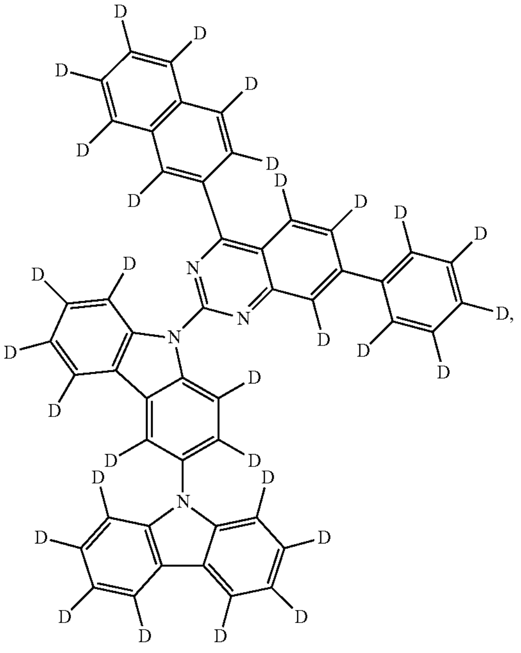

and

-continued

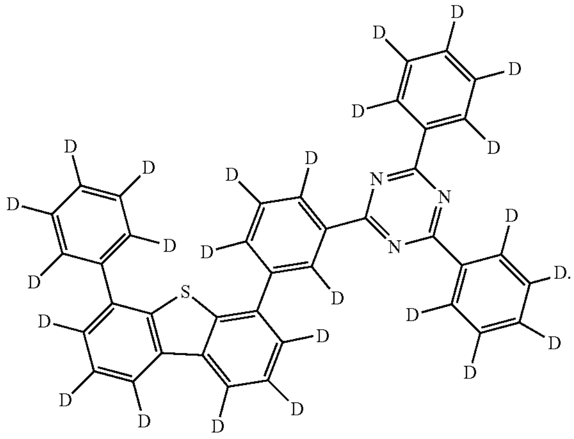

In some embodiments, the metal complex has a ligand $L_A$ comprising a moiety selected from the group consisting of:

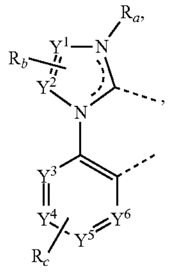

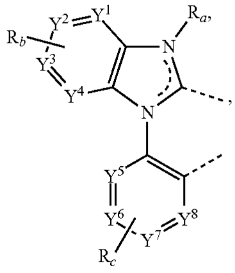

and

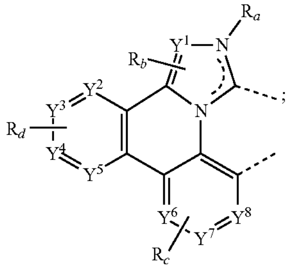

wherein:

each of $Y^1$ to $Y^8$ is independently C or N;

each of $R^b$, $R^c$, and $R^d$ independently represents mono-, up to the maximum substitutions, or no substitutions;

each $R^a$, $R^b$, $R^c$, and $R^d$ is independently a hydrogen or a substituent selected from the group consisting of the General Substituents defined herein.

In some embodiments, at least one $R^a$, $R^b$, $R^c$, and $R^d$ comprises deuterium.

In some embodiments, the metal complex has a structure $M(L_A)_p(L_B)_q(L_C)_r$, wherein p is 1, 2, or 3; q is 0, 1, or 2; r is 0, 1, or 2; and p+q+r is the oxidation state of the metal M; and each of ligand $L_B$ and ligand $L_C$ is independently selected from the group consisting of the structures in the following LIST 3:

-continued
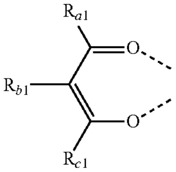,
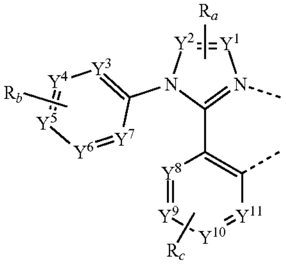,
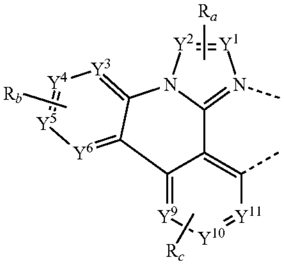,
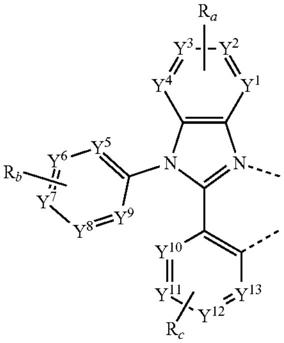,
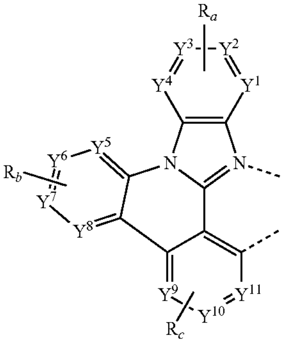,
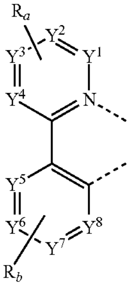,
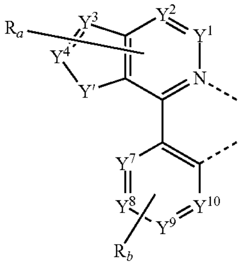,
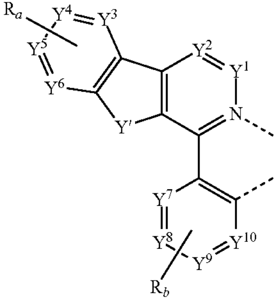,
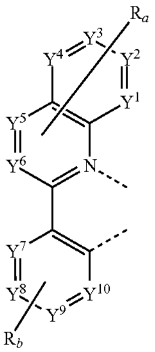,
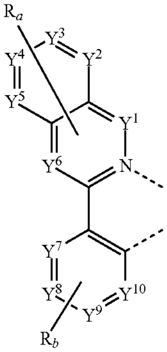,
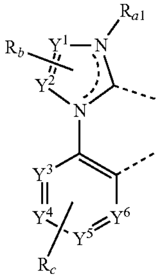,
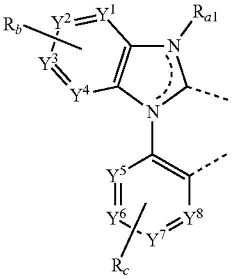,
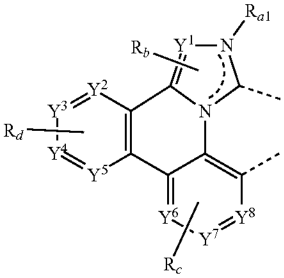,
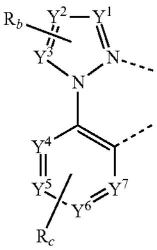,
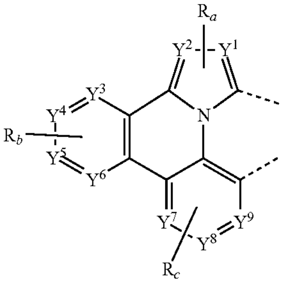,
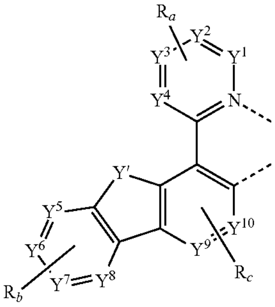,
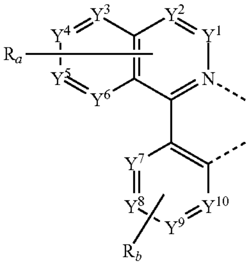,
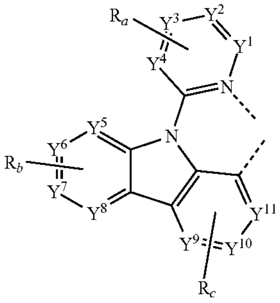, -continued

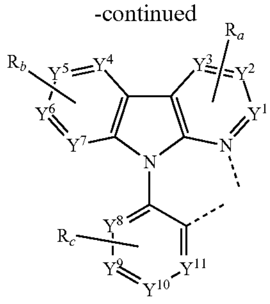

,

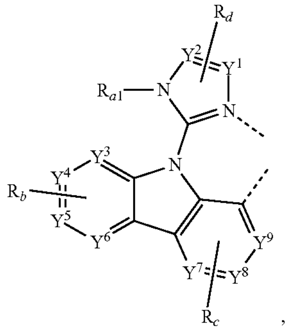

,

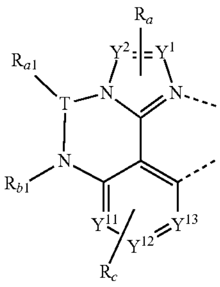

,

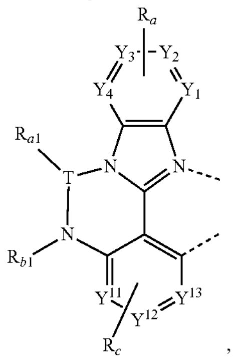

, and

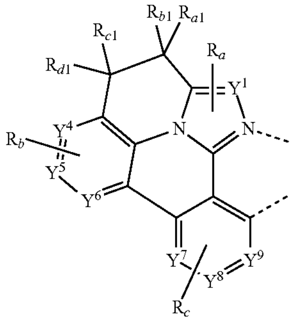

, wherein:

T is selected from the group consisting of B, Al, Ga, and In;

each of $Y^1$ to $Y^{13}$ is independently selected from the group consisting of carbon and nitrogen;

Y' is selected from the group consisting of $BR_e$, $NR_e$, $PR_e$, O, S, Se, C═O, S═O, $SO_2$, $CR_eR_f$, $SiR_eR_f$, and $GeR_eR_f$;

$R_e$ and $R_f$ can be fused or joined to form a ring;

each $R_a$, $R_b$, $R_c$, and $R_d$ independently represents zero, mono, or up to a maximum allowed number of substitutions to its associated ring;

each of $R_{a1}$, $R_{b1}$, $R_{c1}$, $R_{d1}$, $R_a$, $R_b$, $R_c$, $R_d$, $R_e$ and $R_f$ is independently a hydrogen or a substituent selected from the group consisting of the General Substituents defined herein; and any two adjacent $R_a$, $R_b$, $R_c$, $R_d$, $R_e$ and $R_f$ can be fused or joined to form a ring or form a multidentate ligand.

In some embodiments, M is selected from the group consisting of Ir, Pt, Os, Pd, Ag, Au, and Cu.

In some embodiments, each of ligand $L_B$ and ligand $L_C$ is independently selected from the group consisting of the structures in the following LIST 4:

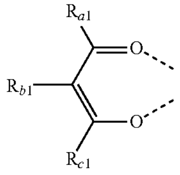

,

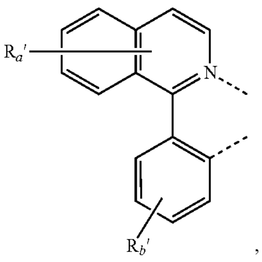

,

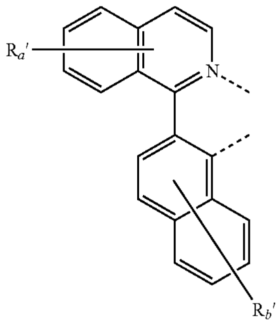

,

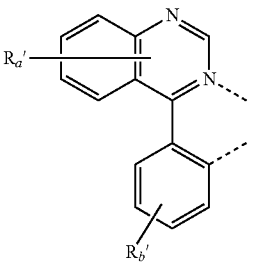

,

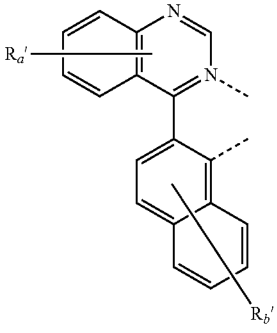

,

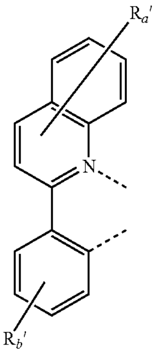

,

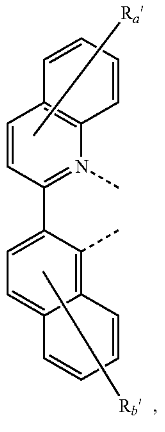

,

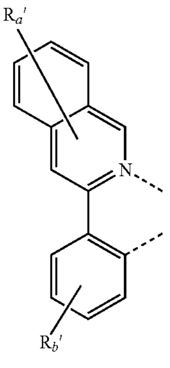

,

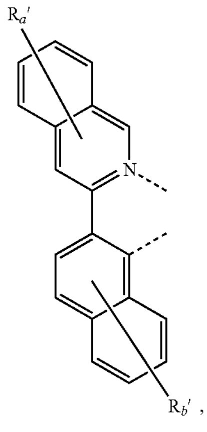

,

-continued
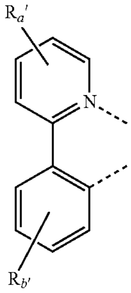
,
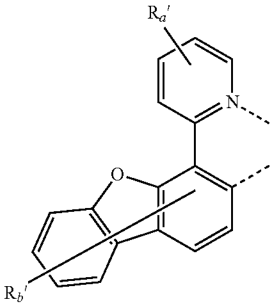
,
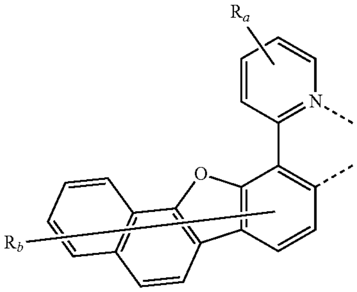
,
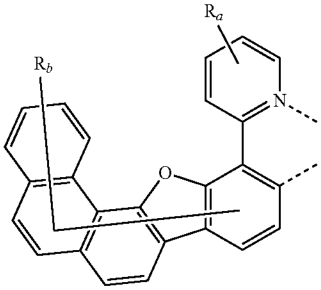
,
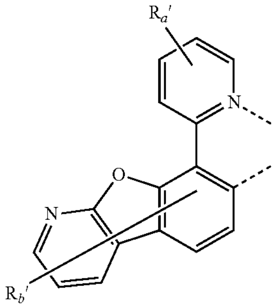
,
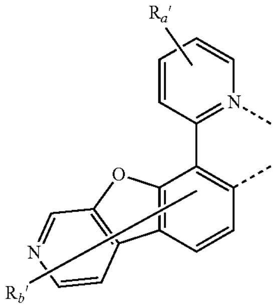
,
-continued
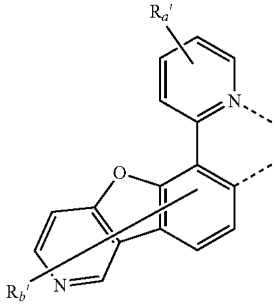
,
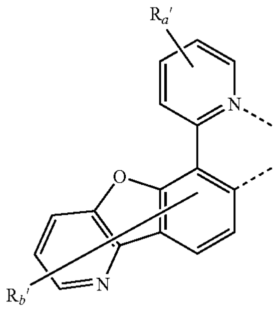
,
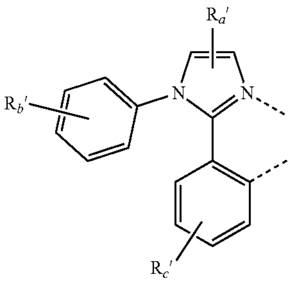
,
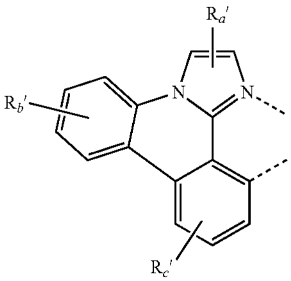
,
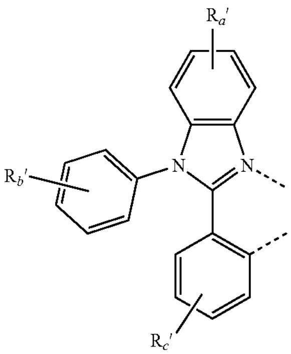
, -continued
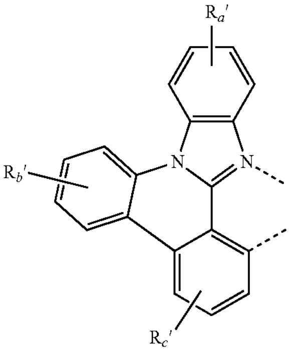
,
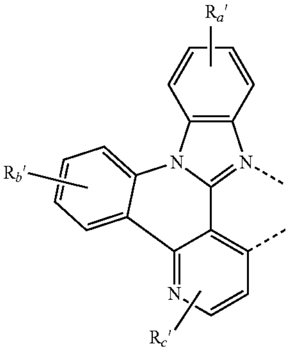
,
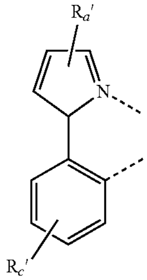
,
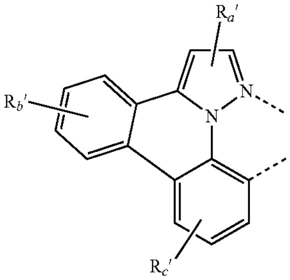
,
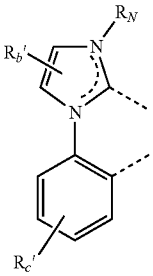
,
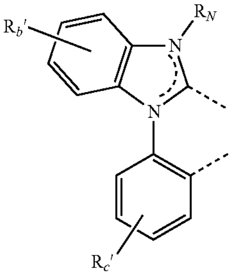
,
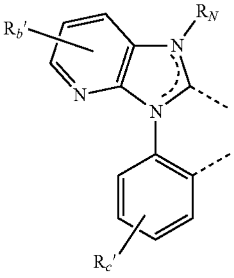
,
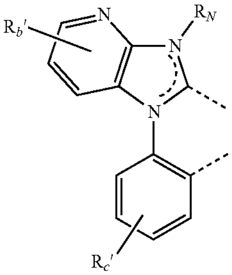
,
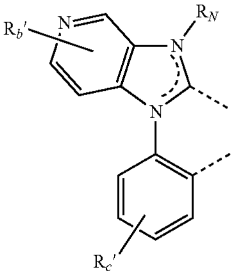
,
-continued
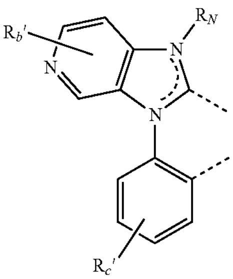
,
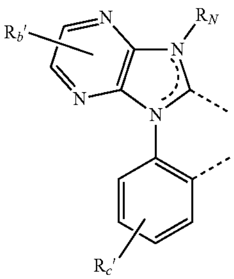
,
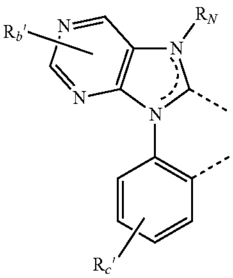
,
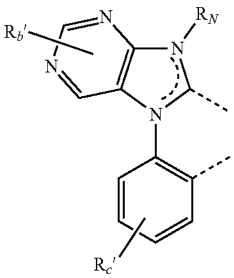
,
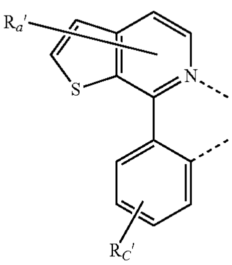
,
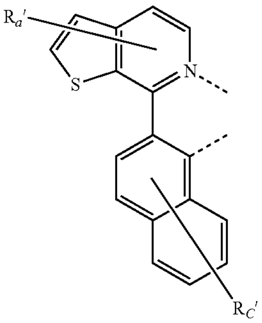
,
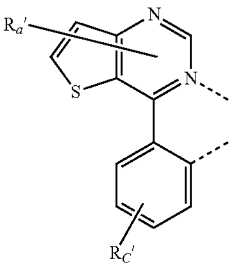
,
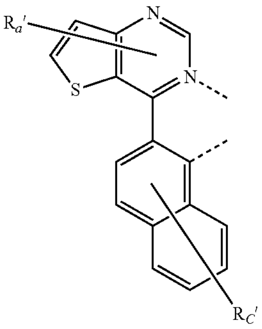
,
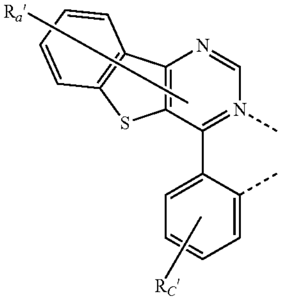
, -continued

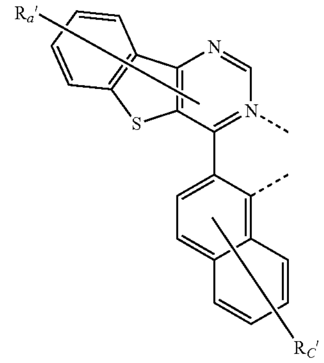

,

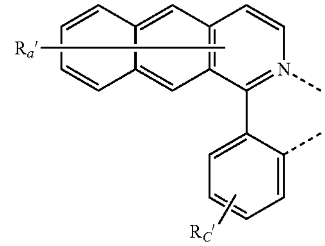

,

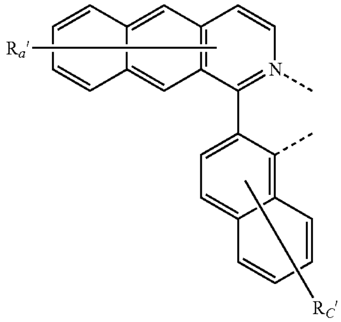

,

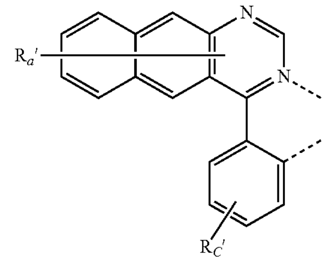

,

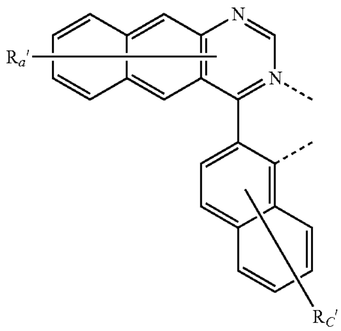

,

-continued

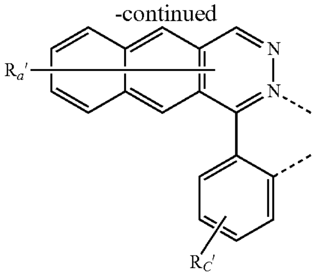

,

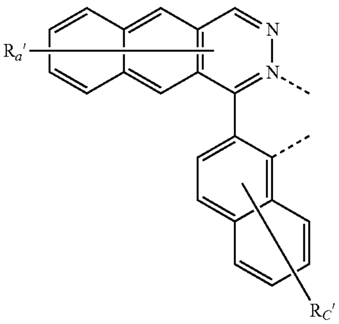

,

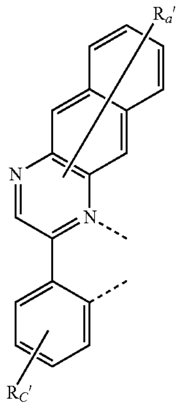

,

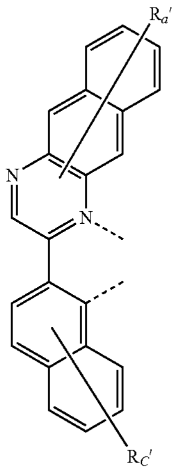

,

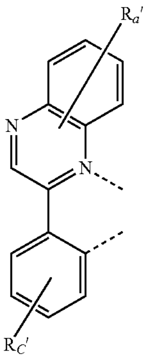

,

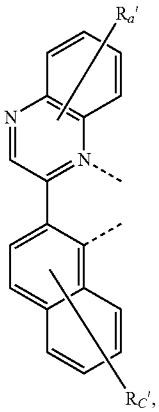

,

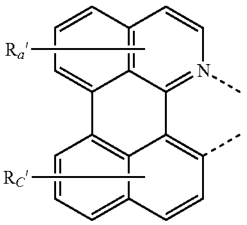

, and

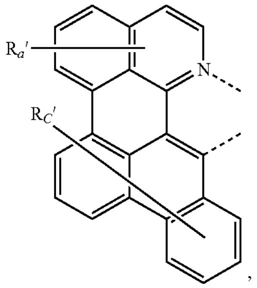

, wherein:

$R_a'$, $R_b'$, and $R_c'$ each independently represent zero, mono, or up to a maximum allowed number of substitutions to its associated ring;

each of $R_{a1}$, $R_{b1}$, $R_{c1}$, $R_a$, $R_b$, $R_c$, $R_N$, $R_a'$, $R_b'$, and $R_c'$ is independently hydrogen or a substituent selected from the group consisting of the General Substituents defined herein; and two adjacent $R_a'$, $R_b'$, and $R_c'$ can be fused or joined to form a ring or form a multidentate ligand.

In some embodiments, the metal complex is selected from the group consisting of the structures in the following LIST 5:
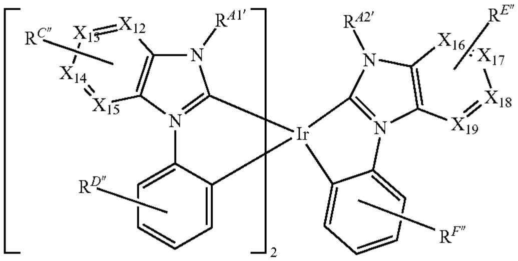
,
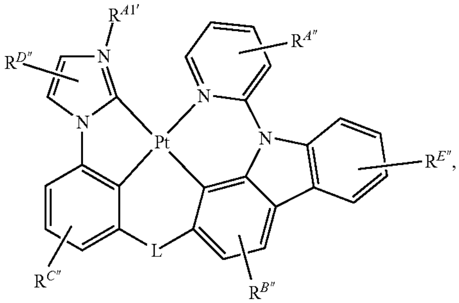
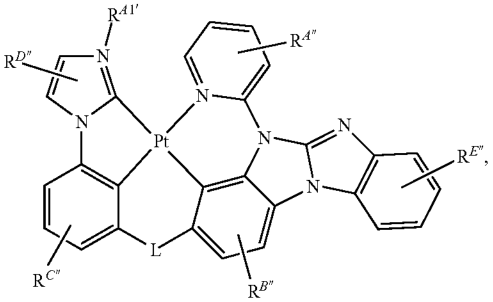
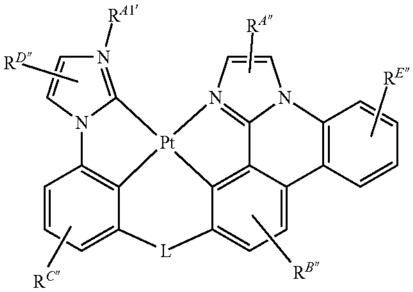
,
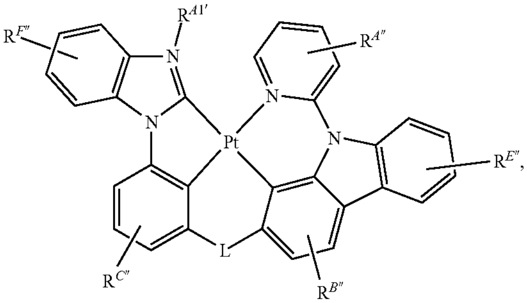
-continued
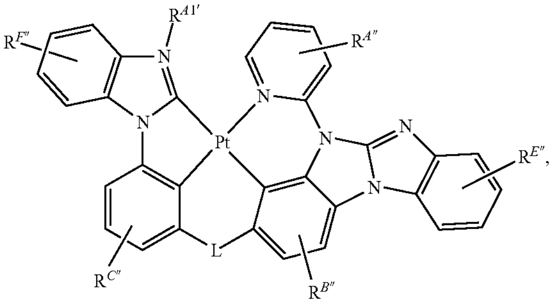
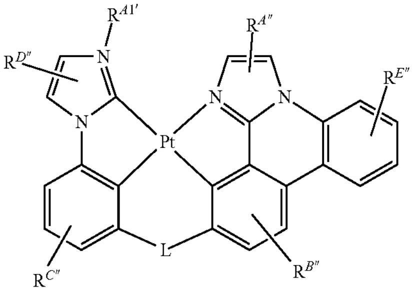
,
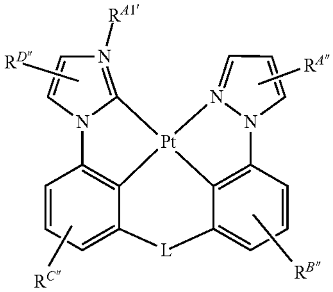
,
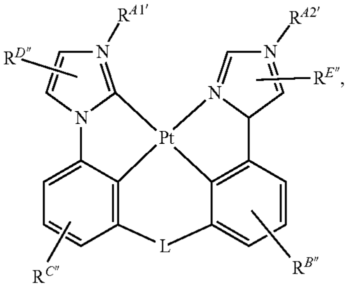
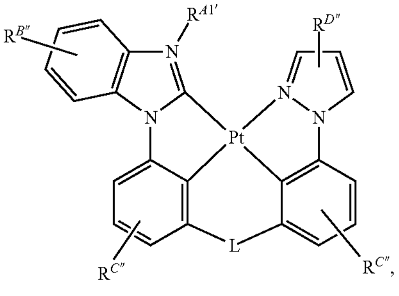

-continued
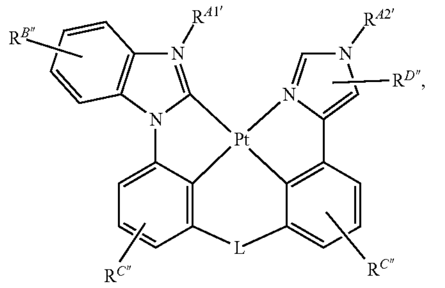
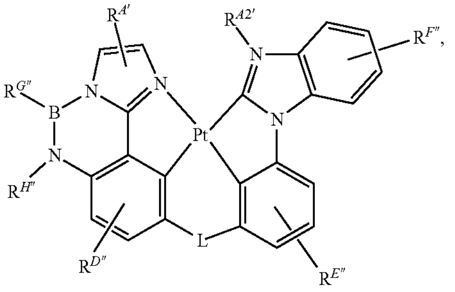
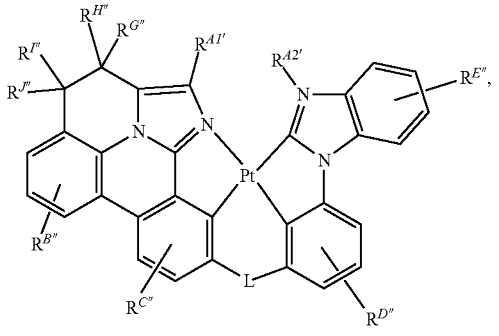
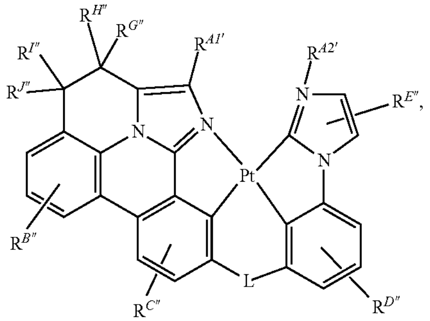
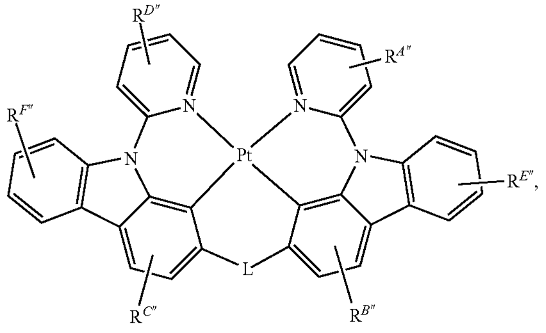
-continued
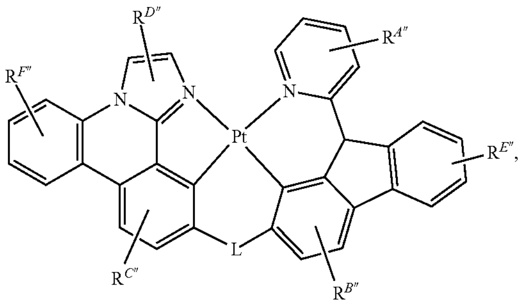
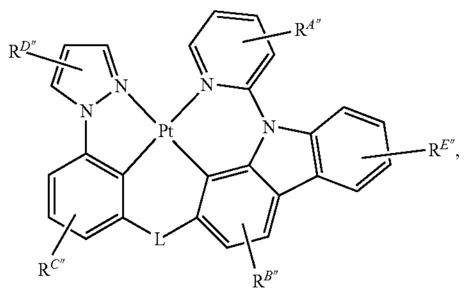
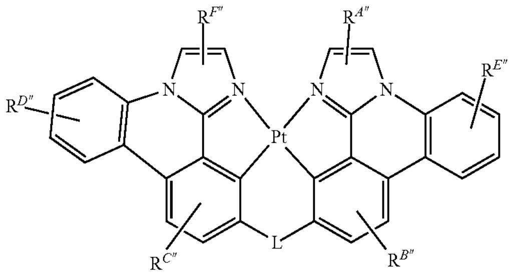
,
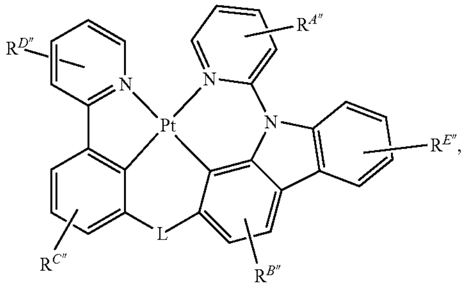
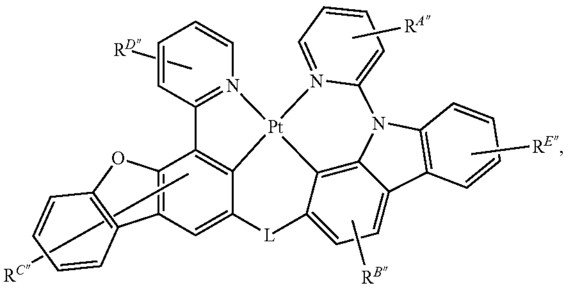
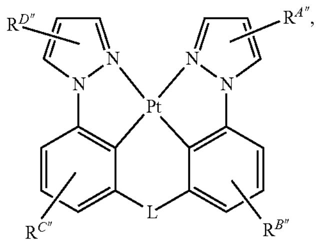

-continued
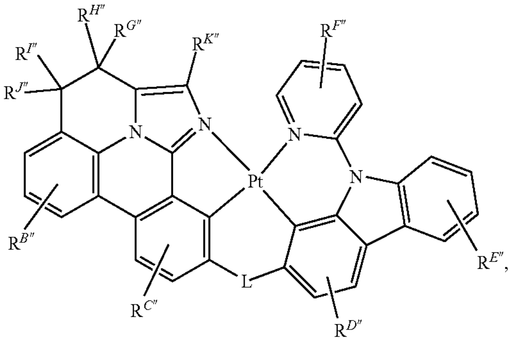
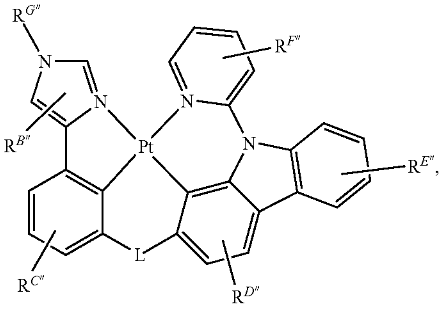
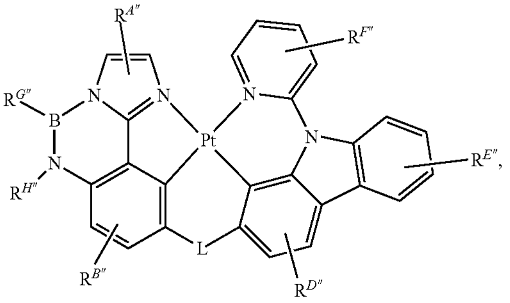
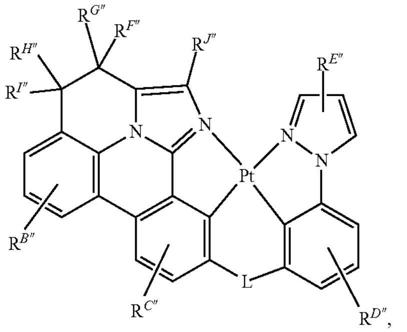
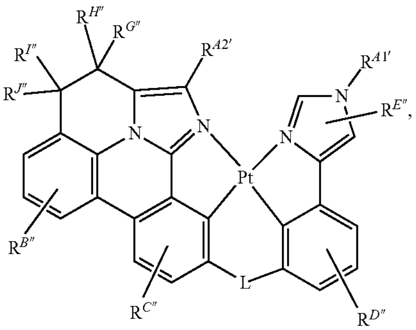
-continued
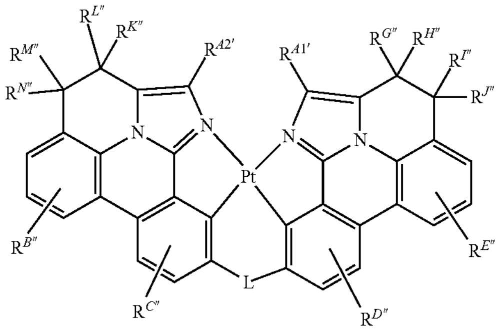
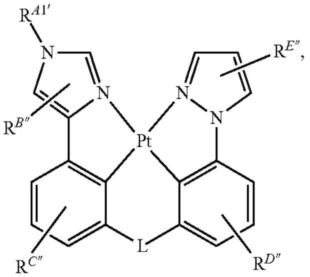
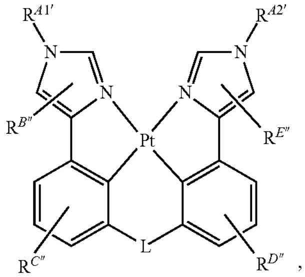
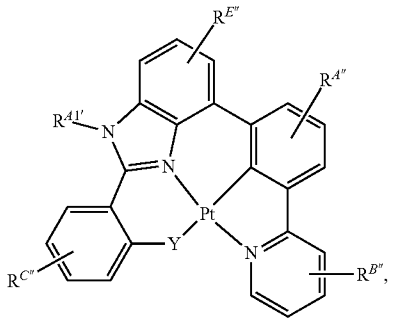
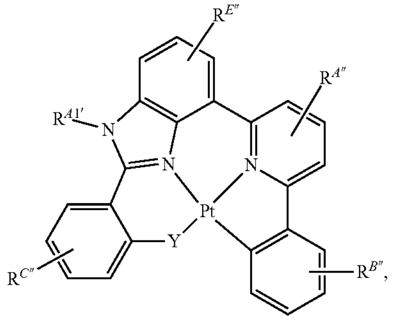

-continued
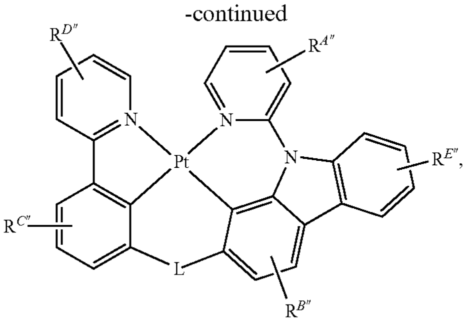
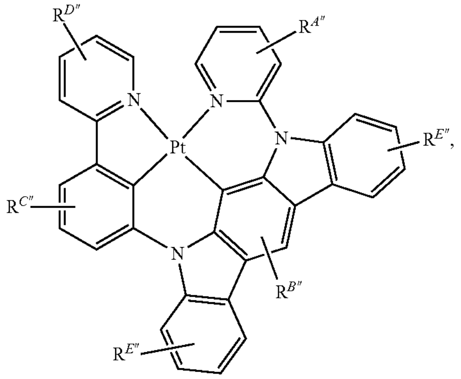
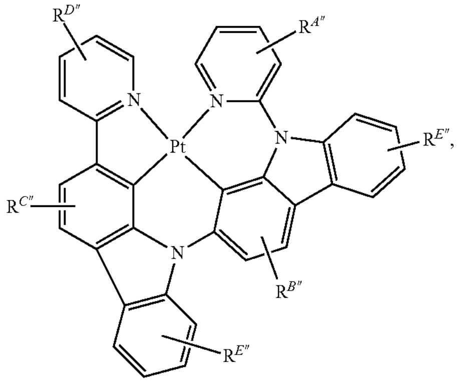
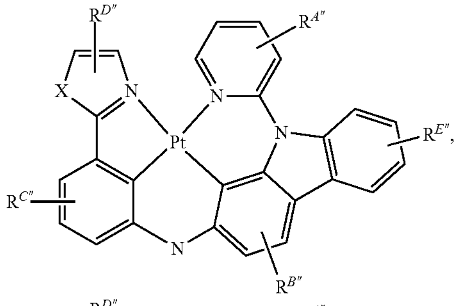
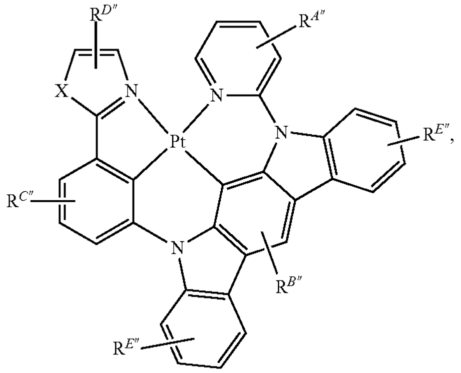
-continued
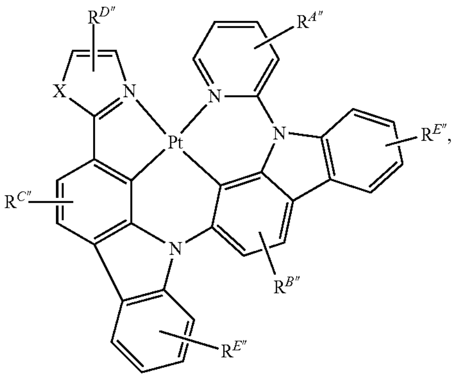
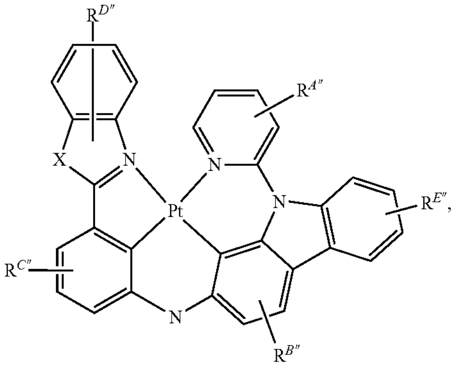
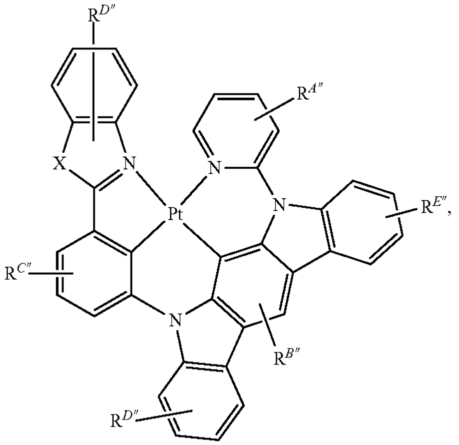
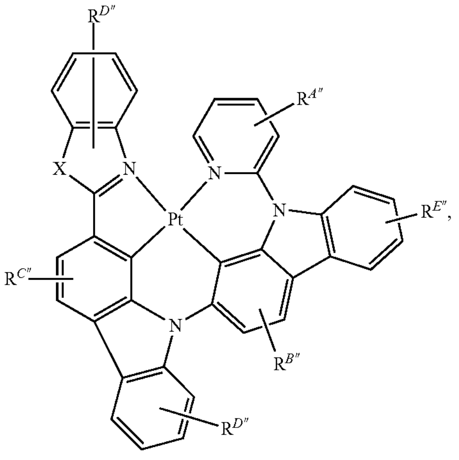

-continued
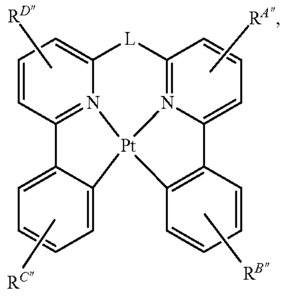
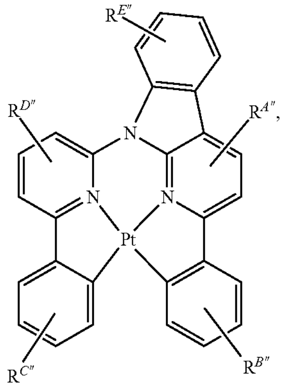
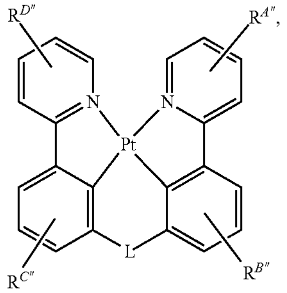
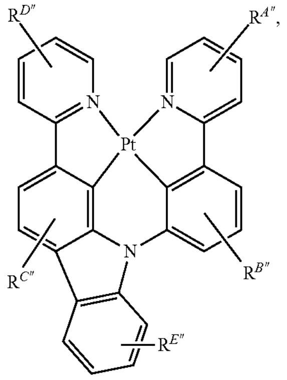
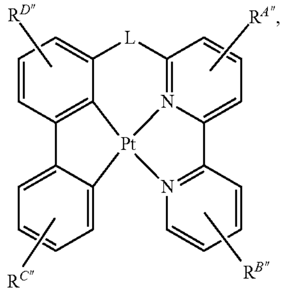
-continued
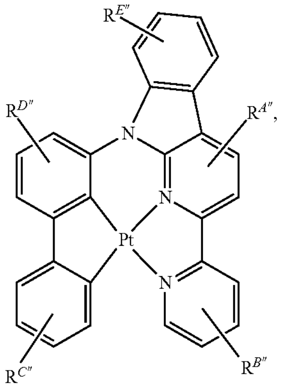
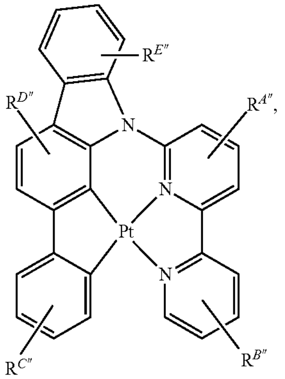
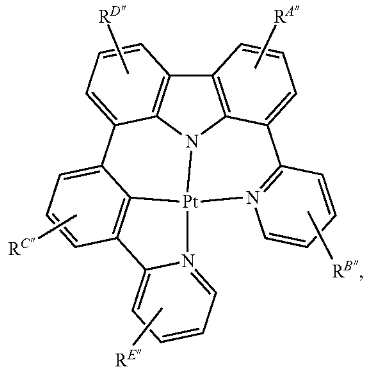
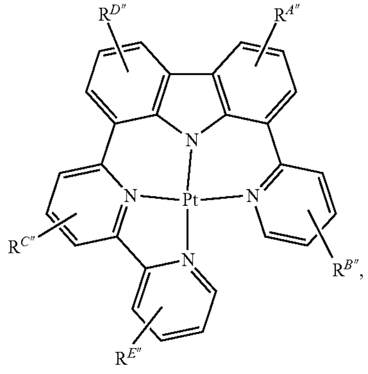

-continued
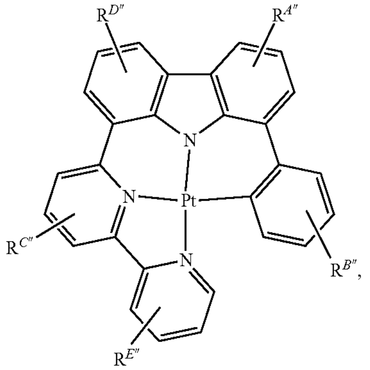
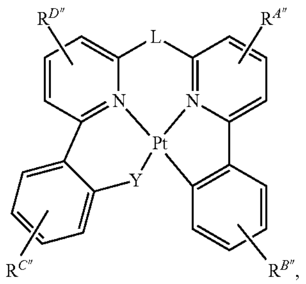
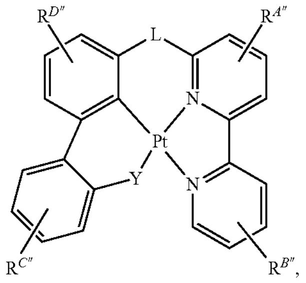
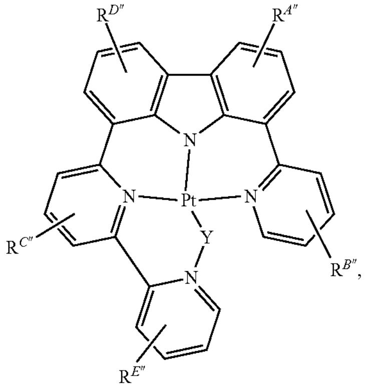
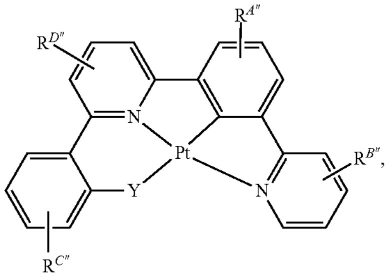
-continued
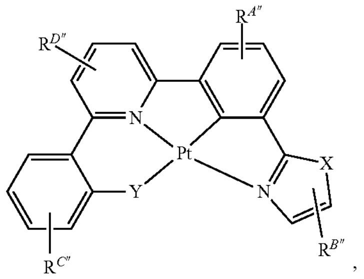
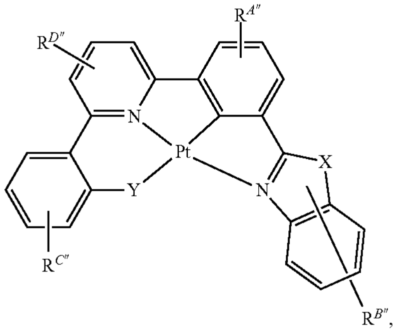
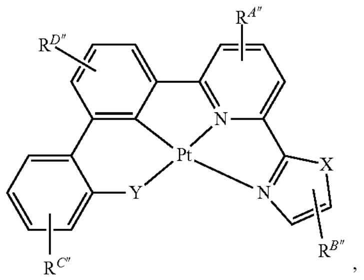
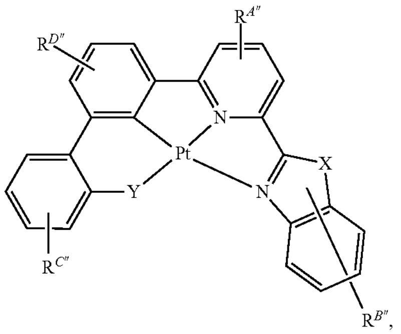
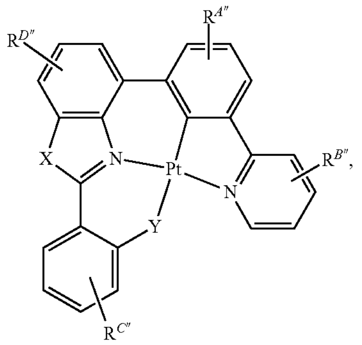

-continued

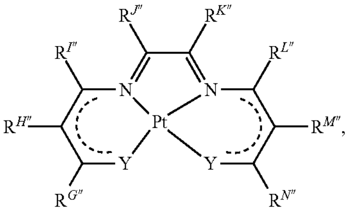

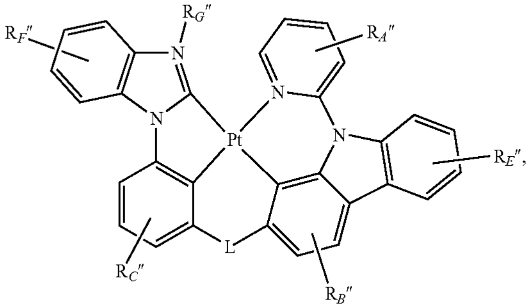

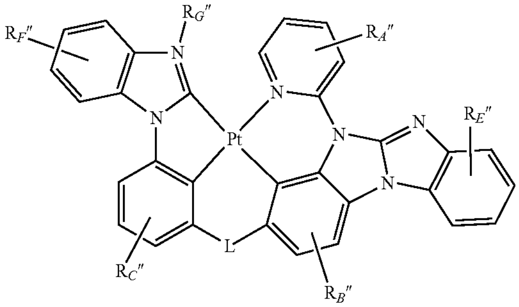

,

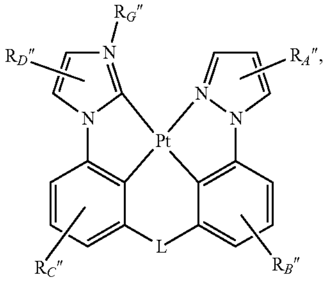

-continued

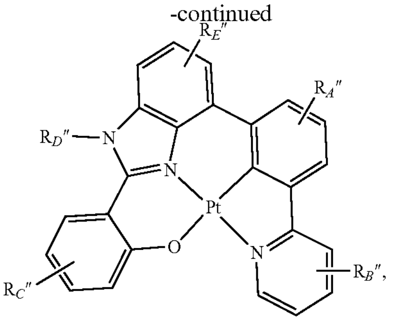

and

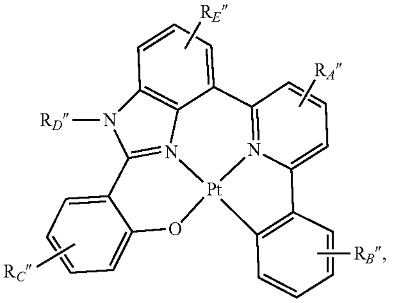

wherein:

each of $X_{12}$ to $X_{19}$ is independently C or N;

each Y is independently selected from the group consisting of a NR, O, S, and Se;

each L is independently selected from the group consisting of a direct bond, BR, BRR', NR, PR, O, S, Se, C═X', S═O, $SO_2$, CR, CRR', SiRR', GeRR', alkyl, cycloalkyl, aryl, heteroaryl, and combinations thereof;

each X and X' is independently selected from the group consisting of O, S, Se, NR", and CR"R'";

each of R, R', R", R'", $R^{A''}$, $R^{B''}$, $R^{C''}$, $R^{D''}$, $R^{E''}$, and $R^{E''}$ independently represents mono-, up to the maximum substitutions, or no substitutions;

each of R, R', $R^{A1'}$, $R^{A2'}$, $R^{A''}$, $R^{B''}$, $R^{C''}$, $R^{D''}$, $R^{E''}$, $R^{F''}$, $R^{G''}$, $R^{H''}$, $R^{I''}$, $R^{J''}$, $R^{K''}$, $R^{L''}$, $R^{M''}$ and $R^{N''}$ is independently a hydrogen or a substituent selected from the group consisting of the General Substituents defined herein.

In some embodiments, the metal carbene complex is selected from the group consisting of the structures in the following LIST 6:

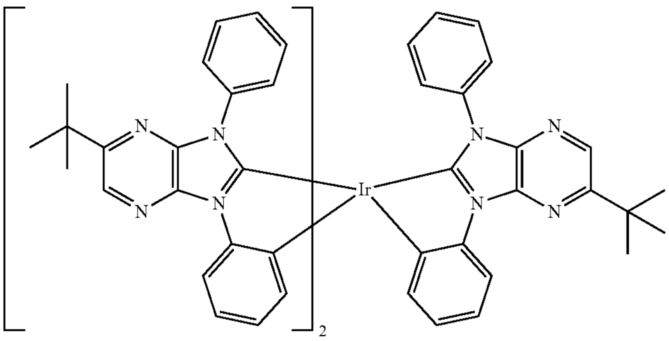

,

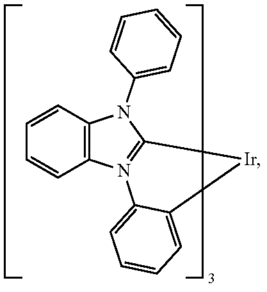

-continued
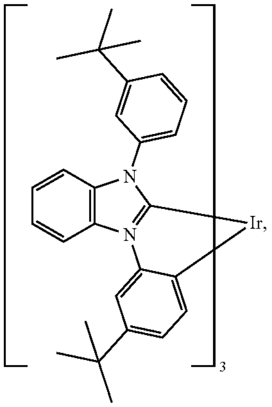
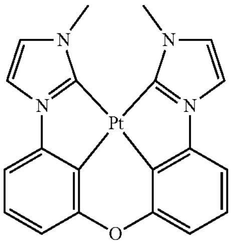
,
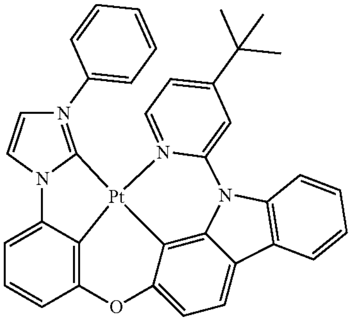
,
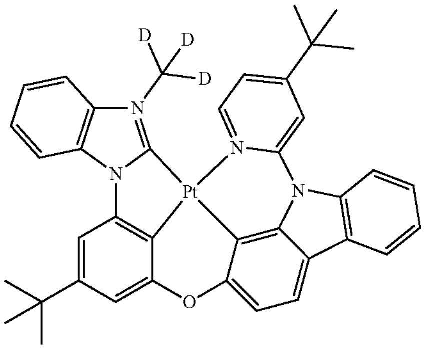
,
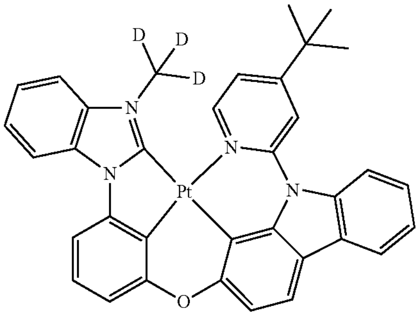
,
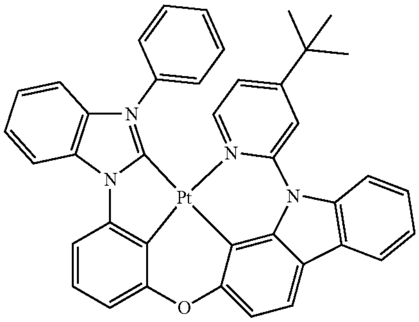
,
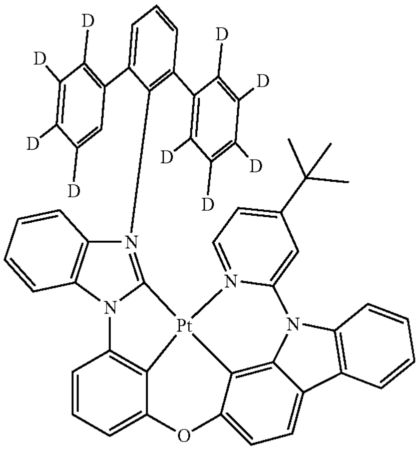
,
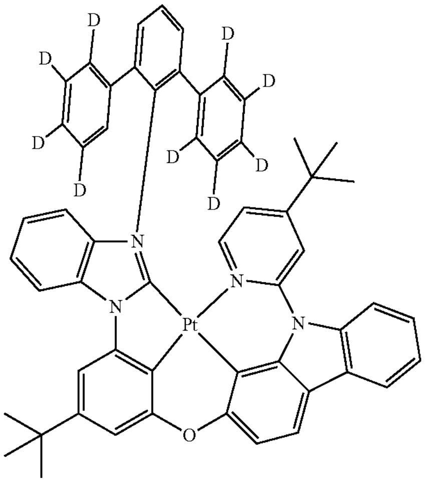
,
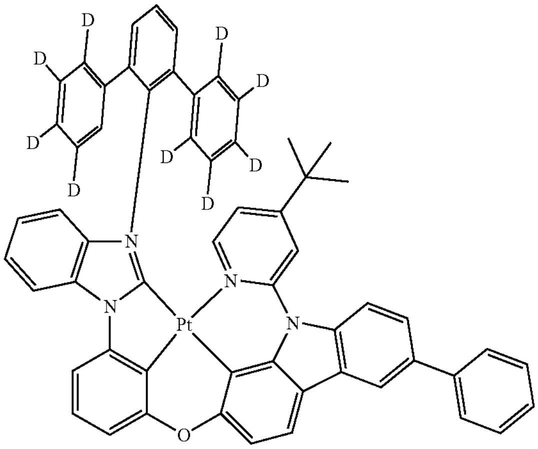
, -continued
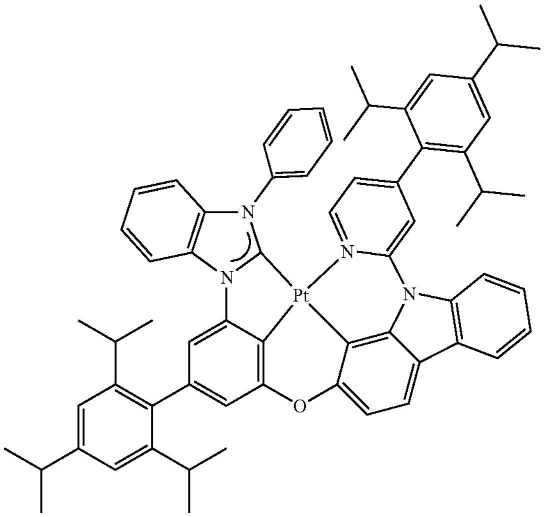
,
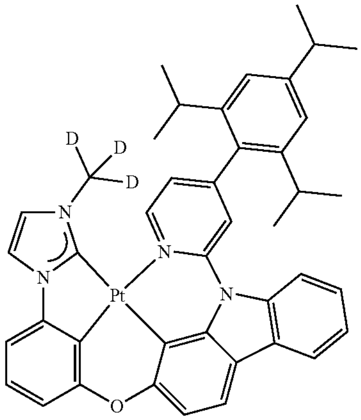
,
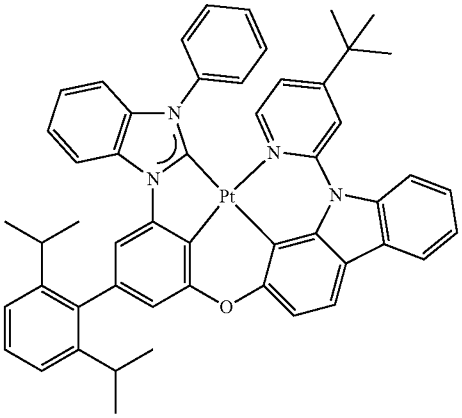
,
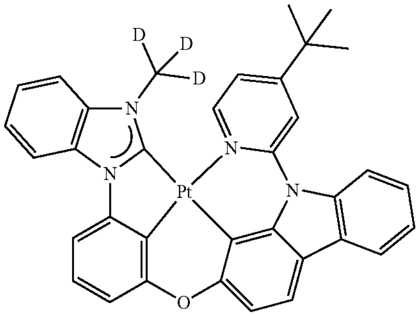
,
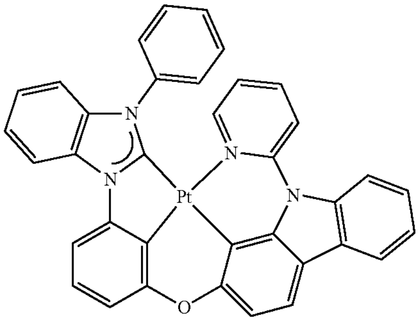
,
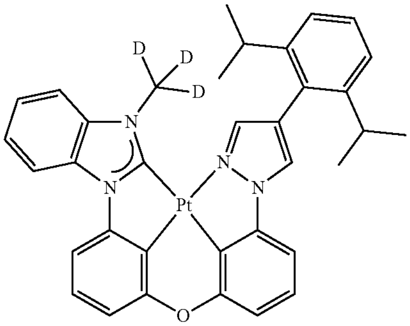
,
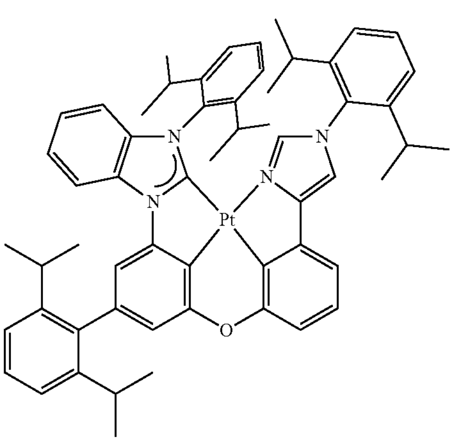
,
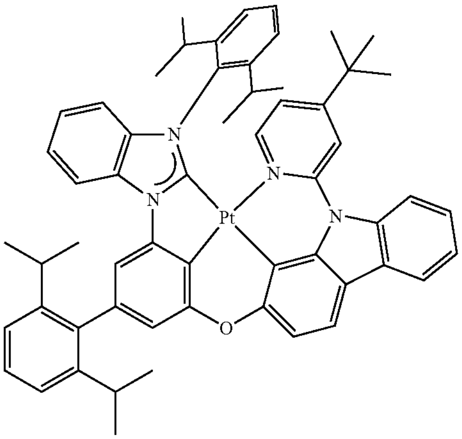
, -continued
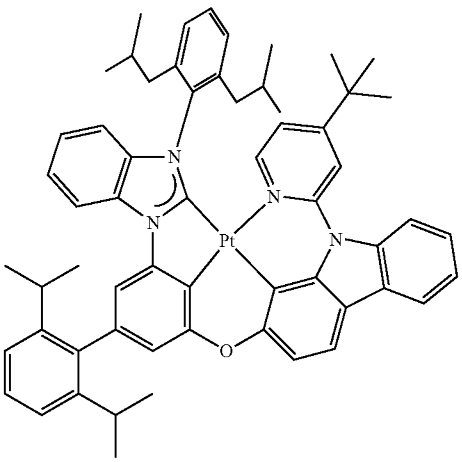
,
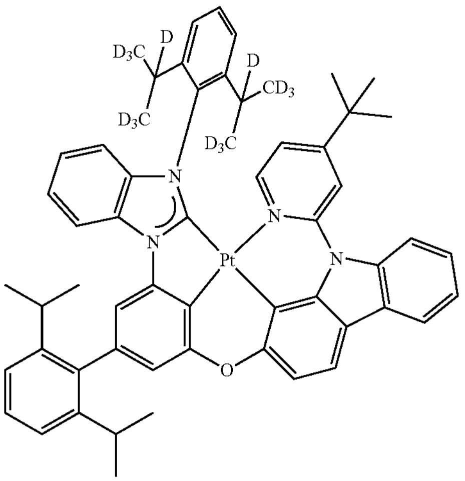
,
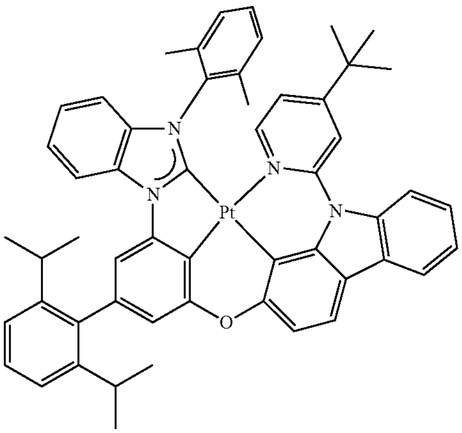
,
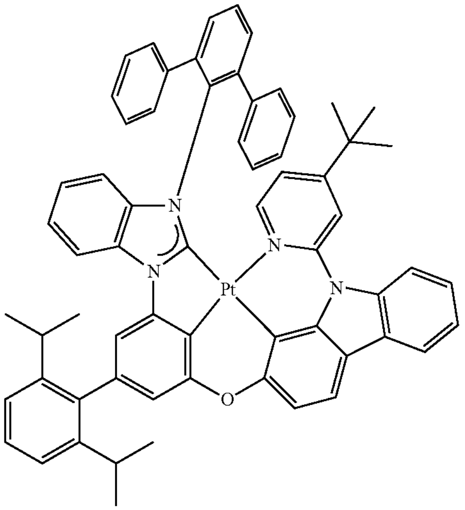
,
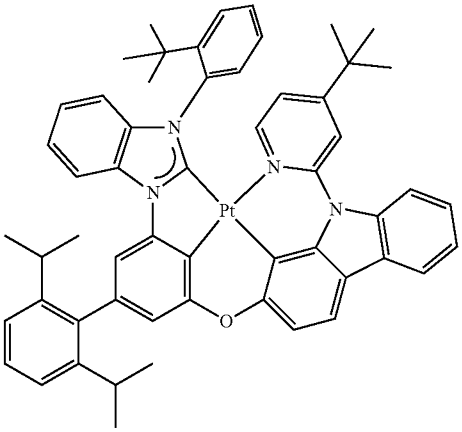
,
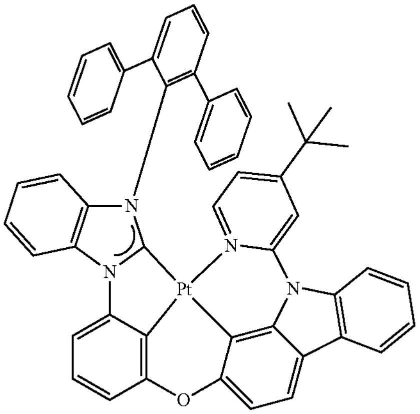
, -continued
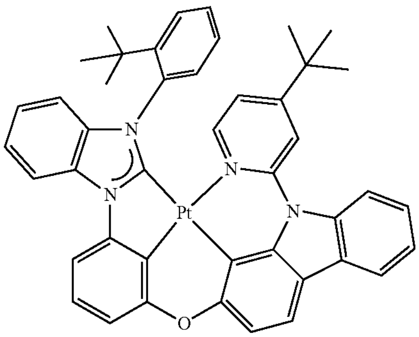,
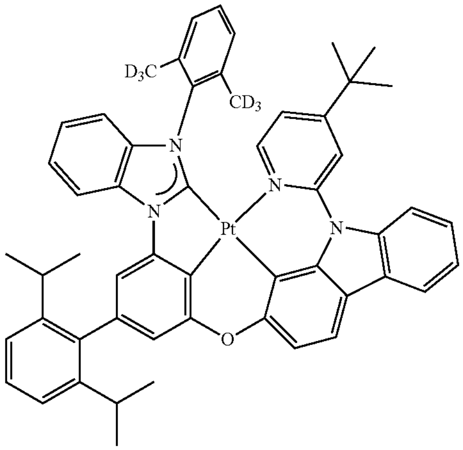,
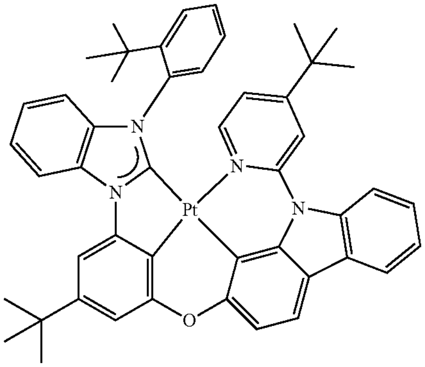,
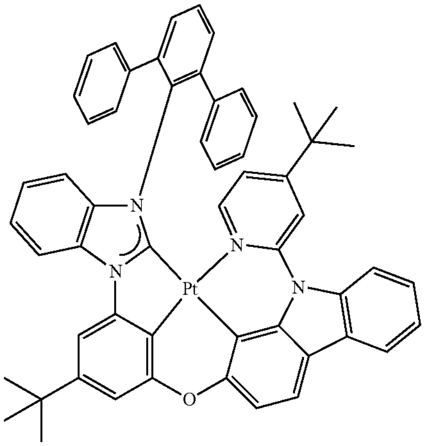,
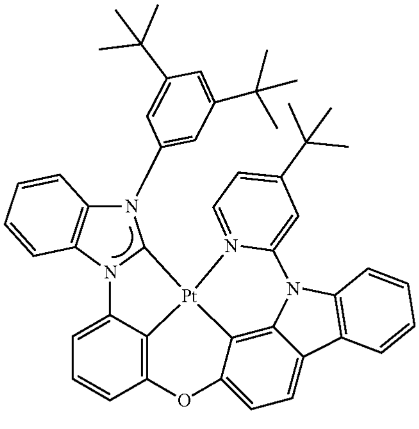,
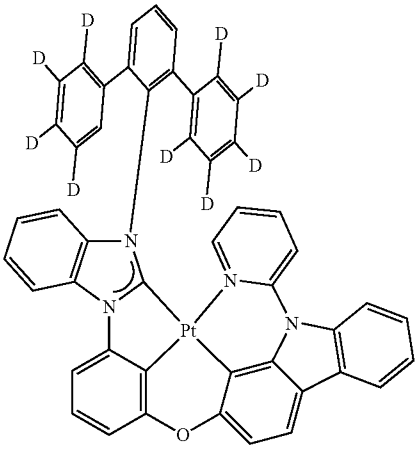, -continued
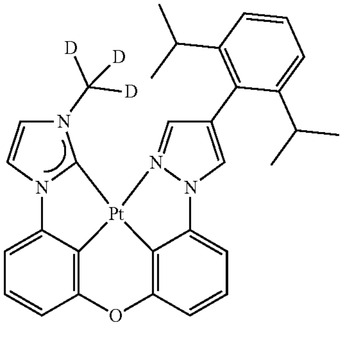,
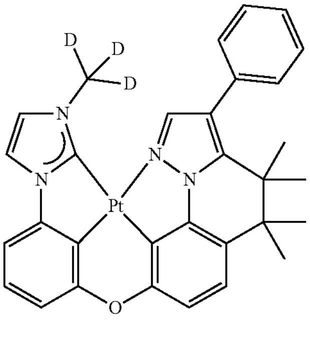,
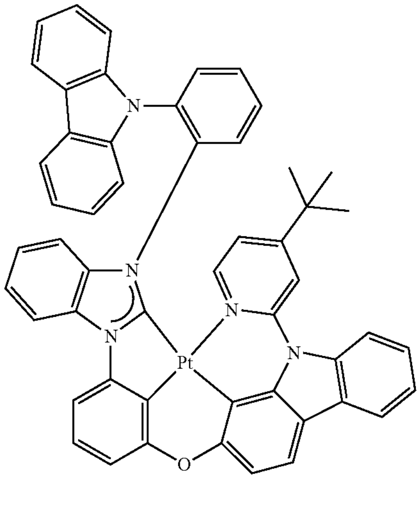,
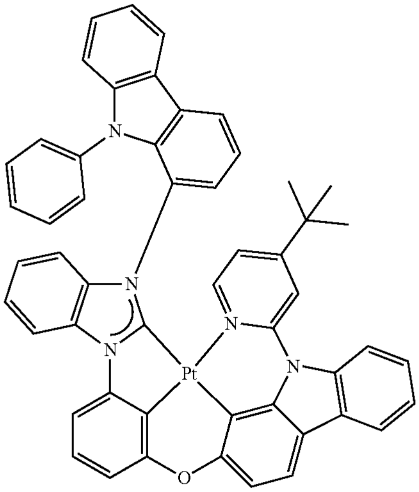,
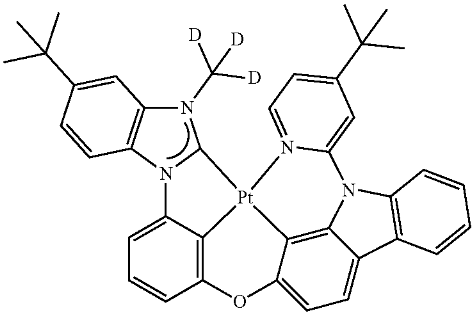,
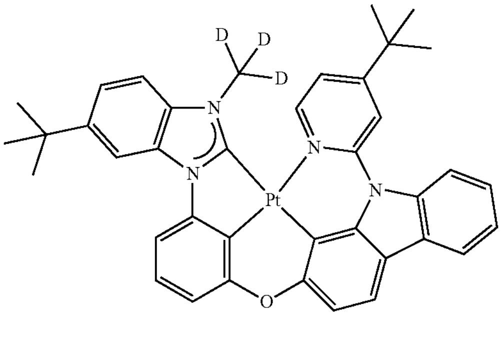,
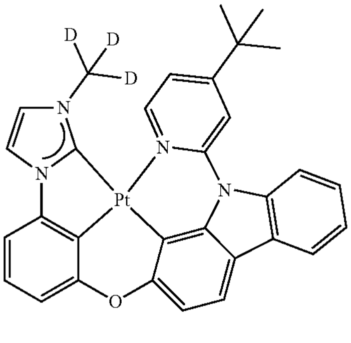, -continued
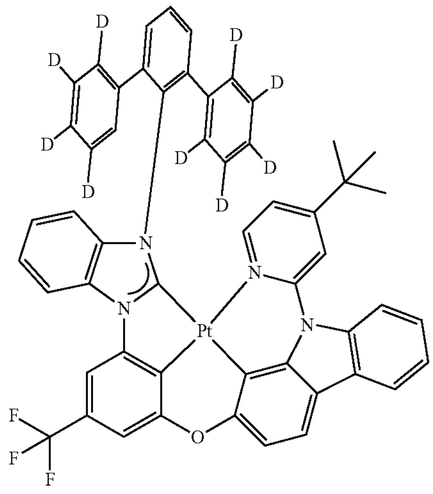,
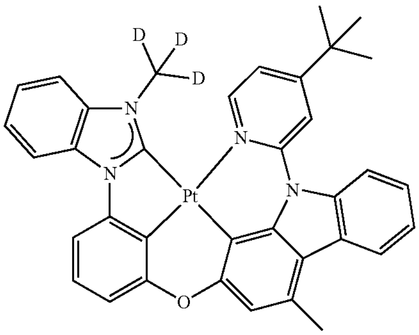,
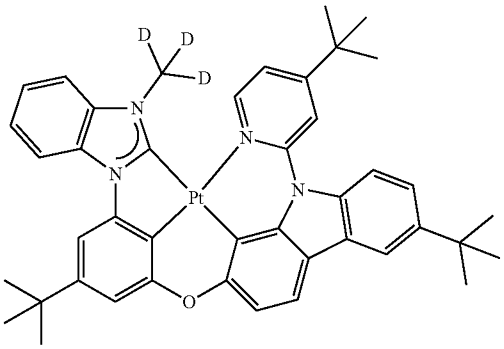,
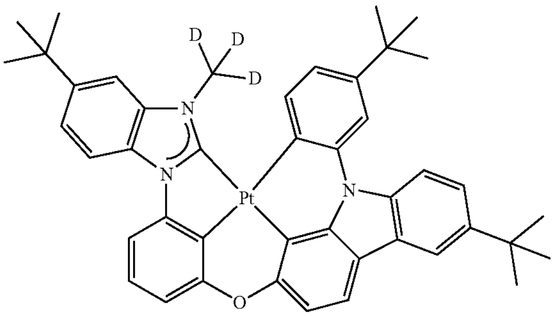,
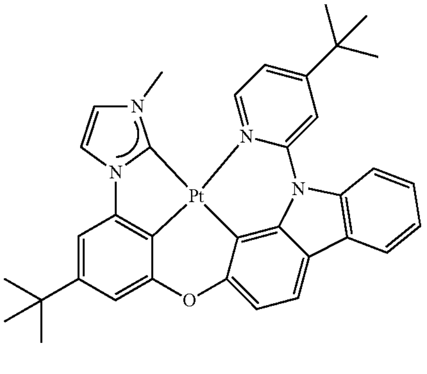,
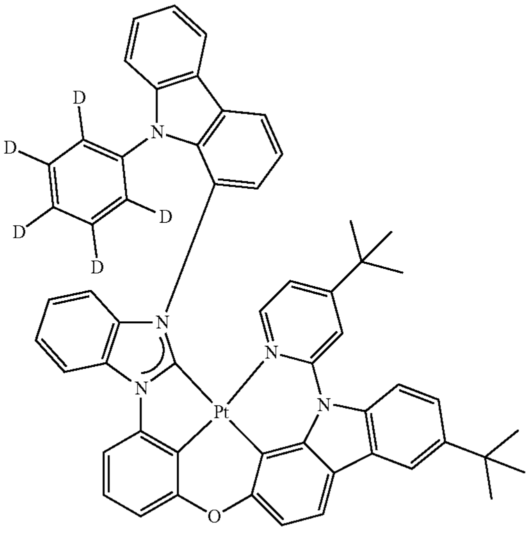, -continued
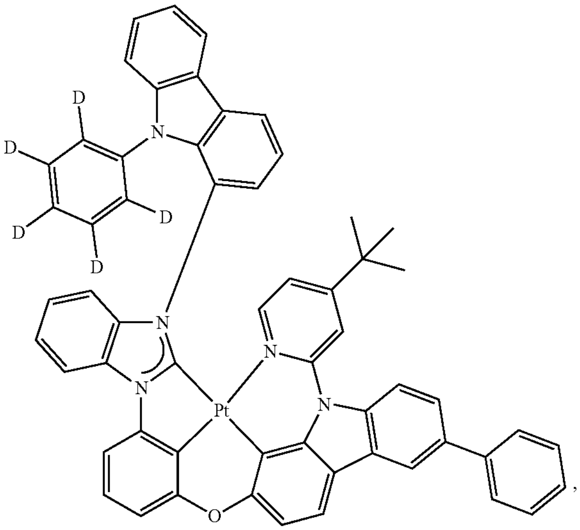
,
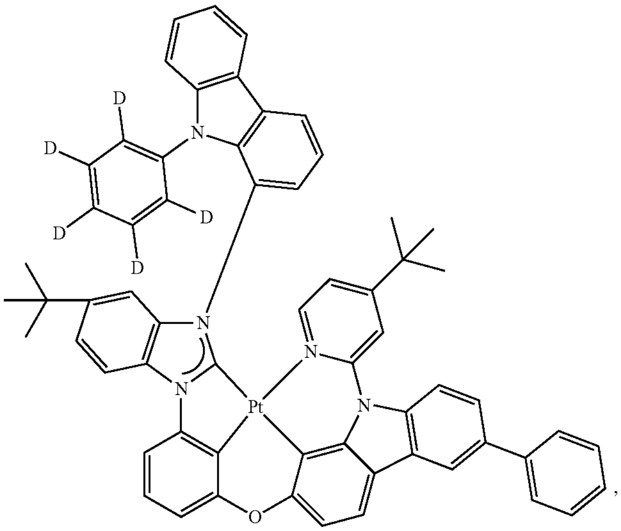
,
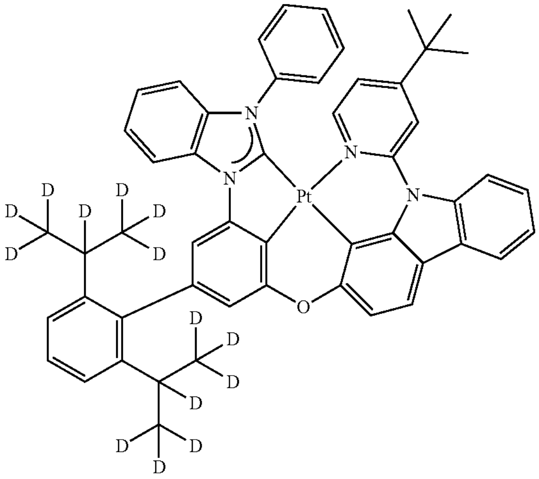
,
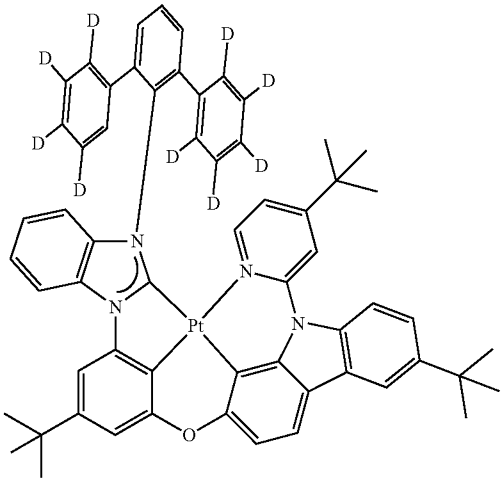
,
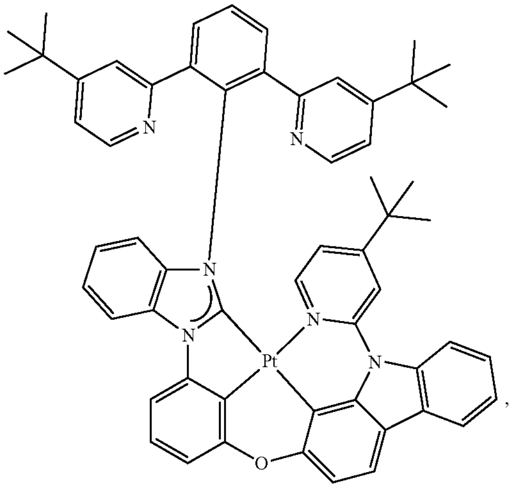
, -continued
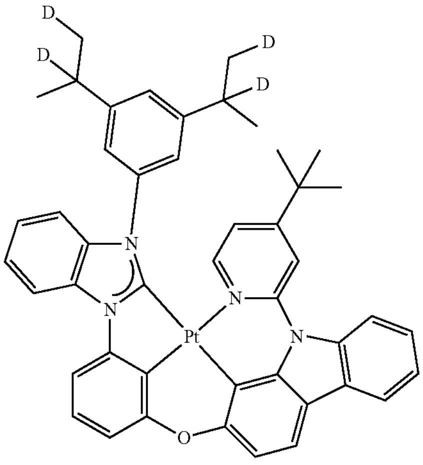
,
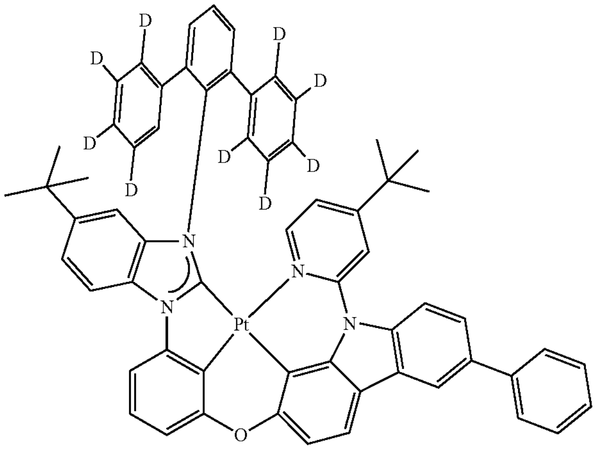
,
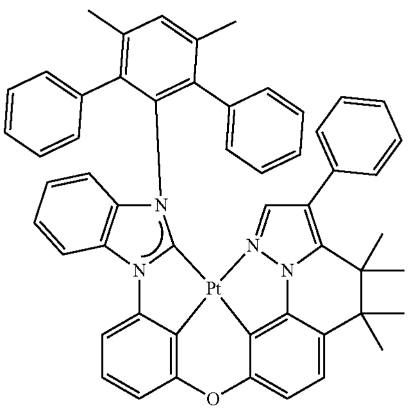
,
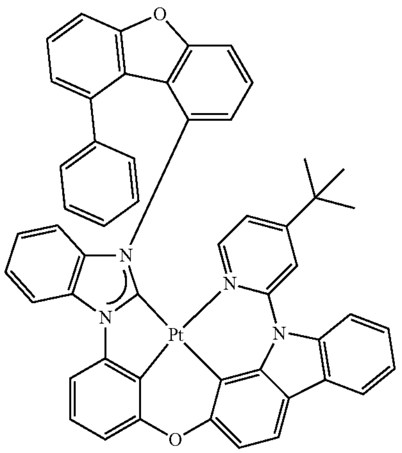
,
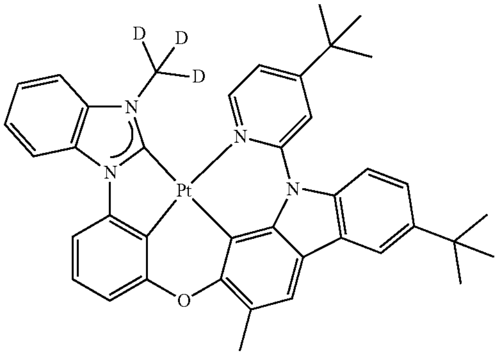
,
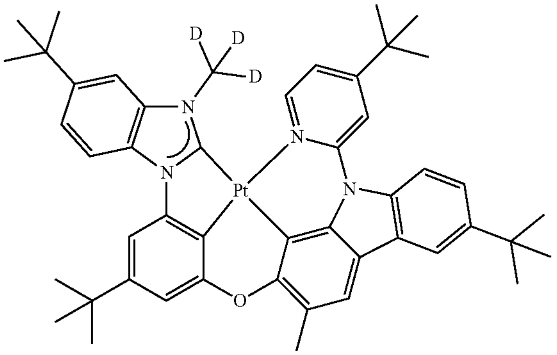
, -continued
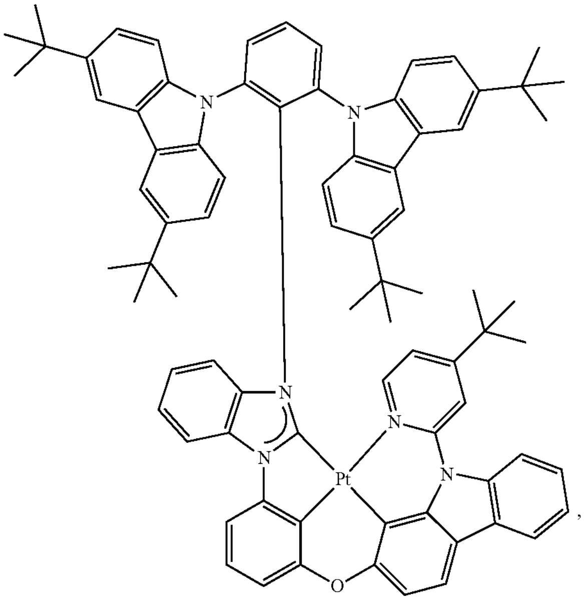
,
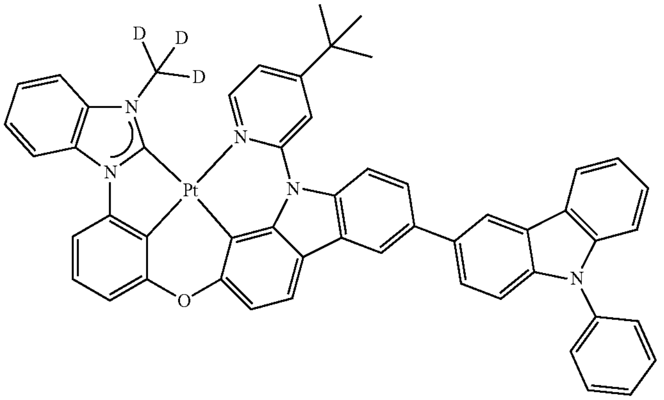
,
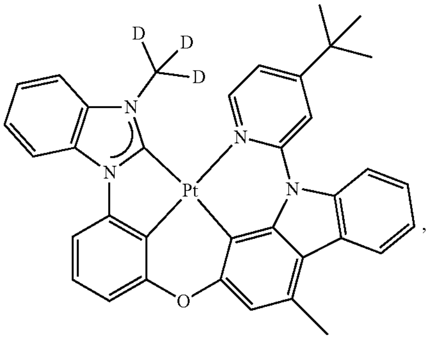
,
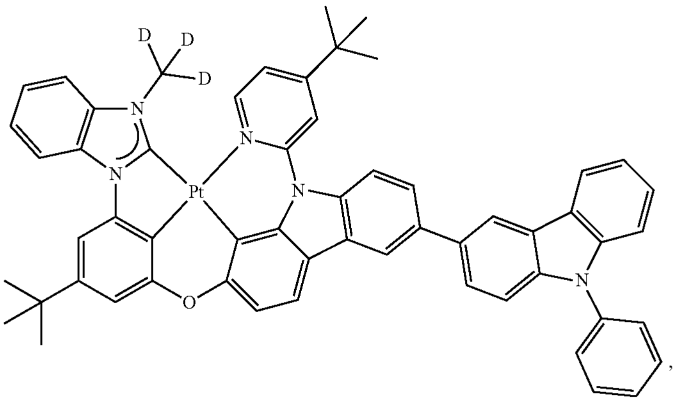
, -continued
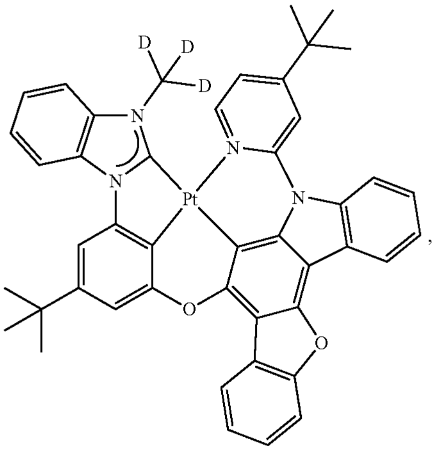
,
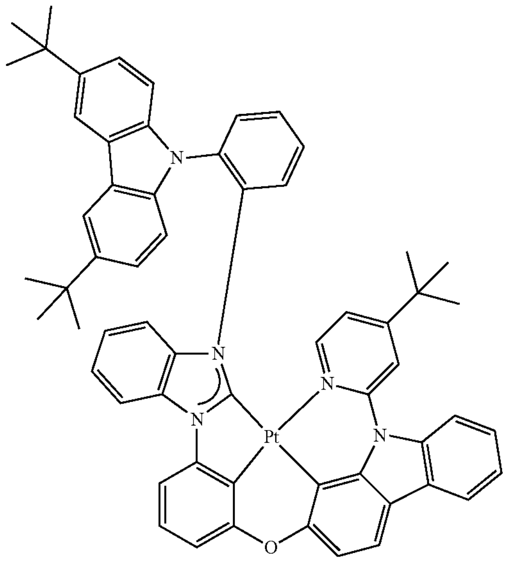
,
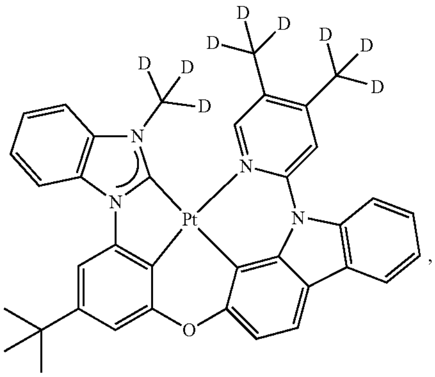
,
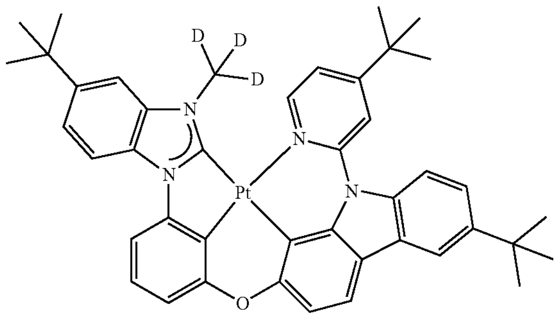
,
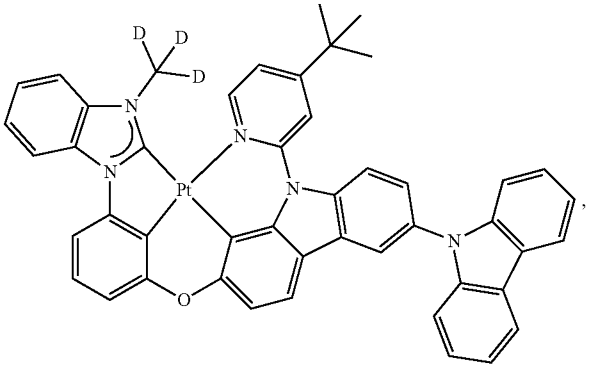
, -continued
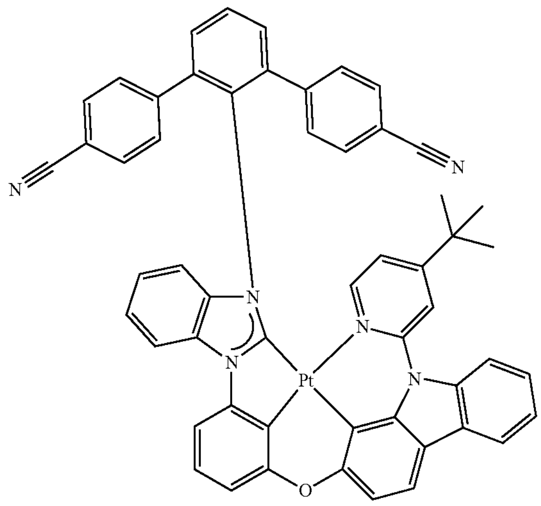,
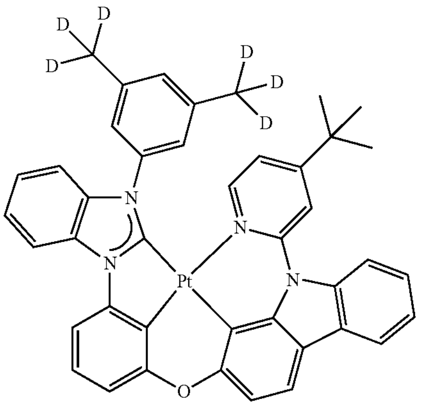,
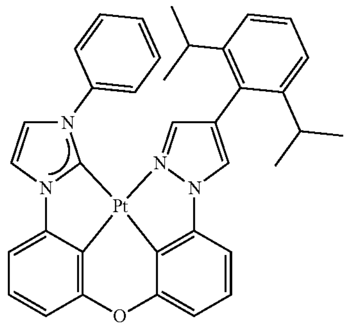,
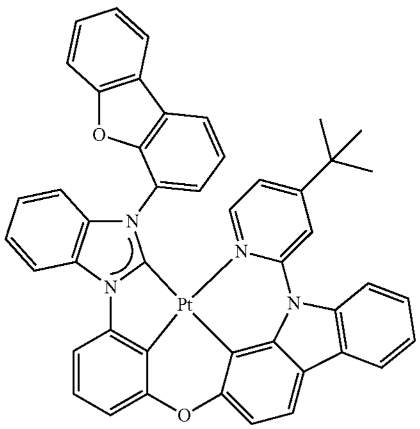,
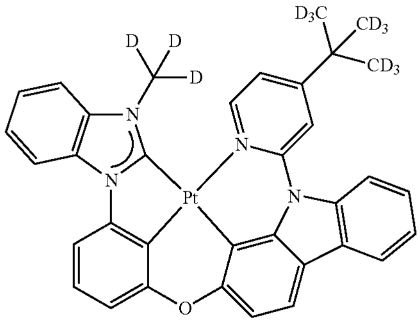,
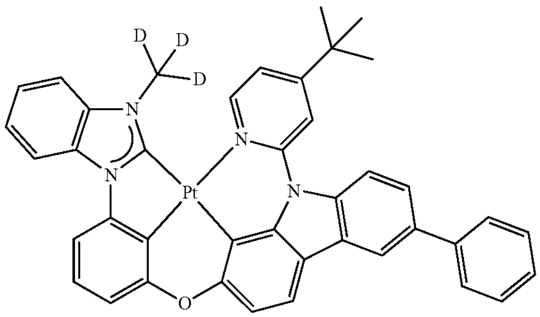,
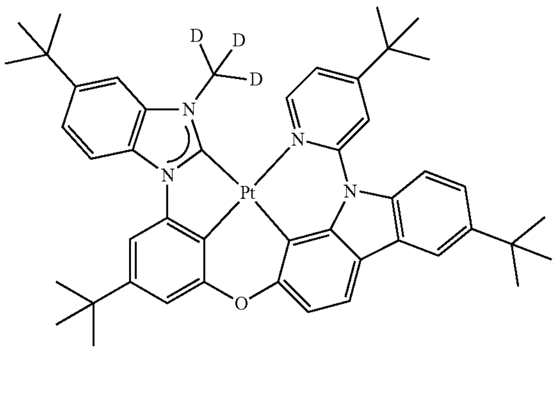,
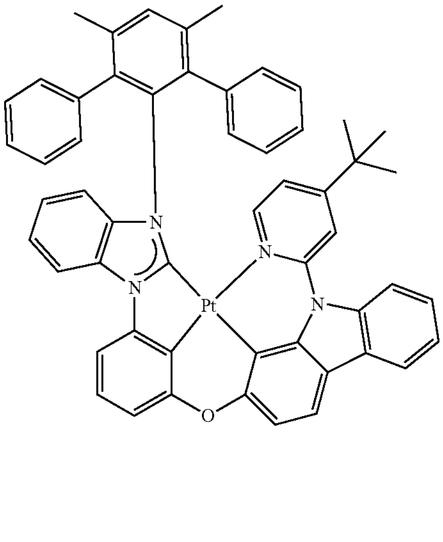, -continued
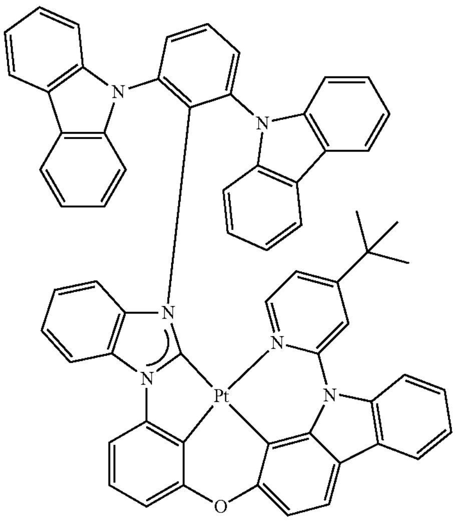
,
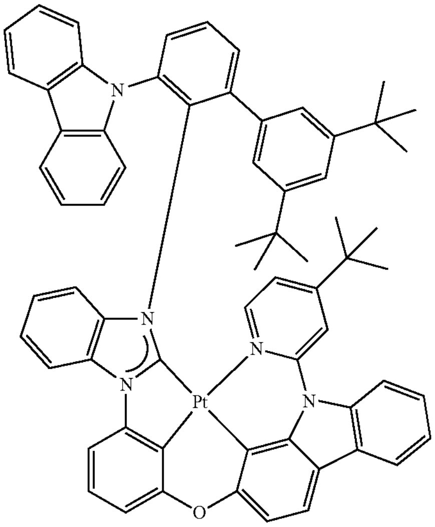
,
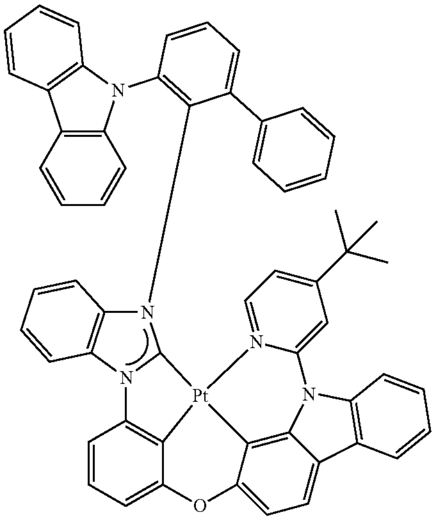
,
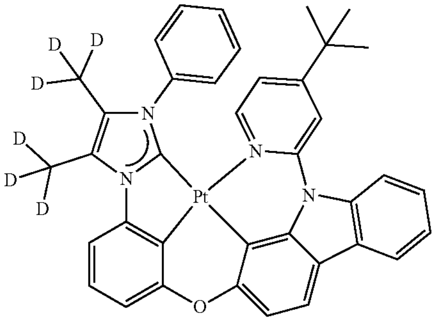
,
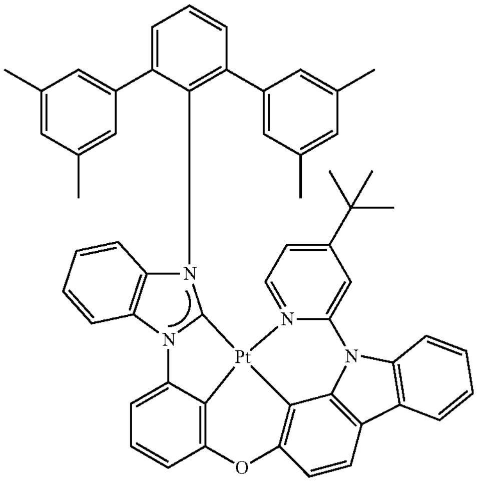
,
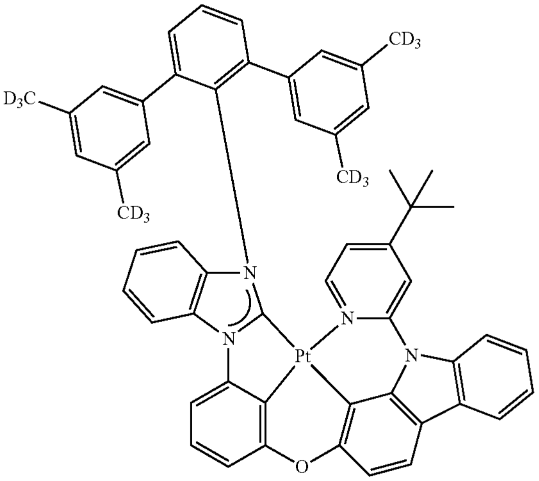
, -continued
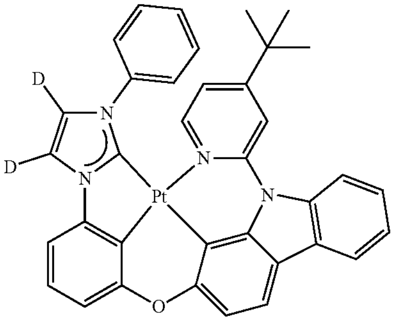
,
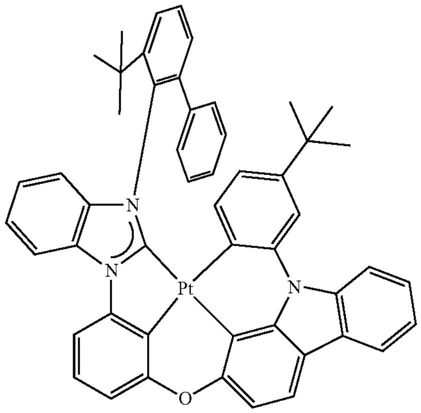
,
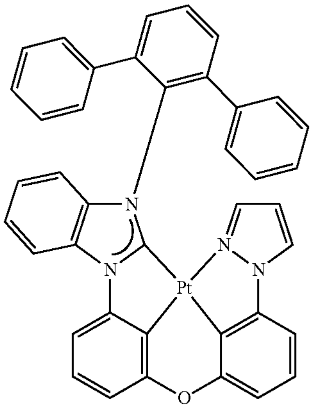
,
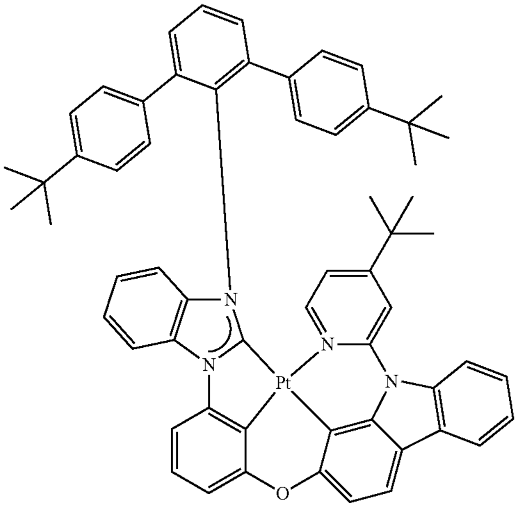
,
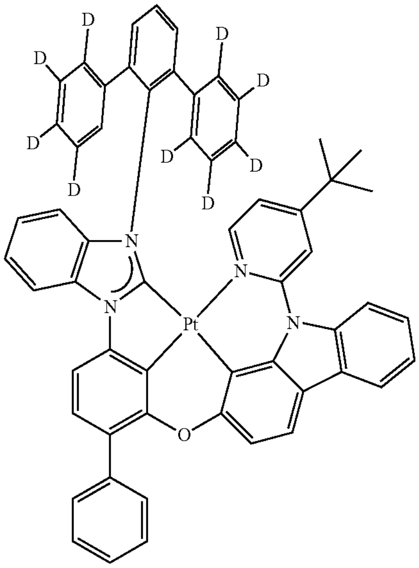
,
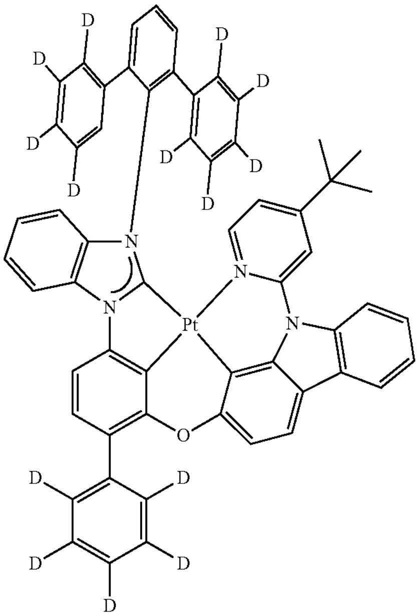
, -continued
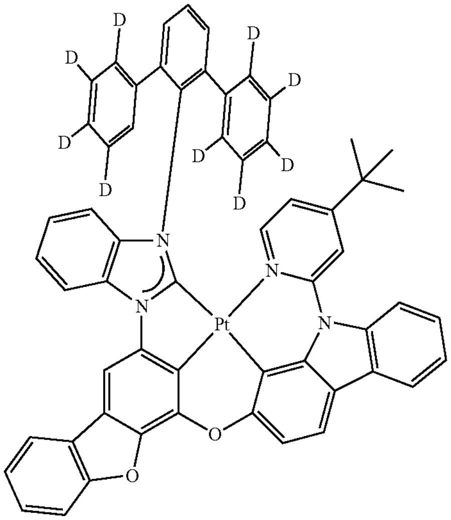
,
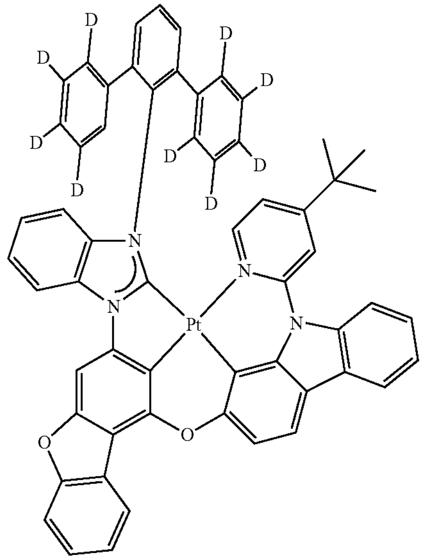
,
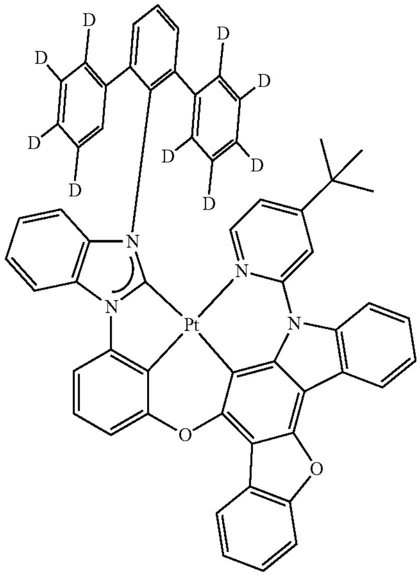
,
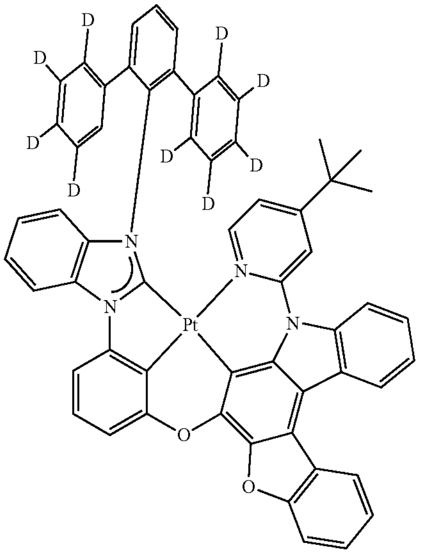
,
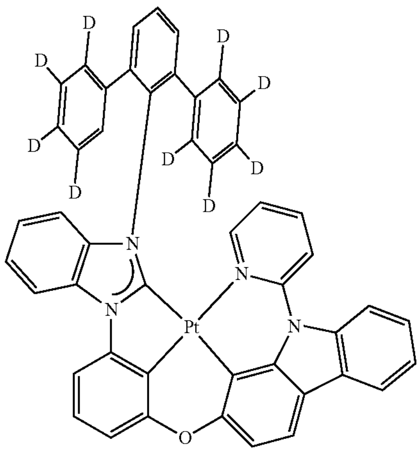
,
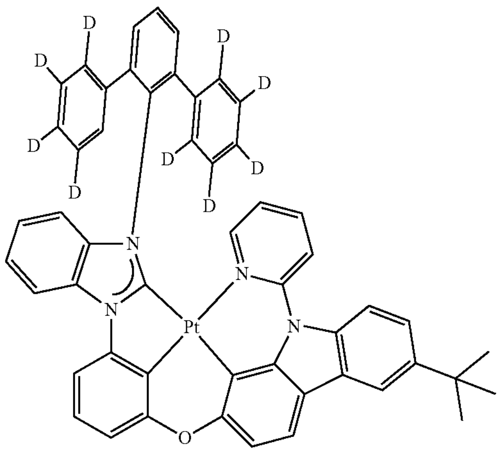
, -continued
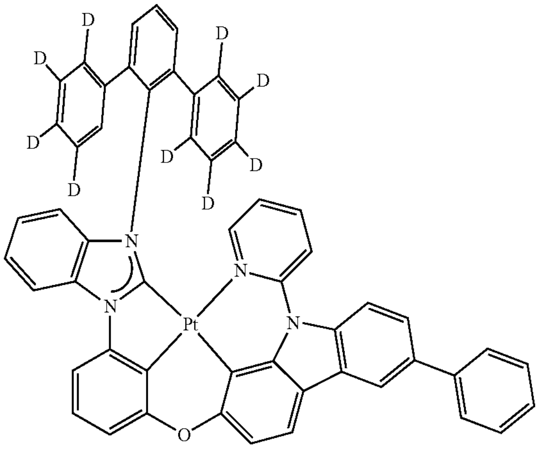,
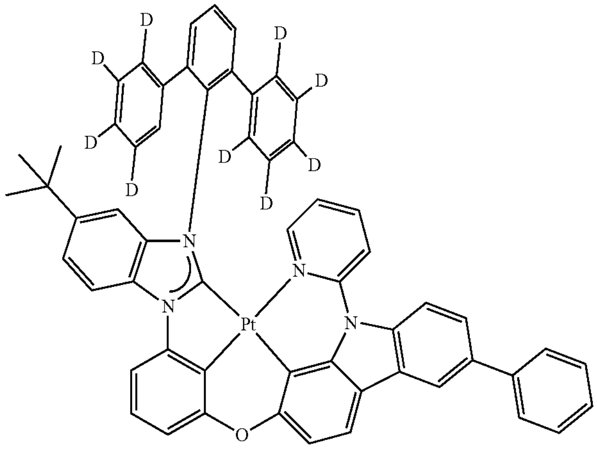,
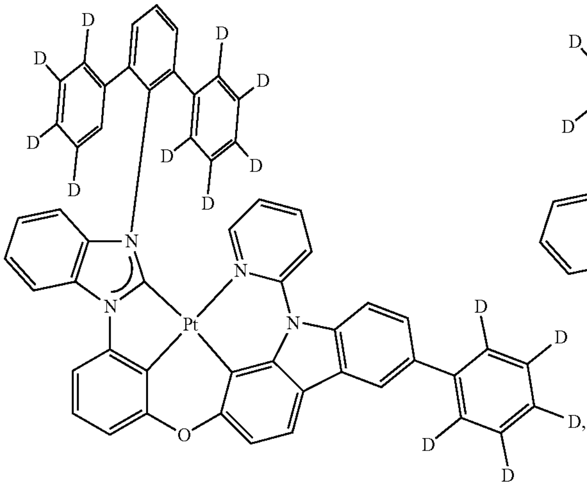,
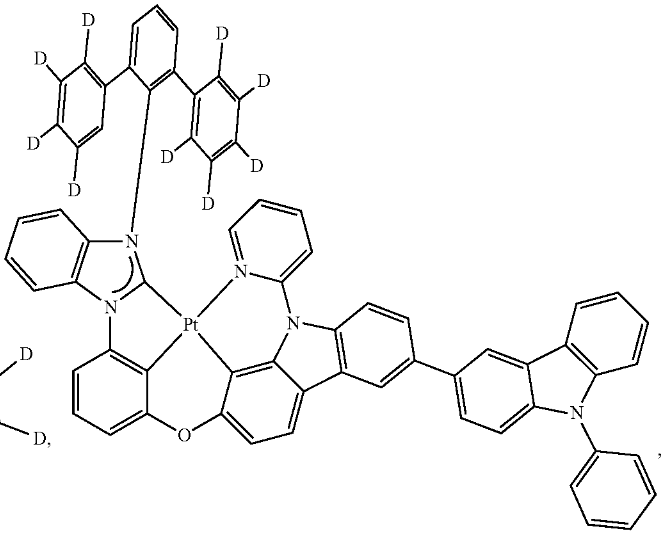,
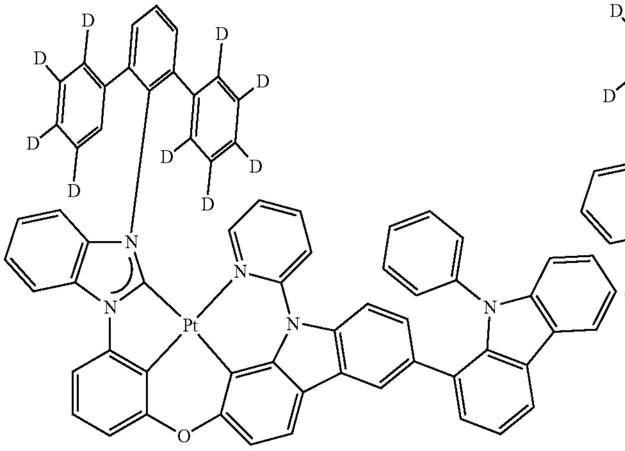,
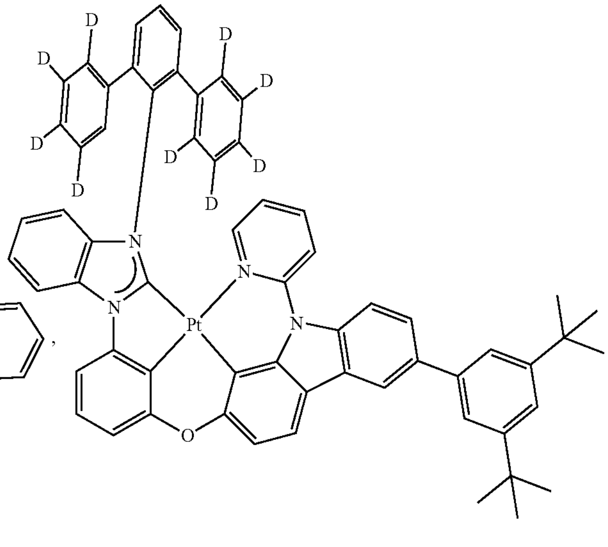, -continued
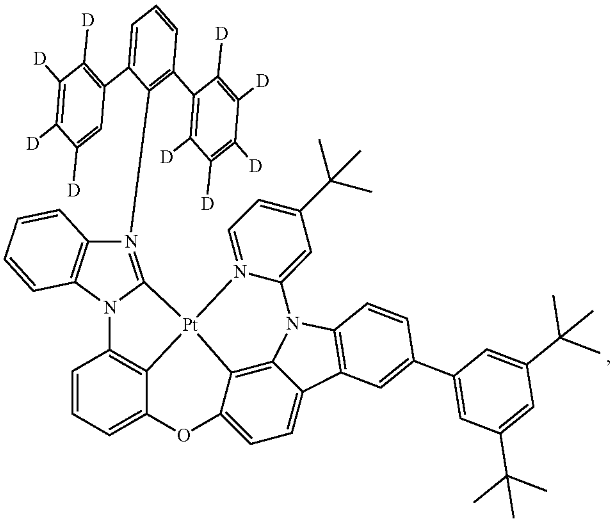
,
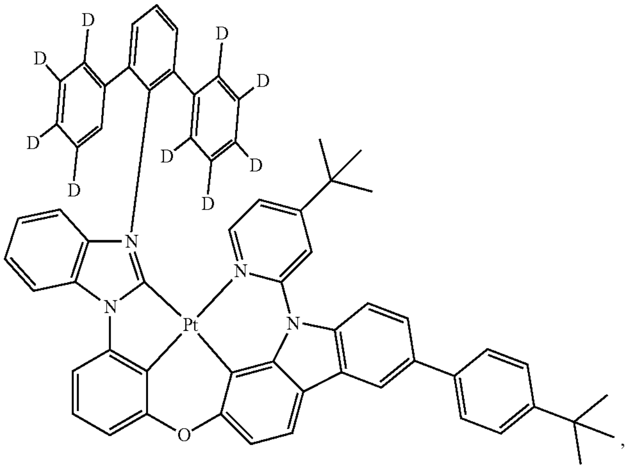
,
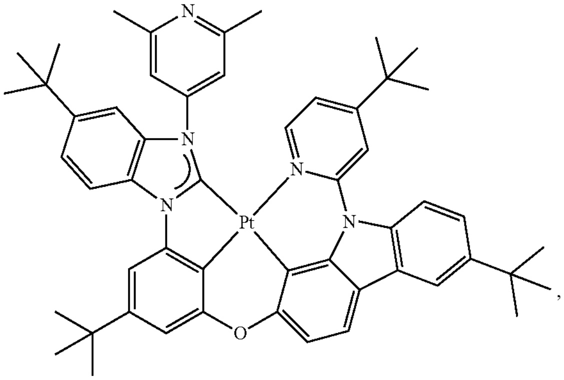
,
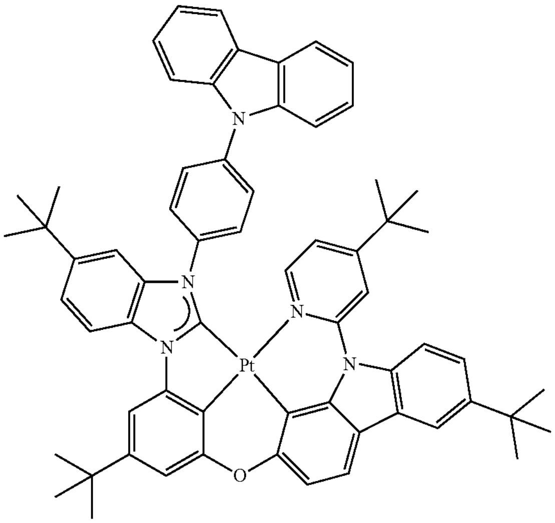
, -continued
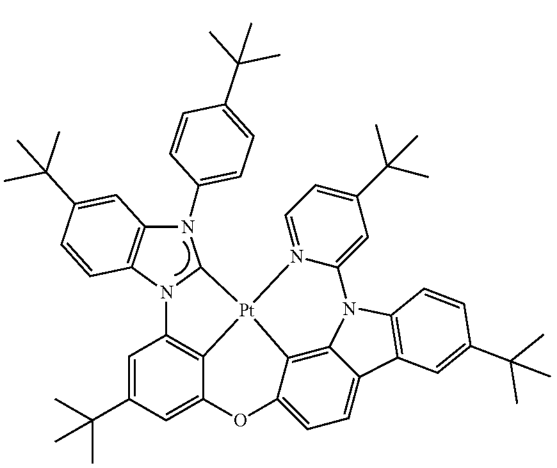
,
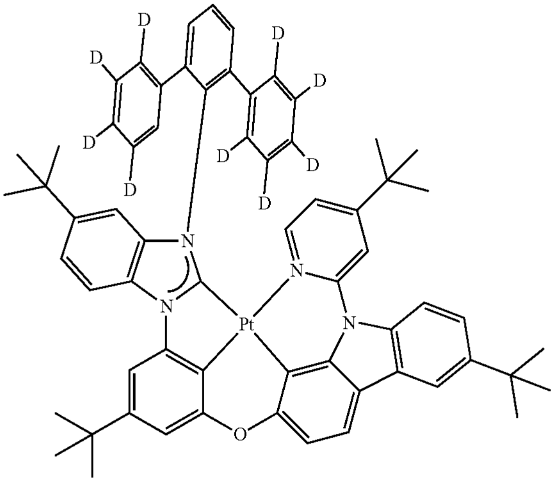
,
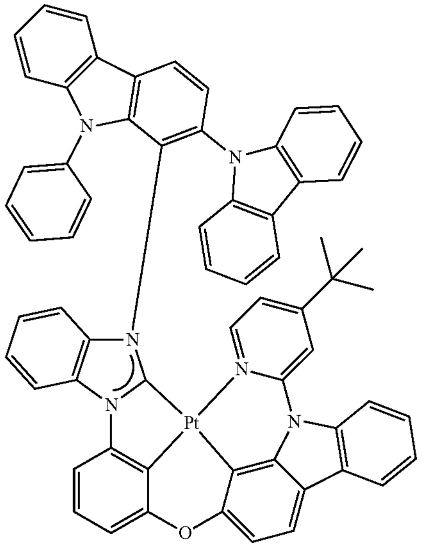
,
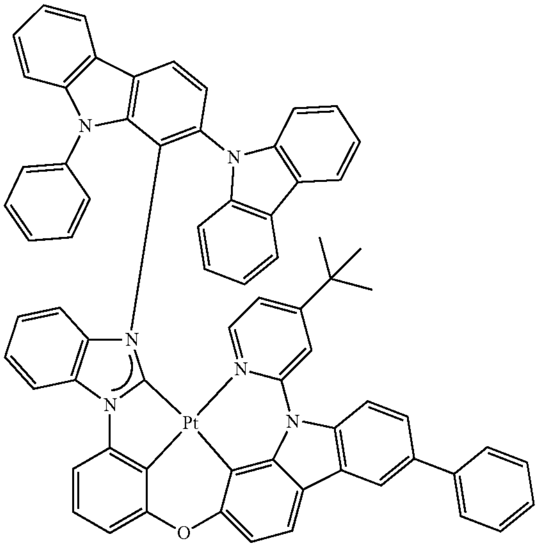
,
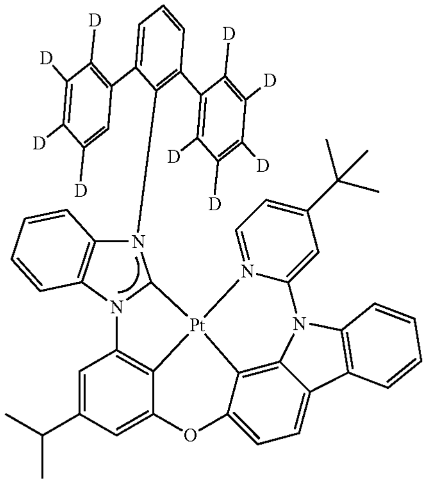
,
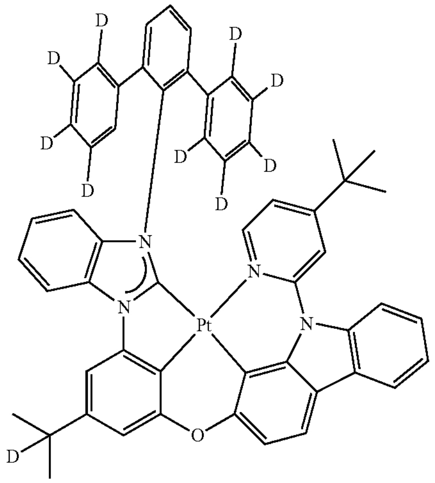
, -continued
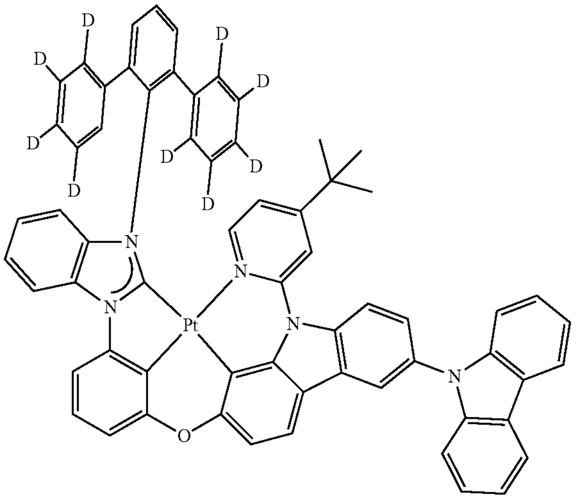
,
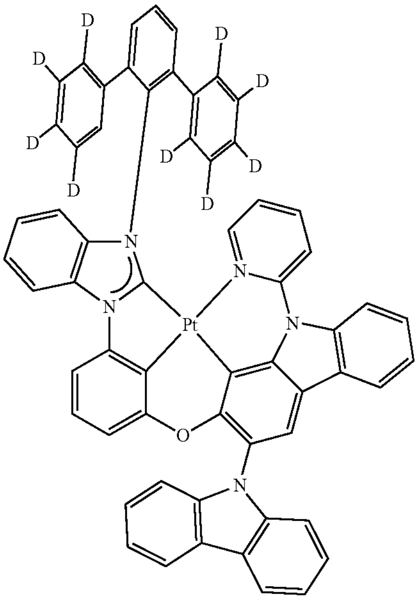
,
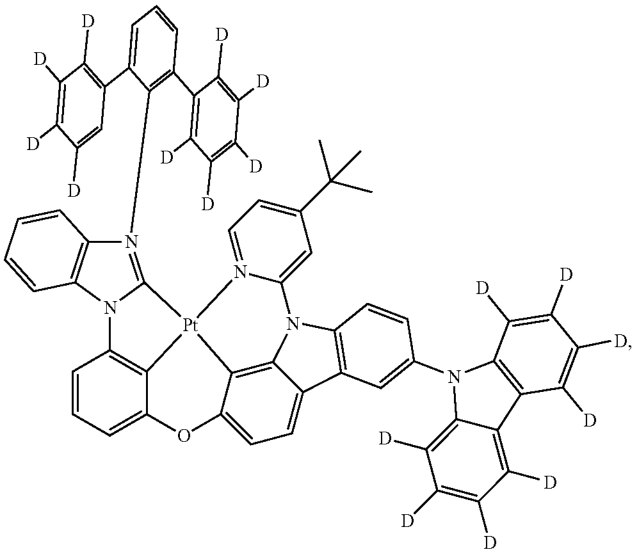
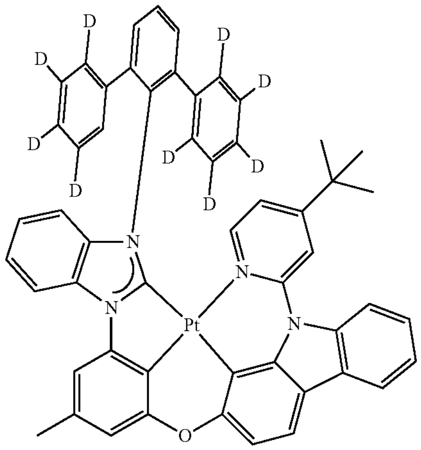
,
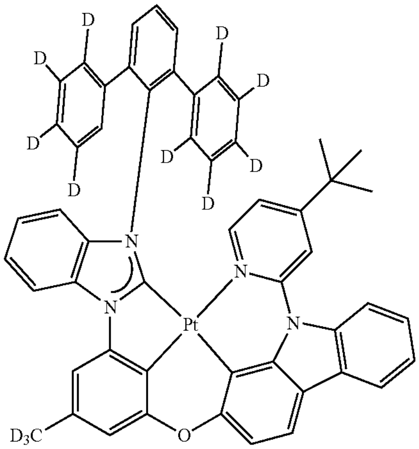
,
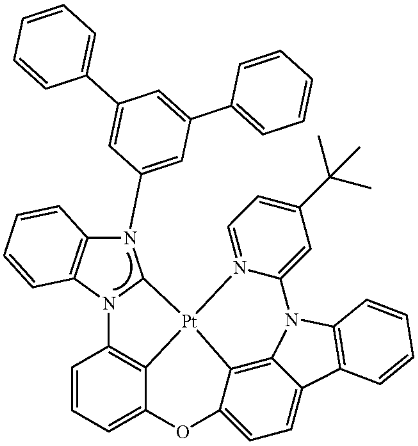
, -continued
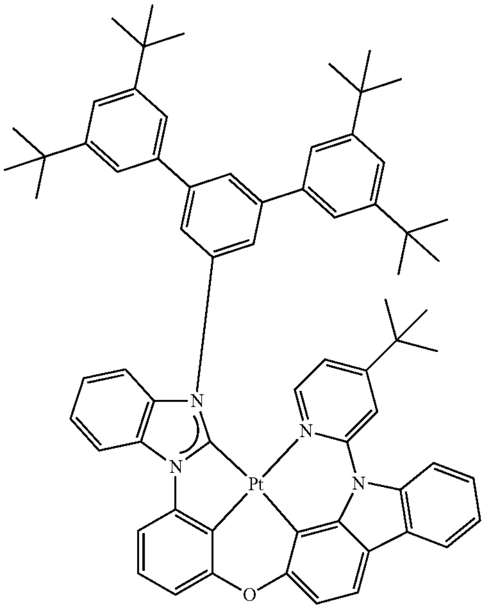,
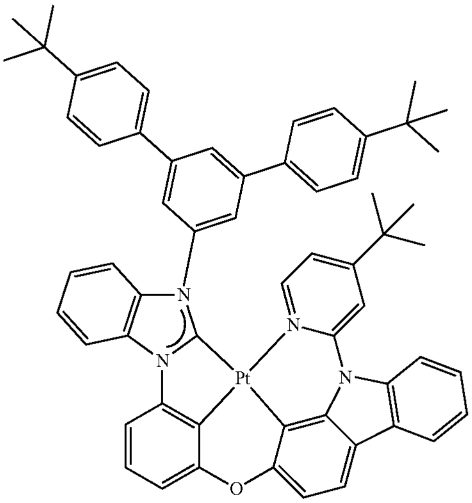,
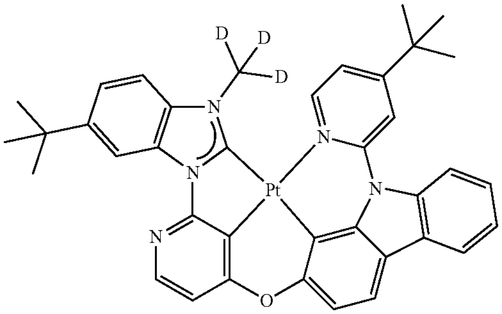,
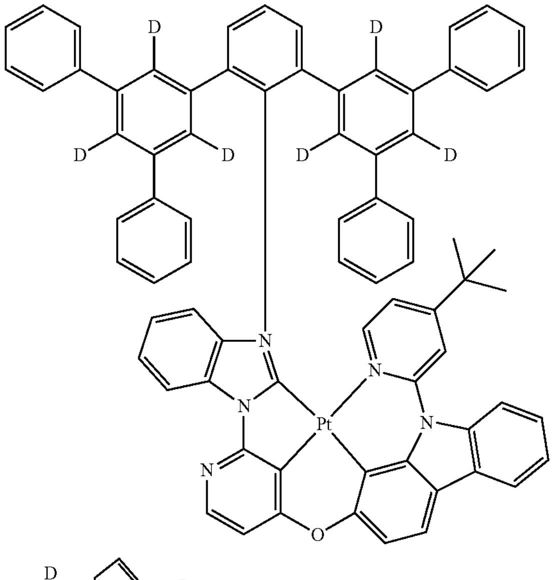,
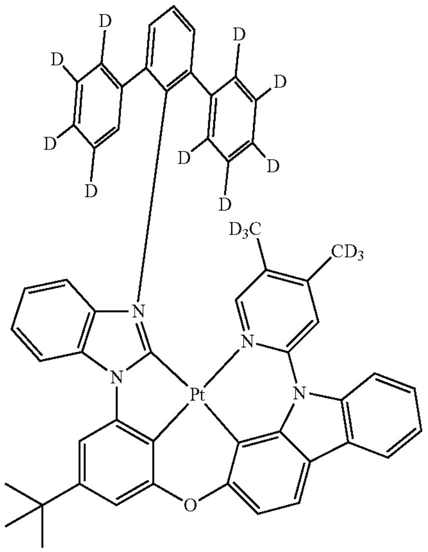,
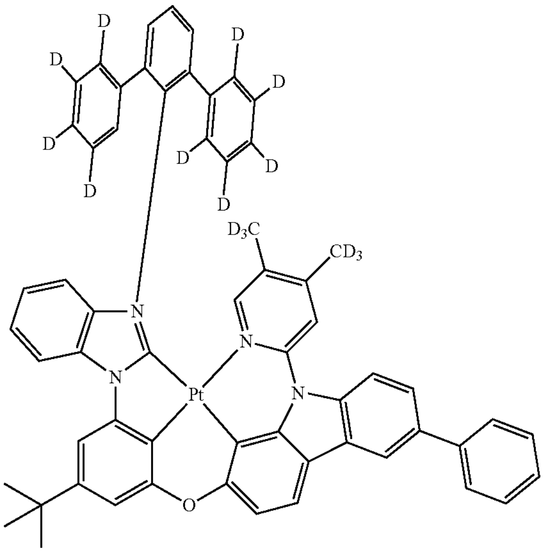, -continued
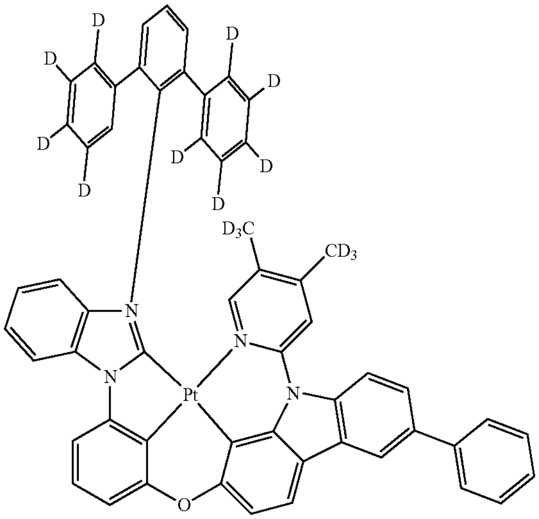
,
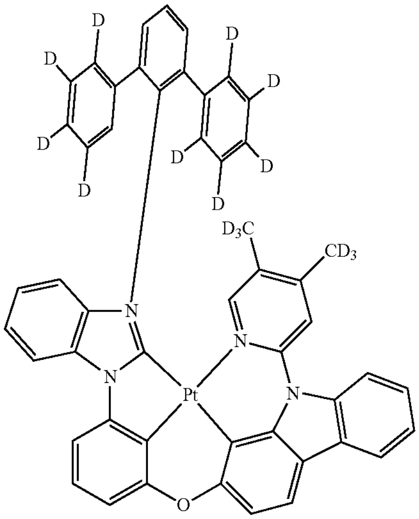
,
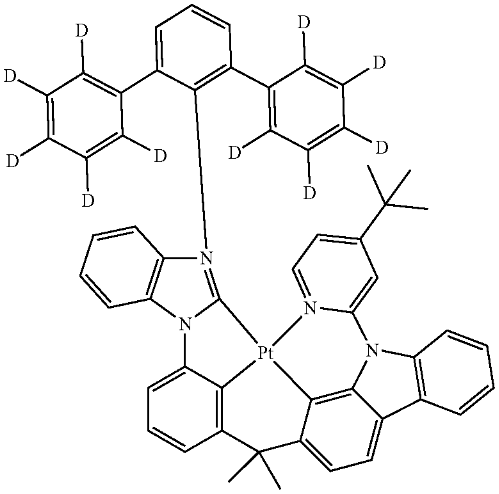
,
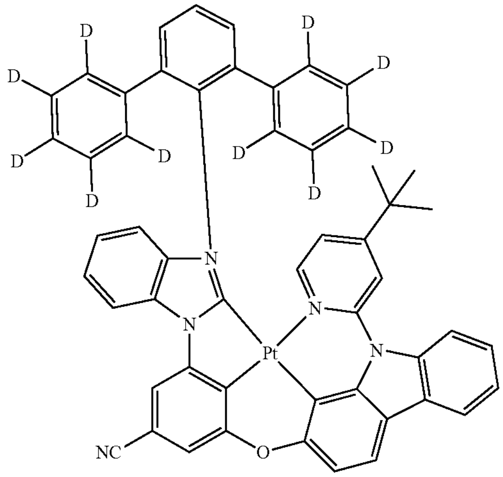
,
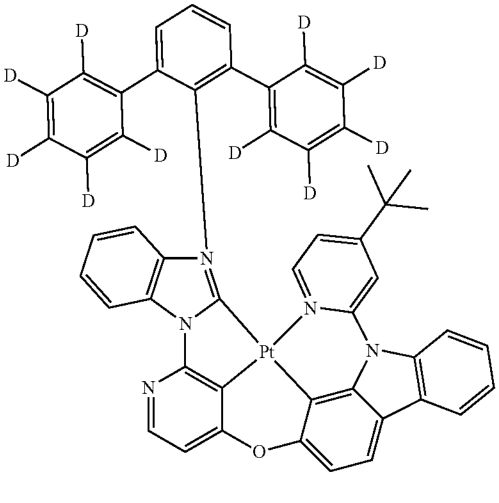
,
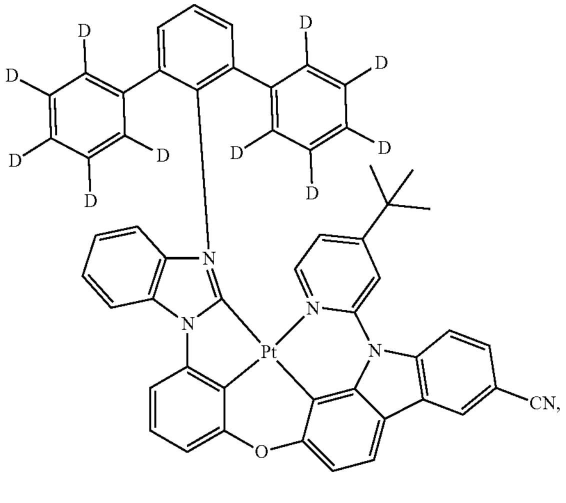

-continued
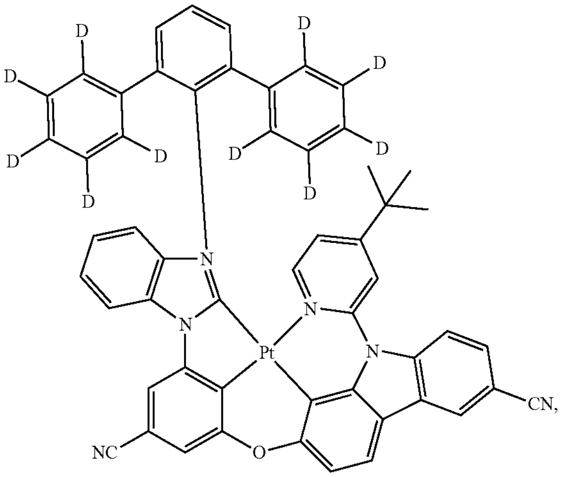
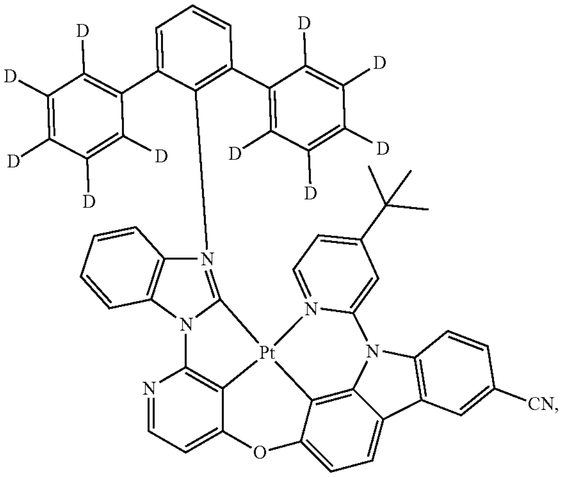
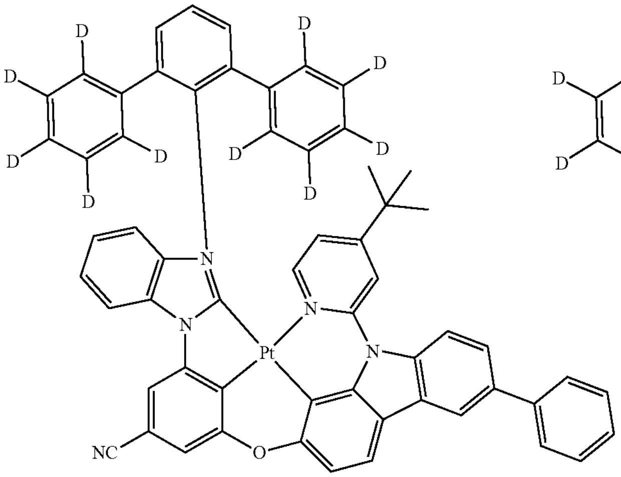
,
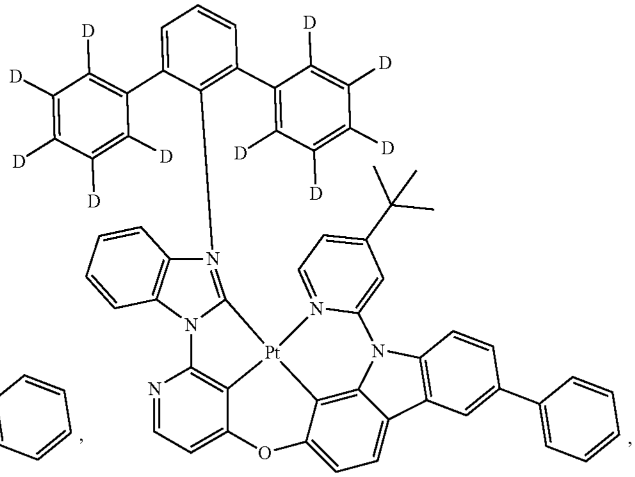
,
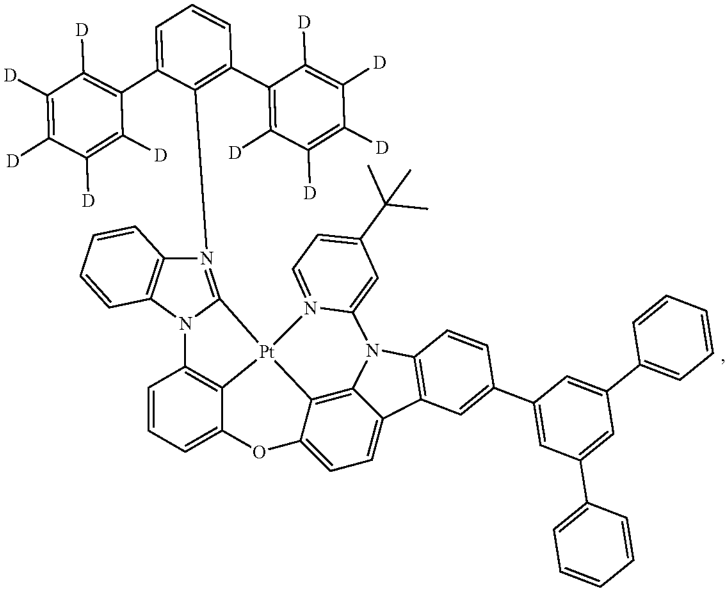
,

-continued
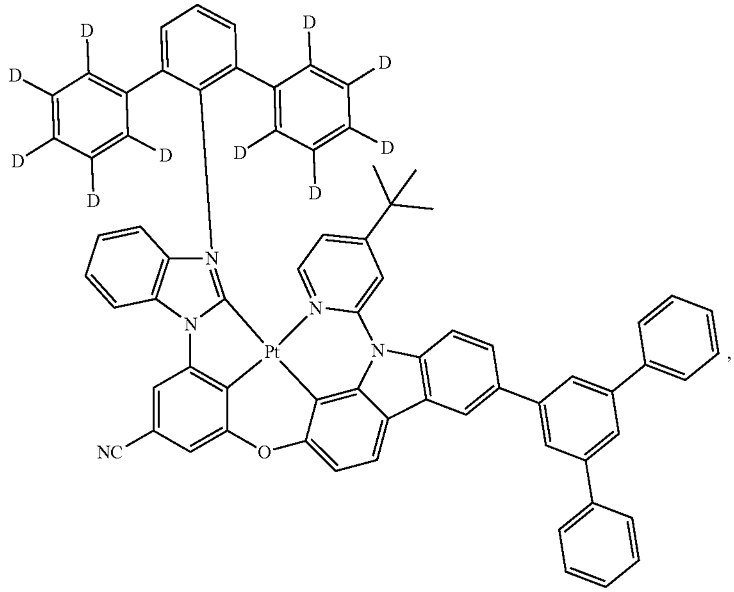
,
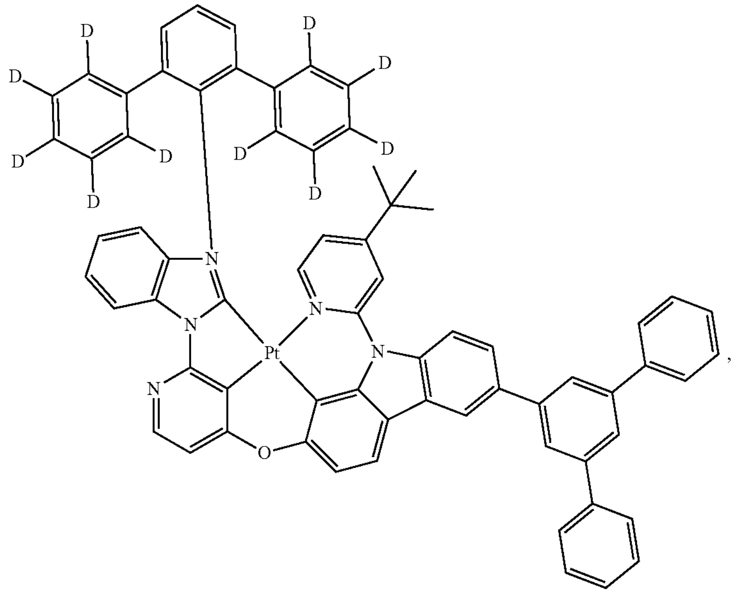
,

-continued
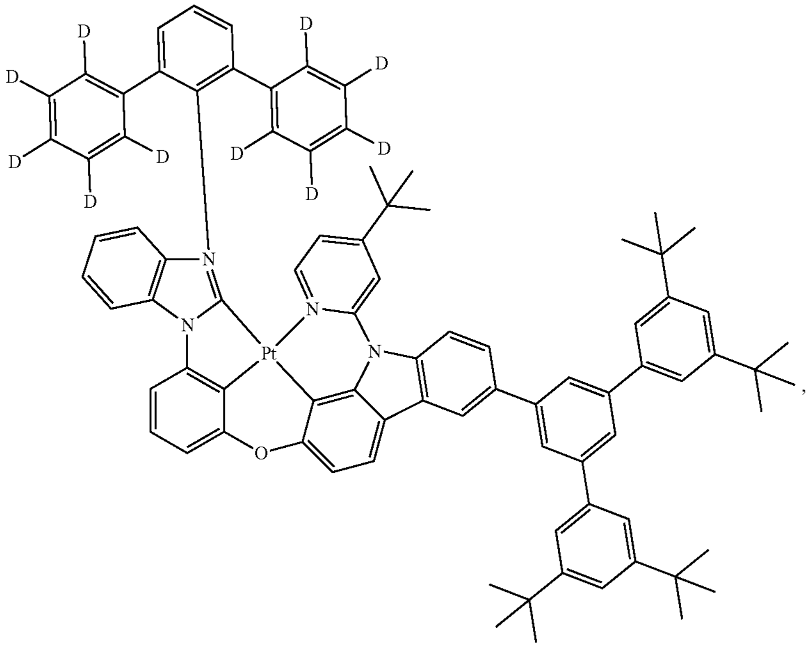
,
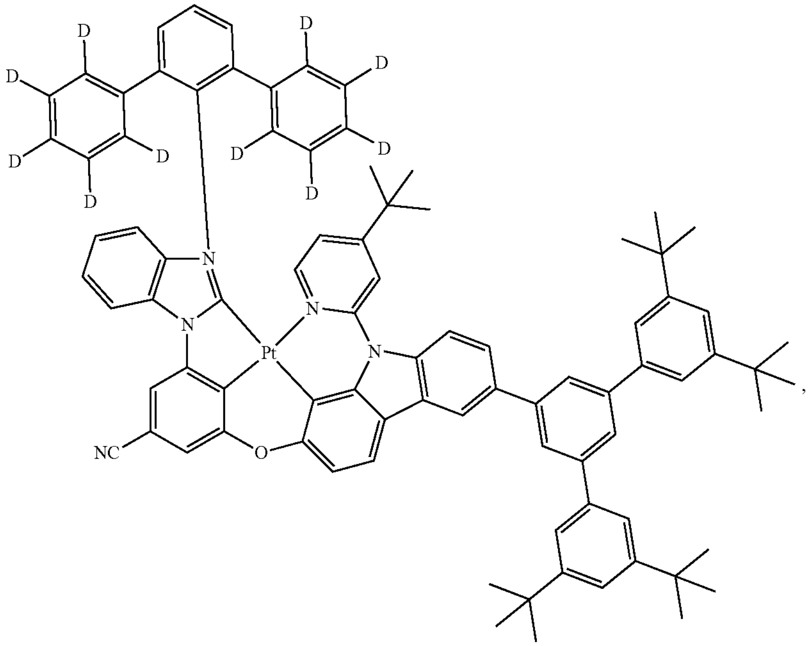
,

-continued
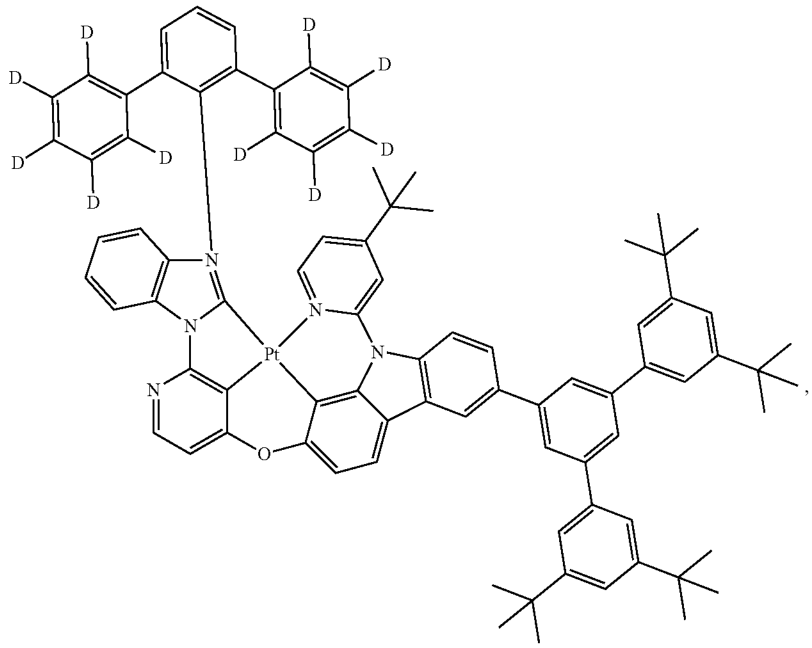
,
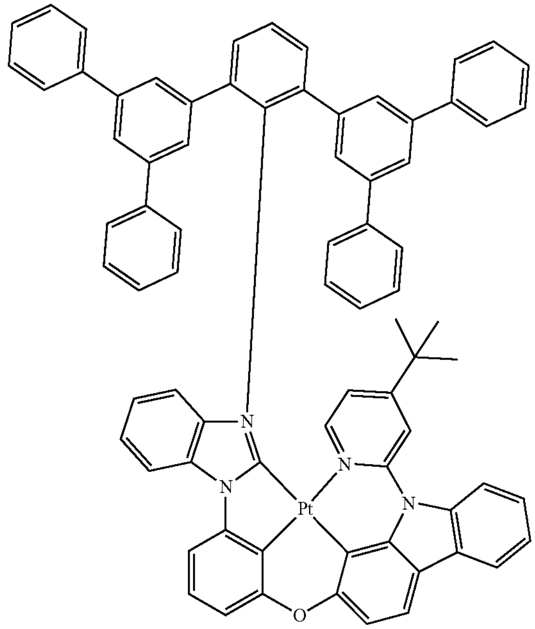
,
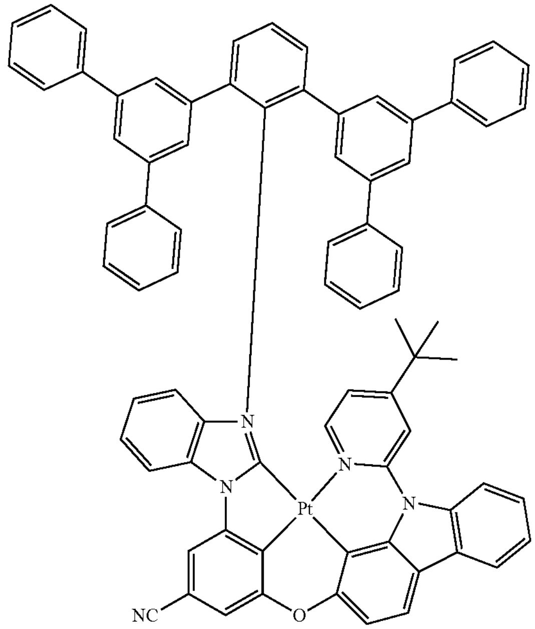
,

-continued
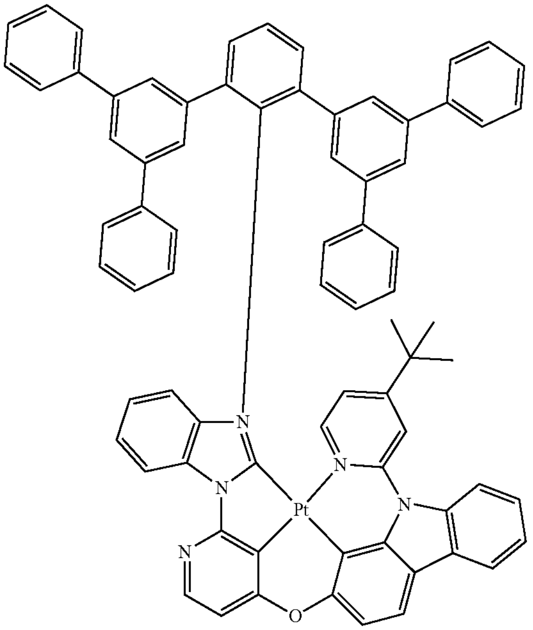
,
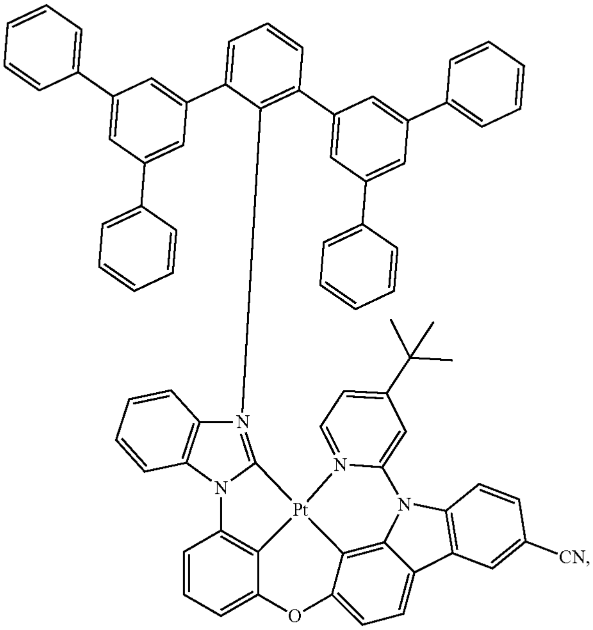
CN,
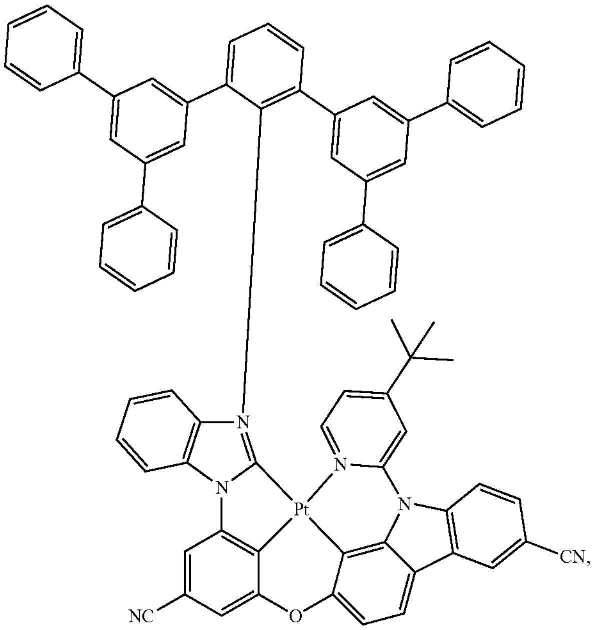
CN,
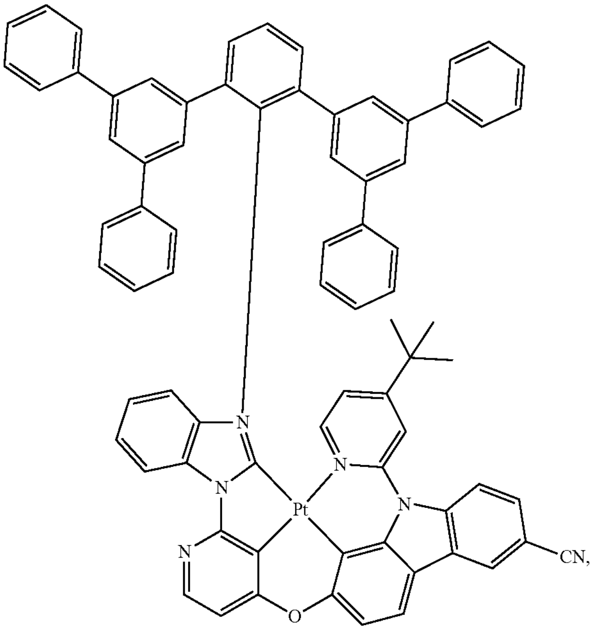
CN,

-continued
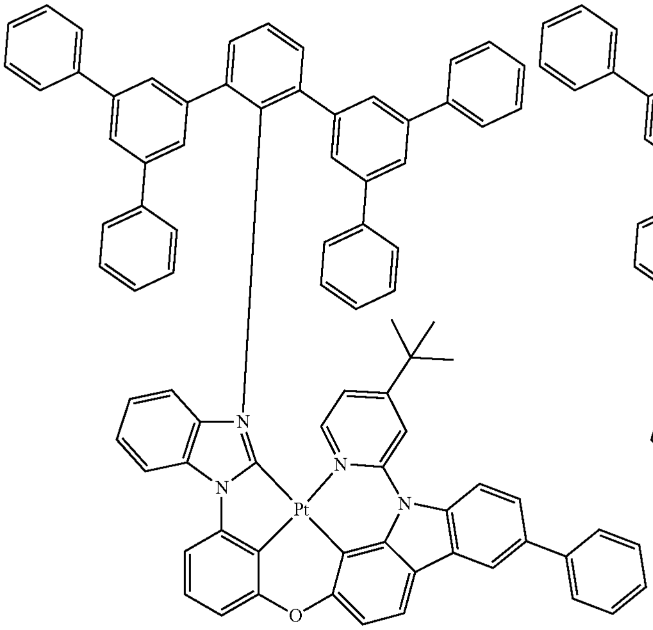
,
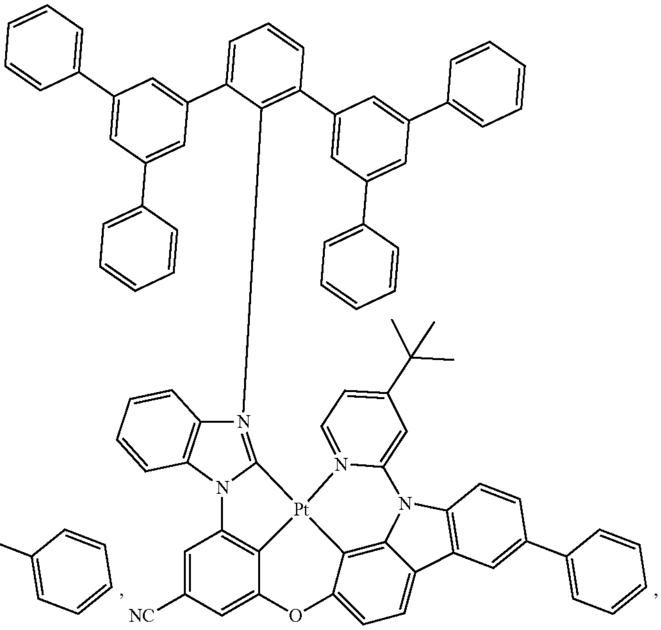
,
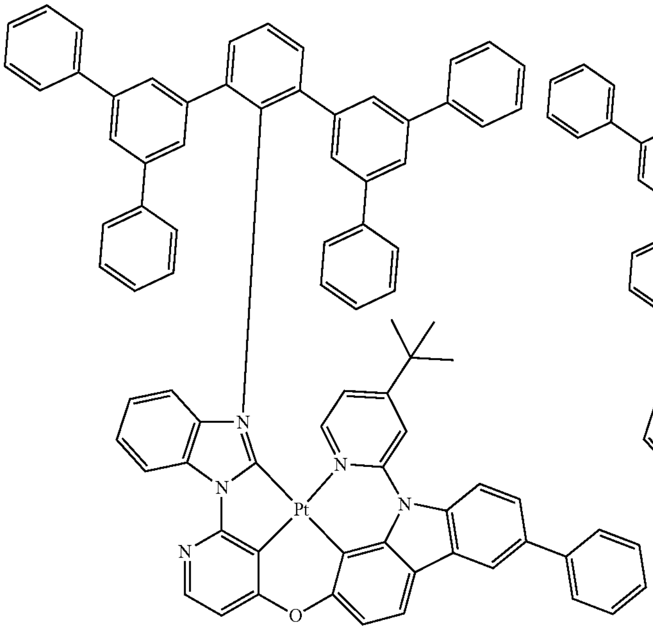
,
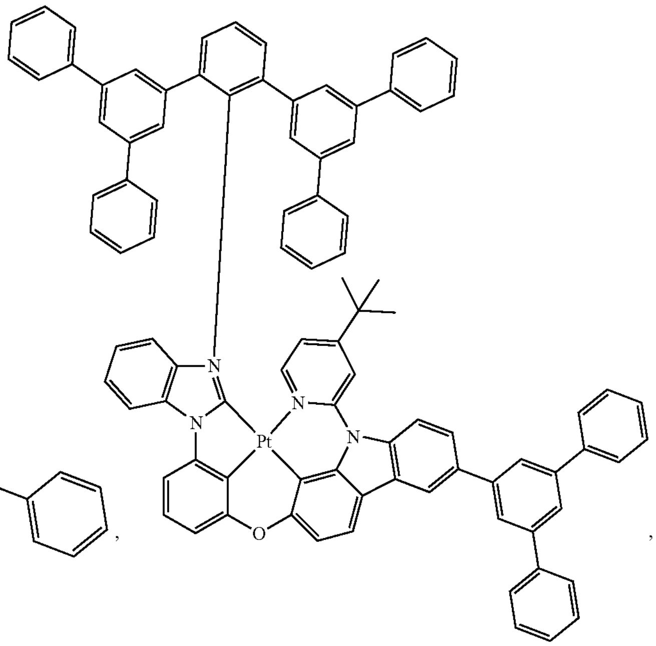
,

-continued
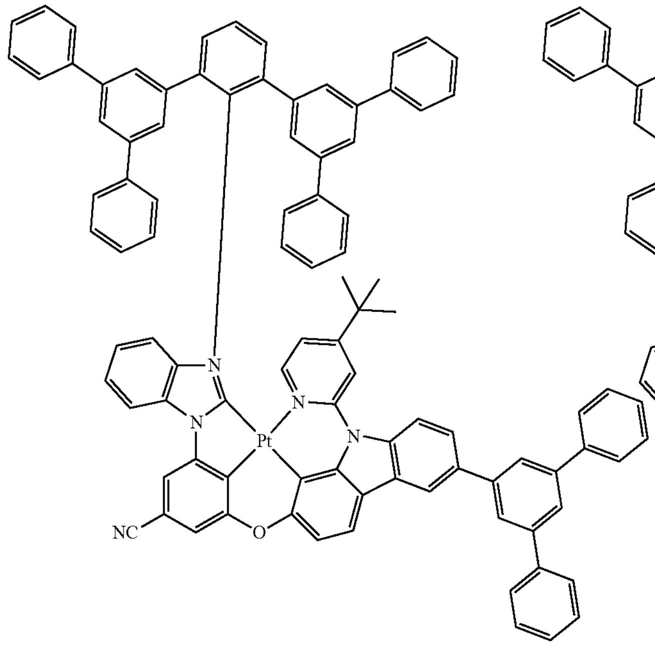
,
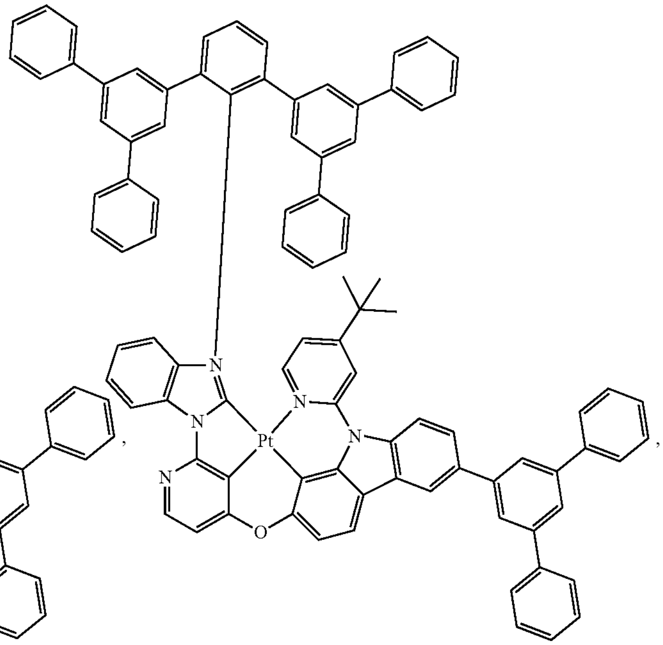
,
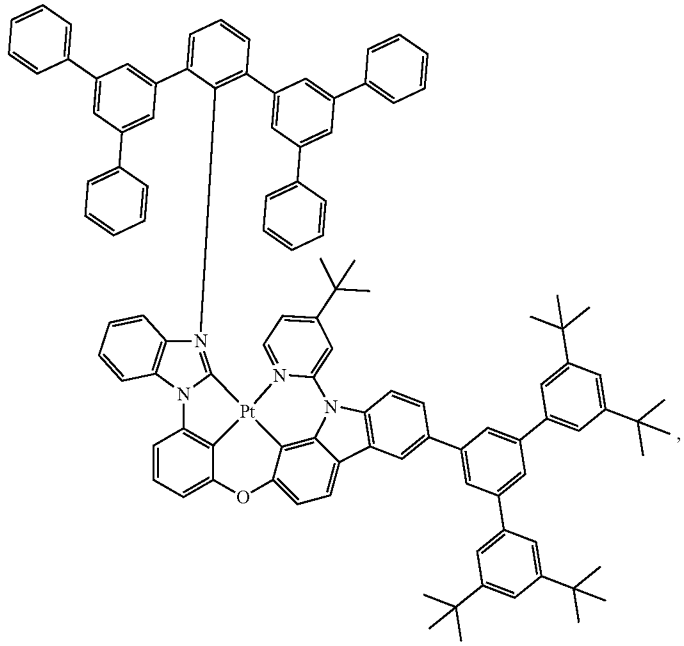
,

-continued
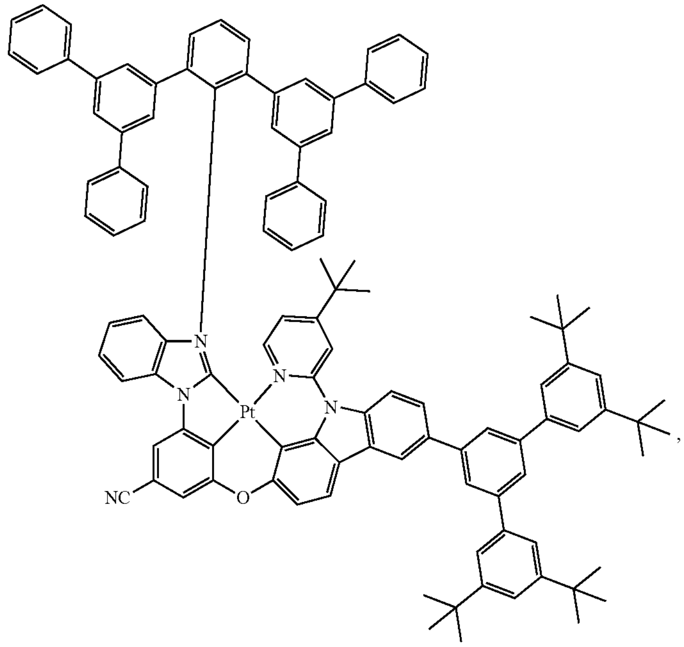
,
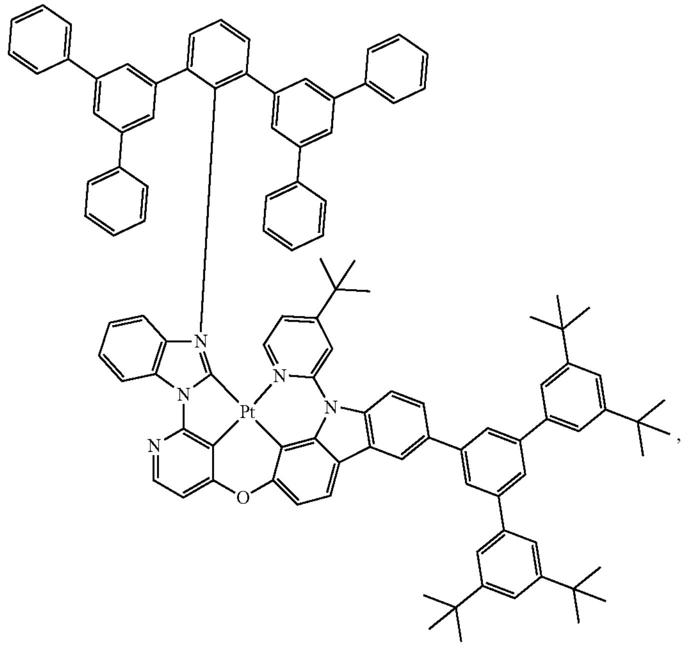
,

-continued
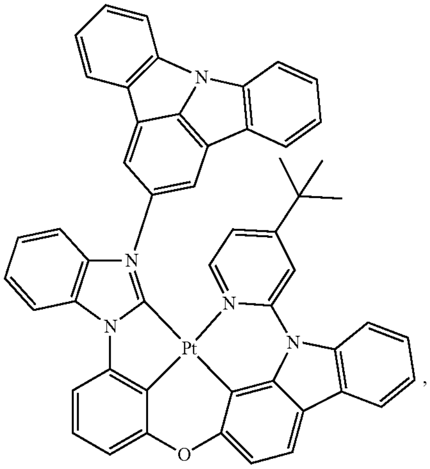,
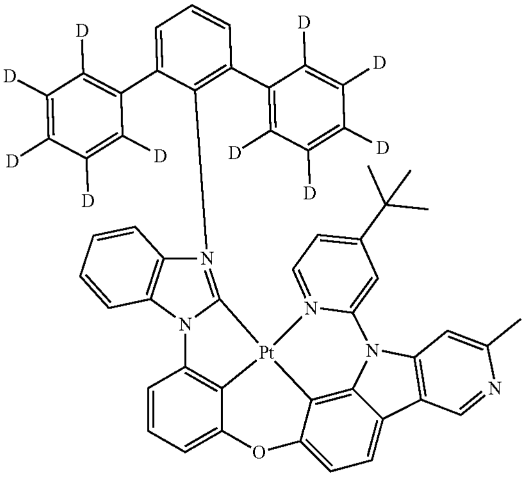,
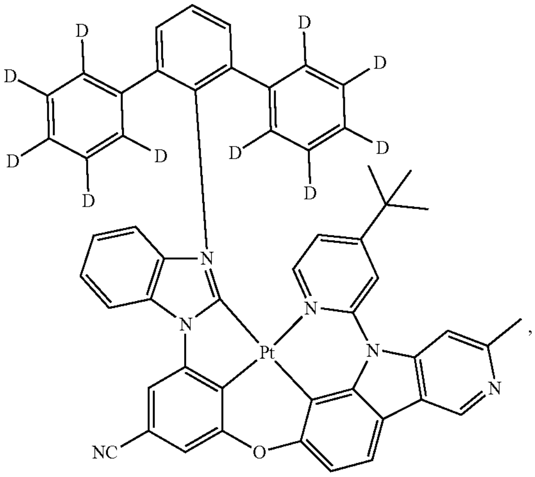,
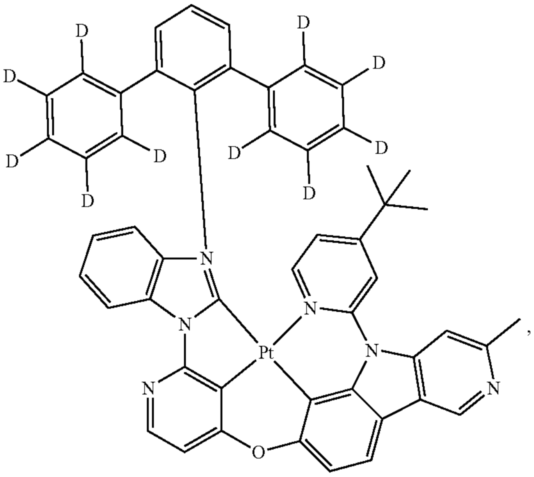,
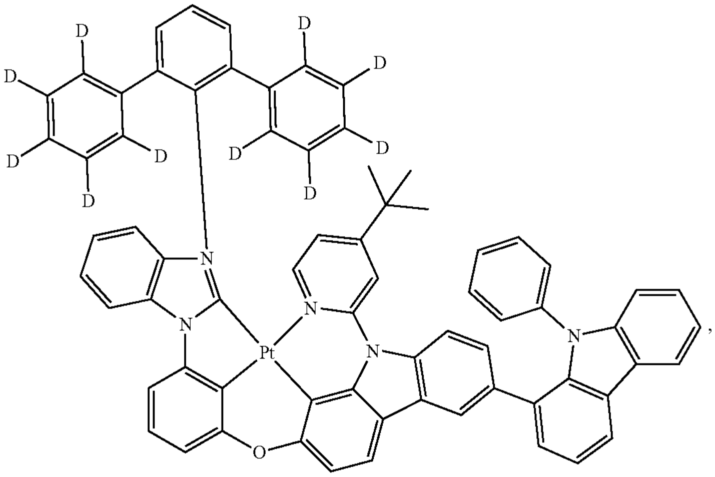,

-continued
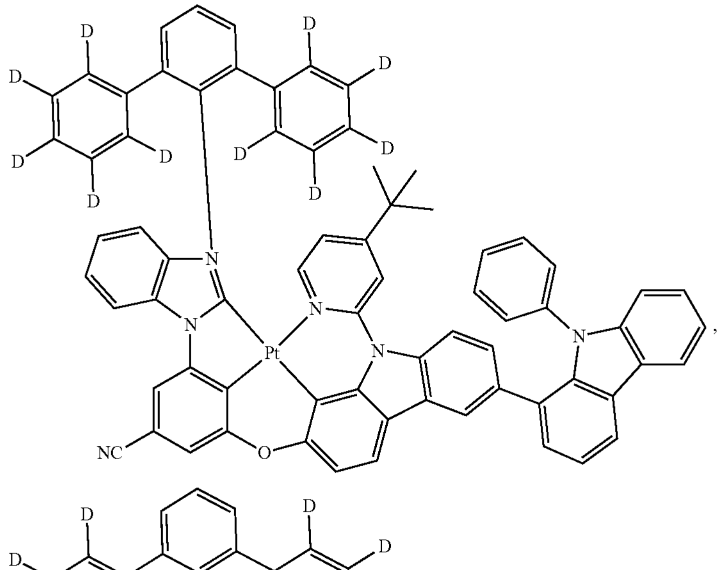
,
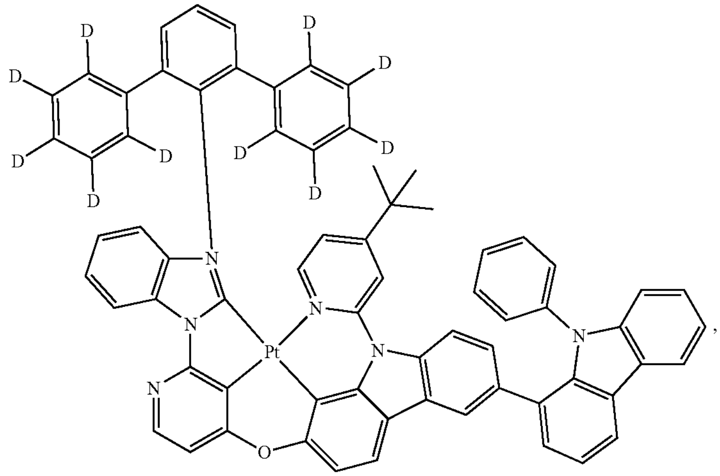
,
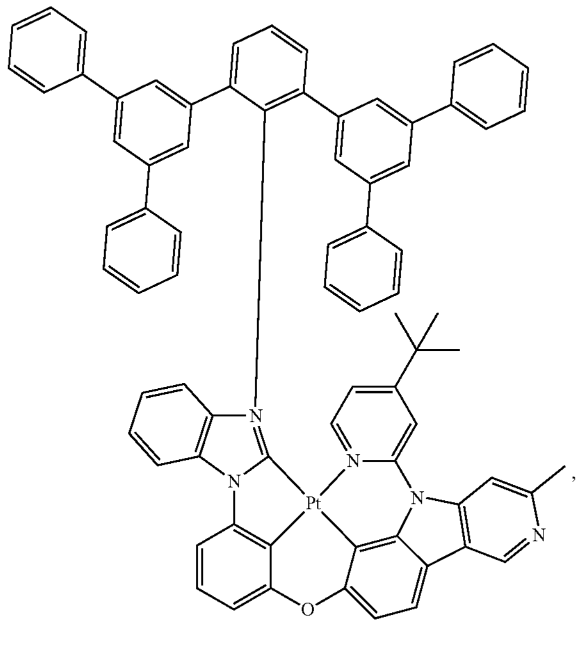
,
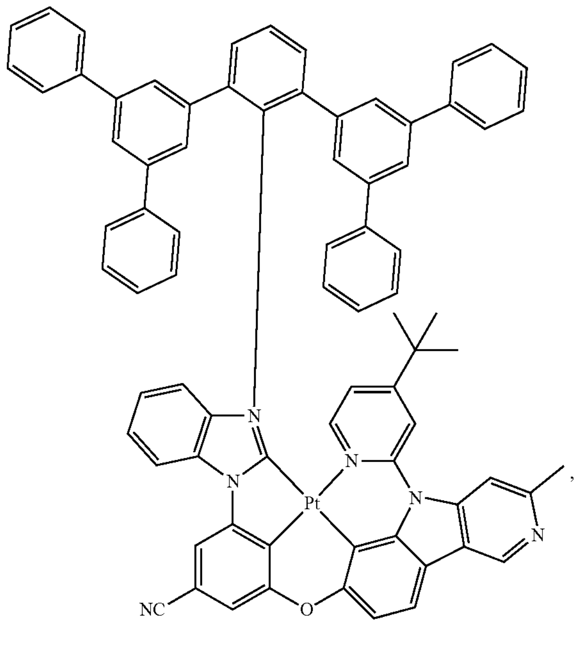
,

-continued
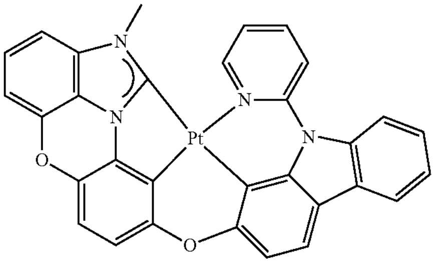
,
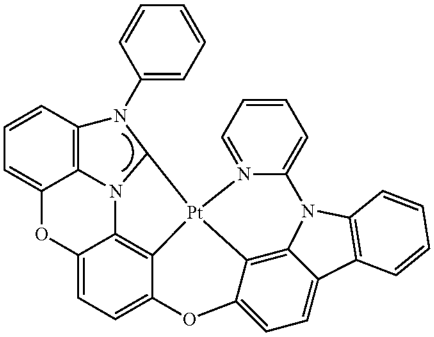
,
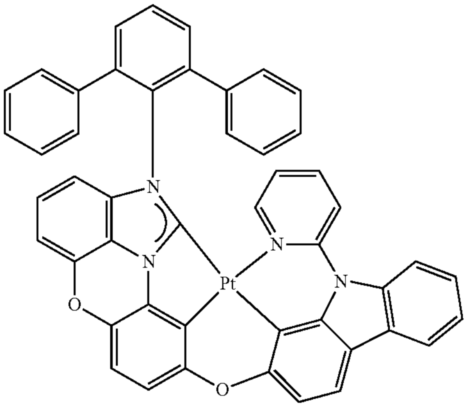
,
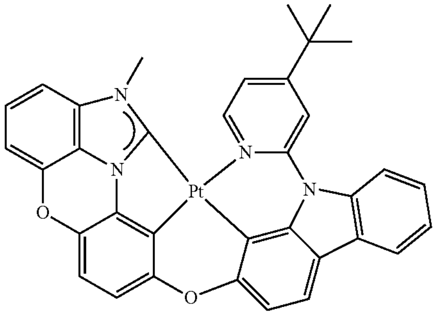
,
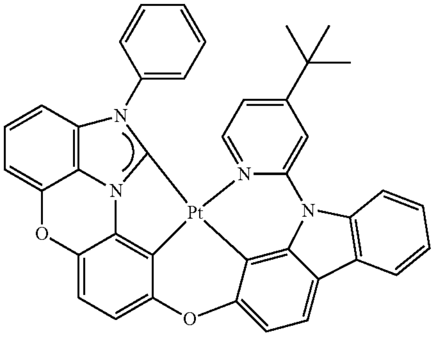
,
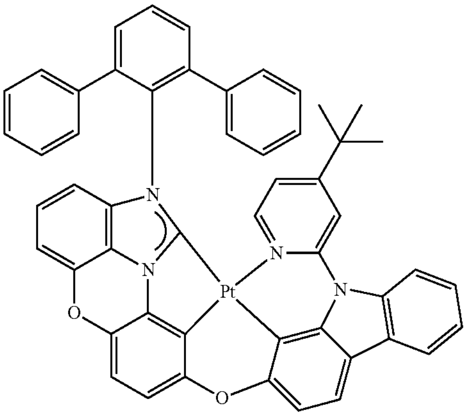
, -continued
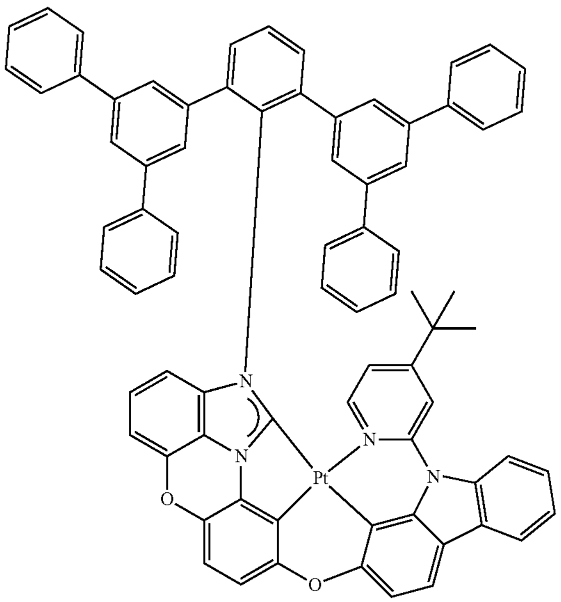
,
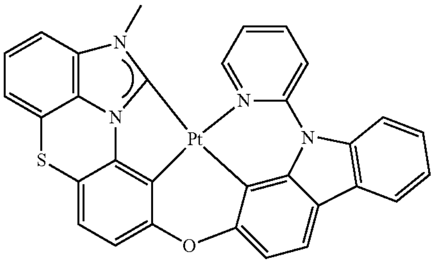
,
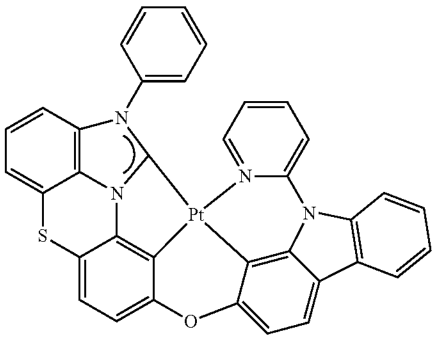
,
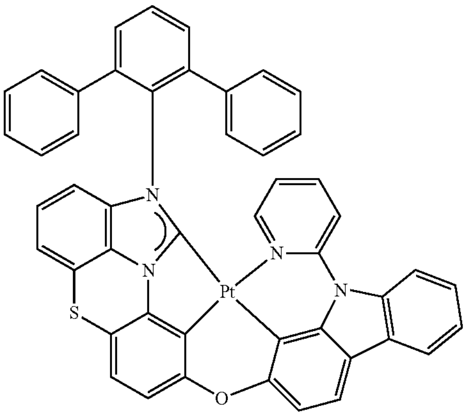
,
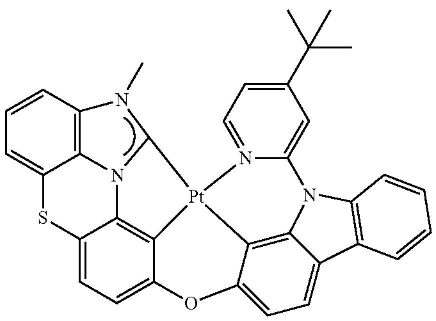
,
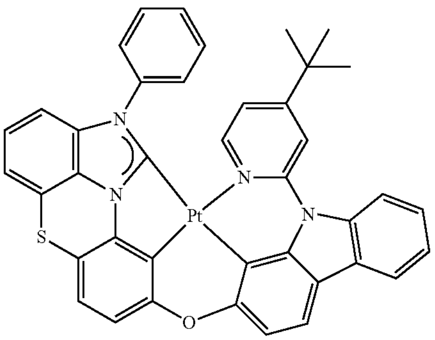
, -continued
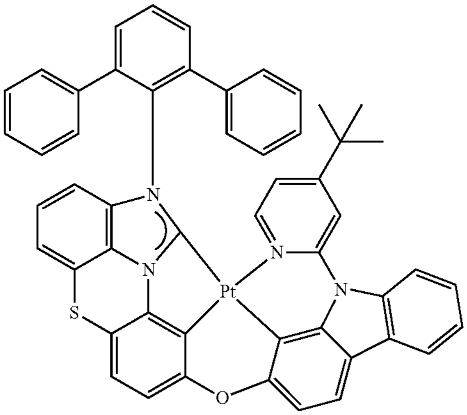
,
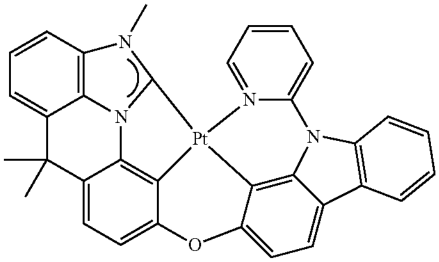
,
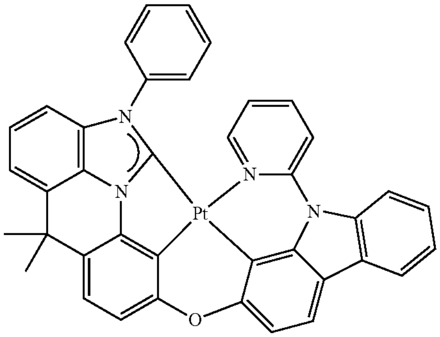
,
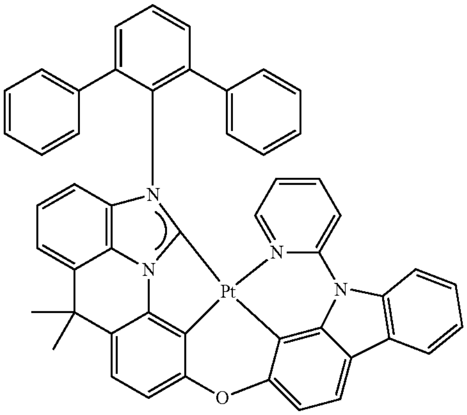
,
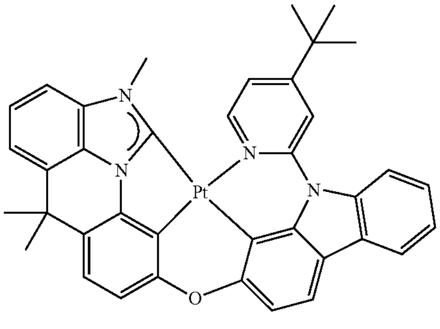
,
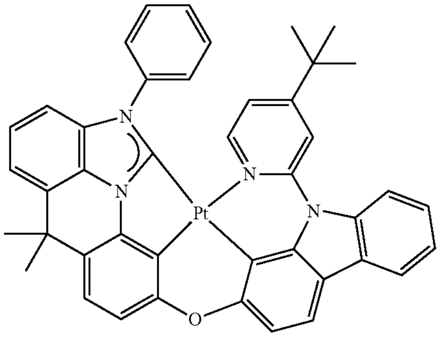
, -continued
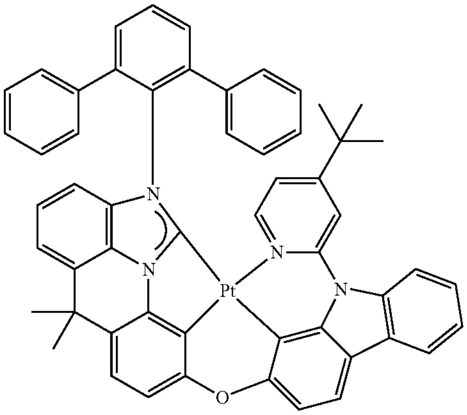,
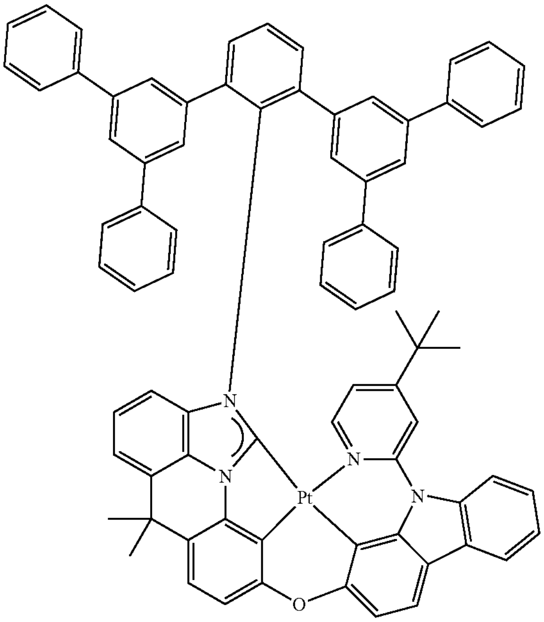,
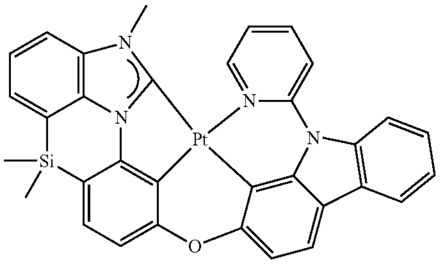,
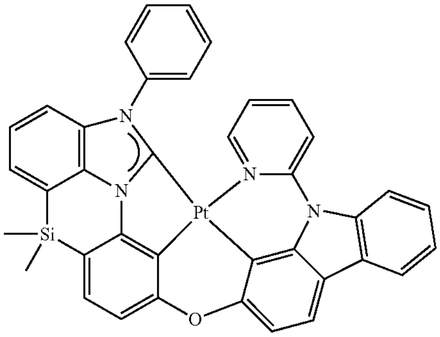,
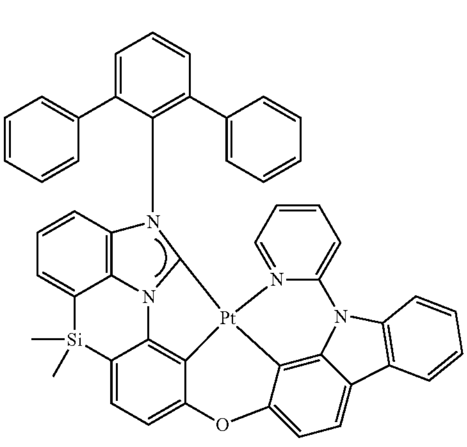,
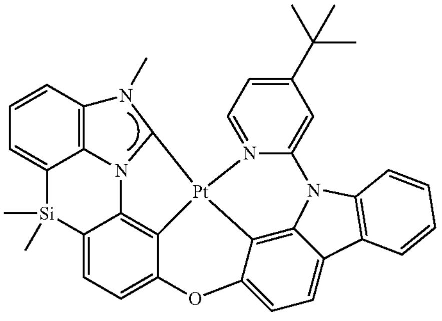, -continued
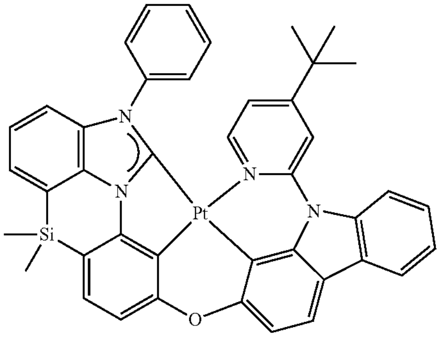
,
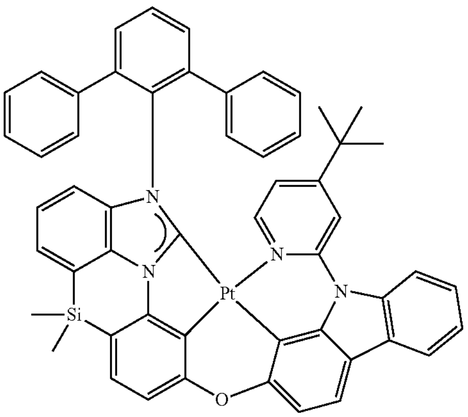
,
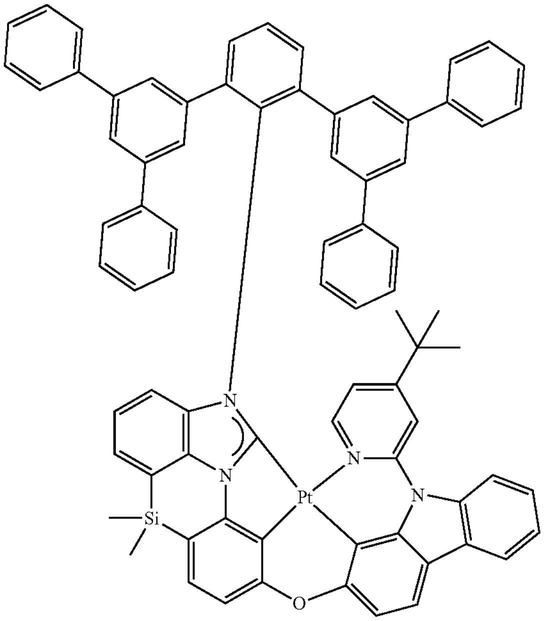
,
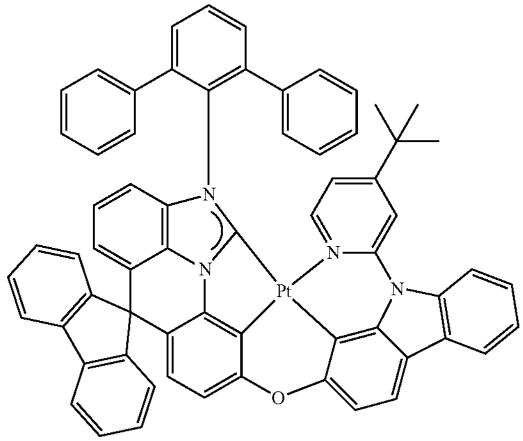
,
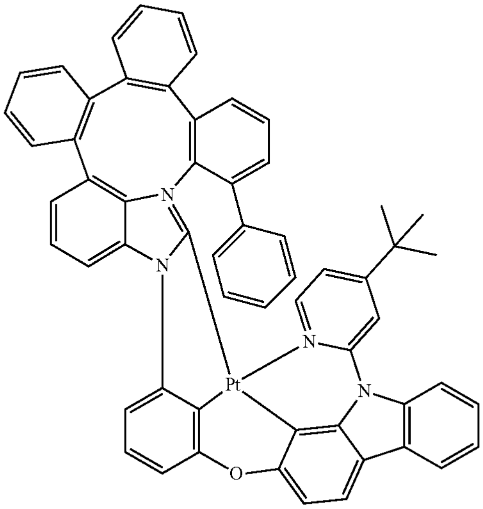
,
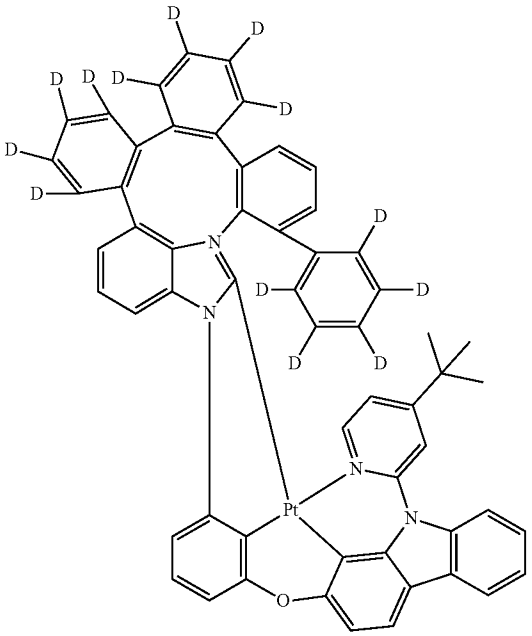
, -continued
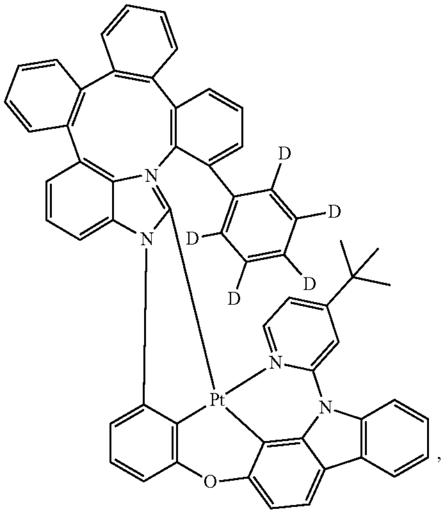
,
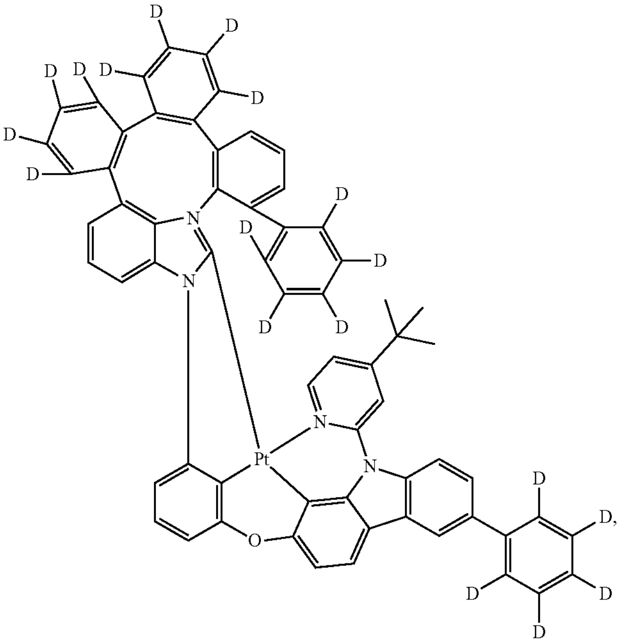
,
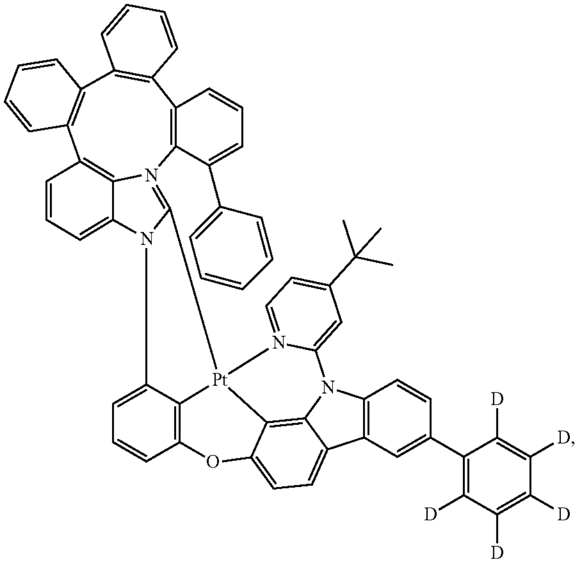
,
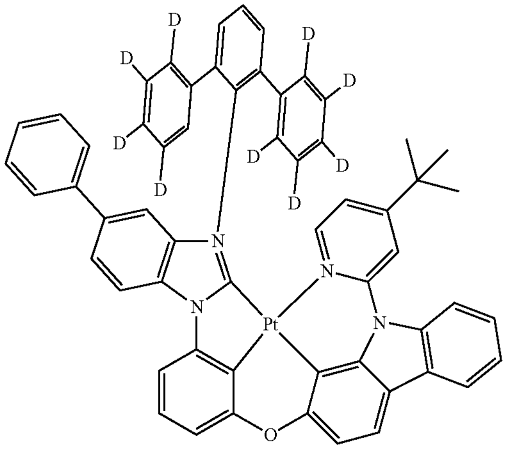
, -continued
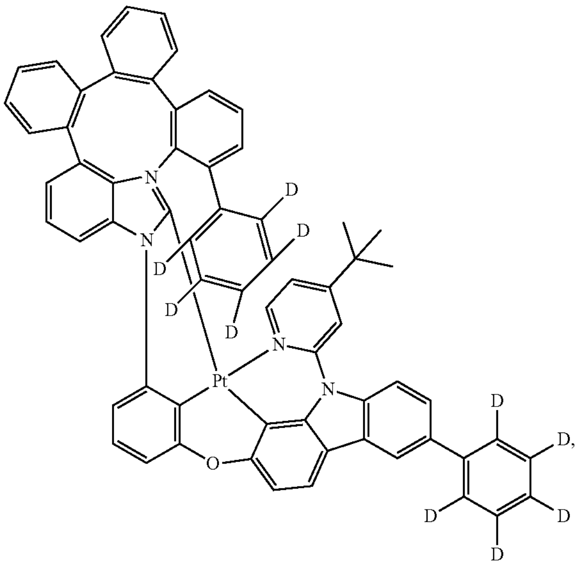
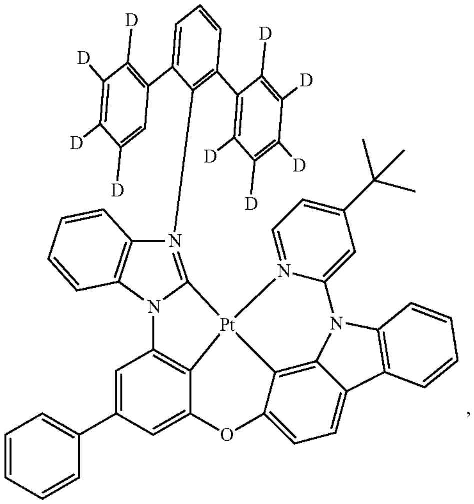
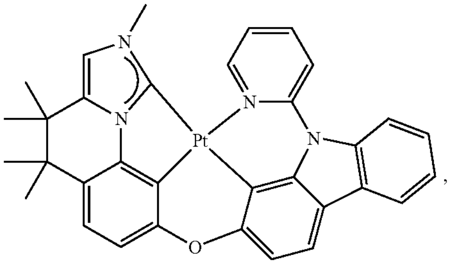
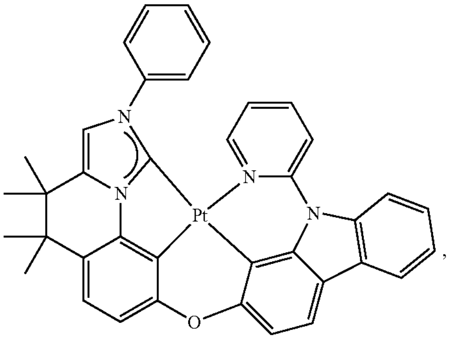
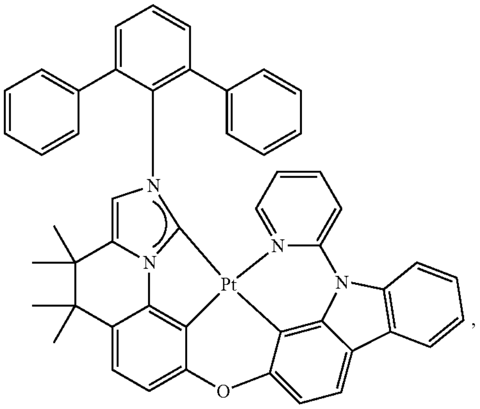
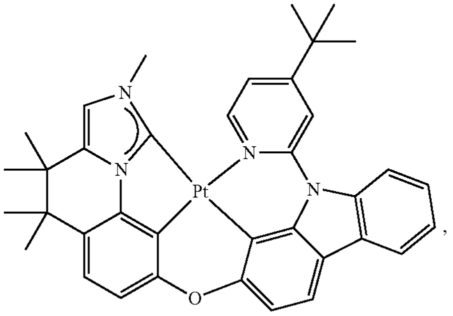

-continued

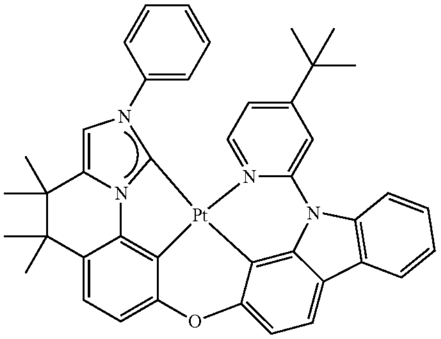
, and
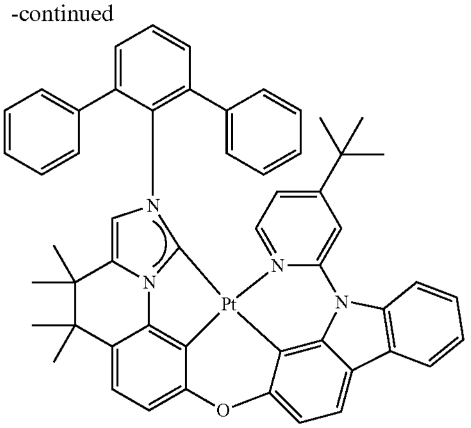
.

In some embodiments, the second host is selected from the group consisting of the structures in LIST 1 and LIST 2 as defined herein.

OLED with Exciplex

In yet another embodiment described herein an OLED is disclosed that includes an anode; a cathode; and an emissive layer, disposed between the anode and the cathode. The emissive layer comprises a first compound and a second compound, where the first compound and the second compound form an exciplex, the first compound is not an organometallic compound, and the first compound is fully or partially deuterated, with the proviso that neither the first nor the second compound is:

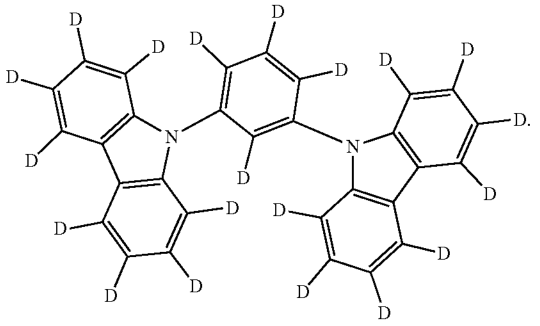

In some embodiments, the first and second compounds are both organic materials.

In some embodiments, the first compound does not include a metal.

In some embodiments, the first compound includes at least two deuterium atoms.

In some embodiments, the first compound is at least 5% deuterated.

In some embodiments, the first and second compounds are both host materials and the emissive layer additionally comprises an emitter.

In some embodiments, each of the first compound and second compound is independently selected from the group consisting of the compounds in LIST 1 defined herein.

In some embodiments, each of the first compound and second compound is independently selected from the group consisting of the compounds in LIST 2 defined herein.

In some embodiments, the emitter is selected from a phosphorescent compound, a fluorescent compound, and a thermally-activated delayed fluorescent (TADF) compound.

In some embodiments, the first compound is a host material and the second compound is an emitter.

In some embodiments, the emitter is a phosphorescent compound comprising a ligand selected from the group consisting of the structures in LIST 3 defined herein.

In some embodiments, the emitter is a phosphorescent compound comprises a ligand selected from the group consisting of the structures in LIST 4 defined herein.

In some embodiments, the emitter is a phosphorescent compound selected from the group consisting of the structures in LIST 5 defined herein.

In some embodiments, the emitter is a TADF compound, and the TADF compound is a multi-resonant-thermally activated delayed fluorescence (MR-TADF) emitter.

In some embodiments, the emitter is a TADF compound, and the TADF compound contains a donor group comprising at least one of the chemical moieties selected from the group consisting of:

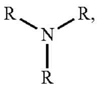
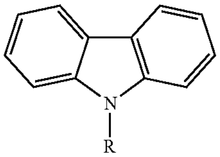
,
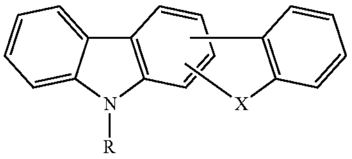
,
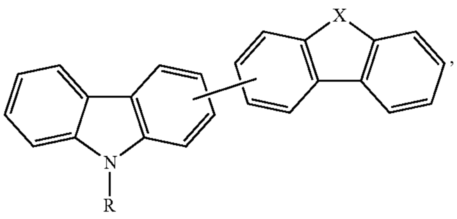
,

-continued

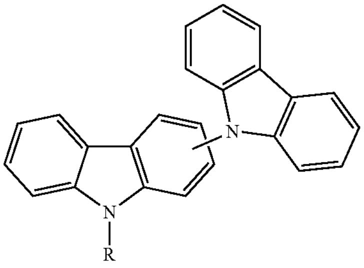

,

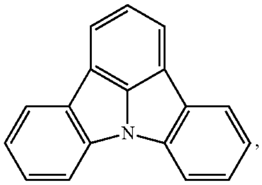

,

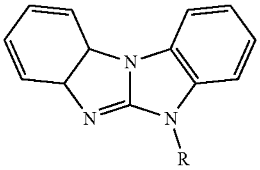

,

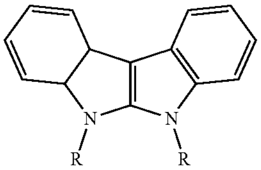

,

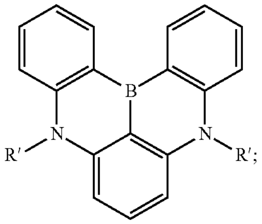

and an acceptor group comprising at least one of the chemical moieties selected from the group consisting of:

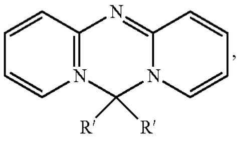

,

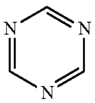

,

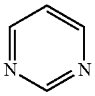

,

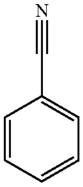

,

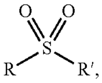

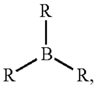

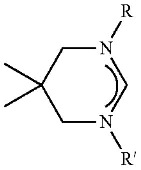

,

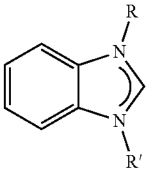

,

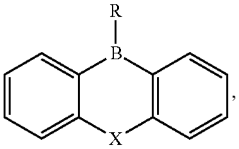

,

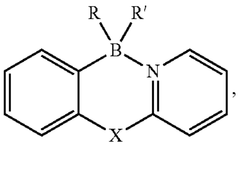

,

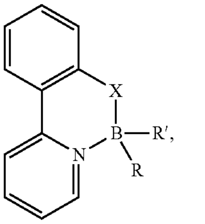

-continued

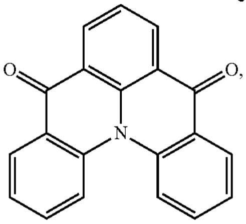

and

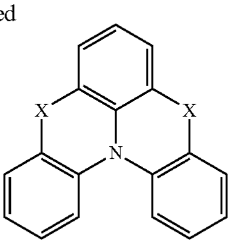

.

wherein X is selected from the group consisting of O, S, Se, and NR;

wherein each R can be the same or different and each R is independently an acceptor group, an organic linker bonded to an acceptor group, or a terminal group selected from the group consisting of alkyl, cycloalkyl, heteroalkyl, heterocycloalkyl, arylalkyl, aryl, heteroaryl, and combinations thereof; and wherein each R' can be the same or different and each R' is independently selected from the group consisting of alkyl, cycloalkyl, aryl, heteroaryl, and combinations thereof.

In some embodiments, the emitter is a TADF compound selected from the group consisting of the structures in the following LIST 10:

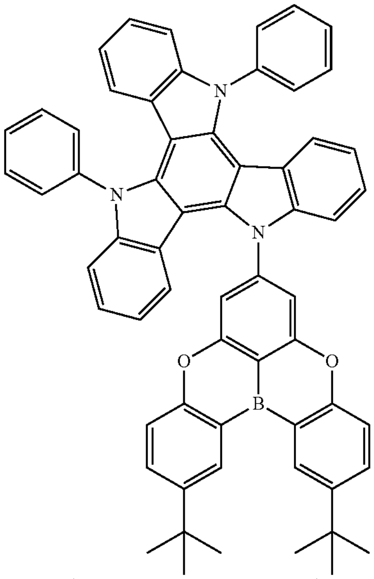

,

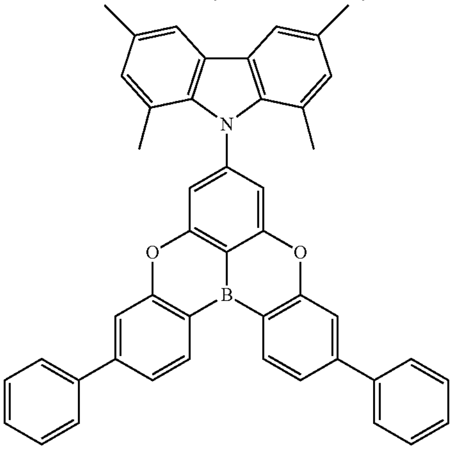

,

-continued
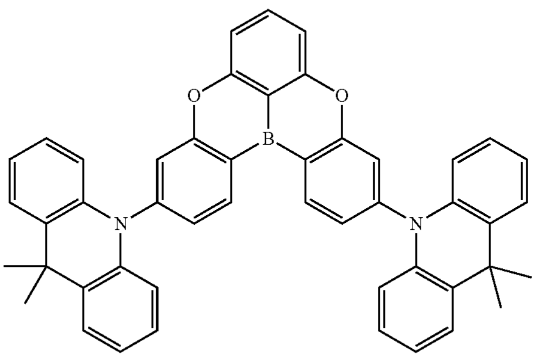
,
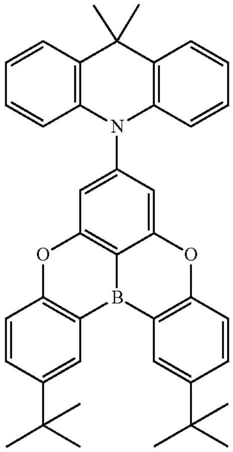
,
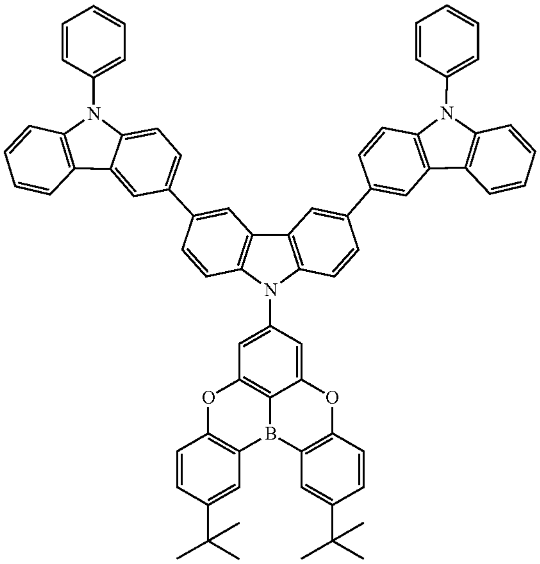
,
-continued
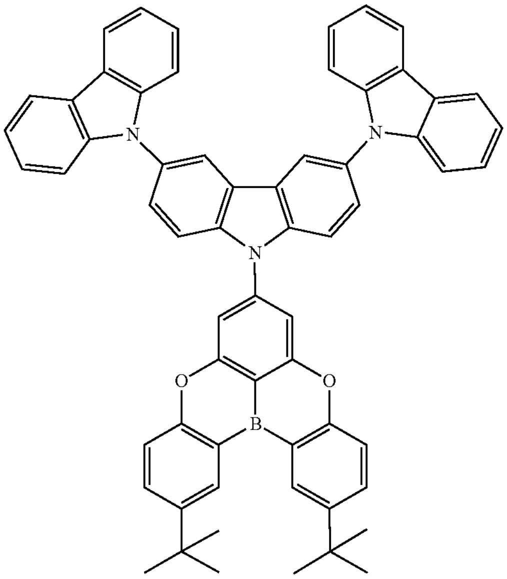
,
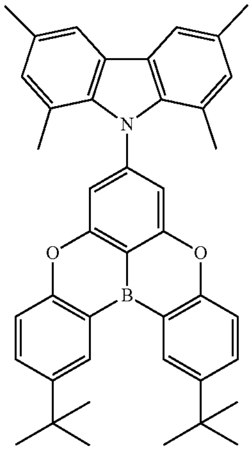
,
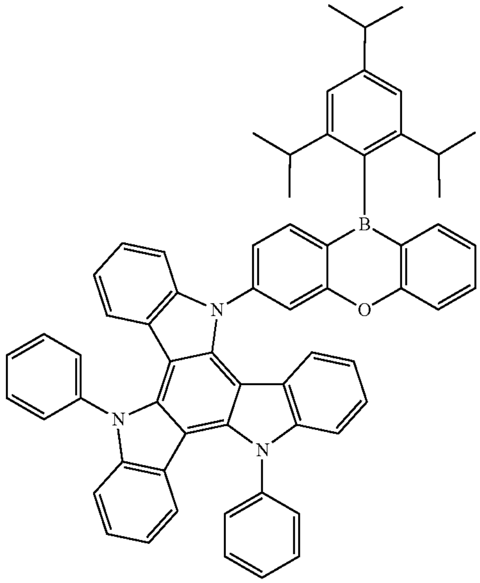
, -continued
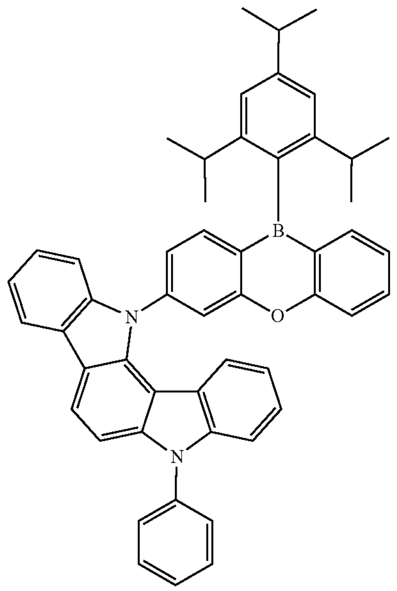
,
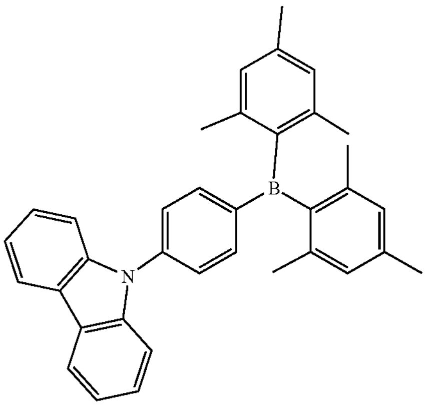
,
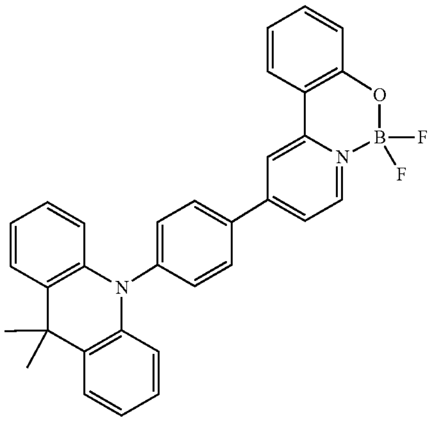
,
-continued
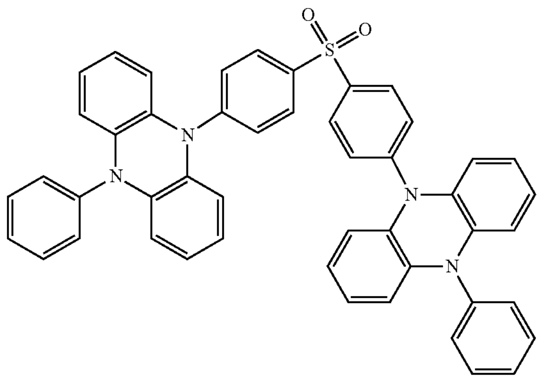
,
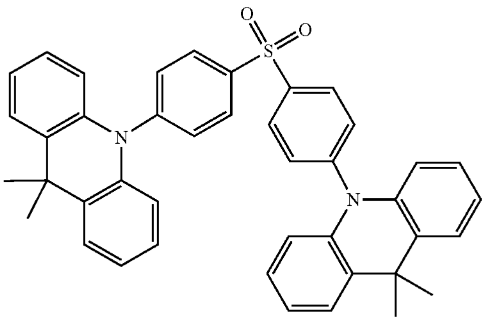
,
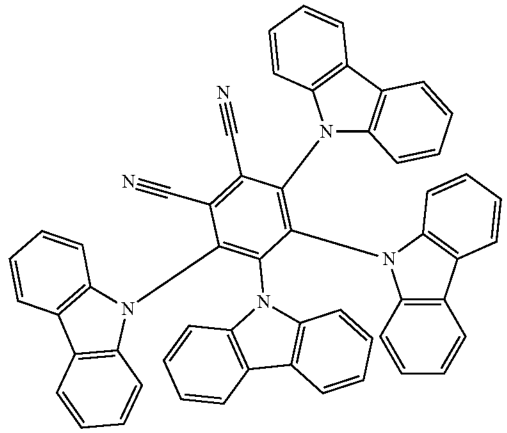
,
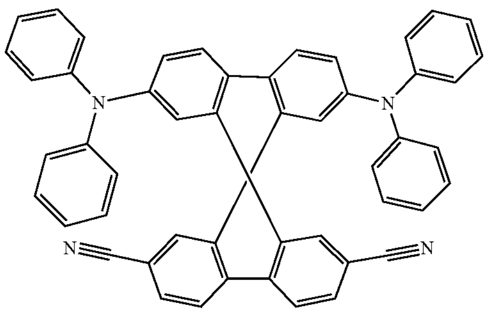
, -continued
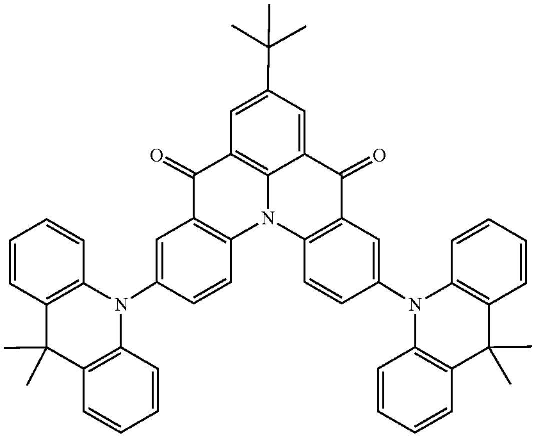
,
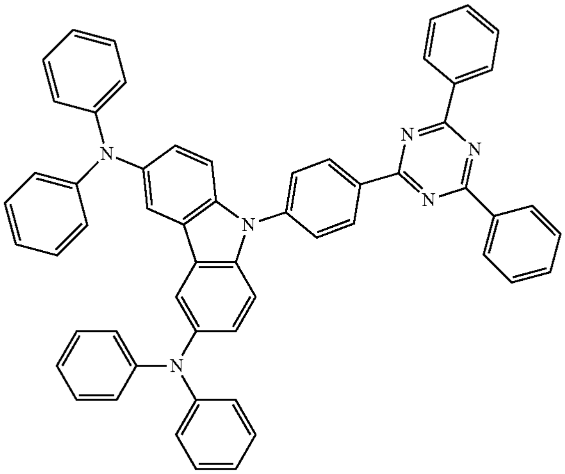
,
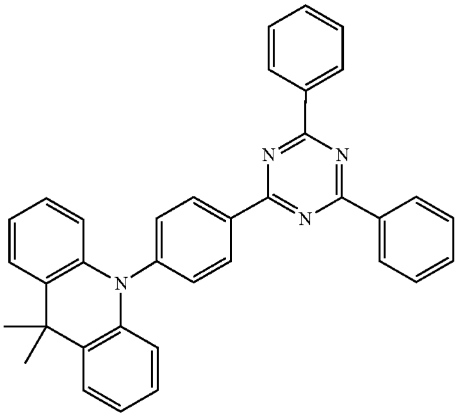
,
-continued
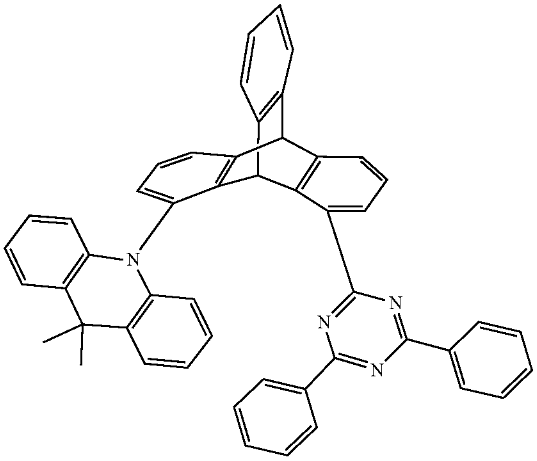
,
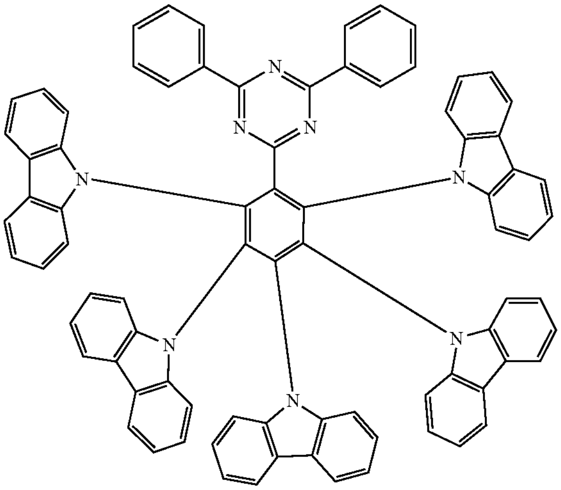
,
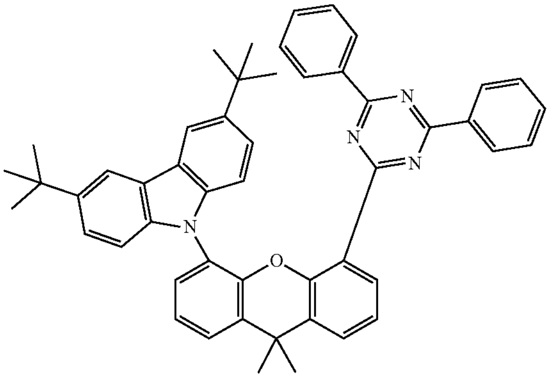
,
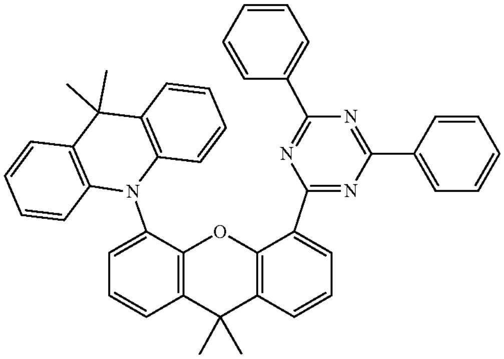
, -continued
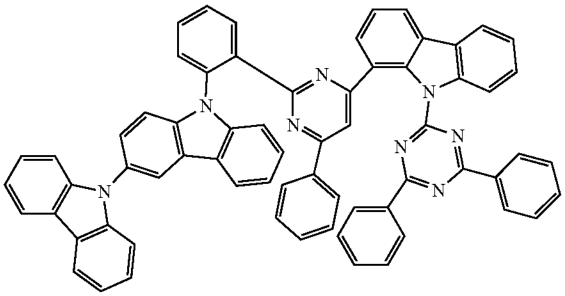
,
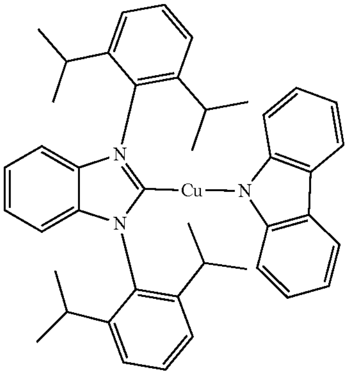
,
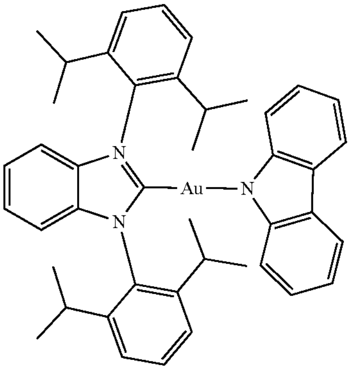
,
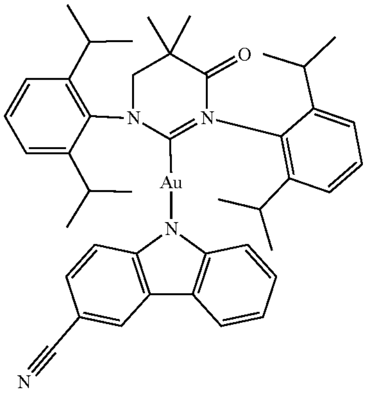
,
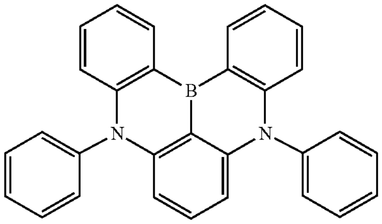
,
-continued
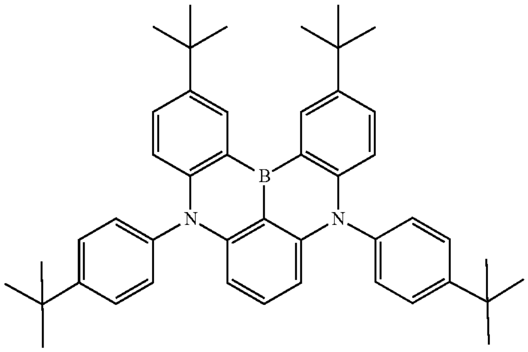
,
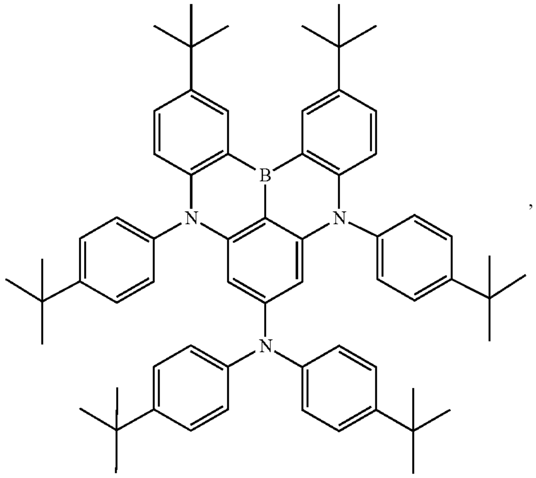
,
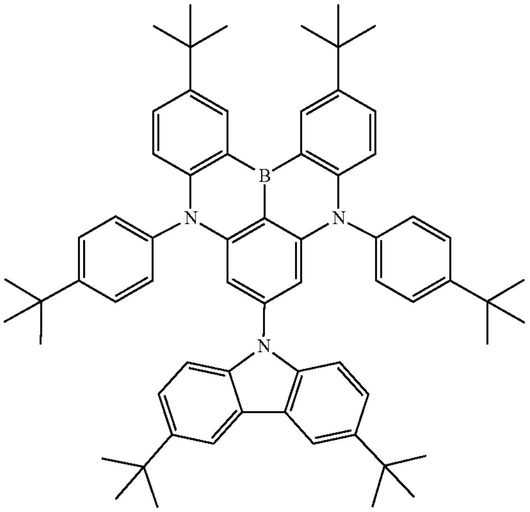
,
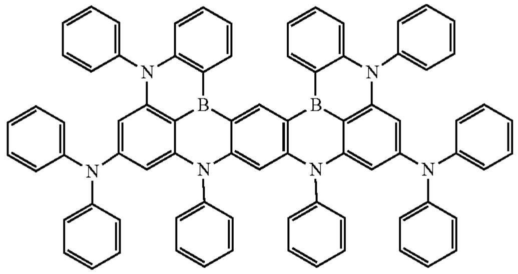
, and -continued
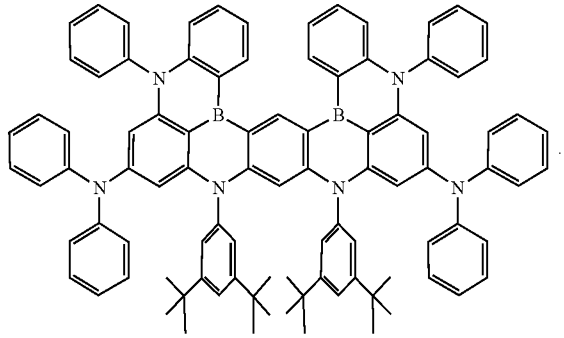
In some embodiments, the emitter is a fluorescent compound selected from the group consisting of the structures in the following LIST 11:
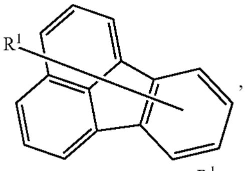
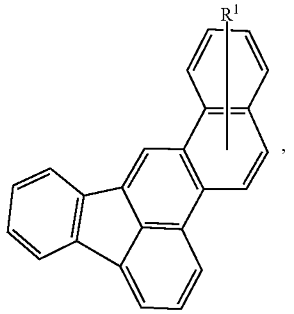
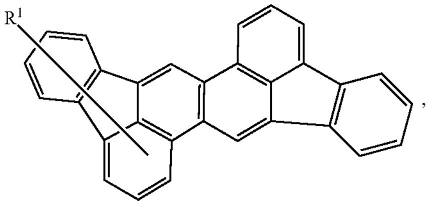
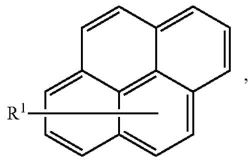
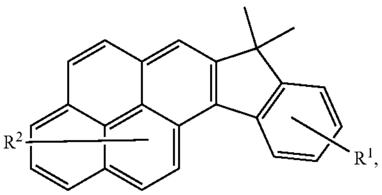
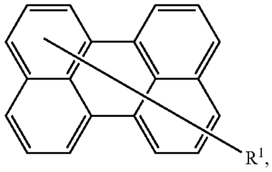
-continued
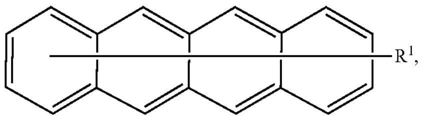
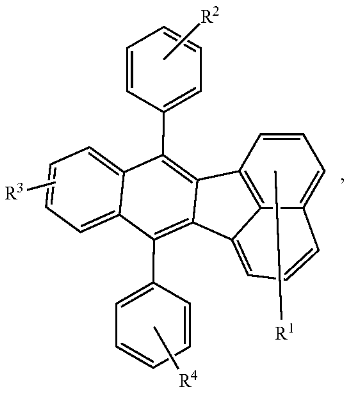
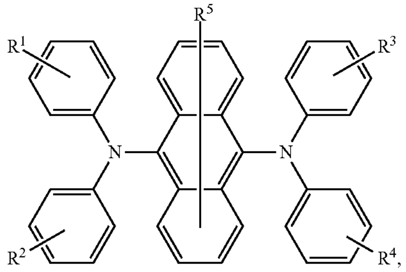
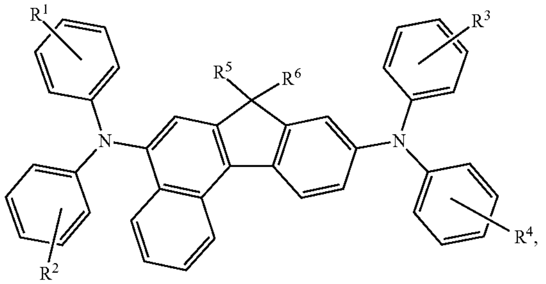
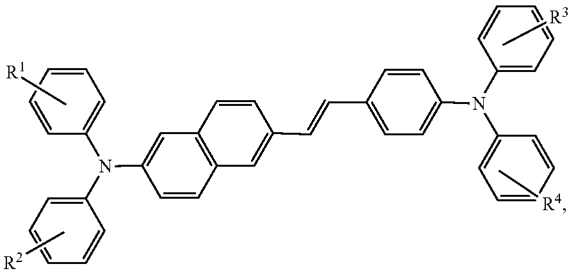
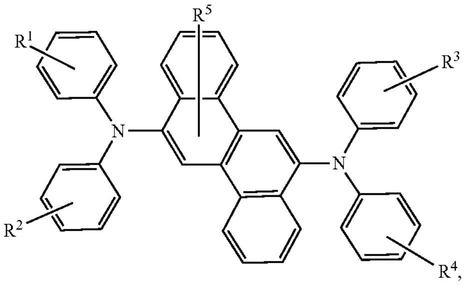

-continued

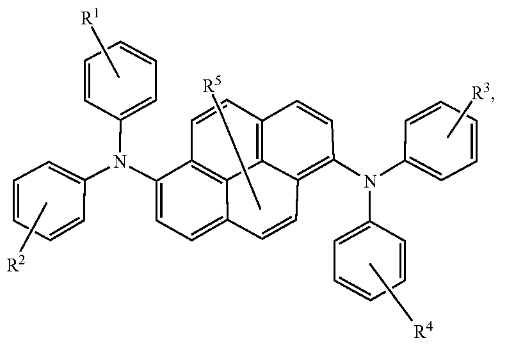

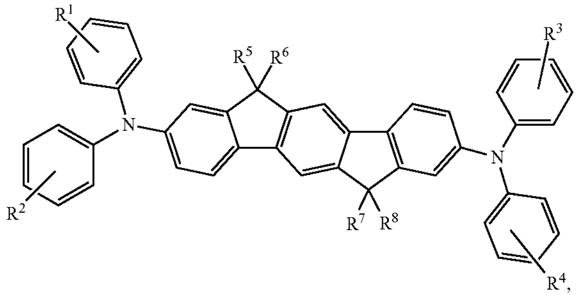

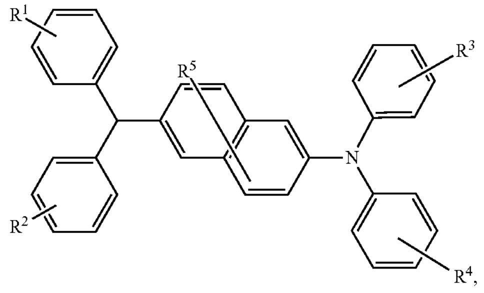

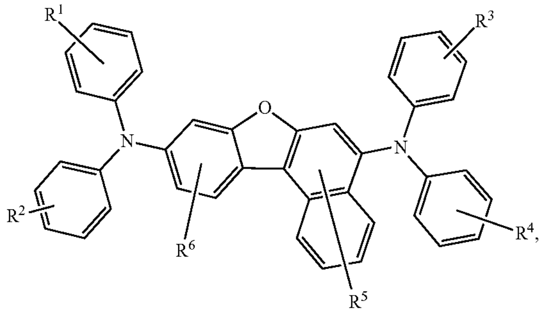

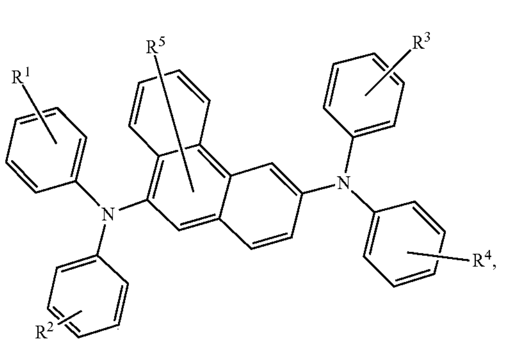

-continued

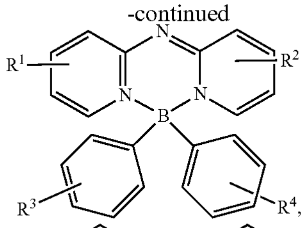

and

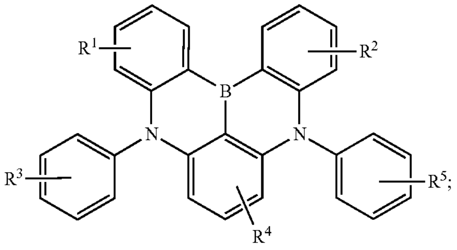

wherein $R^1$ to $R^6$ each independently represents from mono to maximum possible number of substitutions, or no substitution; and wherein each R to $R^6$ is independently a hydrogen or a substituent selected from the group consisting of the general substituents defined herein.

In some embodiments, the second compound is fully or partially deuterated.

In some embodiments, the second compound is a platinum complex and the first compound comprises a triazine moiety.

In some embodiments, the second compound comprises a carbazole moiety.

In some embodiments, the second compound is a platinum complex comprising a tetradentate ligand, and the tetradentate ligand and the platinum atom form 5-6-6 chelating rings.

In some embodiments, the emissive layer has a peak emission equal to or less than 500 nm. In some embodiments, the emissive layer has a peak emission equal to or less than 490 nm. In some embodiments, the emissive layer has a peak emission equal to or less than 480 nm. In some embodiments, the emissive layer has a peak emission equal to or less than 470 nm. In some embodiments, the emissive layer has a peak emission equal to or less than 460 nm. In some embodiments, the emissive layer has a peak emission equal to or less than 450 nm.

In some embodiments, the LUMO of the first compound is less than −2.3 eV. In some embodiments, a LUMO of the first compound is less than −2.4 eV.

In some embodiments, the HOMO of the first compound is greater than −5.8 eV. In some embodiments, the HOMO of the first compound is greater than −5.7 eV.

In some embodiments, the emissive layer further comprises a second host, wherein the first compound has a HOMO level greater than −5.8 eV and the second host has a LUMO level less than −2.3 eV. In some embodiments, the emissive layer further comprises a second host, wherein the first compound has a HOMO level greater than −5.7 eV and the second host has a LUMO level less than −2.4 eV.

In some embodiments, the second compound comprises at least one cyano substituent.

In some embodiments, the second compound is partially fluorinated. In some embodiments, the second compound comprises exactly one F. In some embodiments, the second compound comprises at least two F.

In some embodiments, the second compound comprises at least one tri-aryl amine.

In some embodiments, the second compound comprises at least one partially deuterated alkyl groups.

In some embodiments, the second compound comprises at least one 5-membered chelating ring between a ligand and the metal.

In some embodiments, the second compound has a HOMO level less than −5.2 eV. In some embodiments, the second compound has a HOMO level less than −5.3 eV.

In another aspect, a organic electroluminescent device (OLED) comprising, an anode, a cathode; and an emissive layer, disposed between the anode and the cathode. The emissive layer comprises a phosphorescent dopant and a host, where the phosphorescent dopant is partially or fully deuterated; and the host is partially or fully deuterated.

In some embodiments, the dopant is an Ir or Pt complex. In some embodiments, the dopant is a Pt complex.

In some embodiments, the Pt complex comprises a tetradentate ligand. In some embodiments, the dopant and the host form an exciplex.

In some embodiments, the host is selected from the group consisting of the structures in LIST 1 as defined herein.

In some embodiments, the host is selected from the group consisting of the structures in LIST 2 as defined herein.

In some embodiments, the phosphorescent dopant is a platinum complex and the host comprises a triazine moiety.

In some embodiments, the phosphorescent dopant comprises a carbazole moiety.

In some embodiments, the phosphorescent dopant is a platinum complex comprising a tetradentate ligand, and the tetradentate ligand and the platinum atom form 5-6-6 chelating rings.

In some embodiments, the emissive layer has a peak emission equal to or less than 500 nm. In some embodiments, the emissive layer has a peak emission equal to or less than 490 nm. In some embodiments, the emissive layer has a peak emission equal to or less than 480 nm. In some embodiments, the emissive layer has a peak emission equal to or less than 470 nm. In some embodiments, the emissive layer has a peak emission equal to or less than 460 nm. In some embodiments, the emissive layer has a peak emission equal to or less than 450 nm.

In some embodiments, a LUMO of the host is less than −2.3 eV. In some embodiments, a LUMO of the host is less than −2.4 eV.

In some embodiments, the HOMO of the host is greater than −5.8 eV. In some embodiments, the HOMO of the host is greater than −5.7 eV.

In some embodiments, the emissive layer further comprises a second host, wherein the first host has a HOMO level greater than −5.8 eV and the second host has a LUMO level less than −2.3 eV. In some embodiments, the emissive layer further comprises a second host, wherein the first host has a HOMO level greater than −5.7 eV and the second host has a LUMO level less than −2.4 eV.

In some embodiments, the phosphorescent dopant comprises at least one cyano substituent.

In some embodiments, the phosphorescent dopant is partially fluorinated. In some embodiments, the second compound comprises exactly one F. In some embodiments, the second compound comprises at least two F.

In some embodiments, the phosphorescent dopant comprises at least one tri-aryl amine.

In some embodiments, the phosphorescent dopant comprises at least one partially deuterated alkyl groups.

In some embodiments, the phosphorescent dopant comprises at least one 5-membered chelating ring between a ligand and the metal.

In some embodiments, the phosphorescent dopant has a HOMO level less than −5.2 eV. In some embodiments, the phosphorescent dopant has a HOMO level less than −5.3 eV.

In yet another aspect, an organic electroluminescent device (OLED) comprising, an anode;

a cathode; and an emissive layer, disposed between the anode and the cathode id described. The emissive layer includes a phosphorescent dopant and a first host, where the first host is partially or fully deuterated and the phosphorescent dopant comprises at least one metal-oxygen bond.

In some embodiments, the phosphorescent dopant is an Ir or Pt complex.

In some embodiments, the phosphorescent dopant is a Pt complex.

In some embodiments, the Pt complex comprises a tetradentate ligand.

In some embodiments, the phosphorescent dopant and the host form an exciplex.

In some embodiments, the host is selected from the group consisting of the structures in LIST 1 as defined herein.

In some embodiments, the host is selected from the group consisting of the structures in LIST 2 as defined herein.

In some embodiments, the phosphorescent dopant is a platinum complex and the host comprises a triazine moiety.

In some embodiments, the phosphorescent dopant comprises a benzimidazole moiety.

In some embodiments, the phosphorescent dopant is a platinum complex comprising a tetradentate ligand, and the tetradentate ligand and the platinum atom form 5-6-6 chelating rings.

In some embodiments, the emissive layer further comprises a second host, wherein the first host has a HOMO level greater than −5.8 eV and the second host has a LUMO level less than −2.3 eV.

In some embodiments, the OLEDs described herein can include further features.

Where common terms (e.g., emitter, emissive dopant, host, etc.) are used, compounds from one embodiments can be used in another embodiment.

In some embodiments, the organic layer may further comprise a host, wherein the host comprises a triphenylene containing benzo-fused thiophene or benzo-fused furan, wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH{=}CH{-}C_nH_{2n+1}$, $C{\equiv}CC_nH_{2n+1}$, $Ar_1$, $Ar_1{-}Ar_2$, $C_nH_{2n}{-}Ar_1$, or no substitution, wherein n is from 1 to 10; and wherein $Ar_1$ and $Ar_2$ are independently selected from the group consisting of benzene, biphenyl, naphthalene, triphenylene, carbazole, and heteroaromatic analogs thereof.

In some embodiments, the organic layer may further comprise a host, wherein host comprises at least one chemical group selected from the group consisting of triphenylene, carbazole, dibenzothiphene, dibenzofuran, dibenzoselenophene, azatriphenylene, azacarbazole, aza-dibenzothiophene, aza-dibenzofuran, and aza-dibenzoselenophene.

In some embodiments, the host may be selected from the HOST Group consisting of:
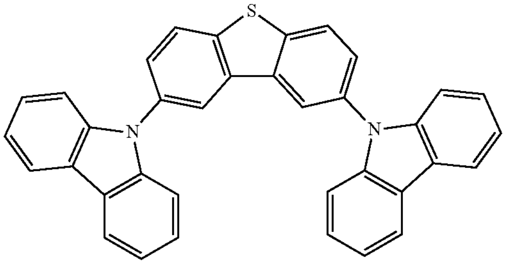
,
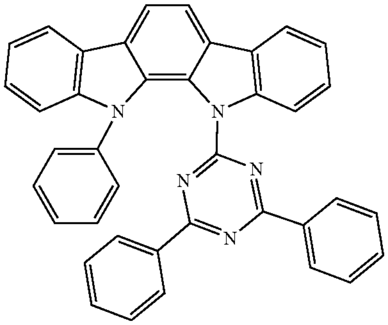
,
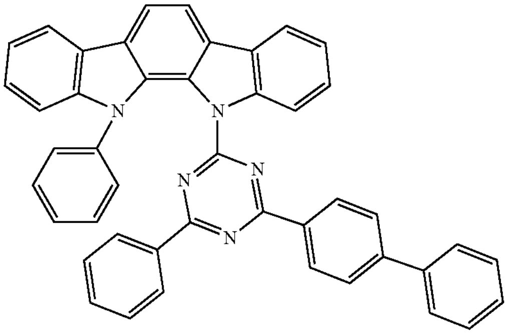
,
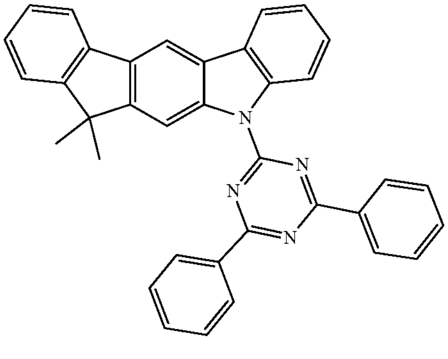
,
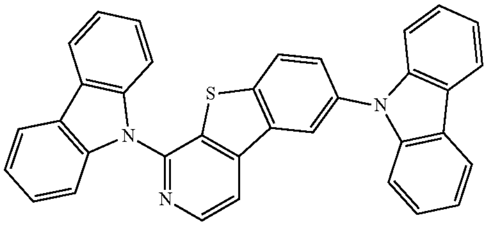
,
-continued
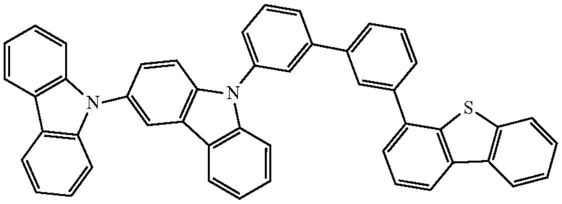
,
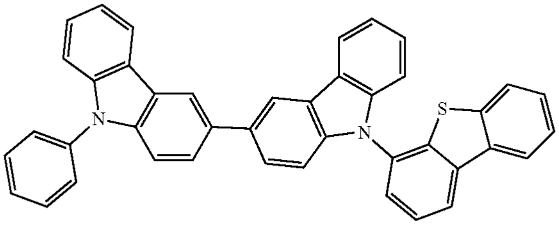
,
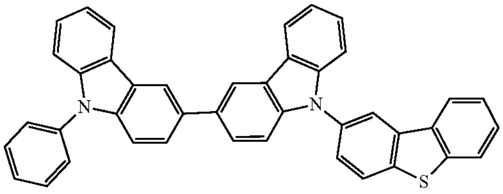
,
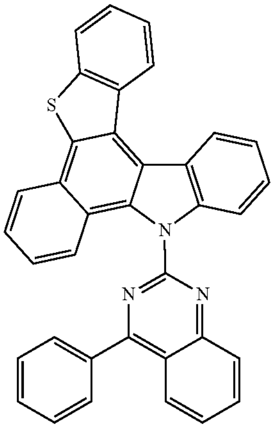
,
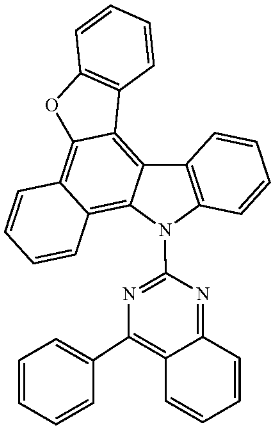
,
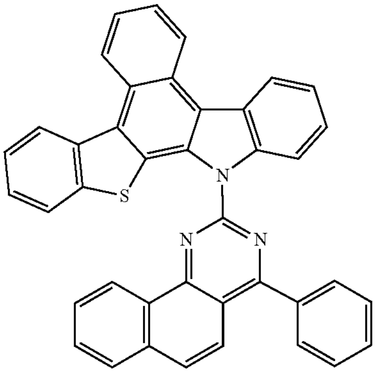
, -continued
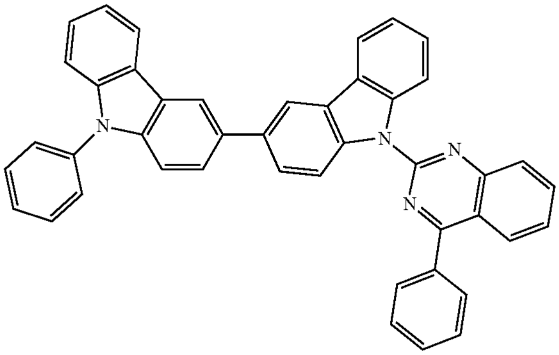
,
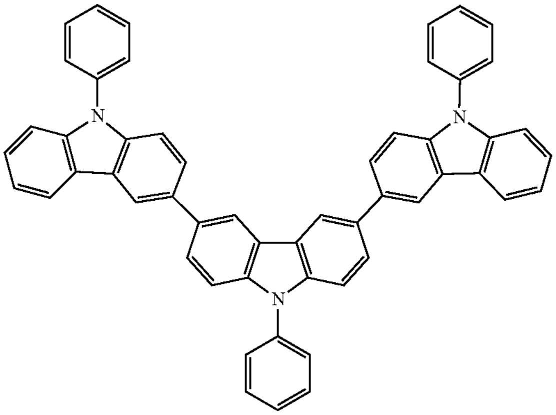
,
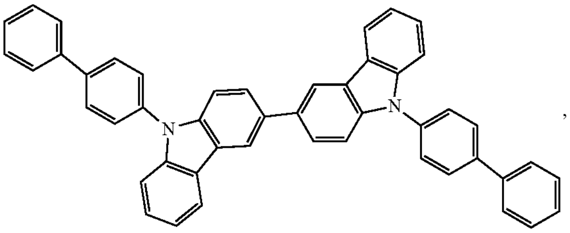
,
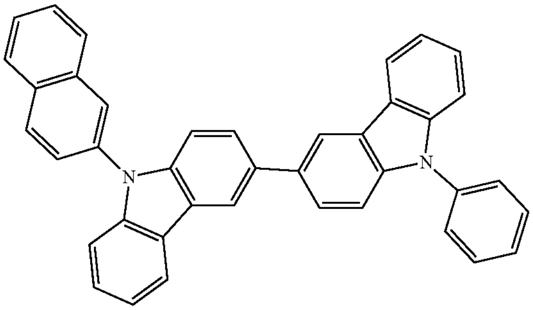
,
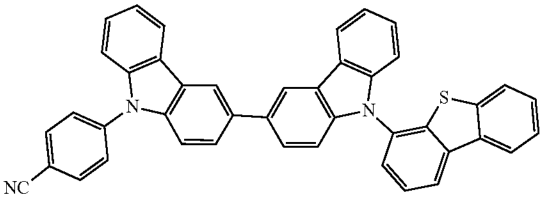
,
-continued
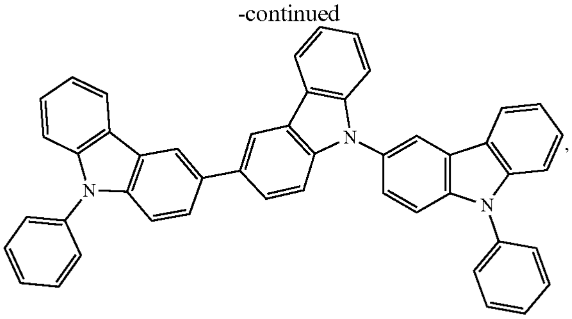
,
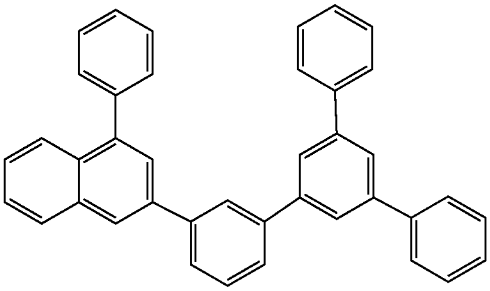
,
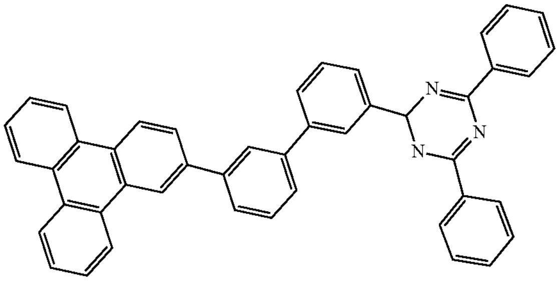
,
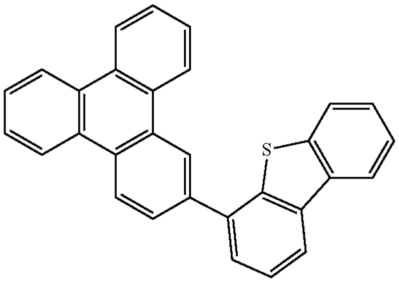
,
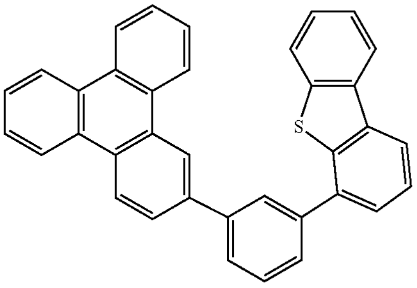
,
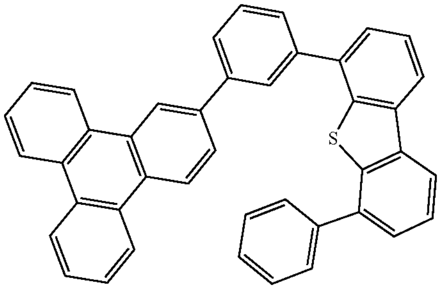
, -continued
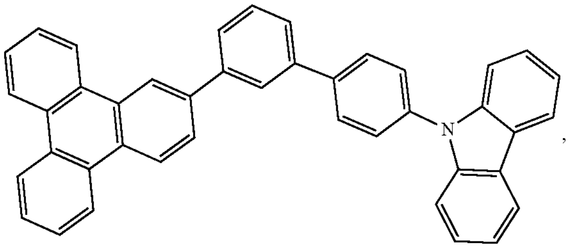
,
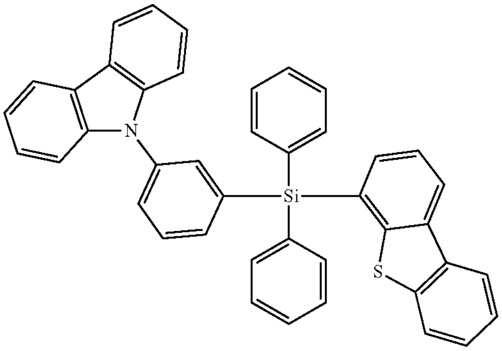
,
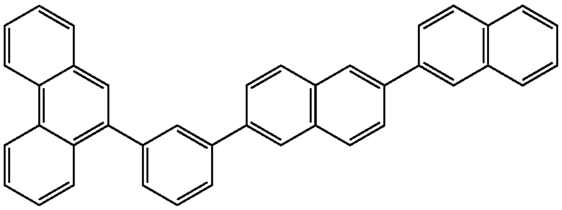
,
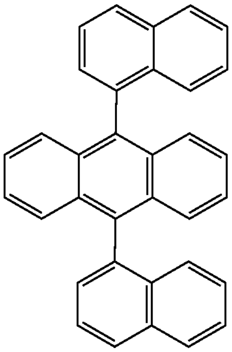
,
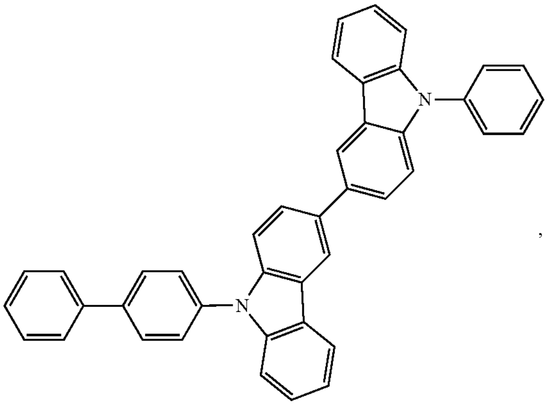
,
-continued
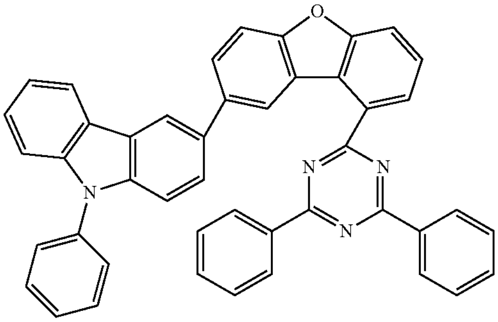
,
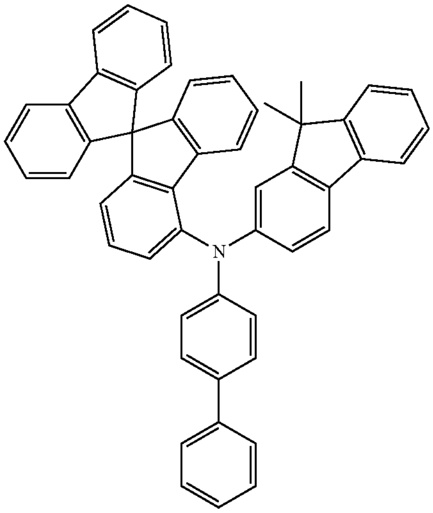
,
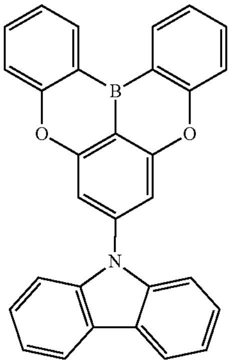
,
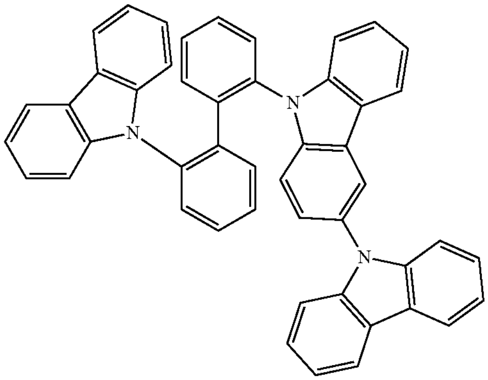
, -continued

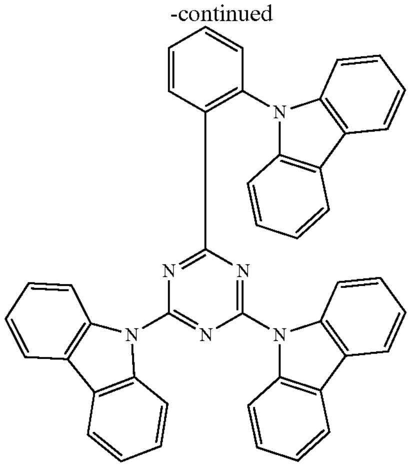

,

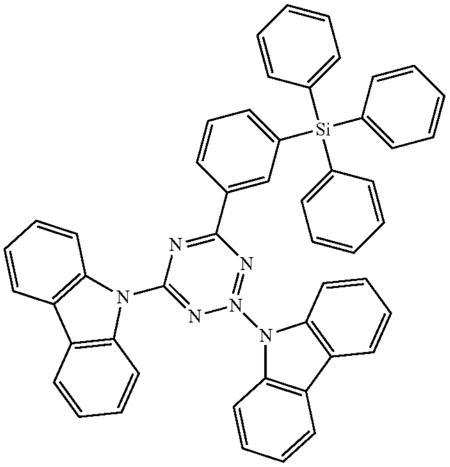

, and combinations thereof.

In some embodiments, the organic layer may further comprise a host, wherein the host comprises a metal complex.

In some embodiments, the compound as described herein may be a sensitizer; wherein the device may further comprise an acceptor; and wherein the acceptor may be selected from the group consisting of fluorescent emitter, delayed fluorescence emitter, and combination thereof.

In yet another aspect, the OLED of the present disclosure may also comprise an emissive region containing a compound as disclosed in the above compounds section of the present disclosure.

In some embodiments, the OLED of the present disclosure comprises an emissive region between a cathode and an anode where the emissive region comprises the emissive layer disclosed herein which includes a first phosphorescent emitter and a first host.

In some embodiments, at least one of the anode, the cathode, or a new layer disposed over the organic emissive layer functions as an enhancement layer. The enhancement layer comprises a plasmonic material exhibiting surface plasmon resonance that non-radiatively couples to the emitter material and transfers excited state energy from the emitter material to non-radiative mode of surface plasmon polariton. The enhancement layer is provided no more than a threshold distance away from the organic emissive layer, wherein the emitter material has a total non-radiative decay rate constant and a total radiative decay rate constant due to the presence of the enhancement layer and the threshold distance is where the total non-radiative decay rate constant is equal to the total radiative decay rate constant. In some embodiments, the OLED further comprises an outcoupling layer. In some embodiments, the outcoupling layer is disposed over the enhancement layer on the opposite side of the organic emissive layer. In some embodiments, the outcoupling layer is disposed on opposite side of the emissive layer from the enhancement layer but still outcouples energy from the surface plasmon mode of the enhancement layer. The outcoupling layer scatters the energy from the surface plasmon polaritons. In some embodiments this energy is scattered as photons to free space. In other embodiments, the energy is scattered from the surface plasmon mode into other modes of the device such as but not limited to the organic waveguide mode, the substrate mode, or another waveguiding mode. If energy is scattered to the non-free space mode of the OLED other outcoupling schemes could be incorporated to extract that energy to free space. In some embodiments, one or more intervening layer can be disposed between the enhancement layer and the outcoupling layer. The examples for intervening layer(s) can be dielectric materials, including organic, inorganic, perovskites, oxides, and may include stacks and/or mixtures of these materials.

The enhancement layer modifies the effective properties of the medium in which the emitter material resides resulting in any or all of the following: a decreased rate of emission, a modification of emission line-shape, a change in emission intensity with angle, a change in the stability of the emitter material, a change in the efficiency of the OLED, and reduced efficiency roll-off of the OLED device. Placement of the enhancement layer on the cathode side, anode side, or on both sides results in OLED devices which take advantage of any of the above-mentioned effects. In addition to the specific functional layers mentioned herein and illustrated in the various OLED examples shown in the figures, the OLEDs according to the present disclosure may include any of the other functional layers often found in OLEDs.

The enhancement layer can be comprised of plasmonic materials, optically active metamaterials, or hyperbolic metamaterials. As used herein, a plasmonic material is a material in which the real part of the dielectric constant crosses zero in the visible or ultraviolet region of the electromagnetic spectrum. In some embodiments, the plasmonic material includes at least one metal. In such embodiments the metal may include at least one of Ag, Al, Au, Ir, Pt, Ni, Cu, W, Ta, Fe, Cr, Mg, Ga, Rh, Ti, Ru, Pd, In, Bi, Ca alloys or mixtures of these materials, and stacks of these materials. In general, a metamaterial is a medium composed of different materials where the medium as a whole acts differently than the sum of its material parts. In particular, we define optically active metamaterials as materials which have both negative permittivity and negative permeability. Hyperbolic metamaterials, on the other hand, are anisotropic media in which the permittivity or permeability are of different sign for different spatial directions. Optically active metamaterials and hyperbolic metamaterials are strictly distinguished from many other photonic structures such as Distributed Bragg Reflectors ("DBRs") in that the medium should appear uniform in the direction of propagation on the length scale of the wavelength of light. Using terminology that one skilled in the art can understand: the dielectric constant of the metamaterials in the direction of propagation can be described with the effective medium approximation. Plasmonic materials and metamaterials provide methods for controlling the propagation of light that can enhance OLED performance in a number of ways.

In some embodiments, the enhancement layer is provided as a planar layer. In other embodiments, the enhancement layer has wavelength-sized features that are arranged periodically, quasi-periodically, or randomly, or sub-wavelength-sized features that are arranged periodically, quasi-periodically, or randomly. In some embodiments, the wavelength-sized features and the sub-wavelength-sized features have sharp edges.

In some embodiments, the outcoupling layer has wavelength-sized features that are arranged periodically, quasi-periodically, or randomly, or sub-wavelength-sized features that are arranged periodically, quasi-periodically, or randomly. In some embodiments, the outcoupling layer may be composed of a plurality of nanoparticles and in other embodiments the outcoupling layer is composed of a plurality of nanoparticles disposed over a material. In these embodiments the outcoupling may be tunable by at least one of varying a size of the plurality of nanoparticles, varying a shape of the plurality of nanoparticles, changing a material of the plurality of nanoparticles, adjusting a thickness of the material, changing the refractive index of the material or an additional layer disposed on the plurality of nanoparticles, varying a thickness of the enhancement layer, and/or varying the material of the enhancement layer. The plurality of nanoparticles of the device may be formed from at least one of metal, dielectric material, semiconductor materials, an alloy of metal, a mixture of dielectric materials, a stack or layering of one or more materials, and/or a core of one type of material and that is coated with a shell of a different type of material. In some embodiments, the outcoupling layer is composed of at least metal nanoparticles wherein the metal is selected from the group consisting of Ag, Al, Au, Ir, Pt, Ni, Cu, W, Ta, Fe, Cr, Mg, Ga, Rh, Ti, Ru, Pd, In, Bi, Ca, alloys or mixtures of these materials, and stacks of these materials. The plurality of nanoparticles may have additional layer disposed over them. In some embodiments, the polarization of the emission can be tuned using the outcoupling layer. Varying the dimensionality and periodicity of the outcoupling layer can select a type of polarization that is preferentially outcoupled to air. In some embodiments the outcoupling layer also acts as an electrode of the device.

In yet another aspect, the present disclosure also provides a consumer product comprising an organic light-emitting device (OLED) having an anode; a cathode; and an organic layer disposed between the anode and the cathode, wherein the organic layer may comprise a compound as disclosed in the above compounds section of the present disclosure.

In some embodiments, the consumer product comprises an organic light-emitting device (OLED) as described herein.

In some embodiments, the consumer product can be one of a flat panel display, a computer monitor, a medical monitor, a television, a billboard, a light for interior or exterior illumination and/or signaling, a heads-up display, a fully or partially transparent display, a flexible display, a laser printer, a telephone, a cell phone, tablet, a phablet, a personal digital assistant (PDA), a wearable device, a laptop computer, a digital camera, a camcorder, a viewfinder, a micro-display that is less than 2 inches diagonal, a 3-D display, a virtual reality or augmented reality display, a vehicle, a video wall comprising multiple displays tiled together, a theater or stadium screen, a light therapy device, and a sign.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

Several OLED materials and configurations are described in U.S. Pat. Nos. 5,844,363, 6,303,238, and 5,707,745, which are incorporated herein by reference in their entirety.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
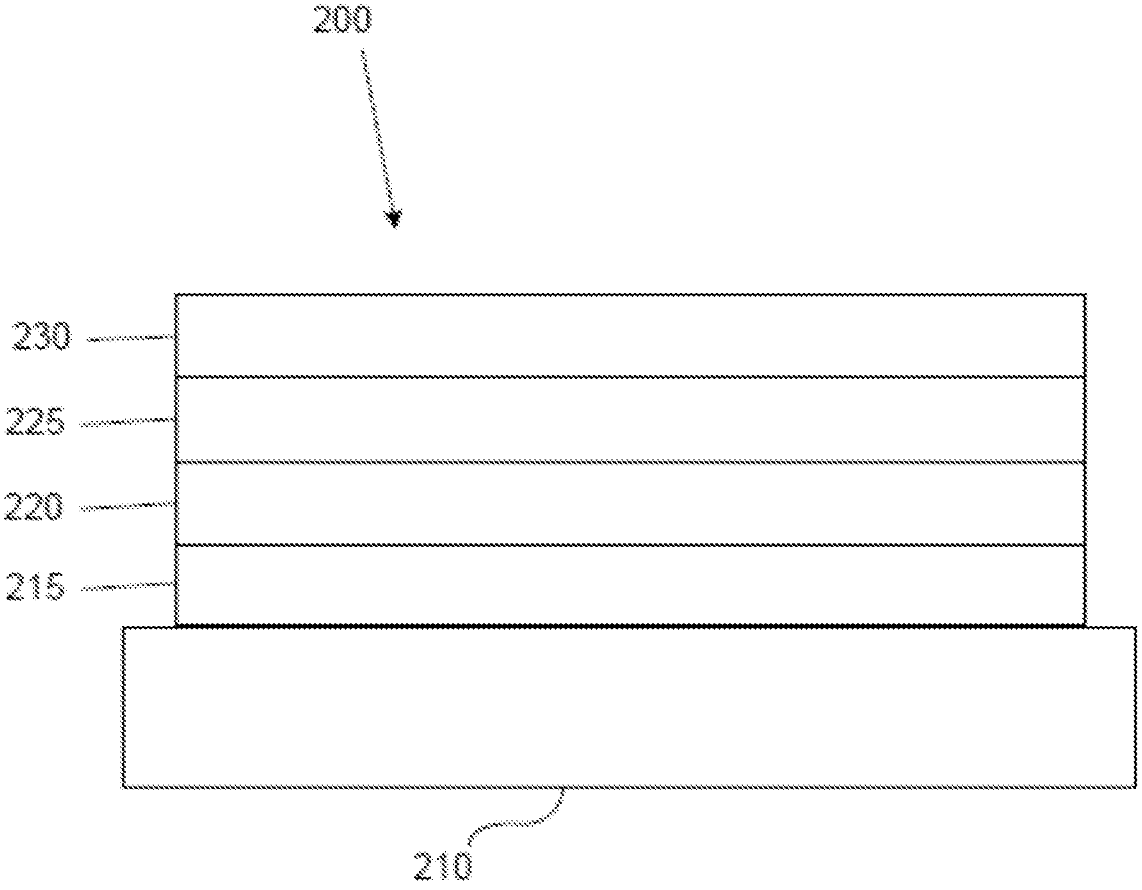
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the present disclosure may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and organic vapor jet printing (OVJP). Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons are a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present disclosure may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the present disclosure can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the present disclosure can be incorporated into a wide variety of consumer products that have one or more of the electronic component modules (or units) incorporated therein. A consumer product comprising an OLED that includes the compound of the present disclosure in the organic layer in the OLED is disclosed. Such consumer products would include any kind of products that include one or more light source(s) and/or one or more of some type of visual displays. Some examples of such consumer products include flat panel displays, curved displays, computer monitors, medical monitors, televisions, billboards, lights for interior or exterior illumination and/or signaling, heads-up displays, fully or partially transparent displays, flexible displays, rollable displays, foldable displays, stretchable displays, laser printers, telephones, mobile phones, tablets, phablets, personal digital assistants (PDAs), wearable devices, laptop computers, digital cameras, camcorders, viewfinders, micro-displays (displays that are less than 2 inches diagonal), 3-D displays, virtual reality or augmented reality displays, vehicles, video walls comprising multiple displays tiled together, theater or stadium screen, a light therapy device, and a sign. Various control mechanisms may be used to control devices fabricated in accordance with the present disclosure, including passive matrix and active matrix. Many of the devices are intended for use in a temperature range comfortable to humans, such as 18 degrees C. to 30 degrees C., and more preferably at room temperature (20-25° C.), but could be used outside this temperature range, for example, from −40 degree C. to +80° C.

More details on OLEDs, and the definitions described above, can be found in U.S. Pat. No. 7,279,704, which is incorporated herein by reference in its entirety.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

In some embodiments, the compound can be an emissive dopant. In some embodiments, the compound can produce emissions via phosphorescence, fluorescence, thermally activated delayed fluorescence, i.e., TADF (also referred to as E-type delayed fluorescence; see, e.g., U.S. application Ser. No. 15/700,352, which is hereby incorporated by reference in its entirety), triplet-triplet annihilation, or combinations of these processes. In some embodiments, the emissive dopant can be a racemic mixture, or can be enriched in one enantiomer. In some embodiments, the compound can be homoleptic (each ligand is the same). In some embodiments, the compound can be heteroleptic (at least one ligand is different from others). When there are more than one ligand coordinated to a metal, the ligands can all be the same in some embodiments. In some other embodiments, at least one ligand is different from the other ligands. In some embodiments, every ligand can be different from each other. This is also true in embodiments where a ligand being coordinated to a metal can be linked with other ligands being coordinated to that metal to form a tridentate, tetradentate, pentadentate, or hexadentate ligands. Thus, where the coordinating ligands are being linked together, all of the ligands can be the same in some embodiments, and at least one of the ligands being linked can be different from the other ligand(s) in some other embodiments.

In some embodiments, the compound can be used as a phosphorescent sensitizer in an OLED where one or multiple layers in the OLED contains an acceptor in the form of one or more fluorescent and/or delayed fluorescence emitters. In some embodiments, the compound can be used as one component of an exciplex to be used as a sensitizer. As a phosphorescent sensitizer, the compound must be capable of energy transfer to the acceptor and the acceptor will emit the energy or further transfer energy to a final emitter. The acceptor concentrations can range from 0.001% to 100%. The acceptor could be in either the same layer as the phosphorescent sensitizer or in one or more different layers. In some embodiments, the acceptor is a TADF emitter. In some embodiments, the acceptor is a fluorescent emitter. In some embodiments, the emission can arise from any or all of the sensitizer, acceptor, and final emitter.

According to another aspect, a formulation comprising the compound described herein is also disclosed.

The OLED disclosed herein can be incorporated into one or more of a consumer product, an electronic component module, and a lighting panel. The organic layer can be an emissive layer and the compound can be an emissive dopant in some embodiments, while the compound can be a non-emissive dopant in other embodiments.

In yet another aspect of the present disclosure, a formulation that comprises the novel compound disclosed herein is described. The formulation can include one or more components selected from the group consisting of a solvent, a host, a hole injection material, hole transport material, electron blocking material, hole blocking material, and an electron transport material, disclosed herein.

The present disclosure encompasses any chemical structure comprising the novel compound of the present disclosure, or a monovalent or polyvalent variant thereof. In other words, the inventive compound, or a monovalent or polyvalent variant thereof, can be a part of a larger chemical structure. Such chemical structure can be selected from the group consisting of a monomer, a polymer, a macromolecule, and a supramolecule (also known as supermolecule). As used herein, a “monovalent variant of a compound” refers to a moiety that is identical to the compound except that one hydrogen has been removed and replaced with a bond to the rest of the chemical structure. As used herein, a “polyvalent variant of a compound” refers to a moiety that is identical to the compound except that more than one hydrogen has been removed and replaced with a bond or bonds to the rest of the chemical structure. In the instance of a supramolecule, the inventive compound can also be incorporated into the supramolecule complex without covalent bonds.

In yet another aspect of the present disclosure, the compound is selected from the group consisting of the compounds in LIST 1 as described above. In some embodiments, the compound is selected from the group consisting of the compounds in LIST 2 as described above.

C. Combination of the Compounds of the Present Disclosure with Other Materials The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

a) Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804, US20150123047, and US2012146012.

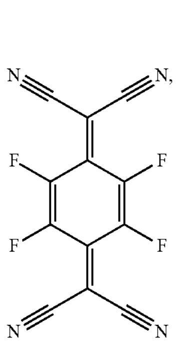

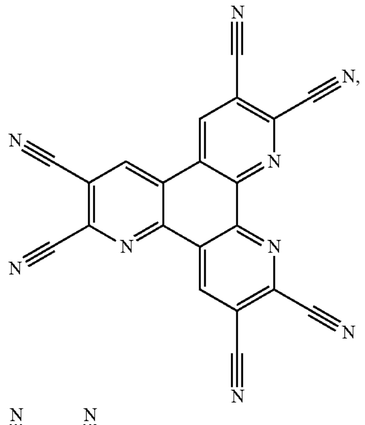

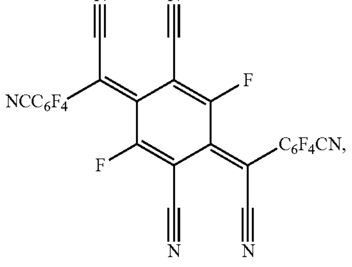

-continued

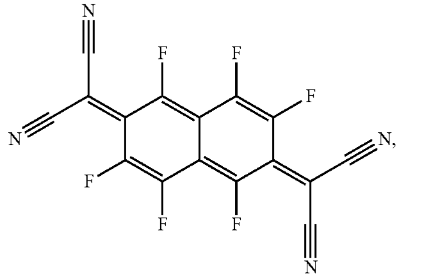

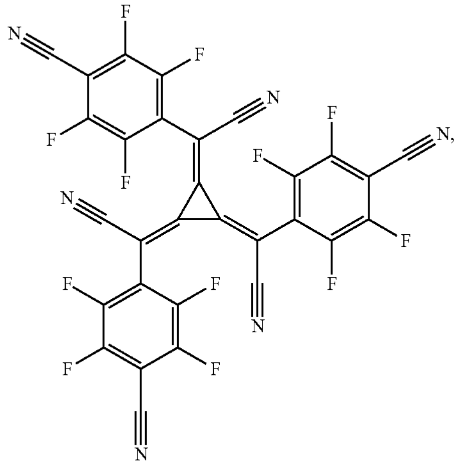

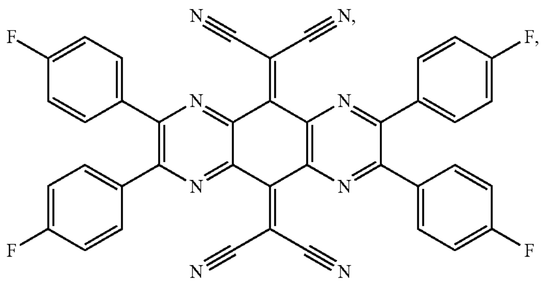

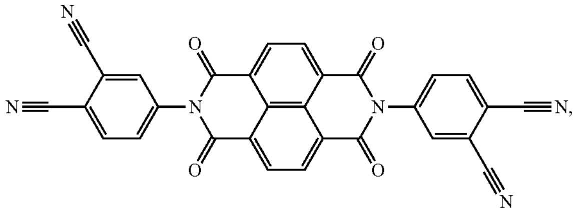

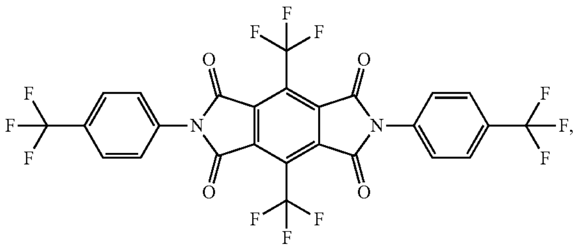

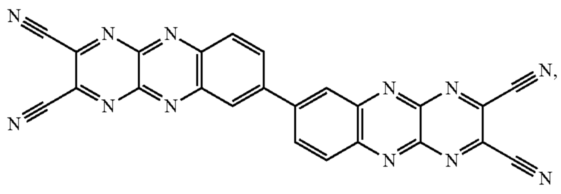

-continued

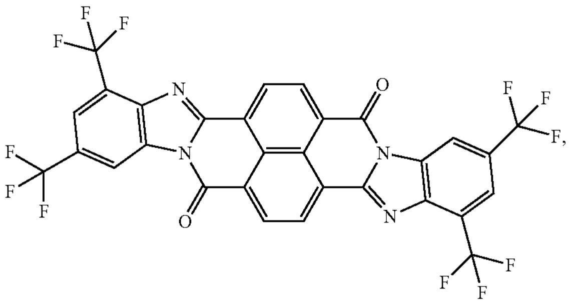

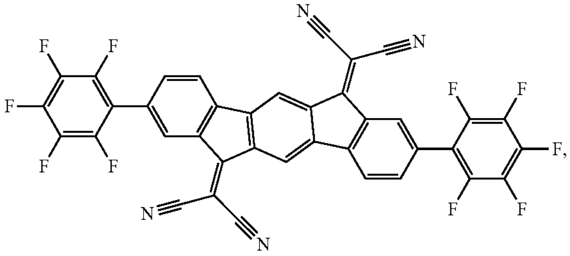

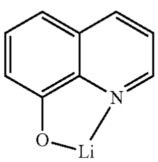,

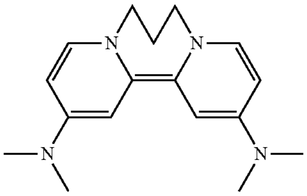

and

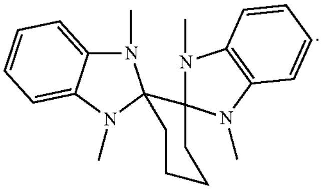.

b) HIL/HTL:

A hole injecting/transporting material to be used in the present disclosure is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

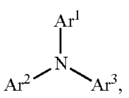

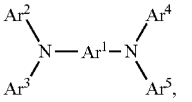

-continued

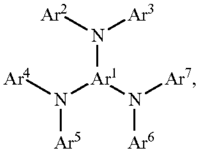

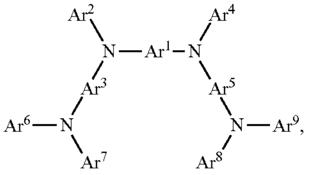

and

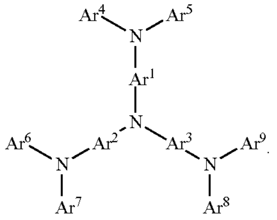

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, $Ar^1$ to $Ar^9$ is independently selected from the group consisting of:

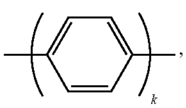,

-continued

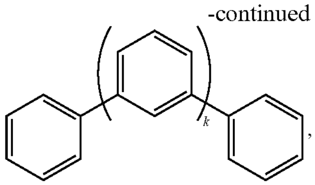
,
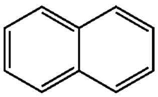
,

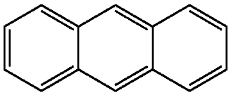
,
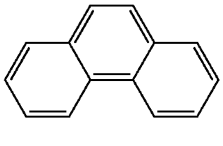
,

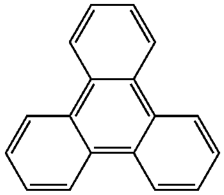
,
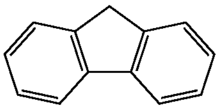
, and

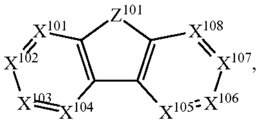

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

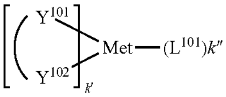

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. $Fc^+$/Fc couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Ser. No. 06/517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018.

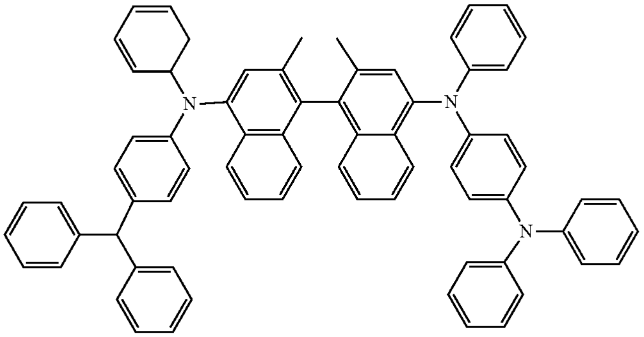
,
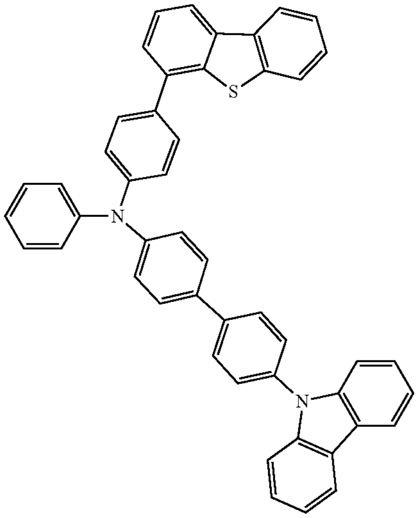
,

-continued
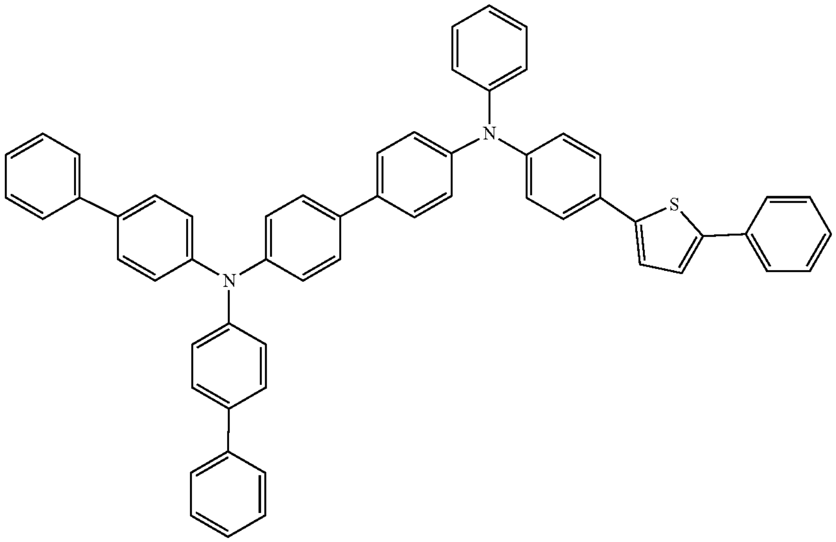
,
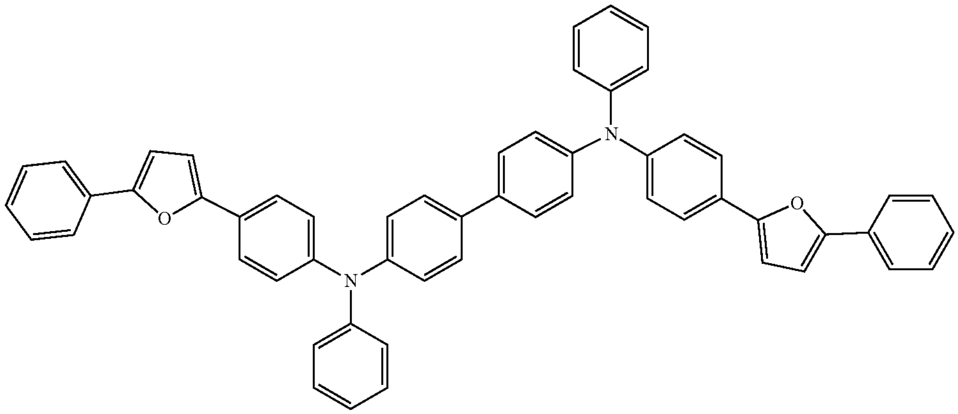
,
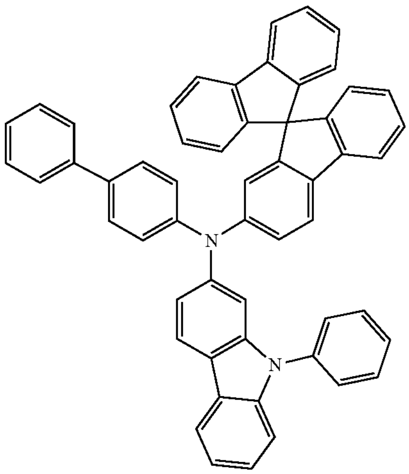
,
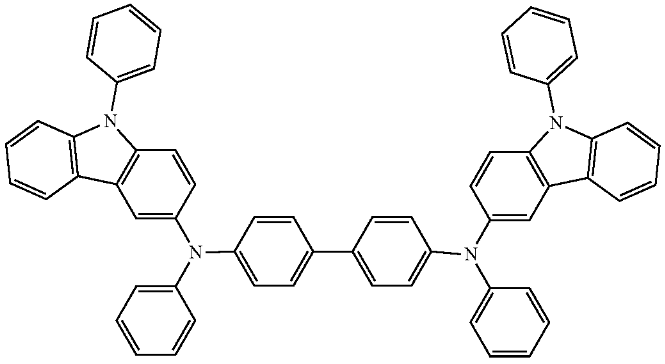
,

-continued
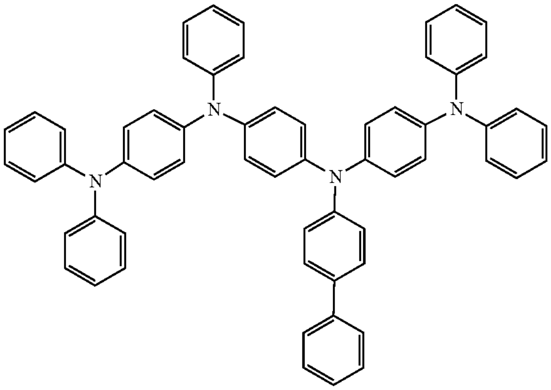
,
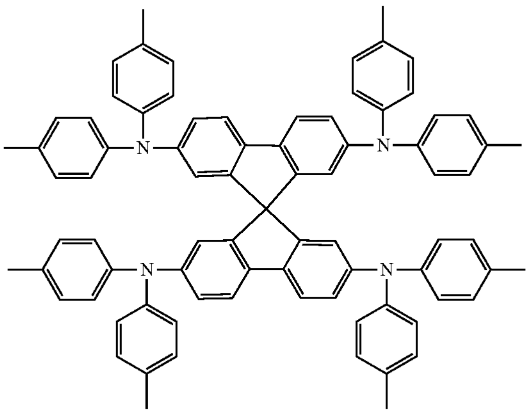
,
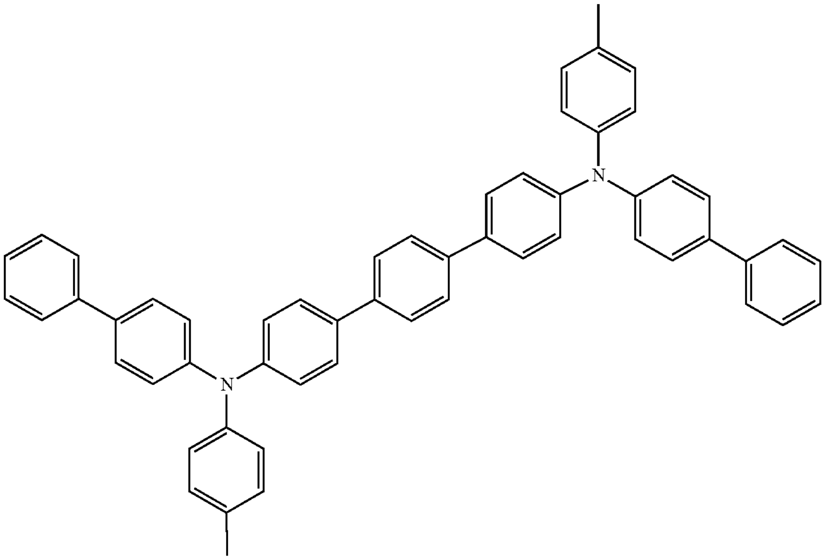
,
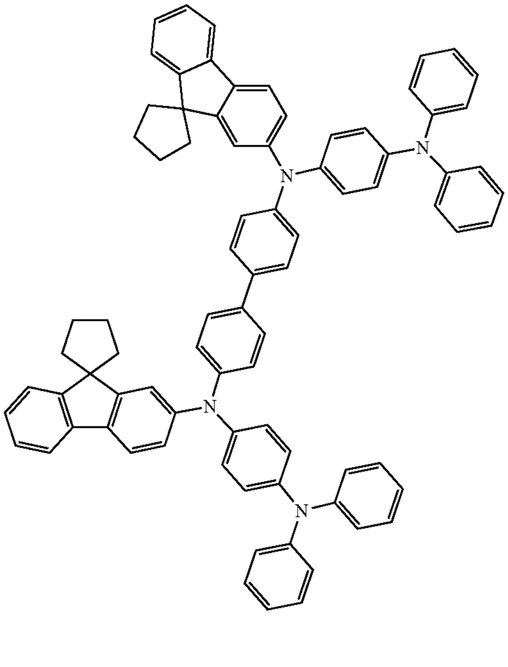
,
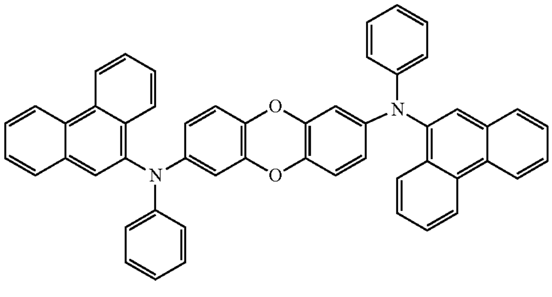
, -continued
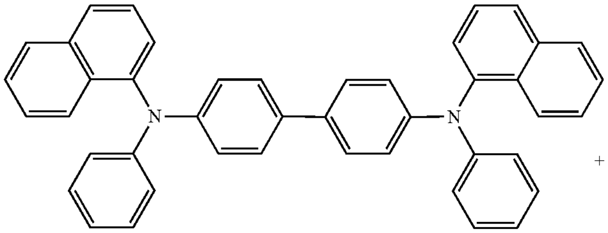
+ $MoO_x$,
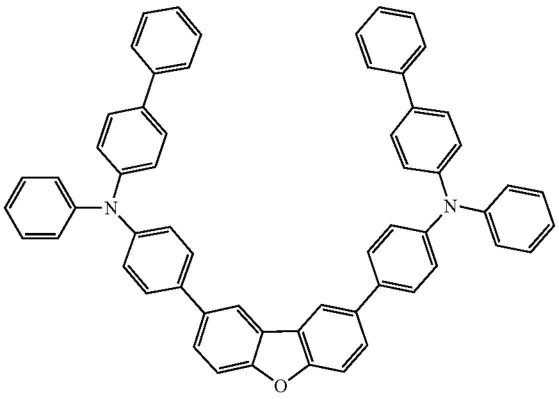
,
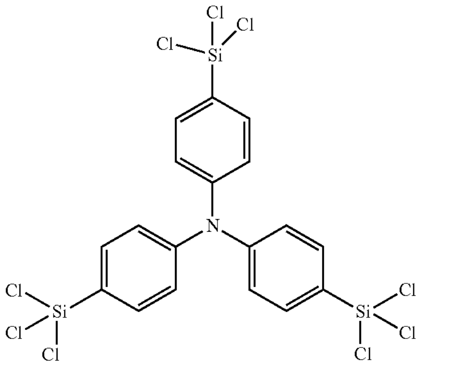
,
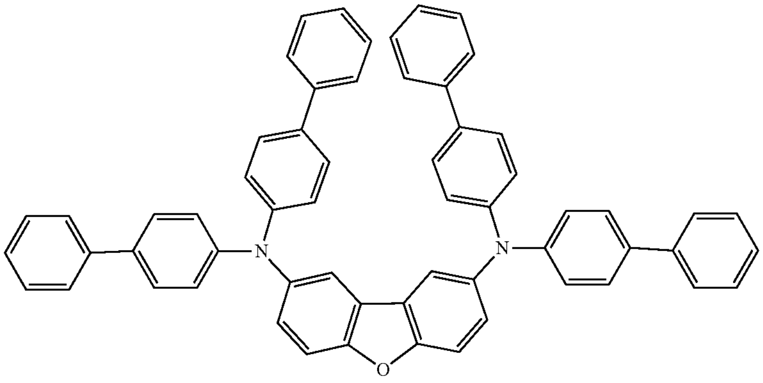
,
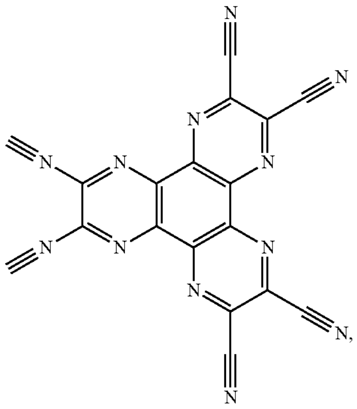
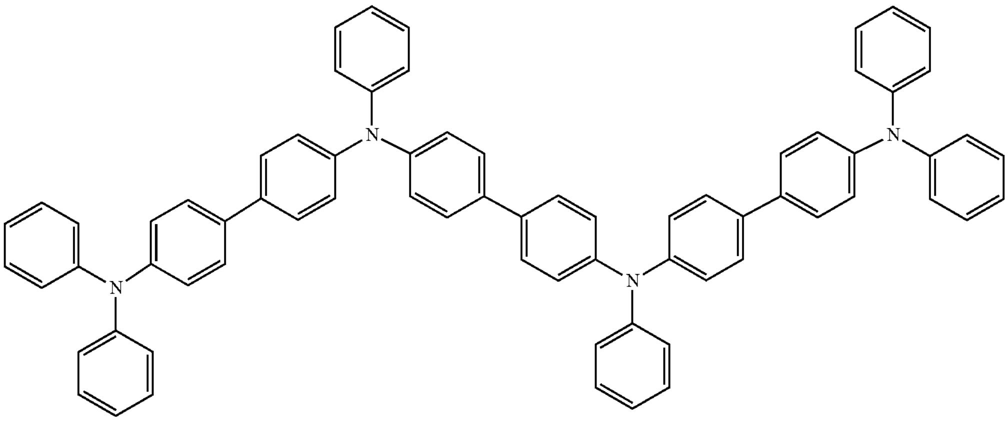
, -continued
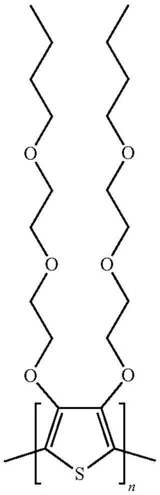
,
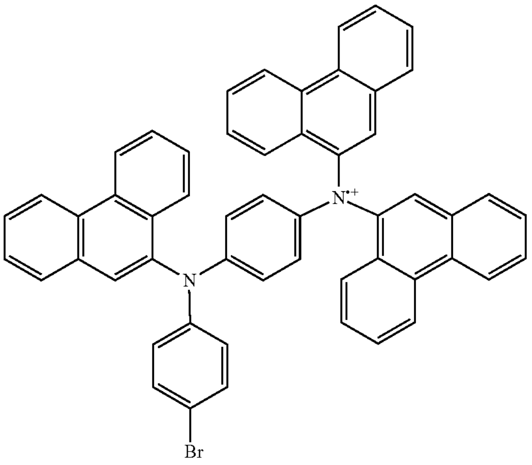
,
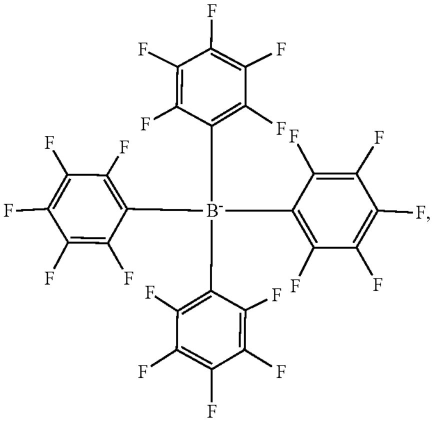
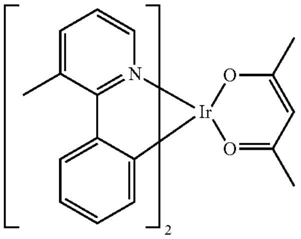
,
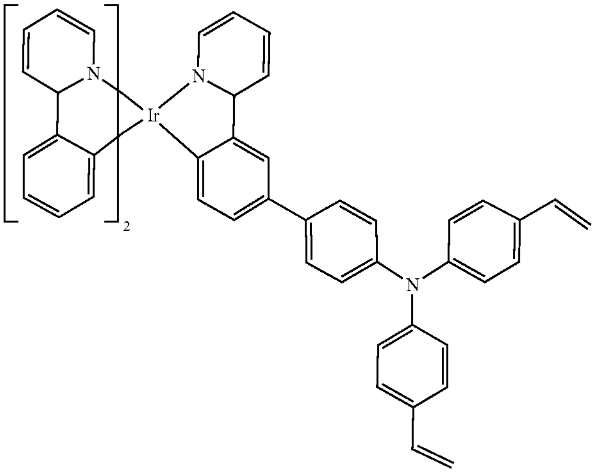
,
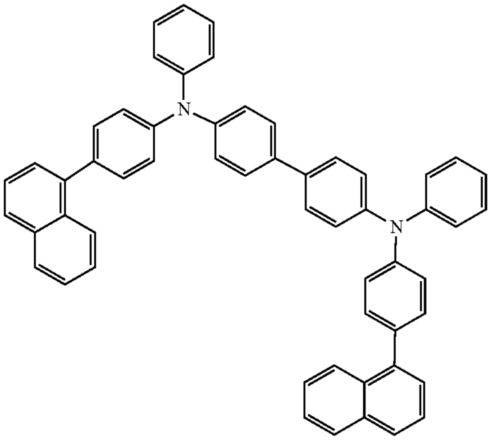
,
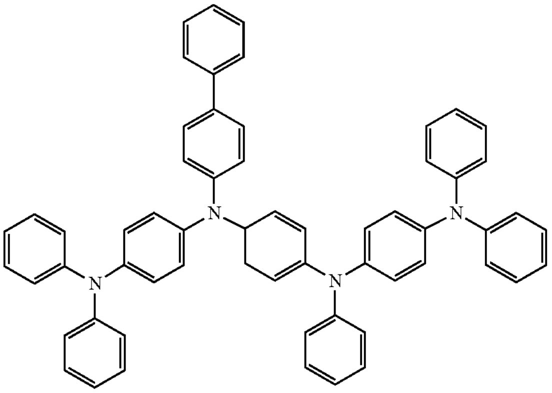
, -continued
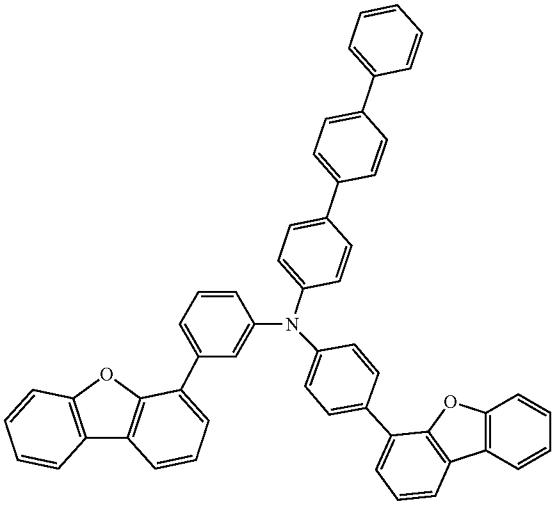
,
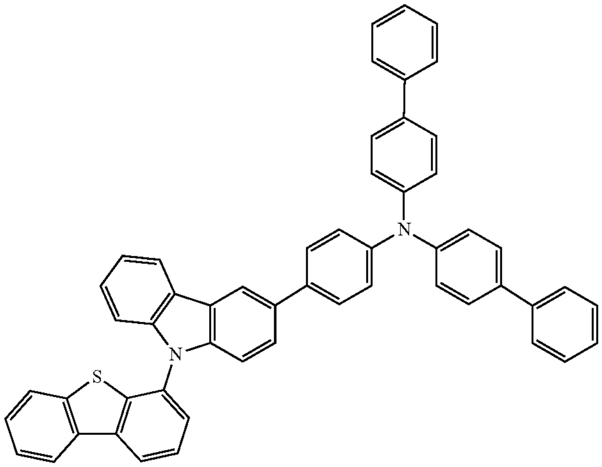
,
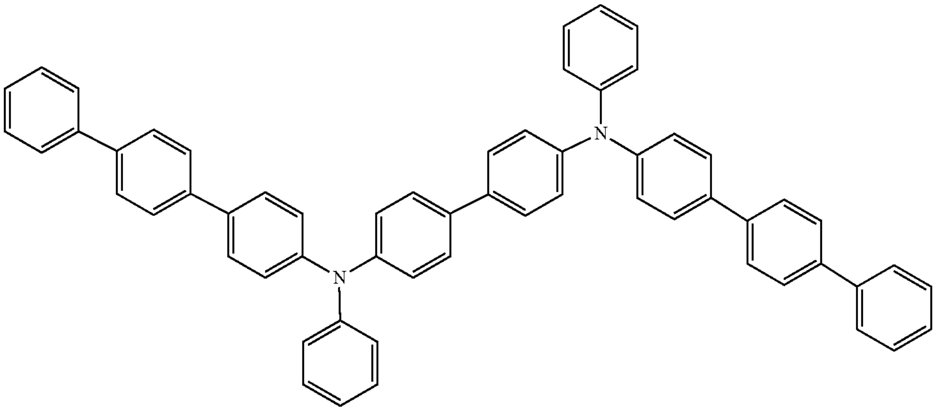
,
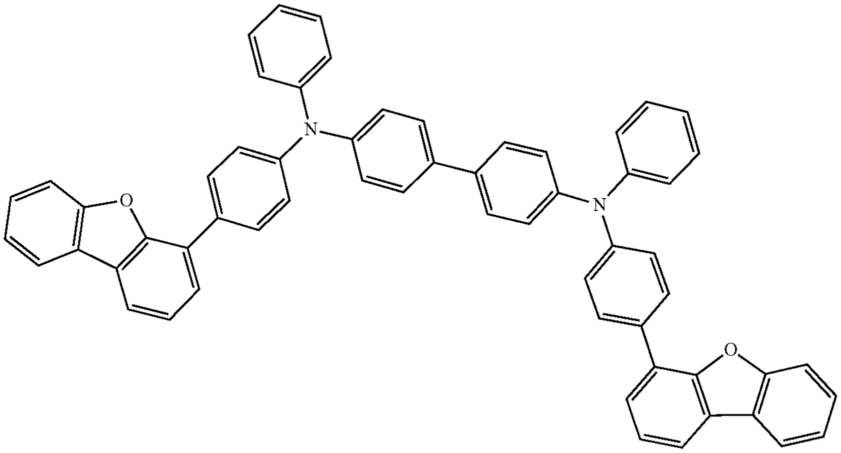
,
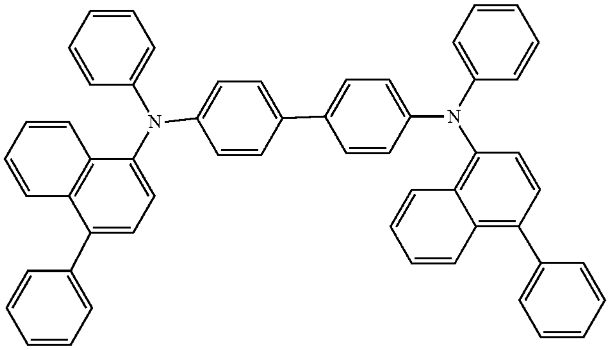
, -continued
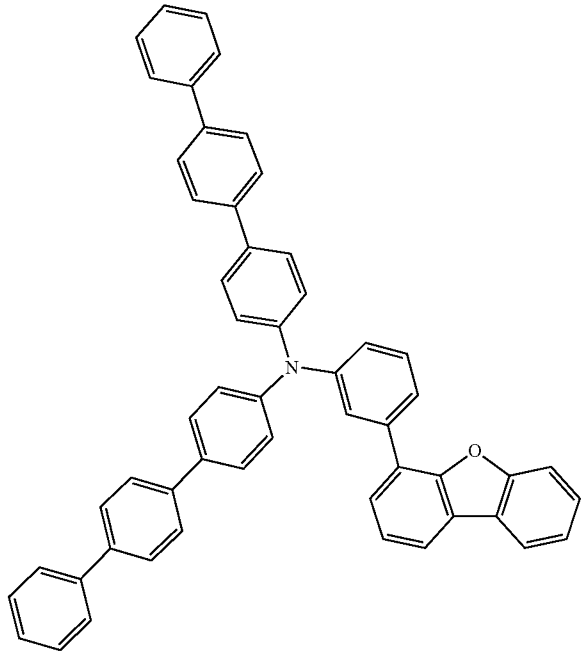
,
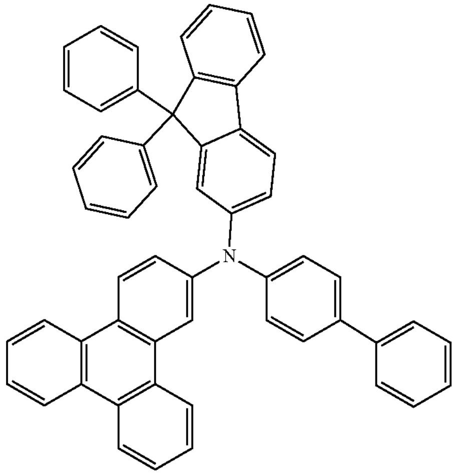
,
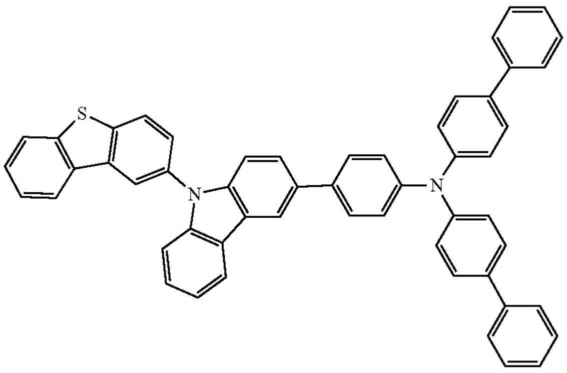
,
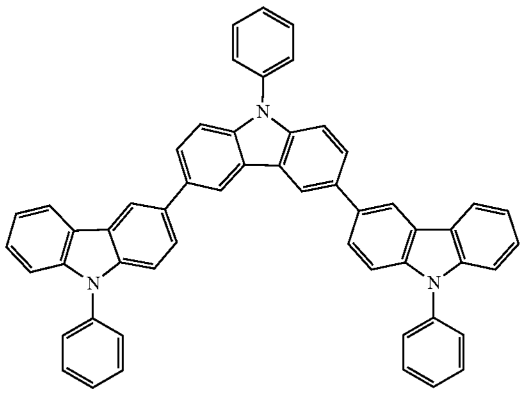
,
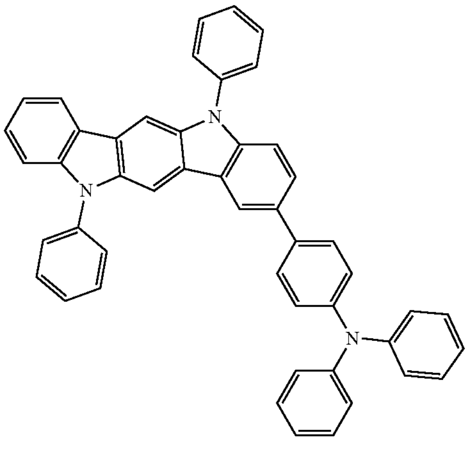
,
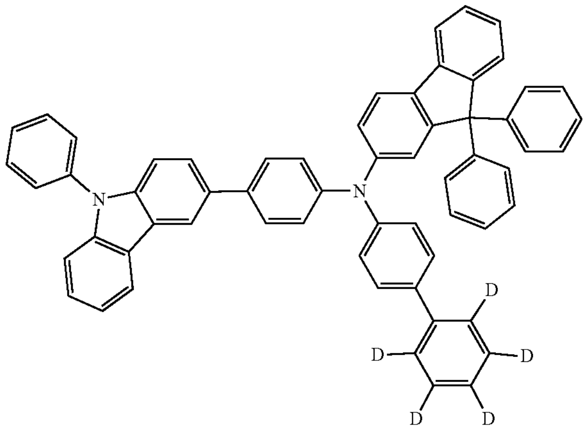
, -continued
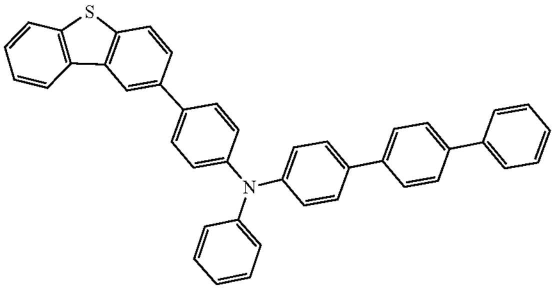
,
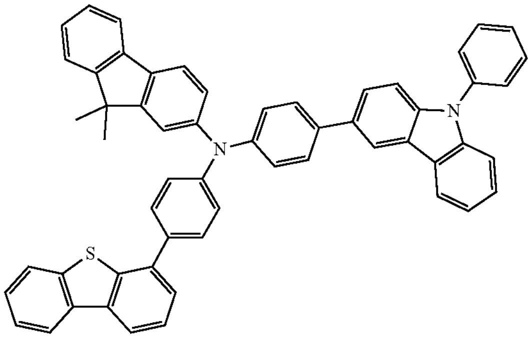
,
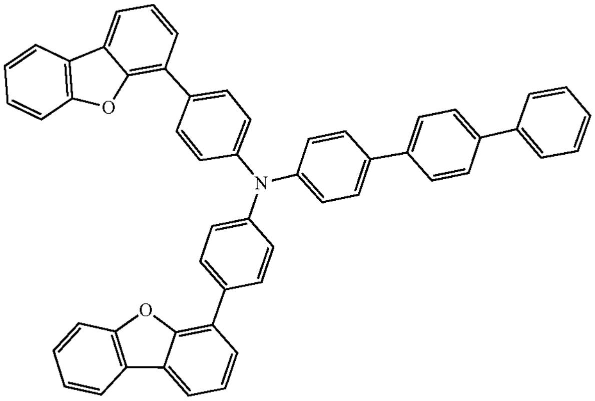
,
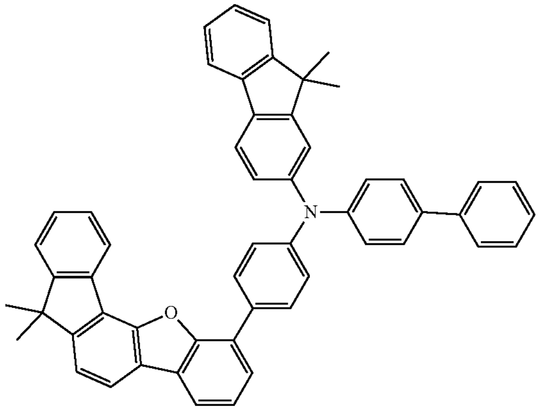
,
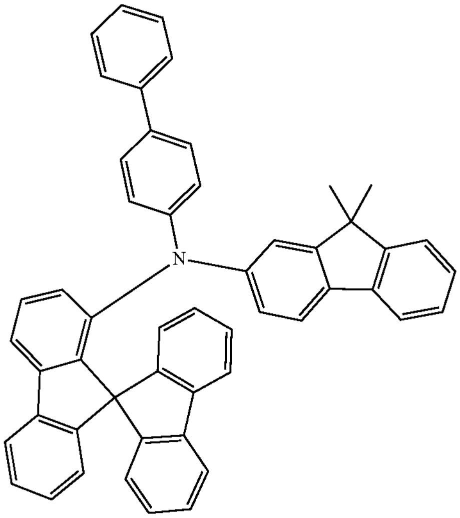
,
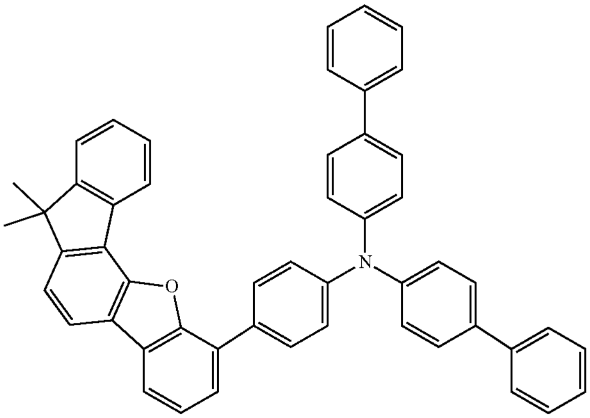
,
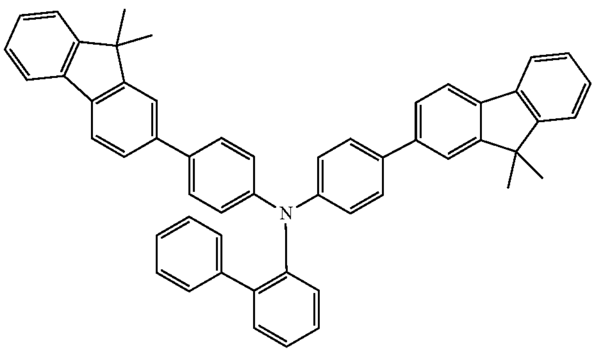
,
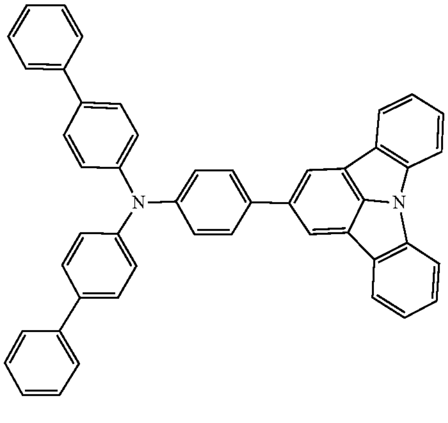
, -continued
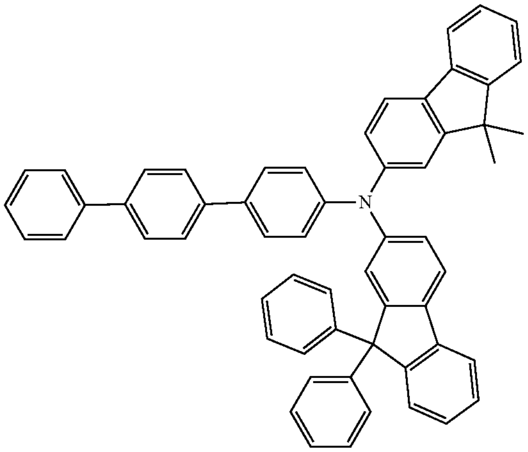
,
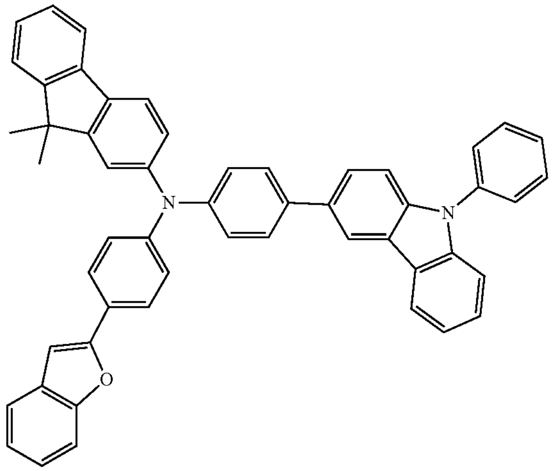
,
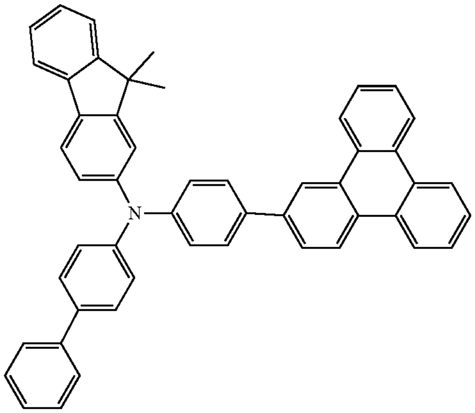
,
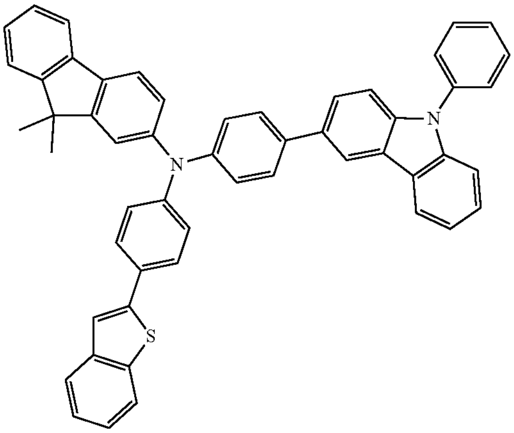
,
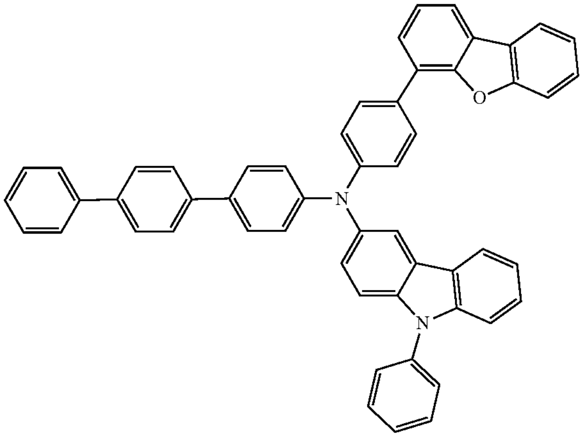
,
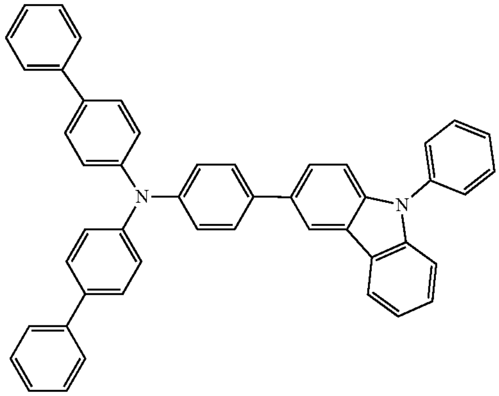
, -continued
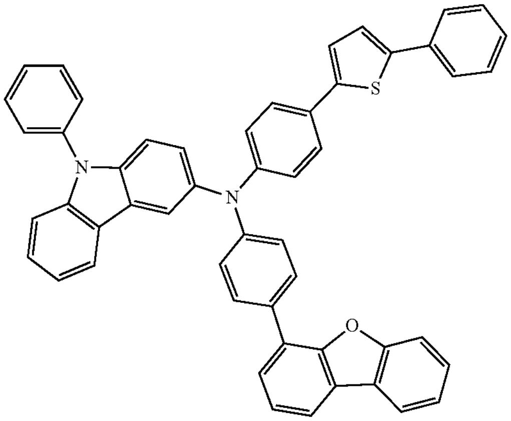
,
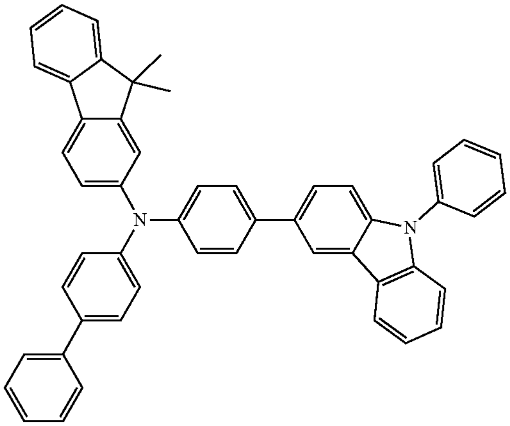
,
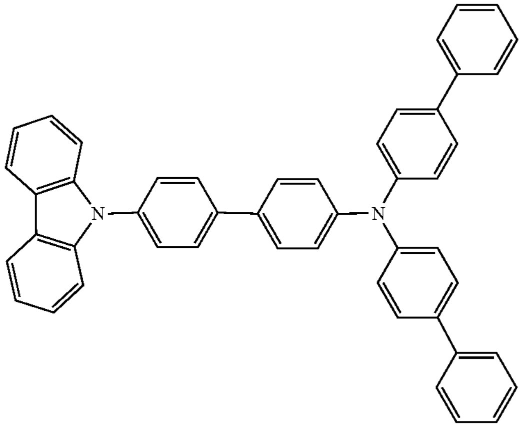
,
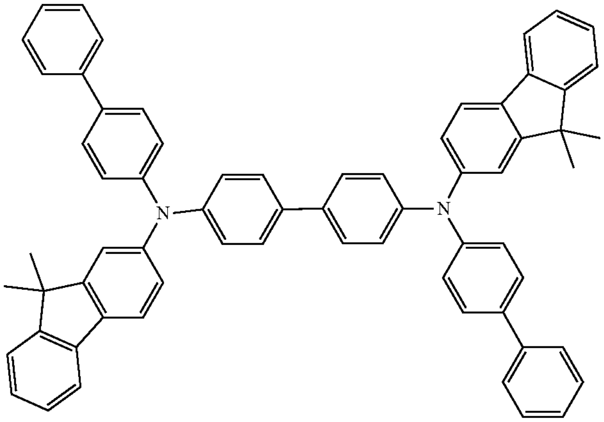
,
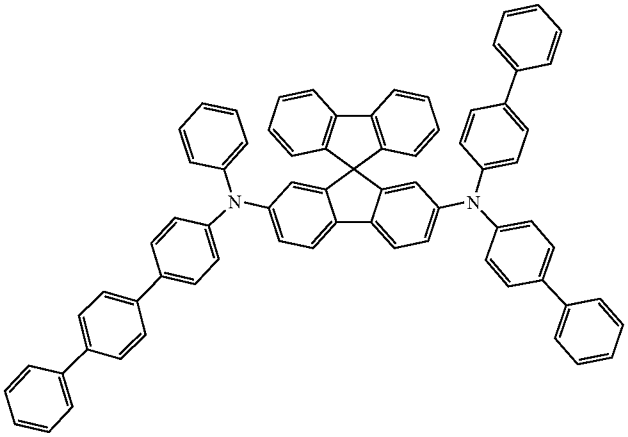
,
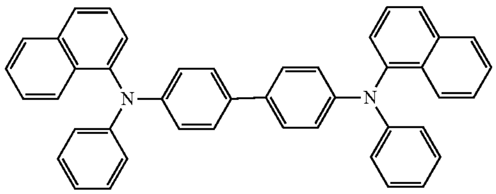
,
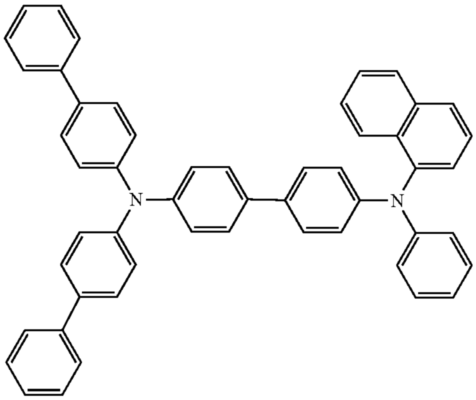
,
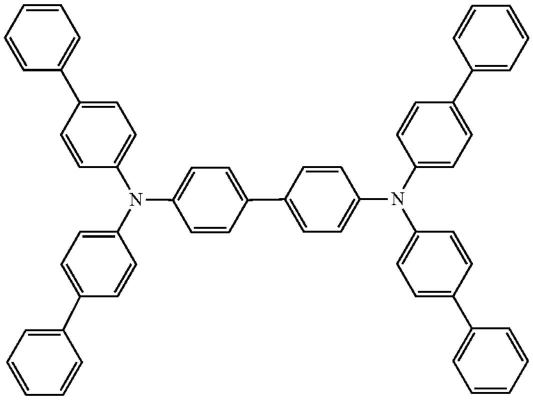
, -continued
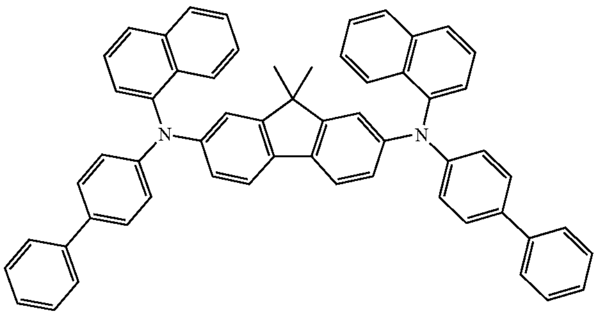
,
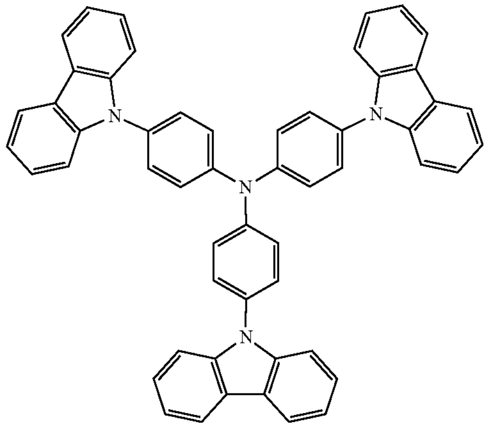
,
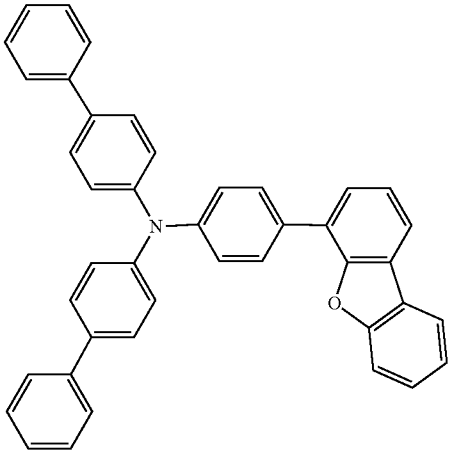
,
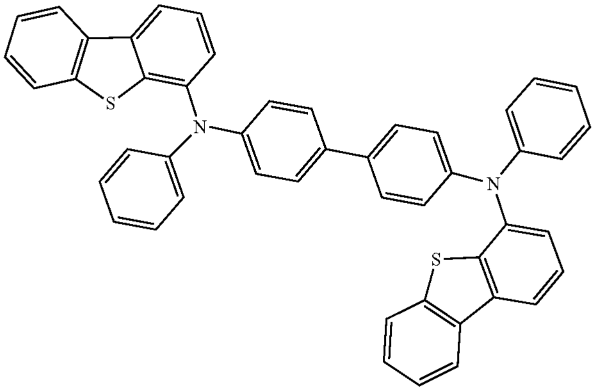
,
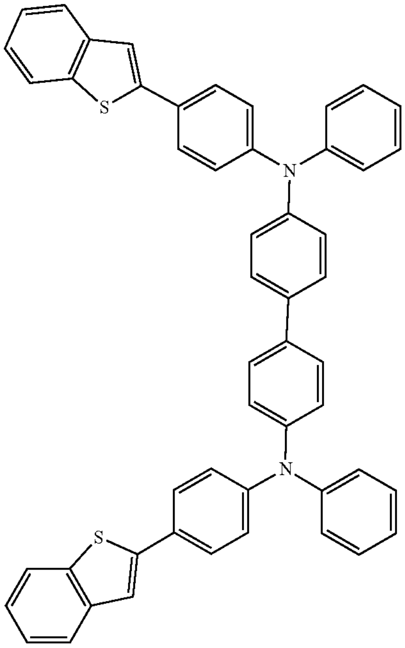
, and -continued

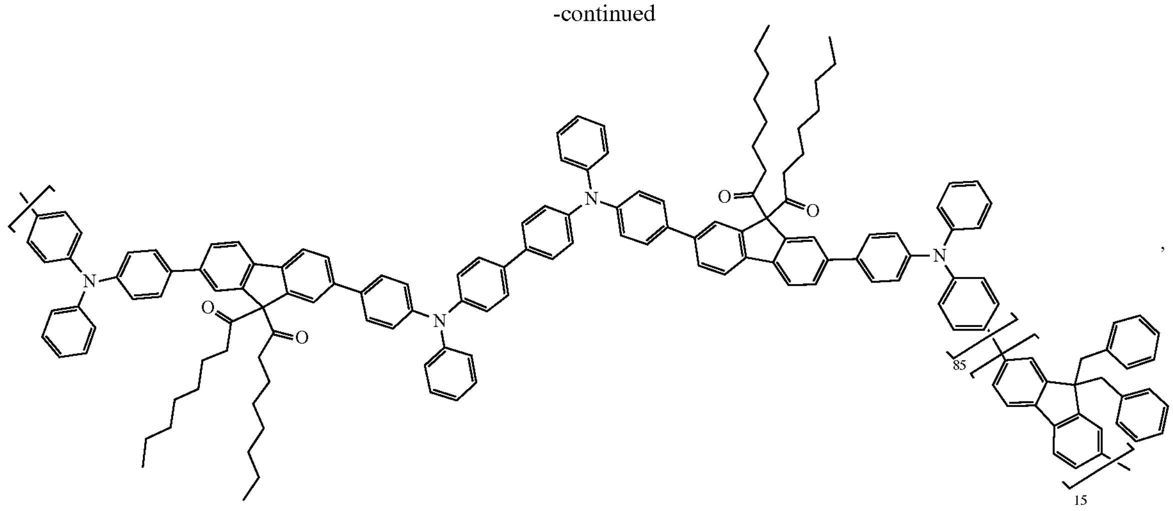

, c) EBL:

An electron blocking layer (EBL) may be used to reduce the number of electrons and/or excitons that leave the emissive layer. The presence of such a blocking layer in a device may result in substantially higher efficiencies, and/or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and/or higher triplet energy than one or more of the hosts closest to the EBL interface. In one aspect, the compound used in EBL contains the same molecule or the same functional groups used as one of the hosts described below.

d) Hosts:

The light emitting layer of the organic EL device of the present disclosure preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

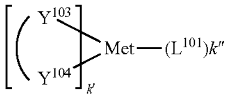

wherein Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

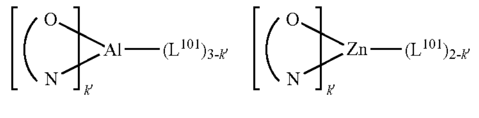

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

In one aspect, the host compound contains at least one of the following groups selected from the group consisting of aromatic hydrocarbon cyclic compounds such as benzene, biphenyl, triphenyl, triphenylene, tetraphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each option within each group may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, the host compound contains at least one of the following groups in the molecule:

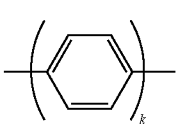,
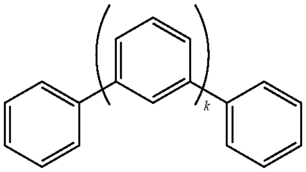,
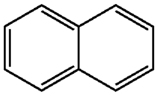,
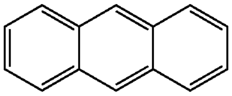,
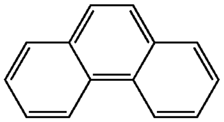,
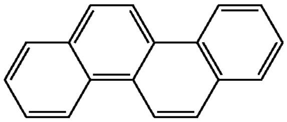,
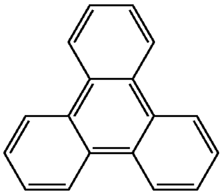,
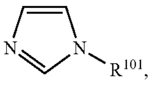,
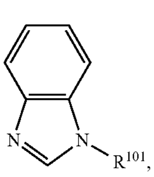,
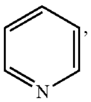,
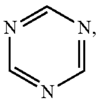,
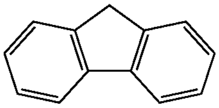,
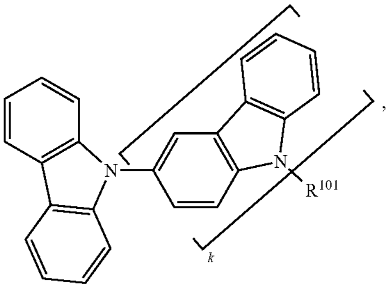,
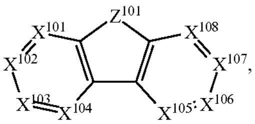,
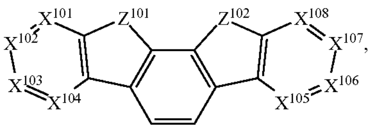,
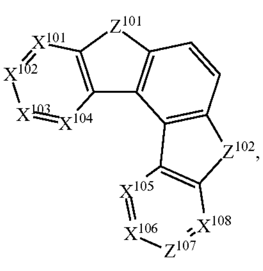, -continued

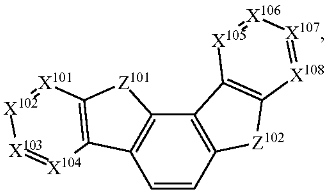,
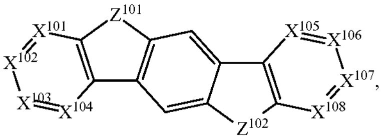, and
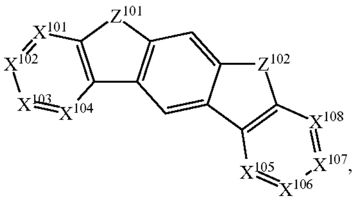, wherein $R^1$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, and when it is aryl or heteroaryl, it has the similar definition as Ar's mentioned above. k is an integer from 0 to 20 or 11 to 20. $X^{101}$ to $X^{108}$ are independently selected from C (including CH) or N. $Z^{101}$ and $Z^{102}$ are independently selected from $NR^{101}$, O, or S.

Non-limiting examples of the host materials that may be used in an OLED in combination with materials disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472, US20170263869, US20160163995, U.S. Pat. No. 9,466,803, -continued
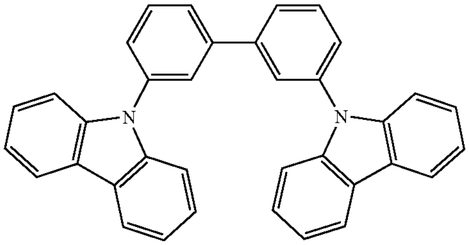
,
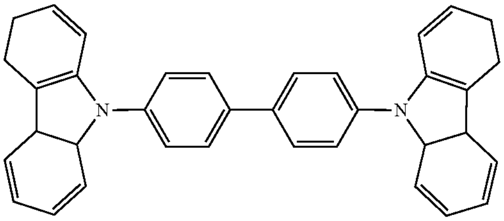
,
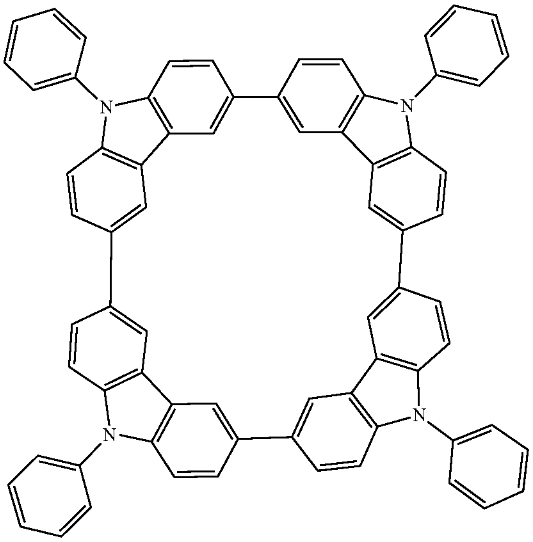
,
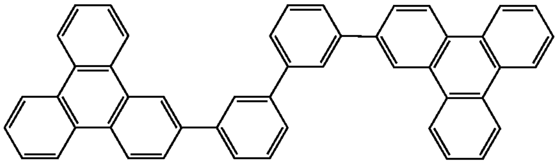
,
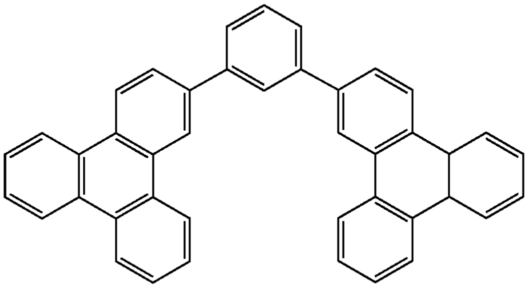
,
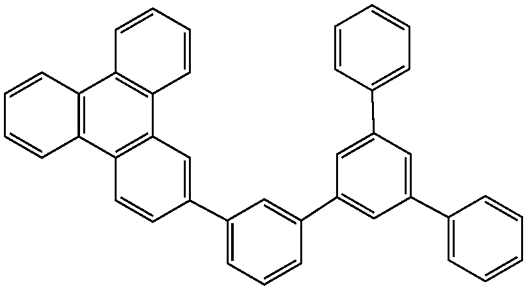
,
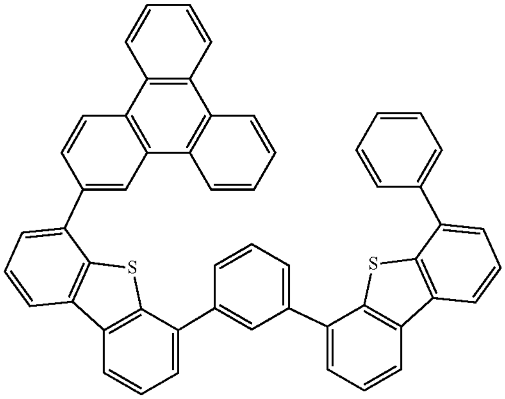
,
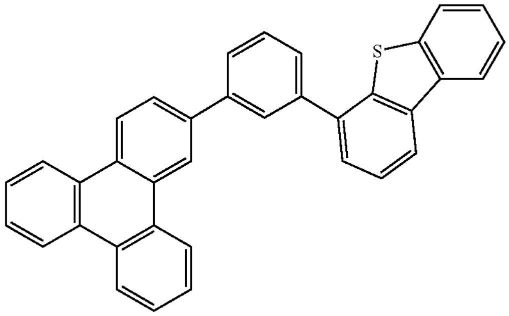
,
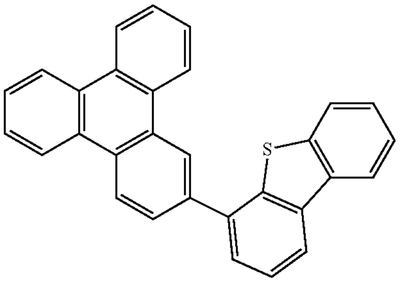
,
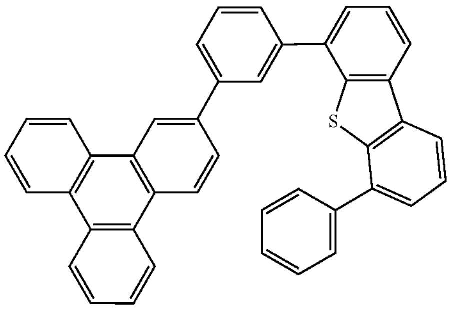
, -continued
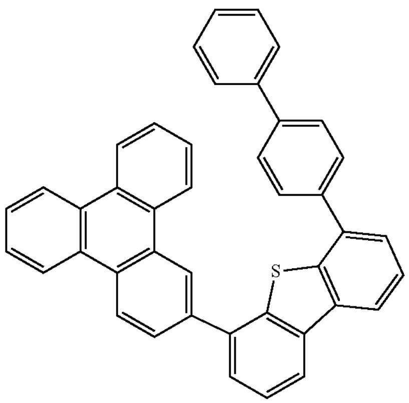
,
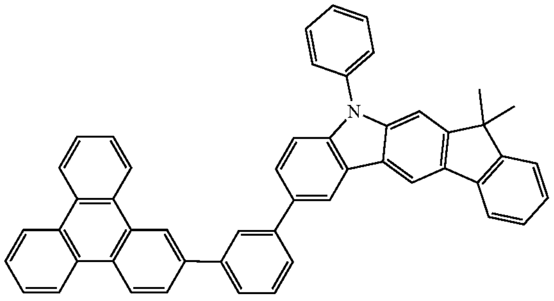
,
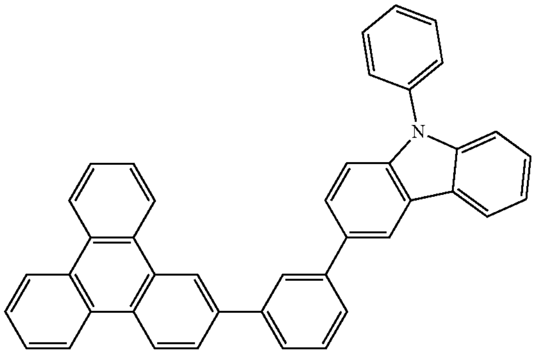
,
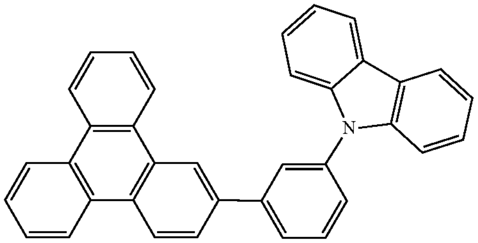
,
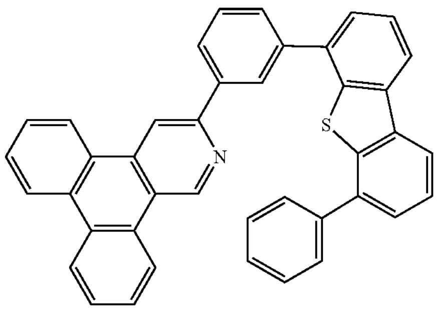
,
-continued
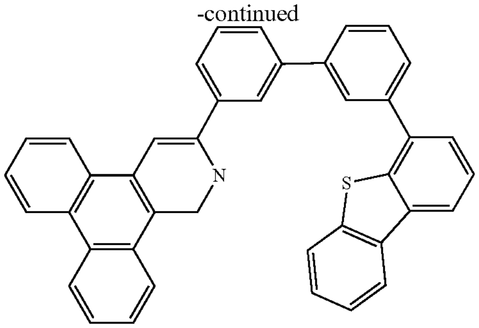
,
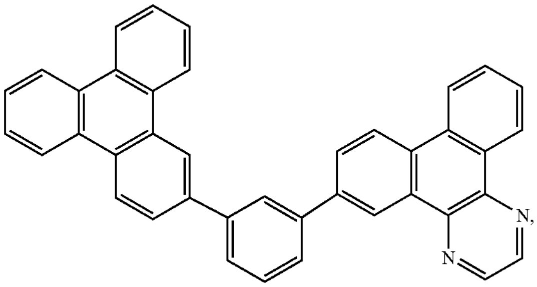
,
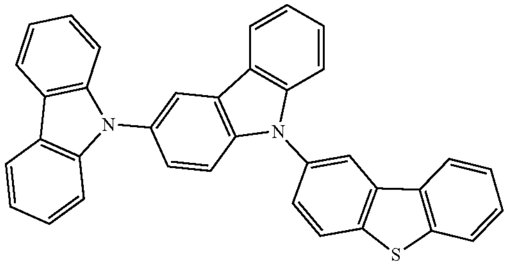
,
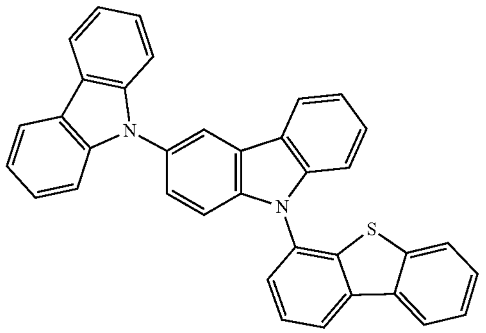
,
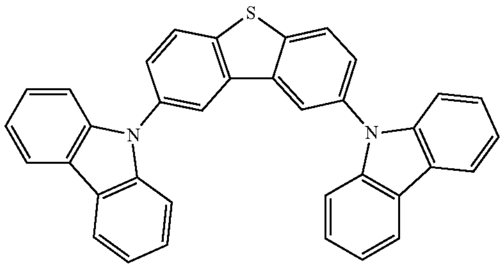
,
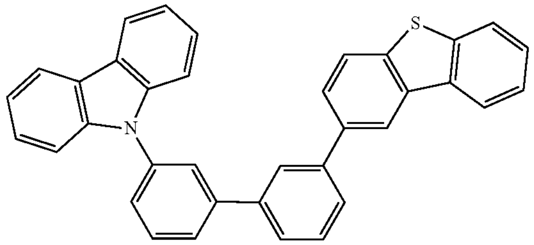
, -continued
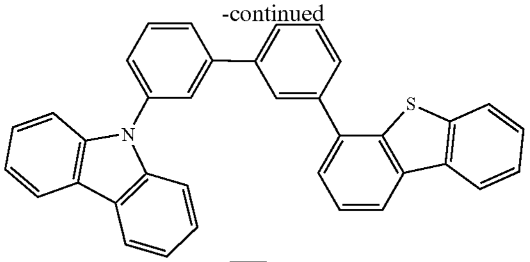
,
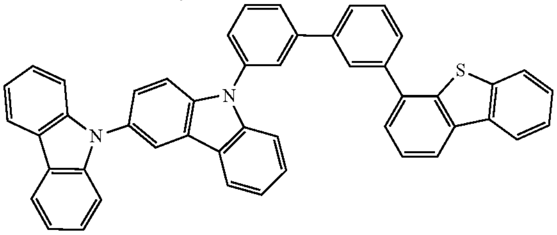
,
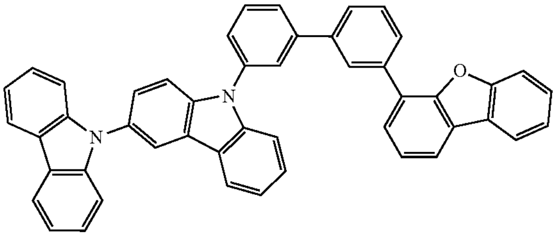
,
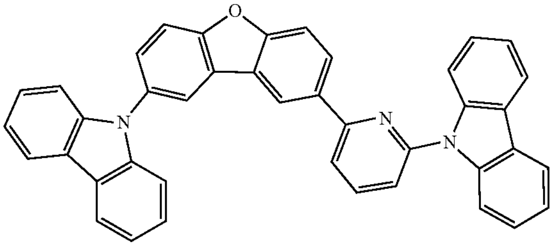
,
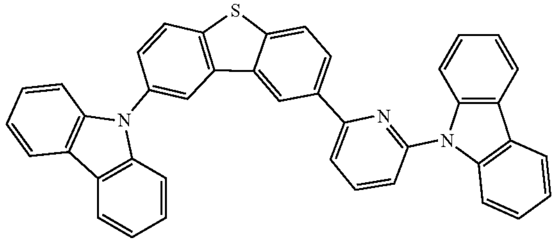
,
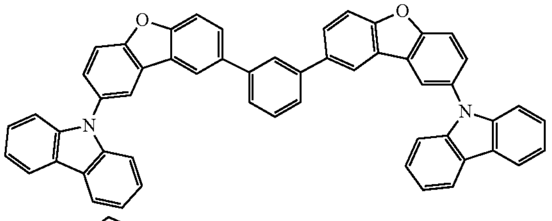
,
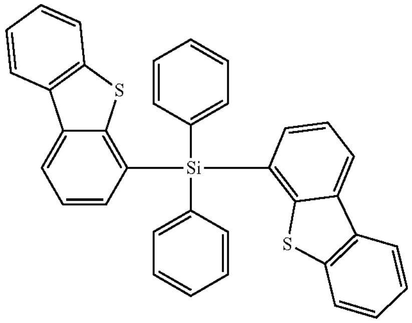
,
-continued
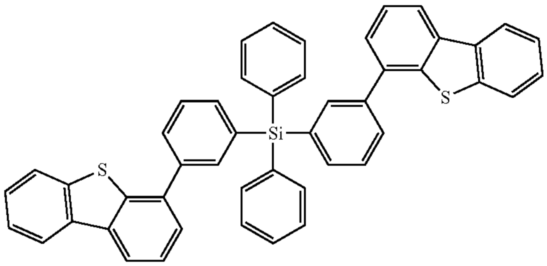
,
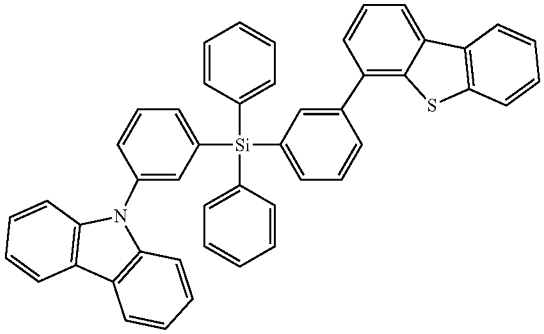
,
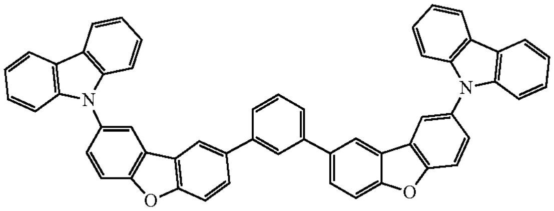
,
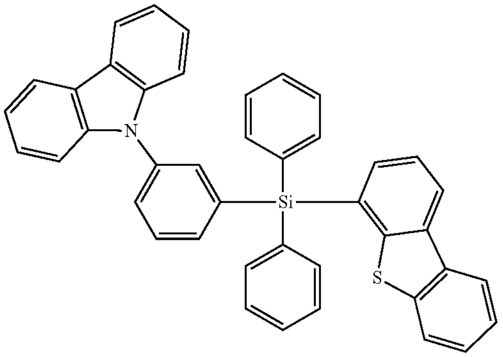
,
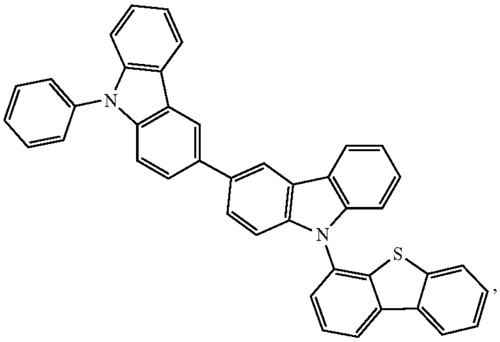
, -continued
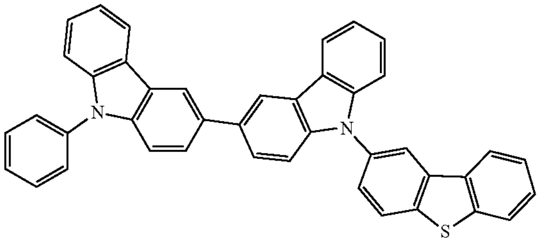
,
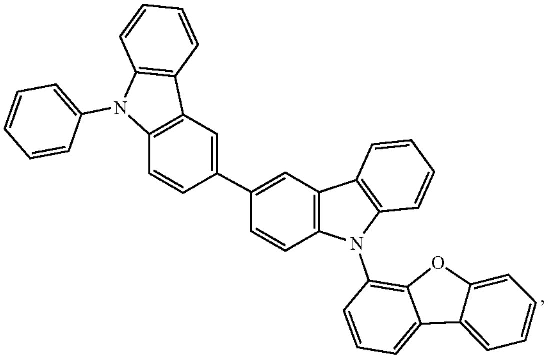
,
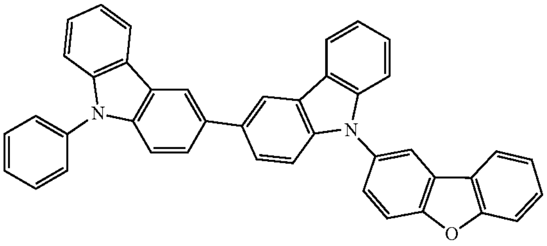
,
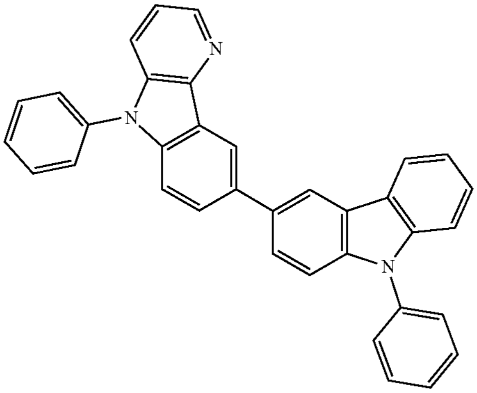
,
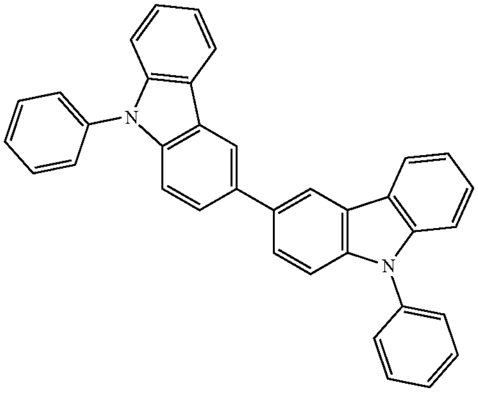
,
-continued
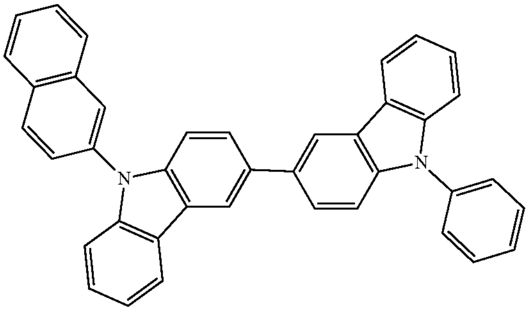
,
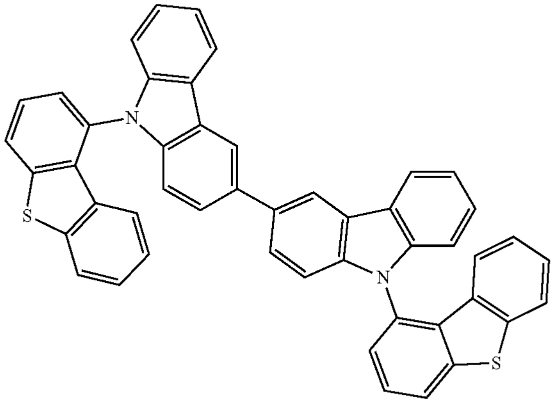
,
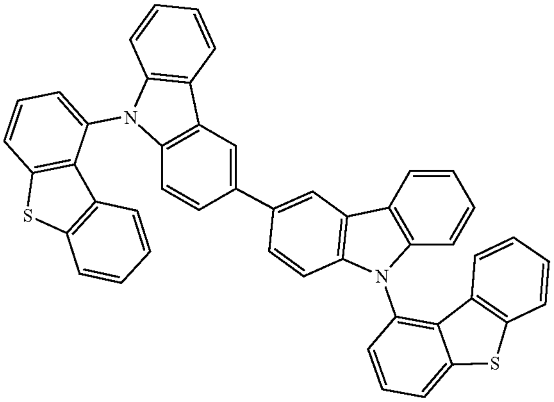
,
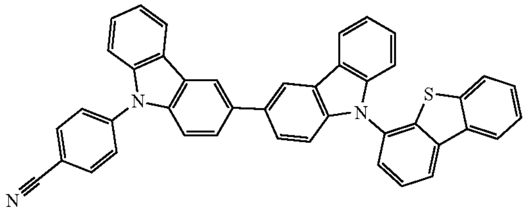
,
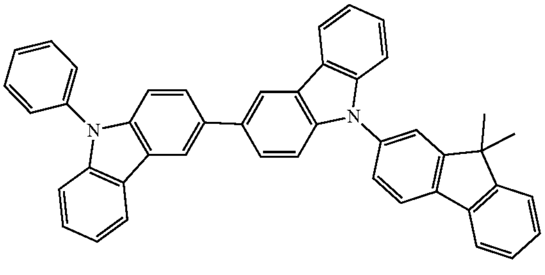
, -continued
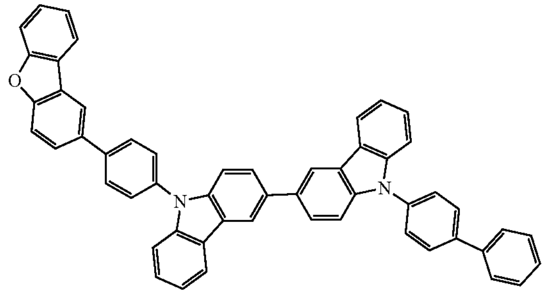
,
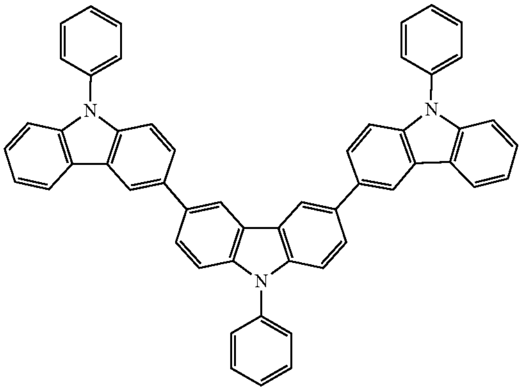
,
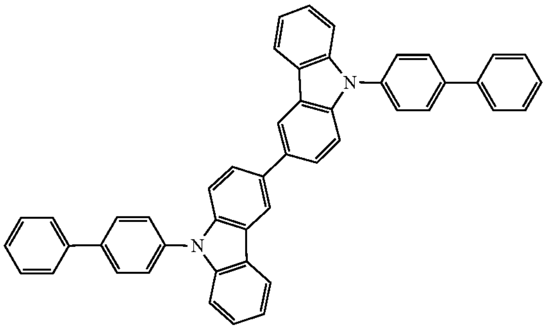
,
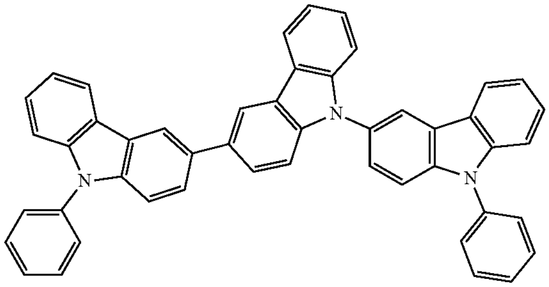
,
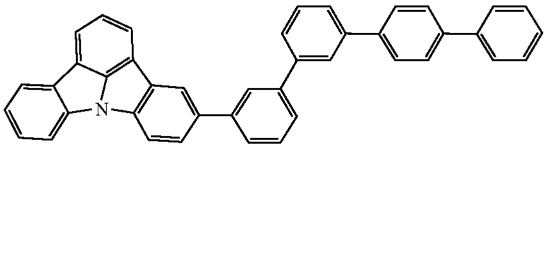
,
-continued
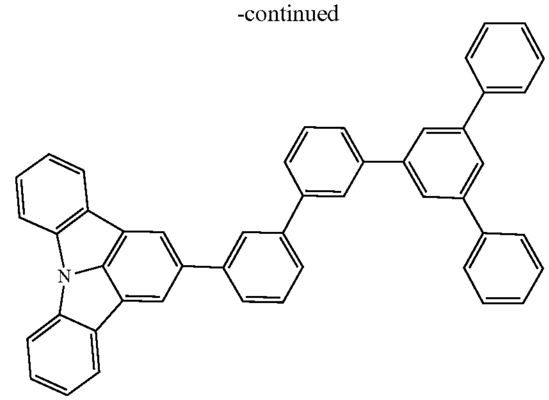
,
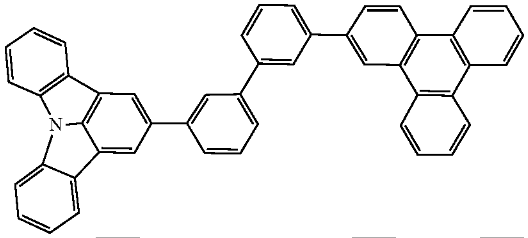
,
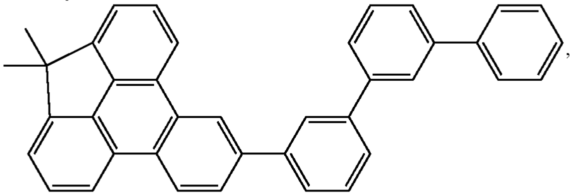
,
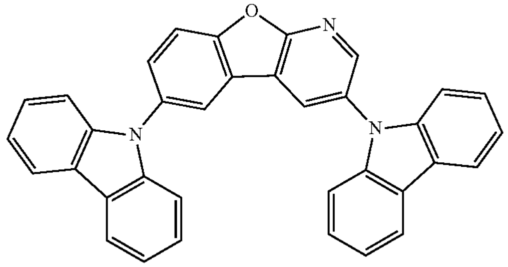
,
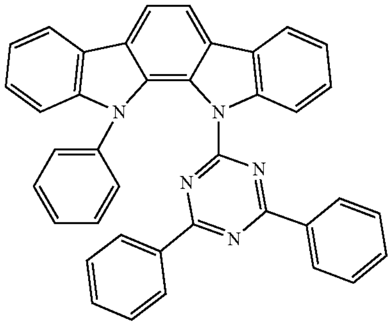
,
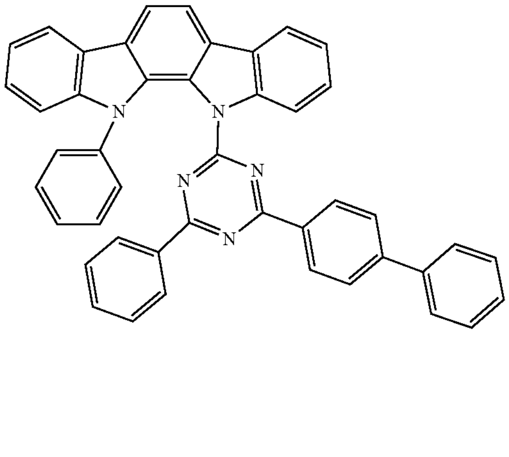
, -continued
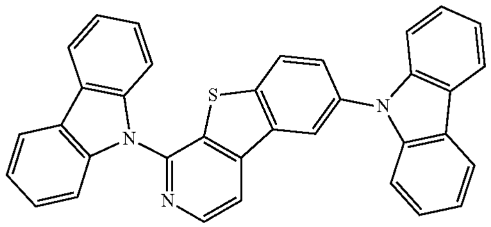
,
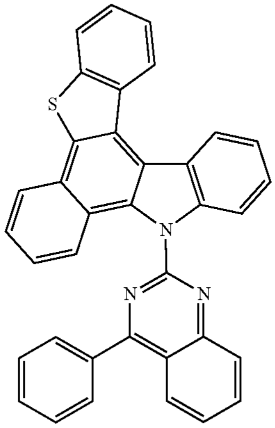
,
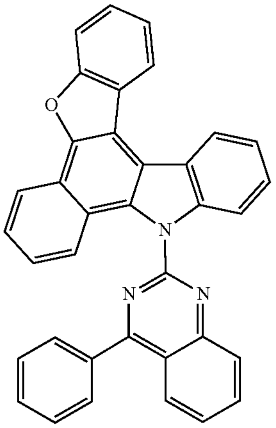
,
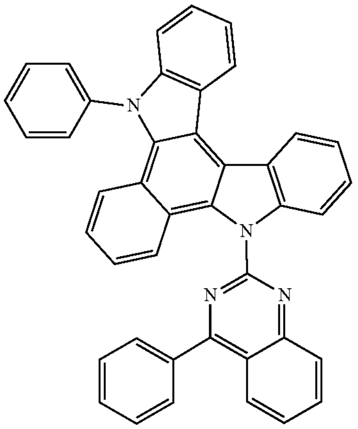
,
-continued
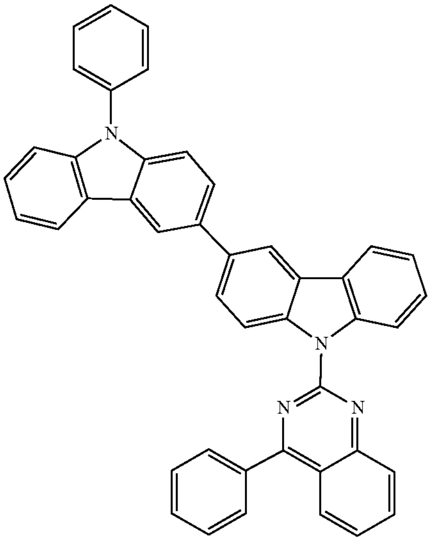
,
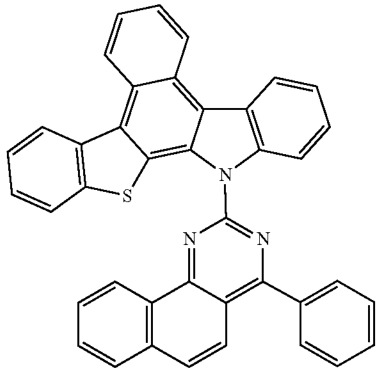
,
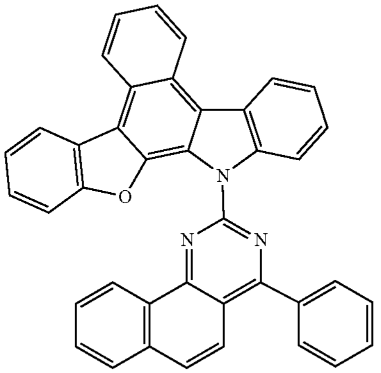
,
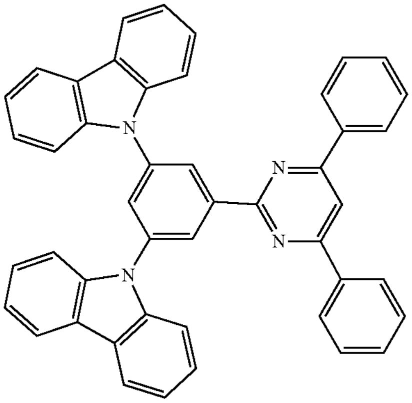
, -continued
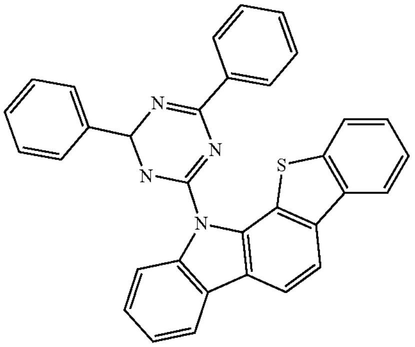
,
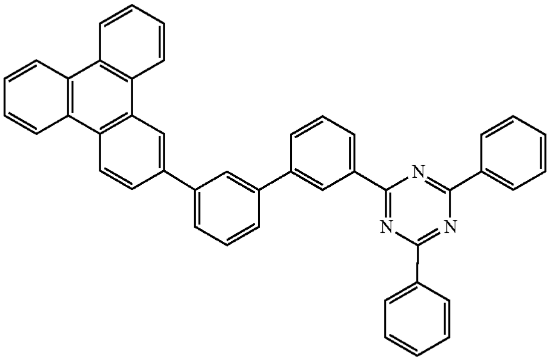
,
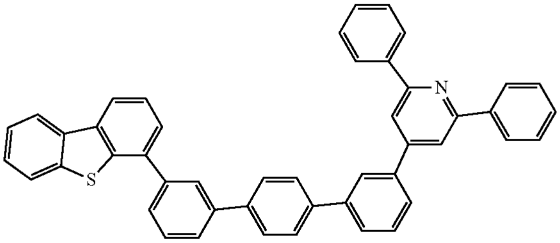
,
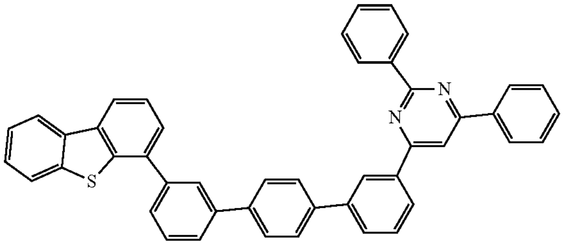
,
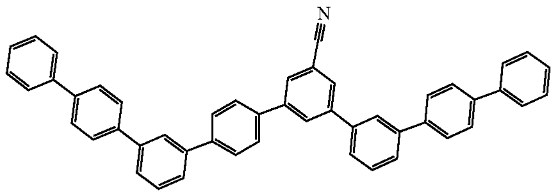
,
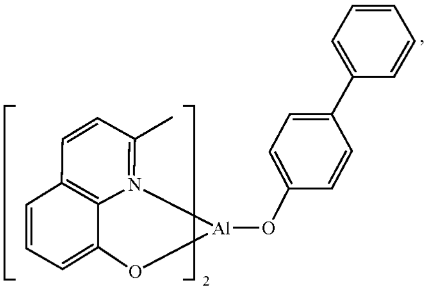
,
-continued
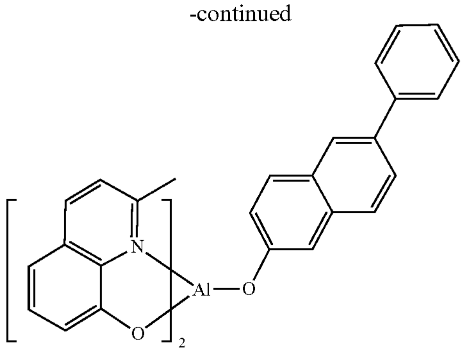
,
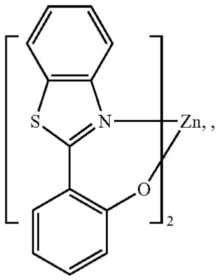
,
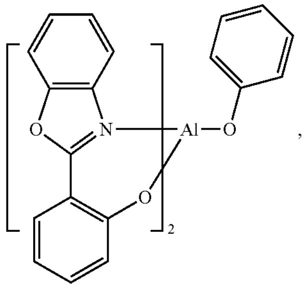
,
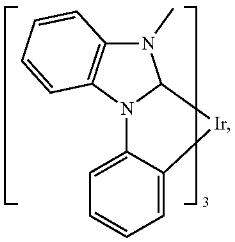
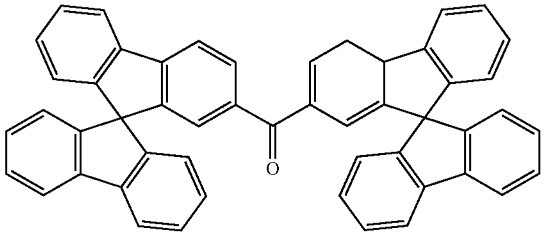
,
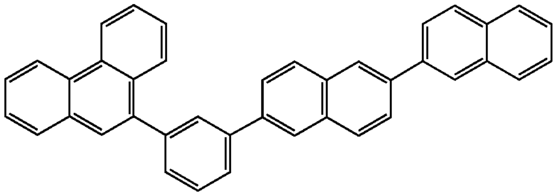
,
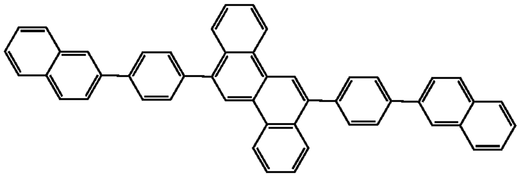
, and
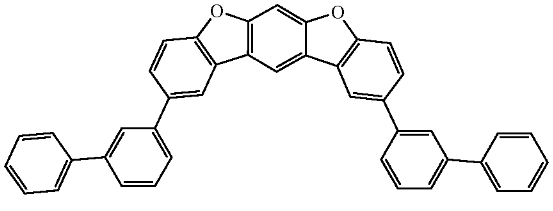
.

e) Additional Emitters:

One or more additional emitter dopants may be used in conjunction with the compound of the present disclosure. Examples of the additional emitter dopants are not particularly limited, and any compounds may be used as long as the compounds are typically used as emitter materials. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Ser. No. 06/699,599, U.S. Ser. No. 06/916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450.

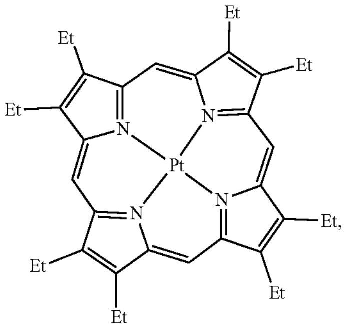

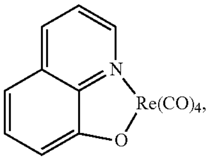

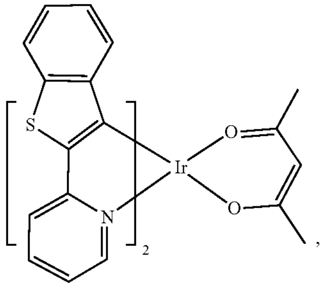

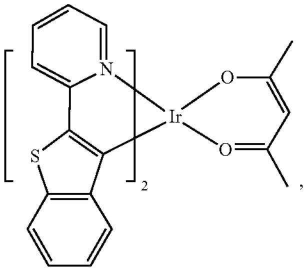

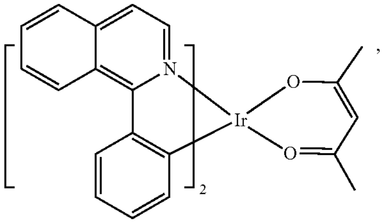

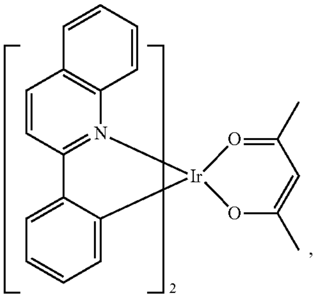

-continued
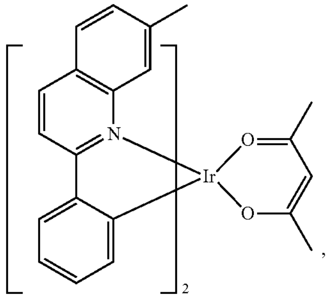
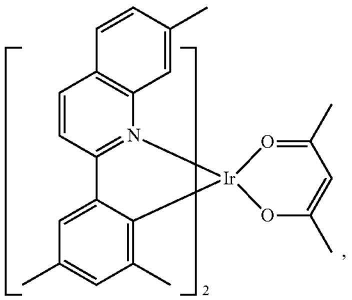
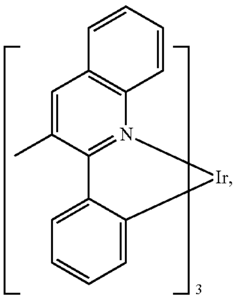
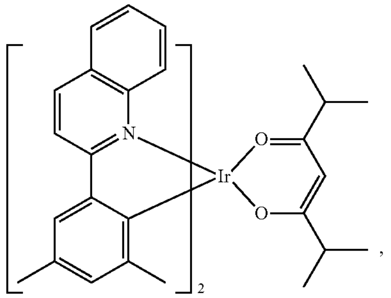
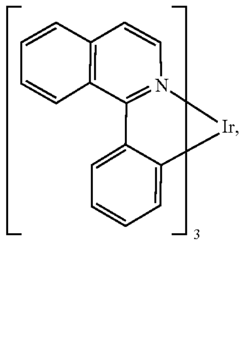
-continued
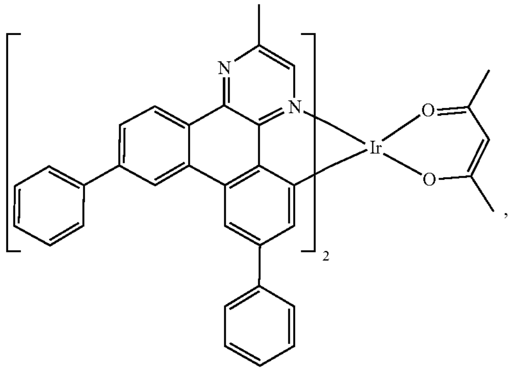
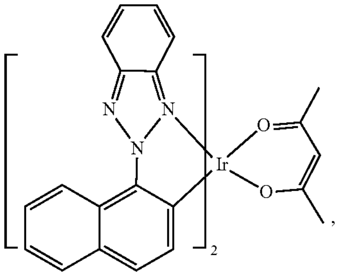
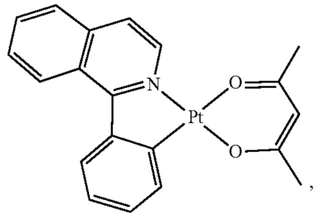
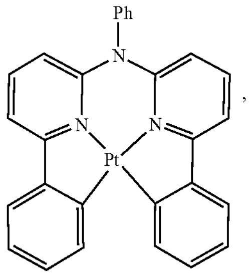
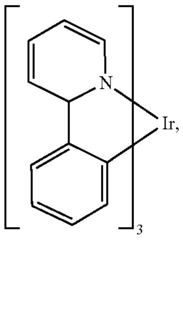
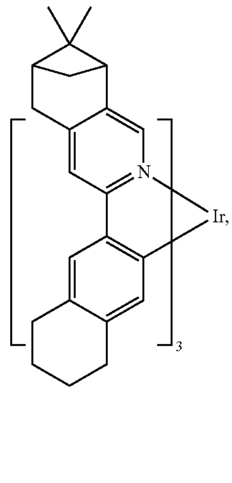

-continued
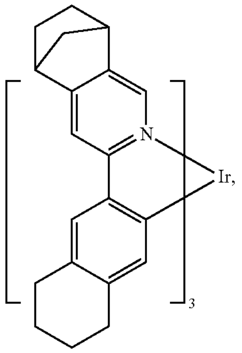
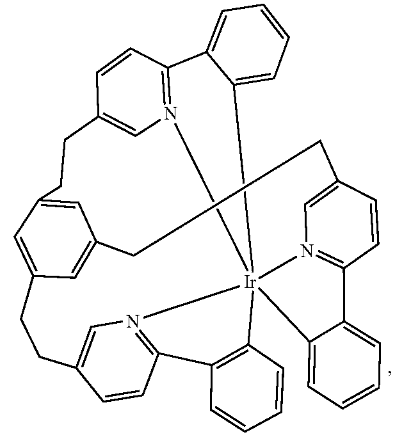
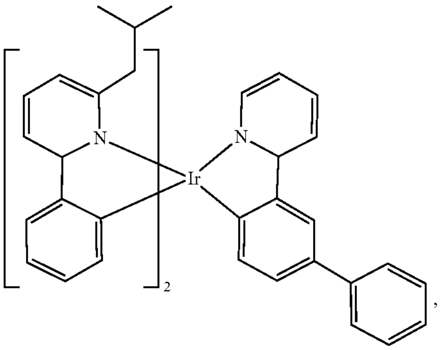
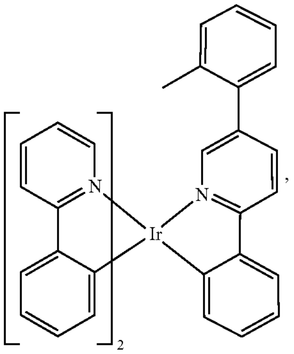
-continued
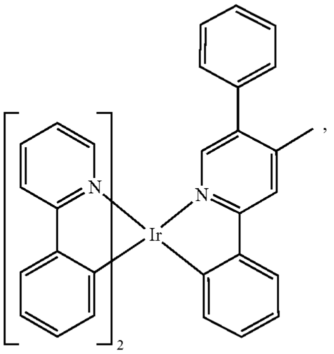
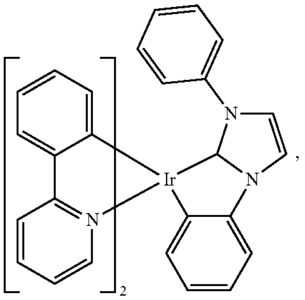
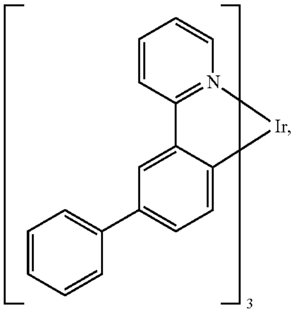
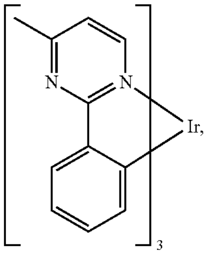
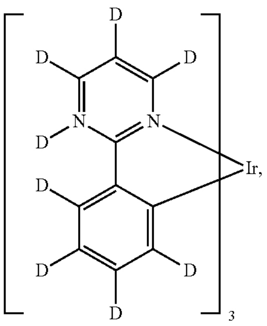
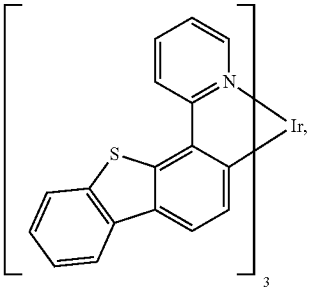

-continued
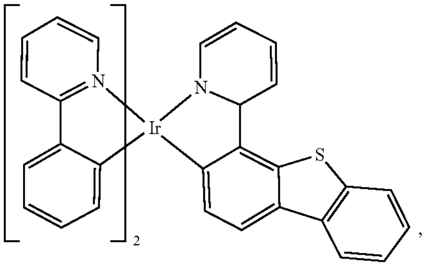
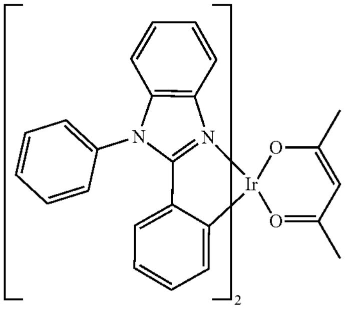
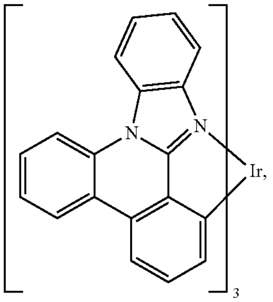
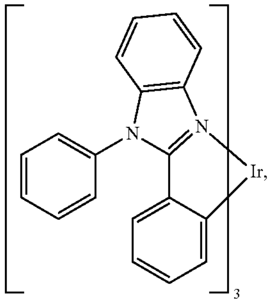
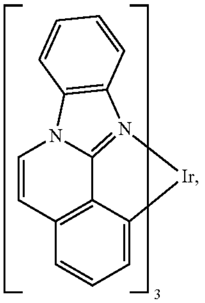
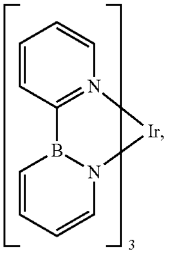
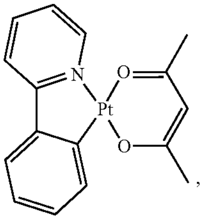
-continued
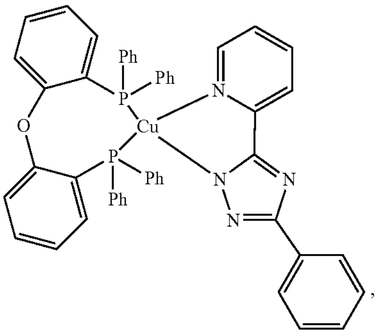
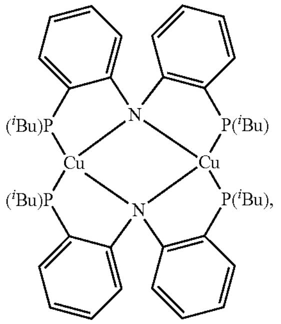
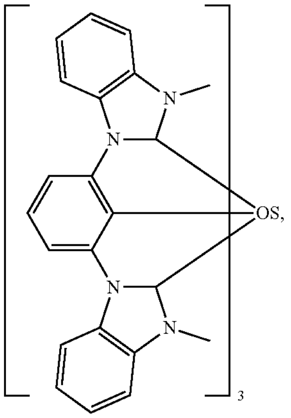
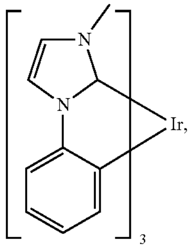
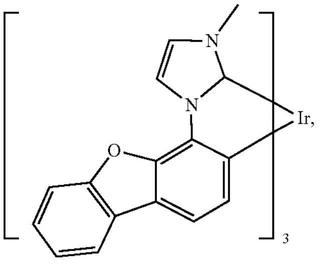
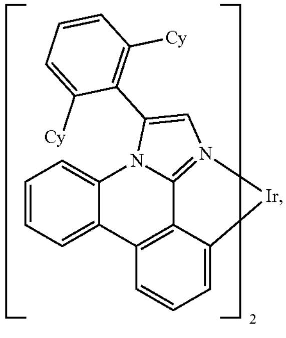

-continued
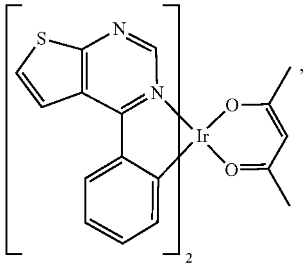
,
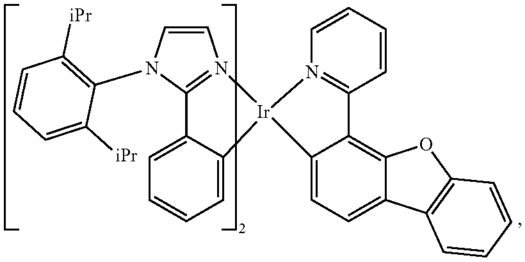
,
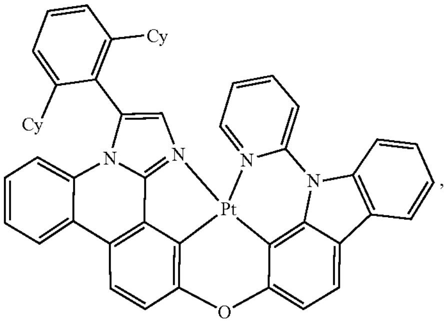
,
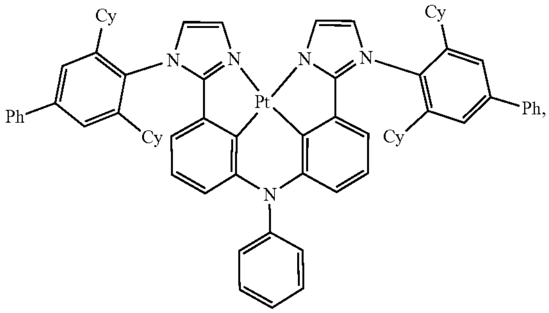
,
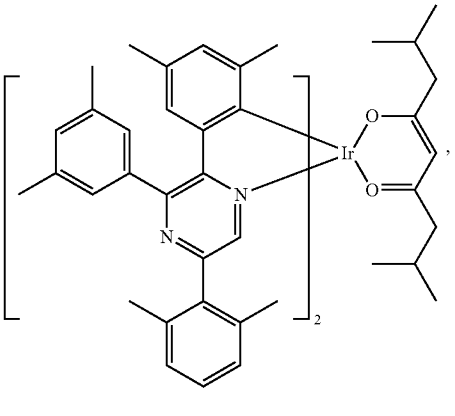
,
-continued
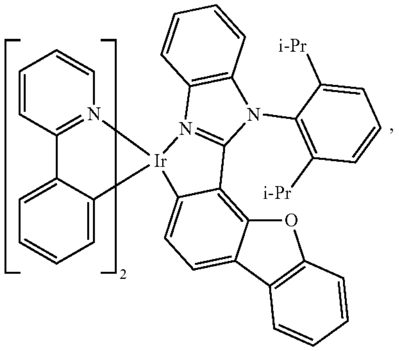
,
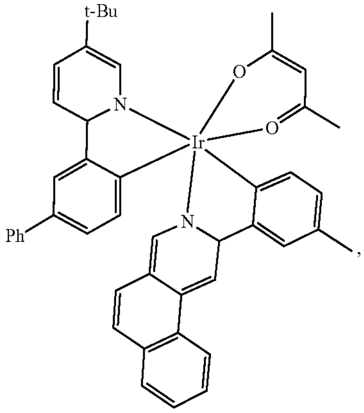
,
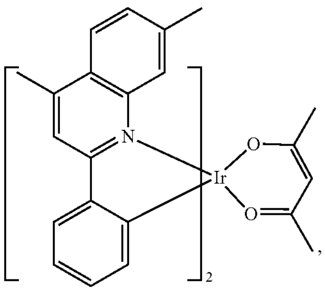
,
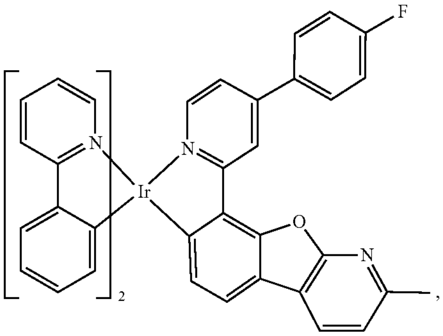
,
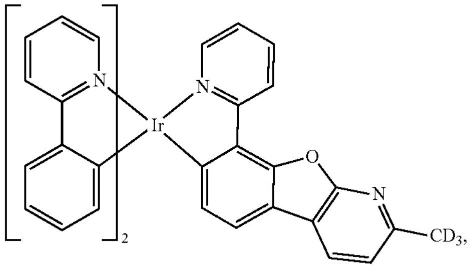
, -continued
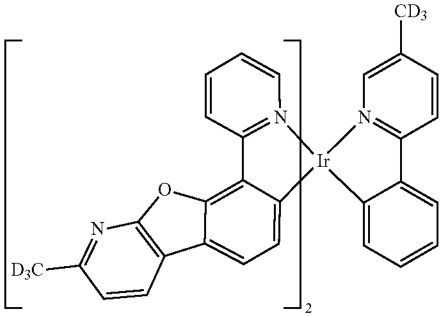
,
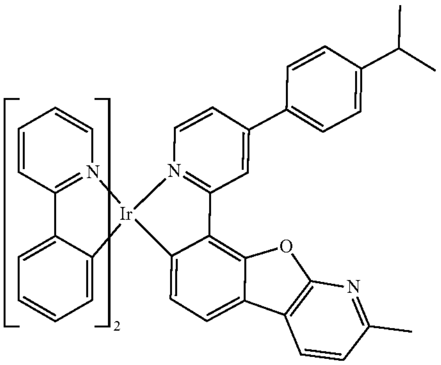
,
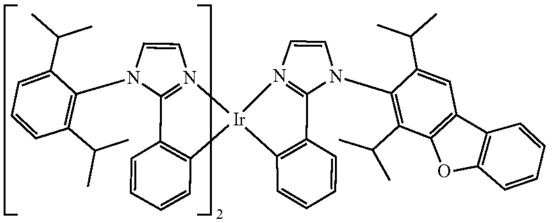
,
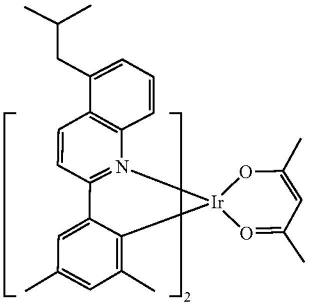
,
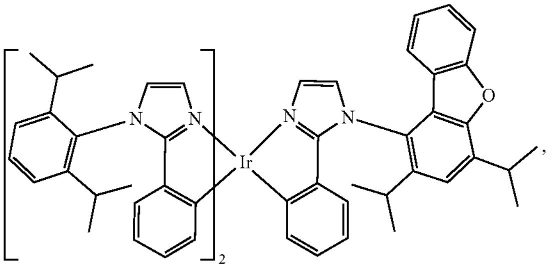
,
-continued
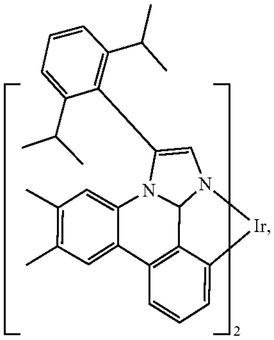
,
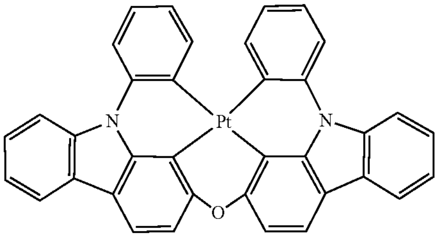
,
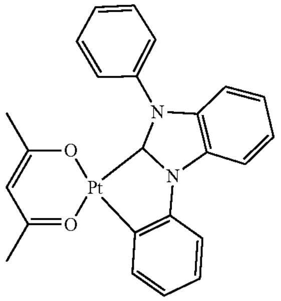
,
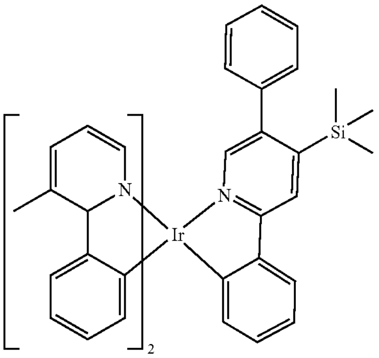
,
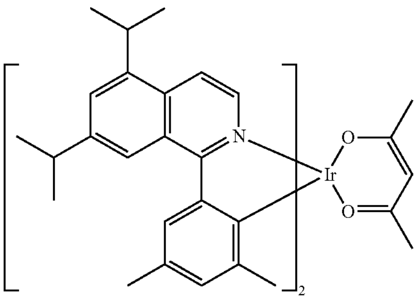
, -continued
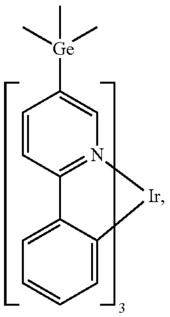
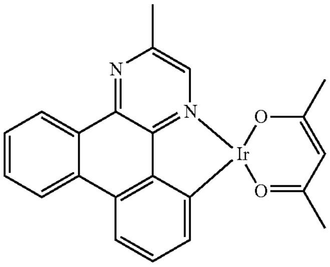
,
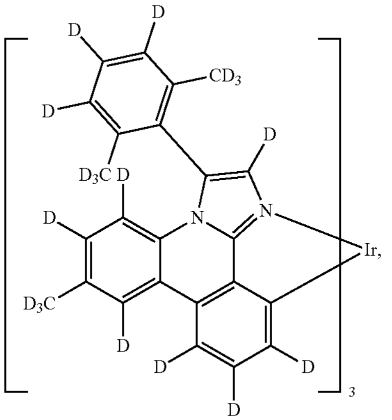
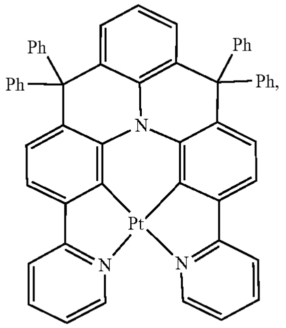
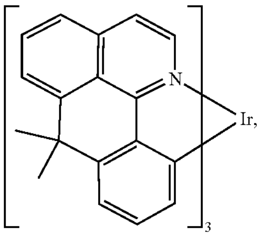
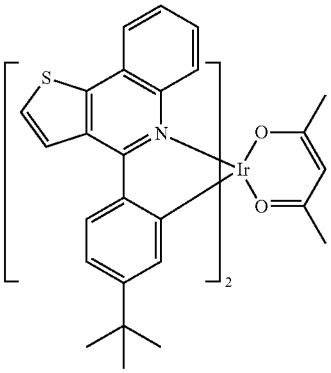
,
-continued
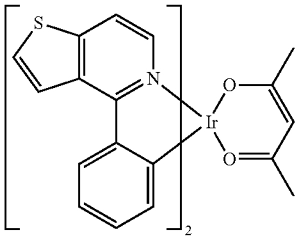
,
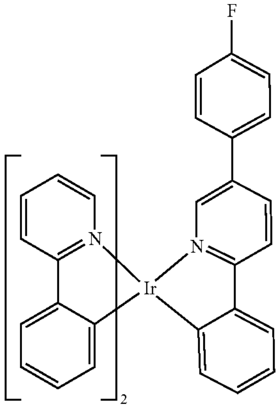
,
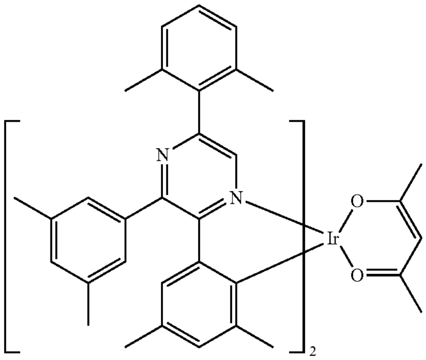
,
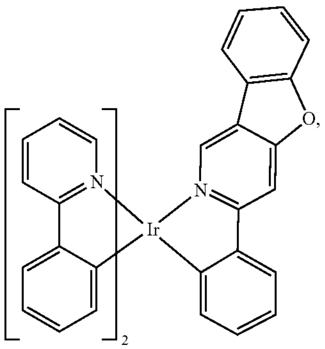

-continued
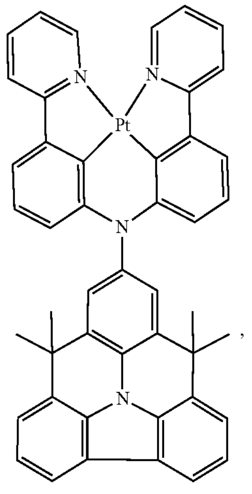
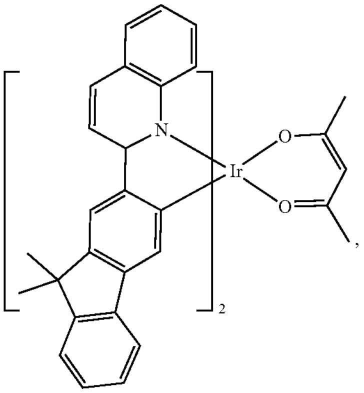
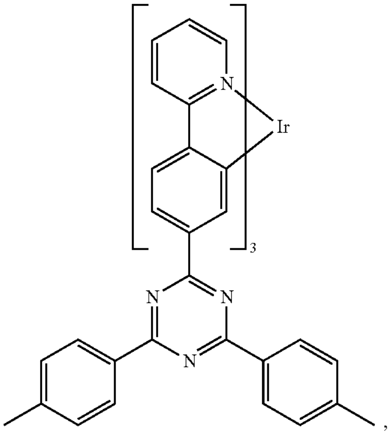
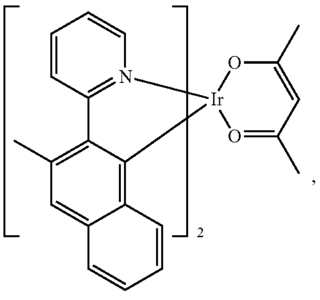
-continued
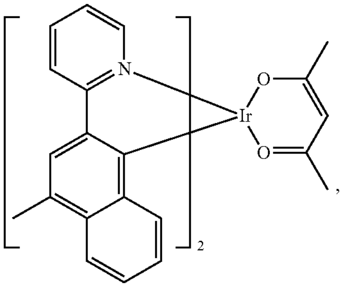
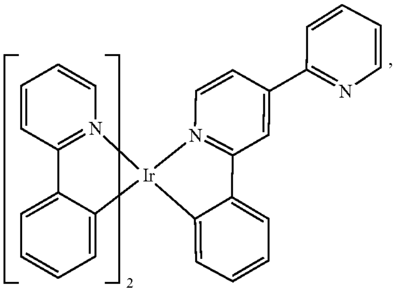
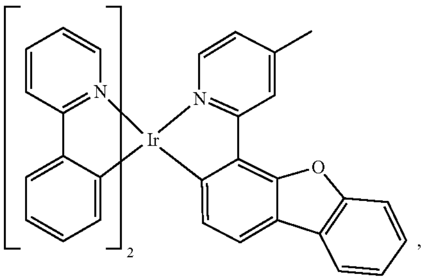
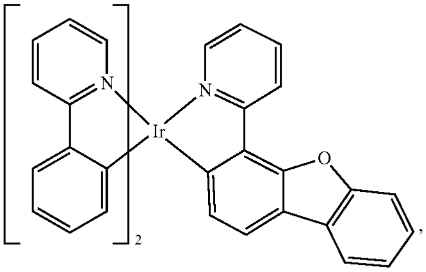
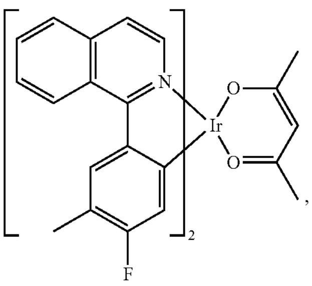

-continued
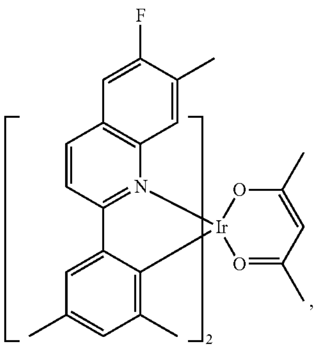
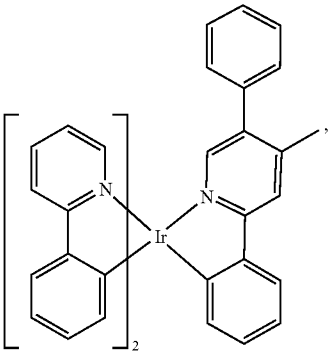
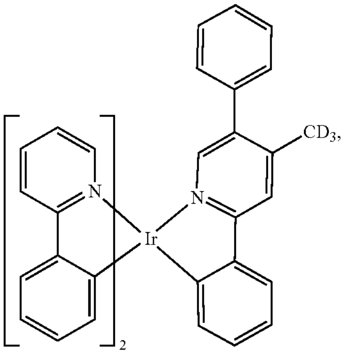
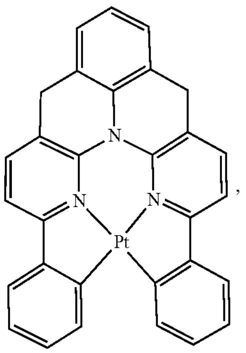
-continued
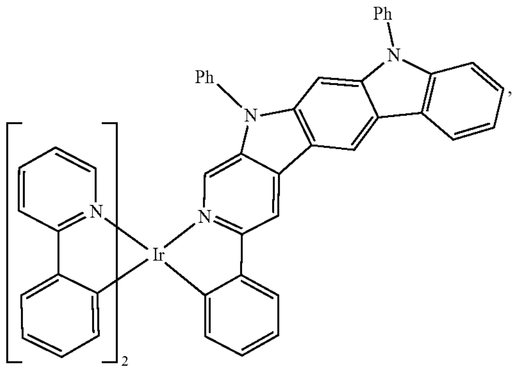
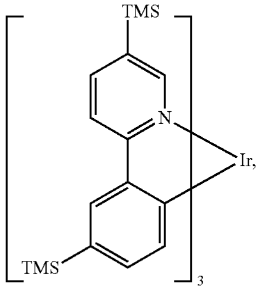
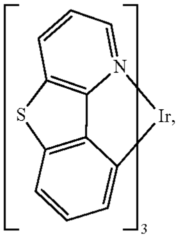
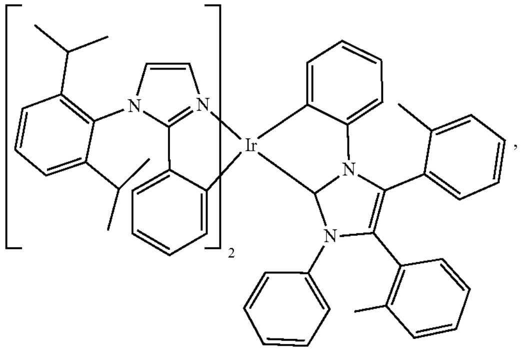
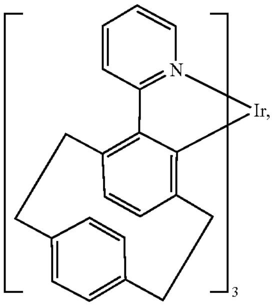
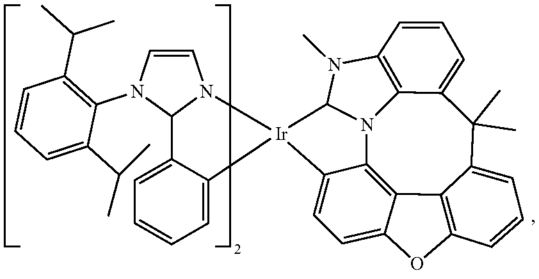

-continued
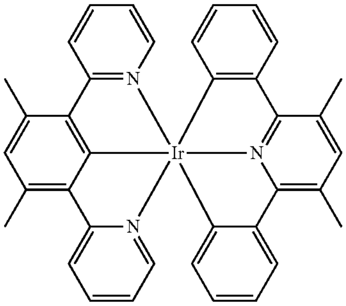
,
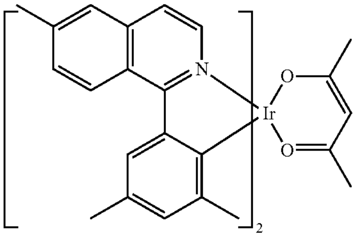
,
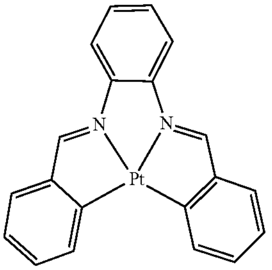
,
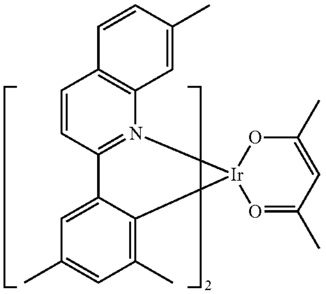
,
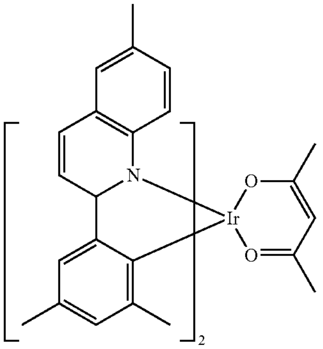
,
-continued
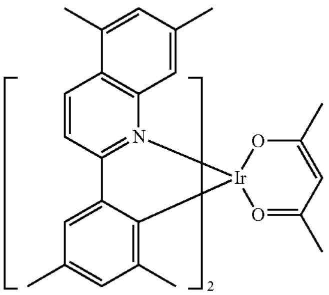
,
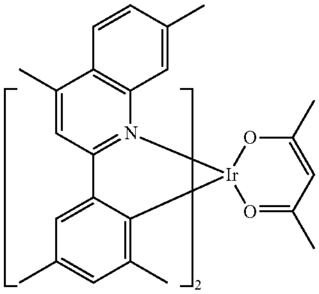
,
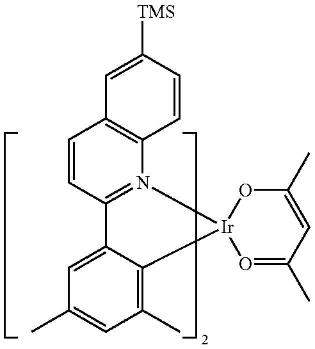
,
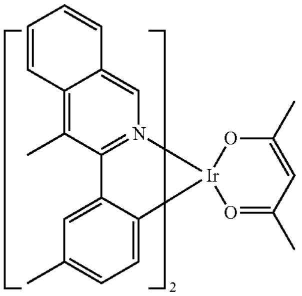
,
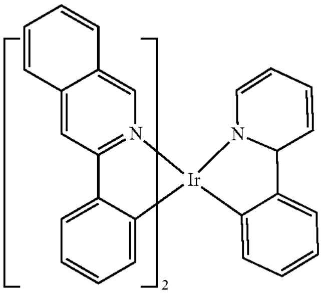
,

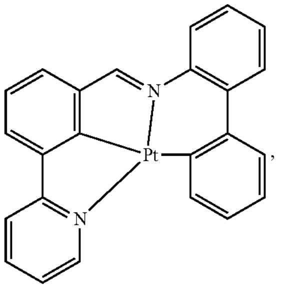
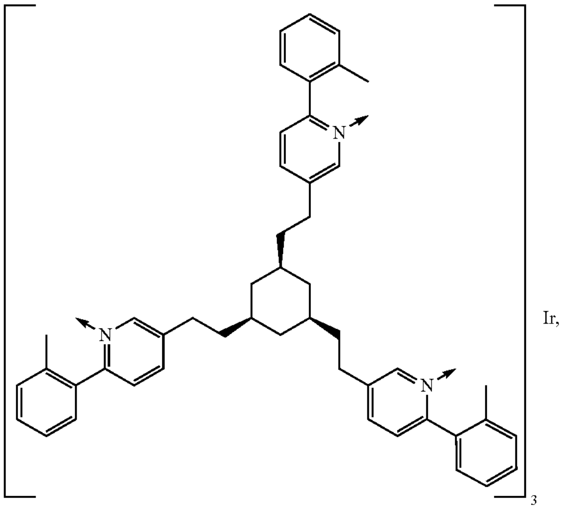
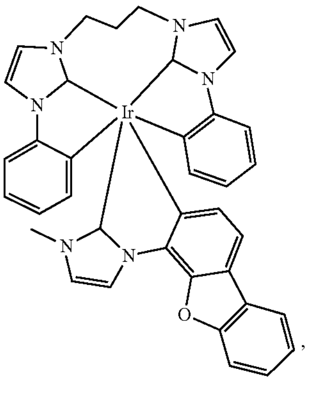
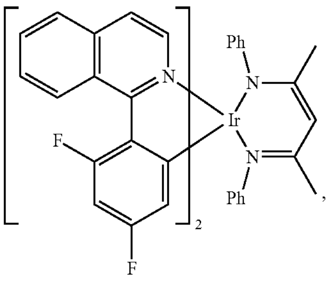
-continued
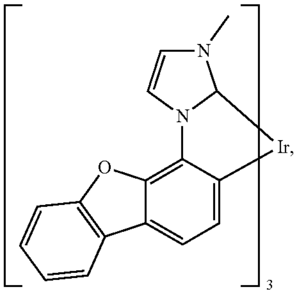
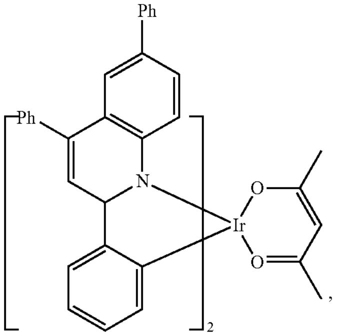
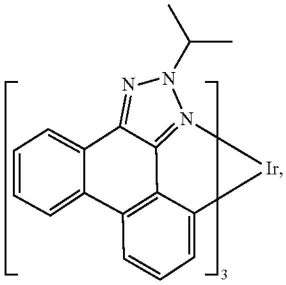
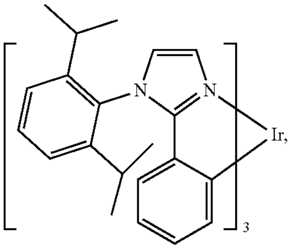
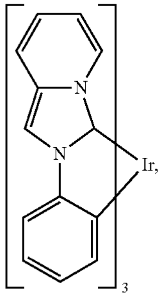
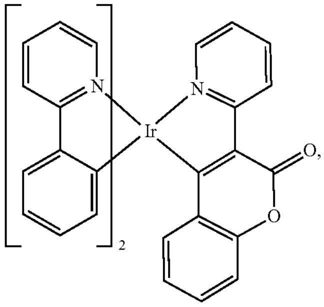

-continued

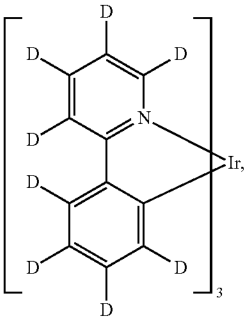

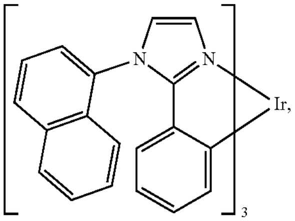

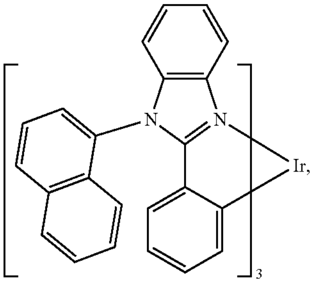

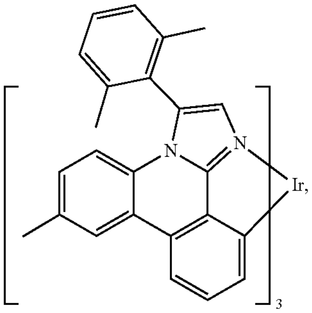

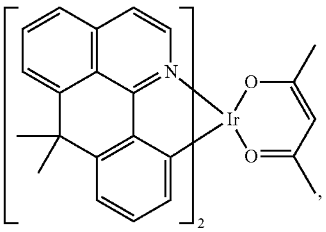

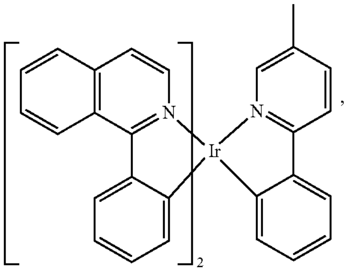

-continued

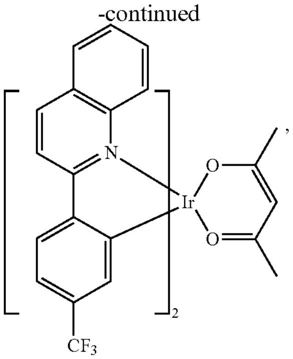

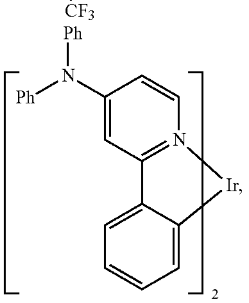

and

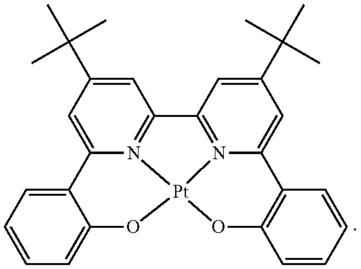

f) HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and/or higher triplet energy than the emitter closest to the HBL interface. In some embodiments, the HBL material has a lower HOMO (further from the vacuum level) and/or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

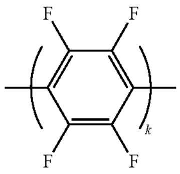

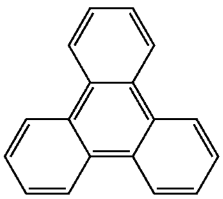

-continued

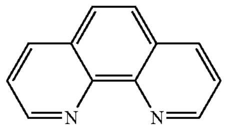

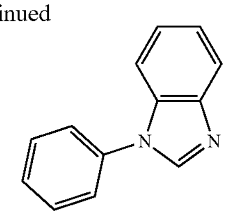

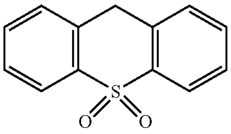

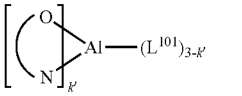

wherein k is an integer from 1 to 20; $L^{101}$ is another ligand, k' is an integer from 1 to 3.

g) ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

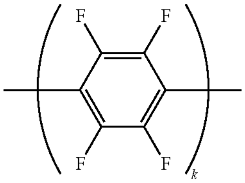

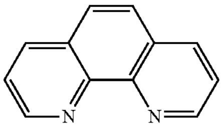

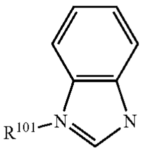

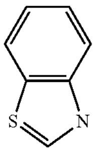

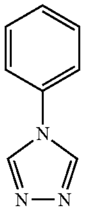

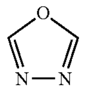

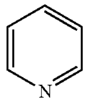

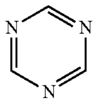

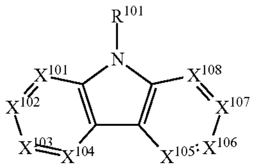

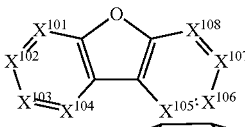

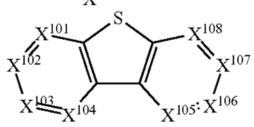

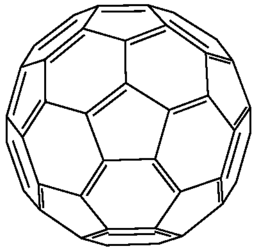

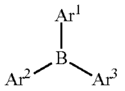

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

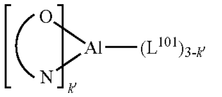

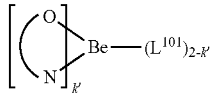

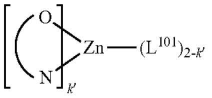

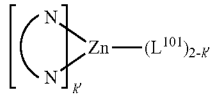

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535,

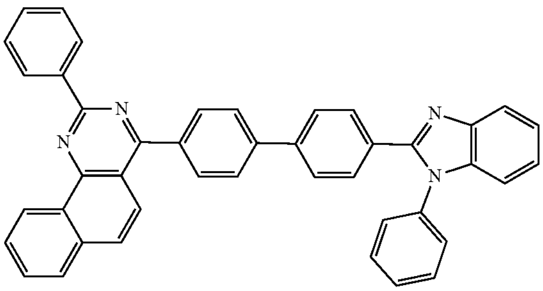

,

-continued
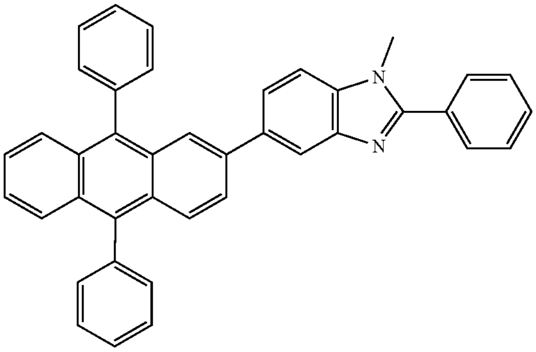
,
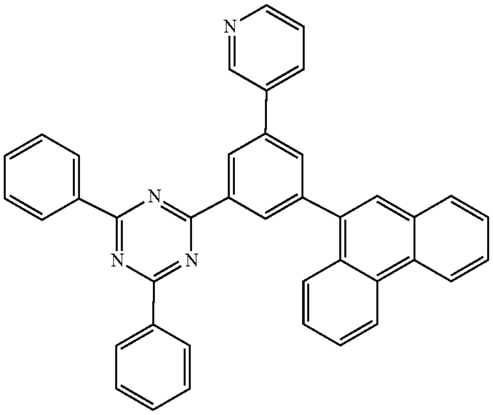
,
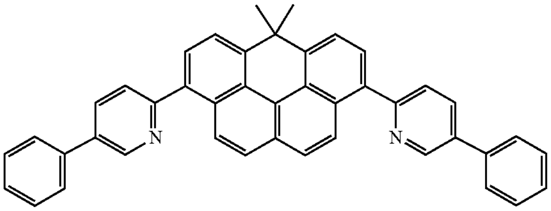
,
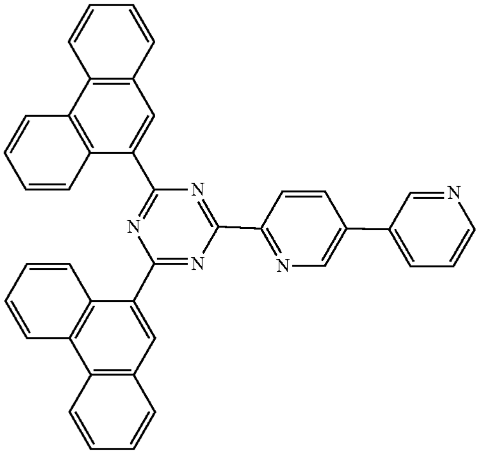
,
-continued
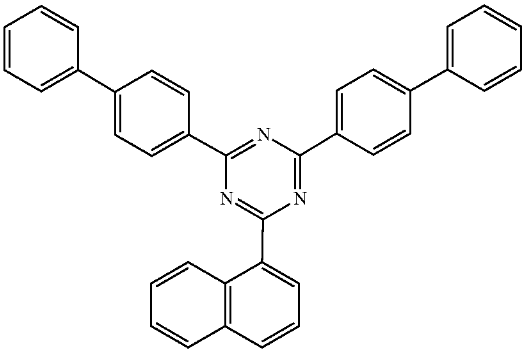
,
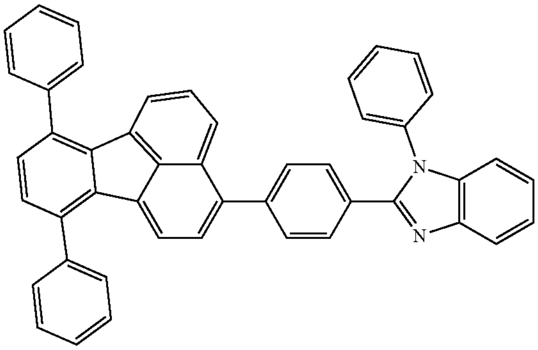
,
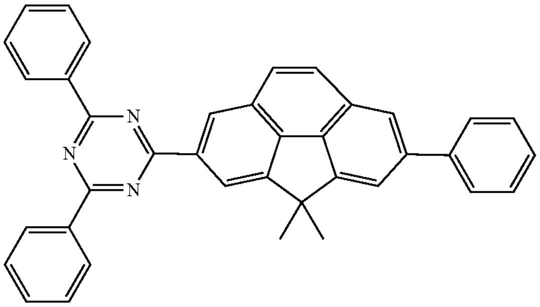
,
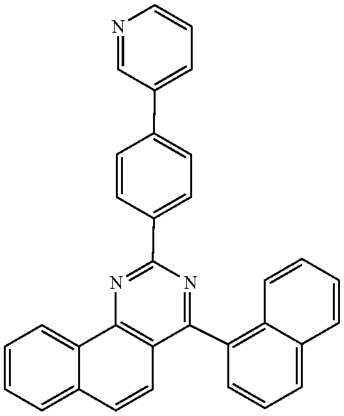
, -continued
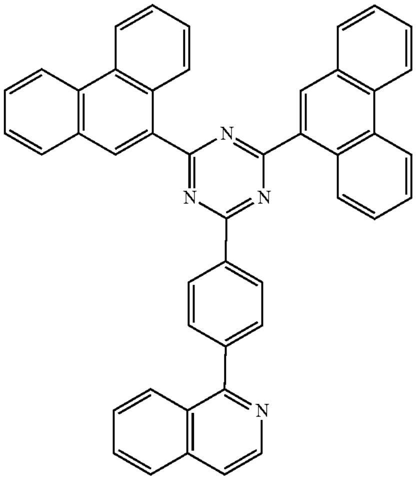
,
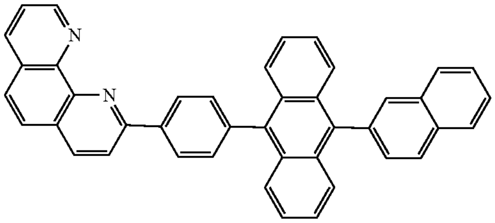
,
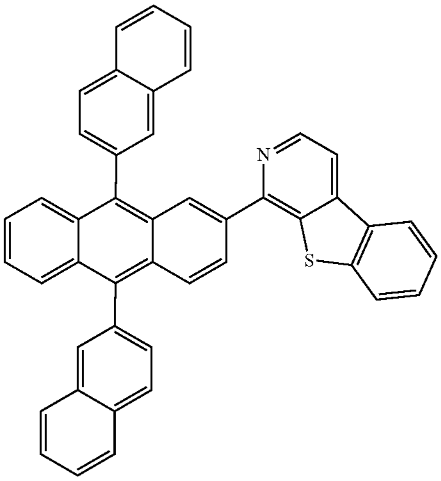
,
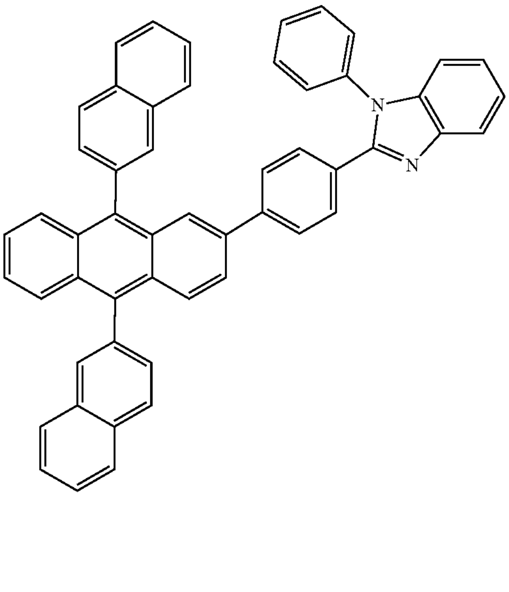
,
-continued
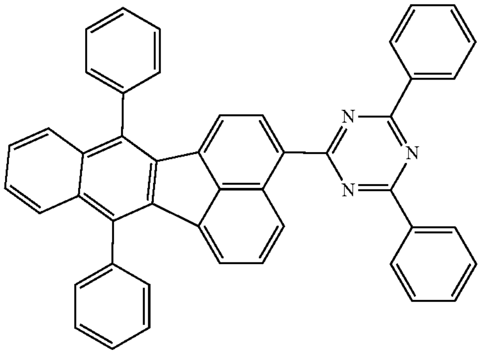
,
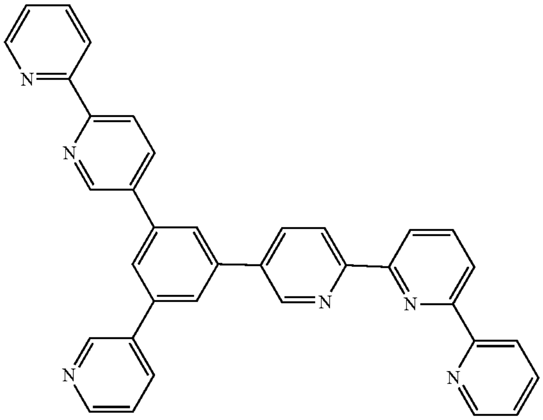
,
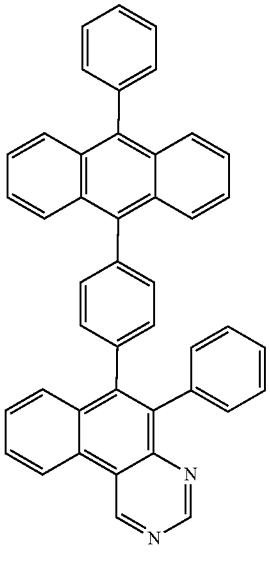
, -continued
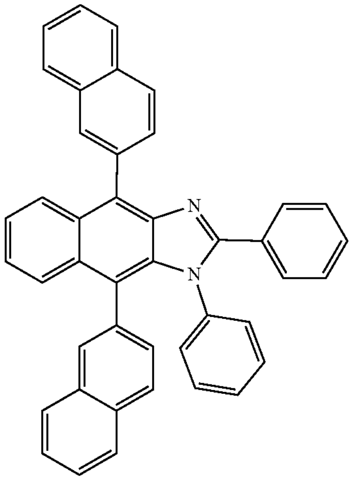
,
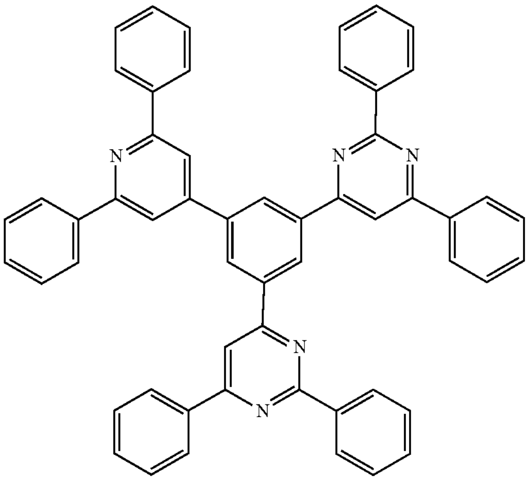
,
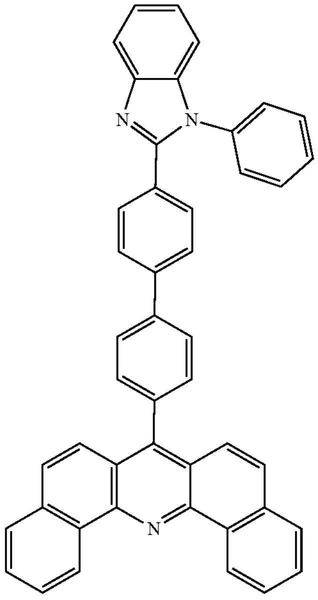
,
-continued
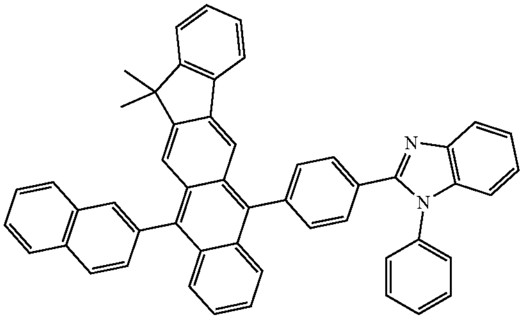
,
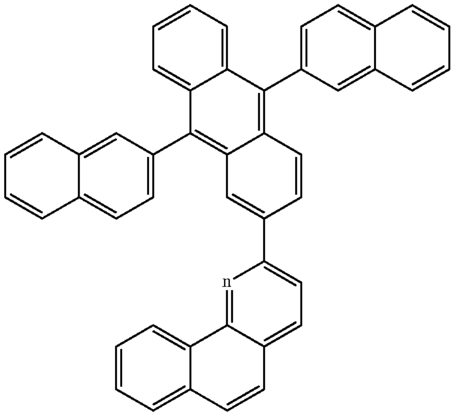
,
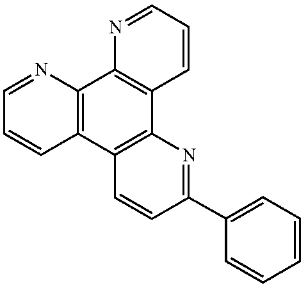
,
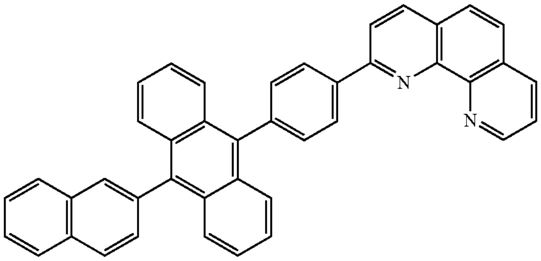
,
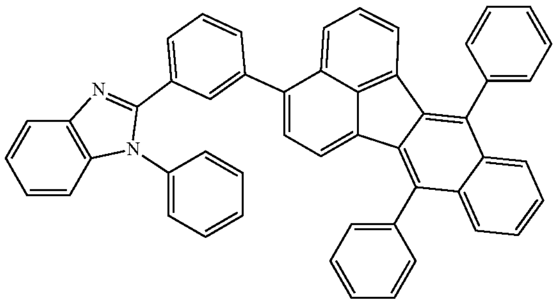
, -continued
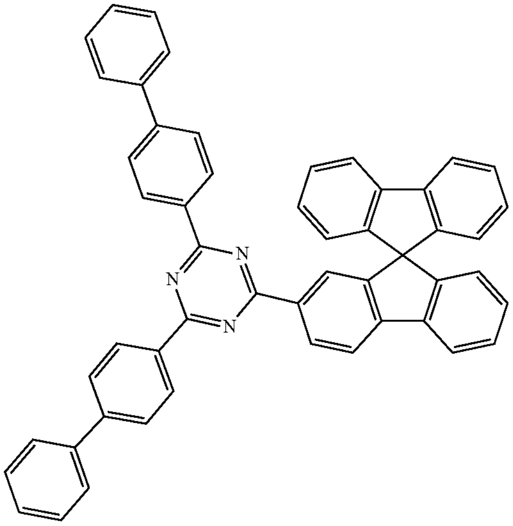,
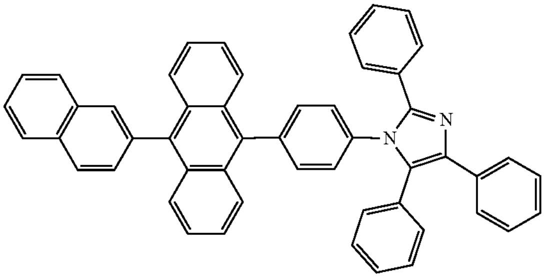,
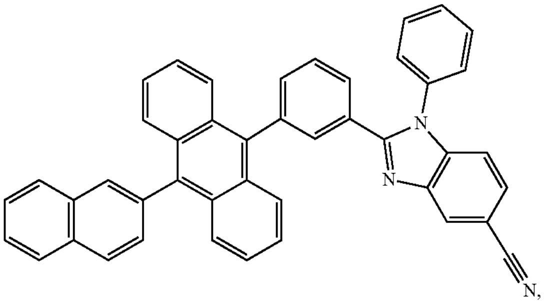,
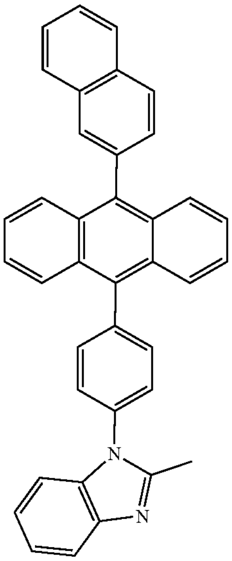,
-continued
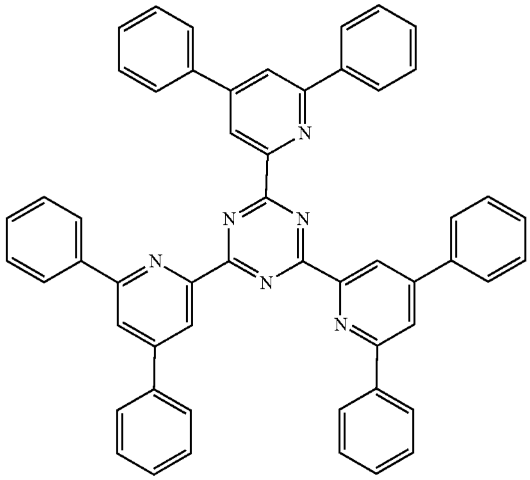,
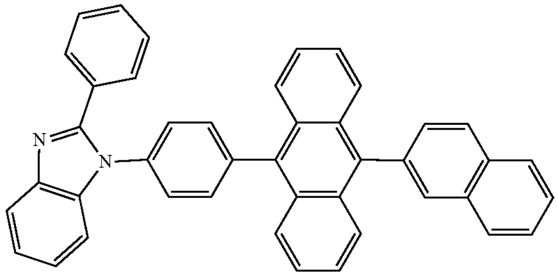,
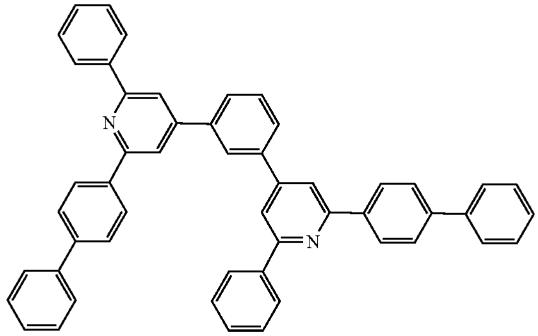,
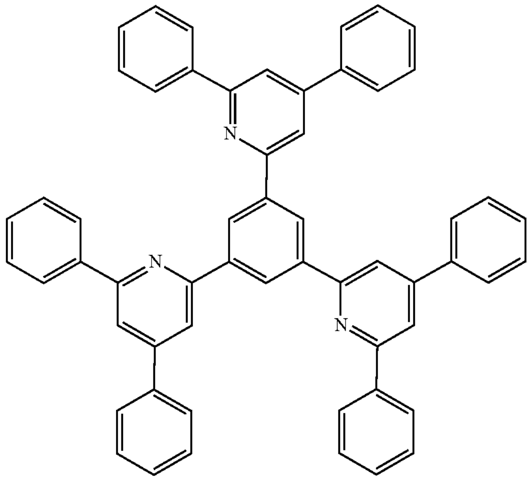, -continued

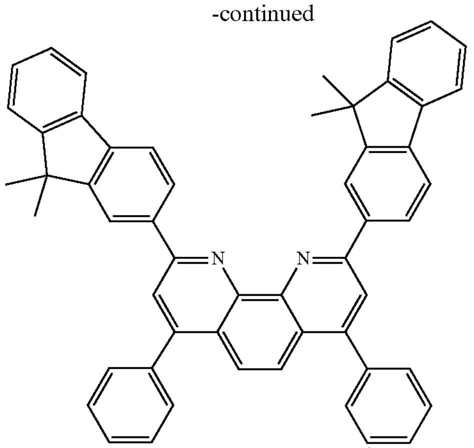

, and

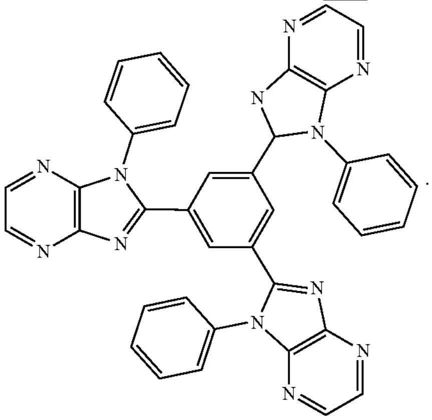

.

h) Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. The minimum amount of hydrogen of the compound being deuterated is selected from the group consisting of 30%, 40%, 50%, 60%, 70%, 80%, 90%, 95%, 99%, and 100%. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

It is understood that the various embodiments described herein are by way of example only and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

EXPERIMENTAL DATA

OLEDs were grown on a glass substrate pre-coated with an indium-tin-oxide (ITO) layer having a sheet resistance of 1542/sq. Prior to any organic layer deposition or coating, the substrate was degreased with solvents and then treated with an oxygen plasma for 1.5 minutes with 50 W at 100 mTorr and with UV ozone for 5 minutes. The devices were fabricated in high vacuum (<10-6 Torr) by thermal evaporation. The anode electrode was 750 Å of indium tin oxide (ITO). All devices were encapsulated with a glass lid sealed with an epoxy resin in a nitrogen glove box (<1 ppm of $H_2O$ and $O_2$) immediately after fabrication with a moisture getter incorporated inside the package. Doping percentages are in volume percent. The devices were grown in several different device structures using the following materials:

Compound 1

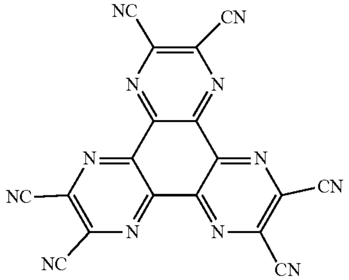

Compound 2

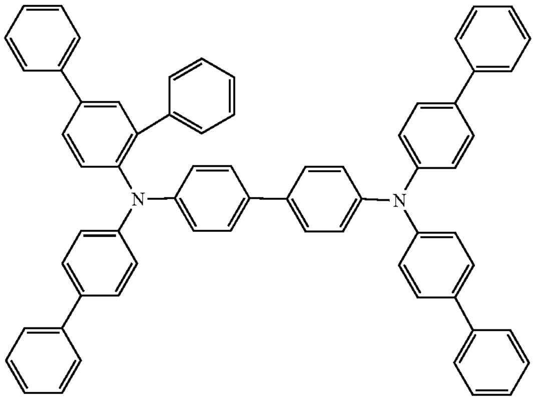

HH1

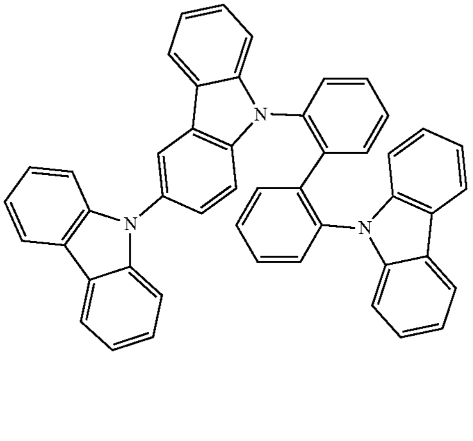

-continued
HH2
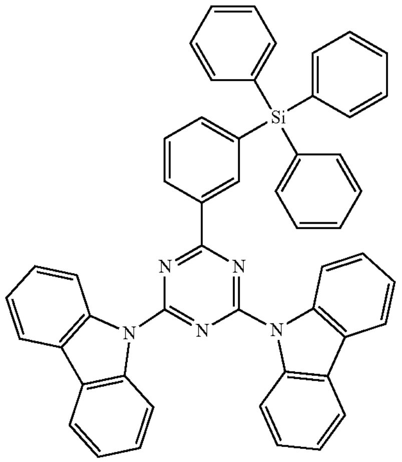
HH3
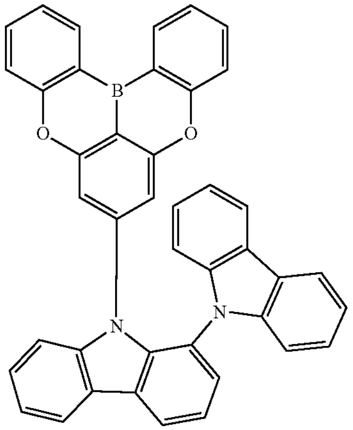
HH4
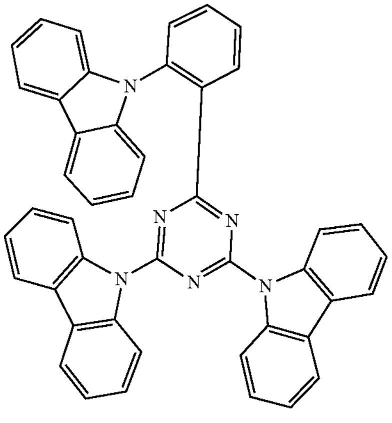
-continued
DH1
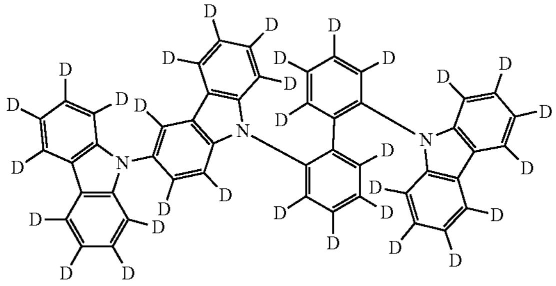
DH2
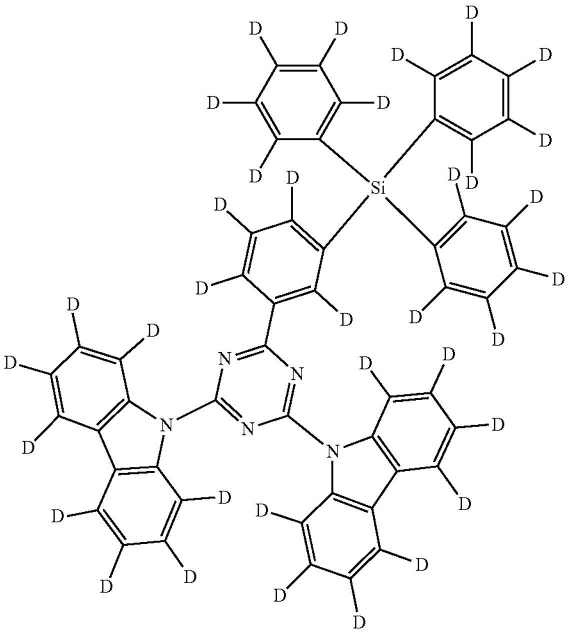
DH3
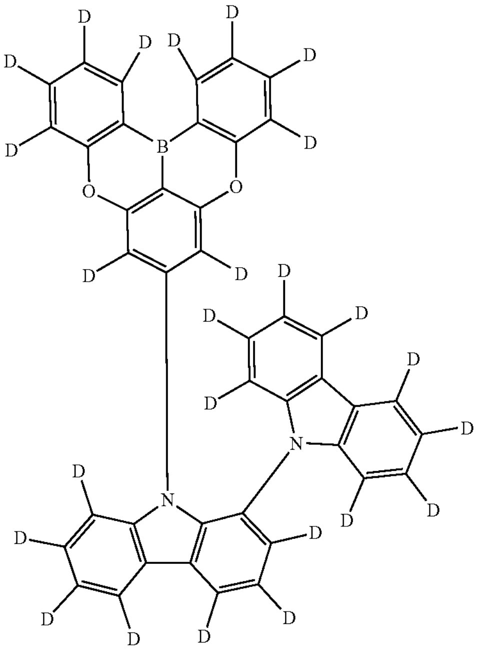

-continued
DH4
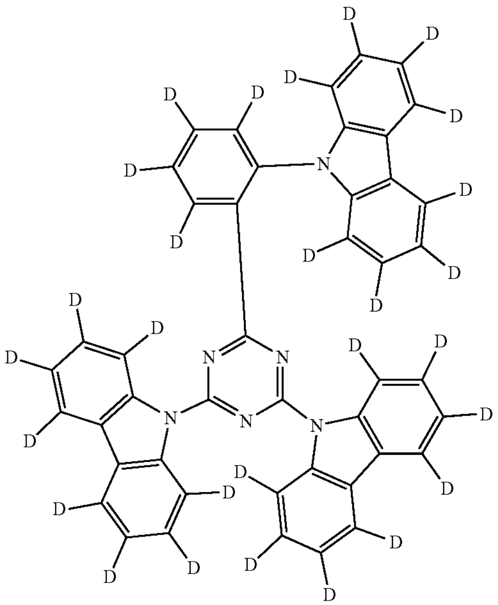
Compound 3
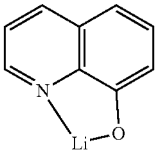
Compound 4
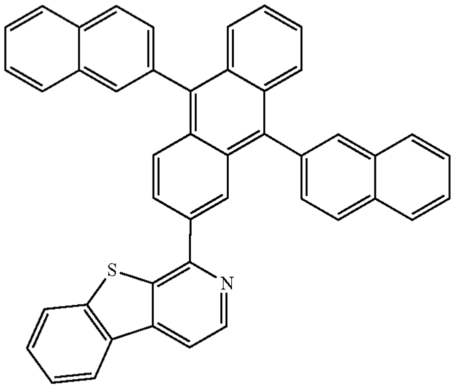
Compound 5
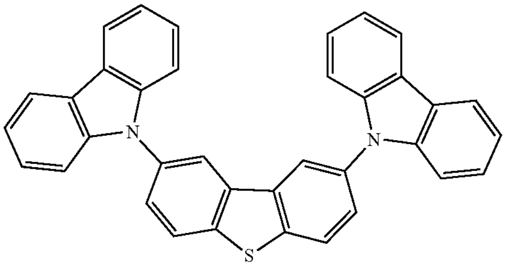
-continued
Compound 6
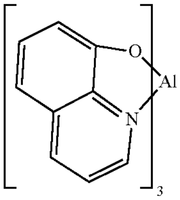
Pt-1
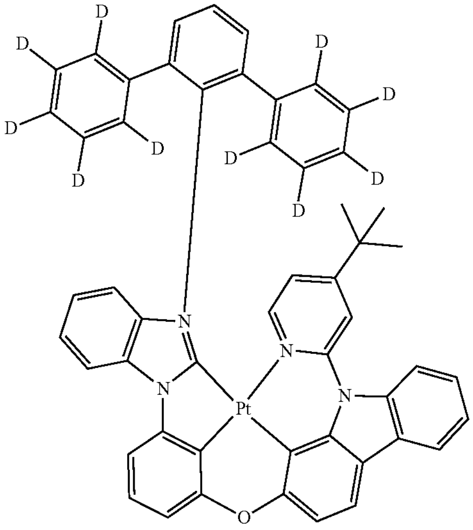
Pt-2
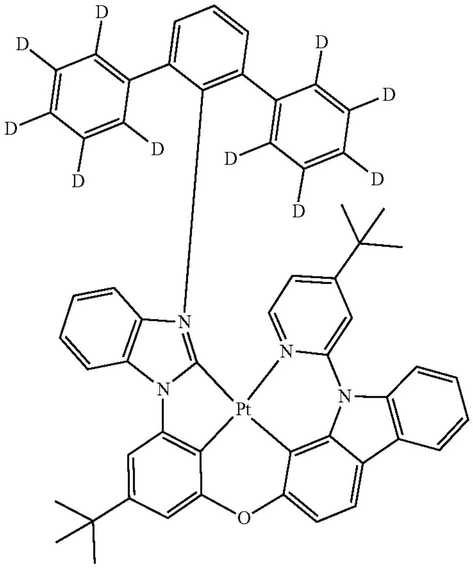

-continued
Pt-3
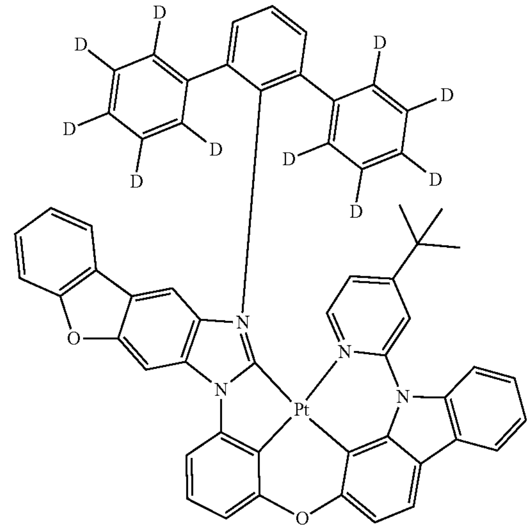
Pt-4
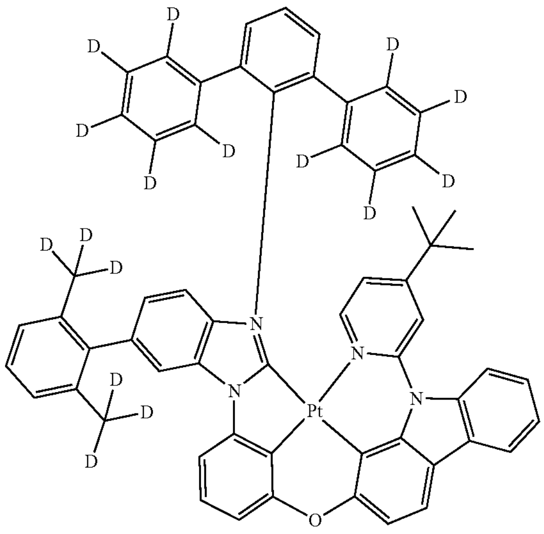
Pt-5
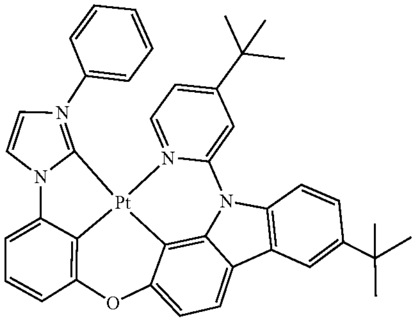
-continued
Pt-6
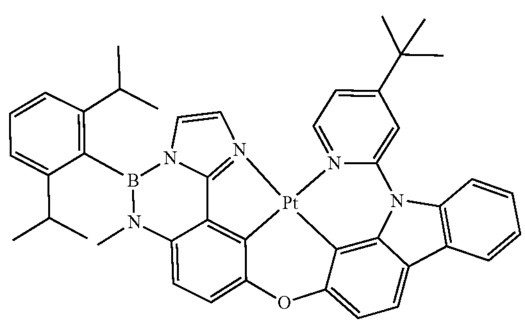
Pt-7
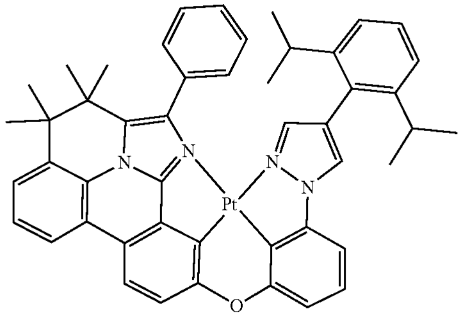
Pt-8
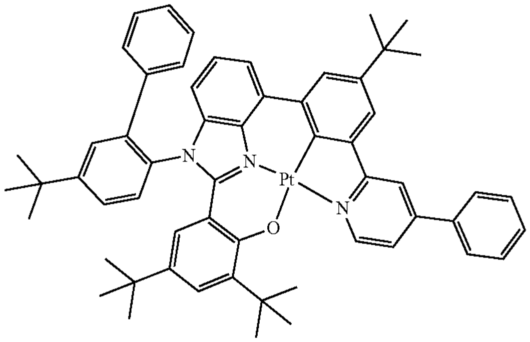
Pt-9
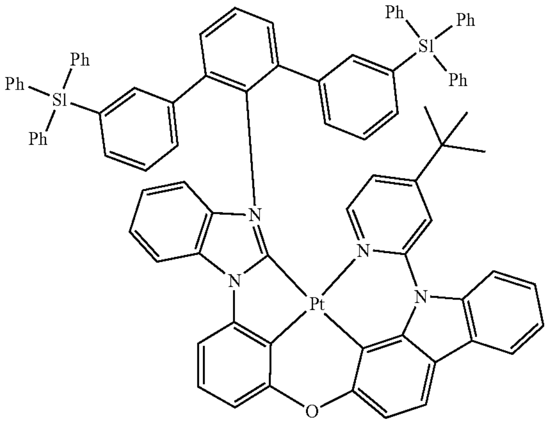

-continued
Pt-10
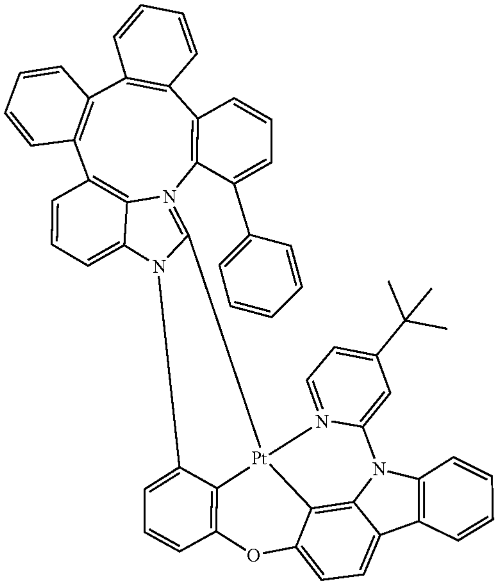
Pt-11
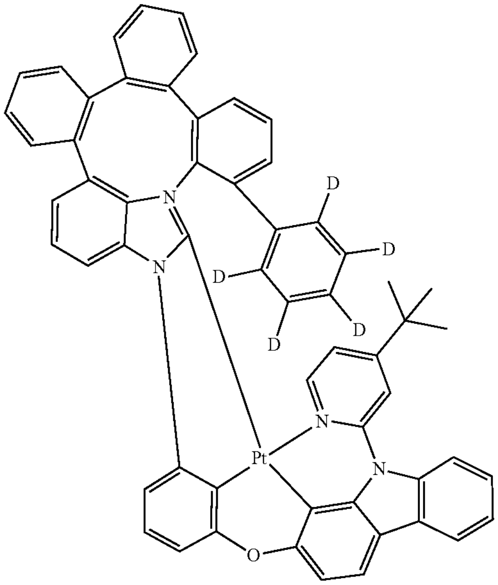
Ir-1
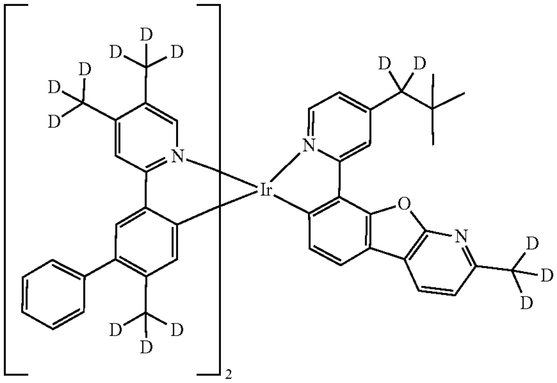
-continued
Ir-2
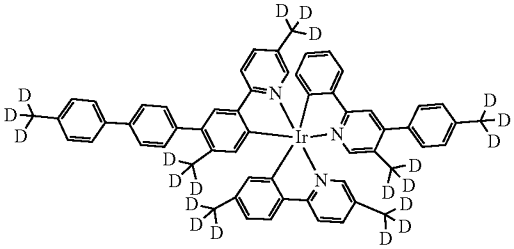
Ir-3
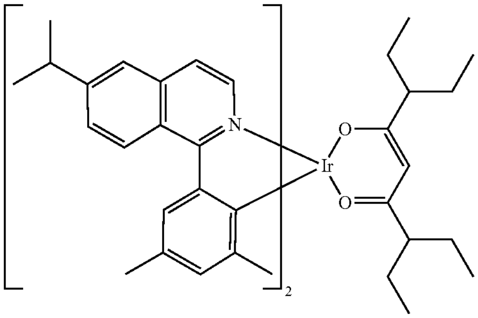
Ir-4
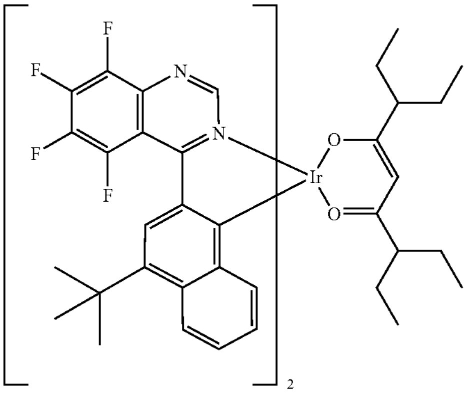
Ir-5
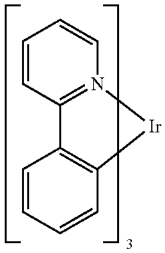
Ir-6
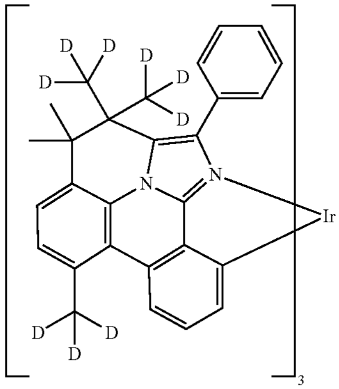

-continued

Ir-7

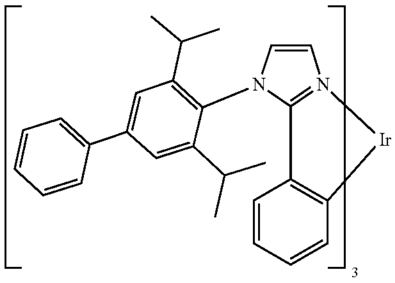

Table 1 shows calculated singlet and triplet energies for DH1 to DH4. Geometry optimization calculations were performed within the Gaussian 09 software package using the B3LYP hybrid functional and CEP-31G basis set which includes effective core potentials. It should be understood that these calculations obtained with the DFT functional set and basis set as identified herein are theoretical. Computational composite protocols, such as Gaussian with the CEP-31G basis set used herein, rely on the assumption that electronic effects are additive and, therefore, larger basis sets can be used to extrapolate to the complete basis set (CBS) limit. However, when the goal of a study is to understand variations in HOMO, LUMO, $S_1$, $T_1$, bond dissociation energies, etc. over a series of structurally-related compounds, the additive effects are expected to be similar. Accordingly, while absolute errors from using the B3LYP may be significant compared to other computational methods, the relative differences between the HOMO, LUMO, $S_1$, $T_1$, and bond dissociation energy values calculated with B3LYP protocol are expected to reproduce experiment quite well. See, e.g., Hong et al., *Chem. Mater.* 2016, 28, 5791-98, 5792-93 and Supplemental Information (discussing the reliability of DFT calculations in the context of OLED materials). Moreover, with respect to iridium or platinum complexes that are useful in the OLED art, the data obtained from DFT calculations correlates very well to actual experimental data. See Tavasli et al., *J. Mater. Chem.* 2012, 22, 6419-29, 6422 (Table 3) (showing DFT calculations closely correlating with actual data for a variety of emissive complexes); Morello, G. R., *J. Mol. Model.* 2017, 23:174 (studying of a variety of DFT functional sets and basis sets and concluding the combination of B3LYP and CEP-31G is particularly accurate for emissive complexes).

TABLE 1

Calculated singlet and triplet energies and the corresponding singlet-triplet gaps.

| Dopant | $S1_{host}$ | $T1_{host}$ | $S1_{host} - T1_{host}$ |
|---|---|---|---|
| DH1 | 3.70 | 3.16 | 0.54 |
| DH2 | 3.50 | 3.13 | 0.37 |
| DH3 | 3.17 | 2.88 | 0.29 |
| DH4 | 3.02 | 2.90 | 0.12 |

The photoluminescent emission spectra of doped PMMA films at room temperature was measured for Pt-1, Pt-2, Pt-3, Pt-4, Pt-5, and Pt-7. The emission spectra of the films were measured on a calibrated Hamamatsu Quantaurus-QY Plus UV-NIR absolute PL quantum yield spectrometer with an excitation wavelength of 340 nm. The films were prepared from solutions of 1% emitter by weight with PMMA in toluene which were filtered and dropcast onto Quartz substrates. The corresponding peak emission wavelength ($\lambda_{max}$) and full width at half maximum (FWHM) are shown in Table 2.

TABLE 2

Photoluminescent emission spectral data of 1% doped PMMA films

| Dopant | λmax (nm) | FWHM |
|---|---|---|
| Pt-1 | 455 | 18 |
| Pt-2 | 460 | 24 |
| Pt-3 | 461 | 19 |
| Pt-4 | 456 | 20 |
| Pt-5 | 448 | 18 |
| Pt-7 | 464 | 47 |

For Examples 1-10 and Comparison 1-2, devices were grown in two different device structures. Device Structure 1 had organic layers consisting of, sequentially, from the ITO surface, 100 Å of Compound 1 (HIL), 250 Å of Compound 2 (HTL), 50 Å of HH1 (EBL), 300 Å of HH1 doped with a fixed percentage of HH2, X % of Dopant (EML), 50 Å of HH2 (BL), 300 Å of Compound 3 doped with 35% of Compound 4 (ETL), 10 Å of Compound 3 (EIL) followed by 1,000 Å of Al (Cathode). Device Structure 2 had organic layers consisting of, sequentially, from the ITO surface, 100 Å of Compound 1 (HIL), 250 Å of Compound 2 (HTL), 50 Å of HH1 (EBL), 300 Å of DH1 doped with a fixed percentage of DH2, X % of Dopant (EML), 50 Å of HH2 (BL), 300 Å of Compound 3 doped with 35% of Compound 4 (ETL), 10 Å of Compound 3 (EIL) followed by 1,000 Å of Al (Cathode). For examples 1-7, examples 10-11, and comparison 1 the doping percentage of HH2 or DH2 was 50%. For examples 8-9 and comparison 2 the doping percentage of HH2 or DH2 was 40%. The dopant and doping concentration for each device are given in Table 4 and Table 5.

For Examples 1-6 and Comparison 1, the measured lifetime (LT90) is the time to reduction of brightness to 90% of the initial luminance at a constant current density of 20 $mA/cm^2$. The Enhancement Factor reported in Table 3 is the ratio of the LT90 for Device Structure 2 to the LT90 for Device Structure 1.

TABLE 3

Enhancement Factors of blue emitting platinum complexes in deuterated hosts

| | Dopant | Conc. | λmax (nm) | CIE | Enhancement Factor |
|---|---|---|---|---|---|
| Example 1 | Pt-1 | 12% | 462 | (0.138, 0.177) | 1.8 |
| Example 2 | Pt-2 | 12% | 468 | (0.139, 0.230) | 1.9 |
| Example 3 | Pt-3 | 12% | 470 | (0.128, 0.215) | 1.8 |
| Example 4 | Pt-4 | 12% | 463 | (0.135, 0.171) | 1.9 |
| Example 5 | Pt-5 | 12% | 488 | (0.225, 0.373) | 1.6 |
| Example 6 | Pt-6 | 12% | 464 | (0.208, 0.364) | 1.7 |
| Example 7 | Pt-9 | 12% | 461 | (0.135, 0.141) | 2.0 |
| Comparison 1 | Pt-7 | 12% | 467 | (0.140, 0.253) | 1.1 |

The above data shows that device Examples 1-7 each exhibited a larger enhancement from deuteration than Comparison 1. The 60%-100% lifetime enhancement is beyond any value that could be attributed to experimental error and the observed improvement is significant. Based on the fact that the devices have the same structure with the only difference being the selection of phosphorescent dopant, the significant performance improvement observed in the above data was unexpected. Without being bound by any theories, this improvement may be attributed to the suppression of intermolecular decomposition reactions between deuterated hosts and dopants with particular molecular structural motifs or particular emission properties. In Examples 1-5 and Example 7, the phosphors are Pt-complexes comprising metal-carbene bonds and show a larger enhancement from deuteration of the host than the comparison compound in Comparison 1 which does not comprise a carbene. In Example 3, the phosphor comprises a fused-ring structure having four rings fused in a linear fashion and shows a larger enhancement from deuteration of the host than the comparison compound in Comparison 1. In Examples 1-4, the terphenyl substituted carbene phosphors comprise a pendant group comprising at least three 6-membered aromatic rings, each of which is not directly fused to another of the at least three 6-membered aromatic rings, and they each shows a larger enhancement from deuteration of the host than the comparison compound in Comparison 1 which does not comprise a terphenyl substitution. In Examples 1-7, each of the phosphors comprise a carbazole moiety which is directly bonded to the metal and show larger enhancements from deuteration of the host than the comparison compound in Comparison 1 which does not comprise a carbazole moiety. In Example 6, the phosphor comprises a boron atom and shows a larger enhancement from deuteration of the host than the comparison compound in Comparison 1 which does not comprise a boron atom. In Examples 1-7 each phosphor comprises a tetradentate ligand that forms at least three adjacent 5-membered or 6-membered chelate rings with at least two neighboring chelate rings being the same size with one 5-membered chelate and two adjacent 6-membered chelates and each show a larger enhancement from deuteration of the host than the comparison compound in Comparison 1 which does not comprise any two neighboring chelate rings of the same size. In Example 7, the phosphor comprises a silicon atom and shows a larger enhancement from deuteration of the host than the comparison compound in Comparison 1 which does not comprise a silicon atom. In Examples 1-4, the phosphors each comprise deuterated phenyl rings and show larger enhancements from deuteration of the host than the comparison compound in Comparison 1 which does not comprise any deuteration. In Example 5, the phosphor forms an exciplex with the host material and shows a larger enhancement from deuteration of the host than the comparison compound in Comparison 1 which does not form an exciplex with the host. In Examples 1-5, the phosphors each exhibit a full width at half maximum of the emission at λmax that is less than 40 nm in a a 1% doped a PMMA film, as shown in Table 2, and they each show a larger enhancement from deuteration of the host than the comparison compound in Comparison 1 which exhibits a full width at half maximum of the emission at λmax that is greater than 40 nm.

For Examples 8-11 and Comparison 2, the measured lifetime (LT95) is the time to reduction of brightness to 95% of the initial luminance at a constant current density of 60 mA/cm$^2$. The enhancement factor reported in Table 4 and Table 5 is the ratio of the LT95 for Device Structure 2 to the LT95 for Device Structure 1. The enhancement factors of devices with Ir-1 to Ir-3 and Ir-5 are shown in Table 5.

TABLE 4

Enhancement Factors of green and red emitting iridium complexes in deuterated hosts

| | Dopant | Conc. | λmax (nm) | CIE | Enhancement Factor |
|---|---|---|---|---|---|
| Example 8 | Ir-1 | 12% | 525 | (0.321, 0.644) | 2.1 |
| Example 9 | Ir-2 | 12% | 528 | (0.341, 0.617) | 2.1 |
| Example 10 | Ir-3 | 5% | 625 | (0.685, 0.313) | 2.0 |
| Comparison 2 | Ir-5 | 12% | 515 | (0.292, 0.638) | 1.2 |

The above data shows that the device Example 8-10 all exhibited a large enhancement from deuteration and have enhancement factors 80% larger than Comparison 2. The 20%-110% lifetime enhancement is beyond any value that could be attributed to experimental error and the observed improvement is significant. Based on the fact that the devices Examples 8-10 have the same structure as Comparison 2 with the only difference being the selection of phosphor, the significant performance improvement observed in the above data was unexpected. Without being bound by any theories, this improvement may be attributed to the suppression of intermolecular decomposition reactions between deuterated hosts and dopants with particular molecular structural motifs or particular emission properties. In Example 8, the phosphor comprises a fused-ring structure comprising at least three rings, including at least one 6-membered heteroaryl ring or a fused ring structure comprising a benzene ring directly bonded to the metal and shows a larger enhancement from deuteration of the host than the comparison compound in Comparison 2 which does not contain any fuse ring structure. In Example 9, the phosphor is an Ir(III) complex comprising three different bidentate ligands and shows a larger enhancement upon deuteration of the host than the comparison compound in Comparison 2 which is a homoleptic Ir(III) complex. In Examples 10, the phosphor comprises an acetylacetonate ligands and shows a larger enhancement than the comparison compound in Comparison 2 which does not comprise an acetylacetonate ligand.

TABLE 5

Enhancement Factor of infrared emitting complex in deuterated hosts

| | Dopant | Conc. | λmax (nm) | CIE | Enhancement Factor |
|---|---|---|---|---|---|
| Example 11 | Ir-4 | 5% | 738 | (0.354, 0.247) | 1.2 |

The photoluminescent quantum yield (PLQY) of a doped PMMA film at room temperature was measured for Ir-4. The PLQY were measured on a calibrated Hamamatsu Quantaurus-QY Plus UV-NIR absolute PL quantum yield spectrometer with an excitation wavelength of 340 nm. The film was prepared from solutions of 1% Ir-4 by weight with PMMA in toluene which was filtered and dropcast onto Quartz substrates. The corresponding peak emission wavelength ($\lambda_{max}$) and PLQY are shown in Table 6.

TABLE 6

| $\lambda_{max}$ and PLQY of Ir-4 | | |
|---|---|---|
| Dopant | λmax (nm) | PLQY |
| Ir-4 | 729 | 60% |

In Example 11, the phosphor which has a $\lambda_{max}$ is in the range of 700-1000 nm with a PLQY value of at least 30% in a 1% doped PMMA film, as shown in Table 6, and contains a fluorinated quinazoline which comprises heteroaryl moiety comprising at least two heteroatoms as well as at least one fluorine atom and shows a significant lifetime enhancement when the host is deuterated.

For Examples 12, devices were grown in two different device structures. Device Structure 3 had organic layers consisting of, sequentially, from the ITO surface, 100 Å of Compound 1 (HIL), 400 Å of Compound 2 (HTL), 50 Å of DH1 (EBL), 400 Å of HH1 doped with 30% HH2, 12% of Pt-8 (EML), 300 Å of Compound 3 doped with 35% of Compound 4 (ETL), 10 Å of Compound 3 (EIL) followed by 1,000 Å of Al (Cathode). Device Structure 4 had organic layers consisting of, sequentially, from the ITO surface, 100 Å of Compound 1 (HIL), 400 Å of Compound 2 (HTL), 50 Å of DH1 (EBL), 400 Å of DH1 doped with 30% DH2, 12% of Pt-8 (EML), 300 Å of Compound 3 doped with 35% of Compound 4 (ETL), 10 Å of Compound 3 (EIL) followed by 1,000 Å of Al (Cathode). The measured lifetime (LT95) is the time to reduction of brightness to 95% of the initial luminance at a constant current density of 80 mA/$cm^2$. The Enhancement Factor reported in Table 7 is the ratio of the LT95 for Device Structure 4 to the LT95 for Device Structure 3.

TABLE 7

| Enhancement Factor of Pt-8 | | | | |
|---|---|---|---|---|
| | Dopant | λmax (nm) | CIE | Enhancement Factor |
| Example 12 | Pt-8 | 528 | (0.328, 0.635) | 1.8 |

The above data shows that the device Example 12 exhibited a larger lifetime enhancement than Comparison 2. The 80% lifetime enhancement is beyond any value that could be attributed to experimental error and the observed improvement is significant. Based on the fact that Example 12 uses the same host materials as Comparison 2 with the major difference between the devices being the selection of phosphor, the significant performance improvement observed in the above data was unexpected. Without being bound by any theories, this improvement may be attributed to the suppressed reactivity of deuterated hosts with Pt-8 which has a tetradentate ligand comprising a coordinating oxygen atom trans to a coordinating carbon atom. Furthermore, the vertical dipole ratio (VDR) for Pt-8 is less than 0.15 which shows that this phosphor with a λmax at 528 nm and a VDR less than 0.15 shows a larger enhancement in lifetime from deuteration of the hosts than Comparison 2 which has a VDR greater than 0.15.

For Examples 13 devices were grown in two different device structures. Device Structure 5 had organic layers consisting of, sequentially, from the ITO surface, 100 Å of Compound 1 (HIL), 250 Å of Compound 2 (HTL), 50 Å of HH1 (EBL), 300 Å of HH1 doped with 30% HH3, 12% of Pt-2 (EML), 50 of HH3 (BL), 300 Å of Compound 3 doped with 35% of Compound 4 (ETL), 10 Å of Compound 3 (EIL) followed by 1,000 Å of Al (Cathode). Device Structure 6 had organic layers consisting of, sequentially, from the ITO surface, 100 Å of Compound 1 (HIL), 250 Å of Compound 2 (HTL), 50 Å of HH1 (EBL), 300 Å of HH1 doped with 30% DH3, 12% of Pt-2 (EML), 50 Å of HH3 (BL), 300 Å of Compound 3 doped with 35% of Compound 4 (ETL), 10 Å of Compound 3 (EIL) followed by 1,000 Å of Al (Cathode). The measured lifetime (LT90) is the time to reduction of brightness to 90% of the initial luminance at a constant current density of 20 mA/cm2. The Enhancement Factor reported in Table 8 is the ratio of the LT90 for Device Structure 6 to the LT90 for Device Structure 5.

TABLE 8

| Relative lifetime of Pt-2 in deuterated boron containing host | | | | |
|---|---|---|---|---|
| | Dopant | λmax (nm) | CIE | Enhancement Factor |
| Example 13 | Pt-2 | 467 | (0.130, 0.196) | 1.3 |

The above data shows that device Example 13 exhibited an elongated lifetime compared to the device without deuteration of the host. The 30% lifetime enhancement is beyond any value that could be attributed to experimental error and the observed improvement is significant. Without being bound by any theories, this improvement may be attributed to the suppressed reactivity of deuterated boron containing host with the phosphor.

For Examples 14, devices were grown in two different device structures. Device Structure 7 had organic layers consisting of, sequentially, from the ITO surface, 100 Å of Compound 1 (HIL), 250 Å of Compound 2 (HTL), 50 Å of DH1 (EBL), 300 Å of HH1 doped with 50% HH4, 12% of Pt-2 (EML), 50 Å of DH4 (BL), 300 Å of Compound 3 doped with 35% of Compound 4 (ETL), 10 Å of Compound 3 (EIL) followed by 1,000 Å of Al (Cathode). Device Structure 8 had organic layers consisting of, sequentially, from the ITO surface, 100 Å of Compound 1 (HIL), 250 Å of Compound 2 (HTL), 50 Å of DH1 (EBL), 300 Å of DH1 doped with 50% DH4, 12% of Pt-2 (EML), 50 Å of DH4 (BL), 300 Å of Compound 3 doped with 35% of Compound 4 (ETL), 10 Å of Compound 3 (EIL) followed by 1,000 Å of Al (Cathode). The measured lifetime (LT90) is the time to reduction of brightness to 90% of the initial luminance at a constant current density of 20 mA/$cm^2$. The Enhancement Factor reported in Table 9 is the ratio of the LT90 for Device Structure 8 to the LT90 for Device Structure 7.

TABLE 9

| Relative lifetime of Pt-2 in deuterated TADF host | | | | |
|---|---|---|---|---|
| | Dopant | λmax (nm) | CIE | Enhancement Factor |
| Example 14 | Pt-2 | 468 | (0.147, 0.241) | 2.8 |

The above data shows that the device Example 14 exhibited an elongated lifetime compared with deuteration of the host. The 180% lifetime enhancement is beyond any value that could be attributed to experimental error and the observed improvement is significant. The enhancement in Example 14 using DH4, which has a small $S1_{host}$–$T1_{host}$, is much larger than any of those observed in using DH2, which has a larger $S1_{host}$–$T1_{host}$. Based on the fact that DH4 and DH2 have the similar structure with the main difference being the smaller $S1_{host}$-$T1_{host}$ for DH4, the significant performance improvement observed in the above data was unexpected. Without being bound by any theories, this improvement may be attributed to the suppressed reaction between the deuteration host and platinum complex being particularly impactful when the host has a difference between $S1_{host}$-$T1_{host}$ that is less than 0.30 eV.

For Examples 15-16 devices were grown in two different device structures. Device Structure 9 had organic layers consisting of, sequentially, from the ITO surface, 100 Å of Compound 1 (HIL), 250 Å of Compound 2 (HTL), 50 Å of DH1 (EBL), 300 Å of HH1 doped with 52% HH2, 13% of dopant (EML), 50 Å of DH2 (BL), 300 Å of Compound 3 doped with 35% of Compound 4 (ETL), 10 Å of Compound 3 (EIL) followed by 1,000 Å of Al (Cathode). Device Structure 10 had organic layers consisting of, sequentially, from the ITO surface, 100 Å of Compound 1 (HIL), 250 Å of Compound 2 (HTL), 50 Å of DH1 (EBL), 300 Å of DH1 doped with 52% DH2, 13% of dopant (EML), 50 Å of DH2 (BL), 300 Å of Compound 3 doped with 35% of Compound 4 (ETL), 10 Å of Compound 3 (EIL) followed by 1,000 Å of Al (Cathode). The measured lifetime (LT90) is the time to reduction of brightness to 90% of the initial luminance at a constant current density of 20 mA/cm2. The Enhancement Factor reported in Table 10 is the ratio of the LT90 for Device Structure 10 to the LT90 for Device Structure 9.

TABLE 10

Enhancement Factors of blue emitting complexes in deuterated hosts

| | Dopant | λmax (nm) | CIE | Enhancement Factor |
|---|---|---|---|---|
| Example 15 | Pt-10 | 461 | (0.142, 0.153) | 2.3 |
| Example 16 | Pt-11 | 468 | (0.142, 0.155) | 1.9 |

In Examples 15-16, each exhibited a larger enhancement from deuteration than Comparison 1. The 90%-130% lifetime enhancement is beyond any value that could be attributed to experimental error and the observed improvement is significant. Based on the fact that the devices have similar structures with the primary difference being the selection of phosphorescent dopant, the significant performance improvement observed in the above data was unexpected. Without being bound by any theories, this improvement may be attributed to the suppression of intermolecular decomposition reactions between deuterated hosts and dopants with particular molecular structural motifs or particular emission properties. Both Pt-10 and Pt-11 comprise a 9 membered ring and show larger enhancements from deuteration of the host than the comparison compound in Comparison 1 which does not have a ring comprising 7 or more atoms.

Comparing Example 15 to Example 16, the device with Pt-10 shows a larger enhancement than the device with Pt-11. Based on the fact that the phosphorescent dopants have an identical structure with the only difference being that Pt-10 contains more deuterium atoms than Pt-11, the significant performance improvement observed in the above data was unexpected. Without being bound by any theories, the larger enhancement factor for Pt-10 may originate by removal of additional hydrogen atoms from the EML. In some embodiments the preferred emitting complex has more than 20% of the protons deuterated, more preferably more than 50% of the protons deuterated, most preferably more than 75% of the proton deuterated.

For Example 17 and Comparison 3 devices were grown in two different device structures. Device Structure 11 had organic layers consisting of, sequentially, from the ITO surface, 100 Å of Compound 1 (HIL), 250 Å of Compound 2 (HTL), 300 Å of HH1 with X % of Dopant (EML), 50 Å of Compound 5 (BL), 300 Å of Compound 6 (ETL), 10 Å of Compound 3 (EIL) followed by 1,000 Å of Al (Cathode). Device Structure 12 had organic layers consisting of, sequentially, from the ITO surface, 100 Å of Compound 1 (HIL), 250 Å of Compound 2 (HTL), 300 Å of DH1 with X % of Dopant (EML), 50 Å of Compound 5 (BL), 300 Å of Compound 6 (ETL), 10 Å of Compound 3 (EIL) followed by 1,000 Å of Al (Cathode). The dopant and doping concentration for each device are given in Table 11. The measured lifetime (LT90) is the time to reduction of brightness to 90% of the initial luminance at a constant current density of 20 mA/cm2. The Enhancement Factor reported in Table 11 is the ratio of the LT90 for Device Structure 12 to the LT90 for Device Structure 11.

TABLE 11

Enhancement Factors of blue emitting complexes in deuterated hosts

| | Dopant | Conc. | λmax (nm) | CIE | Enhancement Factor |
|---|---|---|---|---|---|
| Example 17 | Ir-6 | 18% | 472 | (0.152, 0.320) | 1.9 |
| Comparison 3 | Ir-7 | 20% | 474 | (0.173, 0.392) | 1.3 |

The above data shows that the device Example 17 exhibited a large enhancement from deuteration of the host and has 60% more enhancement than Comparison 2. The 90% lifetime enhancement is beyond any value that could be attributed to experimental error and the observed improvement is significant. Based on the fact that Ir-6 has a similar structure to Ir-7 with the primary difference being the fused ring structure of Ir-6, the significant performance improvement observed in the above data was unexpected. Without being bound by any theories, this improvement may be attributed to the suppression of intermolecular decomposition reactions between deuterated hosts and dopants with a fused ring structure comprising 4 or more fused rings and Example 17 shows a larger enhancement from deuteration of the host than the comparison compound in Comparison 3 which does not contain any fused ring structure.

In each of the Examples 1-17 and Comparison 1-3 the devices tested contain hosts with deuterated carbazole and all showed significant enhancement in device lifetime. Without being bound by any theories, this improvement may be attributed to the suppressed reactivity of deuterated carbazole with the dopants, and particular dopant chemistry shown in Examples 1-17 show significantly larger enhancements than Comparison 1-3. In Examples 1-13 and Examples 15-16 the deuterated host has a difference between $S1_{host}$-$T1_{host}$ which is greater than 0.25 eV and less than 1.50 eV. Example 12 and Examples 14-16 further comprise a blocking layer comprising a deuterated material each of which has amongst the largest enhancement factors.

What is claimed is:

1. An organic electroluminescent device (OLED) comprising:

an anode;

a cathode; and an emissive layer, disposed between the anode and the cathode;

wherein the emissive layer comprises a first phosphorescent emitter and a first host;

wherein the first phosphorescent emitter is a metal complex;

wherein the first host is partially or fully deuterated;

wherein at least one of the following is true:

(a) the metal complex emits light upon photoexcitation at room temperature; wherein the emitted light has an emission spectrum characterized by a peak emission wavelength $\lambda_{max}$ when measured at a mass concentration of 1% in a PMMA film; wherein the metal complex has a $\lambda_{max}$ in the range of 400-500 nm and a VDR value of equal or less than 0.15, or the metal complex has a $\lambda_{max}$ in the range of 500-590 nm and a VDR value of equal or less than 0.15, or the metal complex has a $\lambda_{max}$ in the range of 590-700 nm and a VDR value of equal or less than 0.10, or (b) the OLED comprises a second host that is not deuterated, partially deuterated, or fully deuterated; and wherein at least one of the following conditions is true:

(1) the metal complex is a Pt complex comprising a metal-carbene bond;

(2) the metal complex comprises at least one feature selected from the group consisting of: an imidazole moiety; a fused or unfused heteroaryl moiety comprising at least two heteroatoms; a fused-ring structure comprising at least three rings, including at least one 6-membered heteroaryl ring; a fused-ring structure having at least four rings; a pendant group comprising at least three 6-membered aromatic rings, each of which is not directly fused to another of the at least three 6-membered aromatic rings; a partially or fully deuterated 5- or 6-member carbocyclic or heterocyclic ring directly bonded to the metal; a carbazole moiety which is directly bonded to the metal; a total of at least six 6-membered aromatic rings; at least one boron atom; at least one fluorine atom; a fused ring structure comprising a benzene ring directly bonded to the metal; or a substituted or unsubstituted acetylacetonate ligand; a silicon atom; a ring structure comprising 7 or more atoms;

(3) the metal complex is a tetradentate Pt complex, wherein the tetradentate ligand forms at least three adjacent 5-membered or 6-membered chelate rings with at least two neighboring chelate rings being the same size;

(4) the metal complex is a tetradentate Pt complex, wherein the tetradentate ligand comprises at least one coordinating oxygen atom or sulfur atom trans to a coordinating carbon atom;

(5) the metal complex is partially or fully deuterated;

(6) the metal complex comprises a metal selected from the group consisting of Os, Ag, Au, Cu, and Pd;

(7) the metal complex is an Ir(III) complex comprising three different bidentate ligands;

(8) the metal complex emits light upon photoexcitation at room temperature; wherein the emitted light has an emission spectrum characterized by a peak emission wavelength $\lambda_{max}$ when measured at a mass concentration of 1% in a PMMA film; wherein the metal complex has a λmax in the range of 400-500 nm and a vertical dipole ratio (VDR) value of equal or less than 0.15, or the metal complex has a λmax in the range of 500-590 nm and a VDR value of equal or less than 0.15, or the metal complex has a $\lambda_{max}$ in the range of 590-700 nm and a VDR value of equal or less than 0.10;

(9) the metal complex has a lowest triplet energy $T1_{em}$ and a lowest singlet energy $S1_{em}$, wherein the difference between $S1_{em}-T1_{em}$ is equal or less than 0.3 eV;

(10) the first host comprises a partially or fully deuterated moiety selected from the group consisting of triphenylene, carbazole, indolocarbazole, dibenzothiophene, dibenzofuran, dibenzoselenophene, 5λ2-benzo[d]benzo[4,5]imidazo[3,2-a]imidazole, 5,9-dioxa-13b-boranaphtho[3,2,1-de]anthracene, aza-triphenylene, aza-carbazole, aza-indolocarbazole, aza-dibenzothiophene, aza-dibenzofuran, aza-dibenzoselenophene, aza-5λ2-benzo[d]benzo[4,5]imidazo[3,2-a]imidazole, and aza-(5,9-dioxa-13b-boranaphtho[3,2,1-de]anthracene);

(11) the first host comprises a boryl moiety;

(12) the first host has a lowest triplet energy $T1_{host}$ and a lowest singlet energy $S1_{host}$, wherein the difference between $S1_{host}-T1_{host}$ is equal or greater than 0.25 eV, and equal or less than 1.50 eV;

(13) the metal complex is a Pt complex and the first host has a lowest triplet energy $T1_{host}$ and a lowest singlet energy $S1_{host}$, wherein the difference between $S1_{host}-T1_{host}$ is equal or less than 0.30 eV;

(14) the first host is the only host material in the emissive layer, and the first host comprises a heteroaryl group comprising at least two nitrogen atoms;

(15) the metal complex emits light upon photoexcitation at room temperature; wherein the emitted light has an emission spectrum characterized by a peak emission wavelength $\lambda_{max}$ when measured at a mass concentration of 1% in a PMMA film; and wherein the full width at half maximum of the emission at $\lambda_{max}$ is equal to or less than 40 nm;

(16) the metal complex emits light upon photoexcitation at room temperature; wherein the emitted light has an emission spectrum characterized by a peak emission wavelength $\lambda_{max}$ when measured at a mass concentration of 1% in a PMMA film; wherein the $\lambda_{max}$ is in the range of 700-1000 nm with a PLQY value of at least 30%;

(17) the emissive layer contains two or more materials, which form an exciplex;

(18) the OLED further comprises at least one additional layer comprising at least one partially or fully deuterated material;

(19) the OLED has a first device lifetime LT95 which is measured at 10 $mA/cm^2$, wherein the first device lifetime is at least 1.5 times greater than a second device lifetime which was obtained under the exact condition as the first device lifetime except the first host is non-deuterated;

(20) at least one of the anode, the cathode, or an additional layer disposed over the emissive layer functions as an enhancement layer; wherein the enhancement layer comprises a plasmonic material exhibiting surface plasmon resonance that non-radiatively couples to the first phosphorescent emitter and transfers excited state energy from the emitter material to non-radiative mode of surface plasmon polariton; wherein the enhancement layer is provided no more than a threshold distance away from the emissive layer; and wherein the first phosphorescent emitter has a total non-radiative decay rate constant and a total radiative decay rate constant due to the presence of the enhancement layer and the threshold distance is a distance where the total non-radiative decay rate constant is equal to the total radiative decay rate constant;

(21) the concentration level of the metal complex in the emissive layer along a direction extending perpendicular to the anode toward the cathode, follows a predefined non-constant gradient profile; and

(22) any combination of two or more conditions listed above.

2. The OLED of claim 1, wherein the metal complex is a Pt complex comprising a metal-carbene bond; or the metal complex comprises at least one polydentate ligand that forms a 5-membered chelate ring with the Pt.

3. The OLED of claim 2, wherein the at least one polydentate ligand is a tetradentate ligand, wherein the 5-membered chelate ring can include a carbene bond.

4. The OLED of claim 3, wherein the carbene is substituted by a substituent R, wherein the substituent R is partially or fully deuterated.

5. The OLED of claim 4, wherein the substituent R comprises at least two 6-membered aromatic rings, each of which is not directly fused to the other 6-membered aromatic ring.

6. The OLED of claim 1, wherein the metal complex comprises at least one feature selected from the group consisting of: an imidazole moiety; a fused or unfused heteroaryl moiety comprising at least two heteroatoms; a fused-ring structure comprising at least three rings, including at least one 6-membered heteroaryl ring; a fused-ring structure having at least four rings; a pendant group comprising at least three 6-membered aromatic rings, each of which is not directly fused to another of the at least three 6-membered aromatic rings; a partially or fully deuterated 5- or 6-member carbocyclic or heterocyclic ring directly bonded to the metal; a carbazole moiety which is directly bonded to the metal; a total of at least six 6-membered aromatic rings; at least one boron atom; at least one fluorine atom; a fused ring structure comprising a benzene ring directly bonded to the metal; or a substituted or unsubstituted acetylacetonate ligand.

7. The OLED of claim 1, wherein the metal complex is a tetradentate Pt complex, wherein the tetradentate ligand forms at least three adjacent 5-membered or 6-membered chelate rings with at least two neighboring chelate rings being the same size, wherein the Pt and the tetradentate ligand form at least one 5-membered chelate ring and at least one 6-membered chelate ring.

8. The OLED of claim 7, wherein the Pt and the tetradentate ligand form a 5-membered chelate ring and two 6-membered chelate rings, or form two 5-membered chelate rings and one 6-membered chelate ring.

9. The OLED of claim 1, wherein the metal complex is a tetradentate Pt complex, wherein the tetradentate ligand comprises at least one coordinating oxygen atom or sulfur atom trans to a coordinating carbon atom, or the tetradentate ligand comprises at least one coordinating oxygen atom trans to a coordinating carbon atom.

10. The OLED of claim 1, wherein the metal complex emits light upon photoexcitation at room temperature; wherein the emitted light has an emission spectrum characterized by a peak emission wavelength $\lambda_{max}$ when measured at a mass concentration of 1% in a PMMA film; wherein the metal complex has a $\lambda_{max}$ in the range of 400-500 nm and a VDR value of equal or less than 0.15, or the metal complex has a $\lambda_{max}$ in the range of 500-590 nm and a VDR value of equal or less than 0.15, or the metal complex has a $\lambda_{max}$ in the range of 590-700 nm and a VDR value of equal or less than 0.10.

11. The OLED of claim 1, wherein the first host comprises a boryl moiety that is a three-valence boron atom.

12. The OLED of claim 11, wherein the boron atom is in one of the rings' backbone, in two of the rings' backbones, or in three of the rings' backbones.

13. The OLED of claim 1, wherein the first host is at least 10% deuterated.

14. The OLED of claim 1, wherein the OLED comprises a second host that is not deuterated, partially deuterated, or fully deuterated.

15. The OLED in claim 1, wherein the metal complex is a platinum complex and the first host comprises a moiety selected from the group consisting of triazine, pyridine, pyrimidine, pyrazine, pyridazine, dibenzofuran, dibenzothiophene, aza-dibenzofuran, aza-dibenzothiophene, triphenylene, aza-triphenylene, carbazole, indolocarbazole, aza-carbazole, aza-indolocarbazole, silyl, and boryl.

16. The OLED of claim 1, wherein the metal complex comprises at least one moiety selected from the group consisting of a partially deuterated alkyl group, partially deuterated cycloalkyl group, a partially deuterated aryl or heteroaryl group, a fully deuterated alkyl group, and fully deuterated aryl or heteroaryl group.

17. The OLED of claim 1, wherein the first host is selected from the group consisting of:

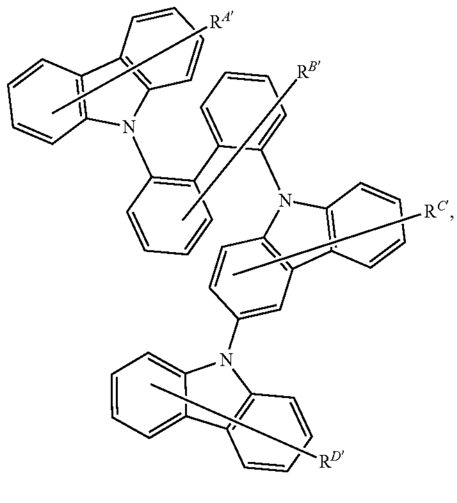
,

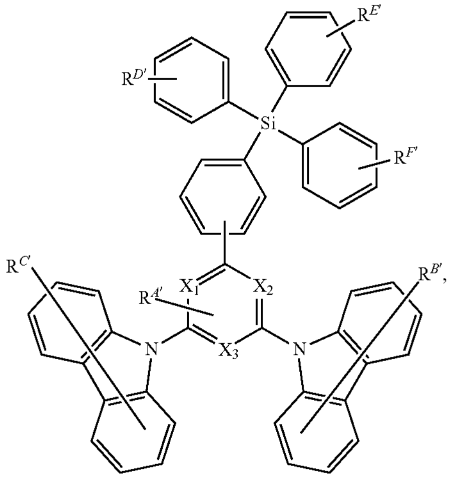
,

-continued
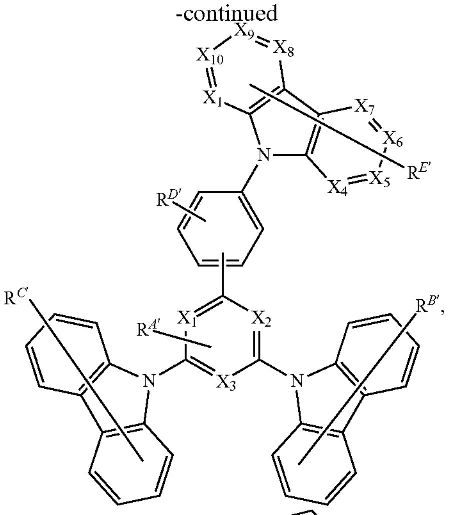
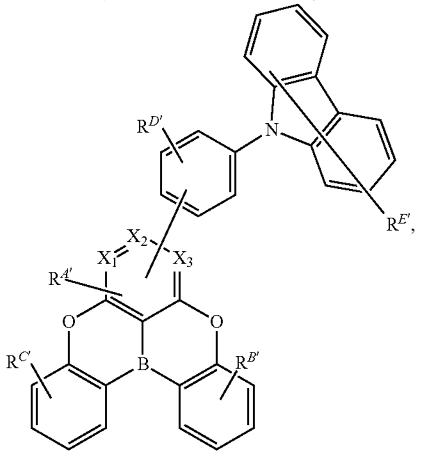
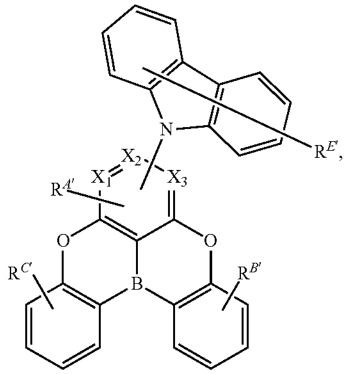
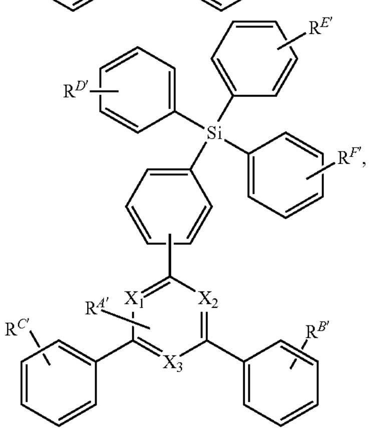
-continued
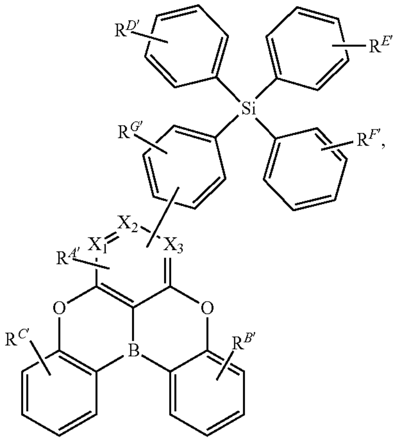
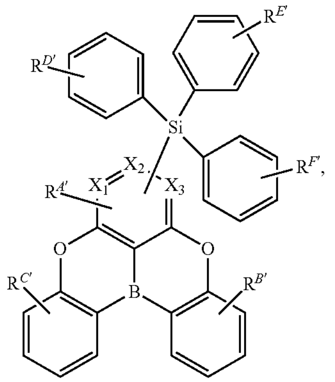
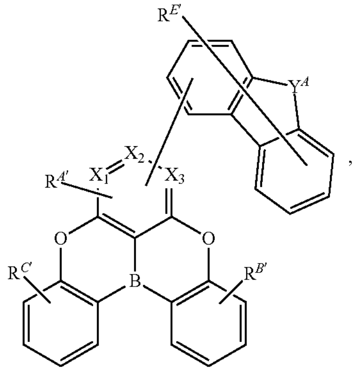
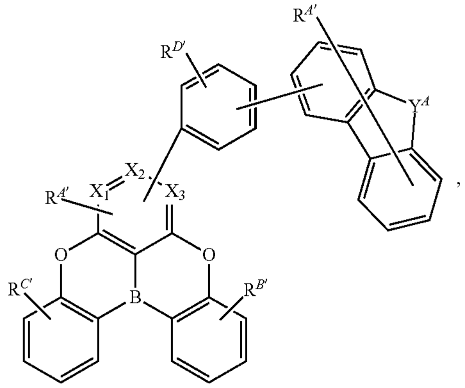

-continued
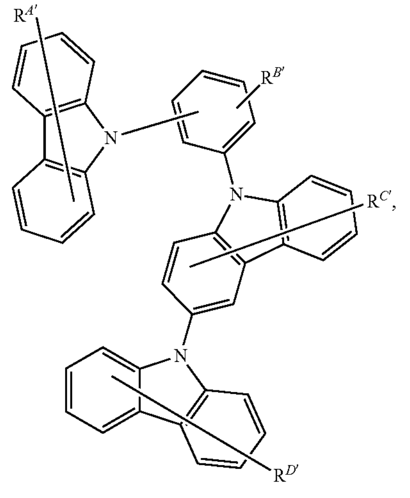
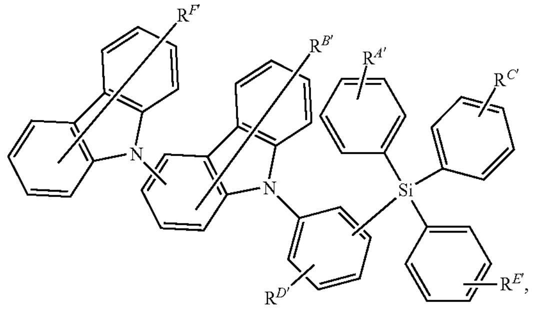
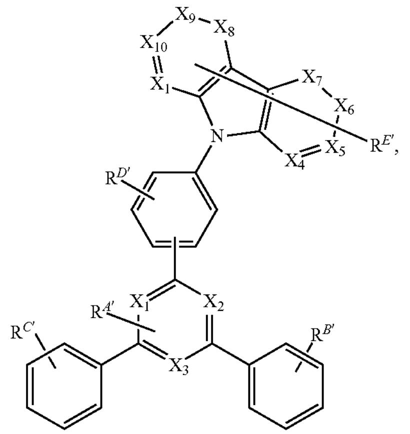
-continued
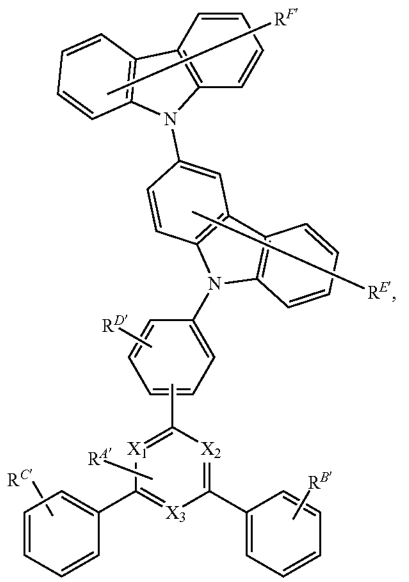
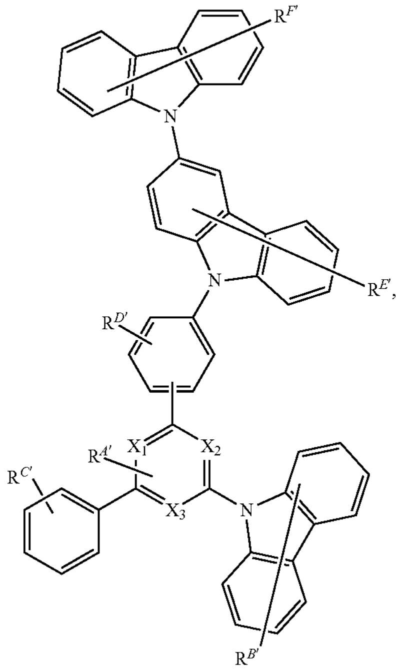
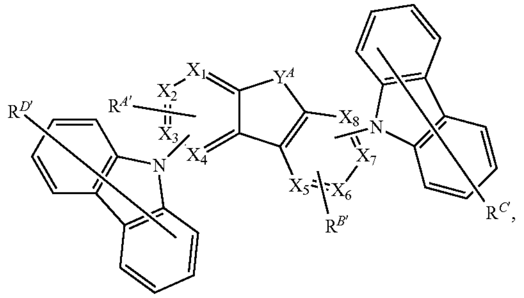

-continued
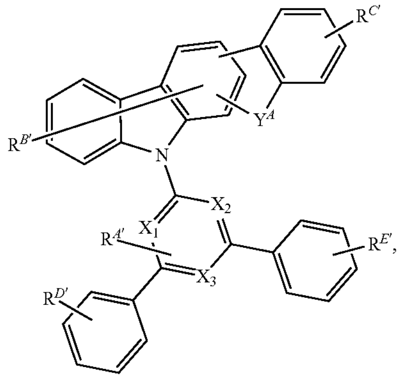
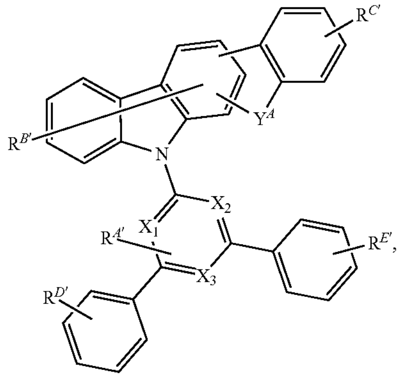
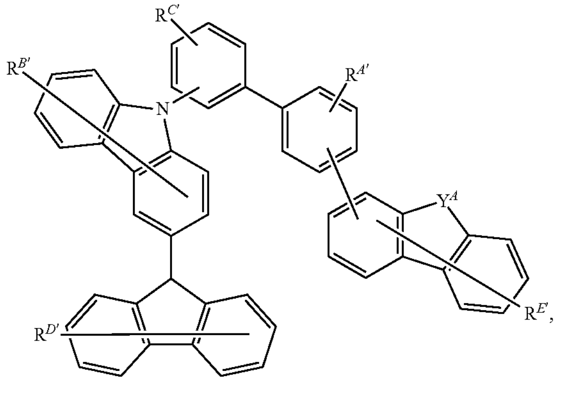
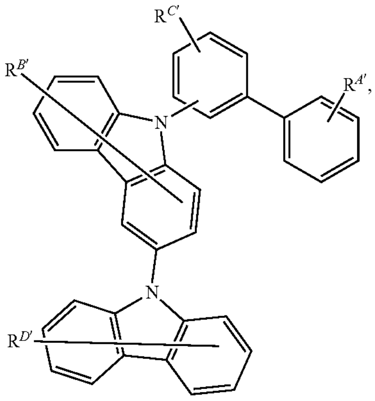
-continued
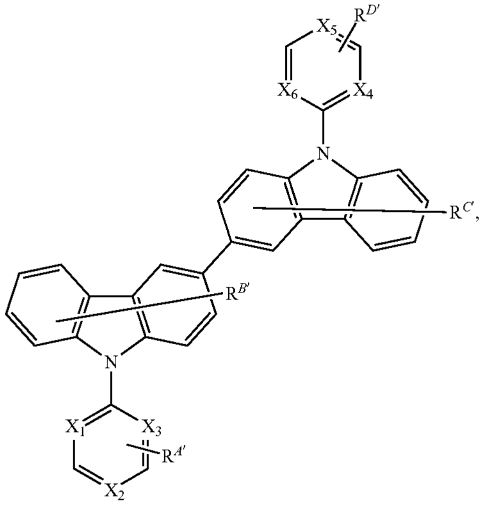
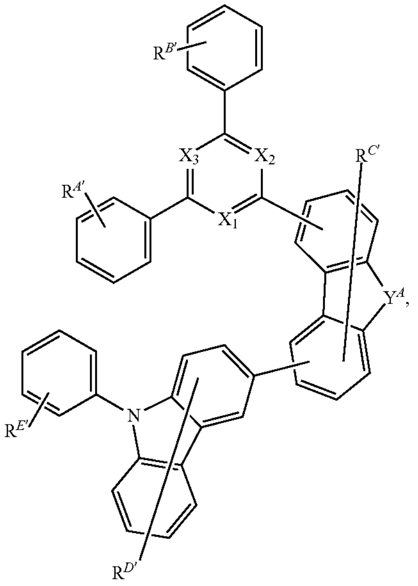
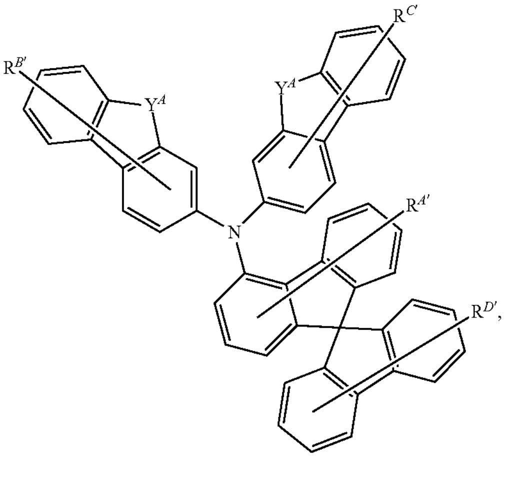

-continued
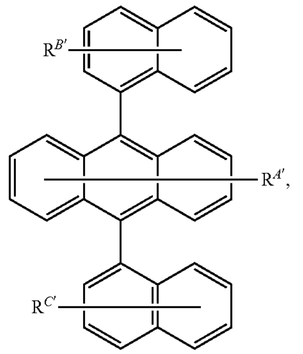
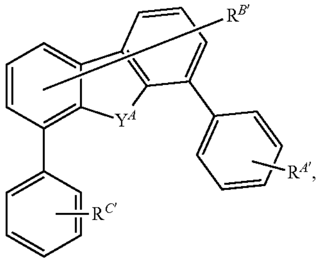
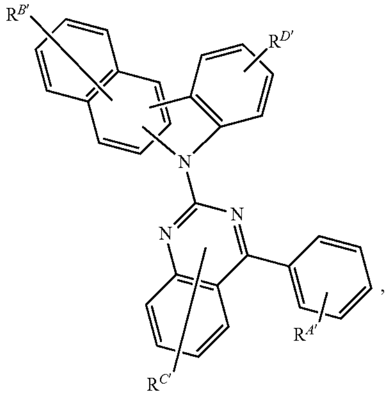
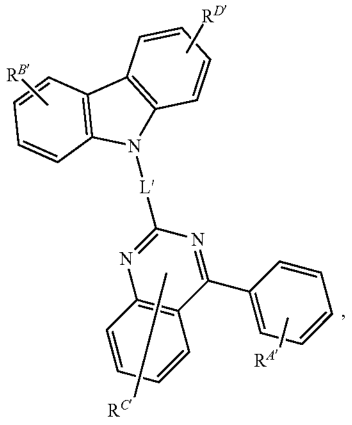
-continued
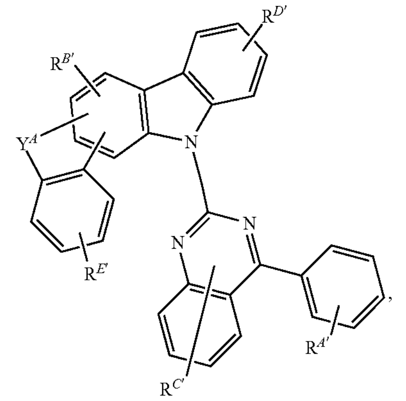
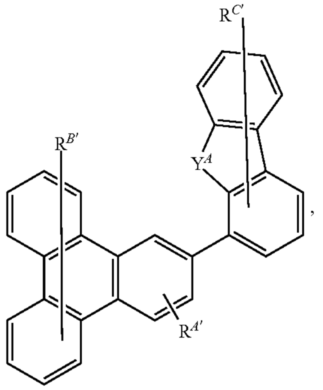
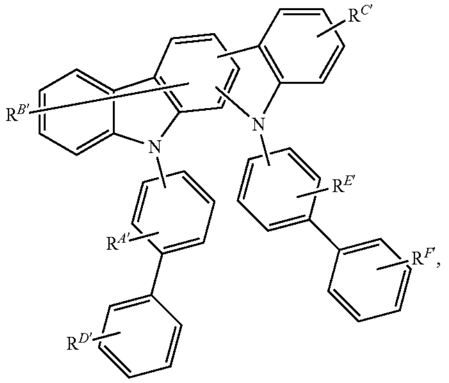
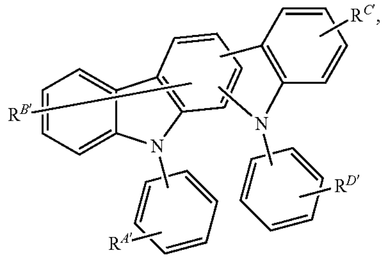

-continued
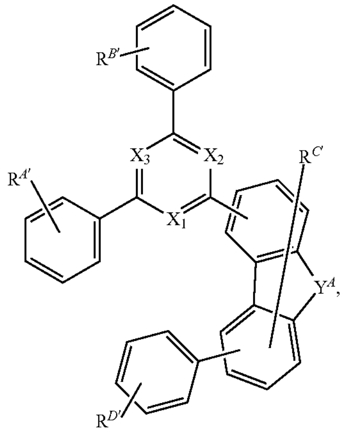
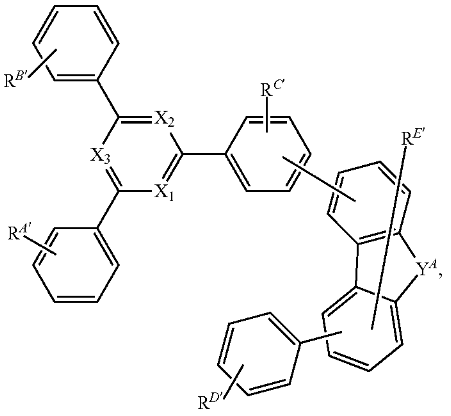
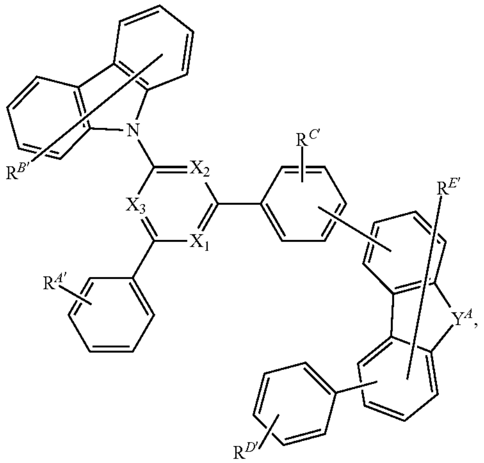
-continued
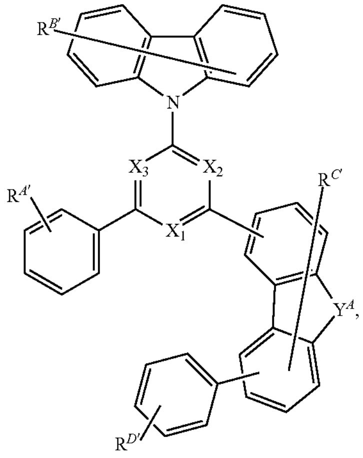
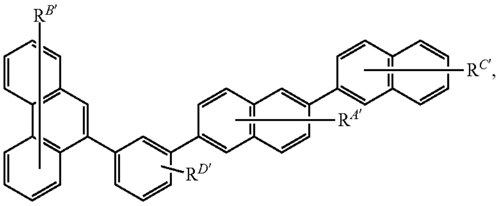
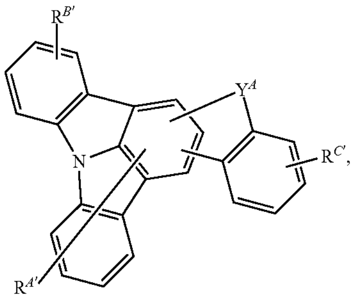
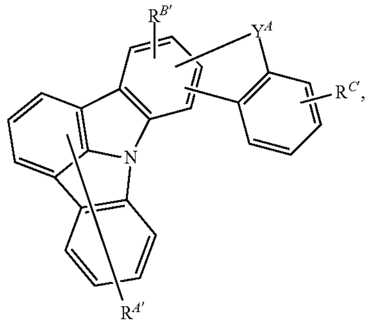
and
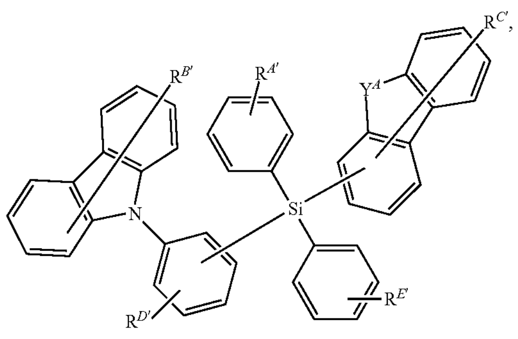

wherein:

each of $X_1$ to $X_{11}$ is independently C or N;

L' is a direct bond or is an organic linker;

each $Y^A$ is independently absent or, when present, is selected from the group consisting of O, S, Se, CRR', SiRR', NR, BR, BRR';

each of $R^{A'}$, $R^{B'}$, $R^{C'}$, $R^{D'}$, $R^{E'}$, $R^{F'}$, and $R^{G'}$ independently represents mono-, up to the maximum substitutions, or no substitutions;

each of R, R', $R^{A'}$, $R^{B'}$, $R^{C'}$, $R^{D'}$, $R^{E'}$, $R^{F'}$, and $R^{G'}$ is independently a hydrogen or a substituent selected from the group consisting of the General Substituents defined herein; and at least one R, R', $R^{A'}$, $R^{B'}$, $R^{C'}$, $R^{D'}$, $R^{E'}$, $R^{F'}$, or $R^{G'}$ comprises deuterium.

18. The OLED of claim 1, wherein the metal complex has a structure $M(L_A)_p(L_B)_q(L_C)_r$, wherein p is 1, 2, or 3; q is 0, 1, or 2; r is 0, 1, or 2; and p+q+r is the oxidation state of the metal M; and each of ligand $L_B$ and ligand $L_C$ is independently selected from the group consisting of:

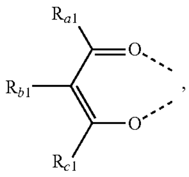

,

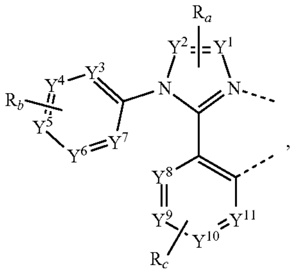

,

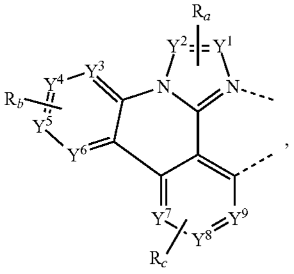

,

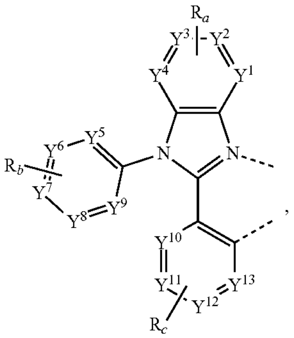

,

-continued

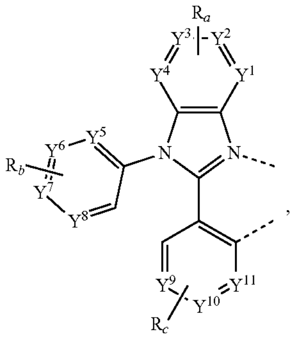

,

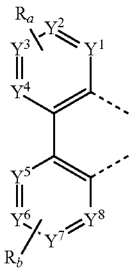

,

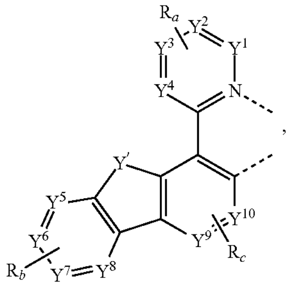

,

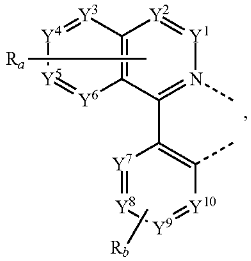

,

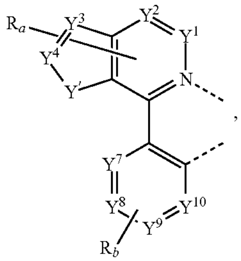

,

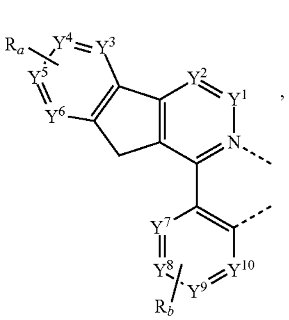

,

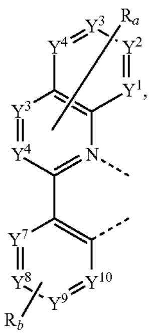

,

-continued

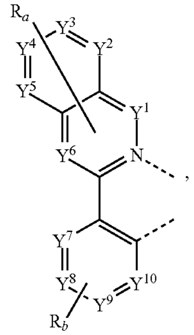,

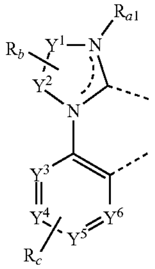,

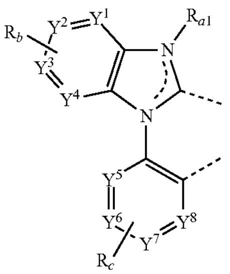,

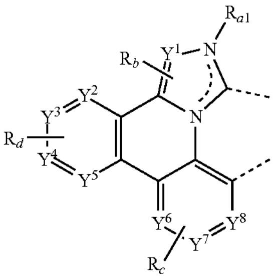,

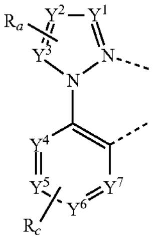,

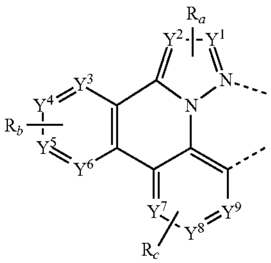,

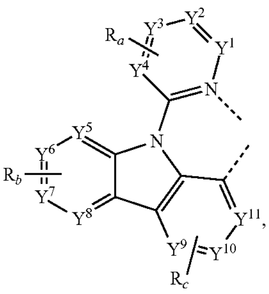

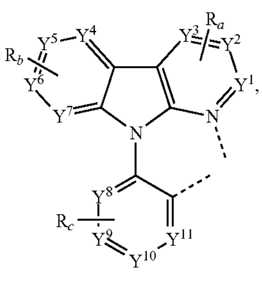

-continued

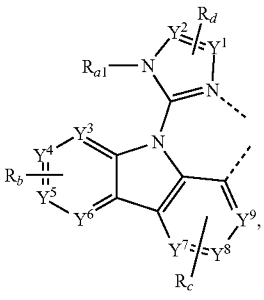

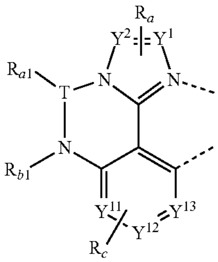,

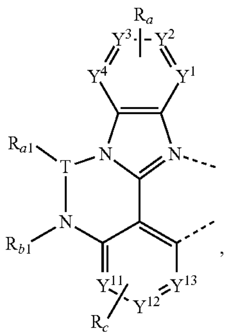,

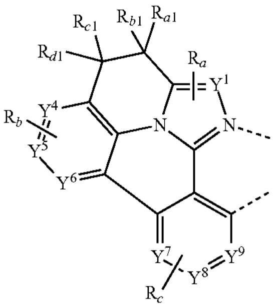, wherein:

T is selected from the group consisting of B, Al, Ga, and In;

each of $Y^1$ to $Y^{13}$ is independently selected from the group consisting of carbon and nitrogen;

Y' is selected from the group consisting of $BR_e$, $BR_eR_f$, $NR_e$, $PR_e$, $P(O)R_e$, O, S, Se, C=O, C=S, C=Se, $C=NR_e$, $C=CR_eR_f$, S=O, $SO_2$, $CR_eR_f$, $SiR_eR_f$, and $GeR_eR_f$;

$R_e$ and $R_f$ can be fused or joined to form a ring;

each $R_a$, $R_b$, $R_c$, and $R_d$ independently represents zero, mono, or up to a maximum allowed number of substitutions to its associated ring;

each of $R_{a1}$, $R_{b1}$, $R_{c1}$, $R_{d1}$, $R_a$, $R_b$, $R_c$, $R_d$, $R_e$ and $R_f$ is independently a hydrogen or a substituent selected from the group consisting of deuterium, halide, alkyl, cycloalkyl, heteroalkyl, arylalkyl, alkoxy, aryloxy, amino, silyl, boryl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and any two adjacent $R_a$, $R_b$, $R_c$, $R_d$, $R_e$ and $R_f$ can be fused or joined to form a ring or form a multidentate ligand.

19. The OLED of claim 1, wherein the OLED further comprises a second host selected from the group consisting of:
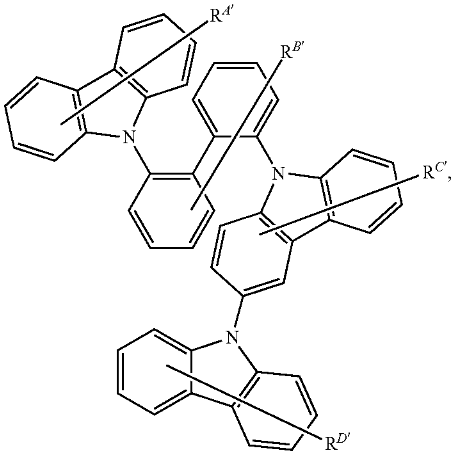
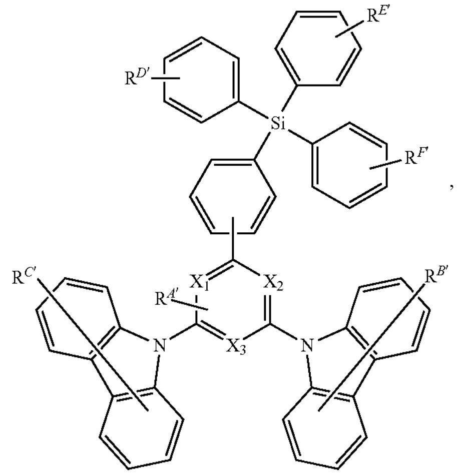
,
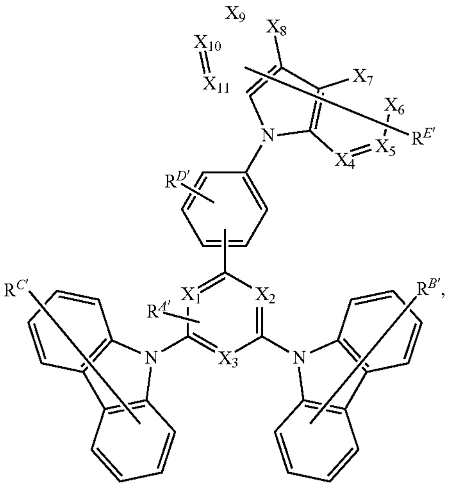
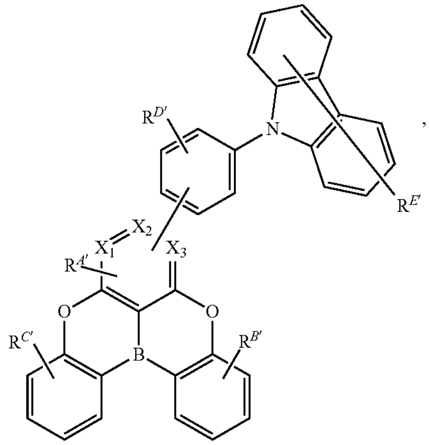
,
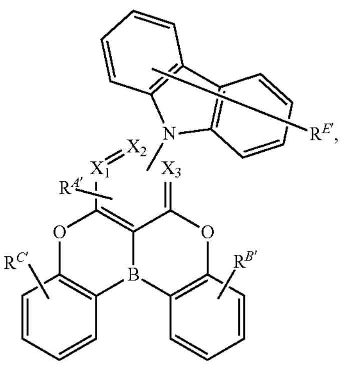
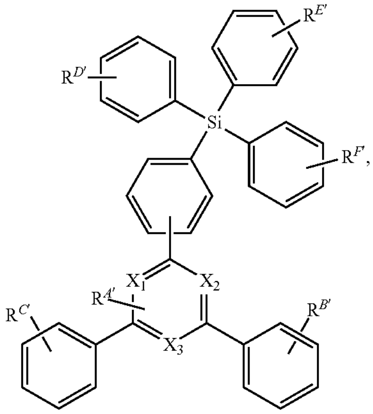
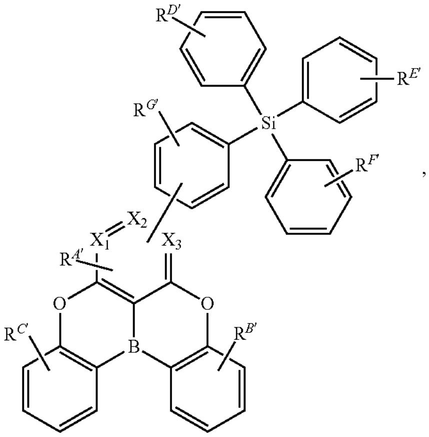
, -continued
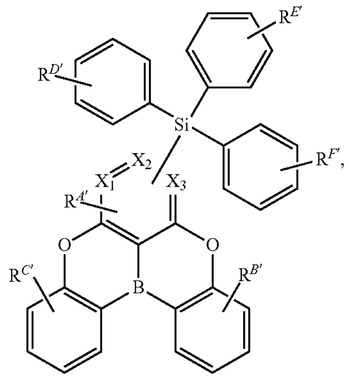
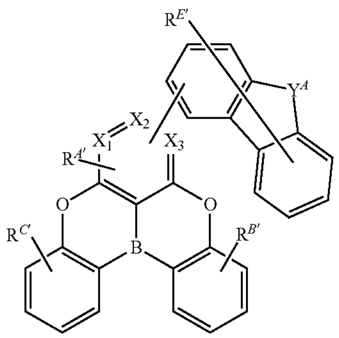
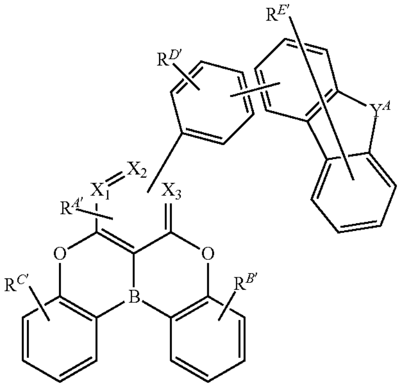
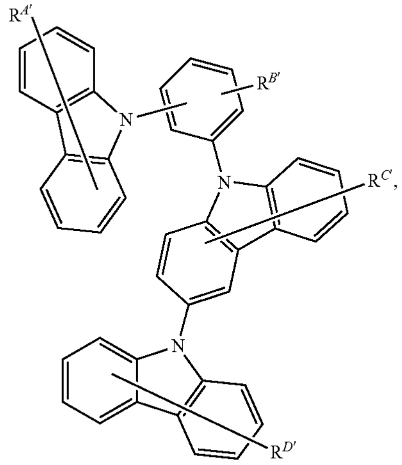
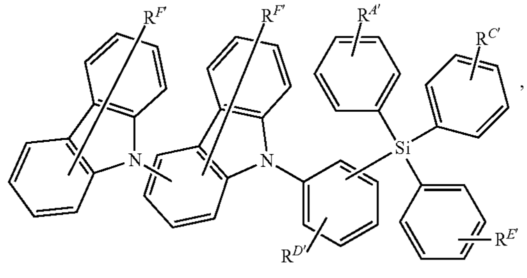
,
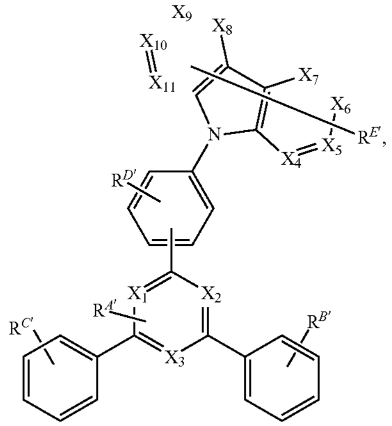
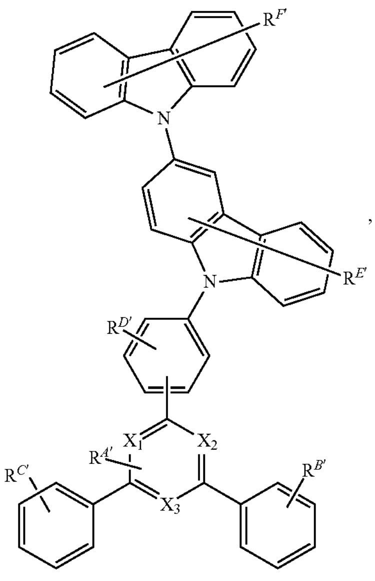
,
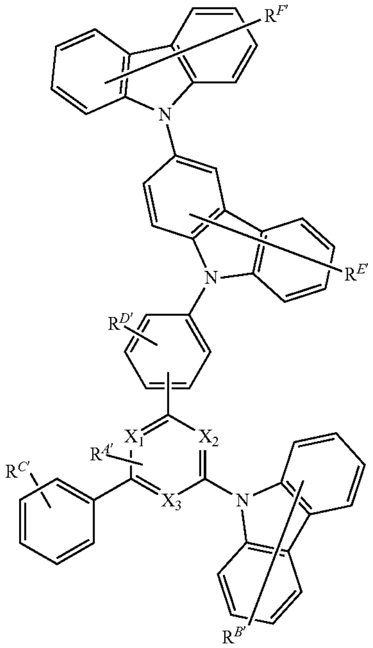
, -continued
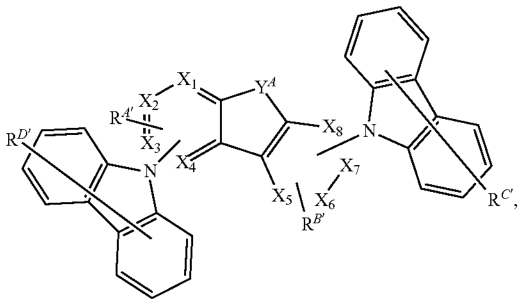
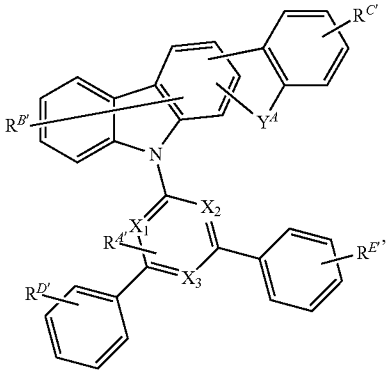
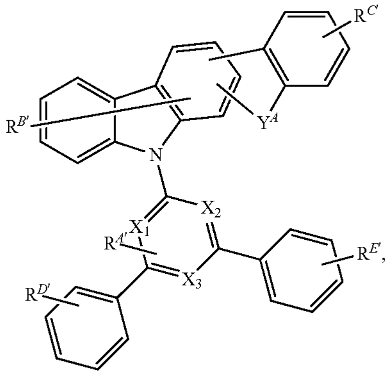
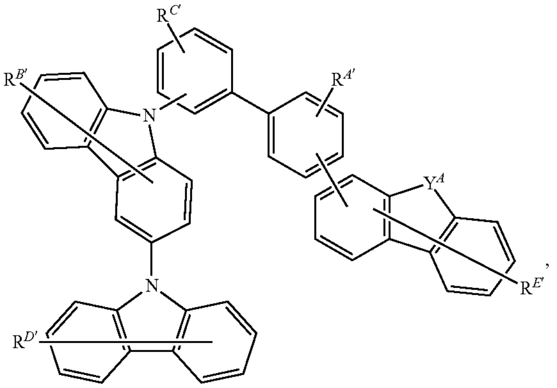
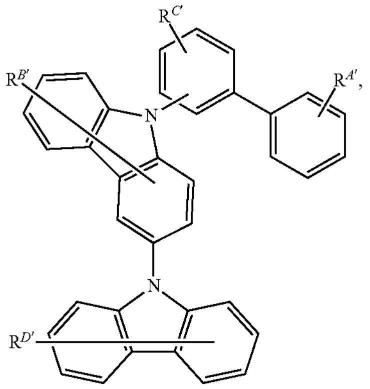
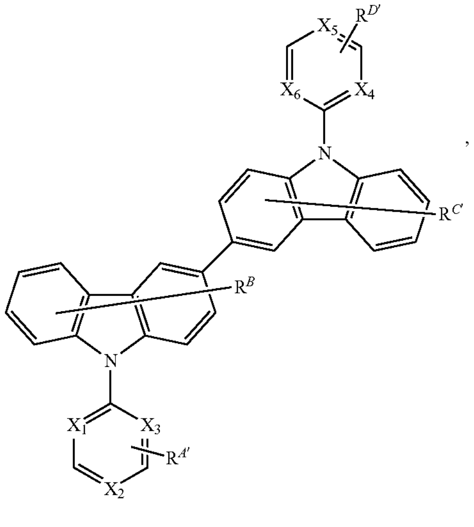

-continued
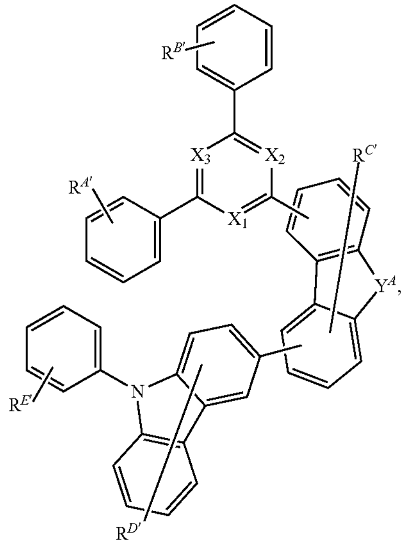,
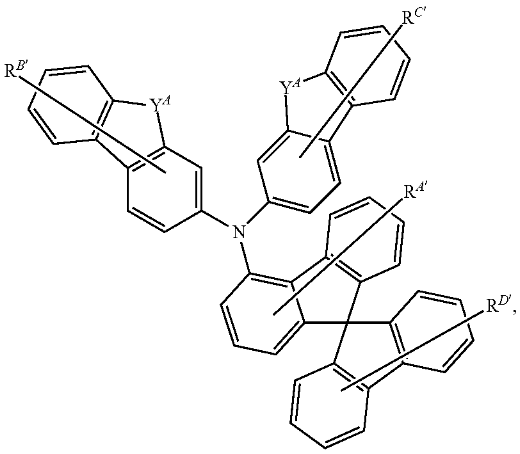,
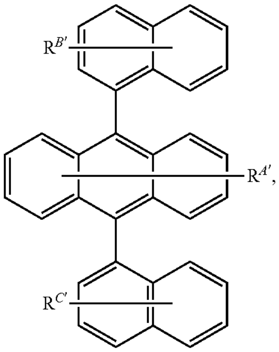,
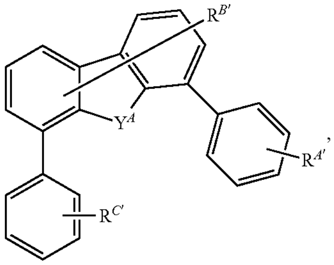,
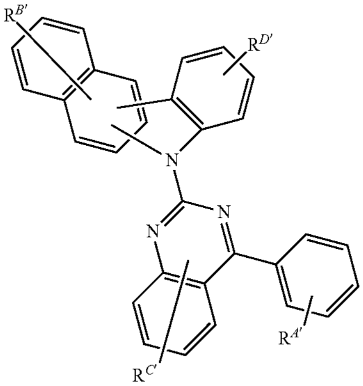,
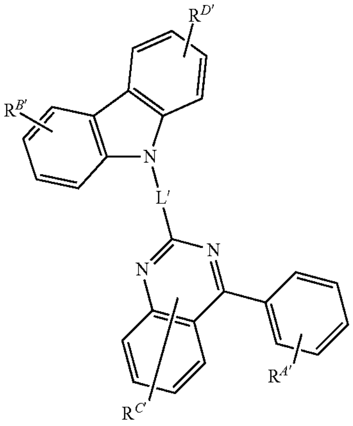,
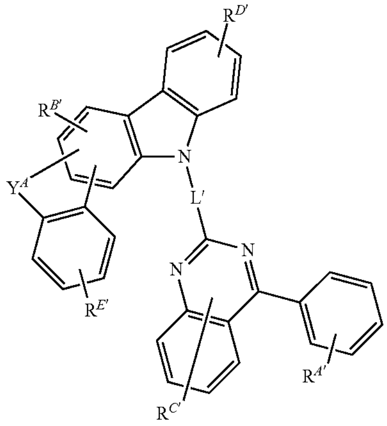,
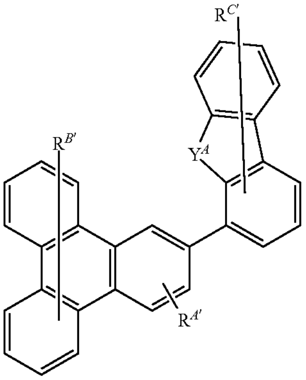,
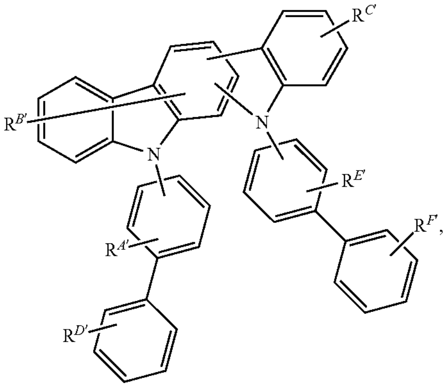,
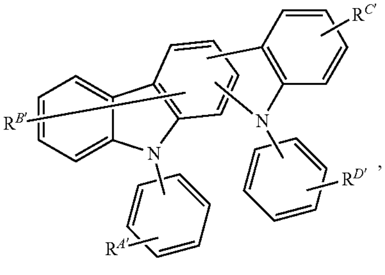, -continued
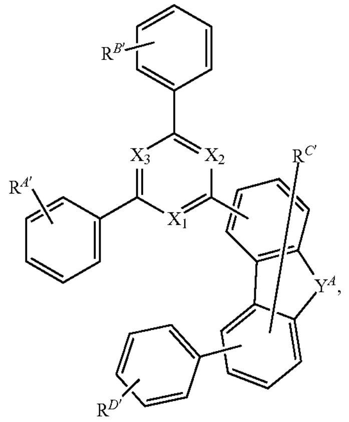
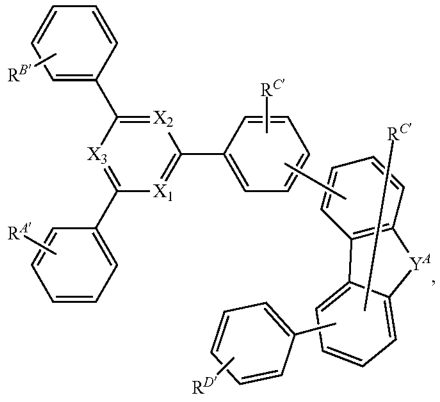
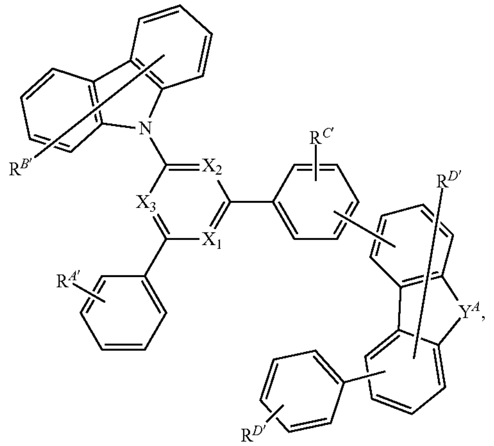
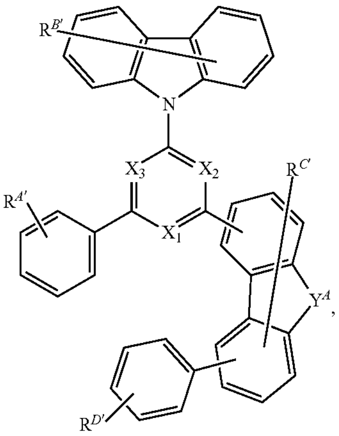
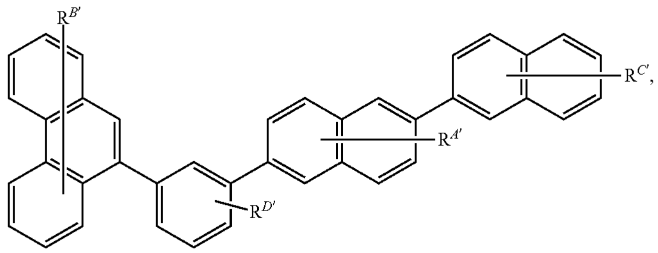
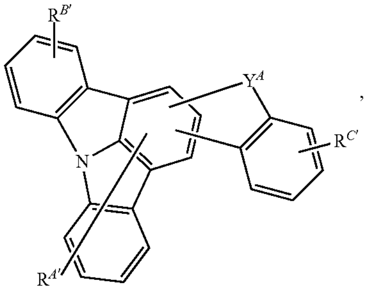
,
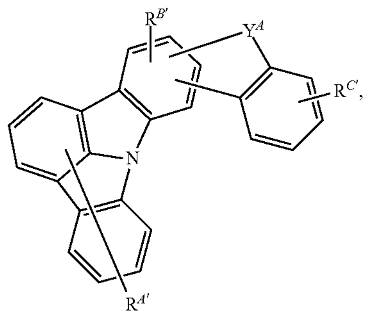
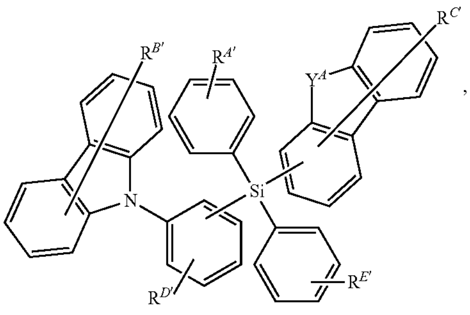
, -continued
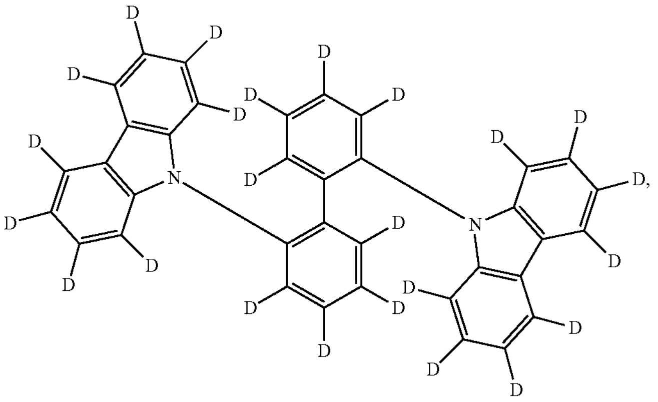
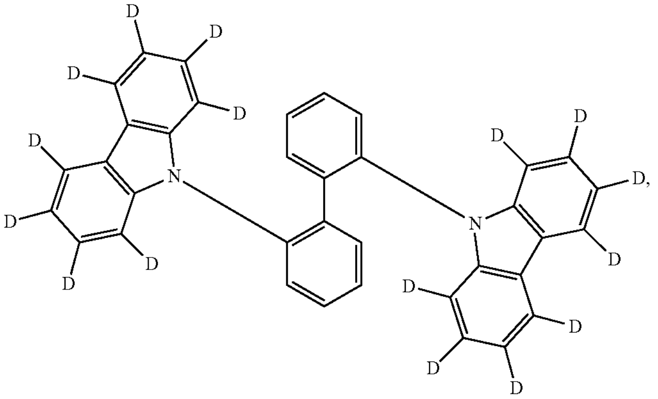
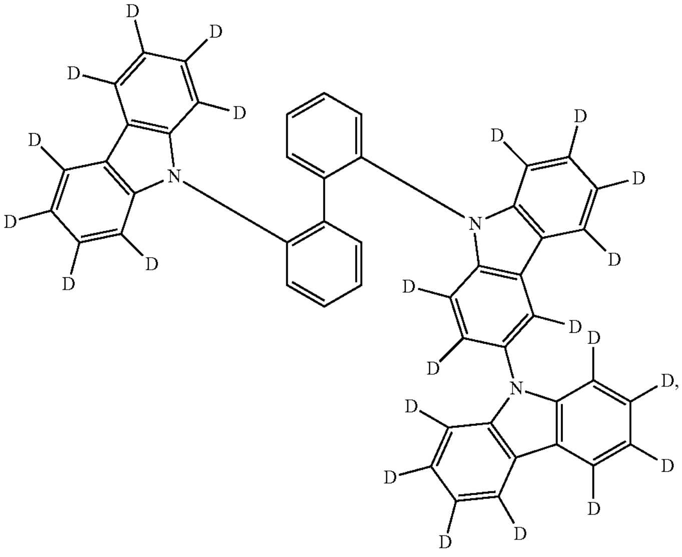

-continued
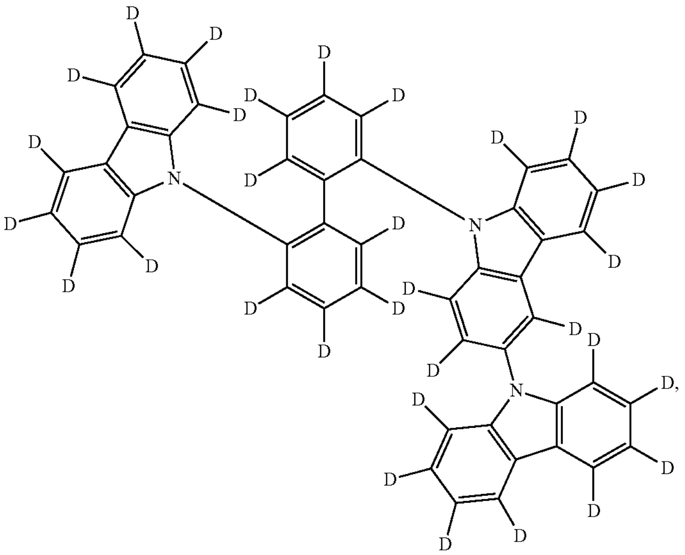
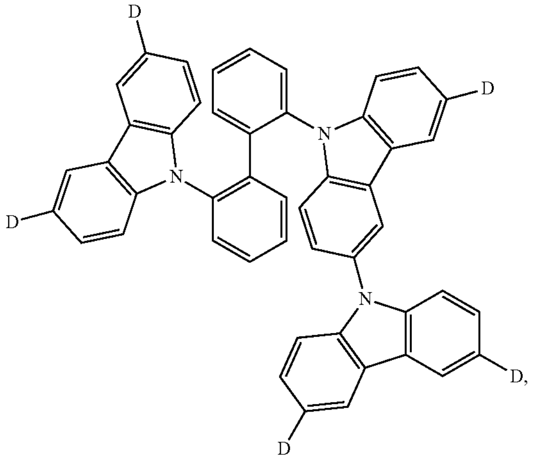
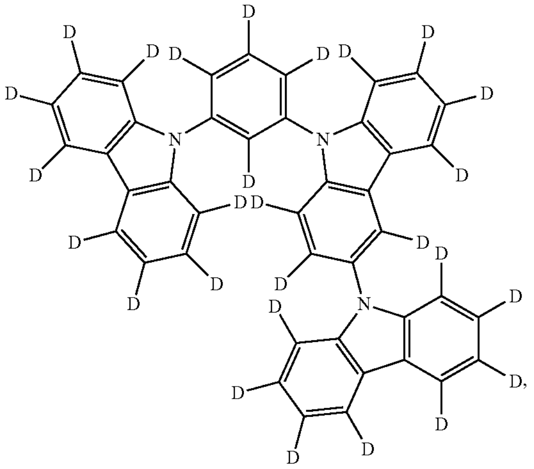
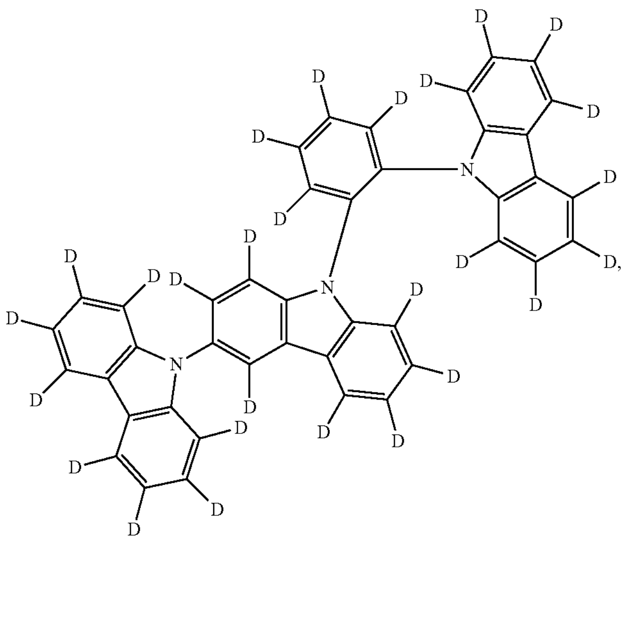

-continued
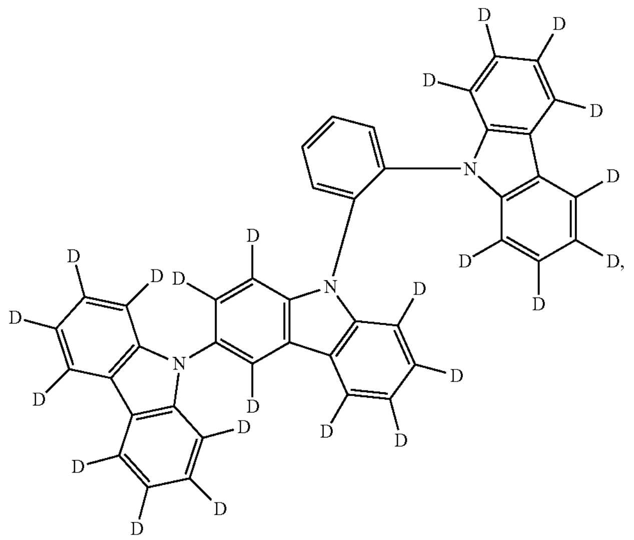
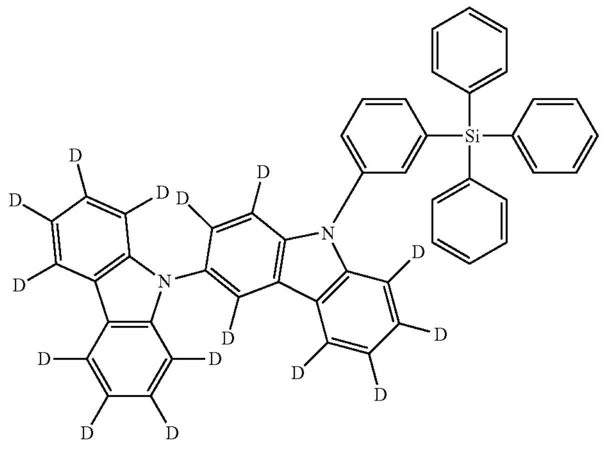
,
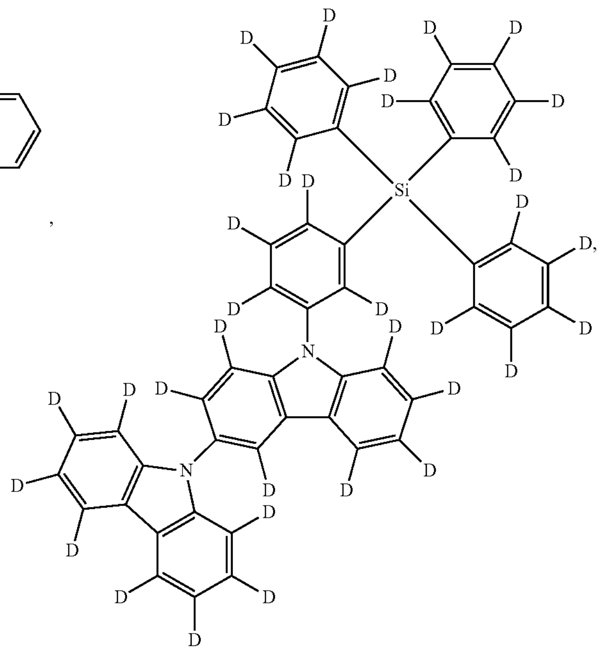

-continued
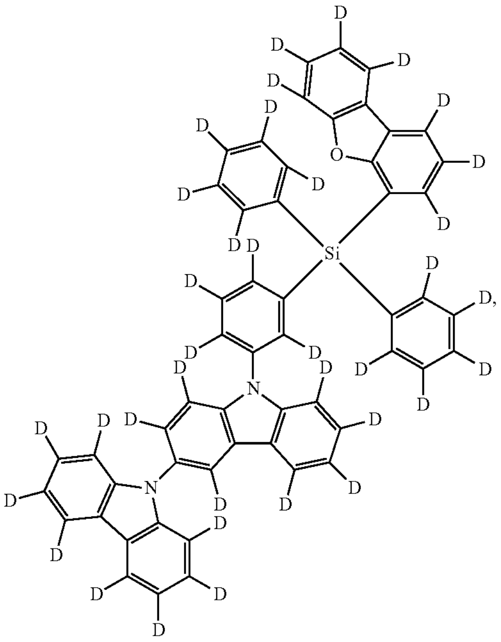,
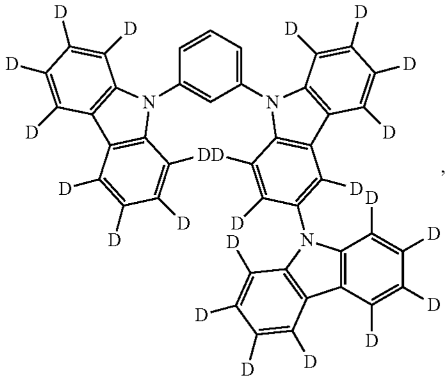,
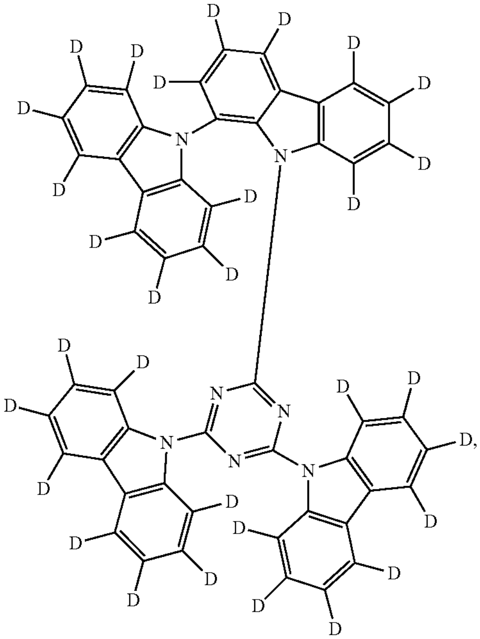,
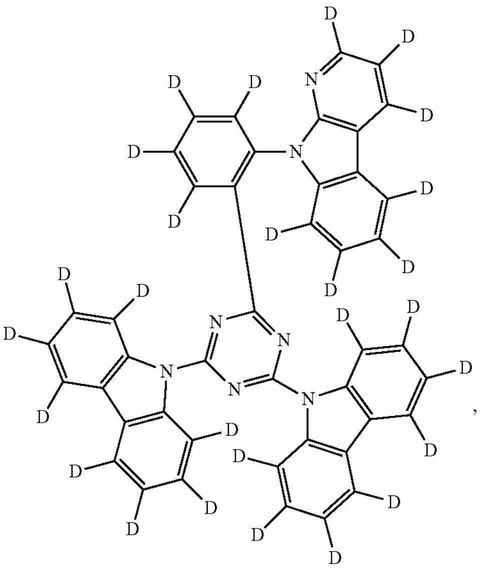,

-continued
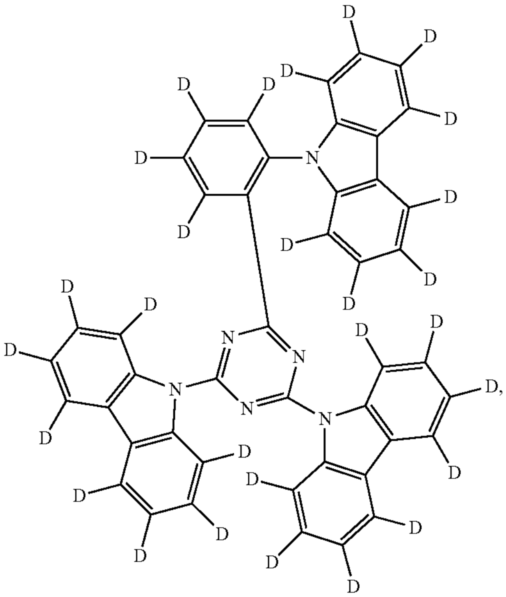,
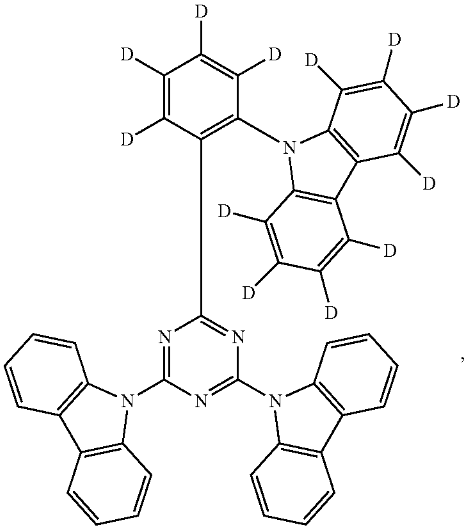,
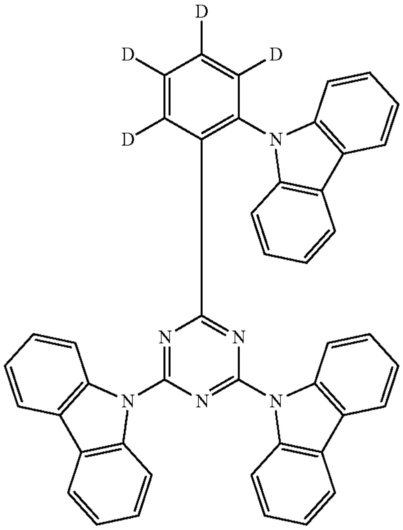,
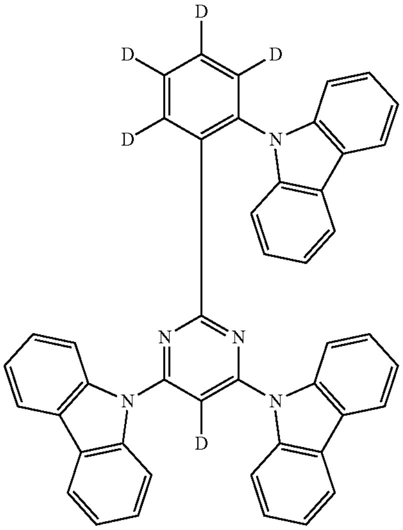,
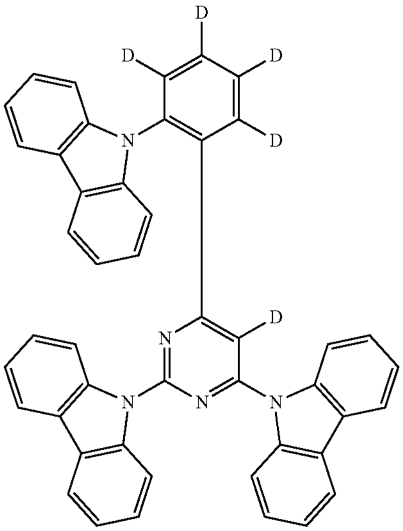,
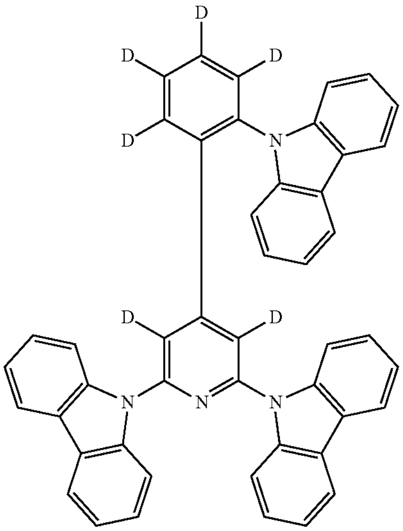, -continued
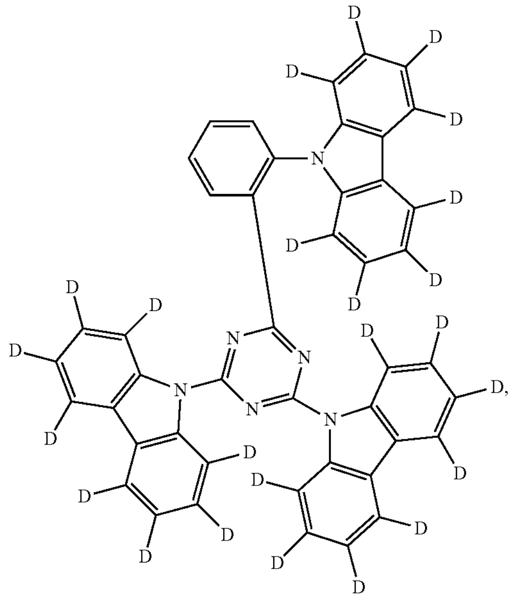
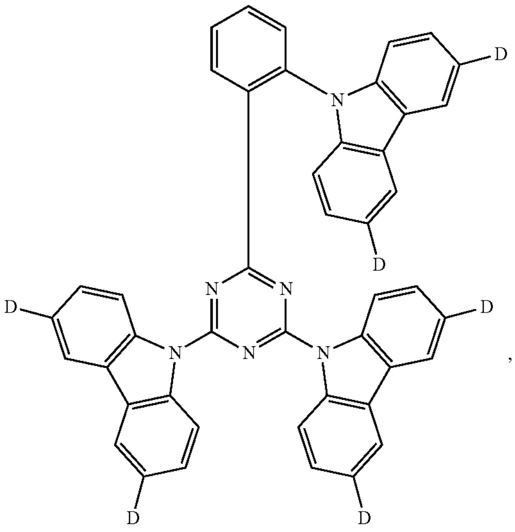
,
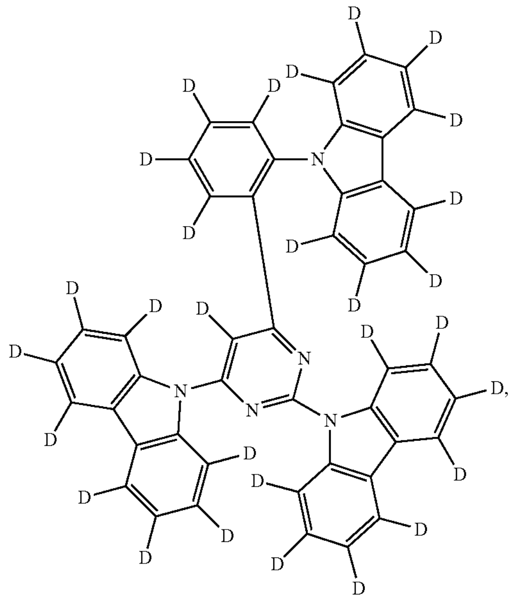
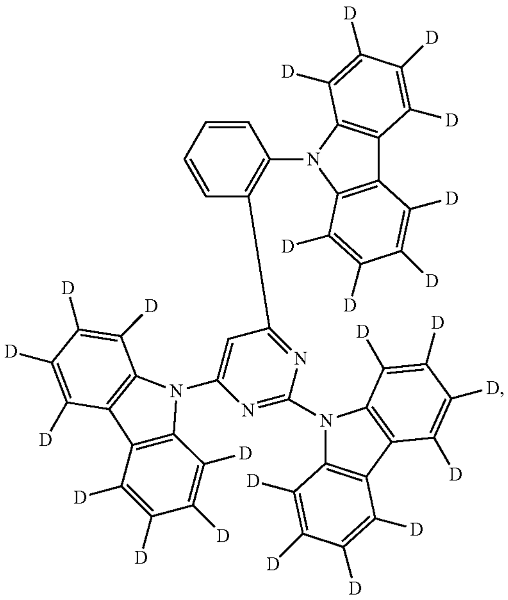
, -continued
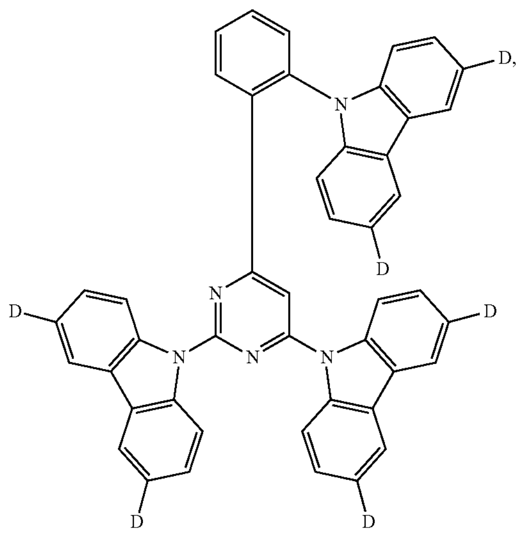
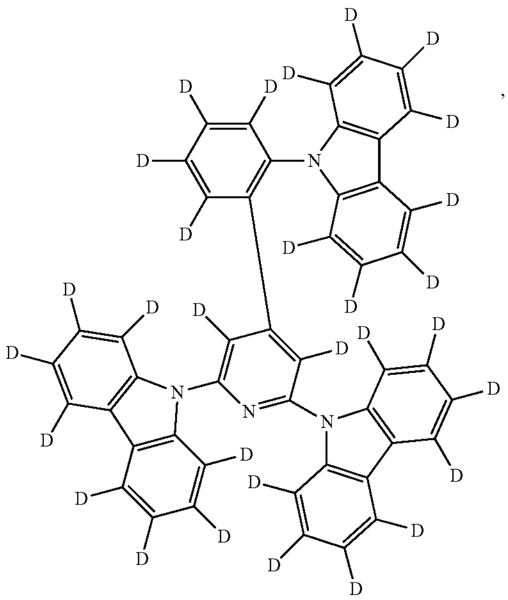
,
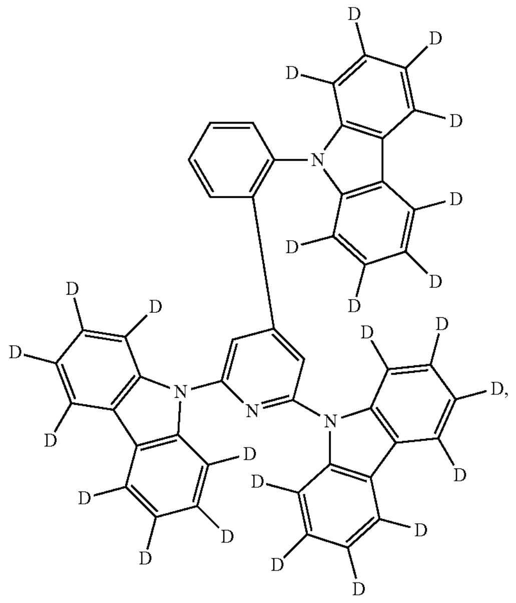
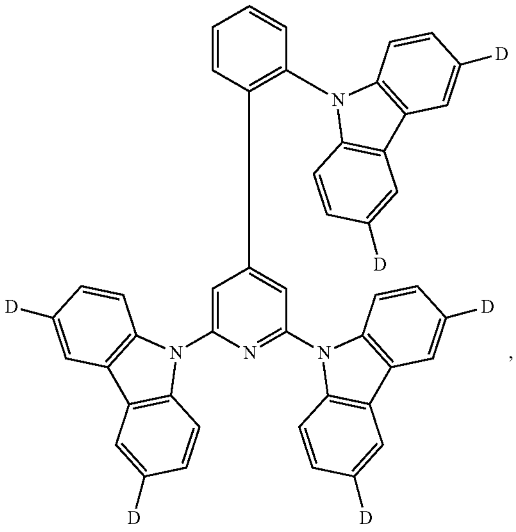
, -continued
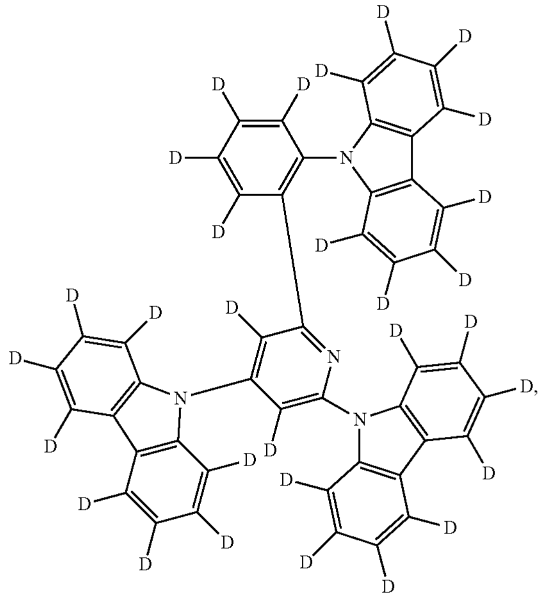
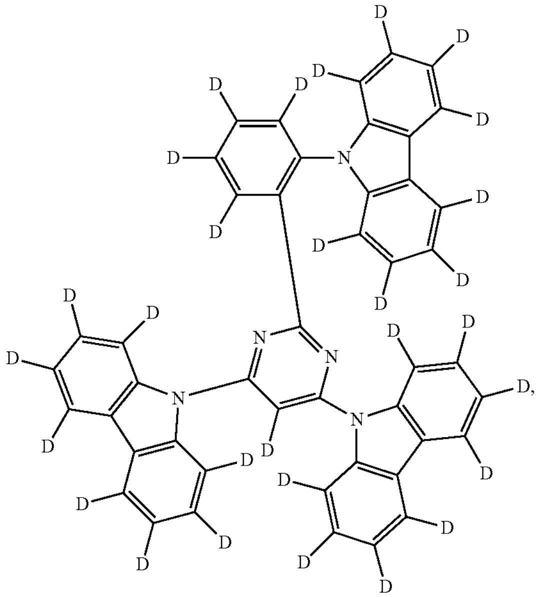
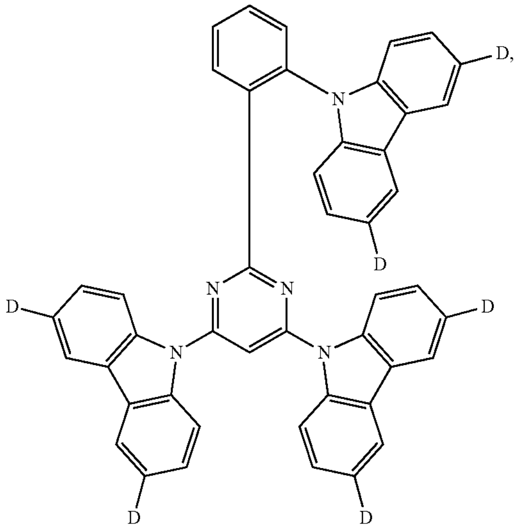
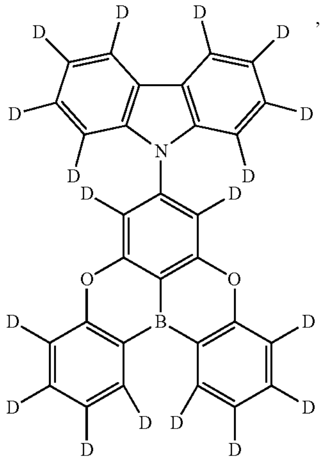
,
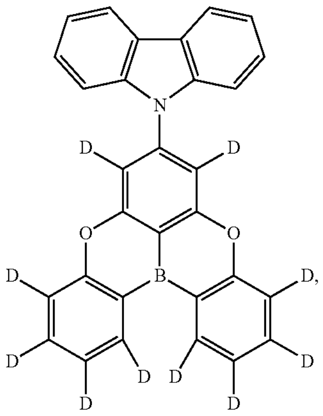
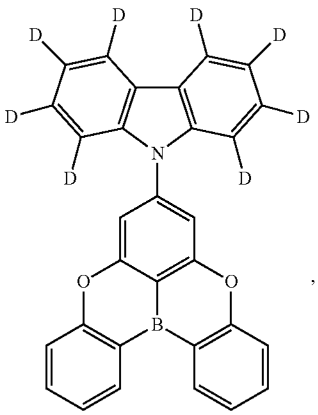
,
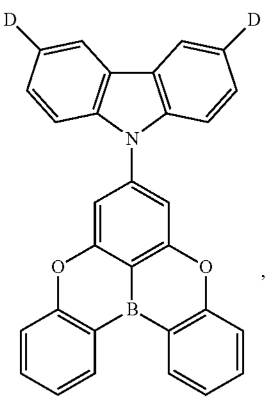
, -continued
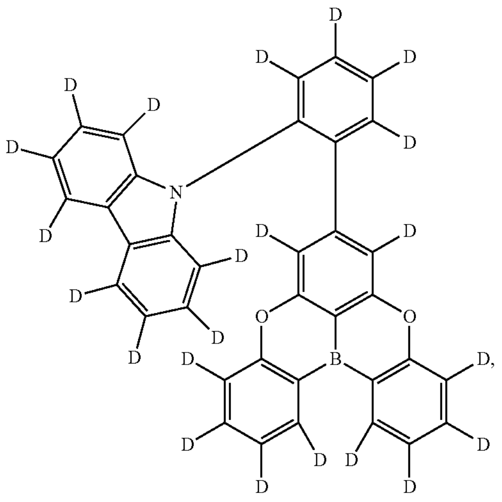
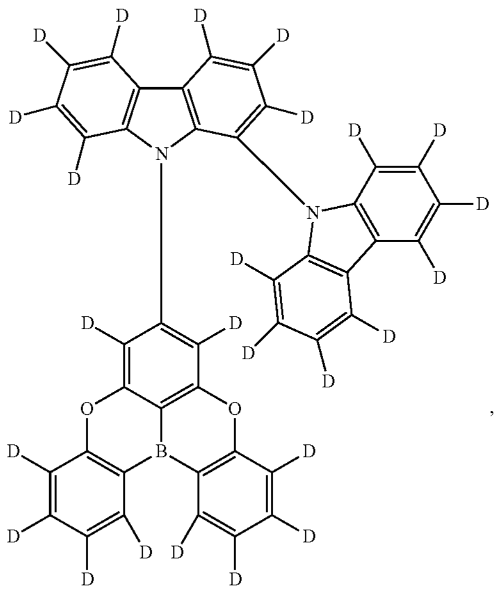
,
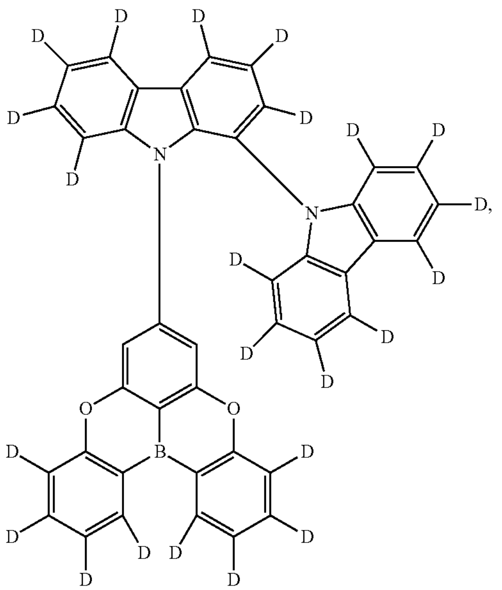
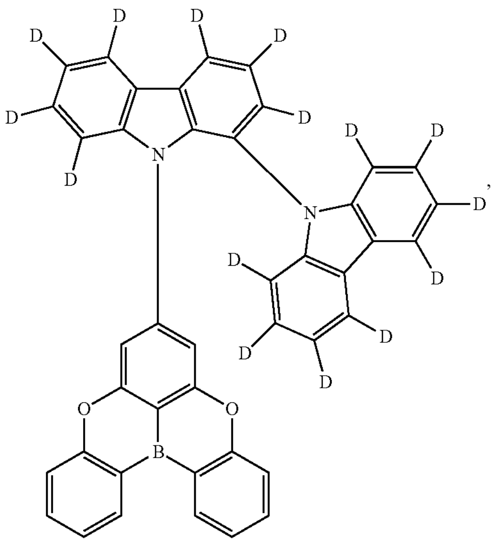
, -continued
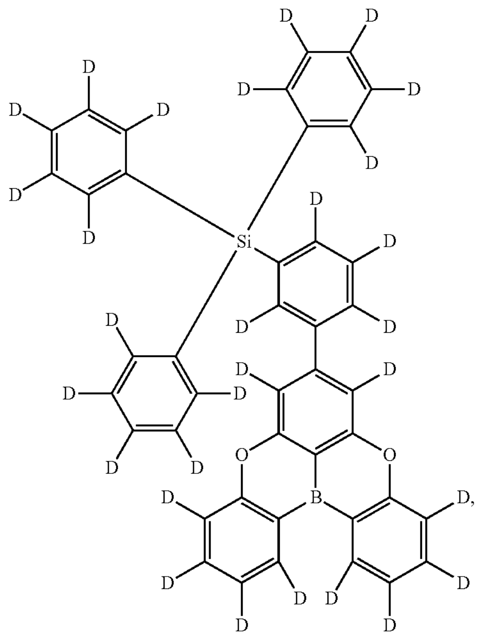
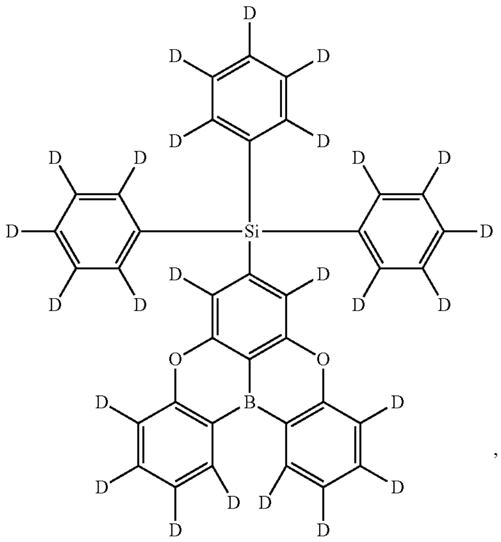
,
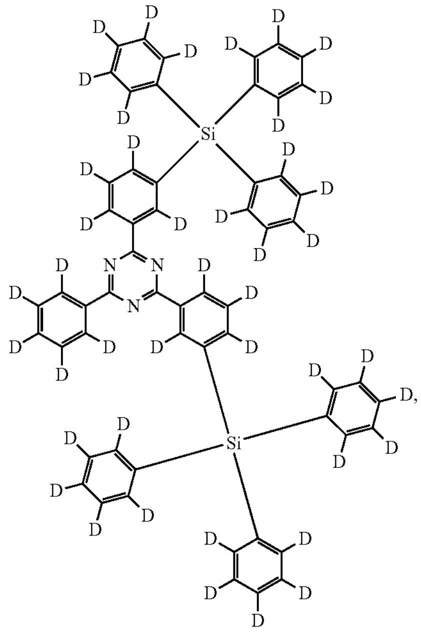
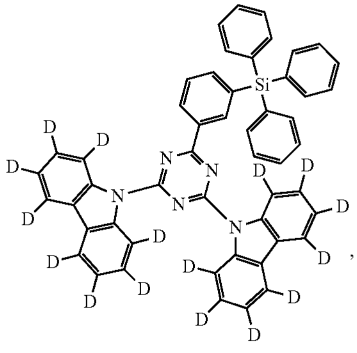
, -continued
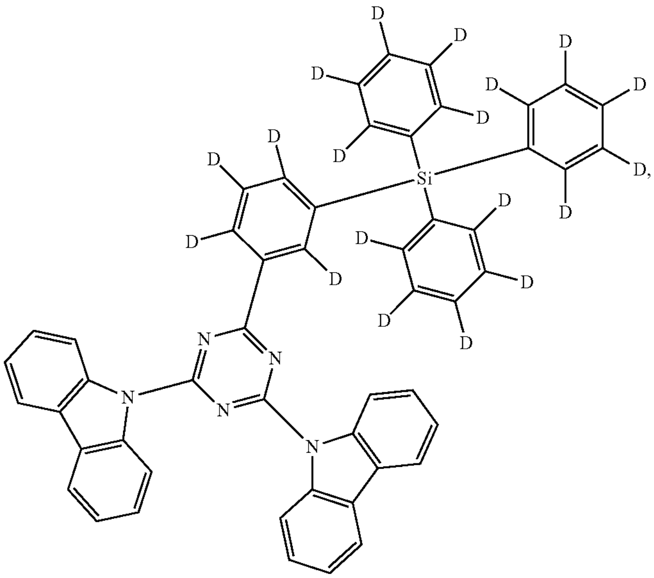
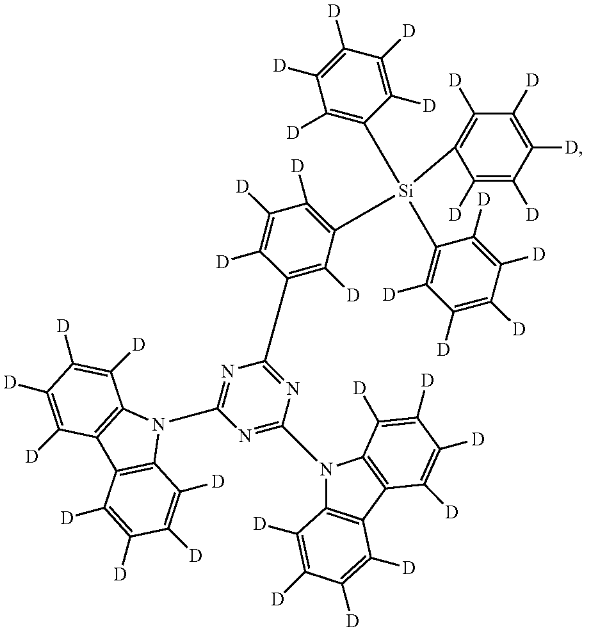
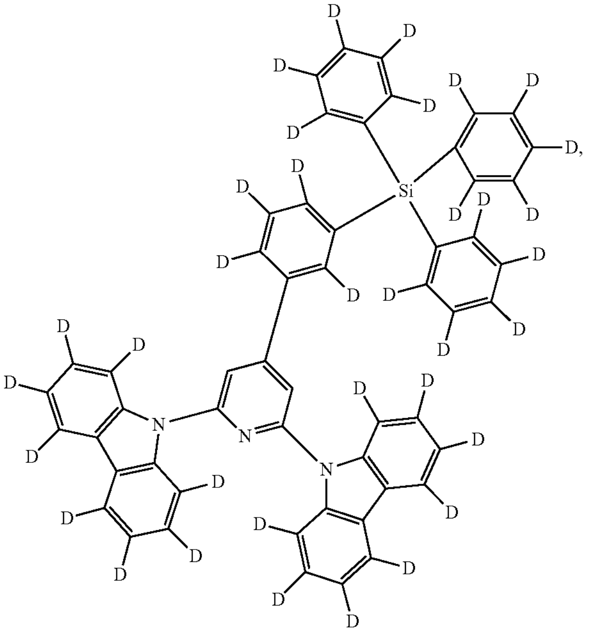

-continued
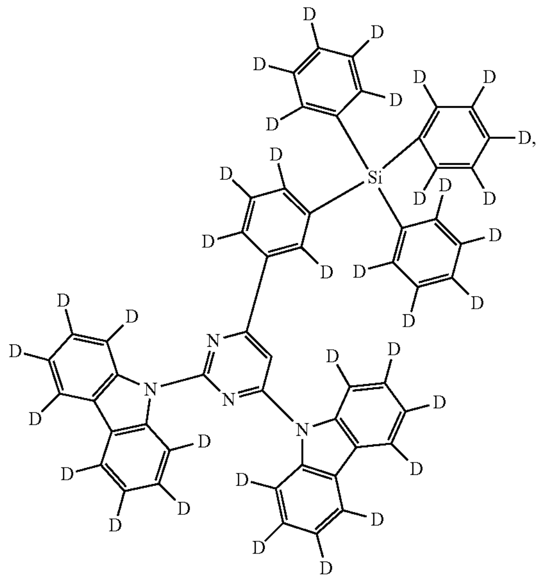,
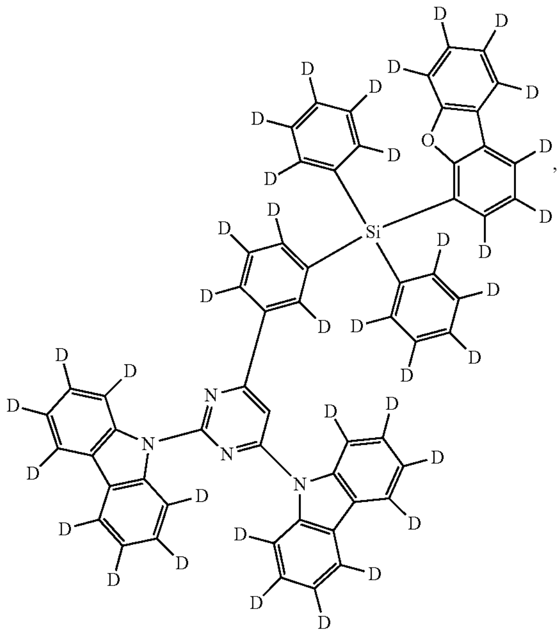,
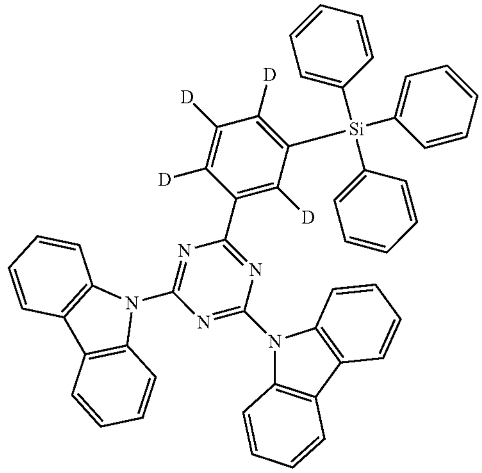,
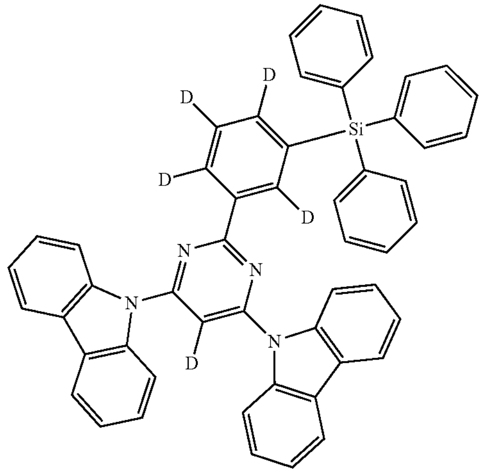,
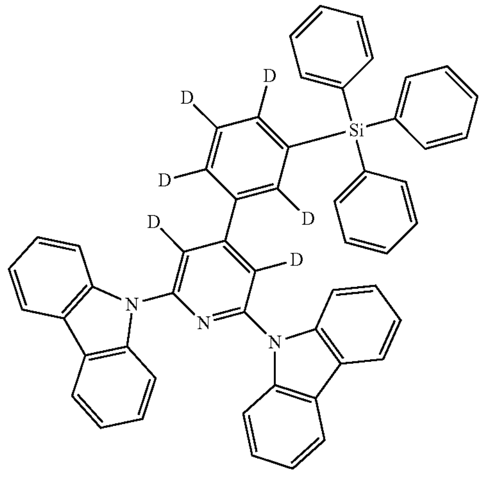,
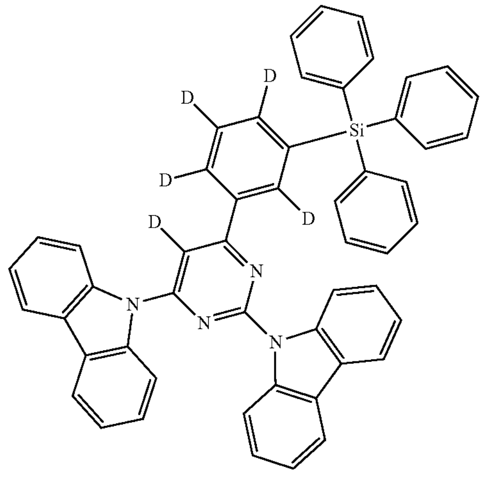, -continued
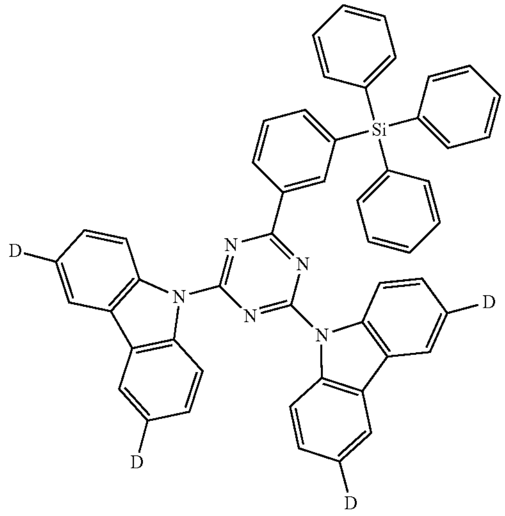
,
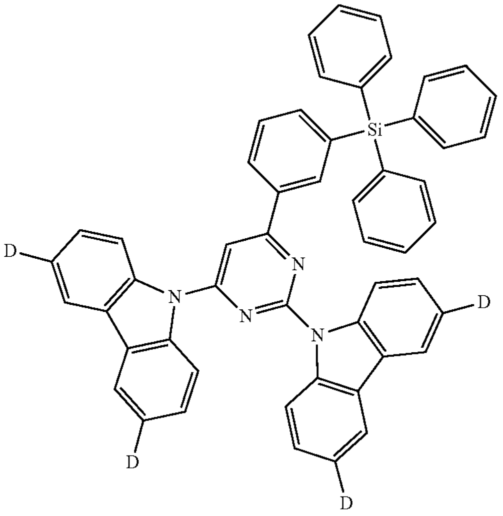
,
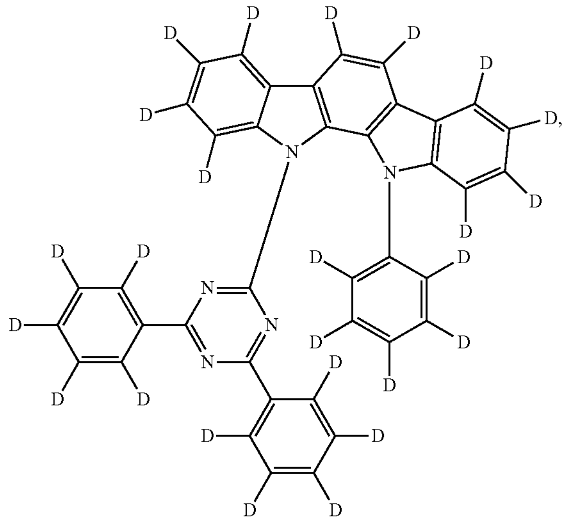
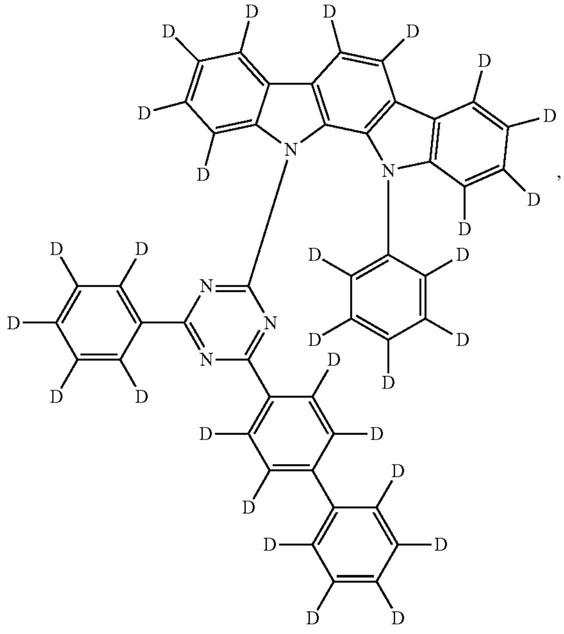
,
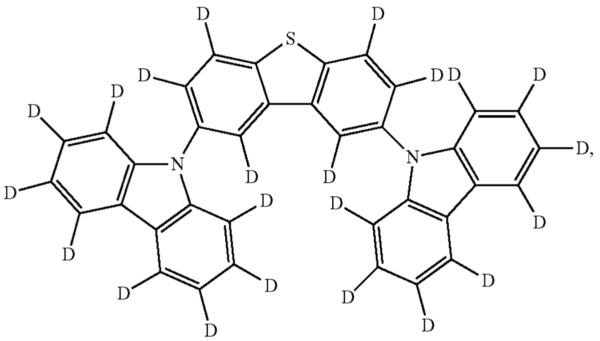
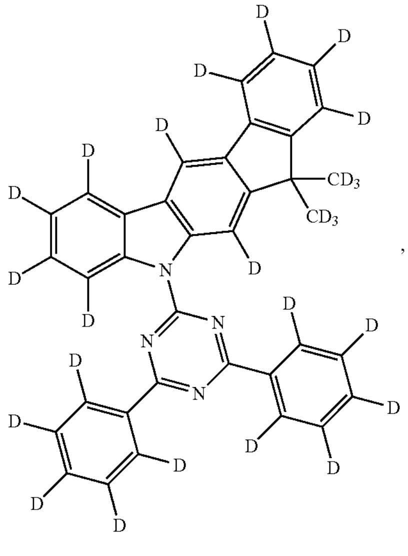
, -continued
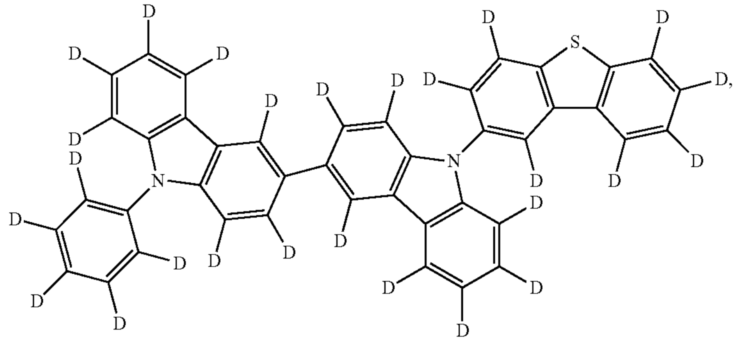
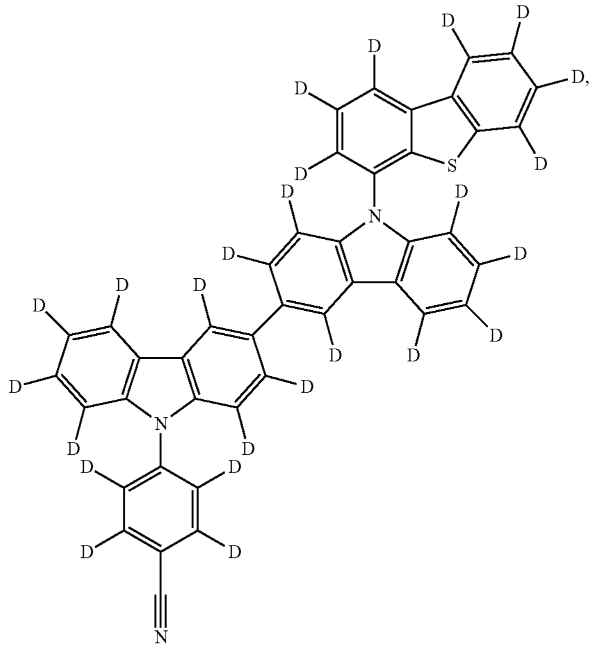
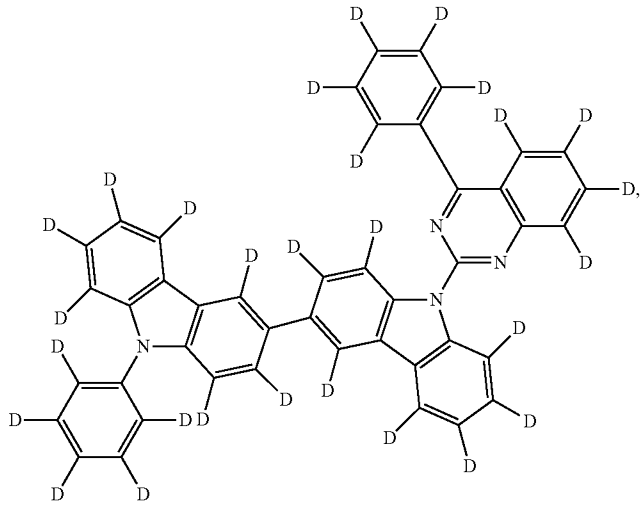

-continued
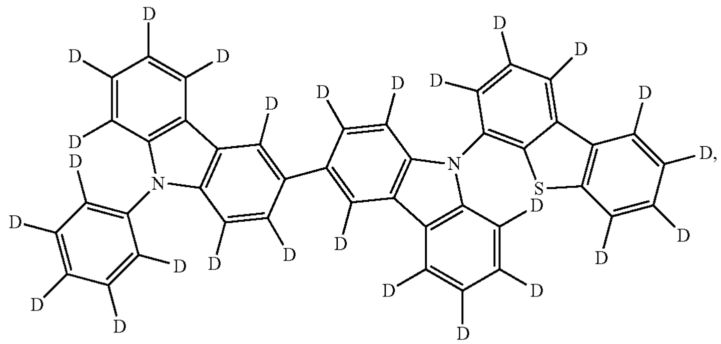
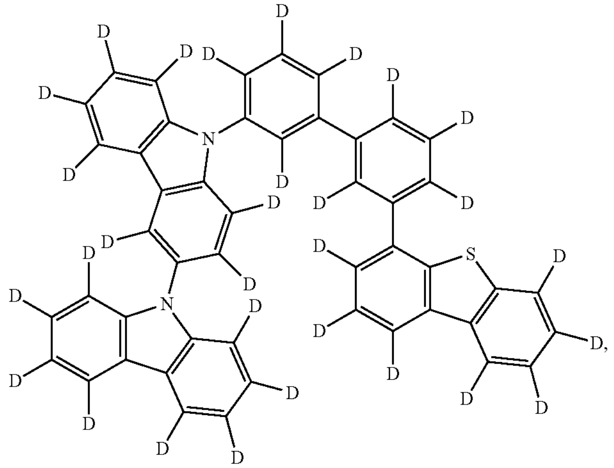
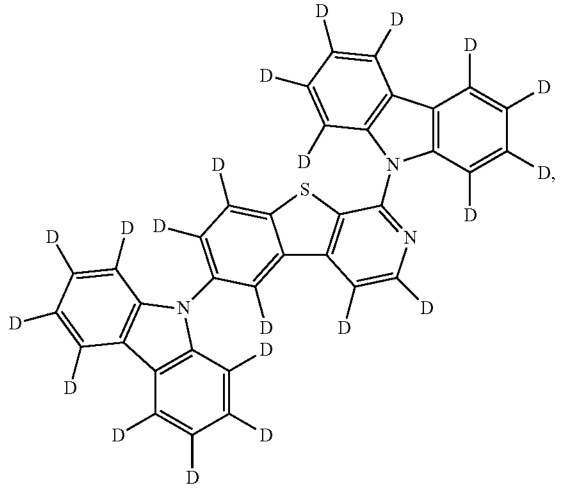
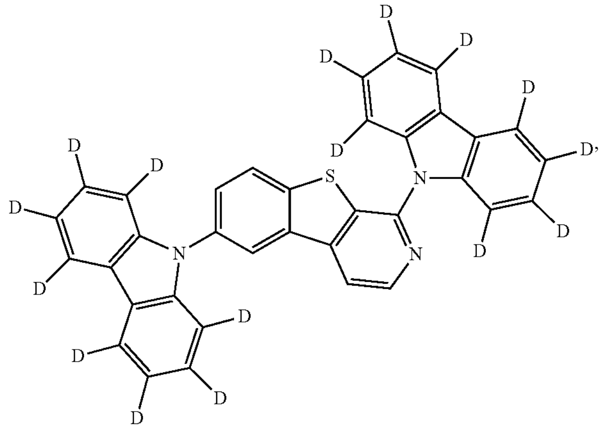

-continued
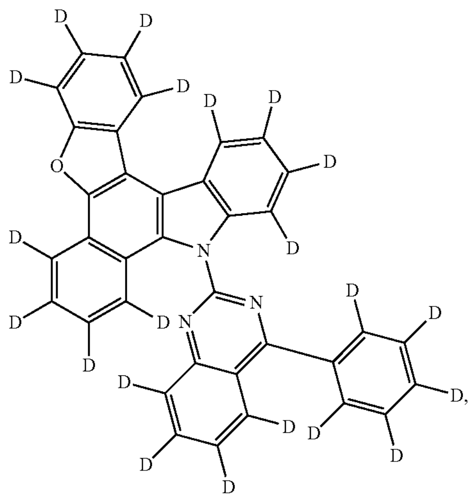
,
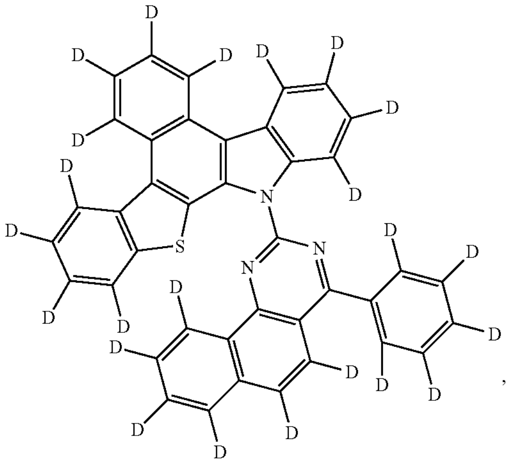
,
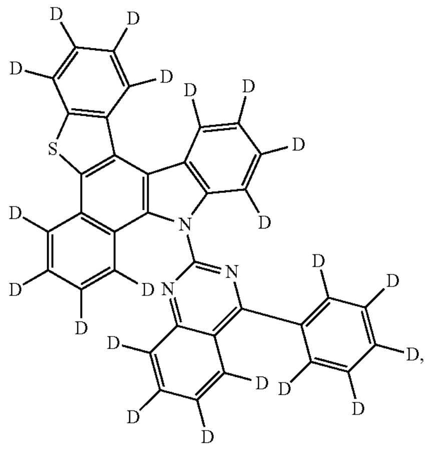
,
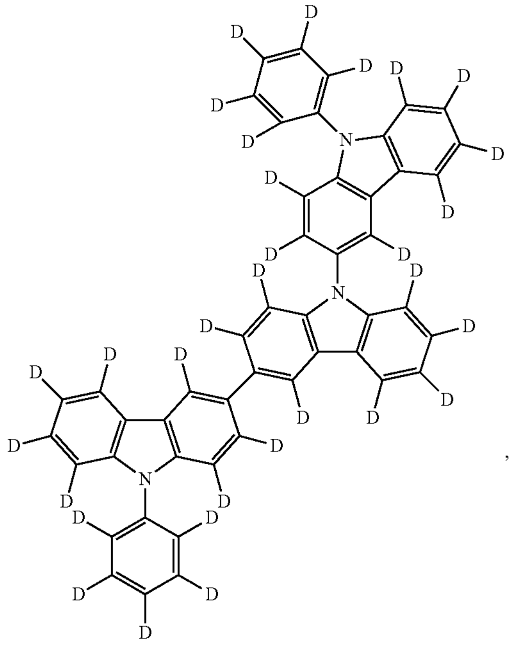
,

-continued
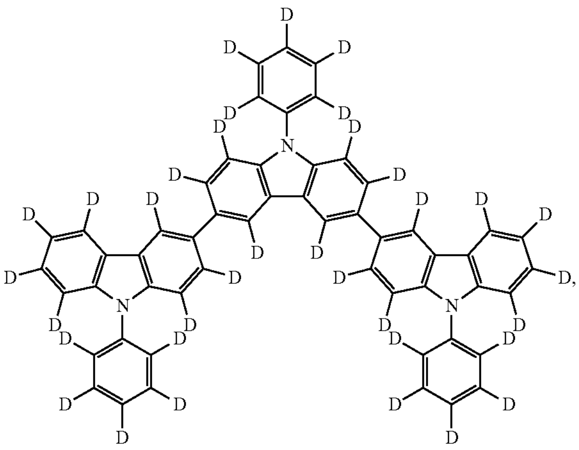
,
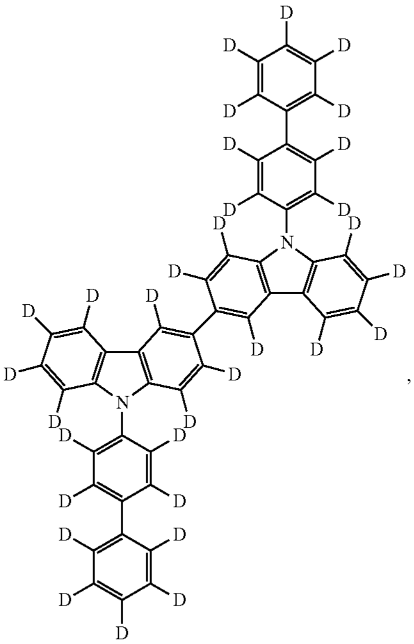
,
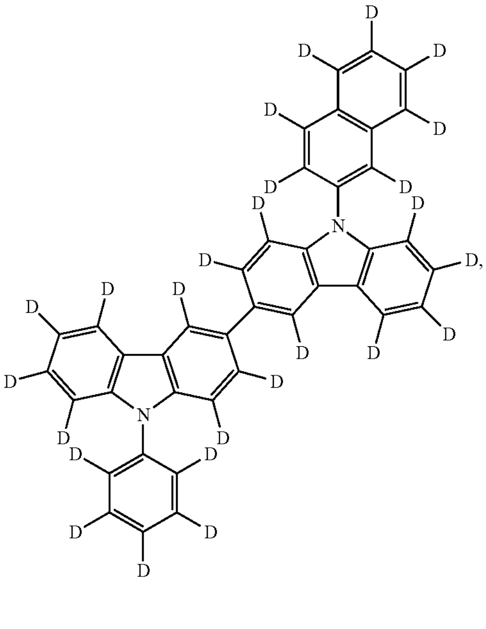
,
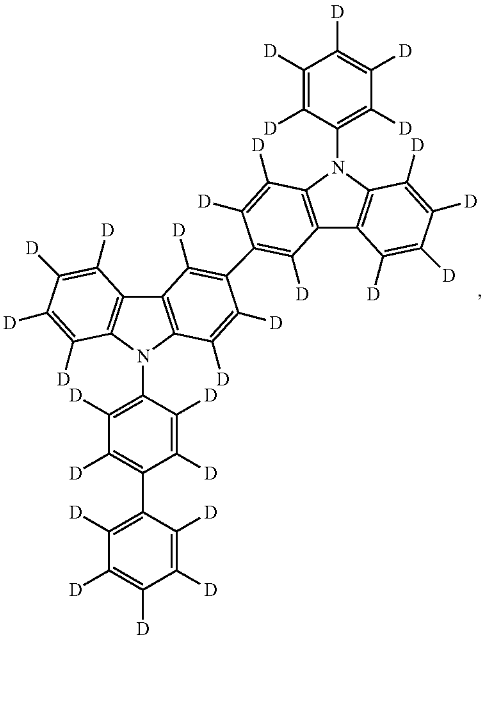
,

-continued
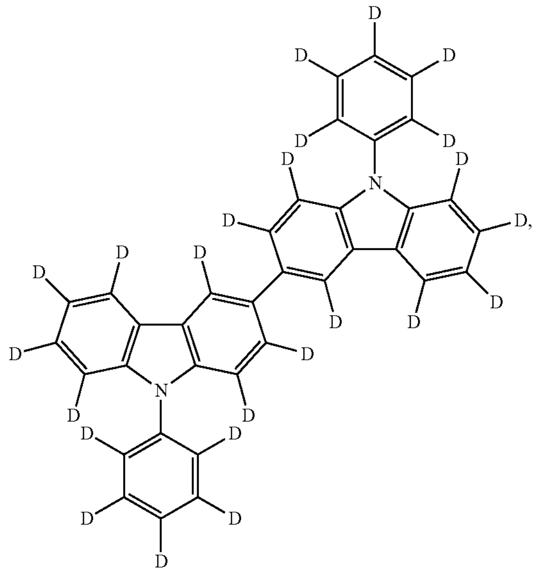
,
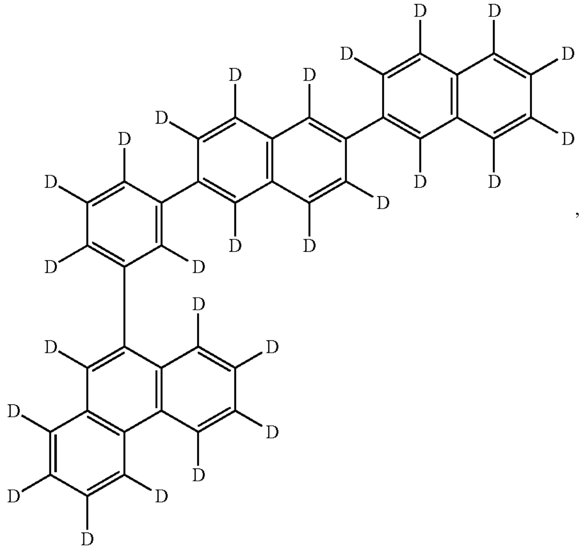
,
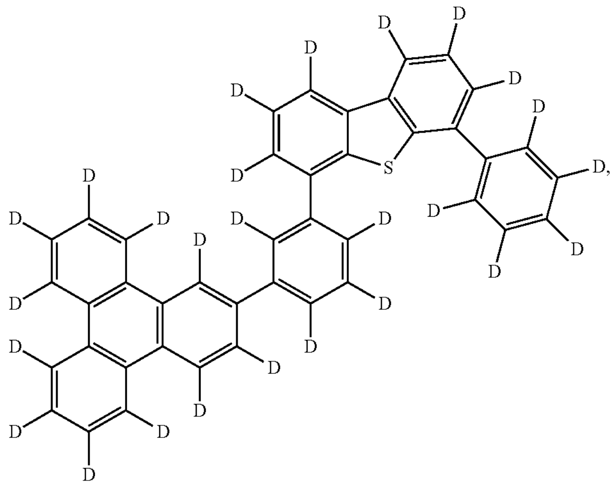
,
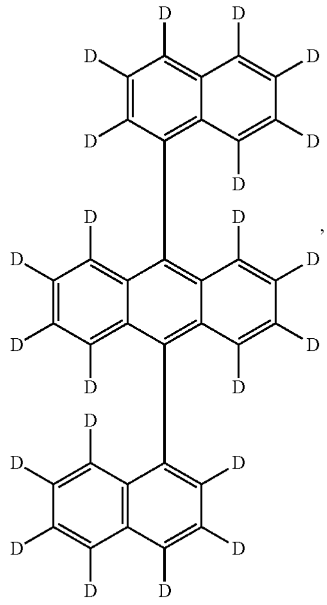
,

-continued
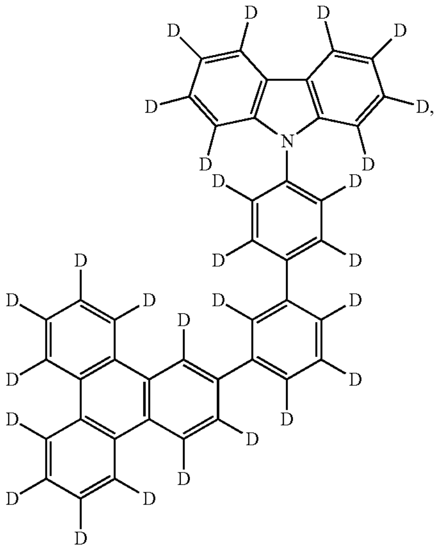
,
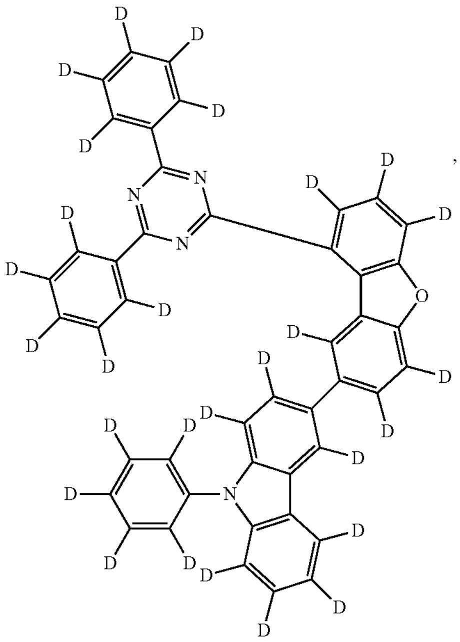
,
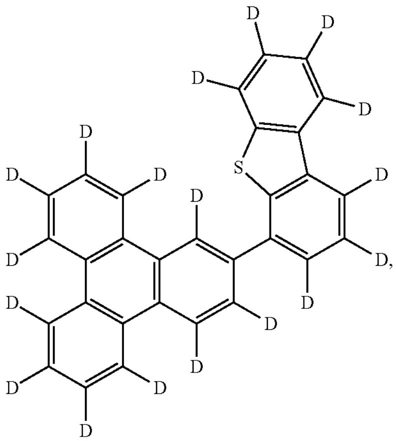
,
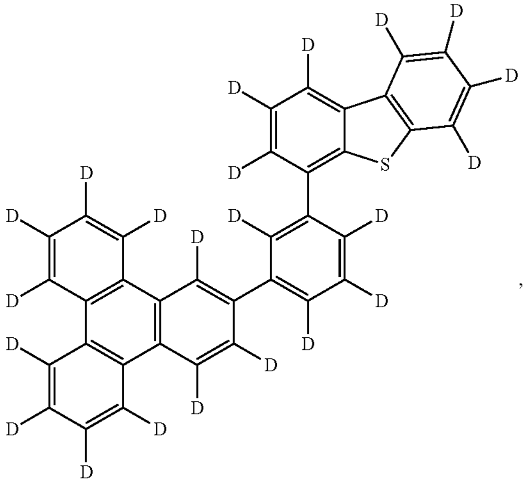
,

-continued
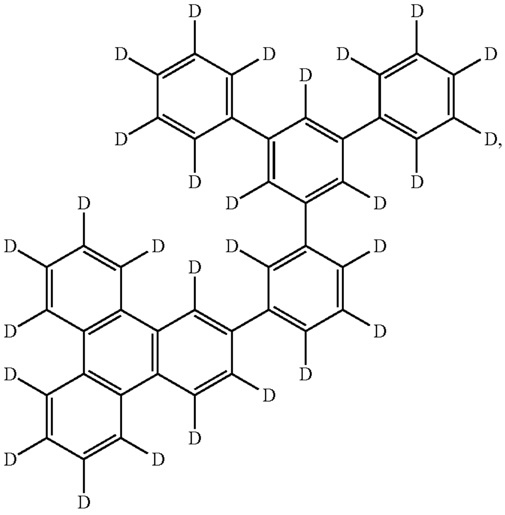
,
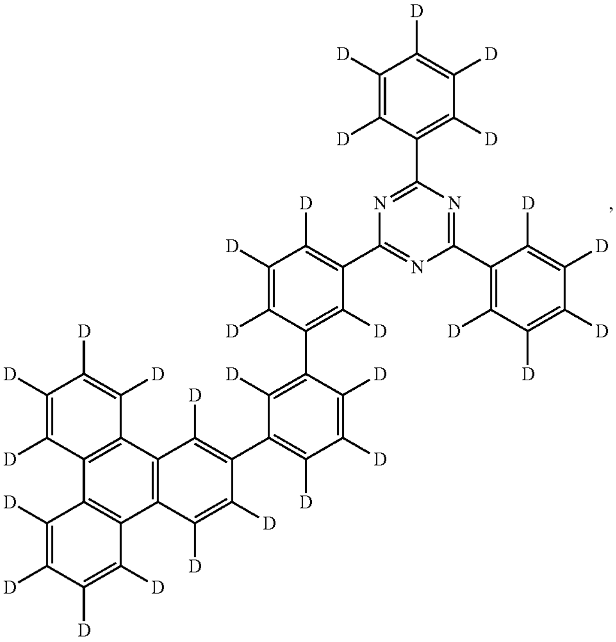
,
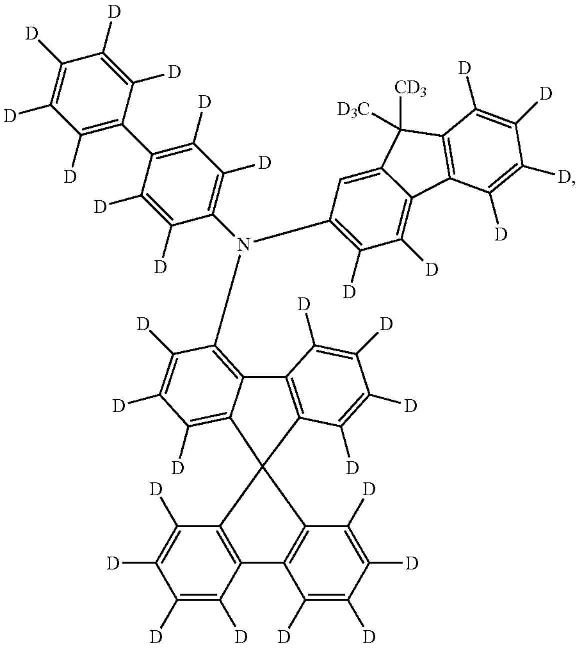
,
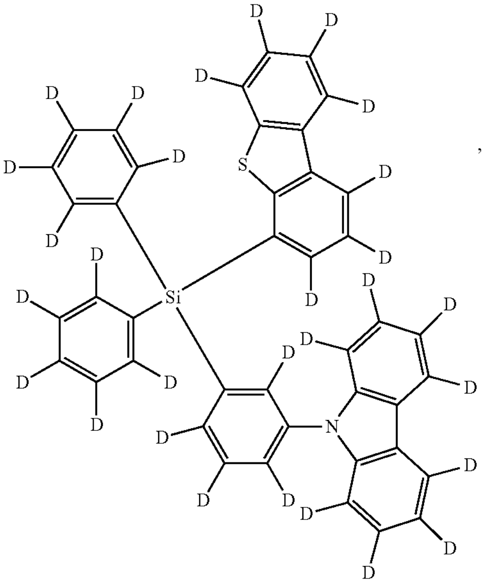
,
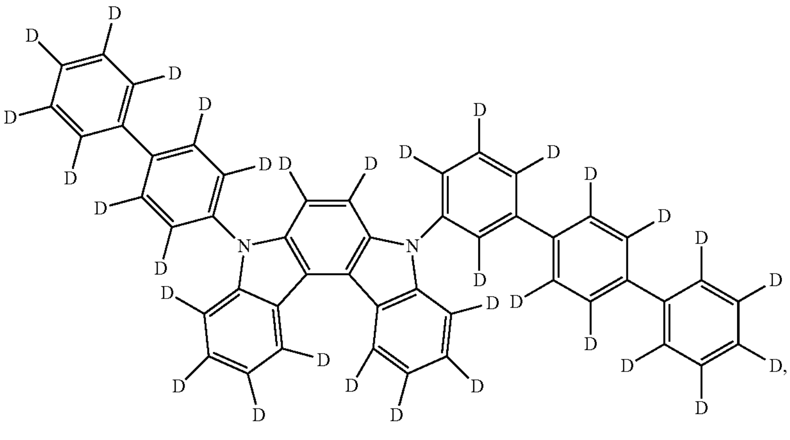
, -continued
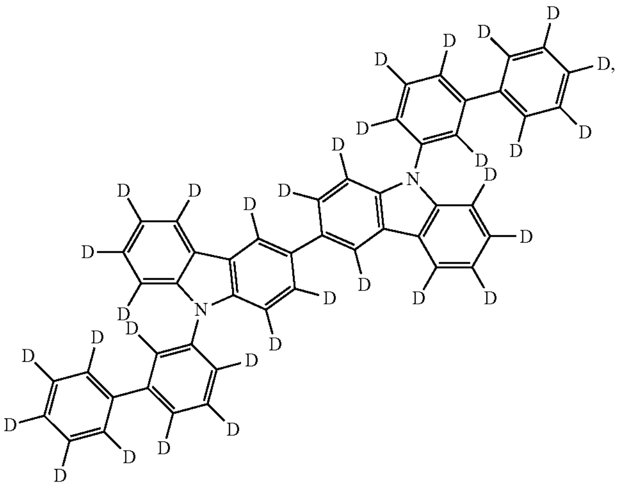
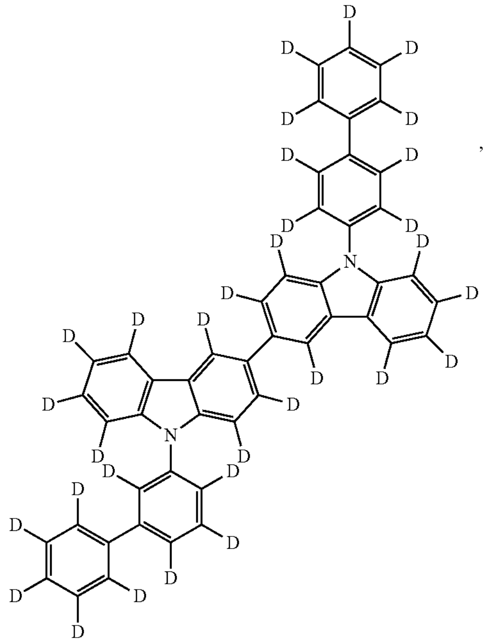
,
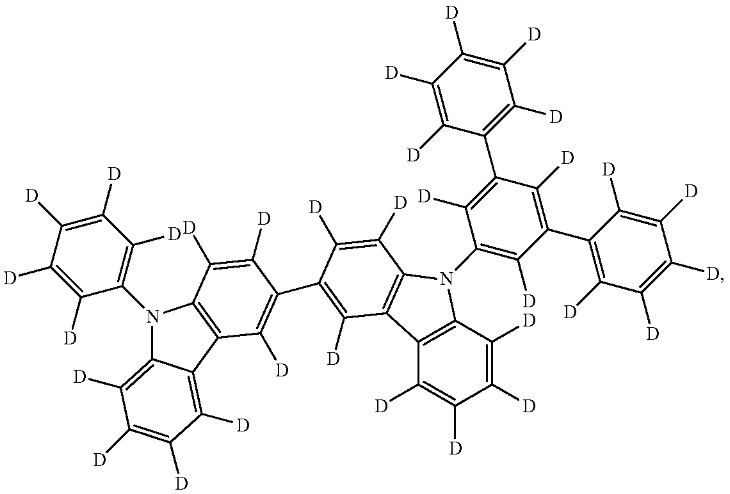

-continued
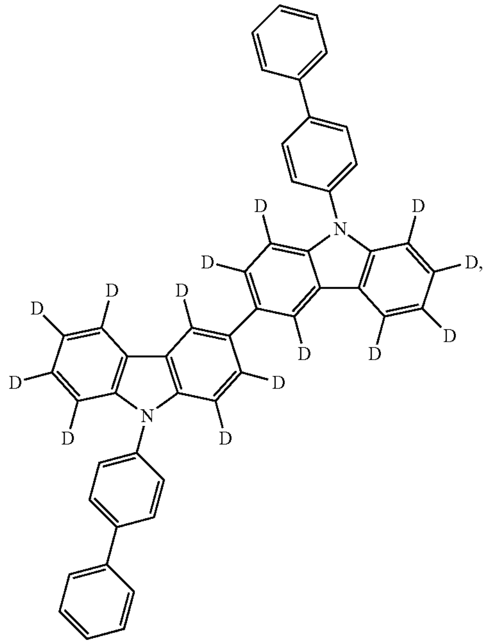
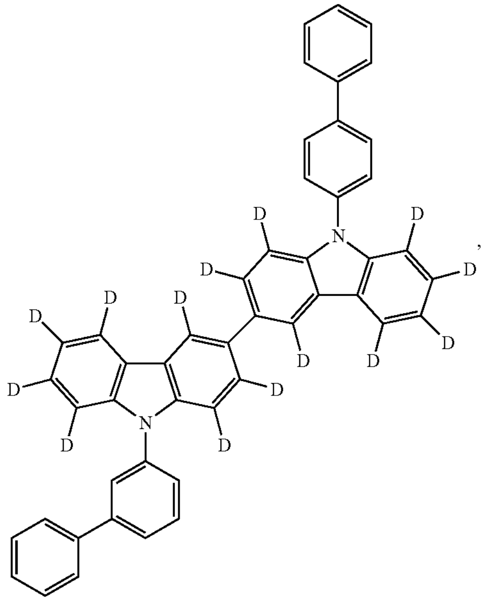
,
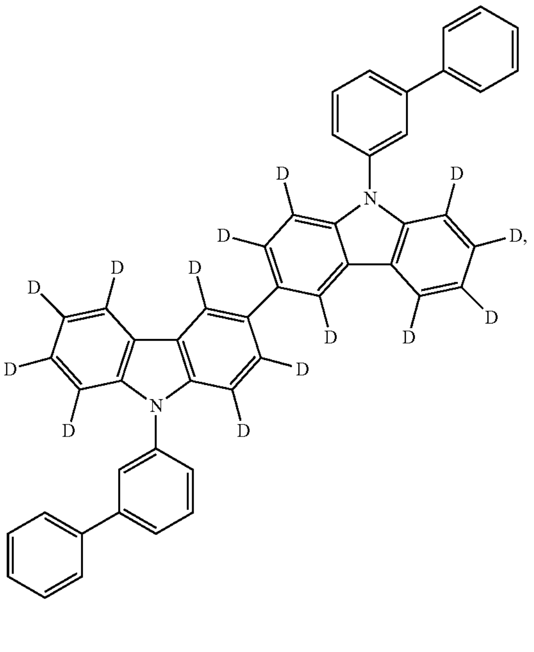
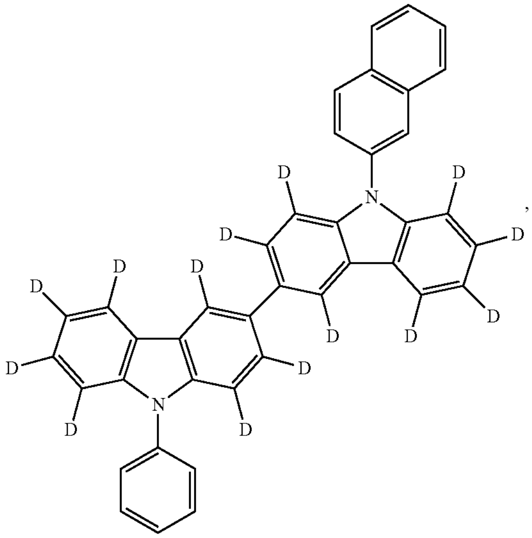
,

-continued
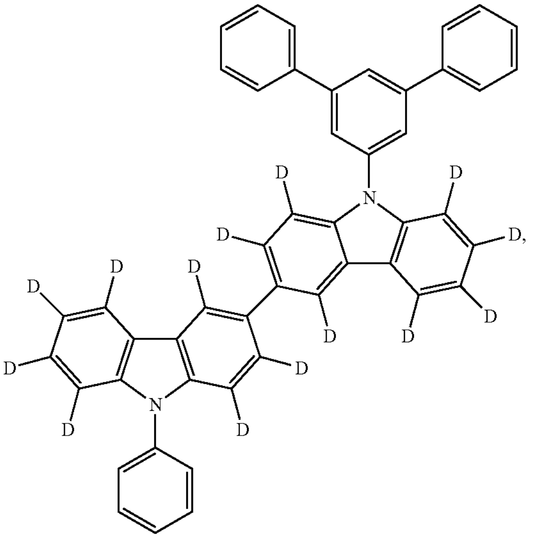
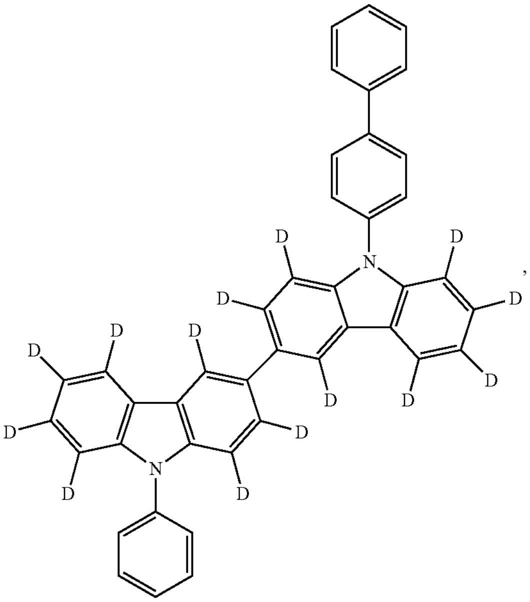
,
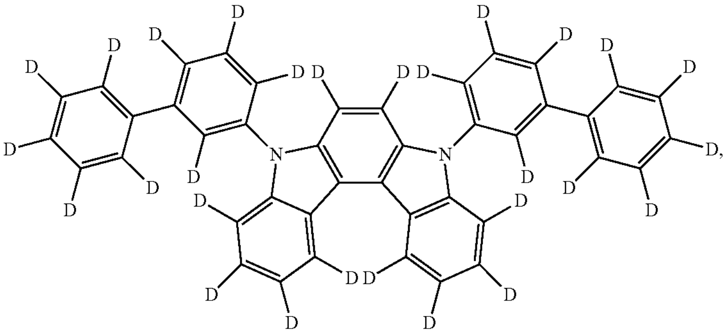
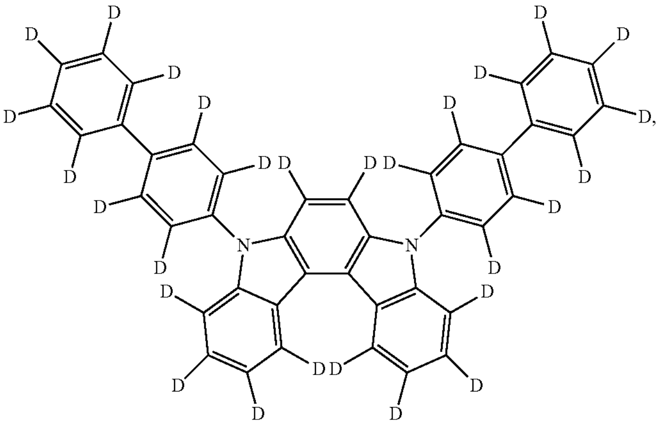
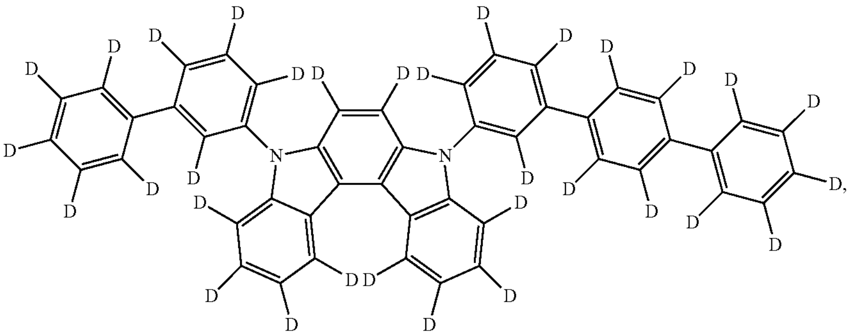

-continued
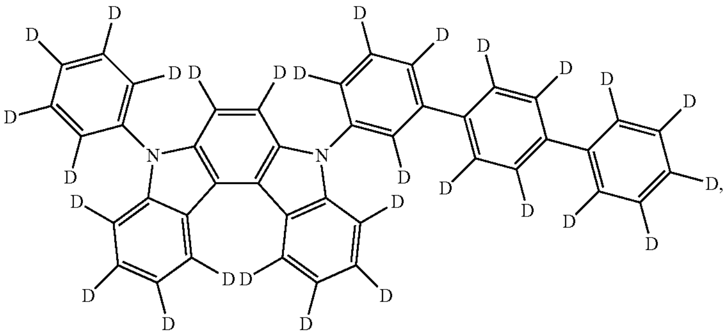
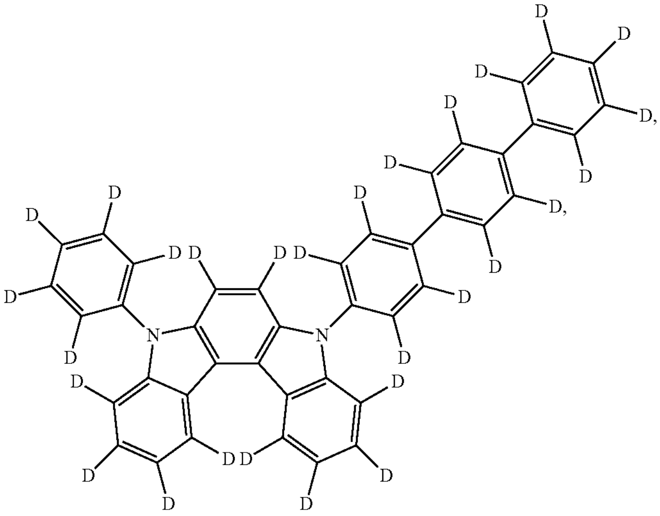
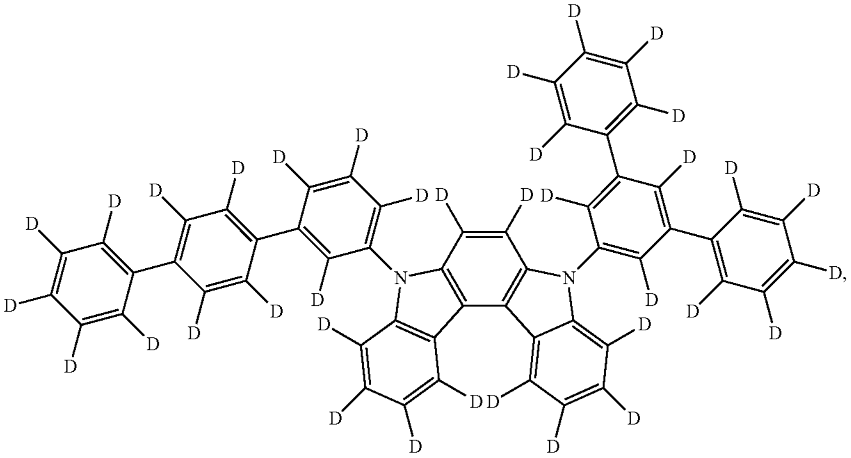
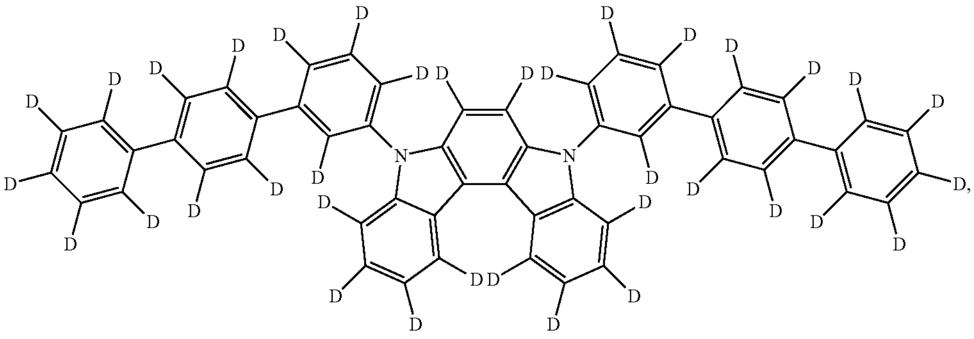

-continued
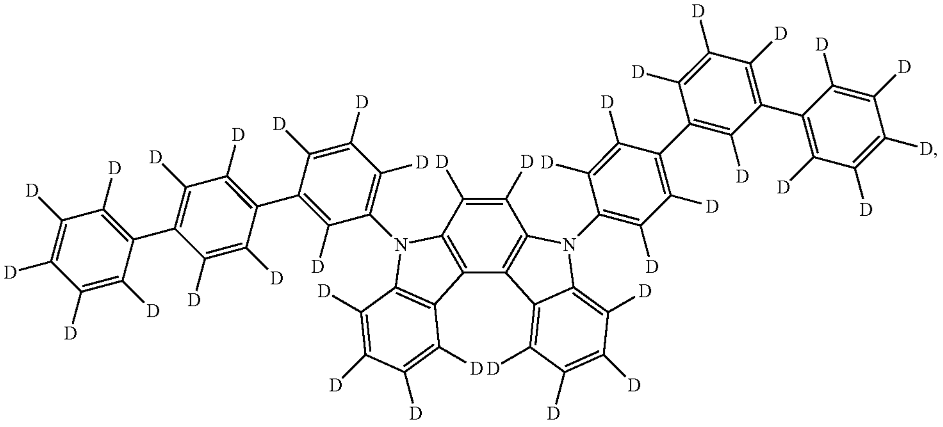
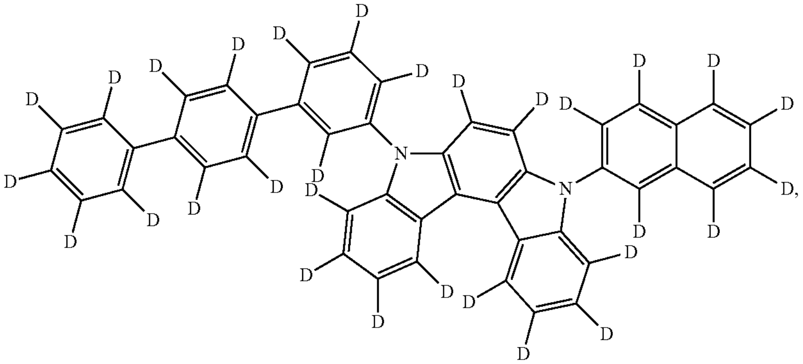
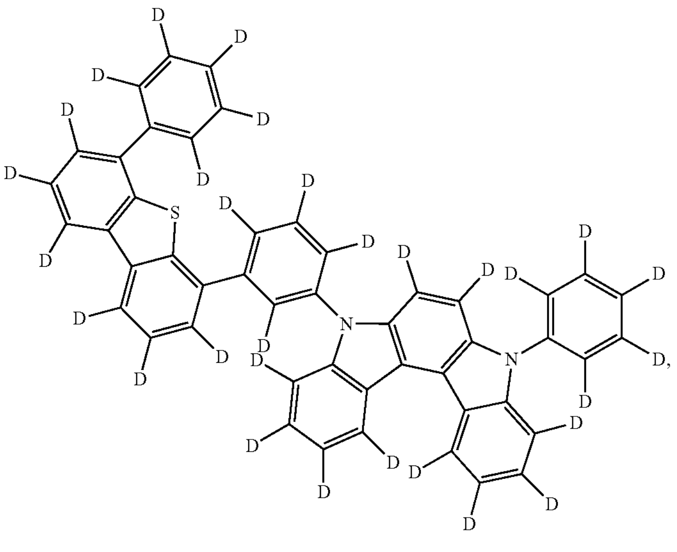

-continued
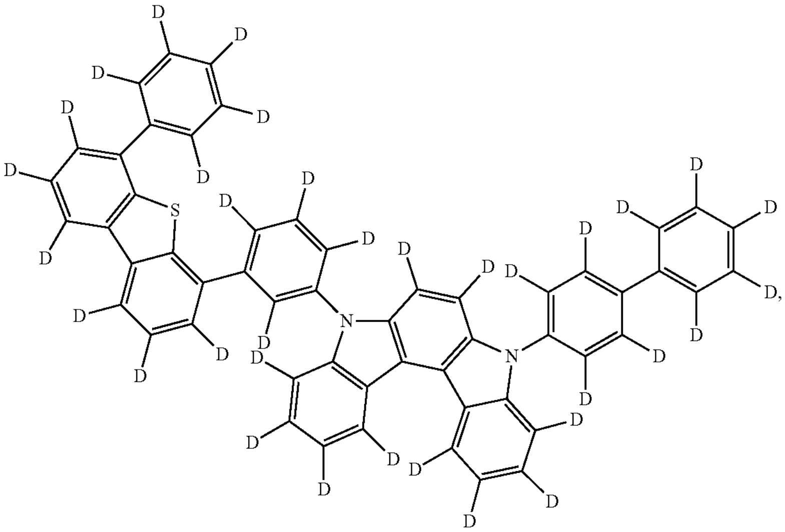
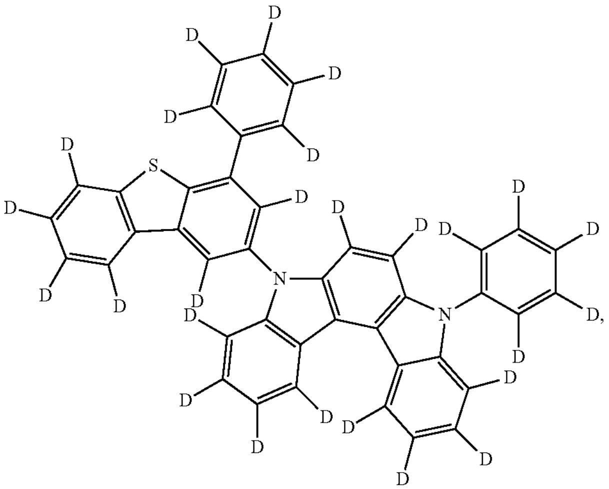
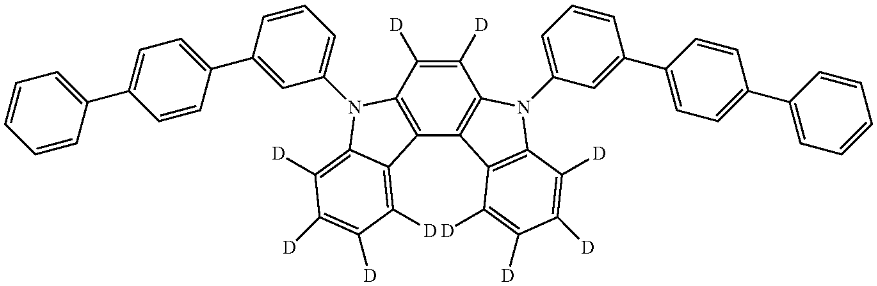
,

-continued
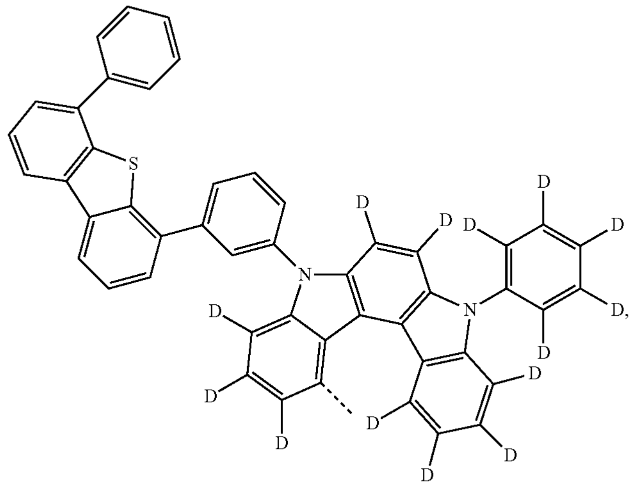
,
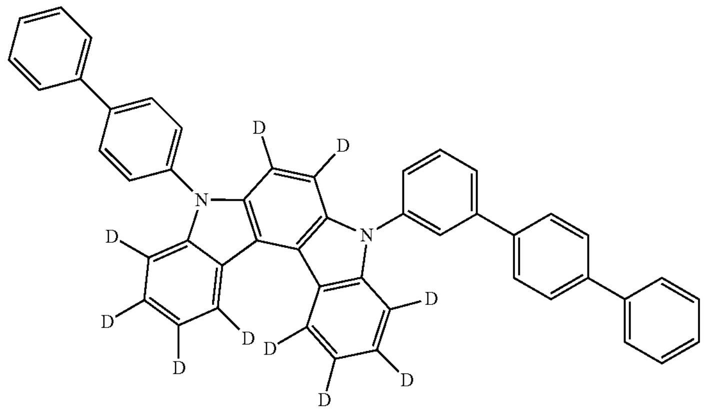
,
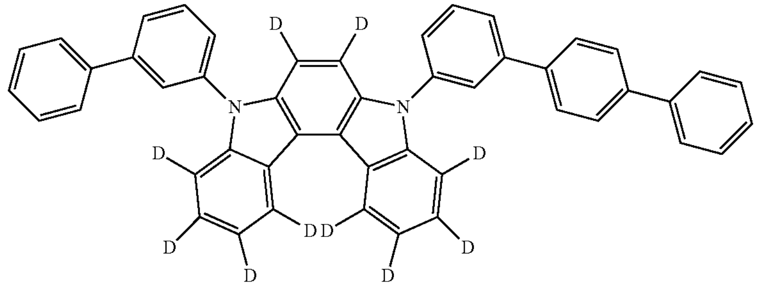
,
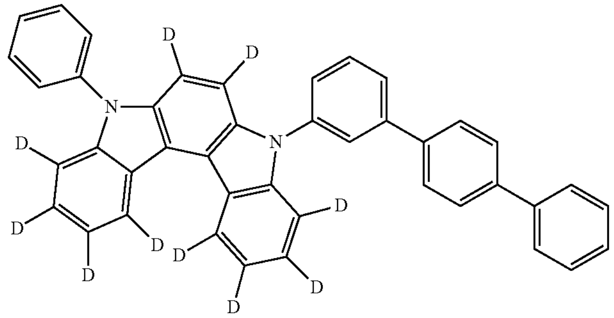
,
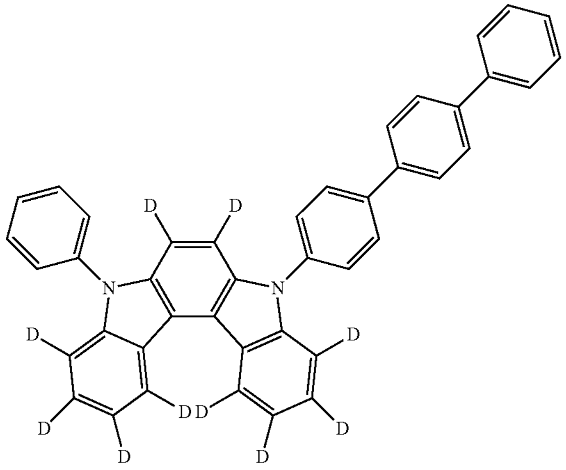
, -continued
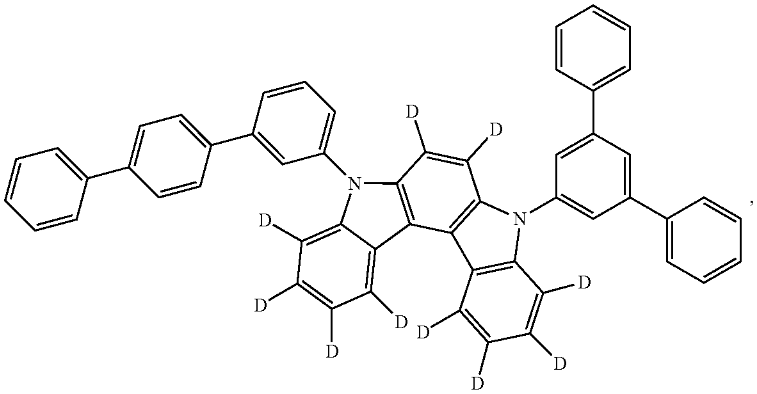
,
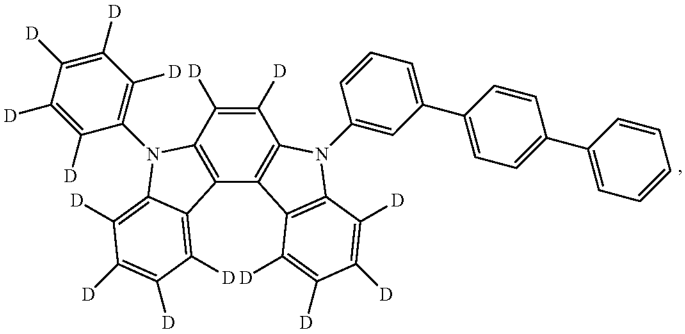
,
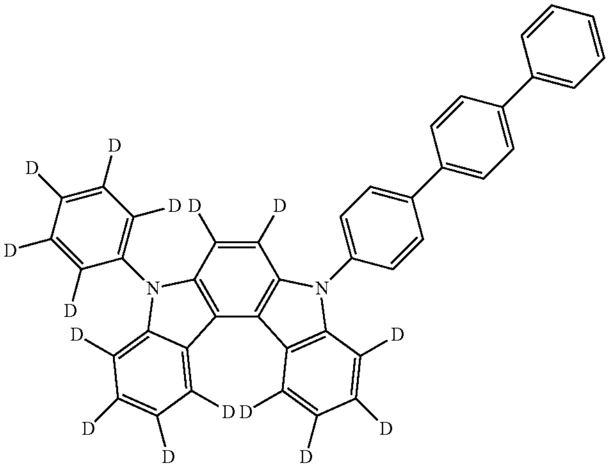
,
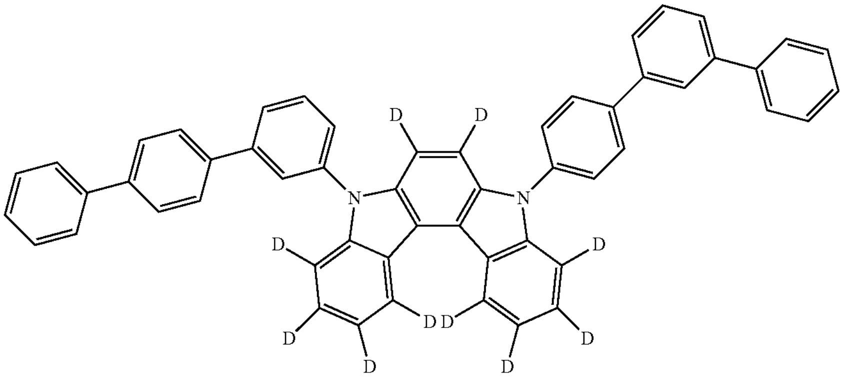
, -continued
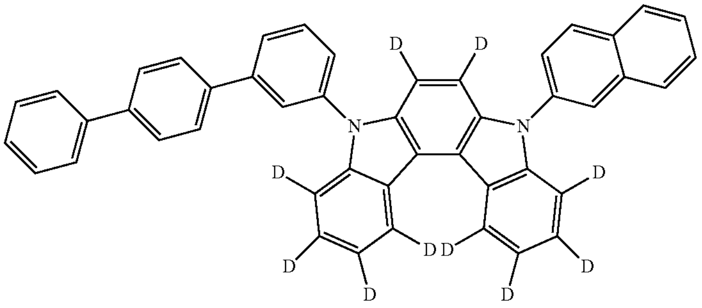
,
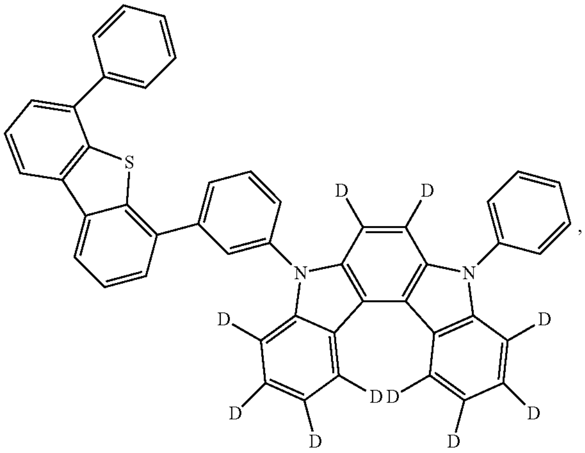
,
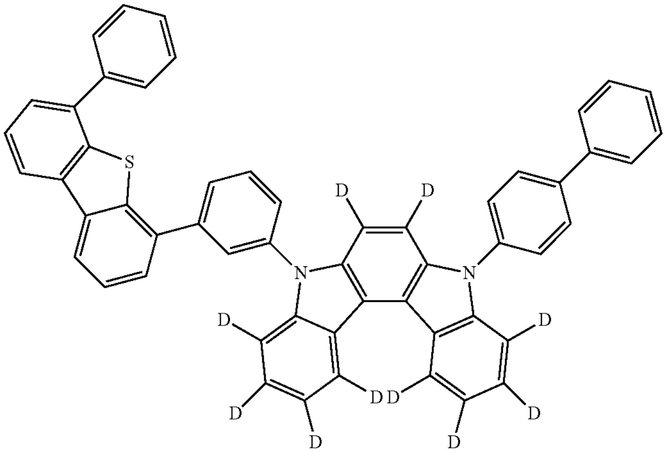
,
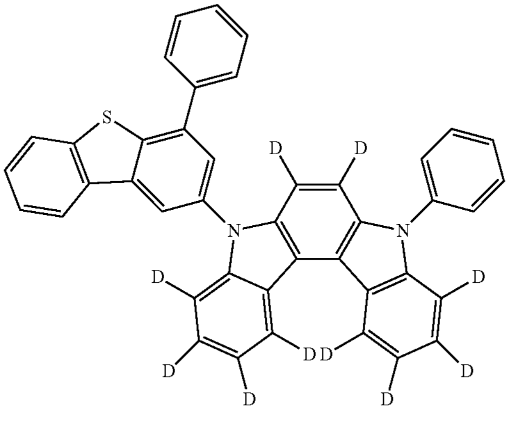
,
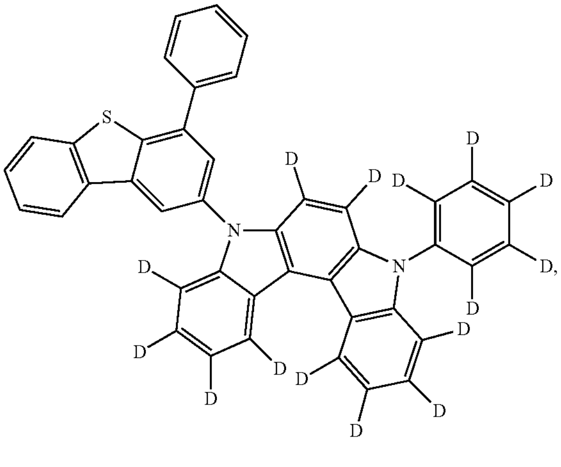
, -continued
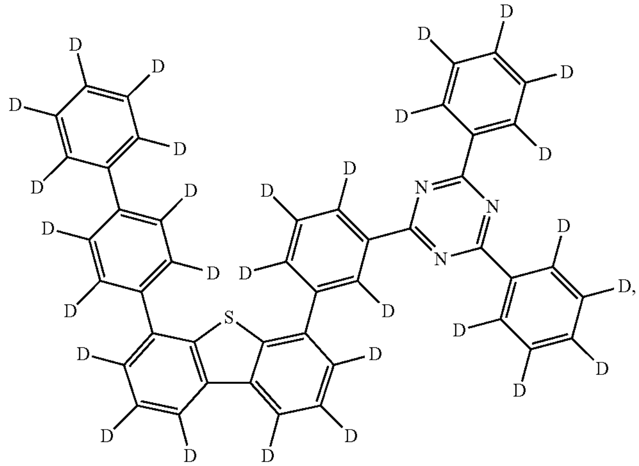
,
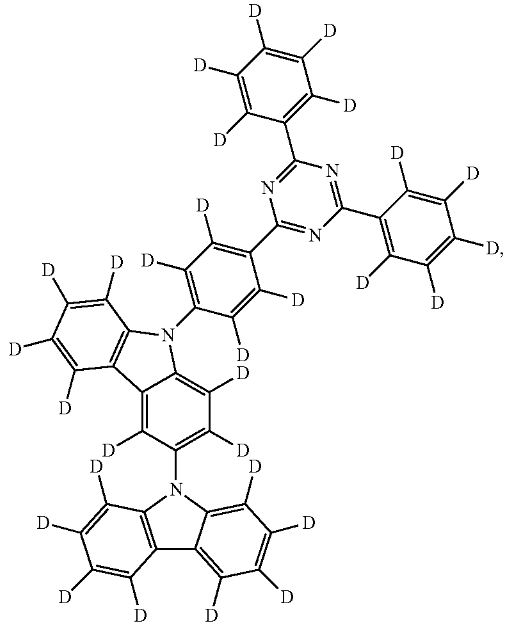
,
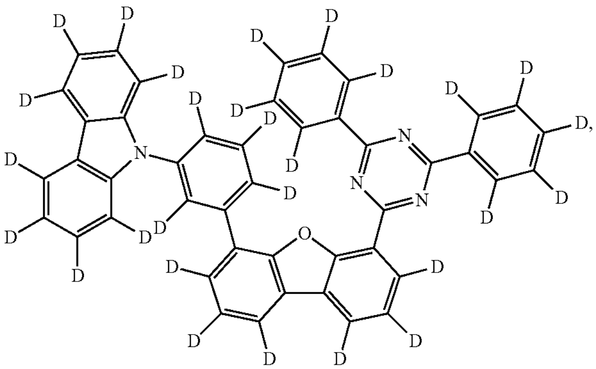
,
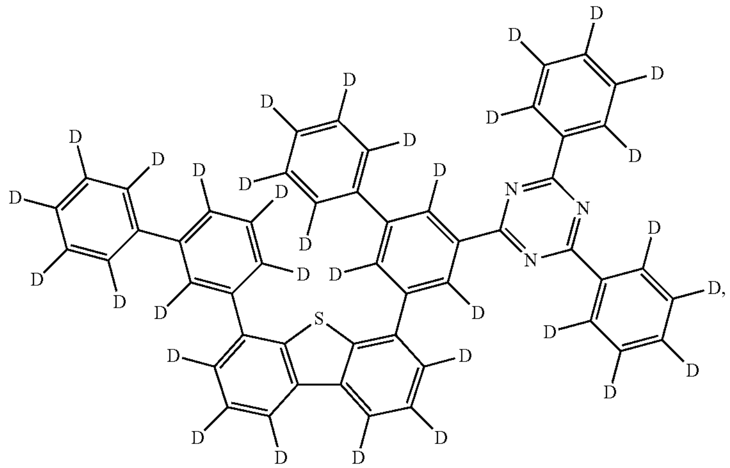
, -continued
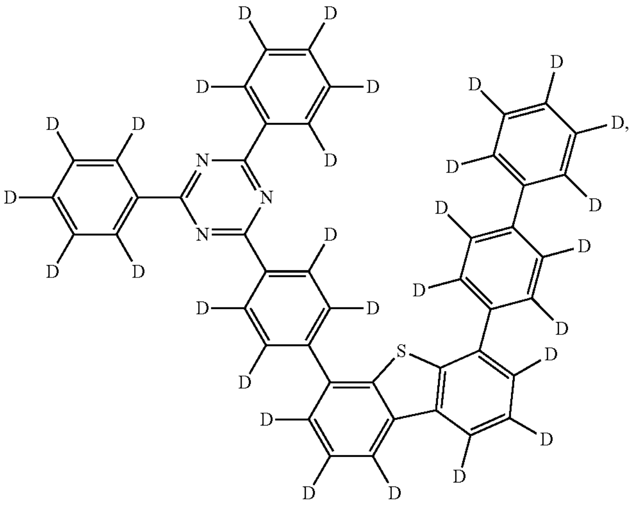
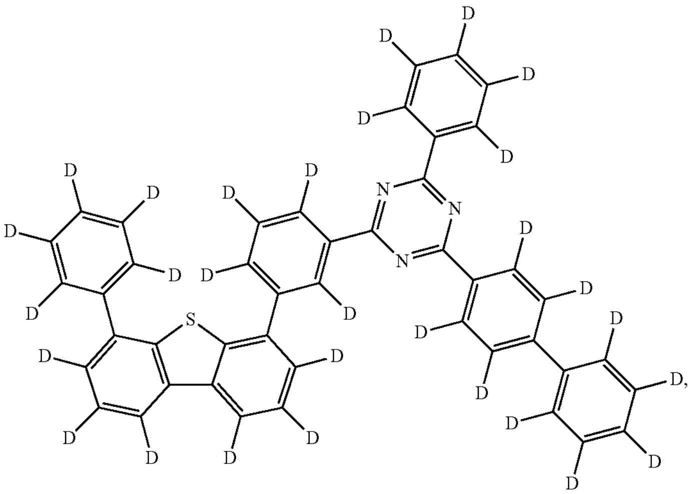
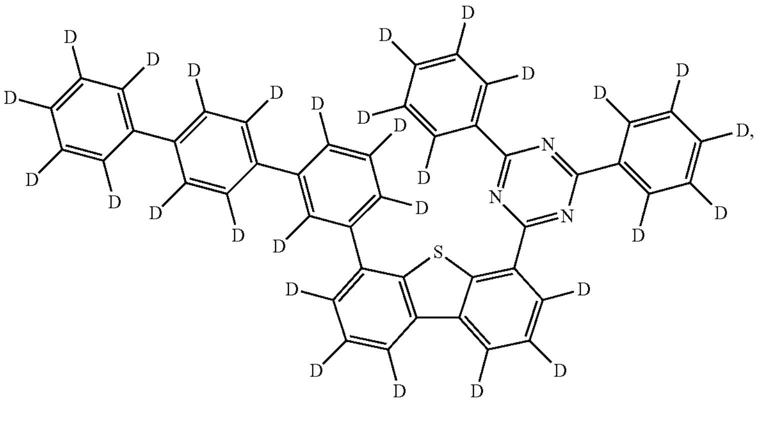

-continued
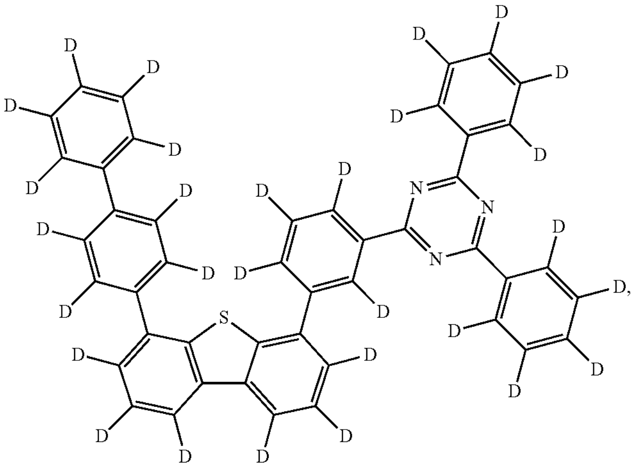
,
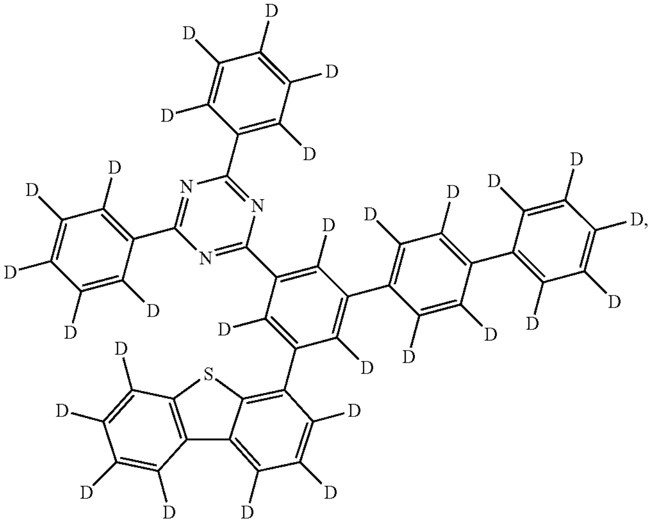
,
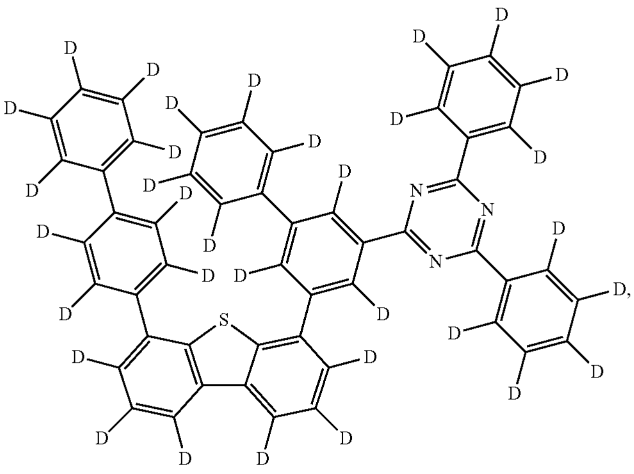
,

-continued
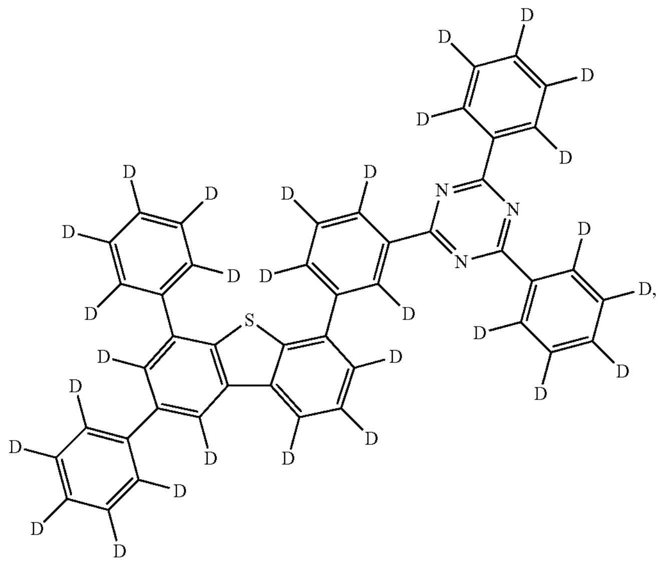
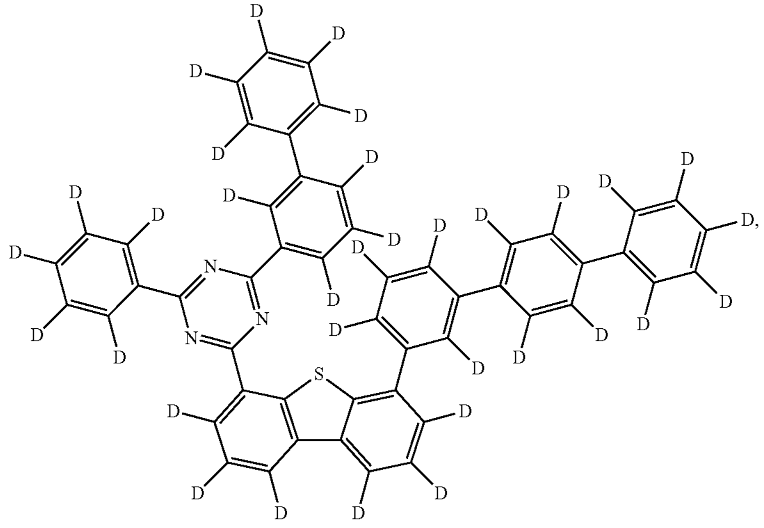
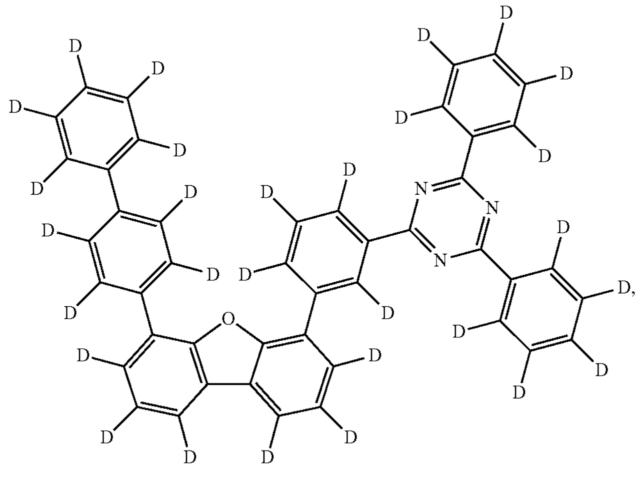

-continued
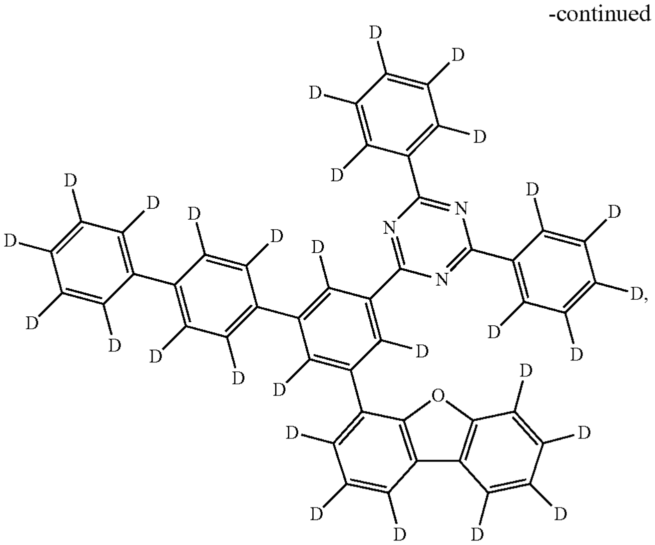
,
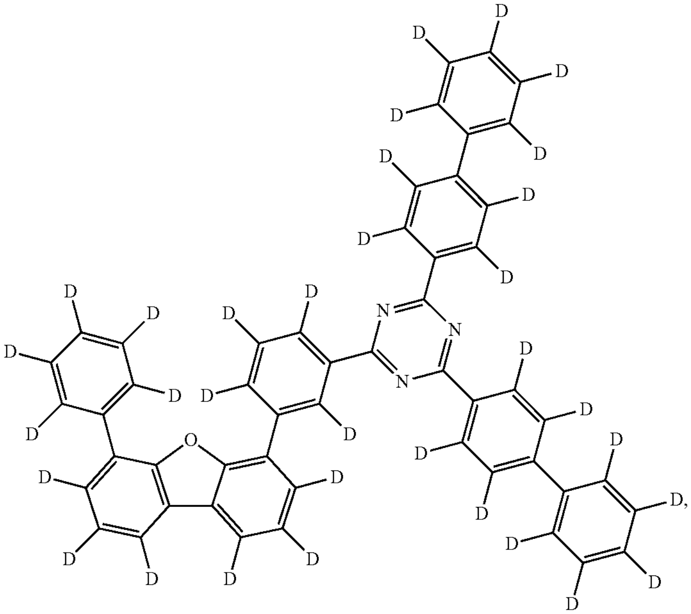
,
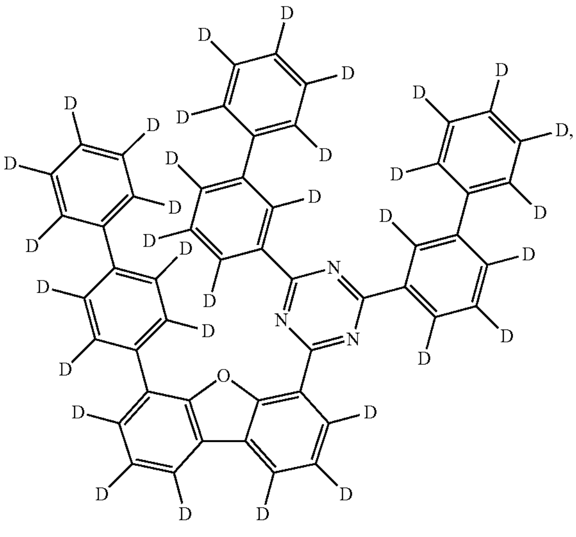
,
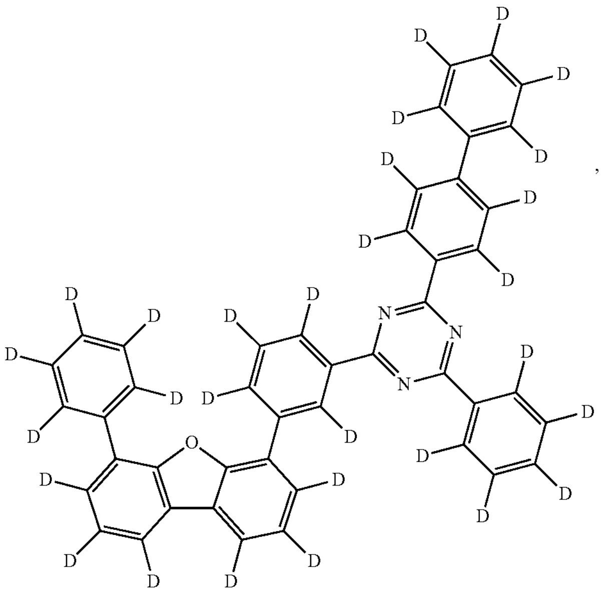
,

-continued
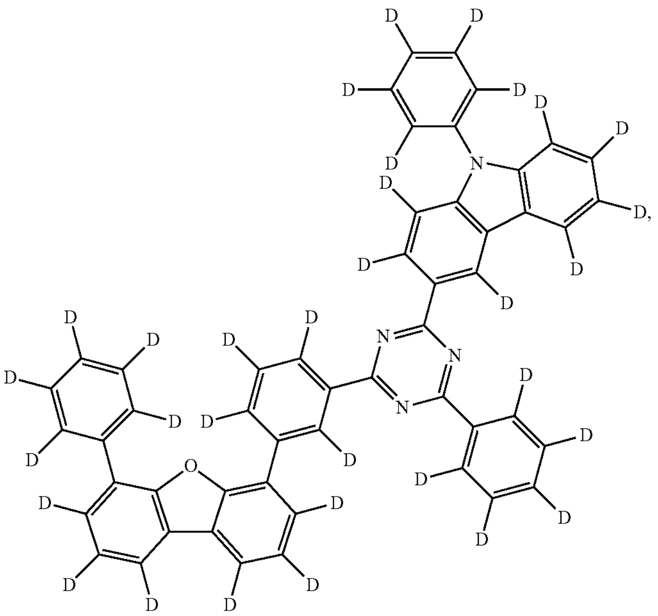
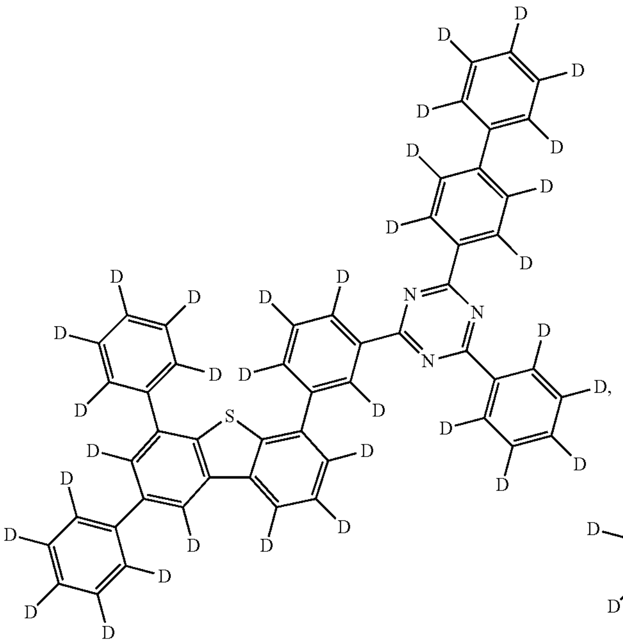
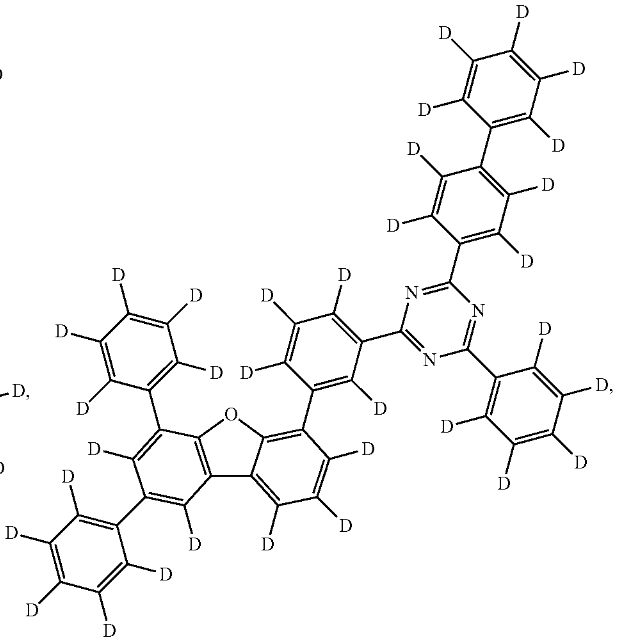

-continued
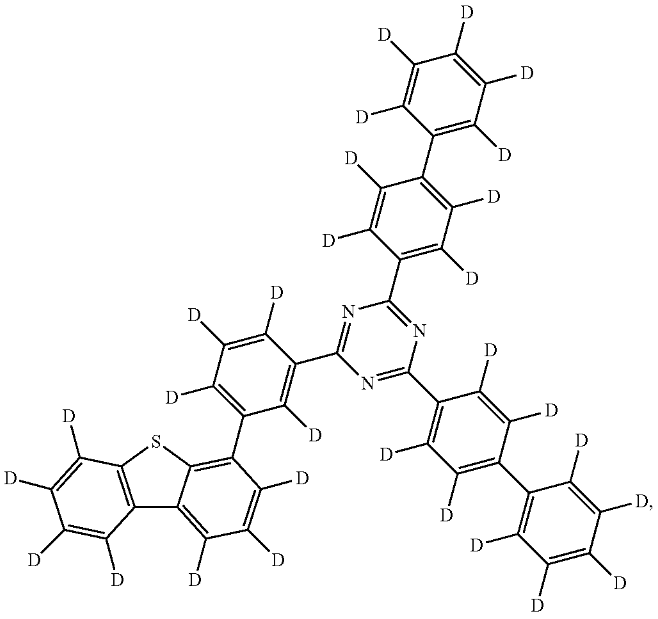
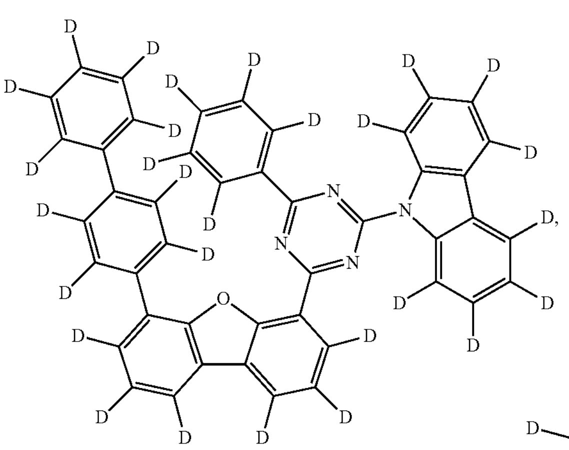
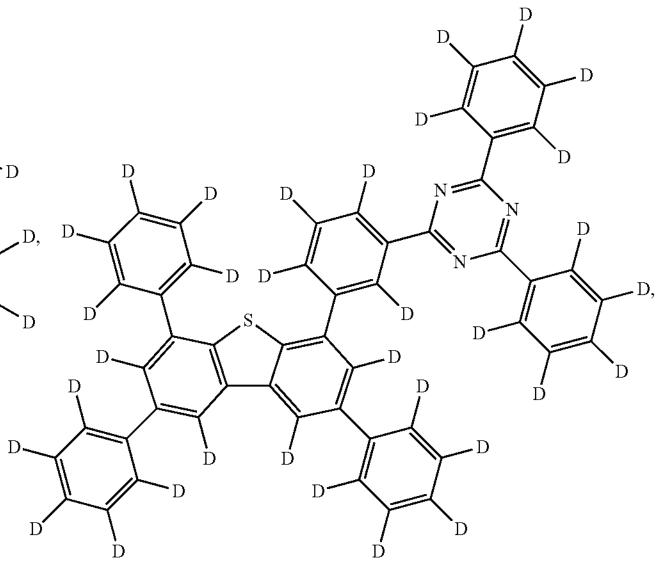

-continued
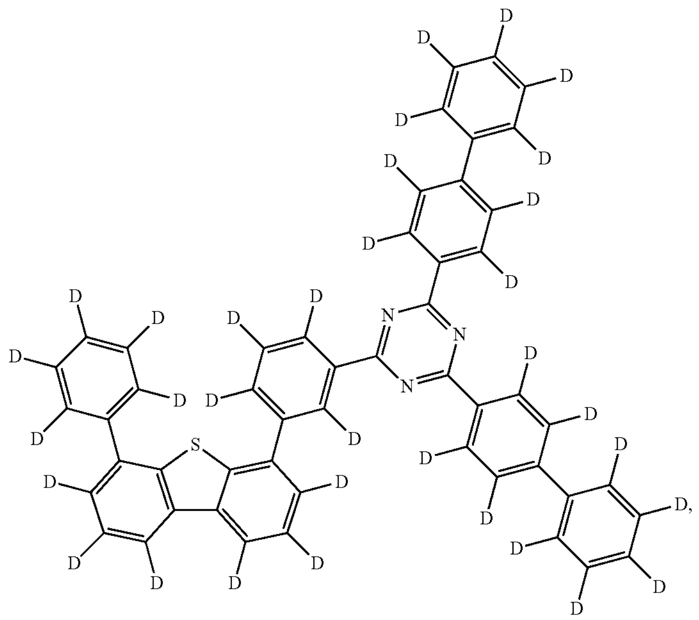
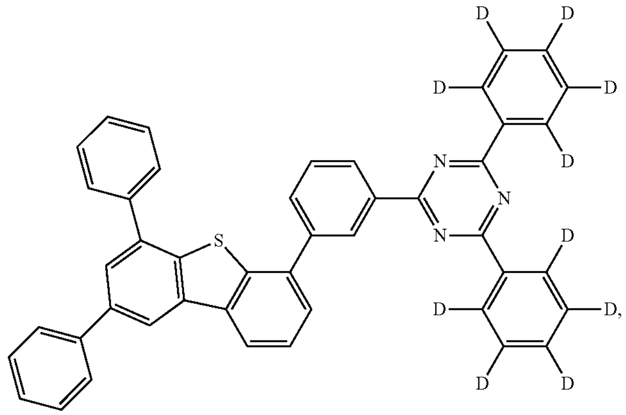
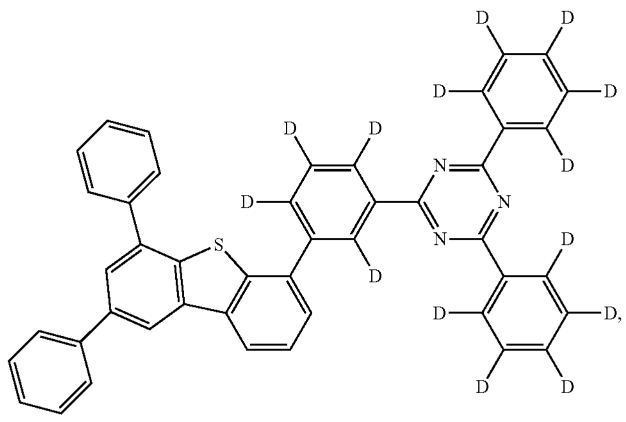
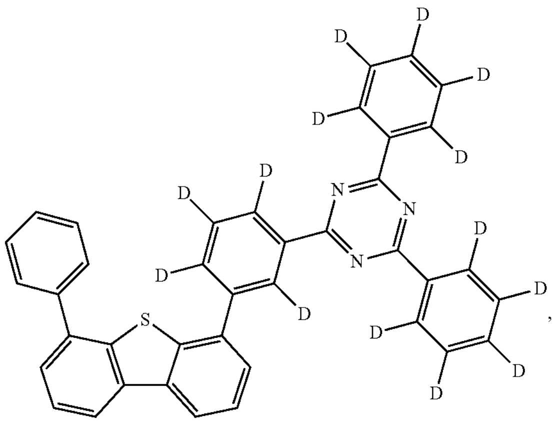
,

-continued
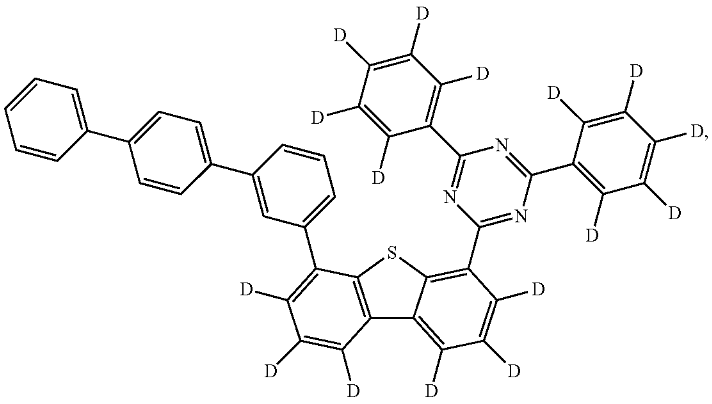
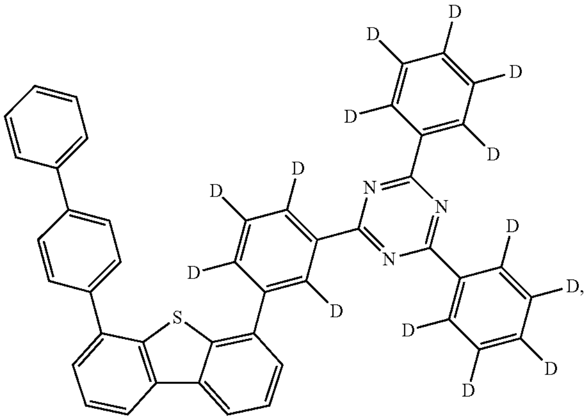
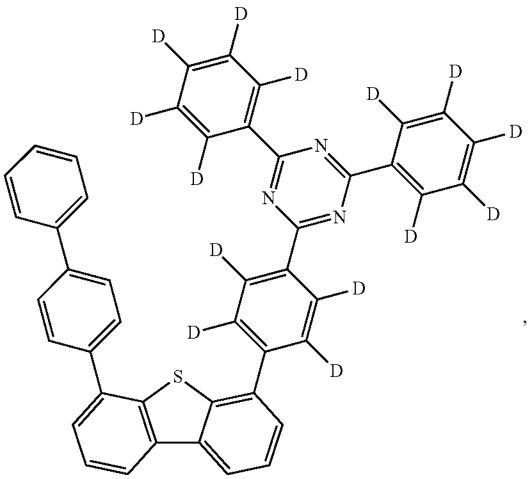
,
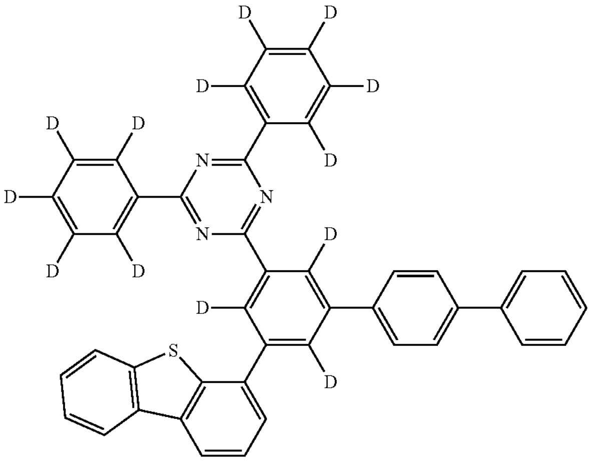
,

-continued
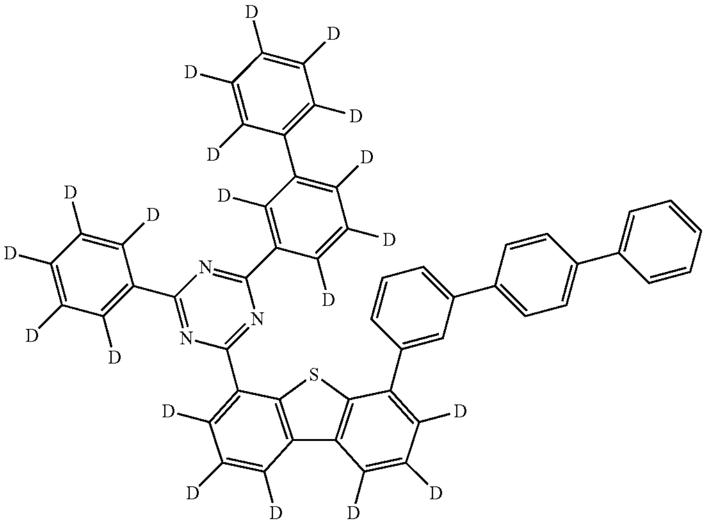
,
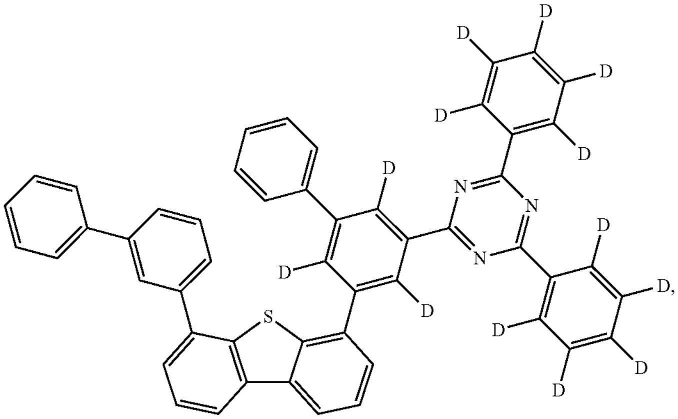
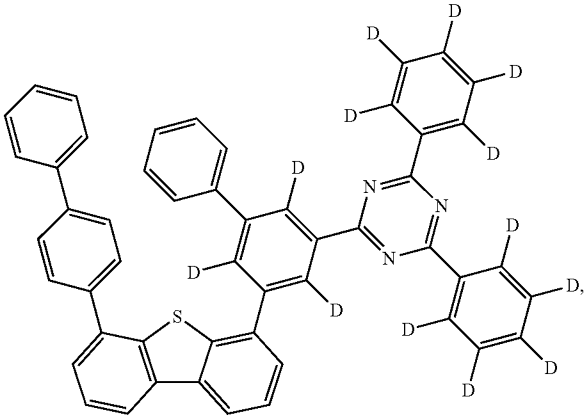
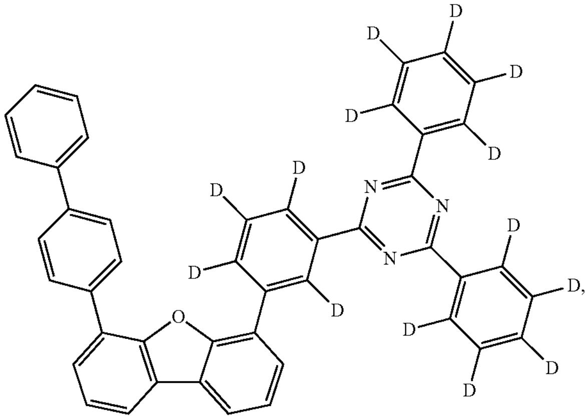

-continued
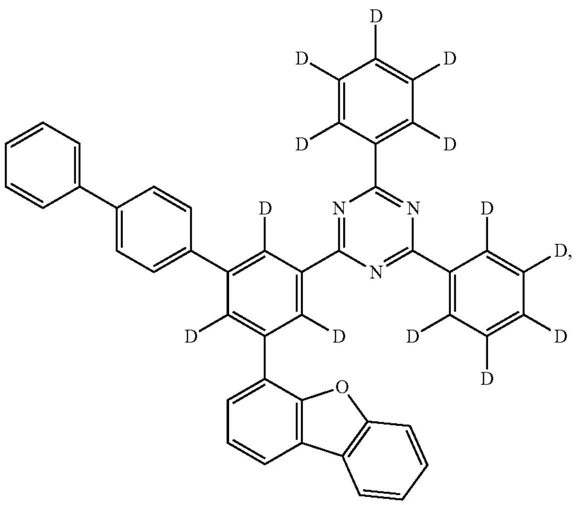
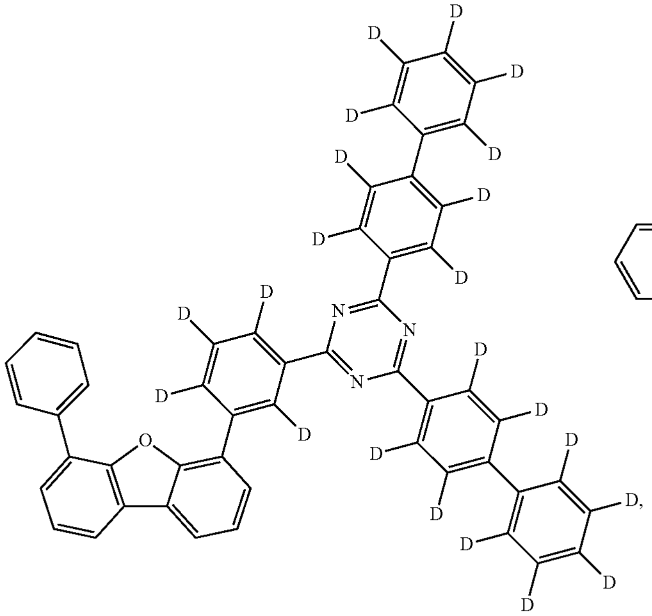
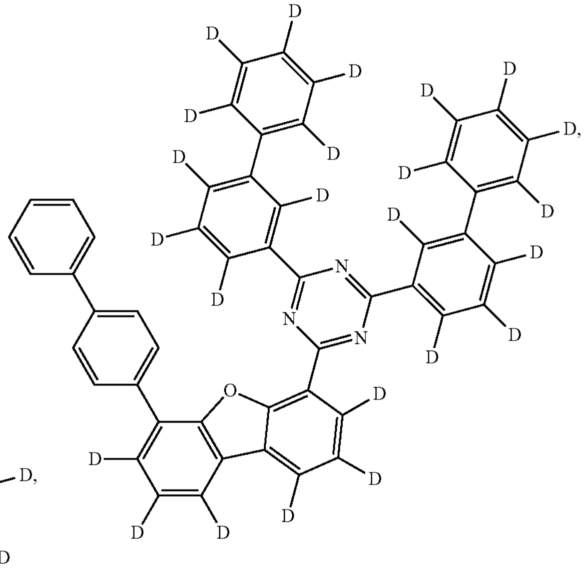
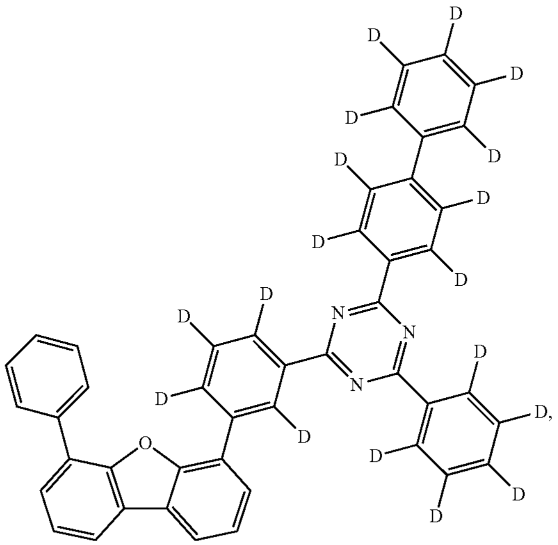
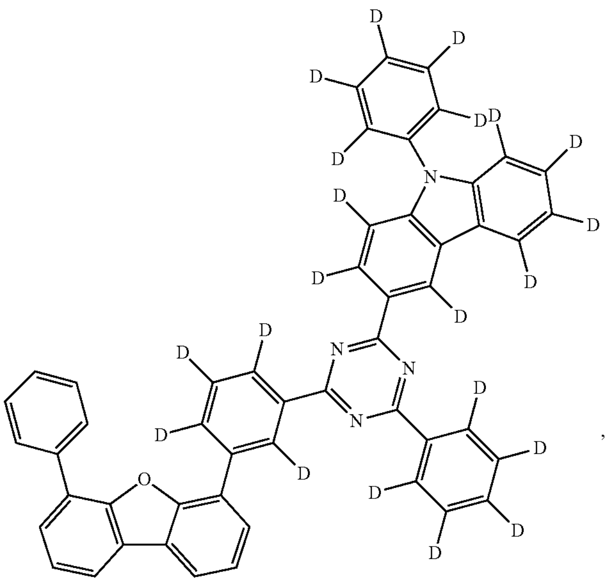
,

-continued
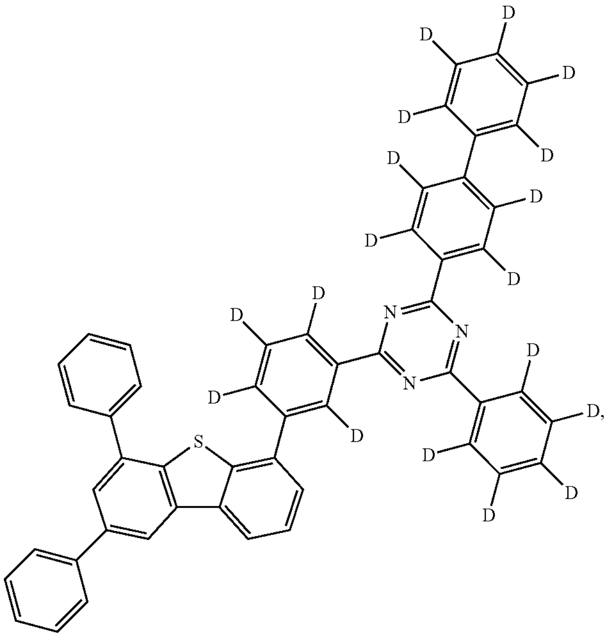
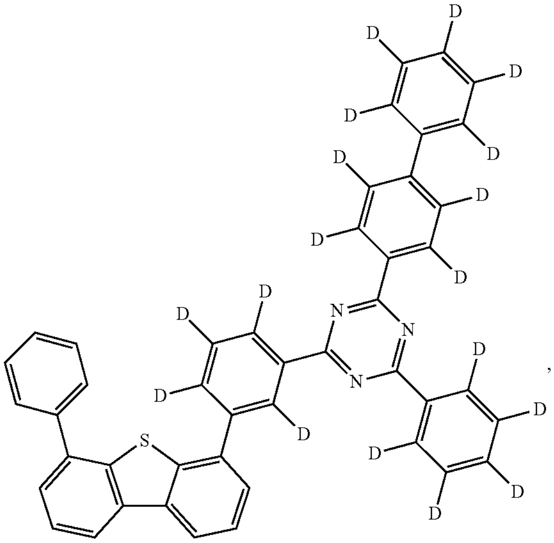
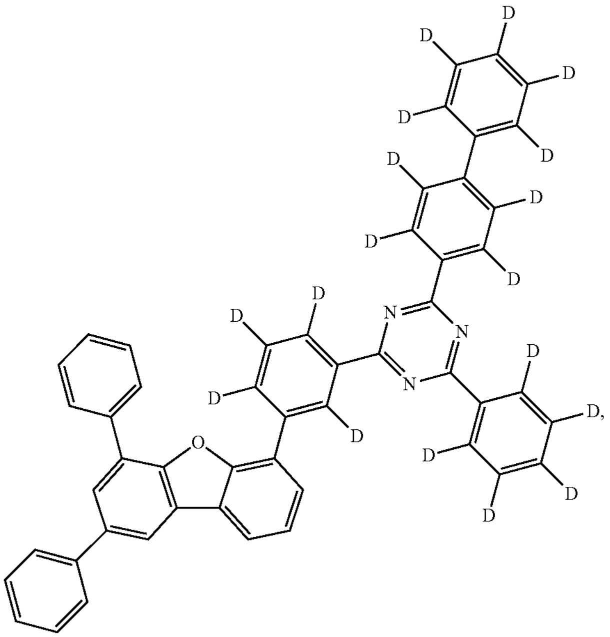

-continued
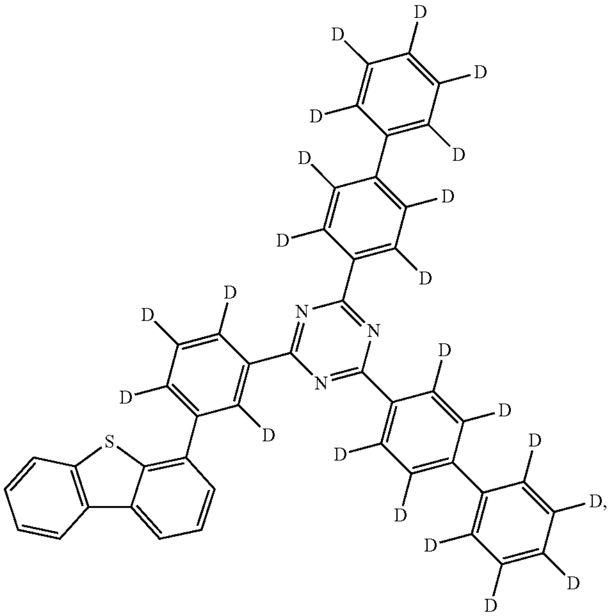
D,
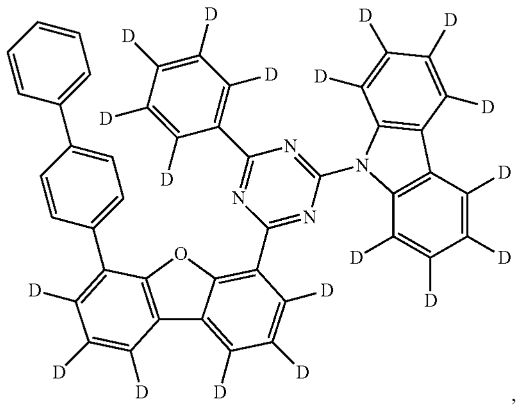
,
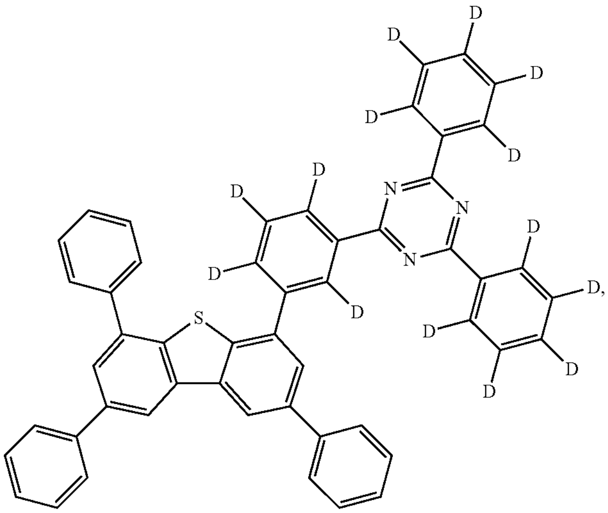
D,

-continued
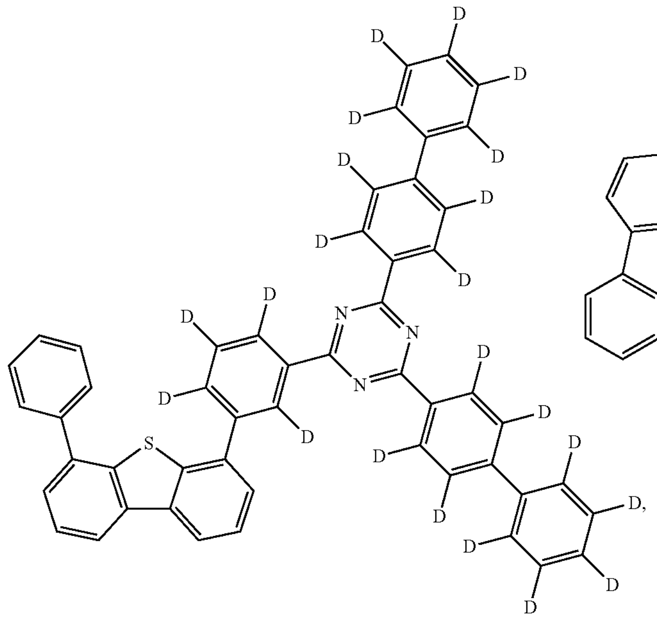
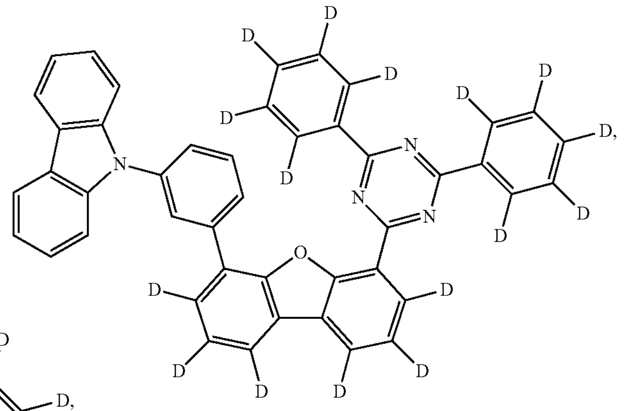
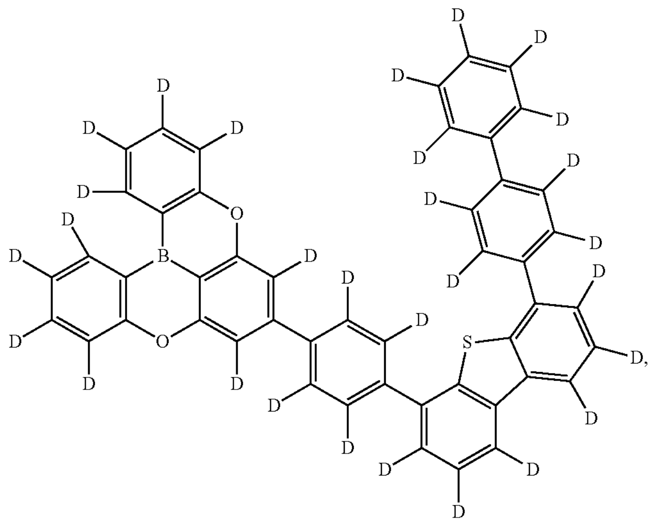
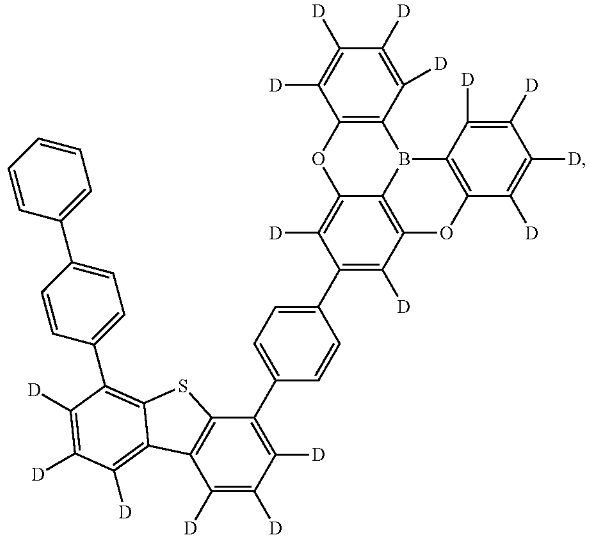
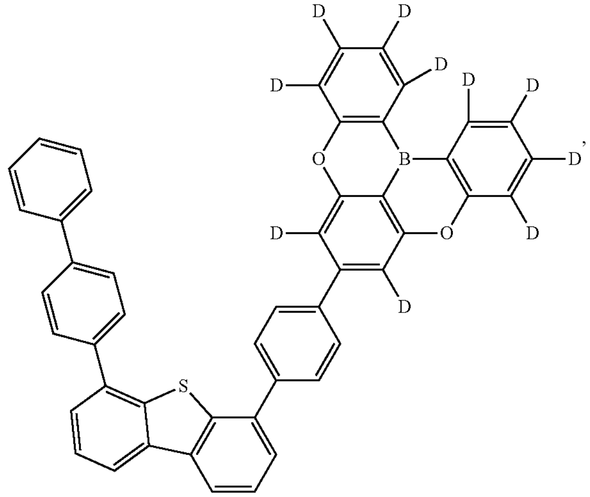

-continued
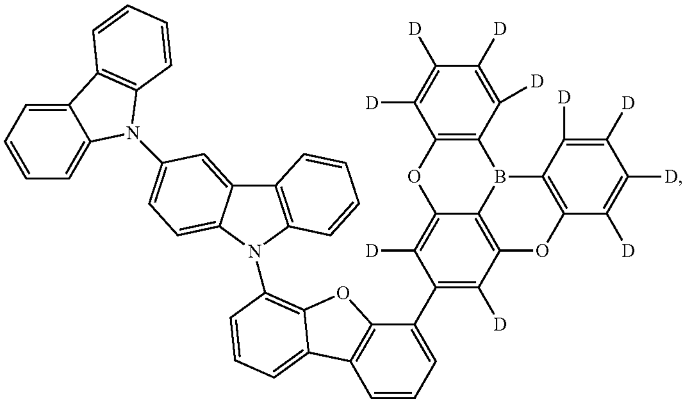
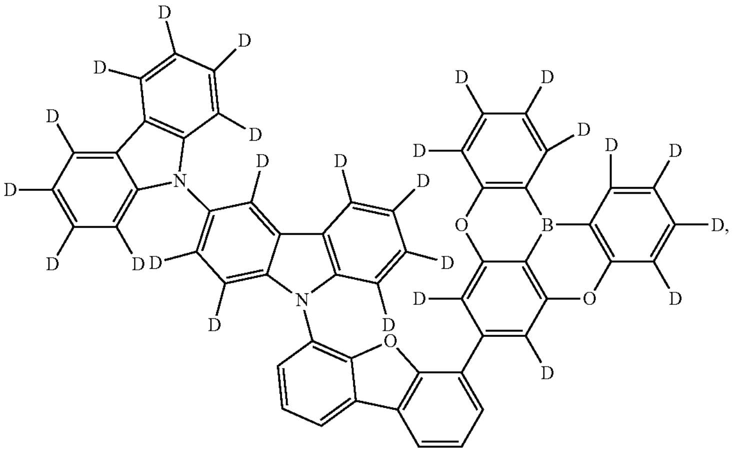
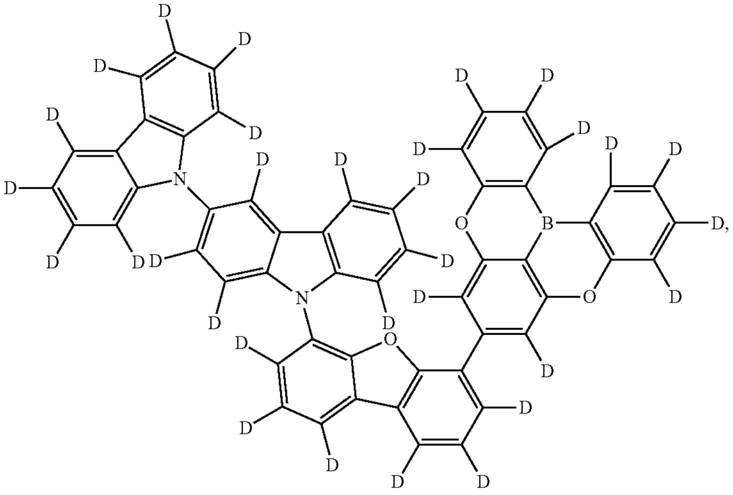

-continued
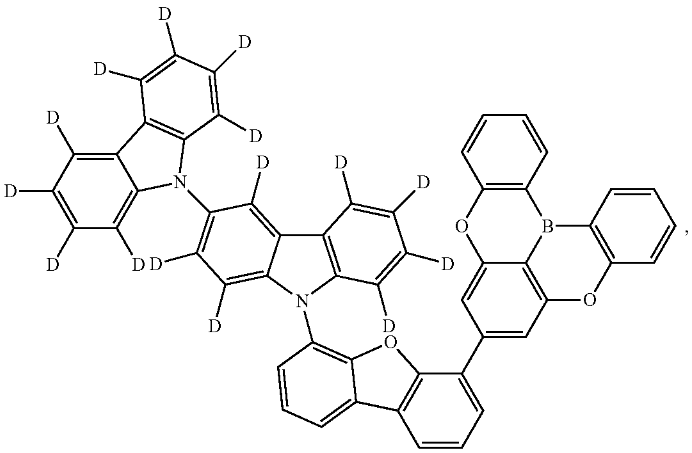
,
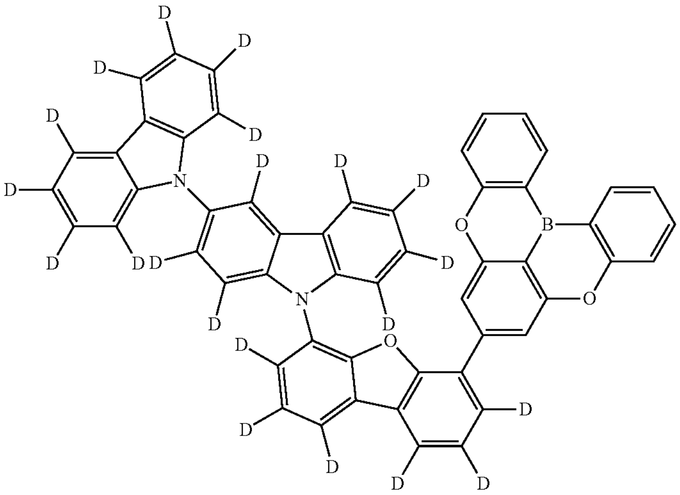
,
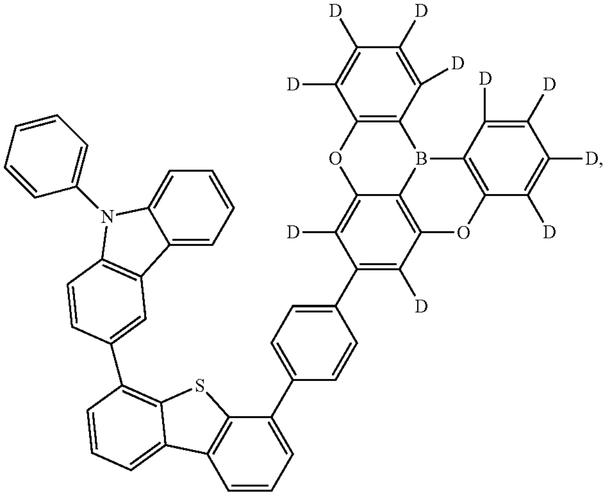
,

-continued
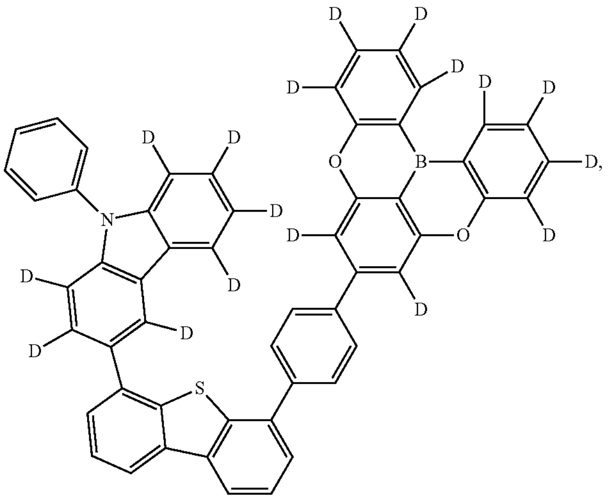
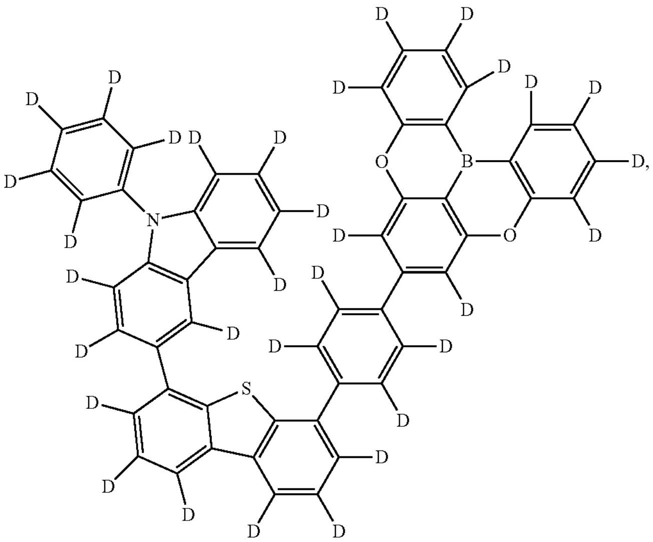
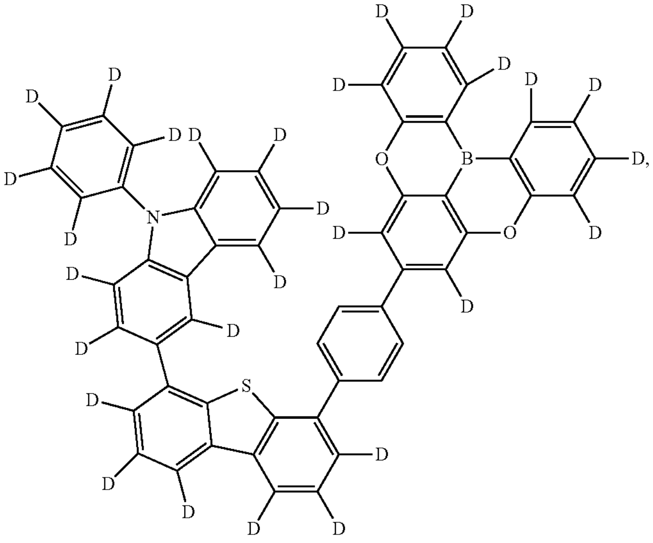

-continued
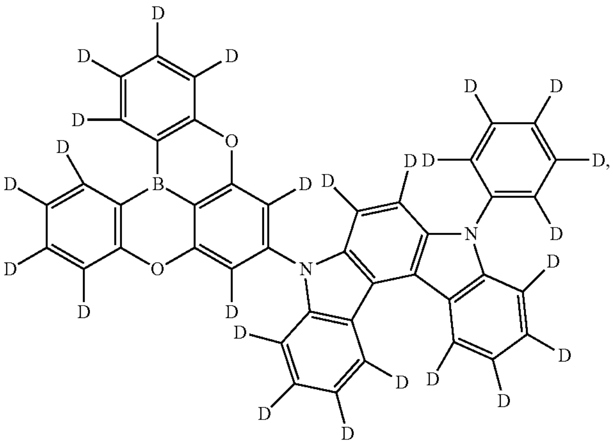
,
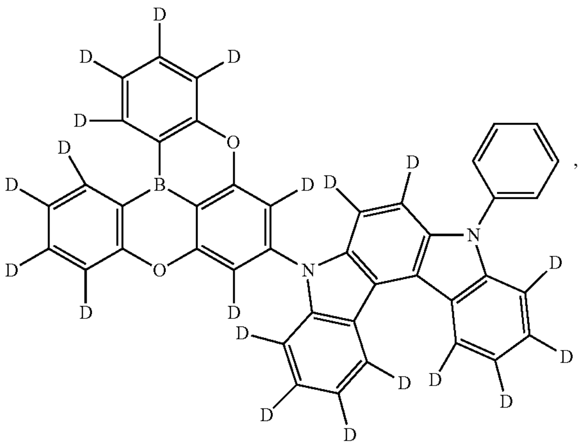
,
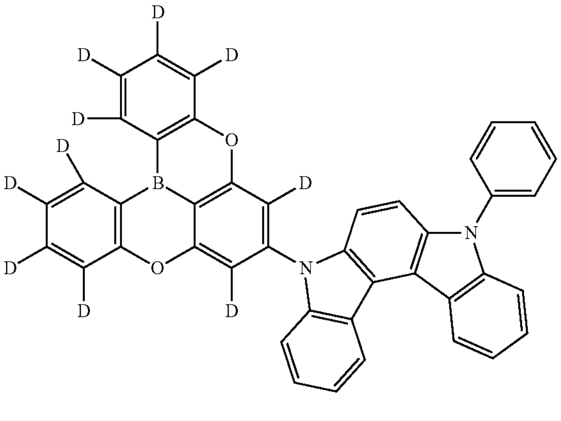
,
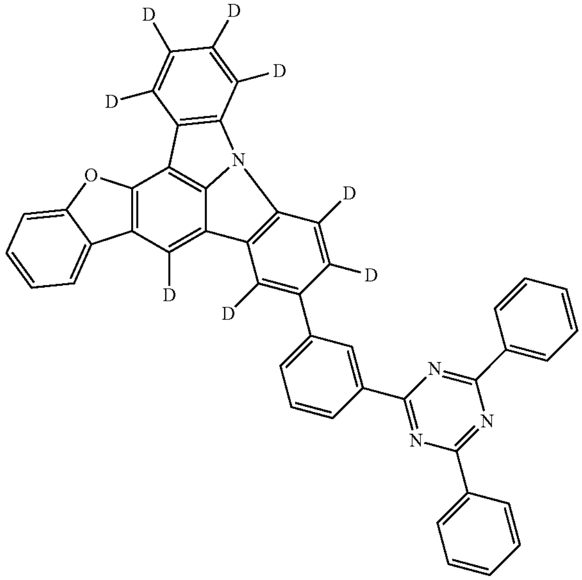
,
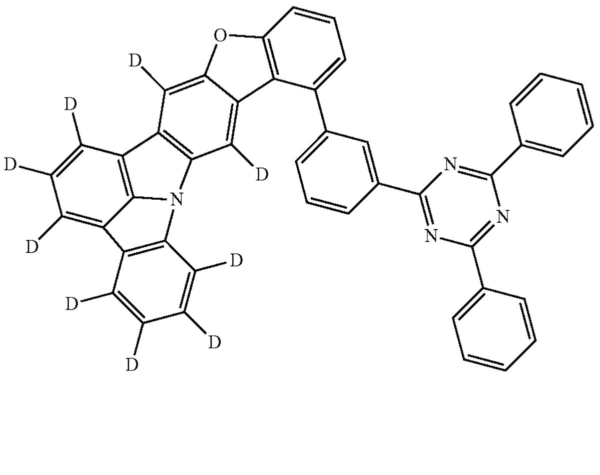
, -continued
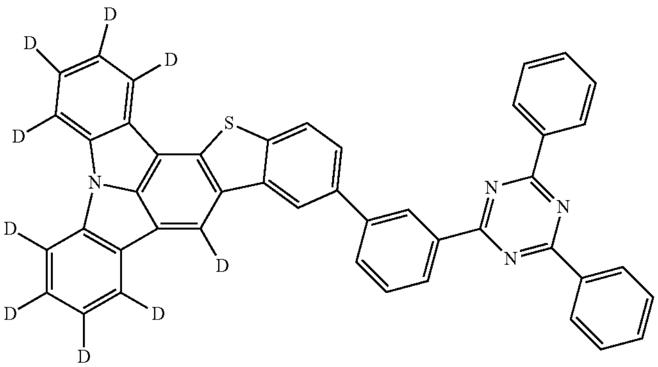
,
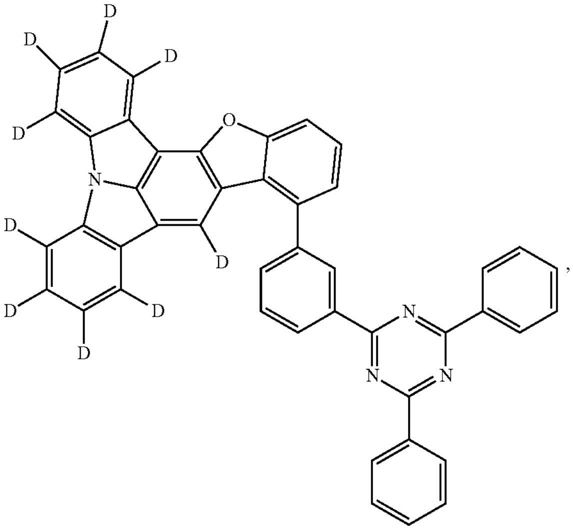
,
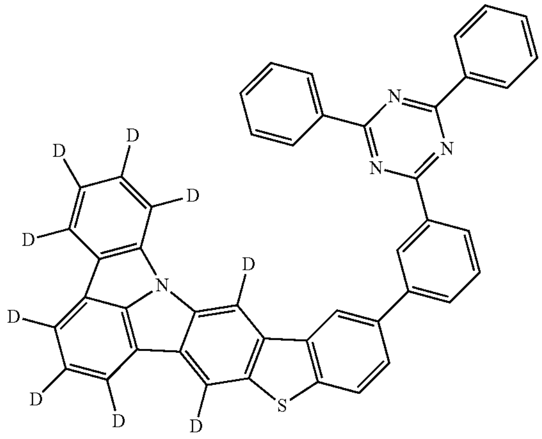
,
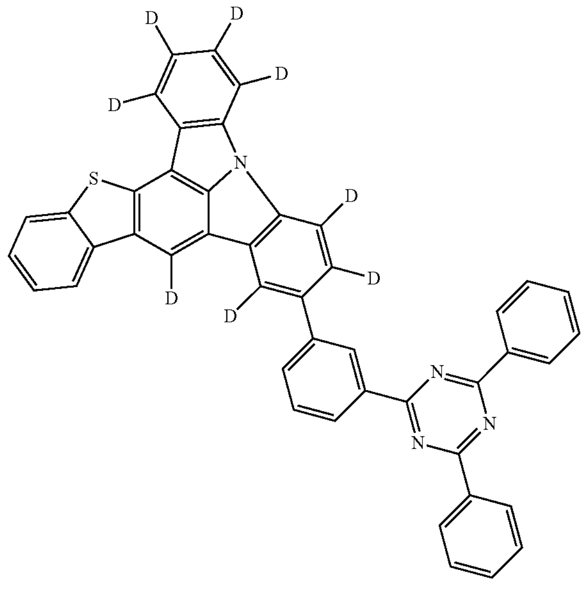
, -continued
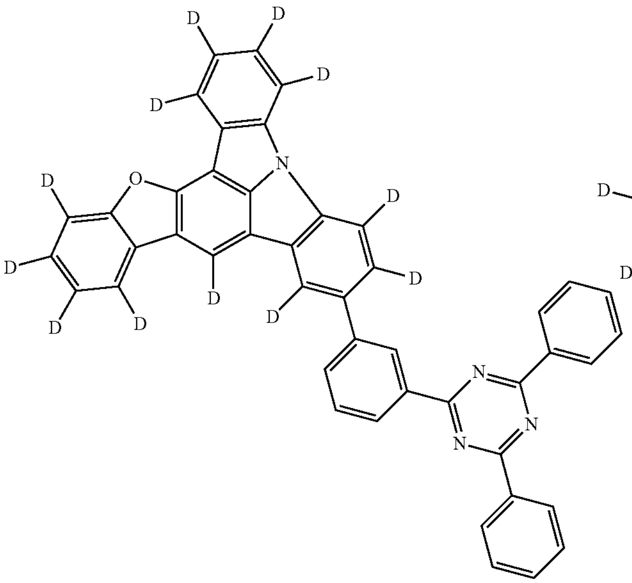
,
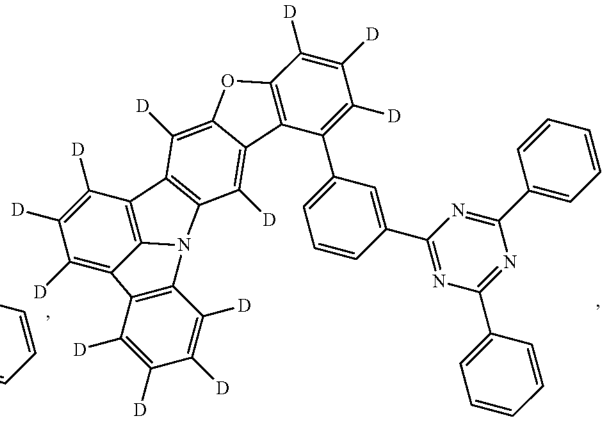
,
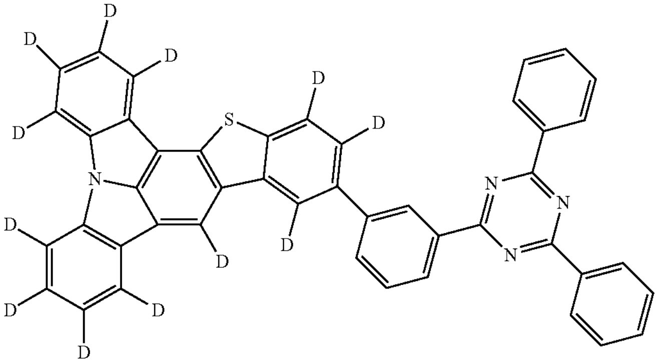
,
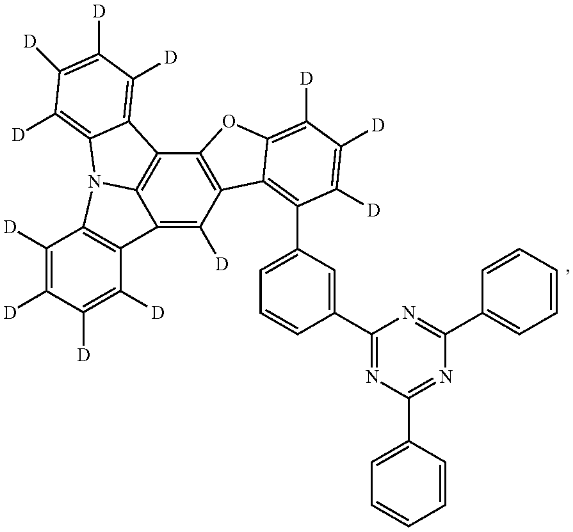
,
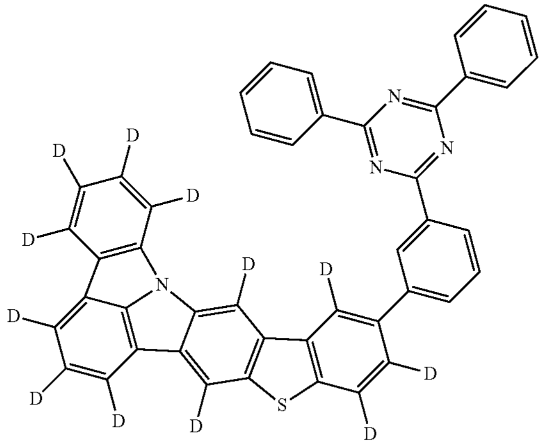
, -continued
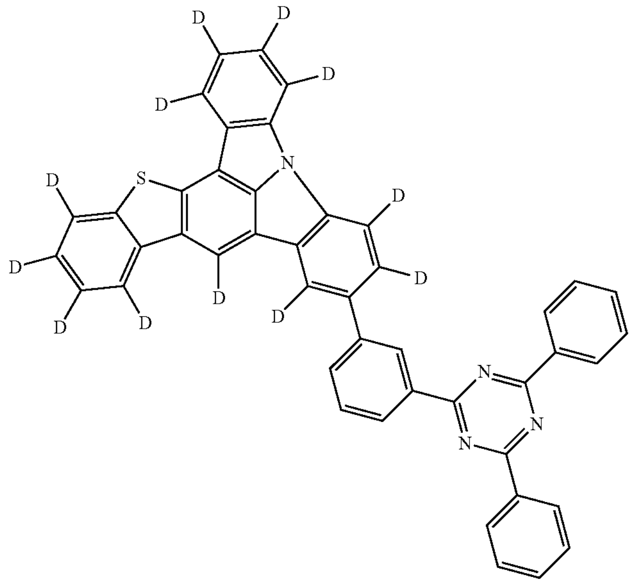
,
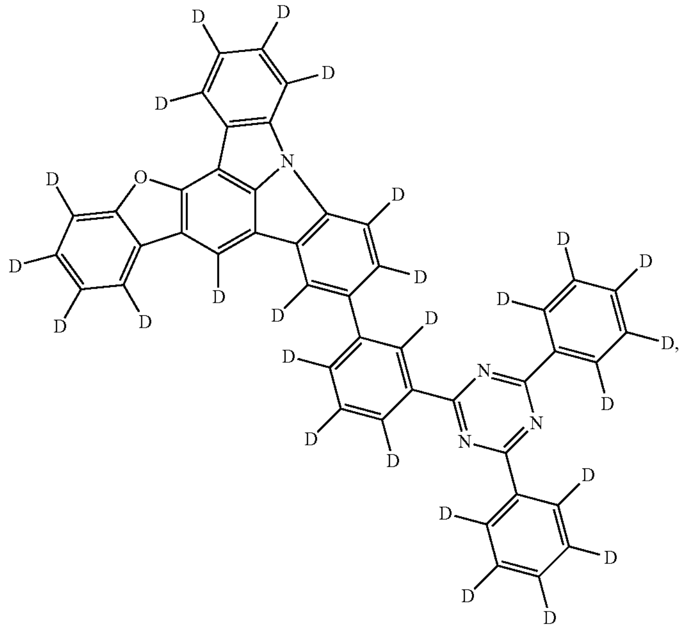
,
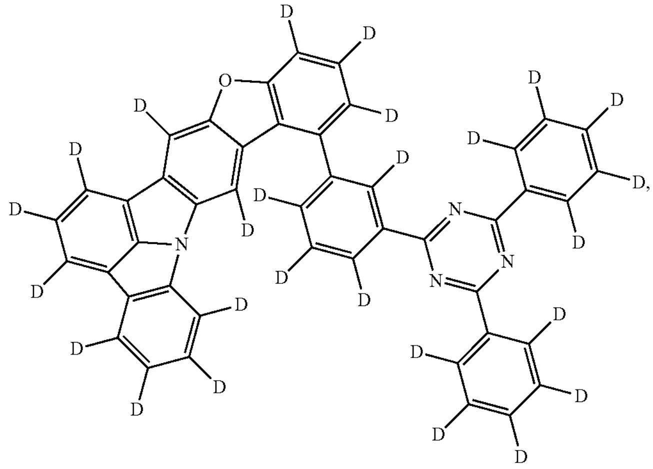
, -continued
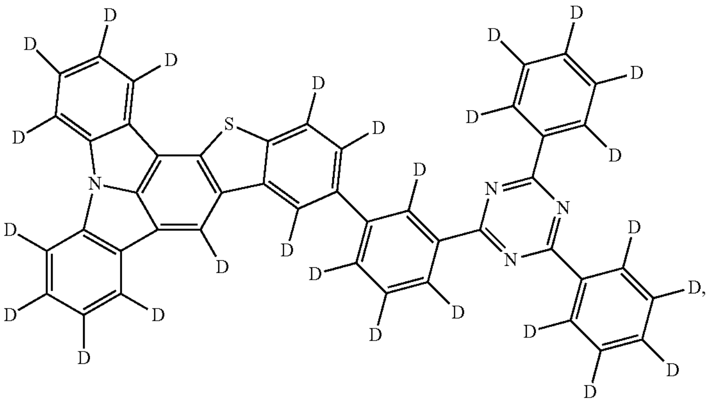
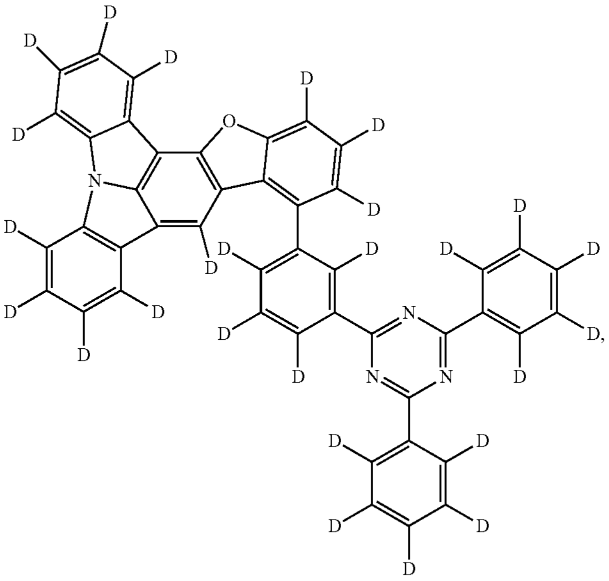
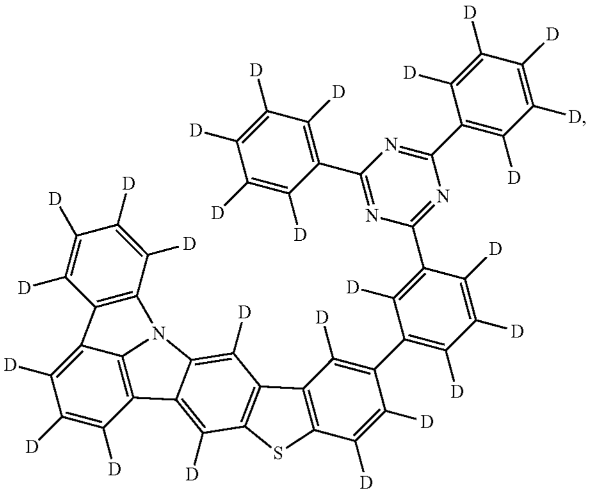

-continued
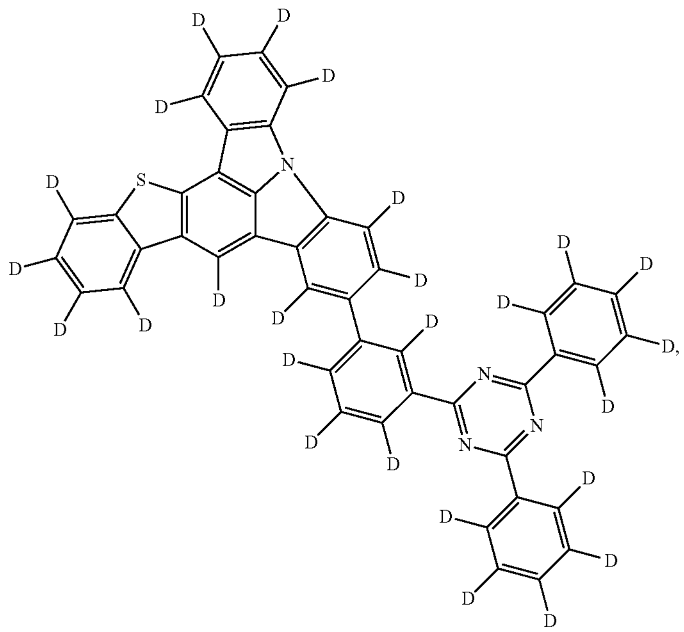
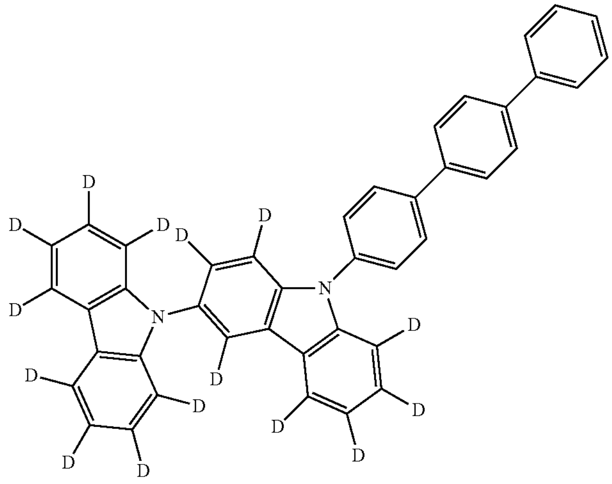
,
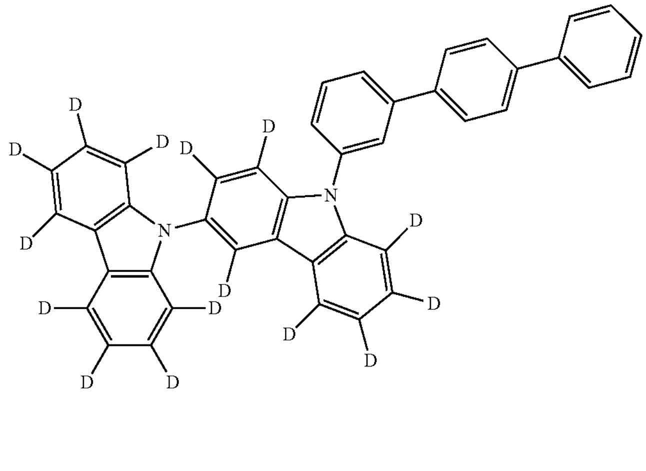
,

-continued
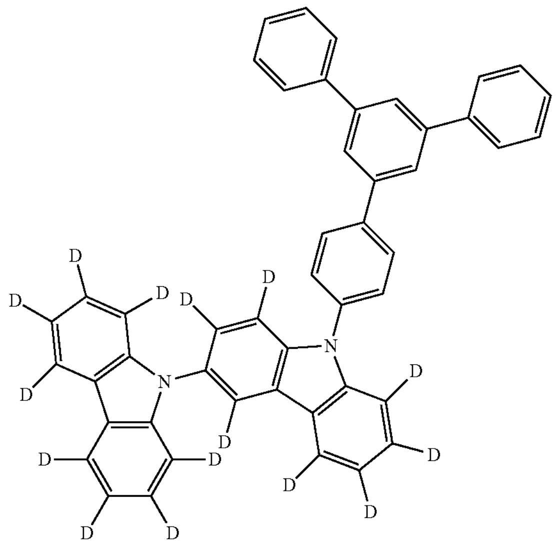
,
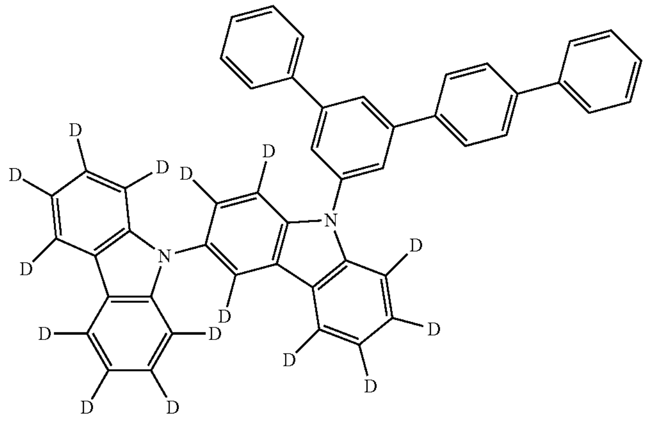
,
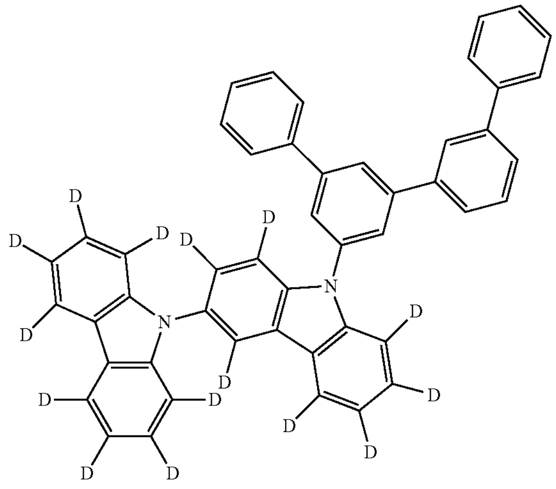
,
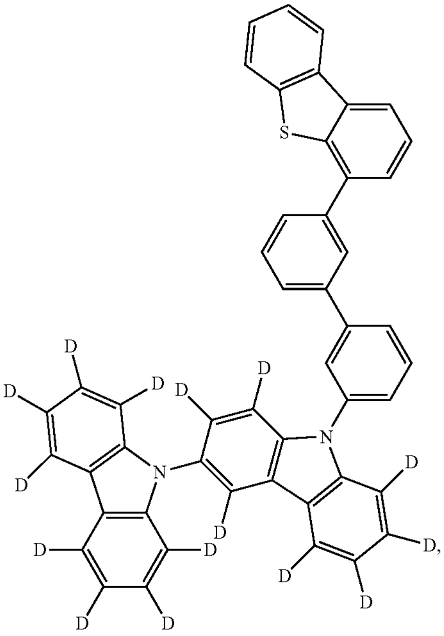
,

-continued
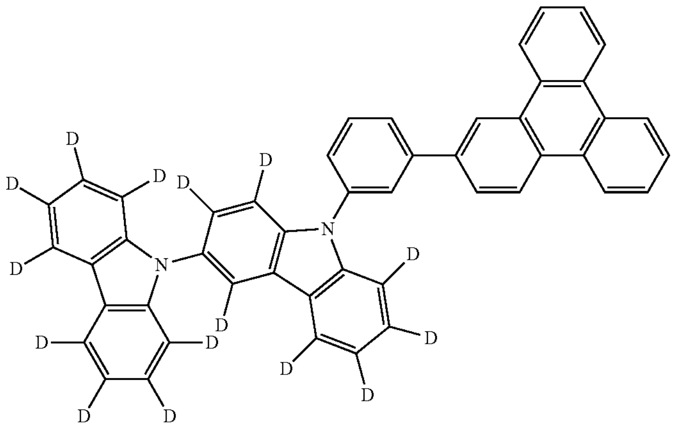
,
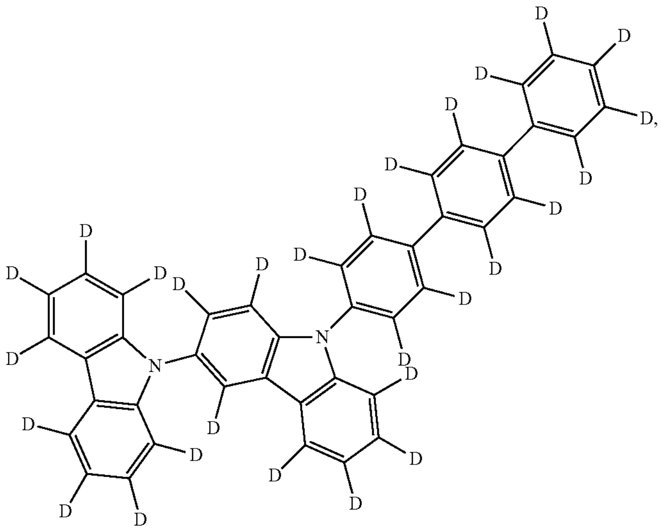
,
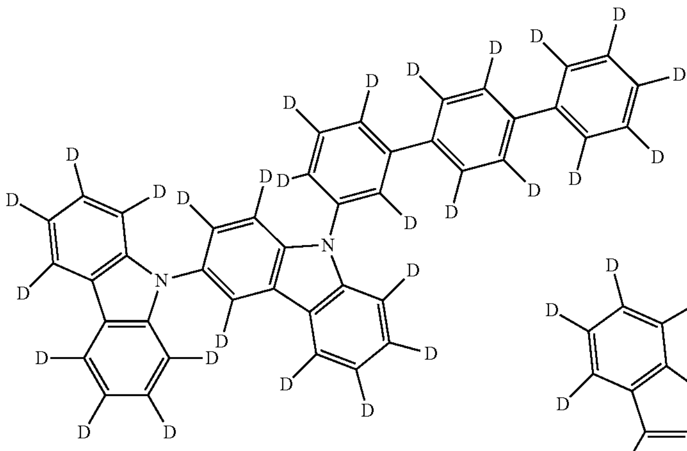
,
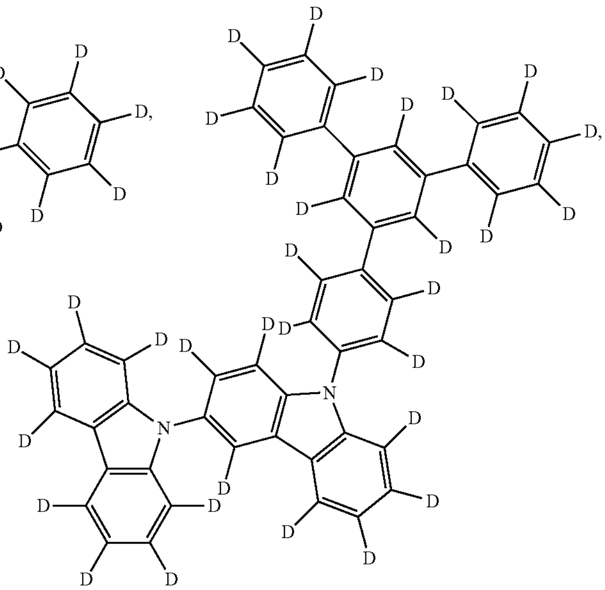
,

-continued
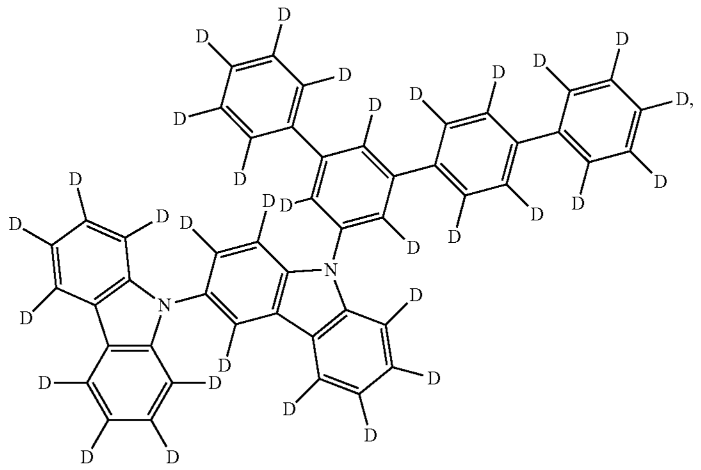
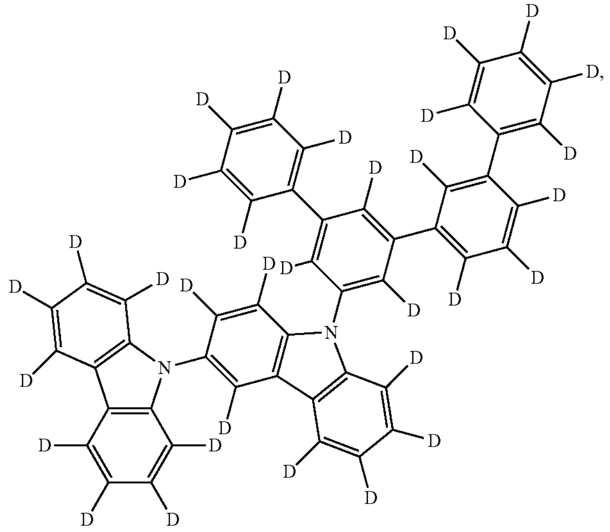
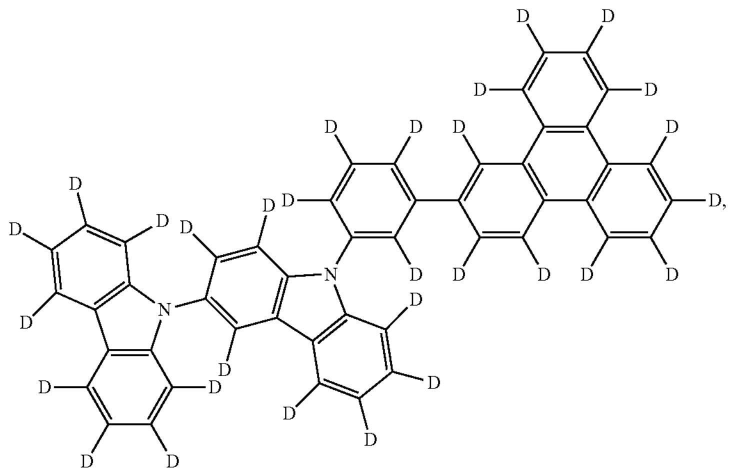

-continued
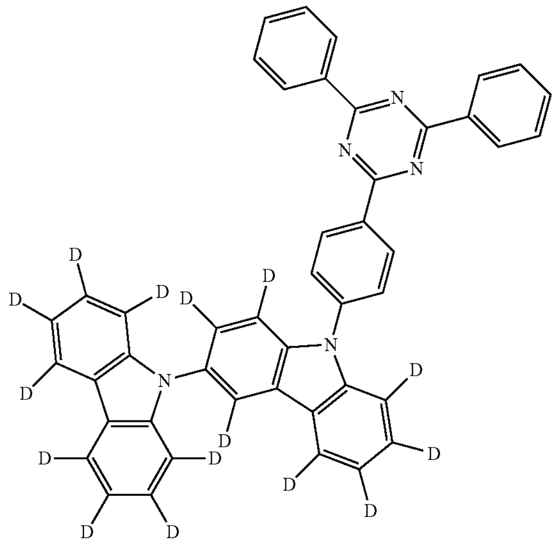
,
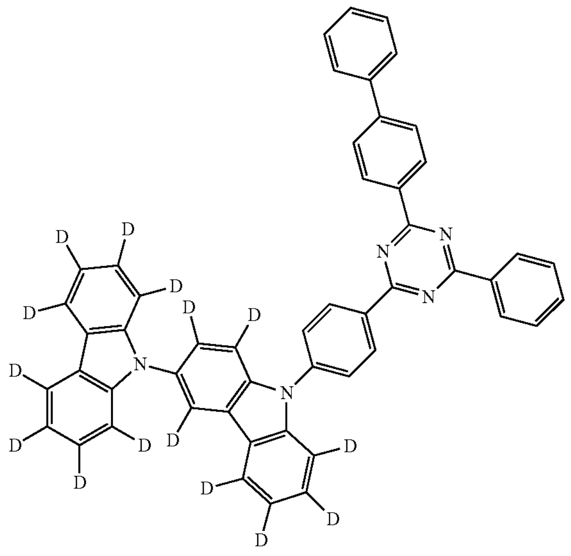
,
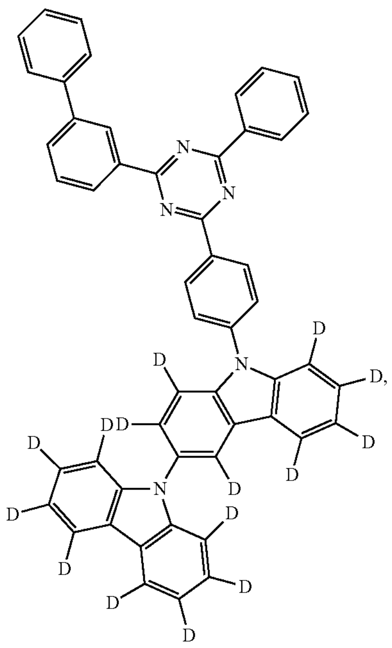
,

-continued
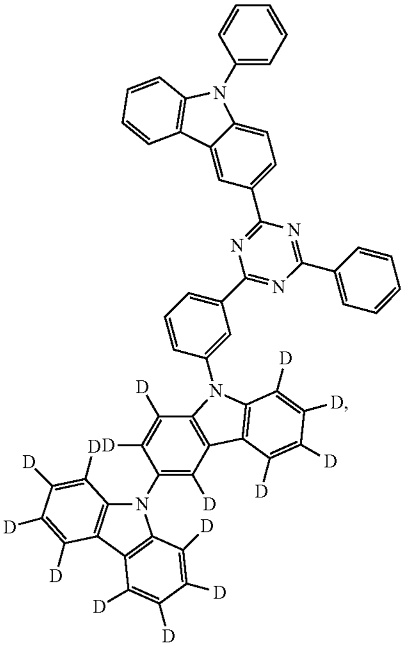
,
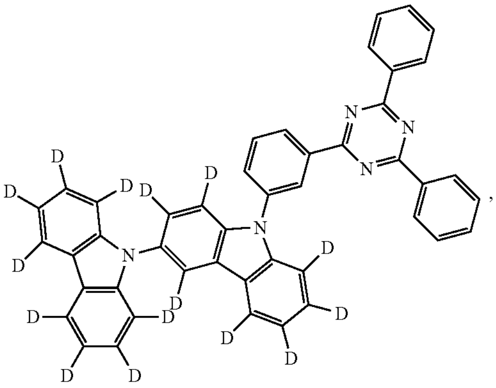
,
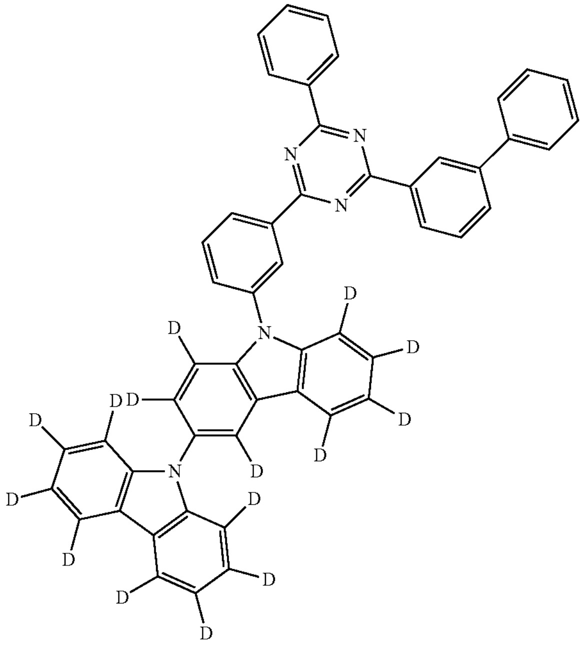
,
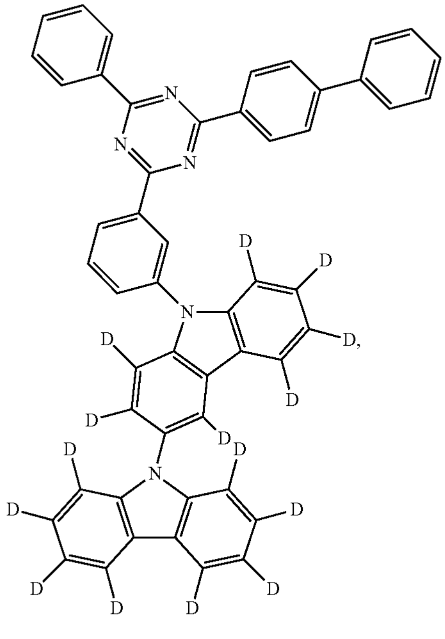
,

-continued
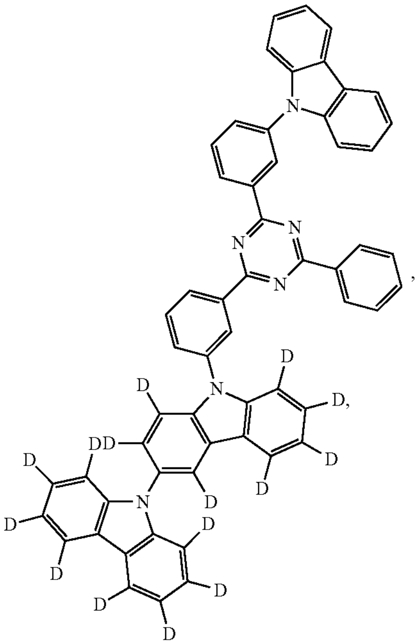
,
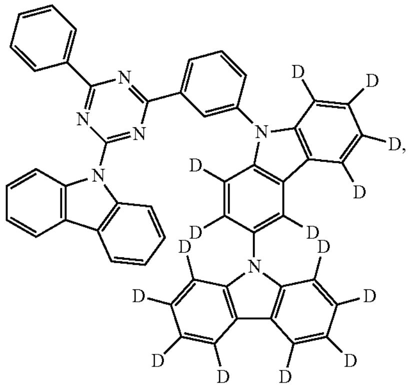
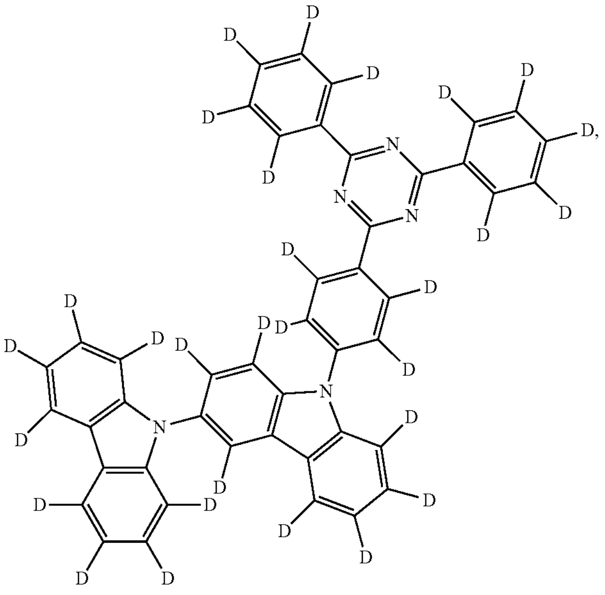

-continued
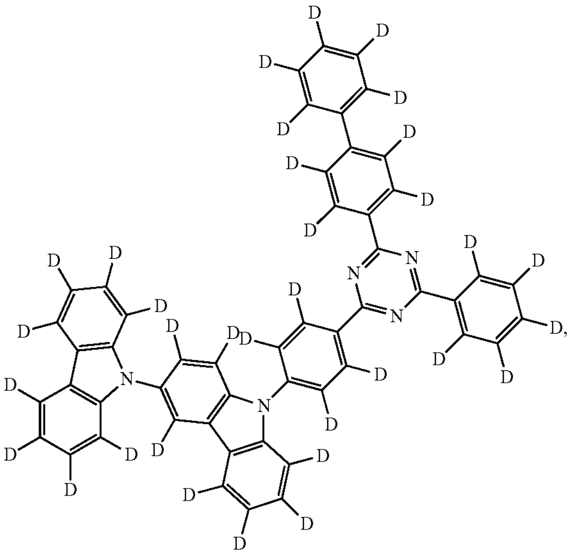
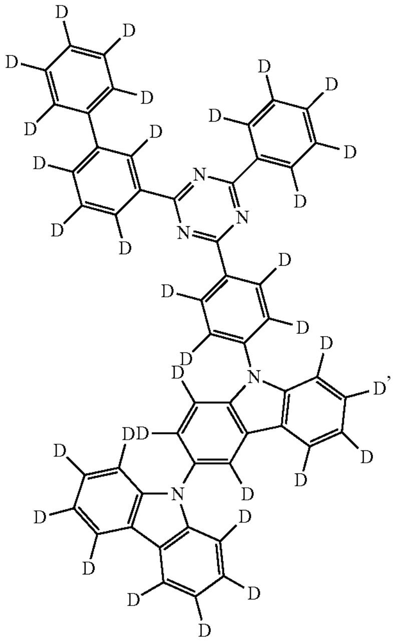
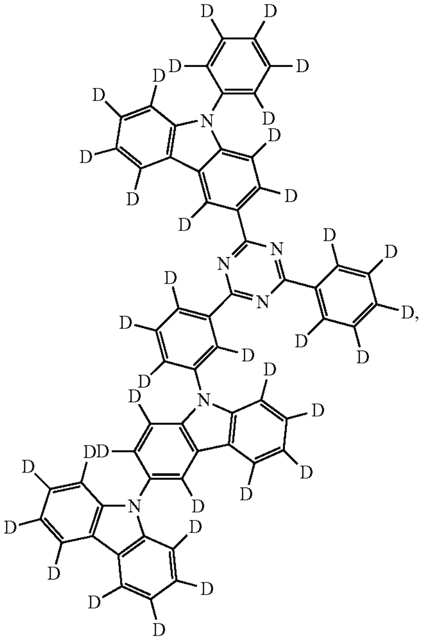
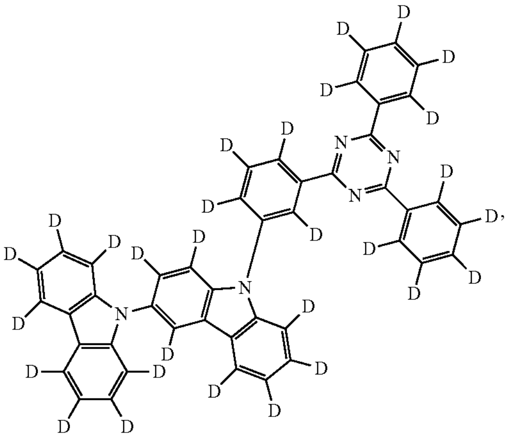

-continued
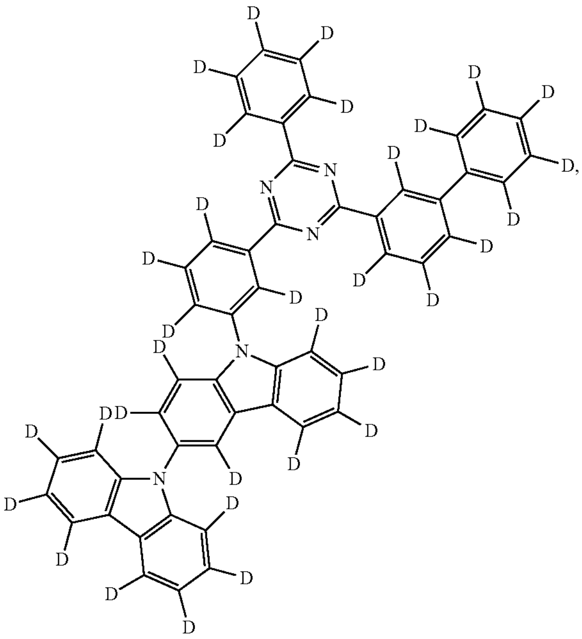
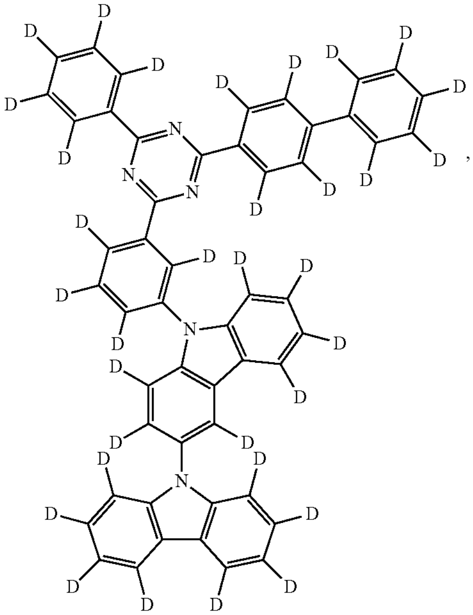
,
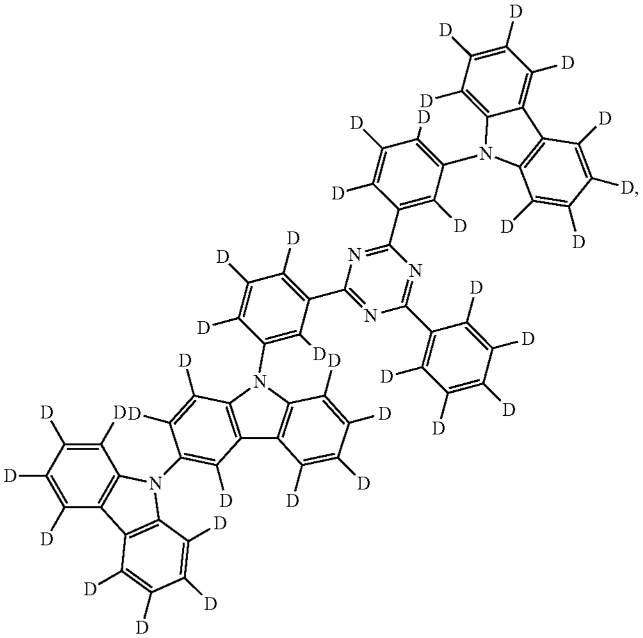
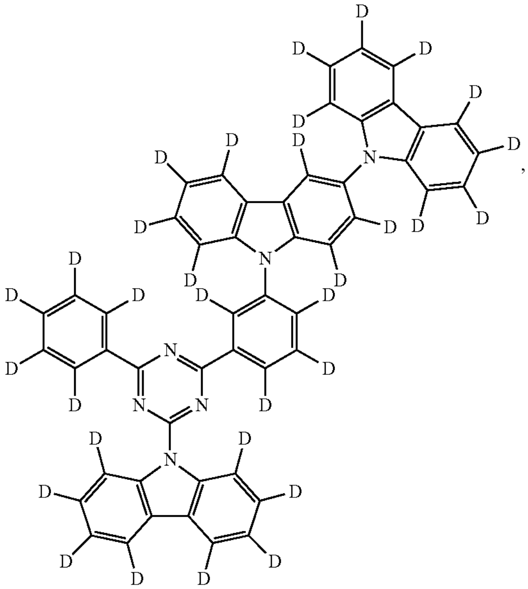
,
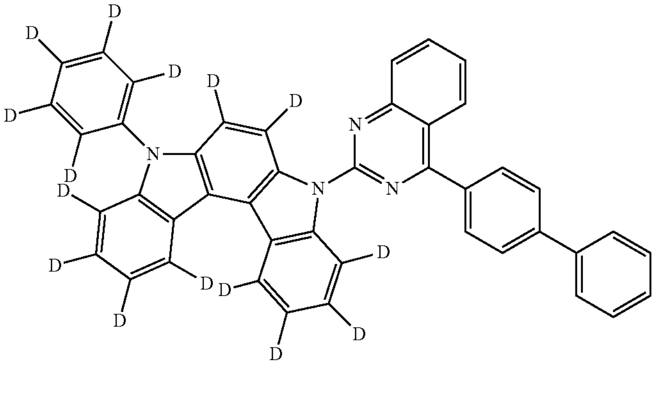
, -continued
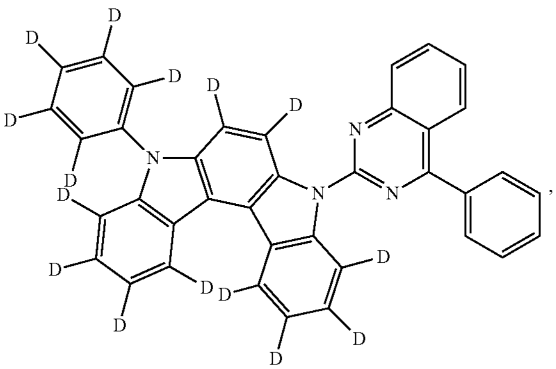
,
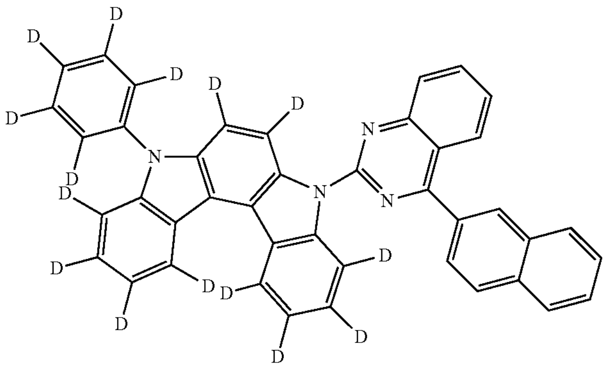
,
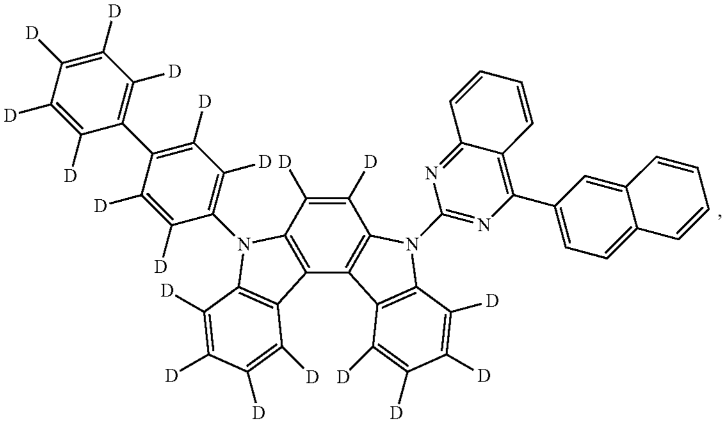
,
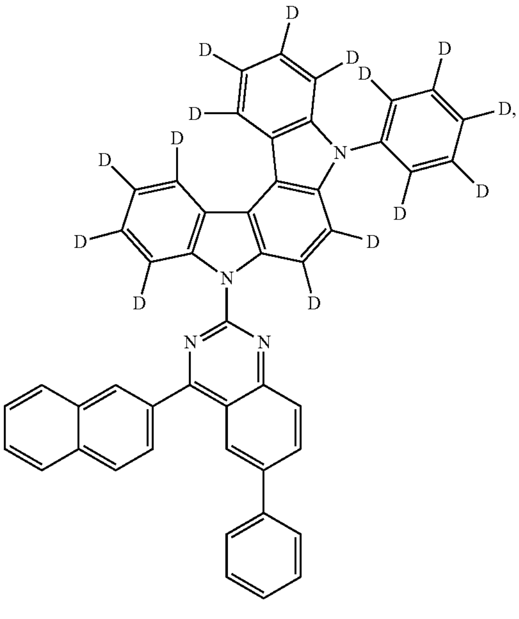
,
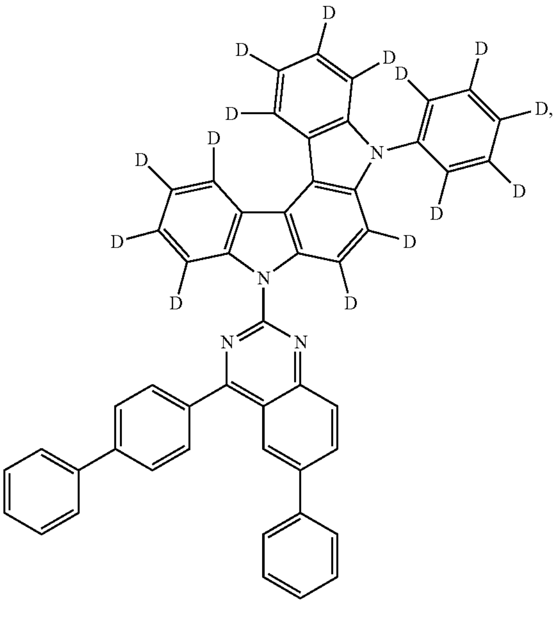
, -continued
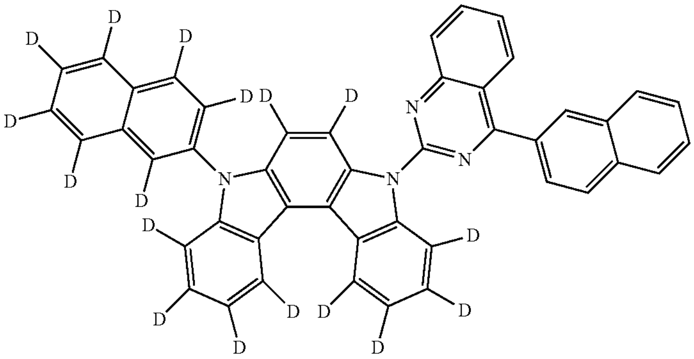
,
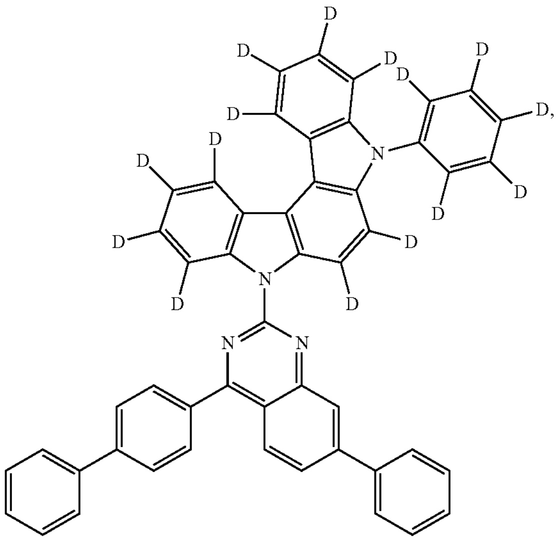
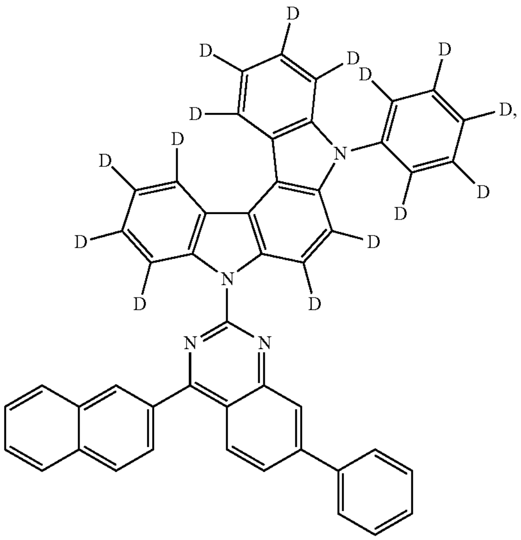
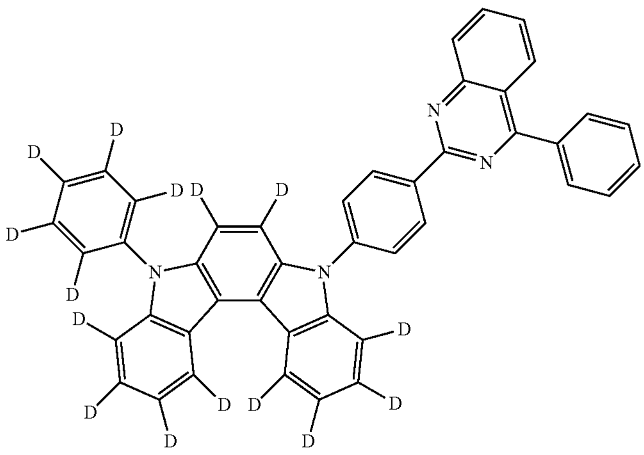
,

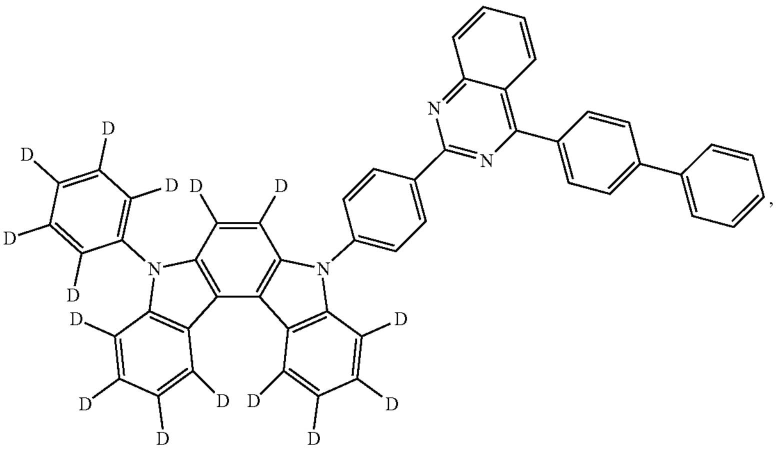
,
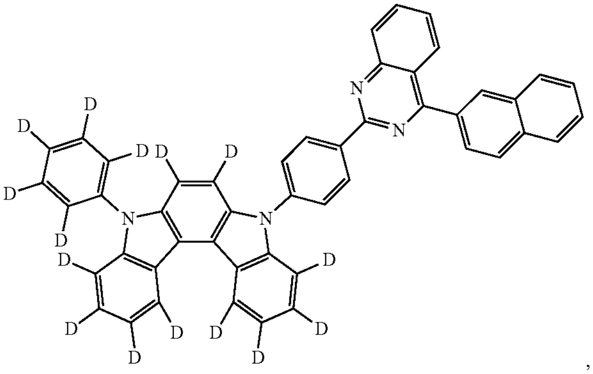
,
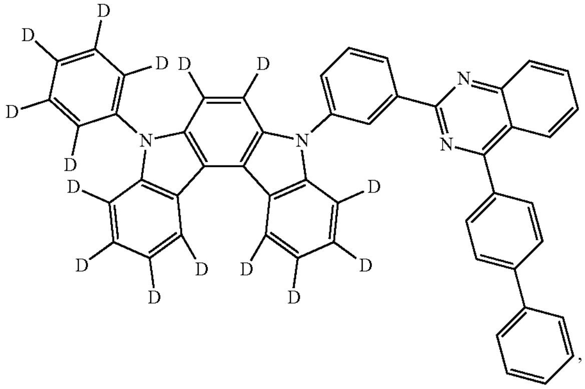
,
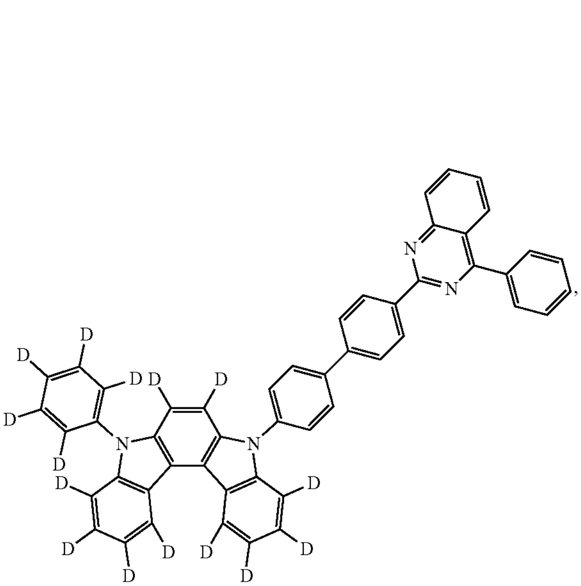
,
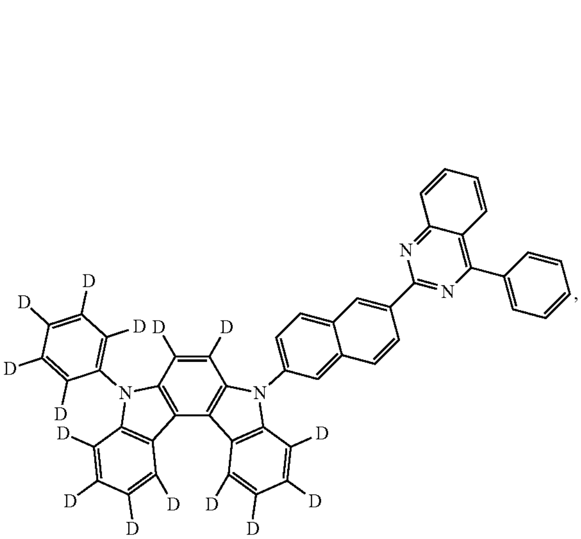
,

-continued
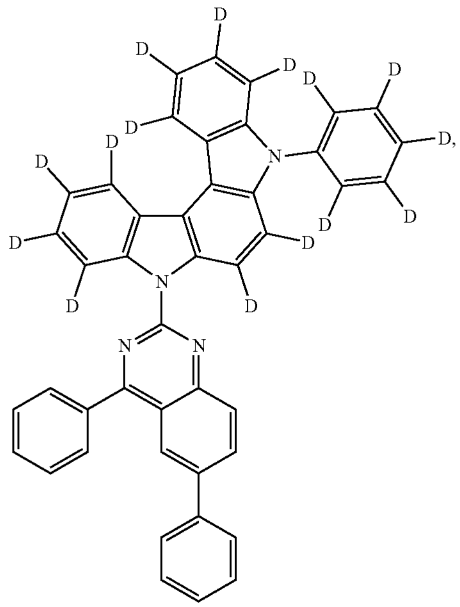
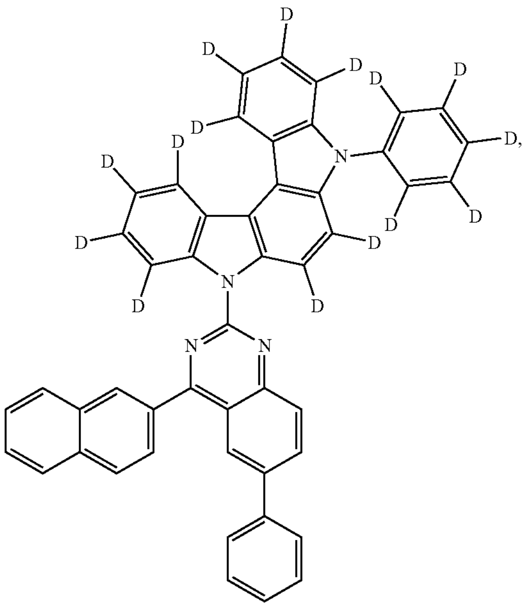
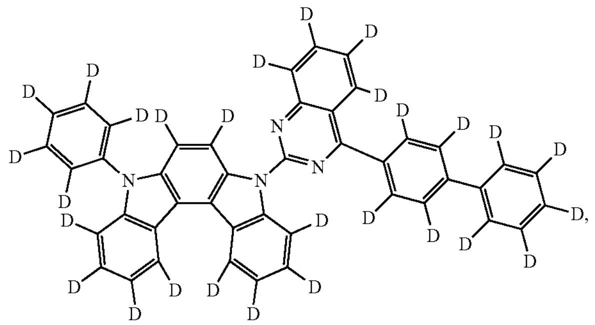
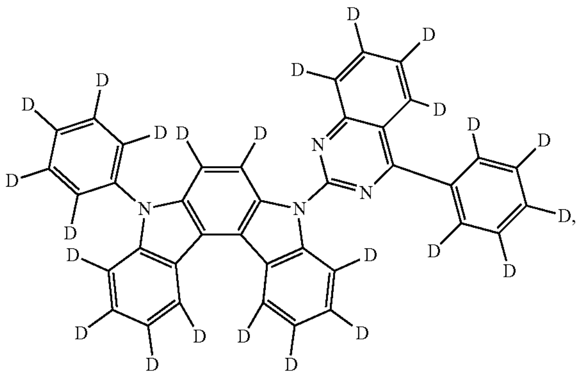
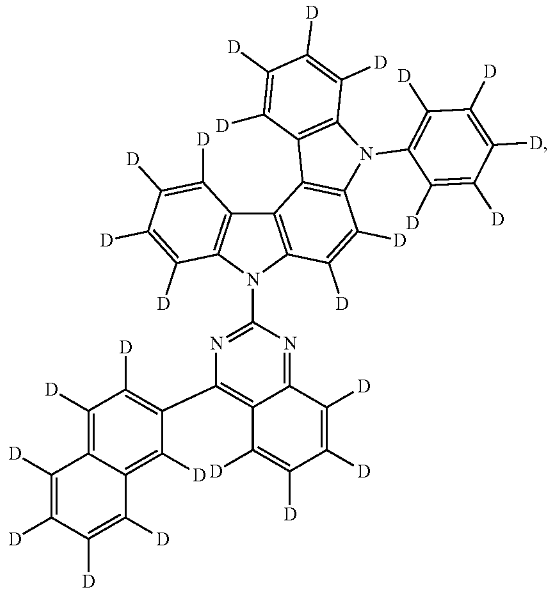

-continued
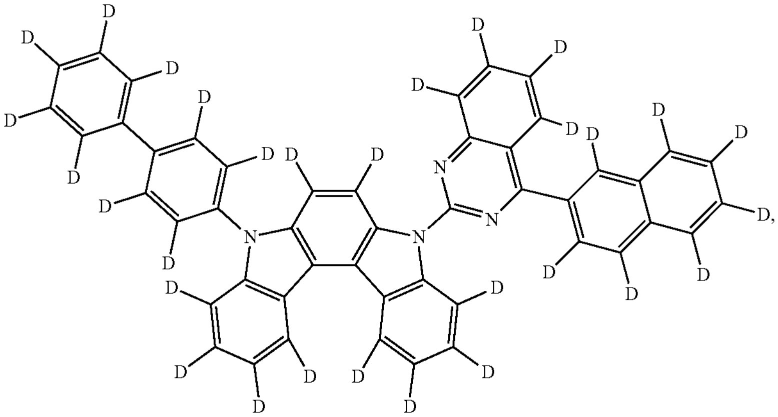
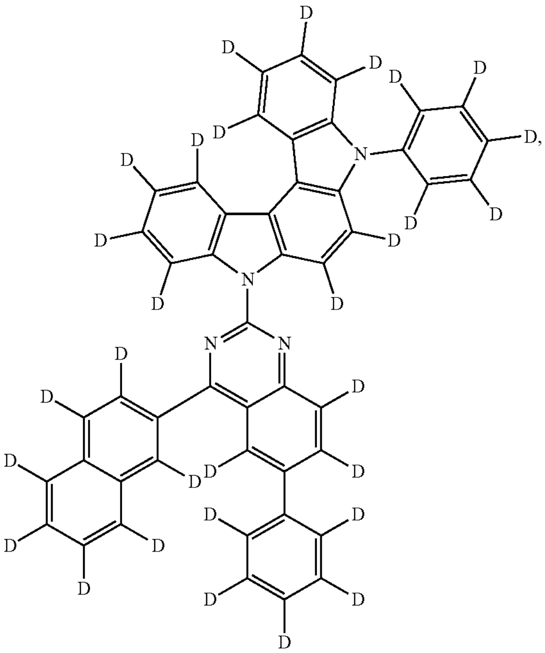
,
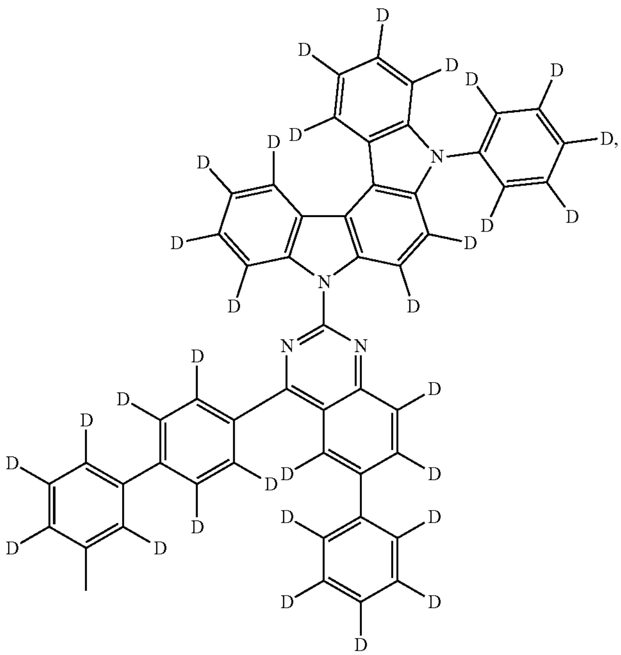
,
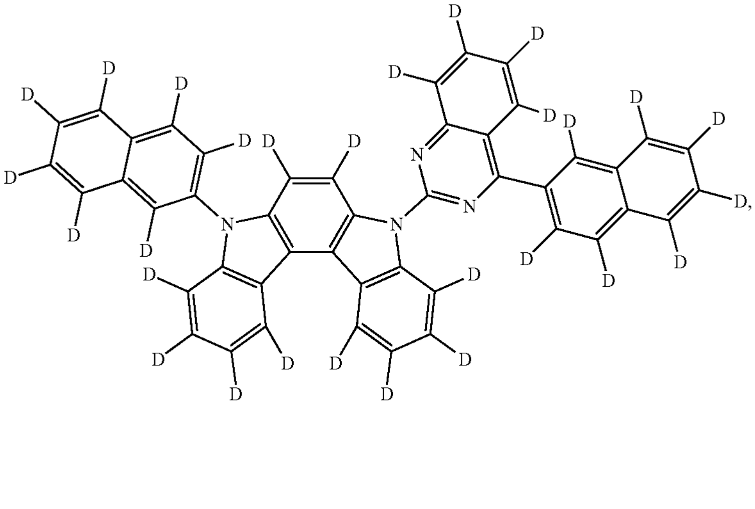
,

-continued
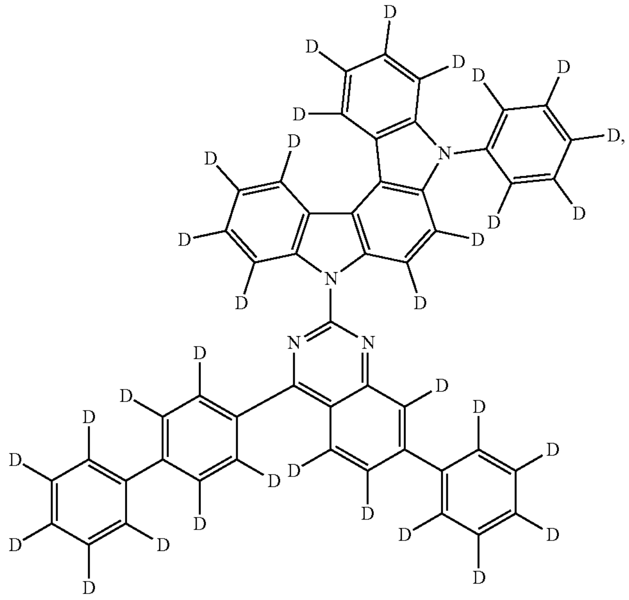
,
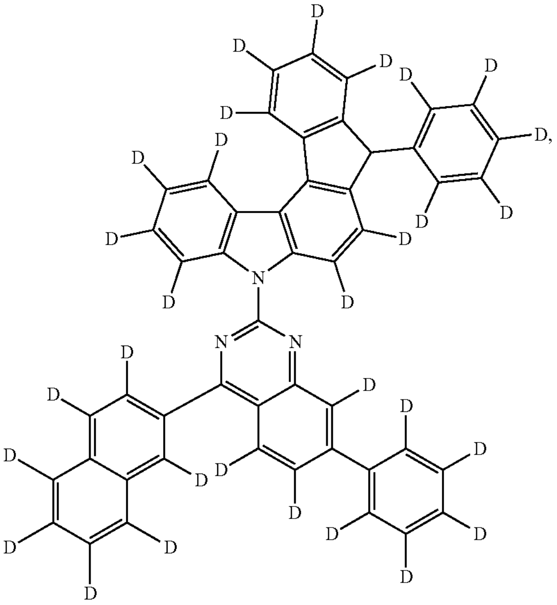
,
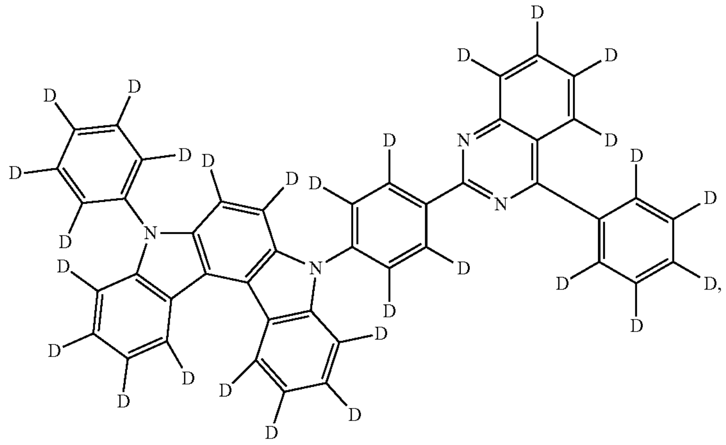
,
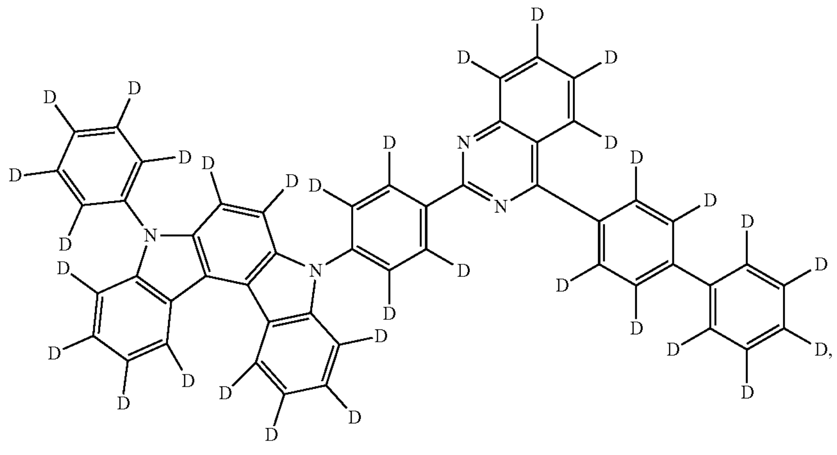
,

-continued
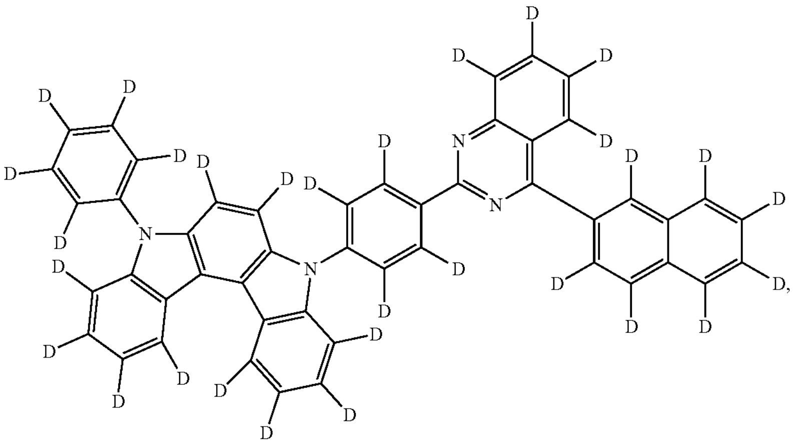
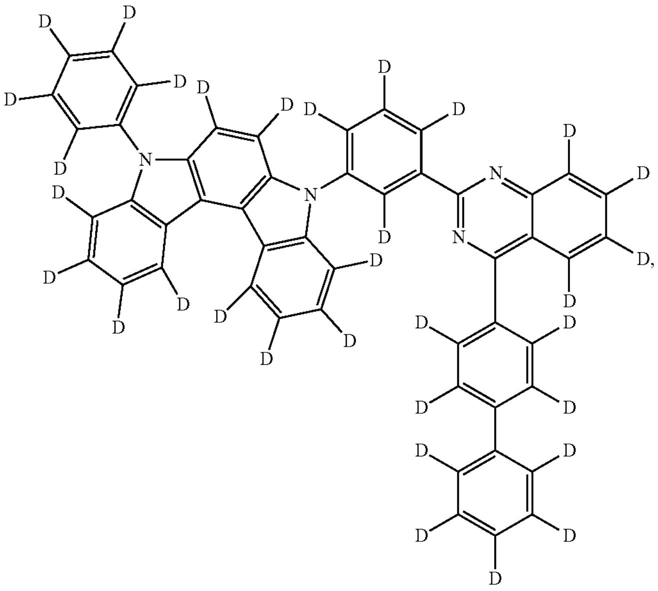
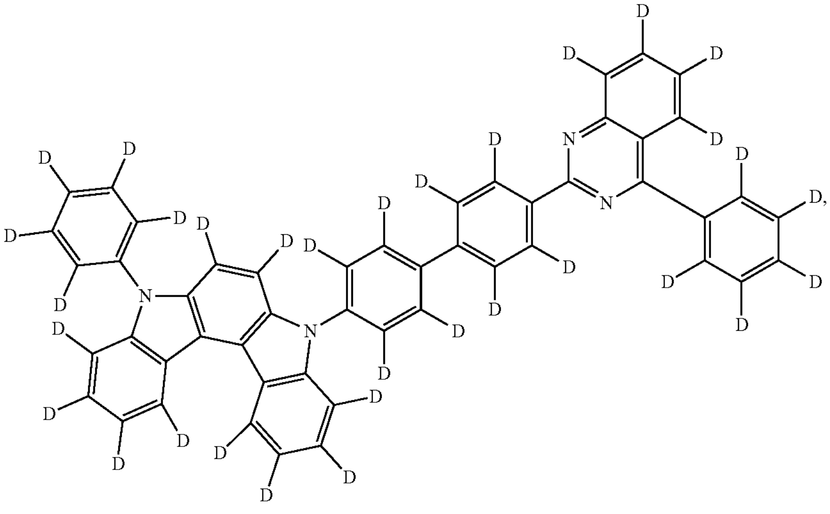

-continued
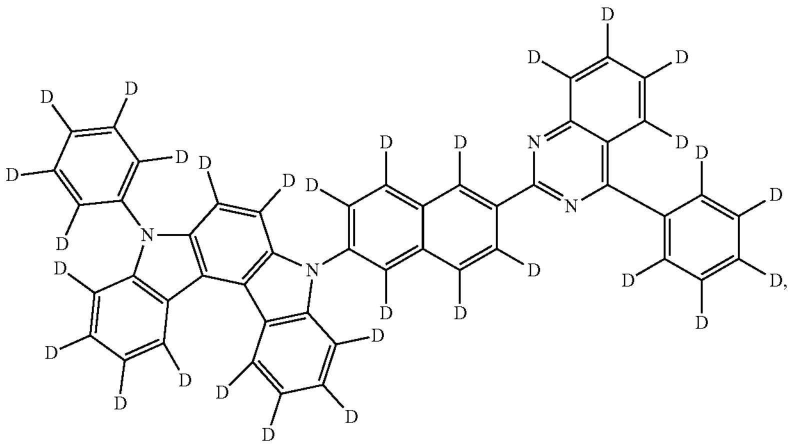
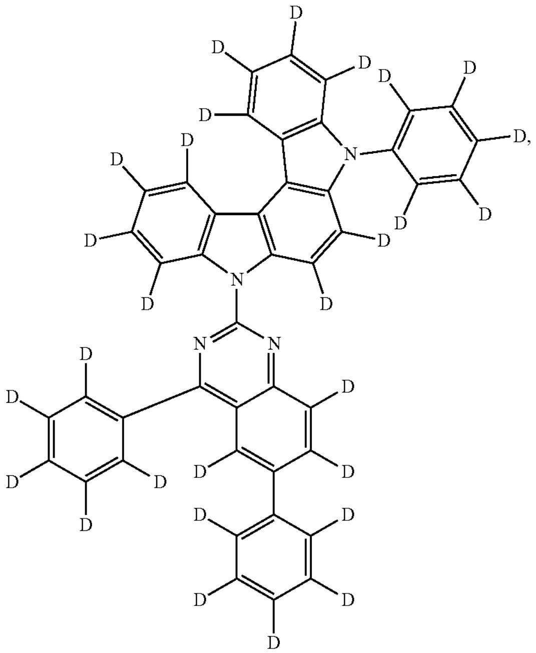
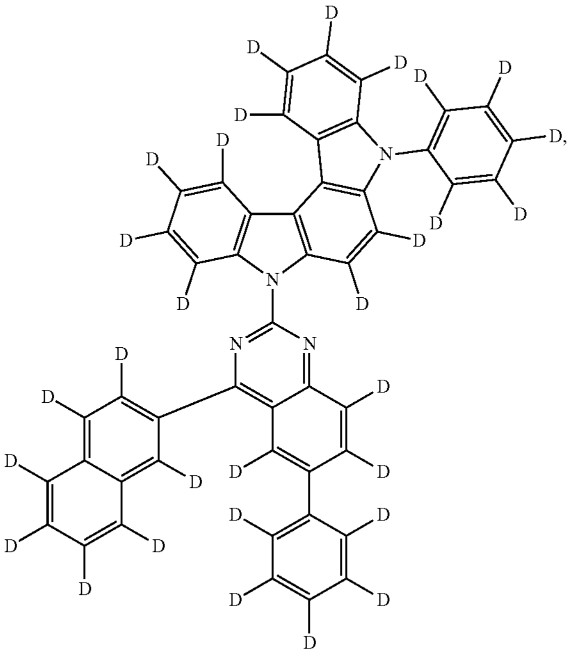
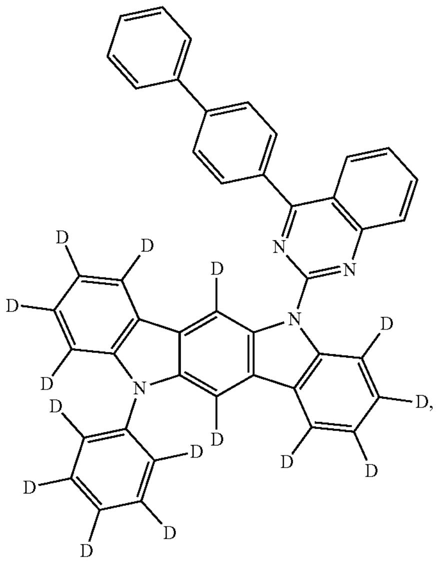
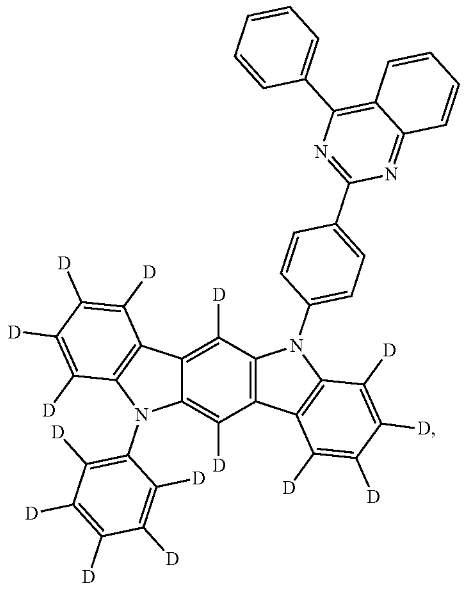

-continued
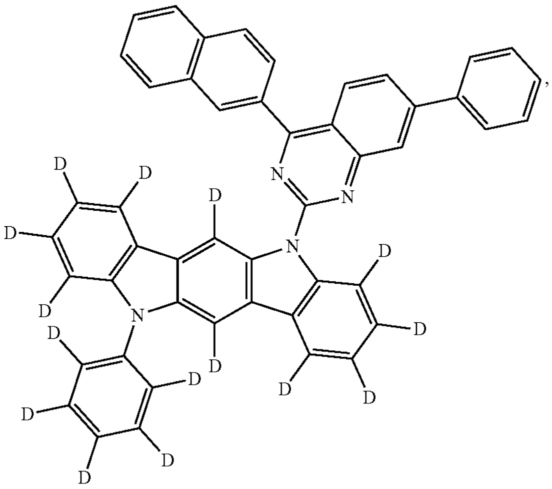
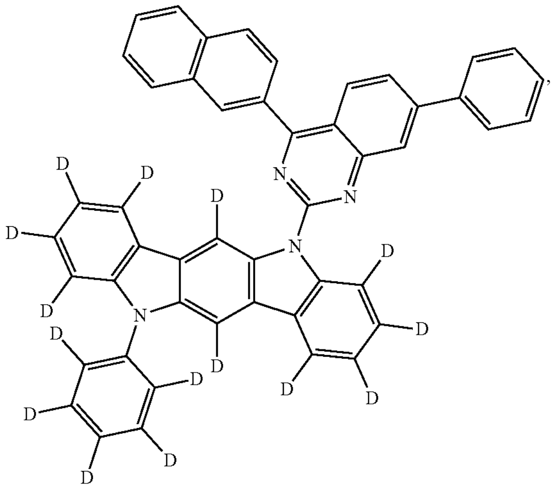
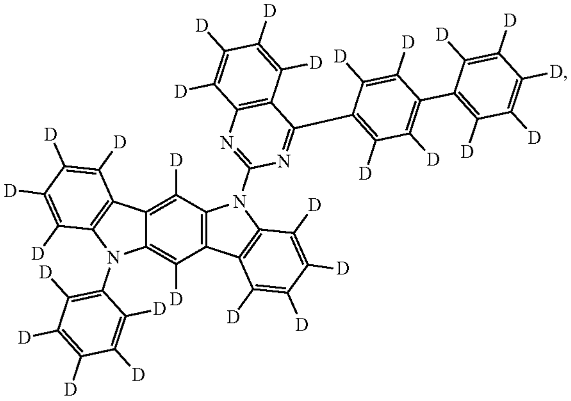
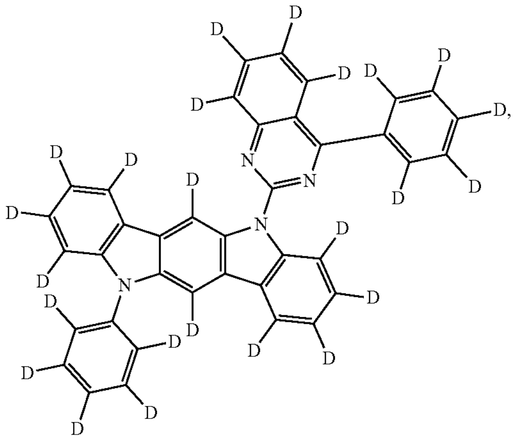
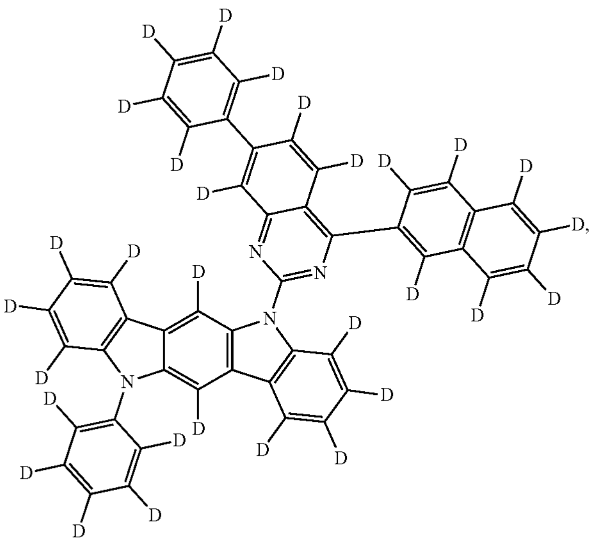
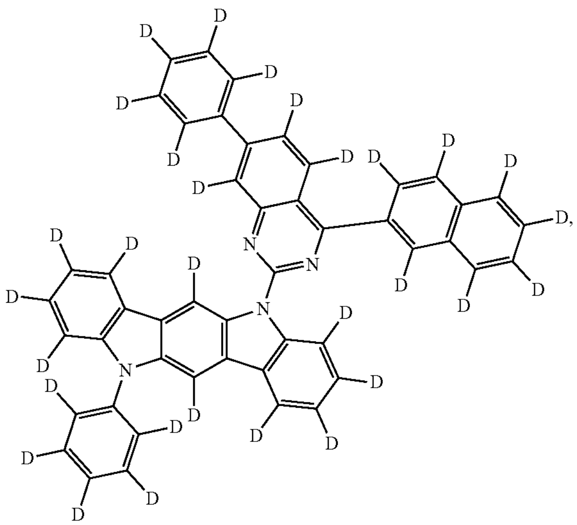

-continued
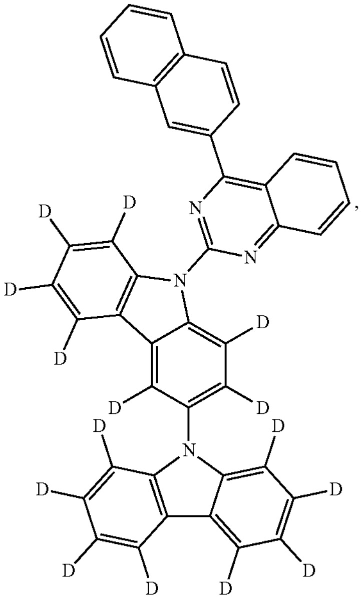
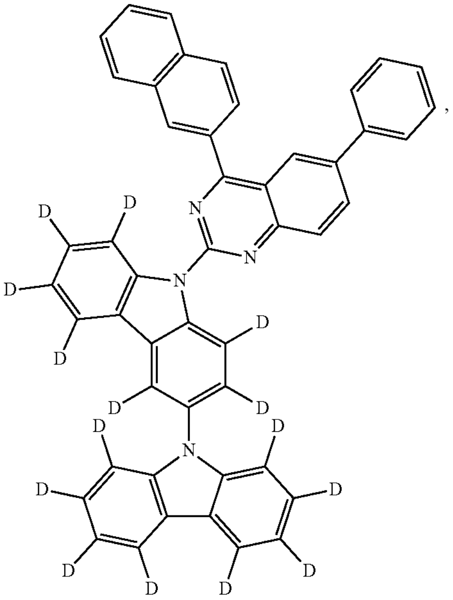
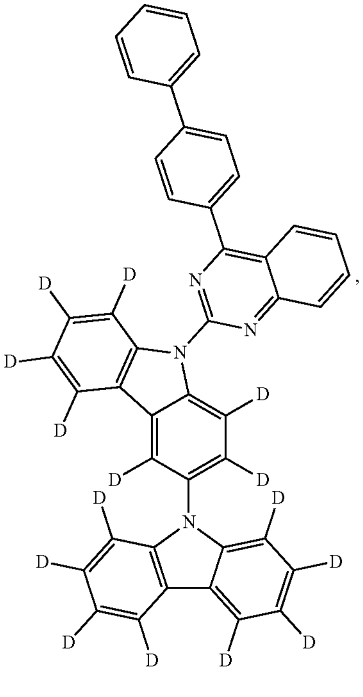
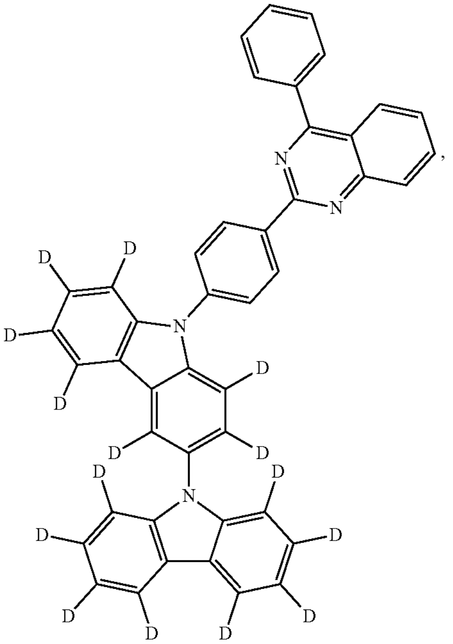

-continued
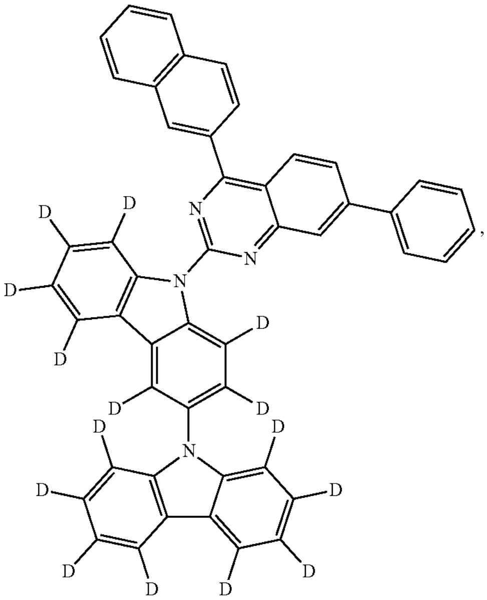
,
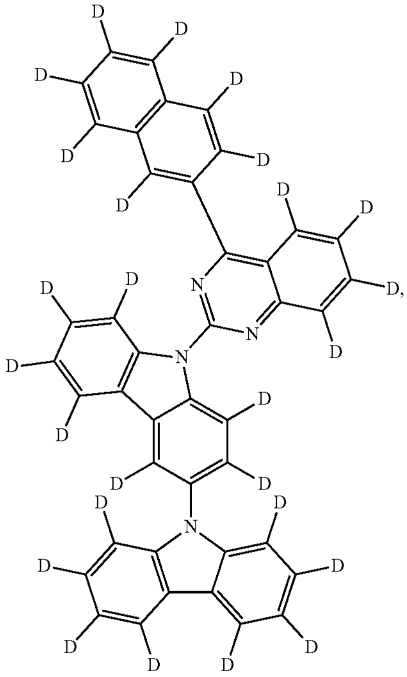
,
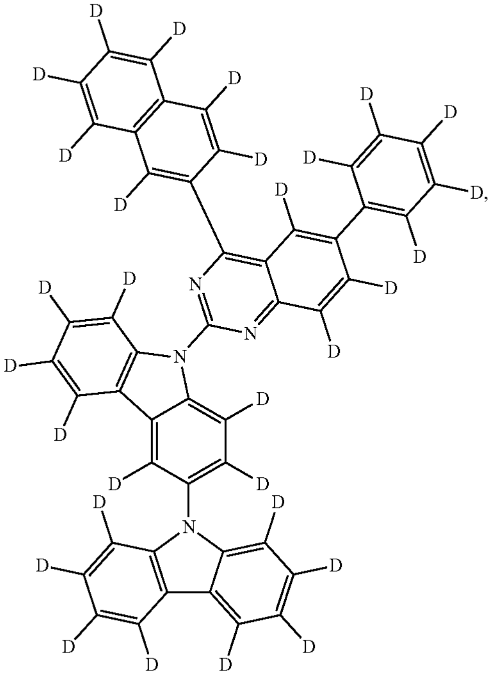
,
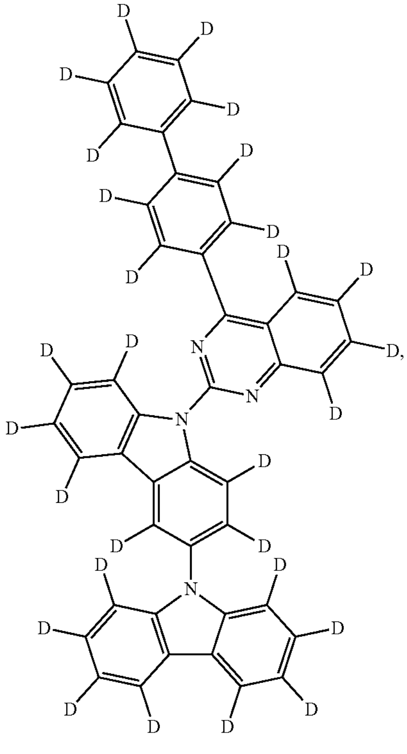
,

-continued

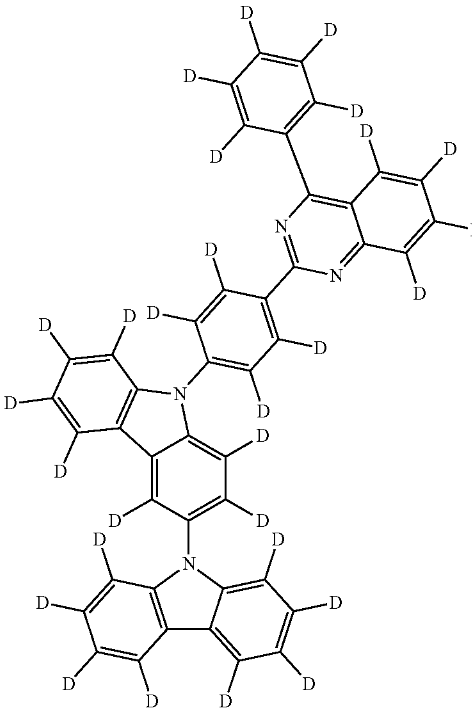

D,

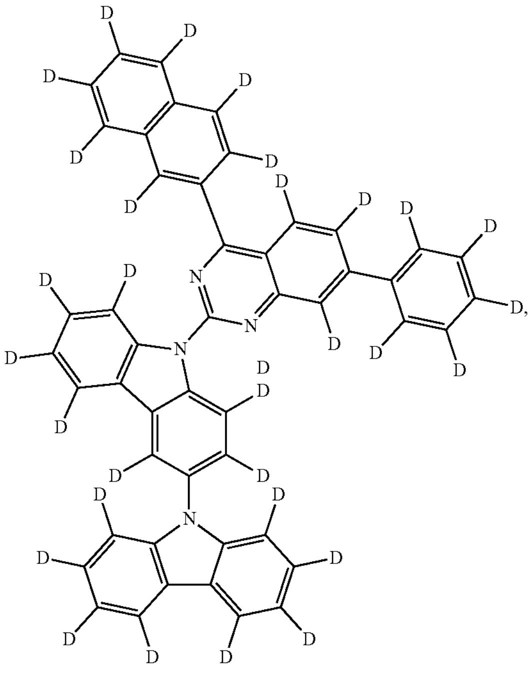

D, and

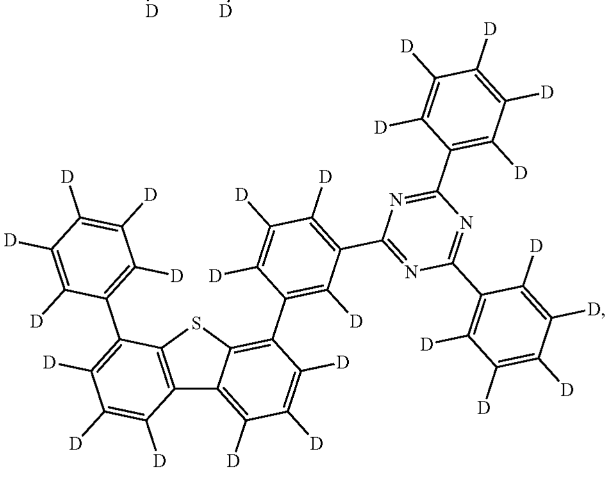

D, wherein:

each of $X_1$ to $X_{11}$ is independently C or N;

each $Y^A$ is independently absent or, when present, is selected from the group consisting of O, S, Se, CRR', SiRR', NR, BR, BRR';

each of $R^{A'}$, $R^{B'}$, $R^{C'}$, $R^{D'}$, $R^{E'}$, $R^{F'}$, and $R^{G'}$ independently represents mono-, up to the maximum substitutions, or no substitutions;

each of R, R', $R^{A'}$, $R^{B'}$, $R^{C'}$, $R^{D'}$, $R^{E'}$, $R^{F'}$, and $R^{G'}$ is independently a hydrogen or a substituent selected from the group consisting of the General Substituents defined herein; and at least one R, R', $R^{A'}$, $R^{B'}$, $R^{C'}$, $R^{D'}$, $R^{E'}$, $R^{F'}$, or $R^{G'}$ comprises deuterium.

* * * * *